US011076875B2

(12) United States Patent
Bonadio et al.

(10) Patent No.: US 11,076,875 B2
(45) Date of Patent: Aug. 3, 2021

(54) TISSUE EXTRACTION DEVICES AND RELATED METHODS

(71) Applicants: Brigham and Women's Hospital, Inc., Boston, MA (US); Freyja Healthcare, LLC, North Andover, MA (US)

(72) Inventors: Frank Bonadio, County Wicklow (IE); Jon I. Einarsson, Boston, MA (US); Jordan Smith, Cambridge, MA (US); Alexander Isakov, Sudbury, MA (US); Debasish Pradhan, Sambalpur (IN); Athar Anwar Solkar, Ratnagiri (IN); Mangesh Ratnakar Patankar, Navi Mumbai (IN); Nikhil Katre, Navi Mumbai (IN); Tejas Chavan, Navi Mumbai (IN)

(73) Assignee: The Brigham and Women's Hospital, Inc., Boston, MA (US)

( * ) Notice: Subject to any disclaimer, the term of this patent is extended or adjusted under 35 U.S.C. 154(b) by 257 days.

(21) Appl. No.: 15/977,251

(22) Filed: May 11, 2018

(65) Prior Publication Data

US 2018/0360481 A1 Dec. 20, 2018

Related U.S. Application Data

(63) Continuation of application No. PCT/US2017/068365, filed on Dec. 23, 2017, which
(Continued)

(51) Int. Cl.
*A61B 17/221* (2006.01)
*A61B 17/3207* (2006.01)
(Continued)

(52) U.S. Cl.
CPC ........ *A61B 17/221* (2013.01); *A61B 10/0266* (2013.01); *A61B 17/02* (2013.01);
(Continued)

(58) Field of Classification Search
None
See application file for complete search history.

(56) References Cited

U.S. PATENT DOCUMENTS 4,368,734 A 1/1983 Banko
5,336,237 A 8/1994 Chin et al.
(Continued)

FOREIGN PATENT DOCUMENTS

EP 0578997 A1 1/1994
WO 9709922 A1 3/1997
(Continued)

OTHER PUBLICATIONS

ISA/US. International Search Report and Opinion for PCT/US2014/020649 (Brigham and Women's Hospital, Inc.) dated Jun. 23, 2014, 17 pages.
(Continued)

*Primary Examiner* — Shaun L David
(74) *Attorney, Agent, or Firm* — Winthrop & Weinstine, P.A.

(57) ABSTRACT

In accordance with an aspect of the present disclosure, a tissue extraction device may include a bag having an interior and a plurality of cutting elements extending through the interior of the bag. The cutting elements can have a common end.

15 Claims, 272 Drawing Sheets

Related U.S. Application Data is a continuation-in-part of application No. PCT/US2016/061595, filed on Nov. 11, 2016.

(60) Provisional application No. 62/569,293, filed on Oct. 6, 2017, provisional application No. 62/470,625, filed on Mar. 13, 2017, provisional application No. 62/438,916, filed on Dec. 23, 2016, provisional application No. 62/400,915, filed on Sep. 28, 2016, provisional application No. 62/255,065, filed on Nov. 13, 2015.

(51) Int. Cl.

| | | |
|---|---|---|
| *A61B 17/22* | (2006.01) | |
| *A61B 10/02* | (2006.01) | |
| *A61B 17/34* | (2006.01) | |
| *A61B 17/3205* | (2006.01) | |
| *A61B 17/02* | (2006.01) | |
| A61B 17/32 | (2006.01) | |
| A61B 90/92 | (2016.01) | |
| A61B 17/00 | (2006.01) | |
| A61M 13/00 | (2006.01) | |
| A61B 17/42 | (2006.01) | |
| A61B 18/14 | (2006.01) | |
| A61B 18/00 | (2006.01) | |
| A61B 18/12 | (2006.01) | |
| A61B 90/00 | (2016.01) | |

(52) U.S. Cl.
CPC .. *A61B 17/22031* (2013.01); *A61B 17/32056* (2013.01); *A61B 17/320758* (2013.01); *A61B 17/3421* (2013.01); *A61B 17/0218* (2013.01); A61B 17/320068 (2013.01); A61B 17/42 (2013.01); A61B 18/12 (2013.01); A61B 90/37 (2016.02); A61B 90/92 (2016.02); A61B 2017/00287 (2013.01); A61B 2017/00398 (2013.01); A61B 2017/00407 (2013.01); A61B 2017/00557 (2013.01); A61B 2017/2212 (2013.01); A61B 2017/2215 (2013.01); A61B 2017/320004 (2013.01); A61B 2017/32006 (2013.01); A61B 2017/320024 (2013.01); A61B 2017/320064 (2013.01); A61B 2017/320775 (2013.01); A61B 2017/345 (2013.01); A61B 2018/00285 (2013.01); A61B *2018/00601* (2013.01); *A61B 2018/144* (2013.01); *A61B 2018/1407* (2013.01); *A61M 13/003* (2013.01)

(56) References Cited

U.S. PATENT DOCUMENTS

| | | |
|---|---|---|
| 5,354,303 A | 10/1994 | Spaeth et al. |
| 5,569,284 A | 10/1996 | Young et al. |
| 5,611,803 A | 3/1997 | Heaven et al. |
| 5,735,289 A * | 4/1998 | Pfeffer ............ A61B 17/00234 600/562 |
| 5,836,953 A | 11/1998 | Yoon |
| 6,451,036 B1 | 9/2002 | Heitzmann et al. |
| 6,537,273 B1 | 3/2003 | Sosiak et al. |
| 9,522,034 B2 | 12/2016 | Johnson et al. |
| 9,629,618 B2 | 4/2017 | Davis et al. |
| 2004/0002683 A1 | 1/2004 | Nicholson et al. |
| 2005/0267492 A1 | 12/2005 | Poncet et al. |
| 2008/0221604 A1 | 9/2008 | Kondoh et al. |
| 2009/0326546 A1 | 12/2009 | Mohamed et al. |
| 2011/0040314 A1 | 2/2011 | McGuckin, Jr. et al. |
| 2011/0046637 A1 | 2/2011 | Patel et al. |
| 2012/0203241 A1 | 8/2012 | Williamson, IV |
| 2016/0030073 A1 | 2/2016 | Isakov et al. |
| 2016/0100857 A1* | 4/2016 | Wachli ............... A61B 17/3423 600/204 |
| 2016/0346000 A1 | 12/2016 | Abreu |

FOREIGN PATENT DOCUMENTS

| | | |
|---|---|---|
| WO | 2014158880 A1 | 10/2014 |
| WO | 2015164591 A1 | 10/2015 |
| WO | 2017083694 A1 | 5/2017 |
| WO | 2018119473 A1 | 6/2018 |

OTHER PUBLICATIONS

ISA/EPO. International Search Report for PCT/US2016/061595 (Lattis Surgical Inc.) dated Jan. 24, 2017, 4 pages.

ISA/RU international Search Report and Opinion for PCT/US 2017/068365 ( Brigham and Women's Hospital, Inc. et al. ) dated Apr. 19, 2018, 9 pages.

Extended European Search Report dated Aug. 10, 2020 for corresponding European Patent Application 17884362.9.

* cited by examiner

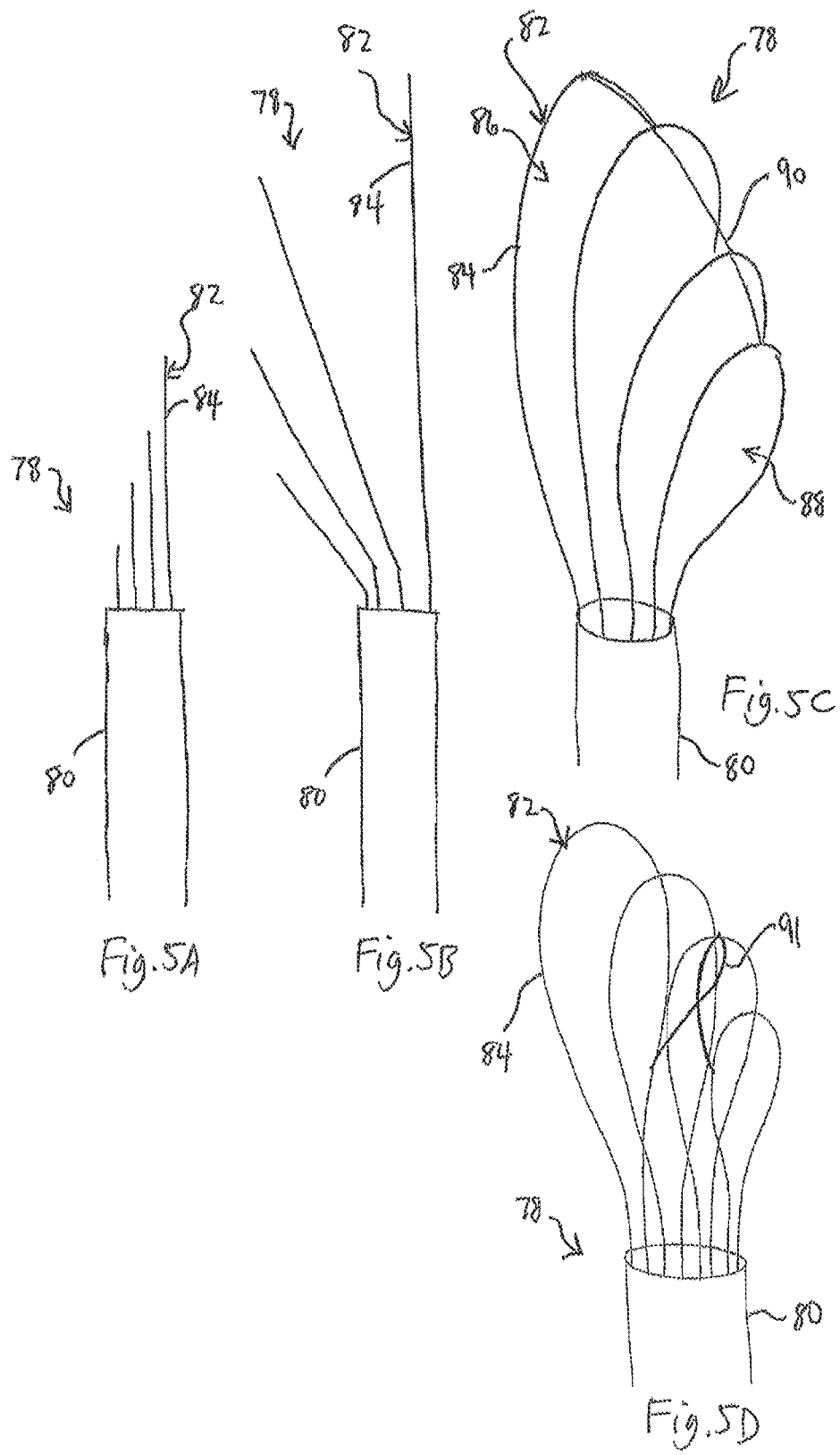

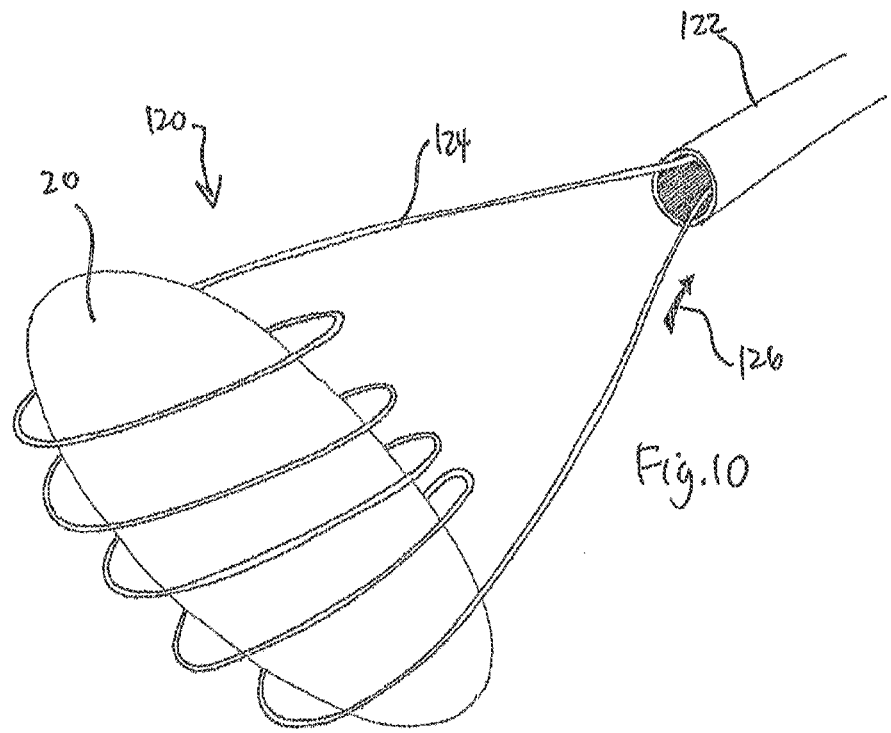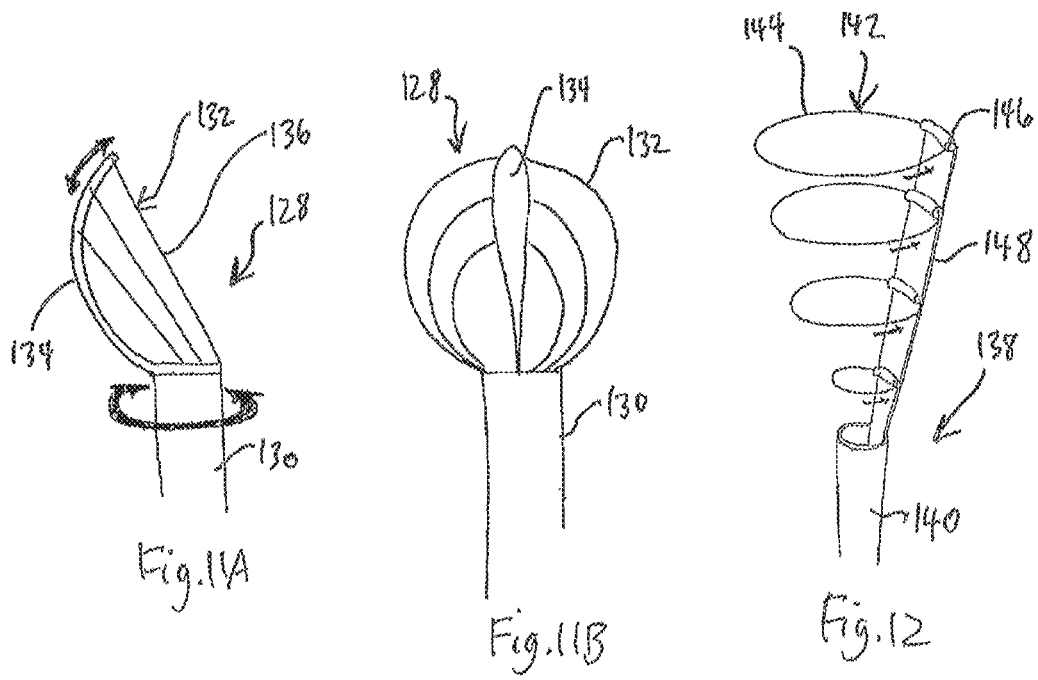

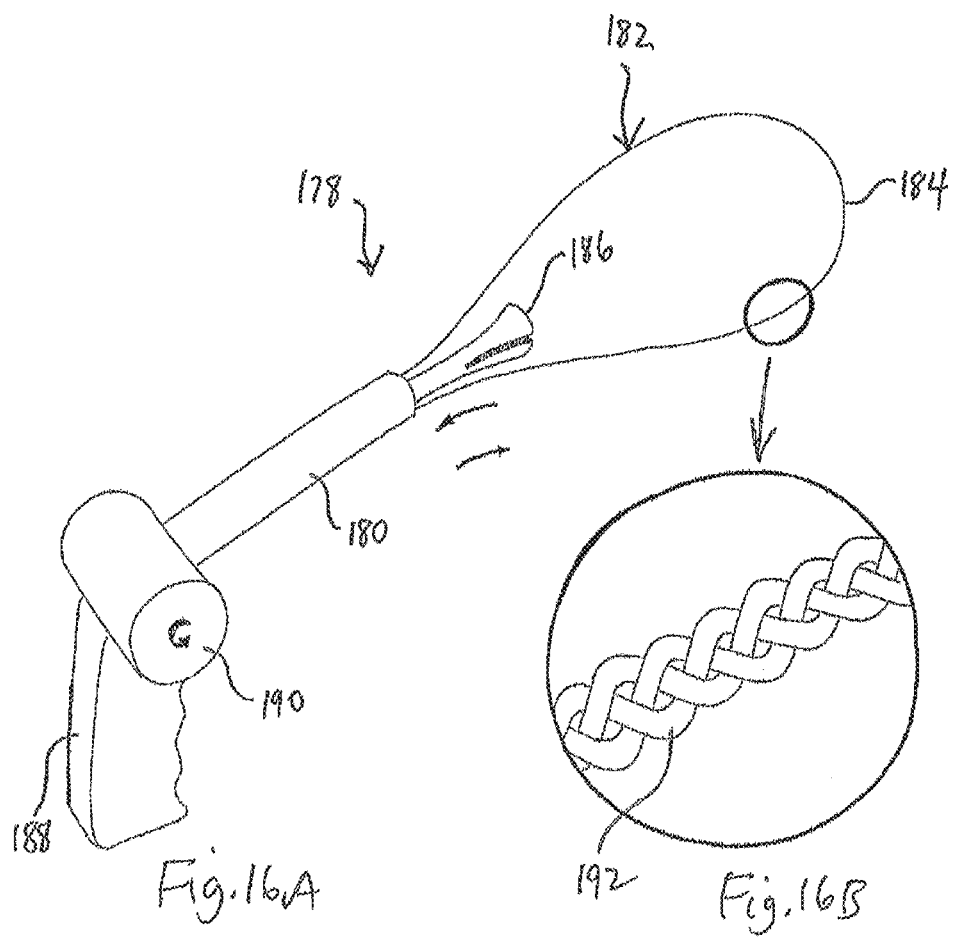

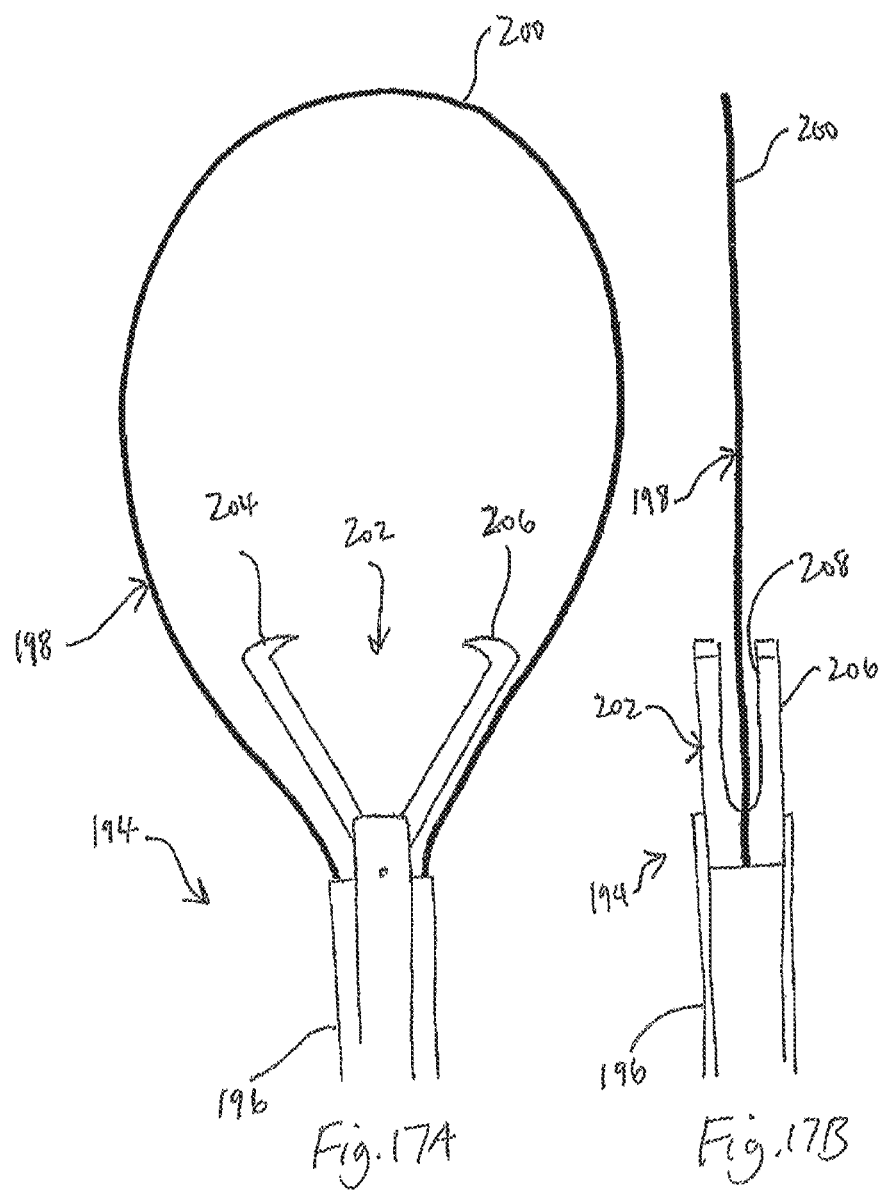

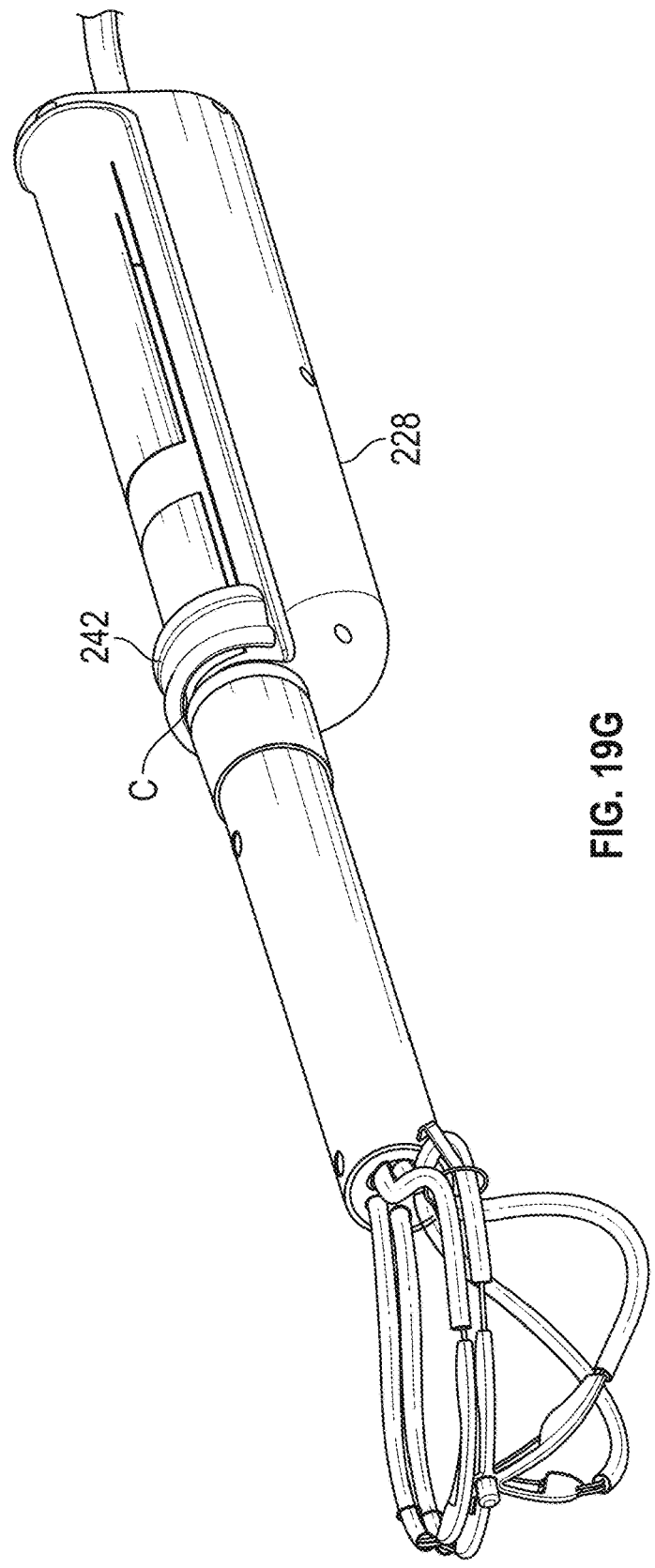
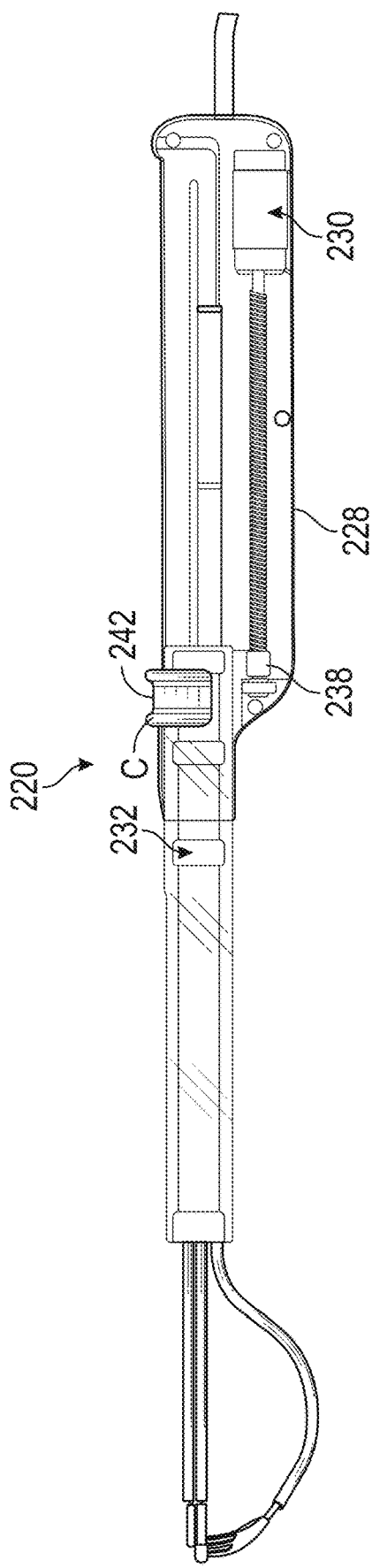
FIG. 19G
FIG. 19H

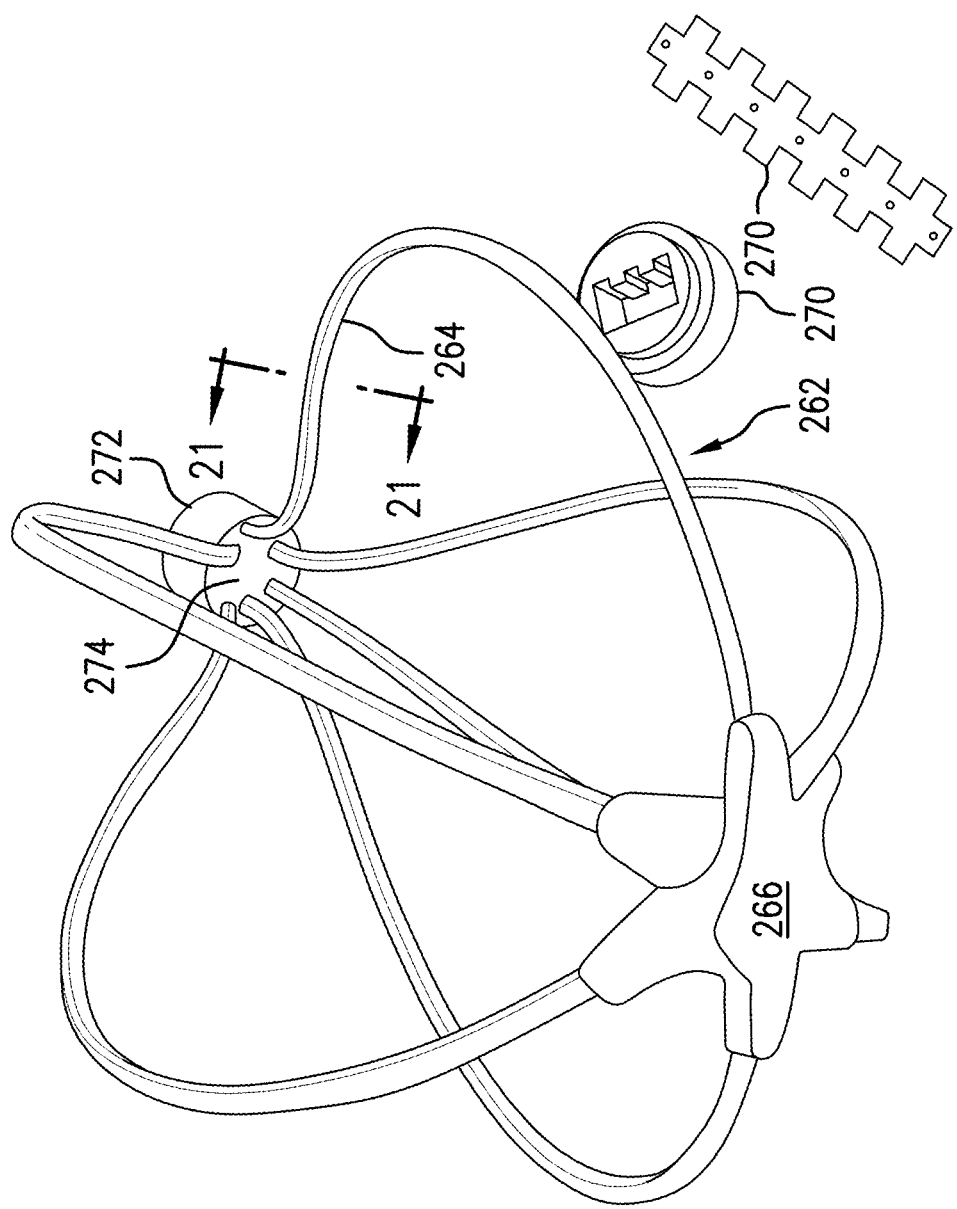

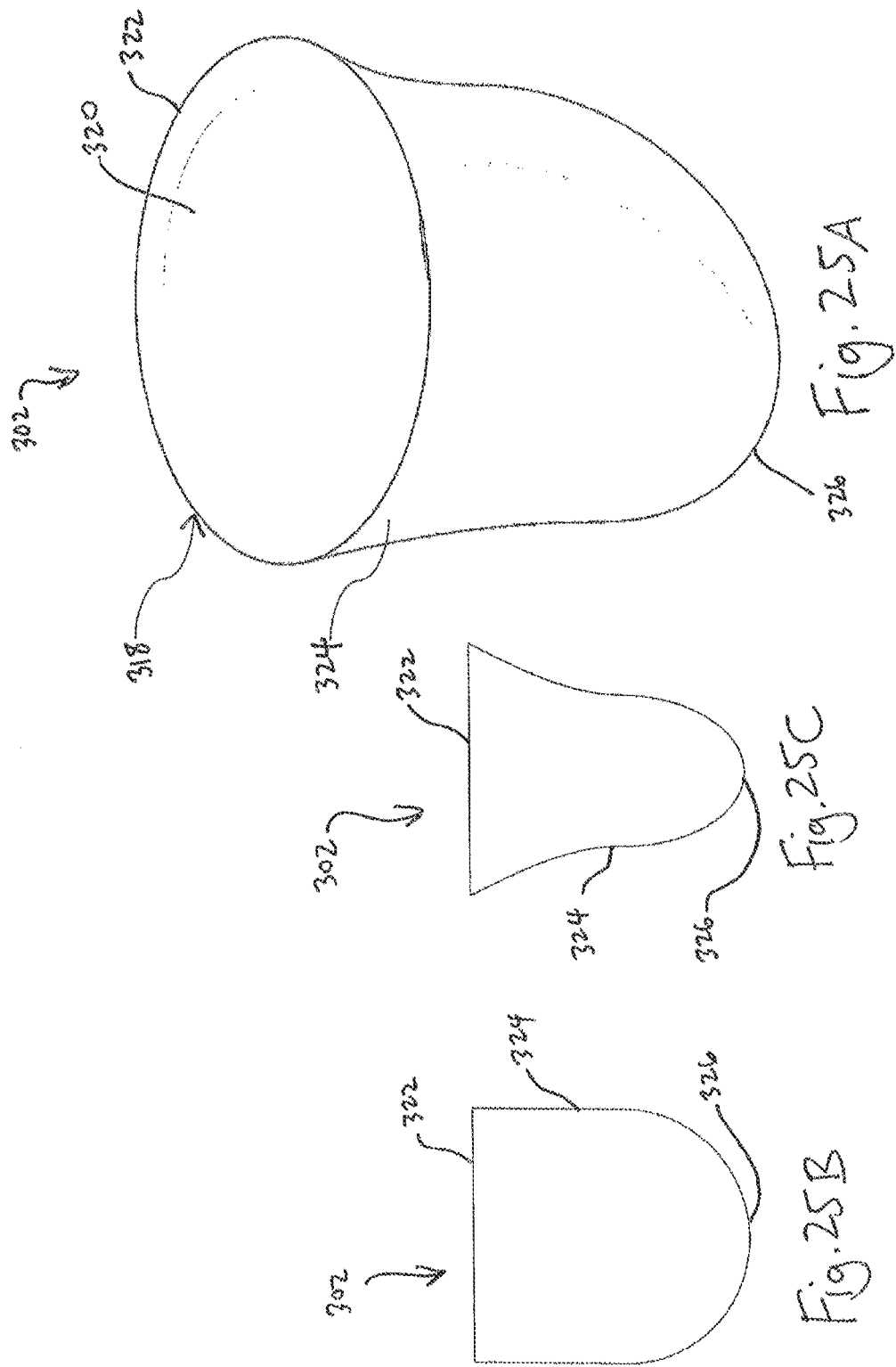

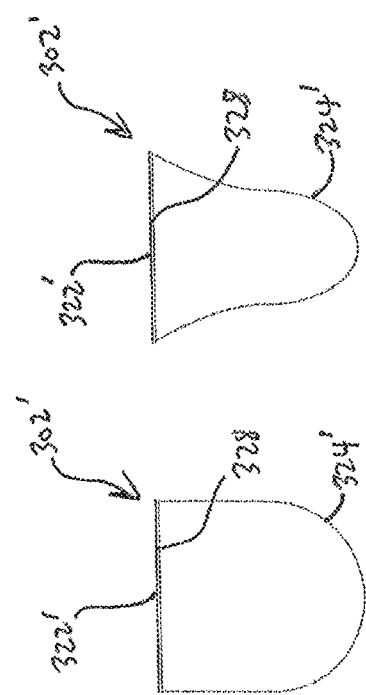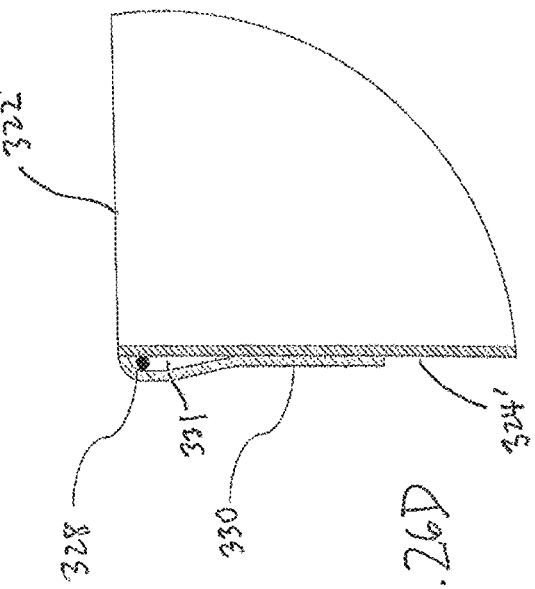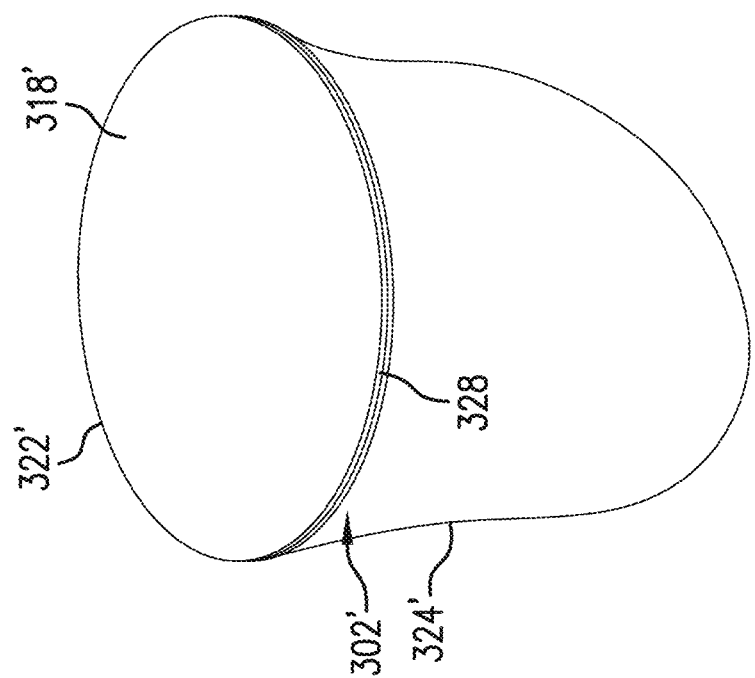
FIG. 26A, fig. 26B, fig. 26C, fig. 26D

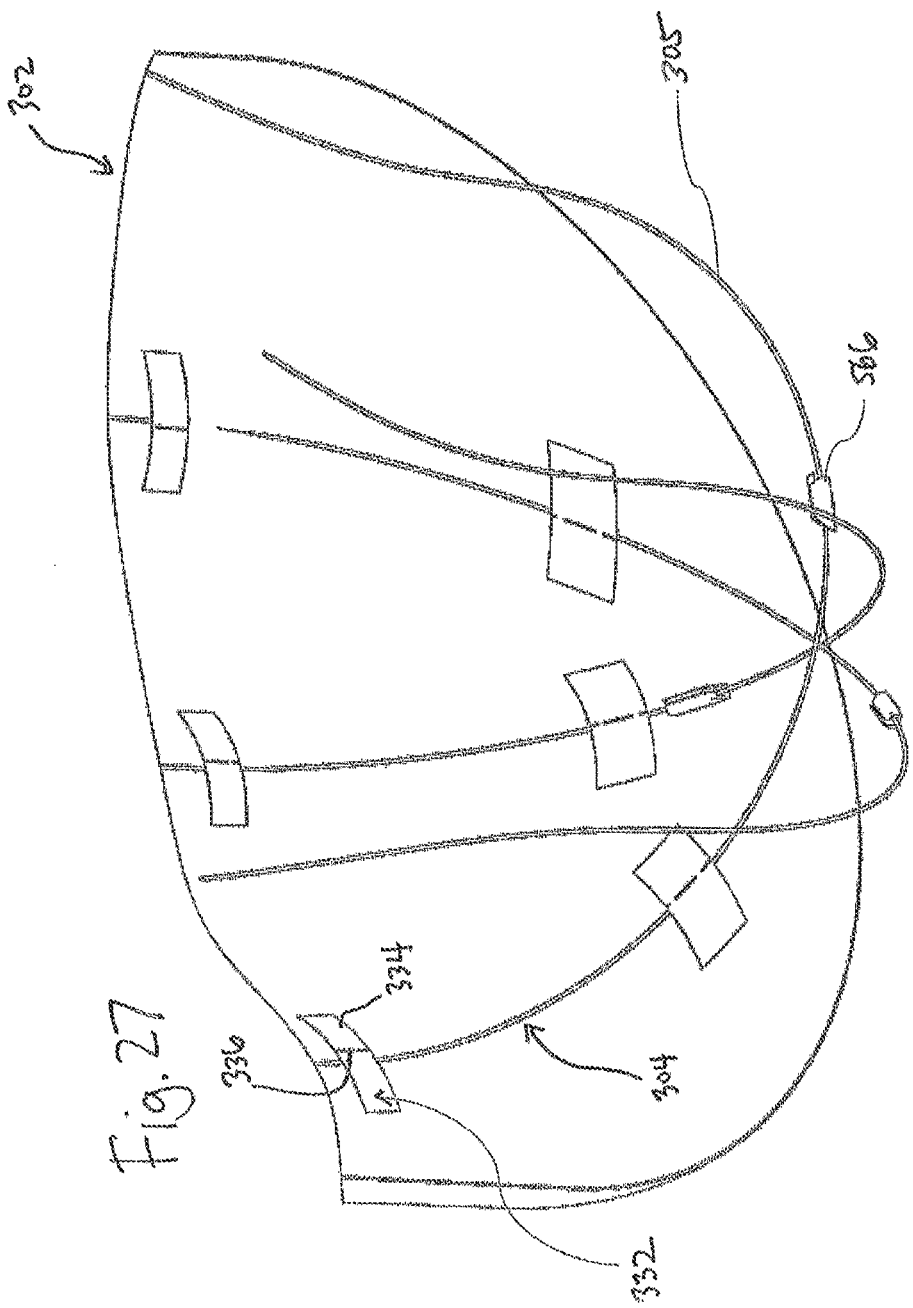

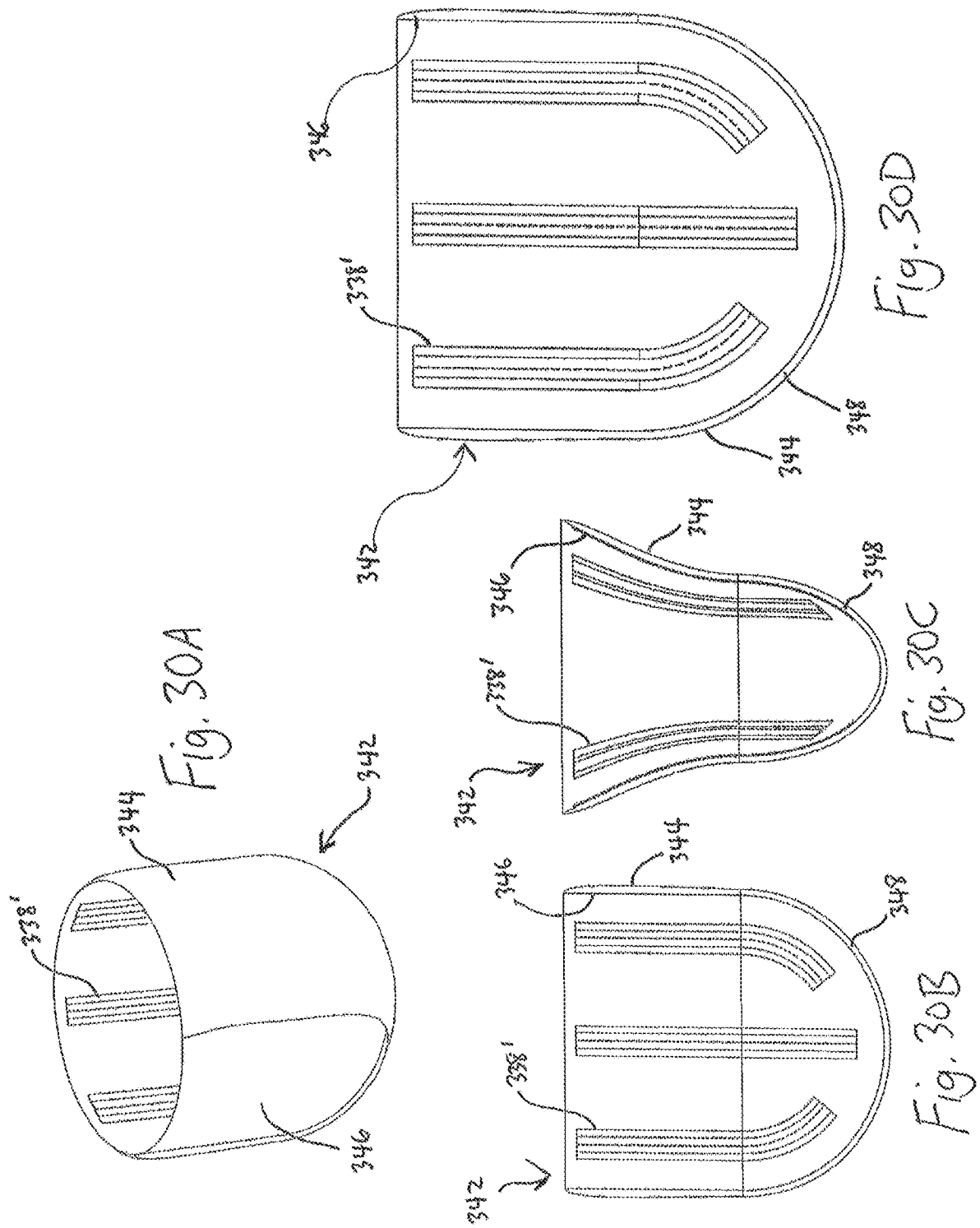

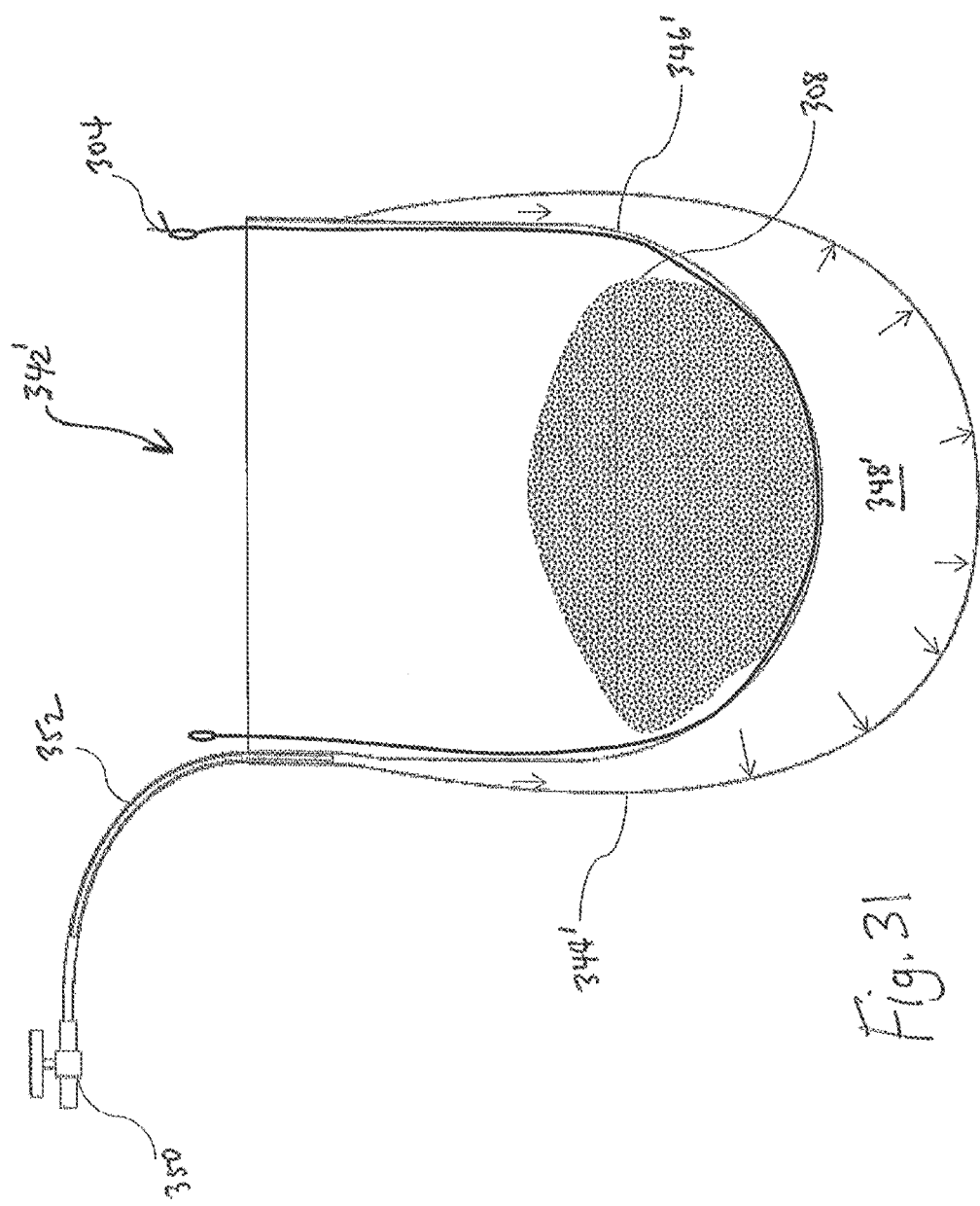

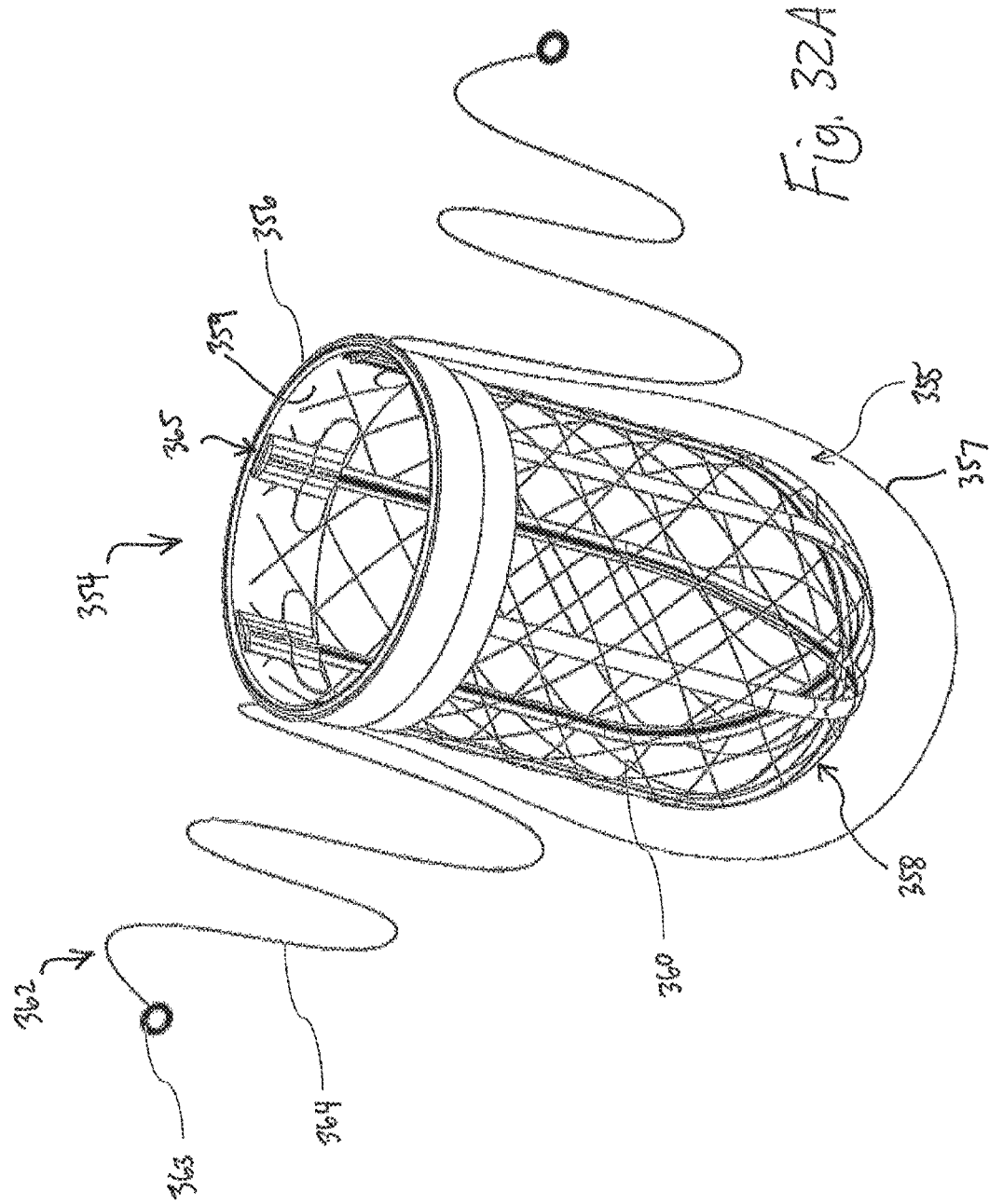

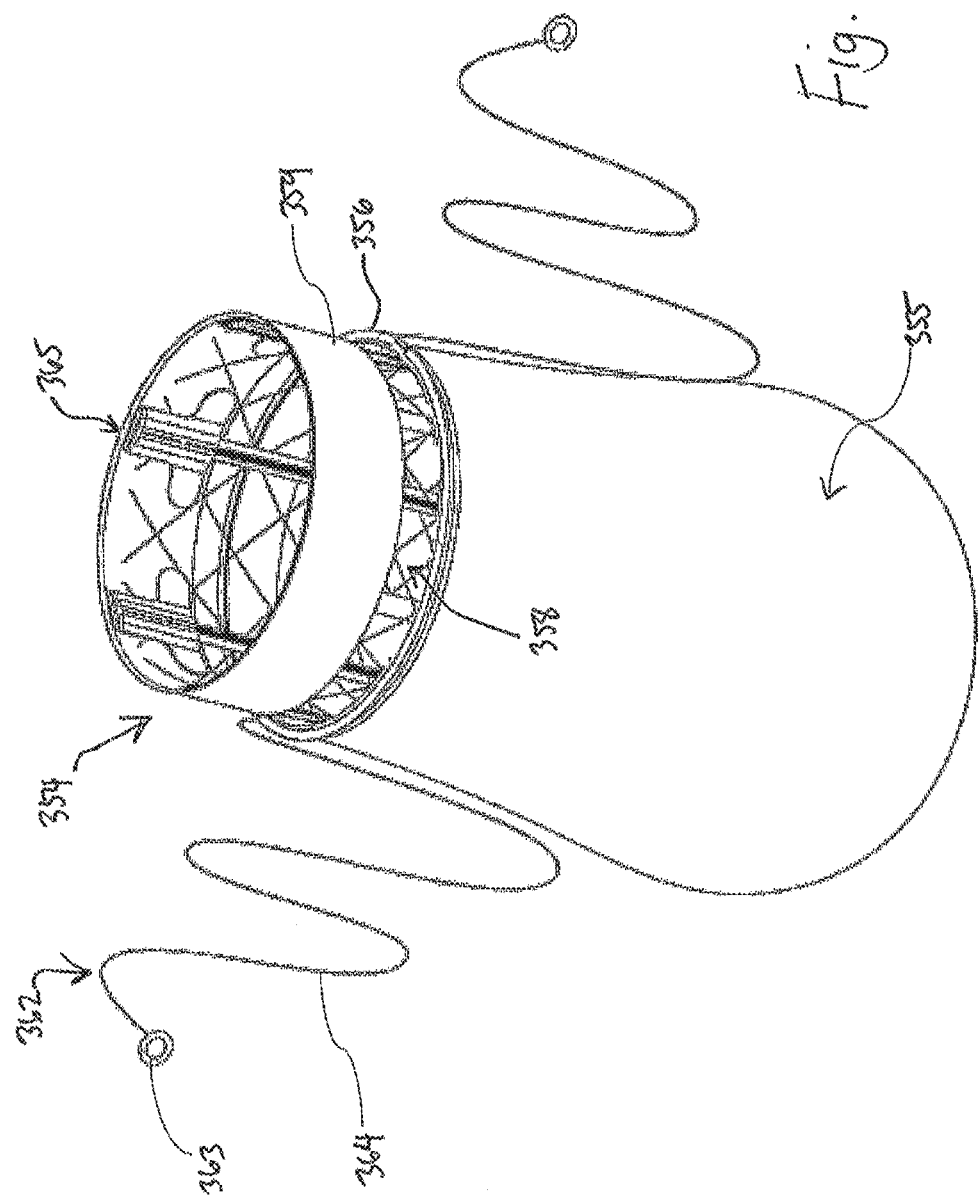

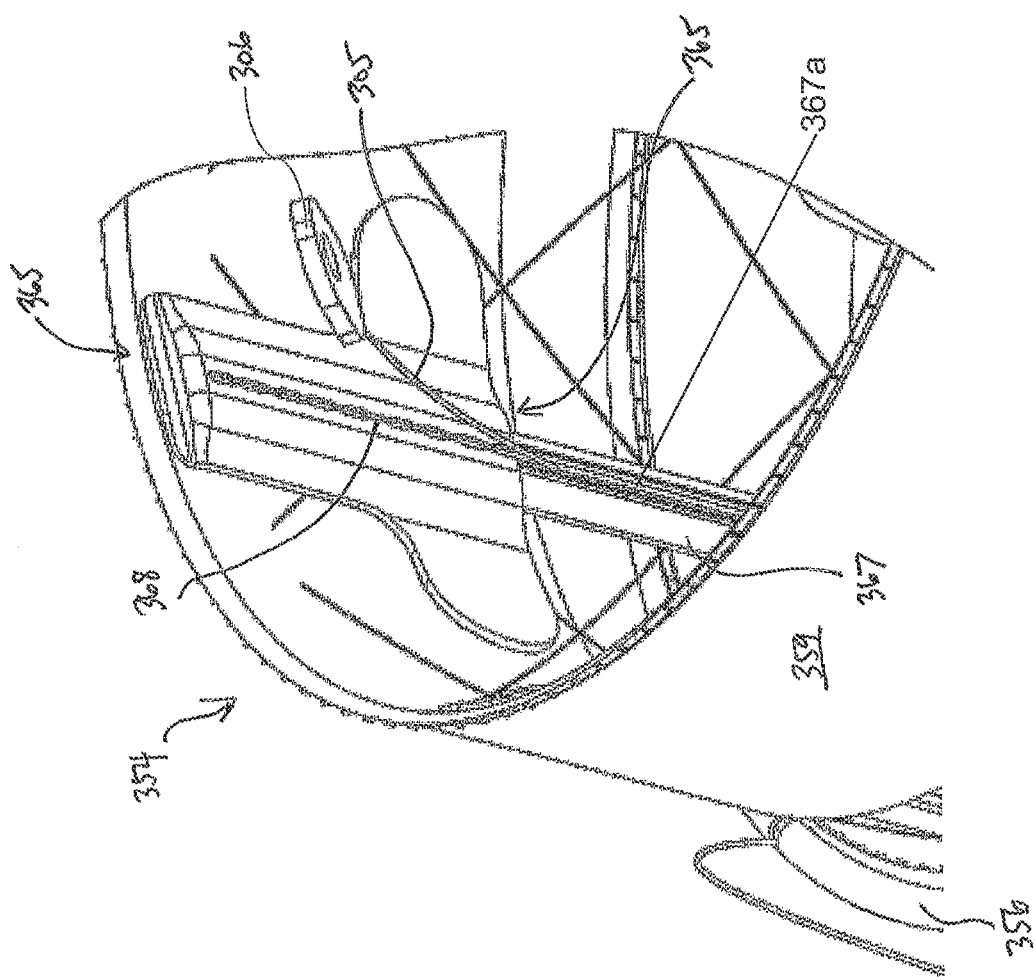

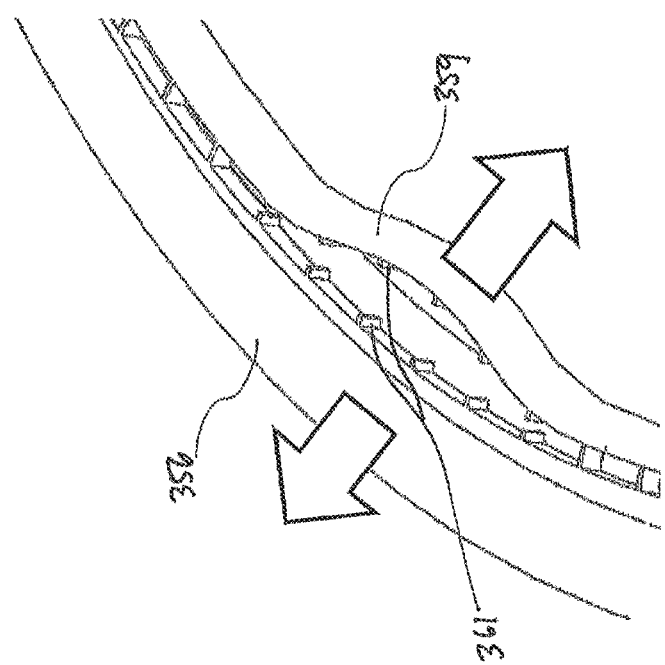
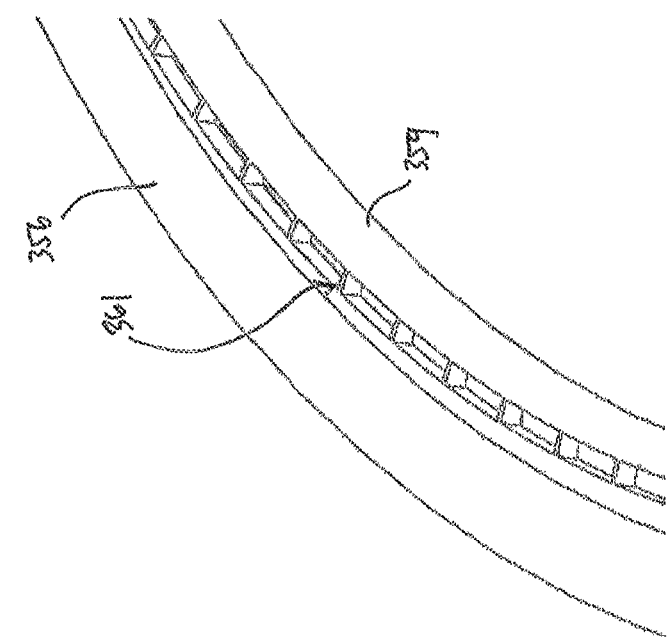

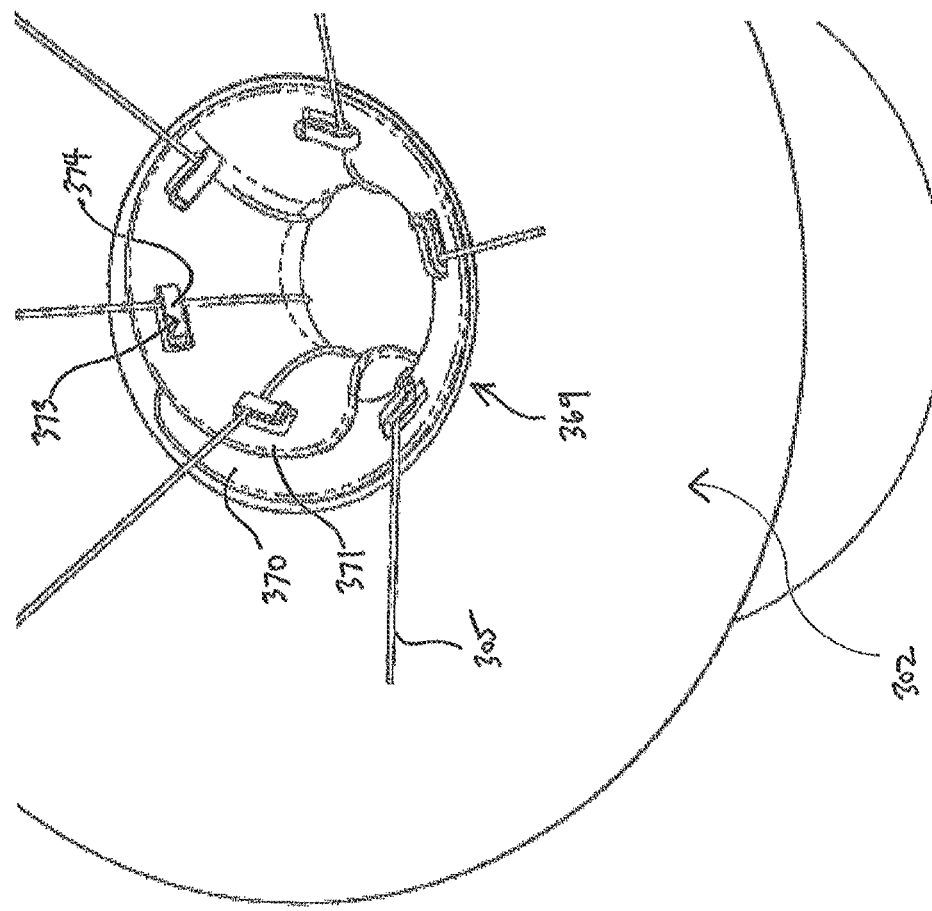
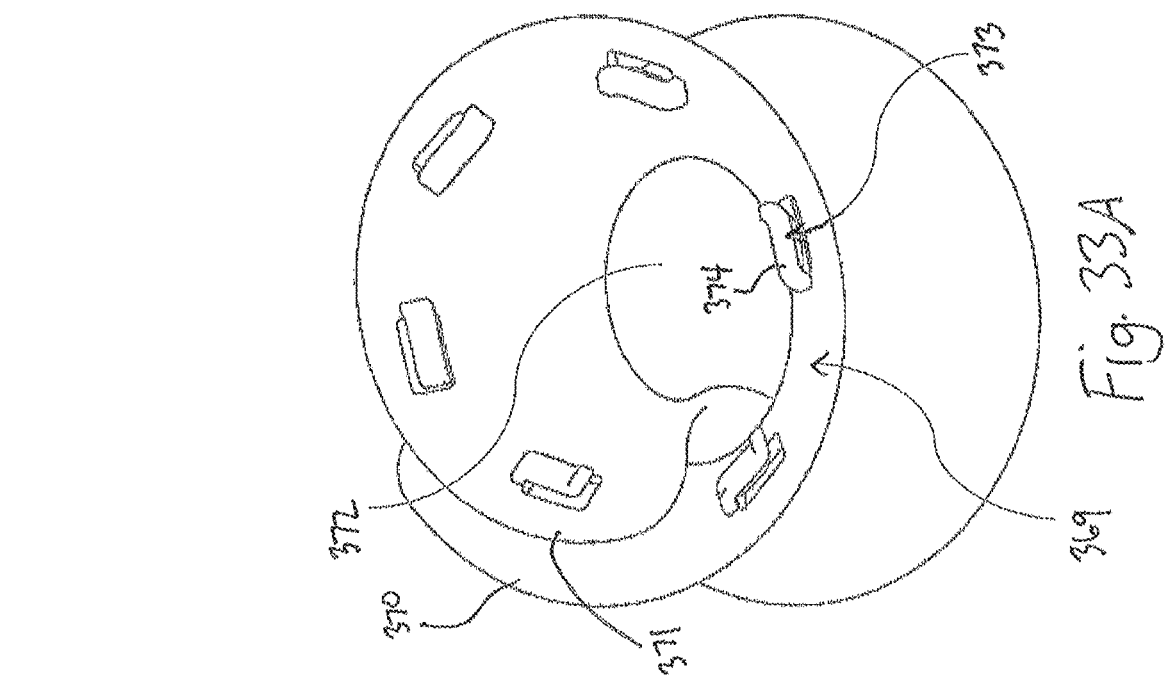

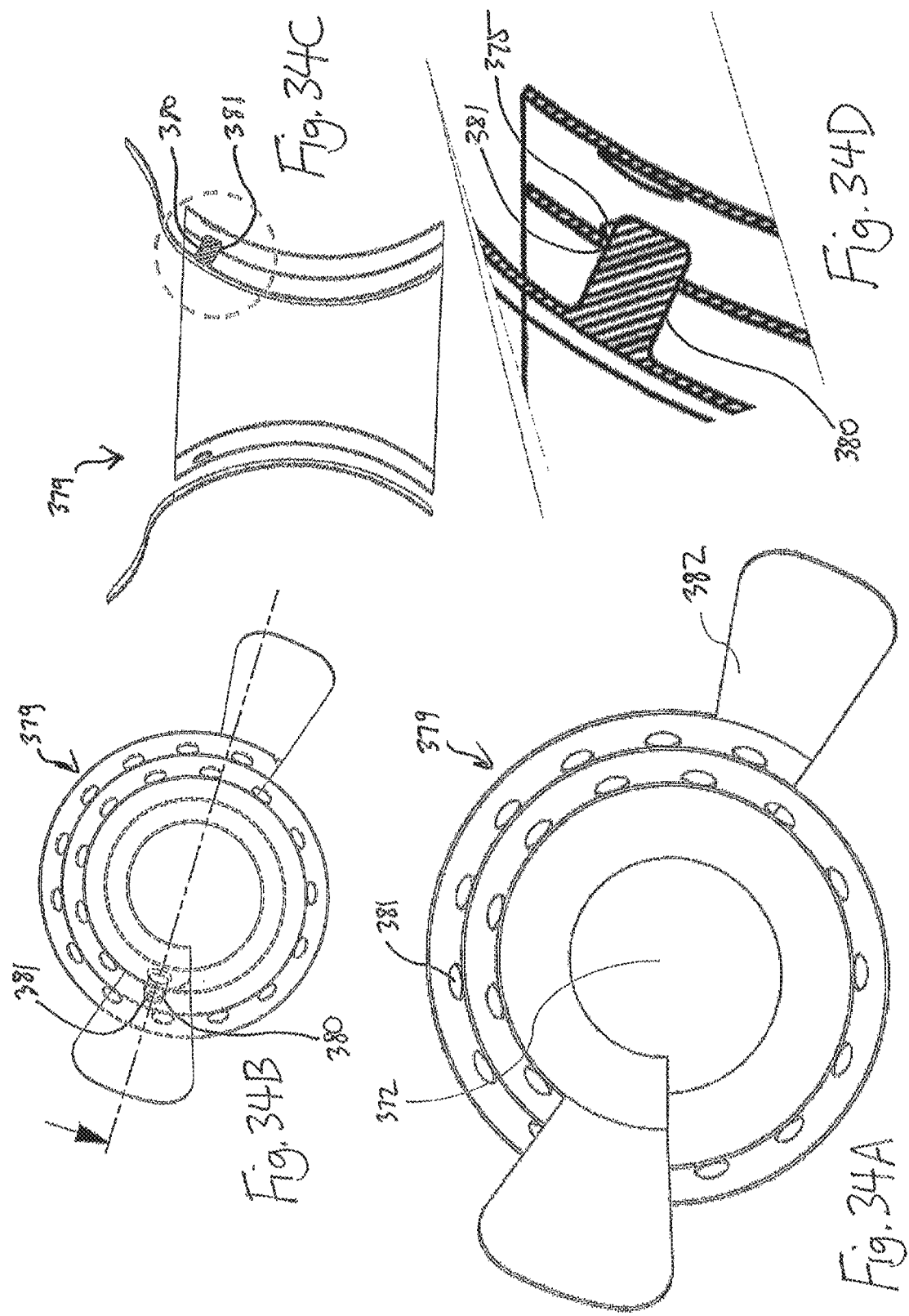

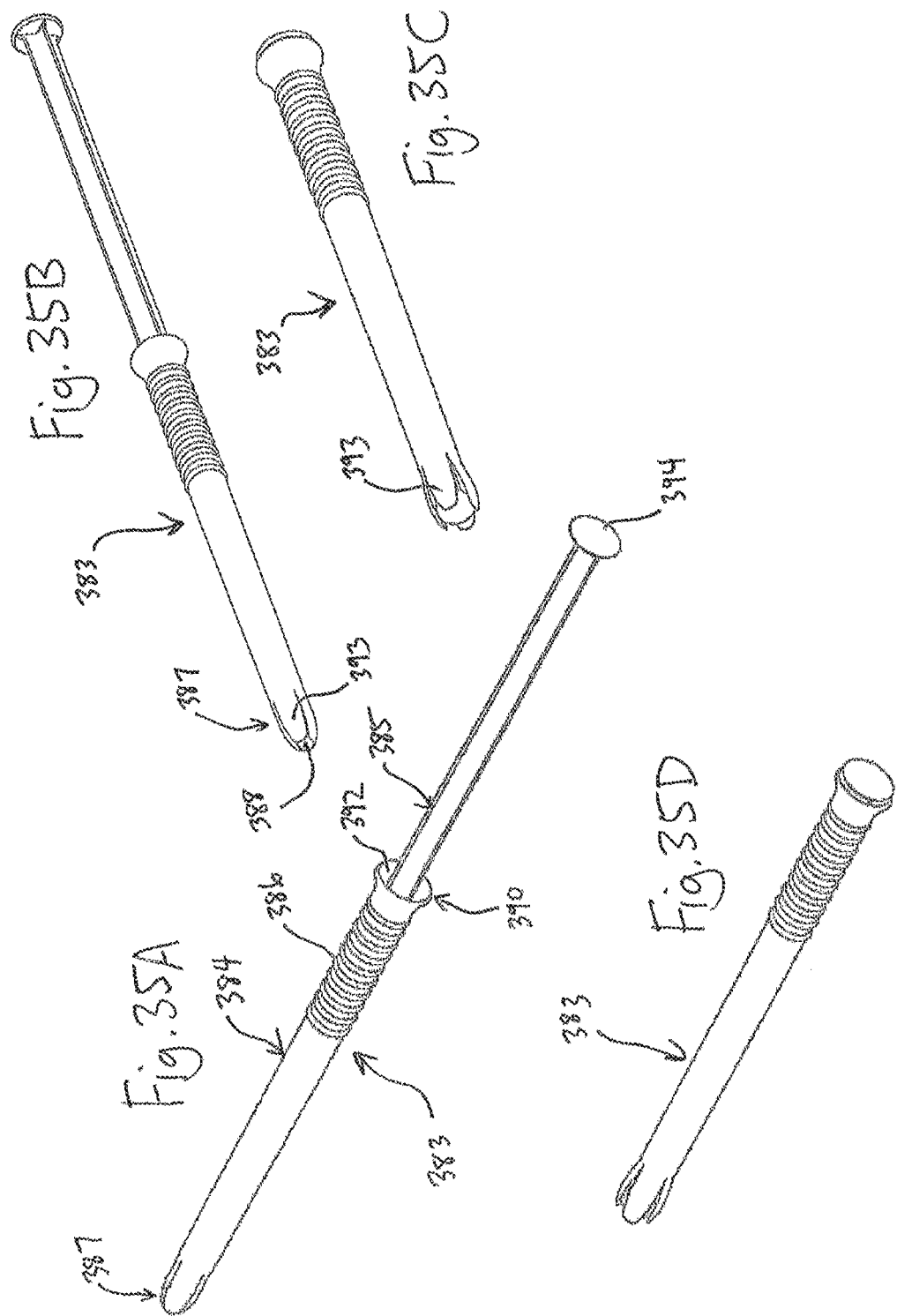

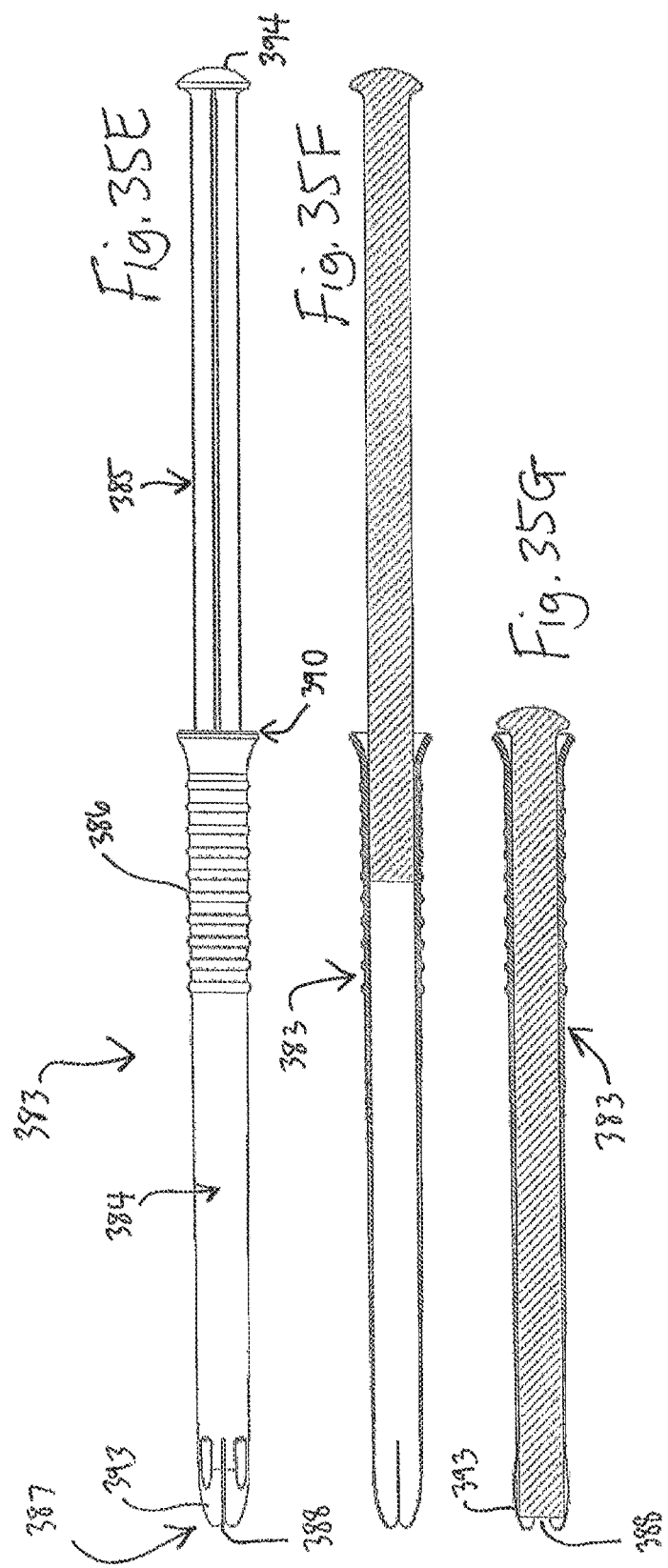

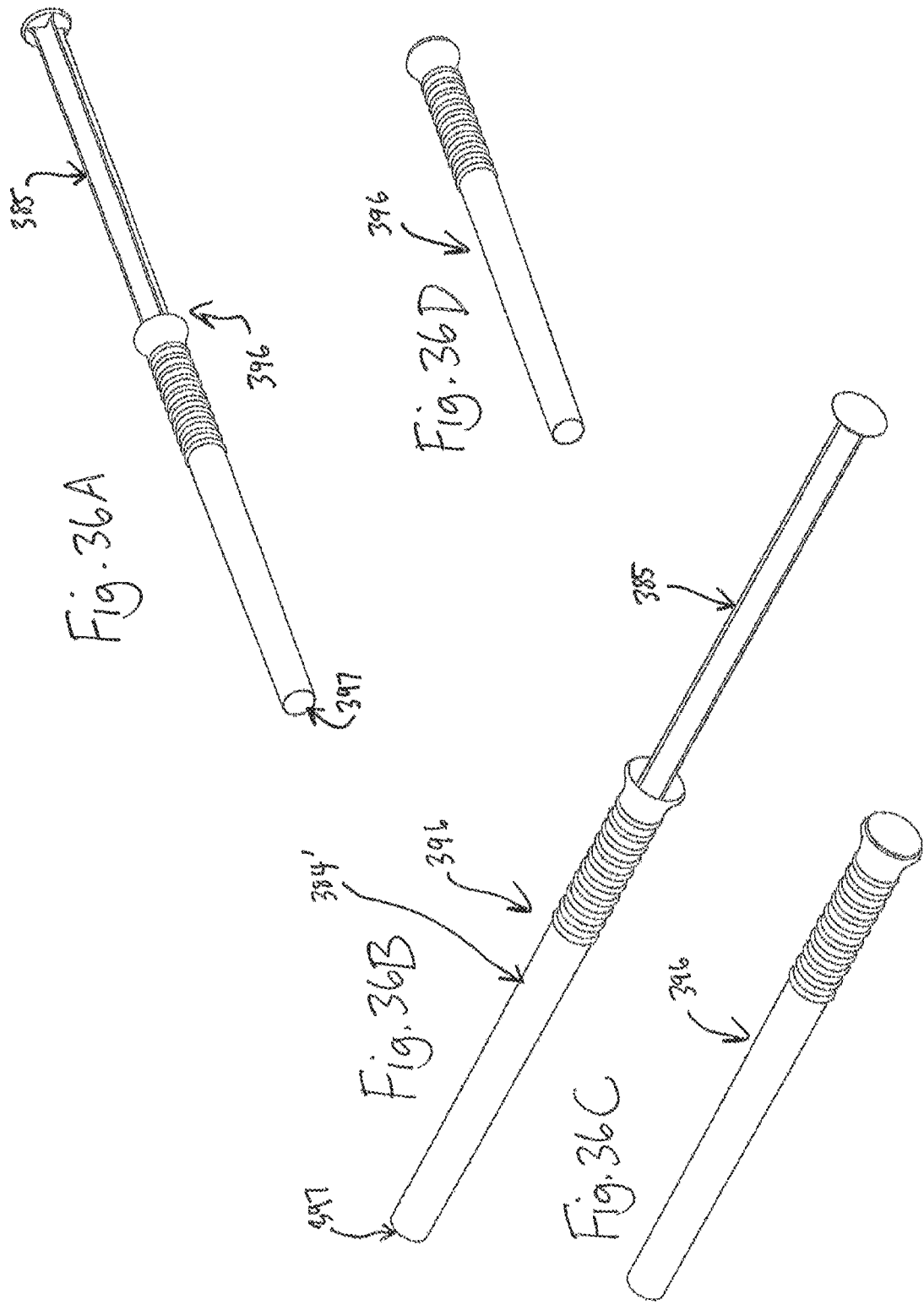

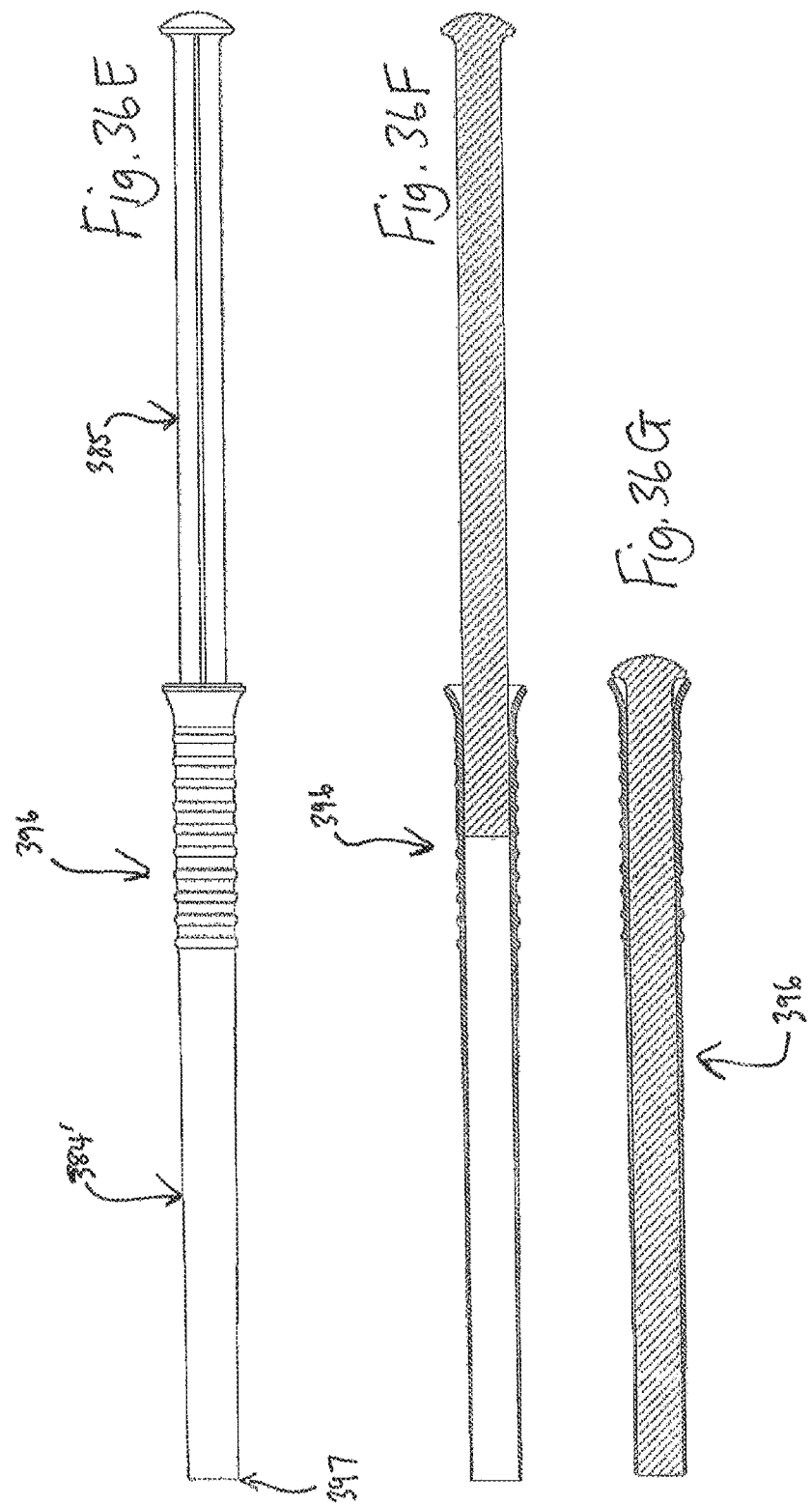

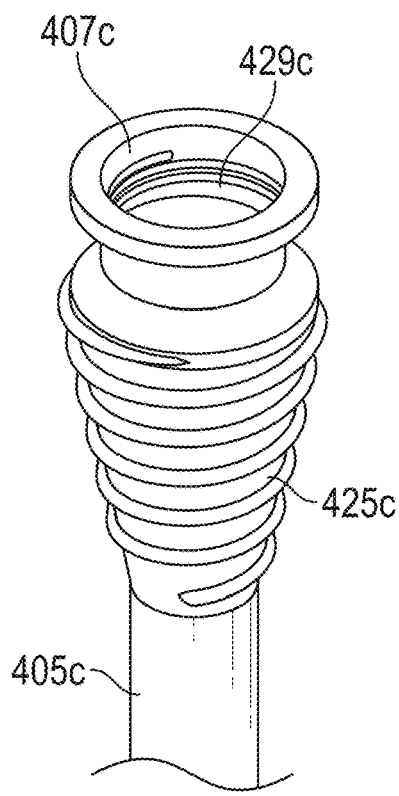
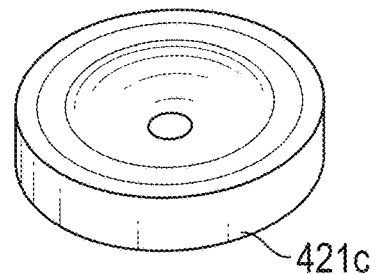
FIG. 37M
FIG. 37N
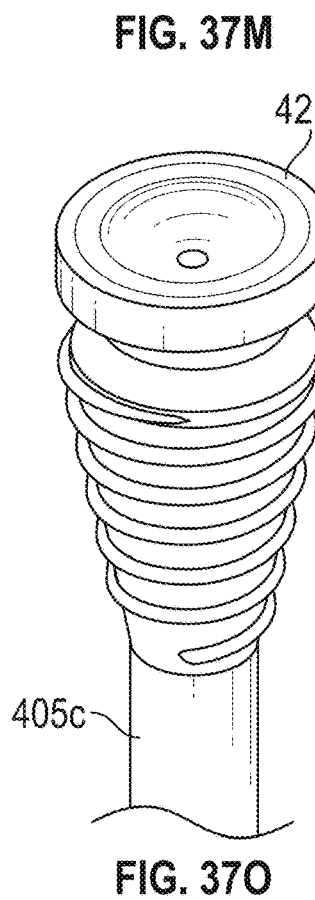
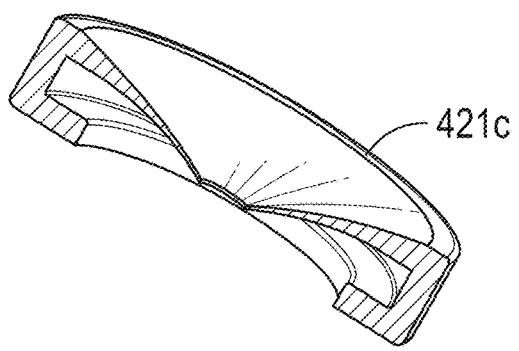
FIG. 37O
FIG. 37P

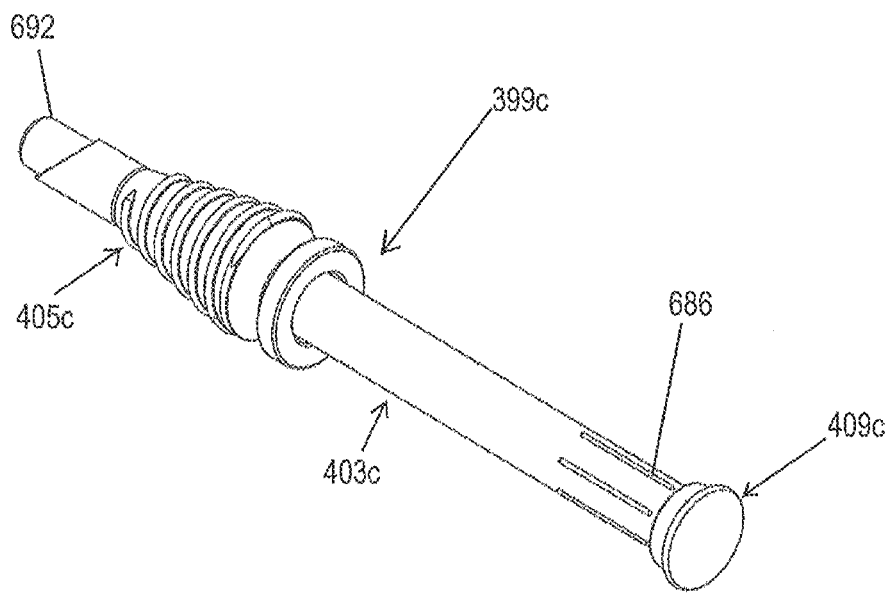
Fig. 37Q(i)
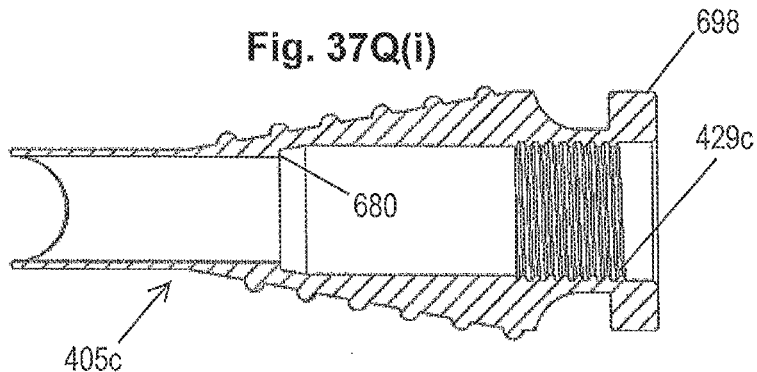
Fig. 37Q(ii)
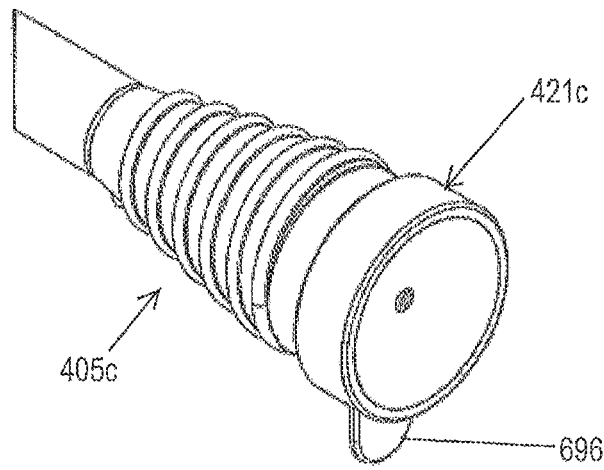
Fig. 37Q(iii)

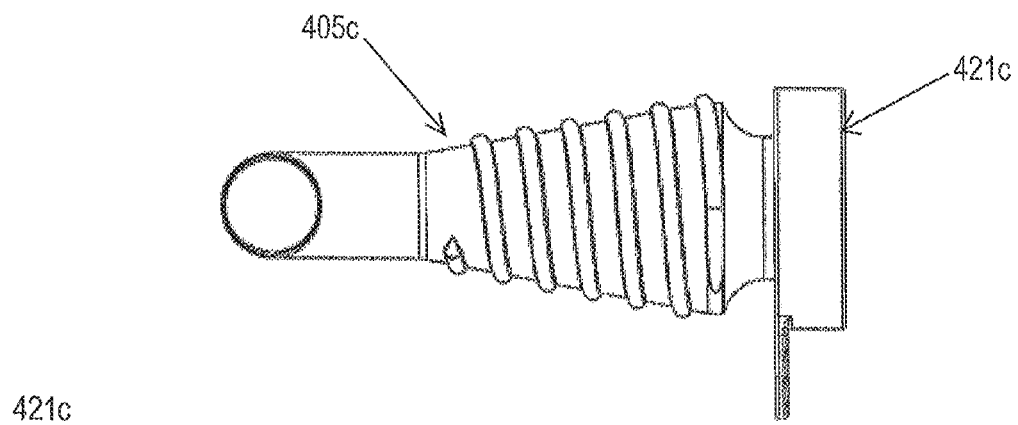
Fig. 37Q(iv)
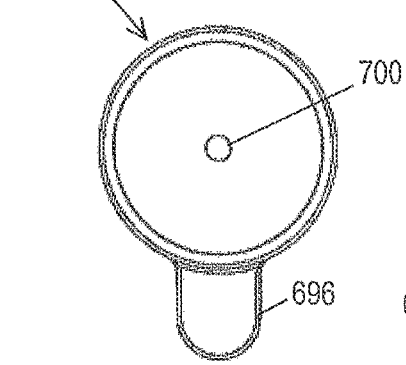
Fig. 37Q(v)
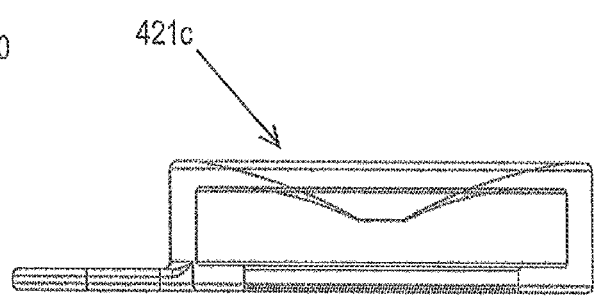
FIG. 37Q(vi)
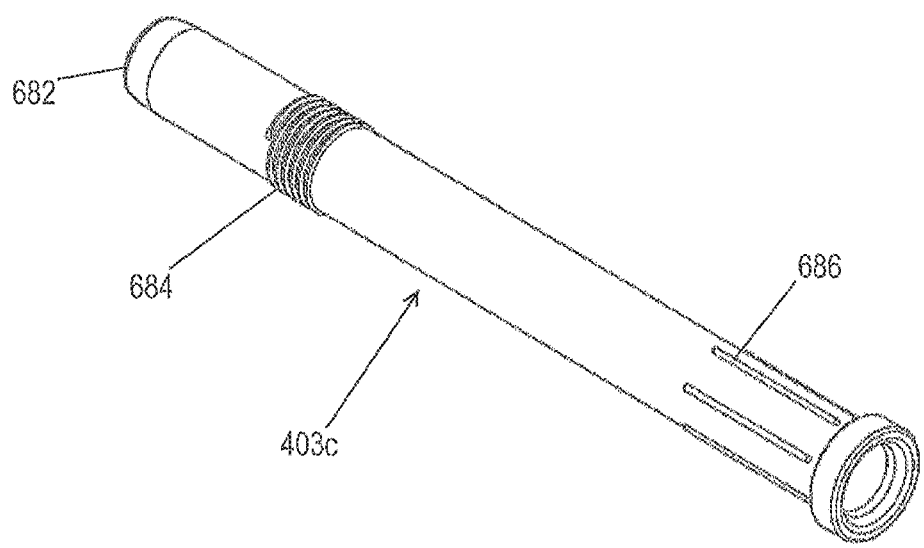
Fig. 37Q(vii)

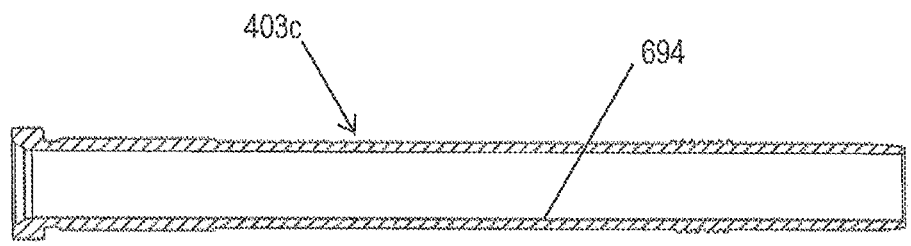
Fig. 37Q(viii)
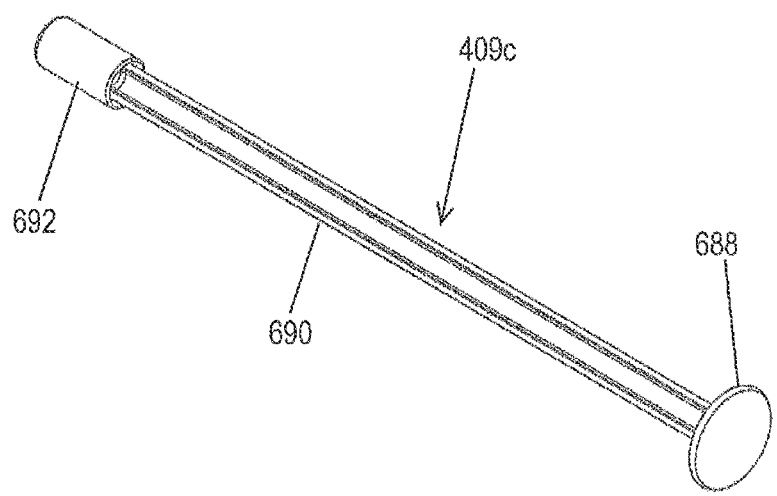
Fig. 37Q(ix)
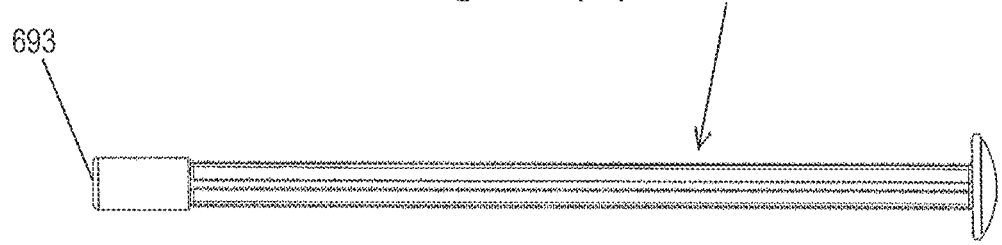
Fig. 37Q(x)

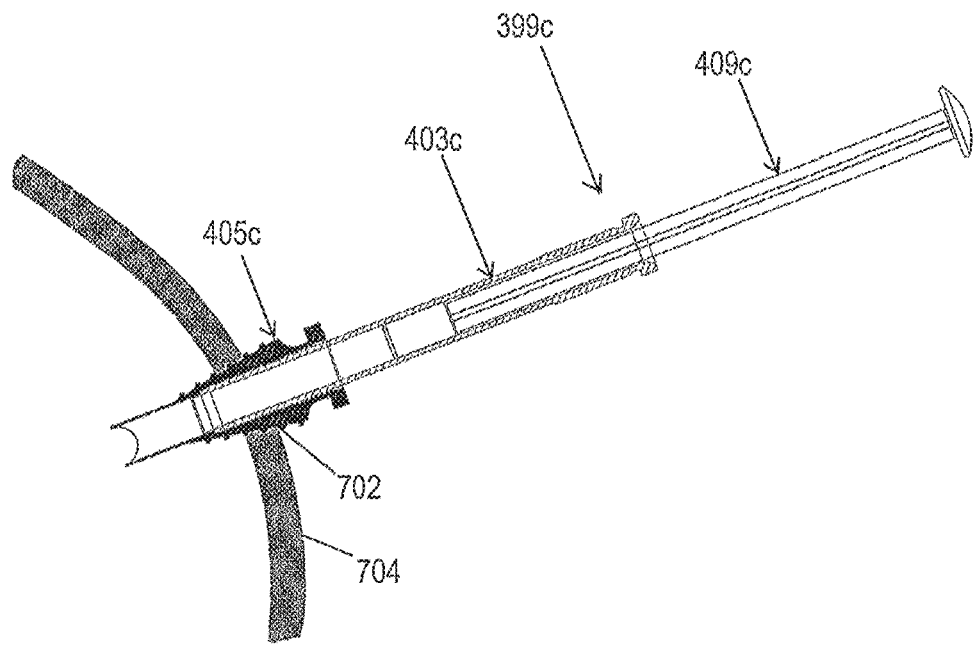
Fig. 37Q(xi)
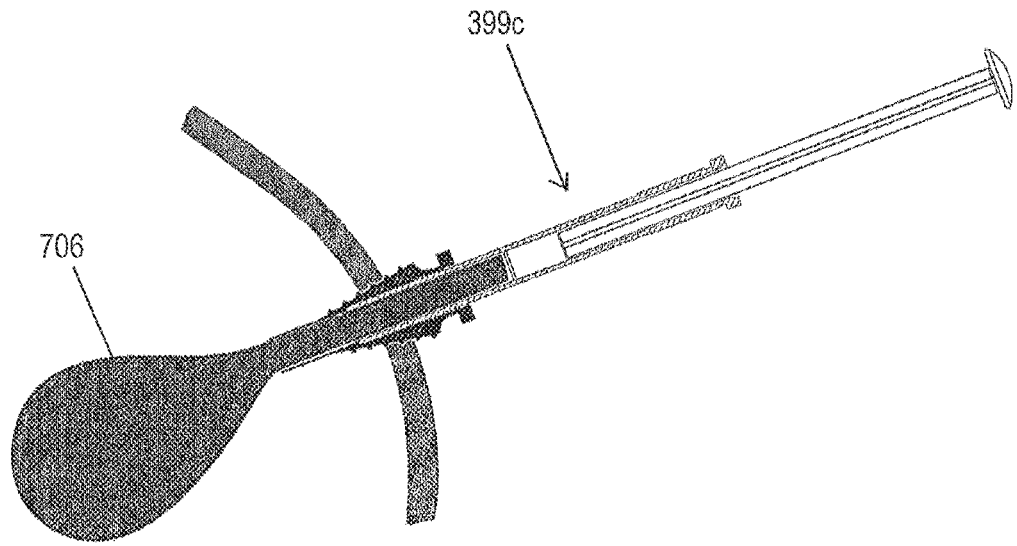
Fig. 37Q(xii)

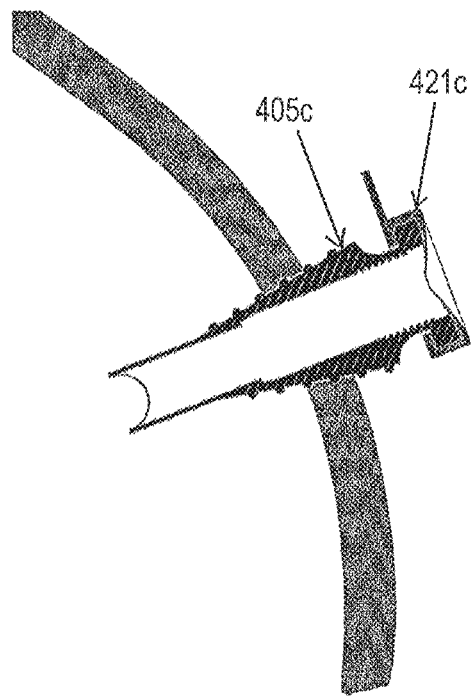
Fig. 37Q(xiii)
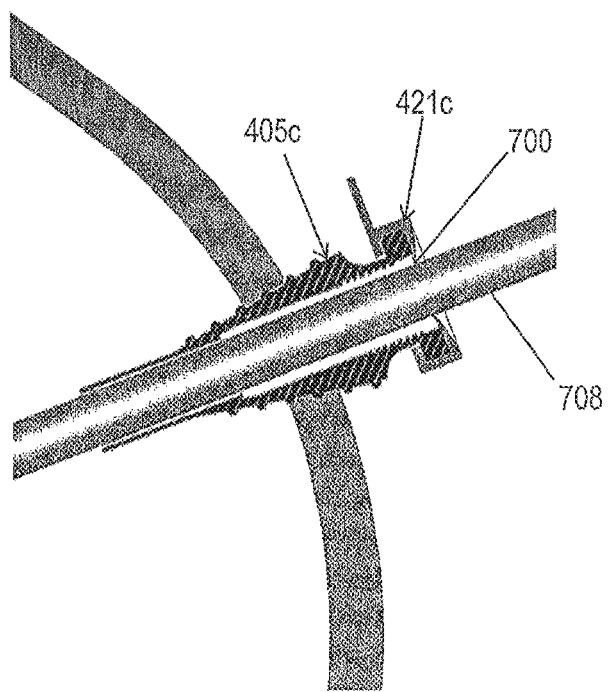
Fig. 37Q(xiv)

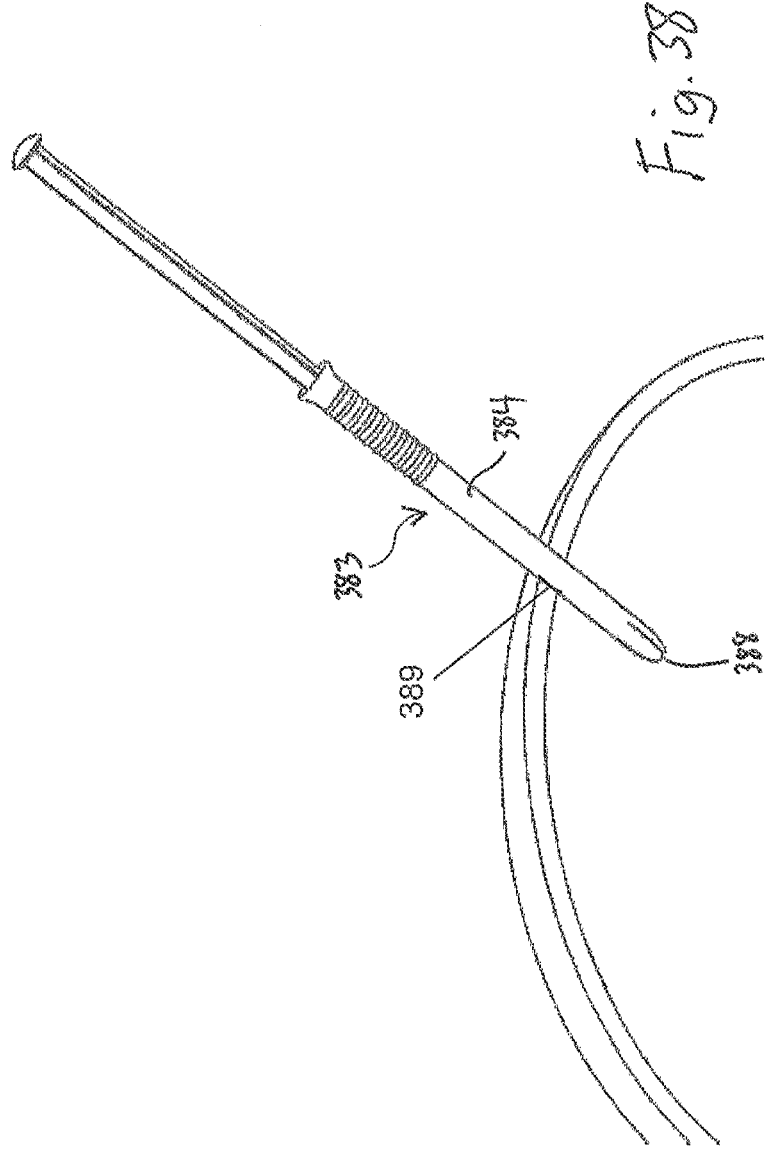

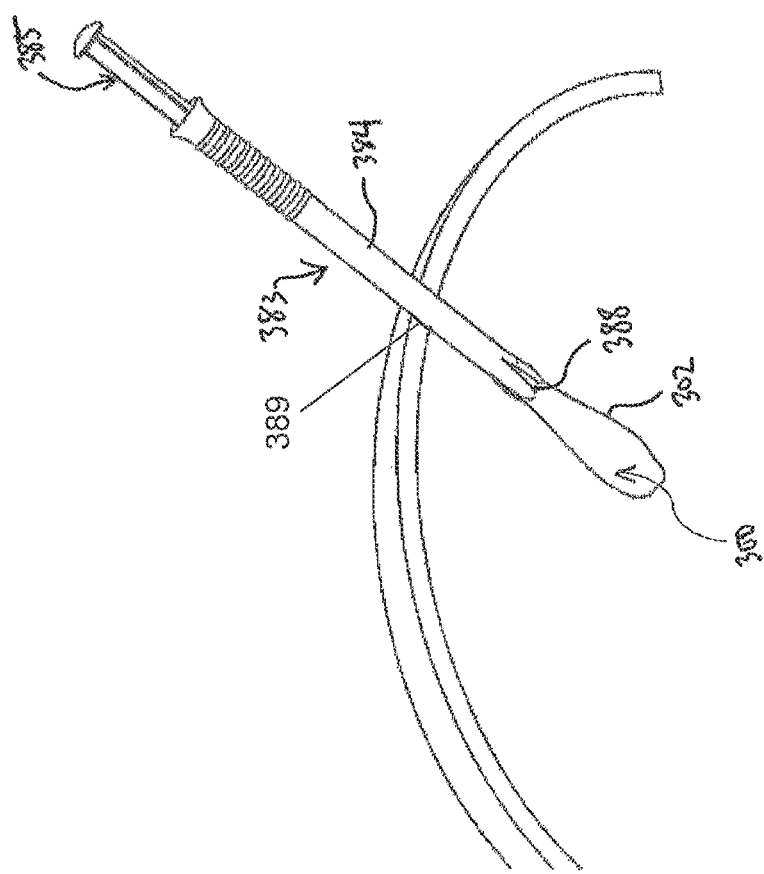

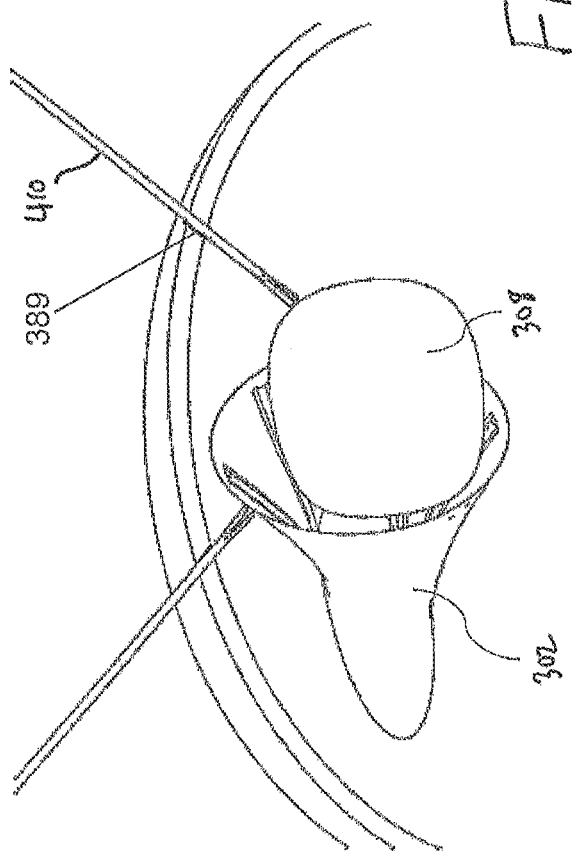

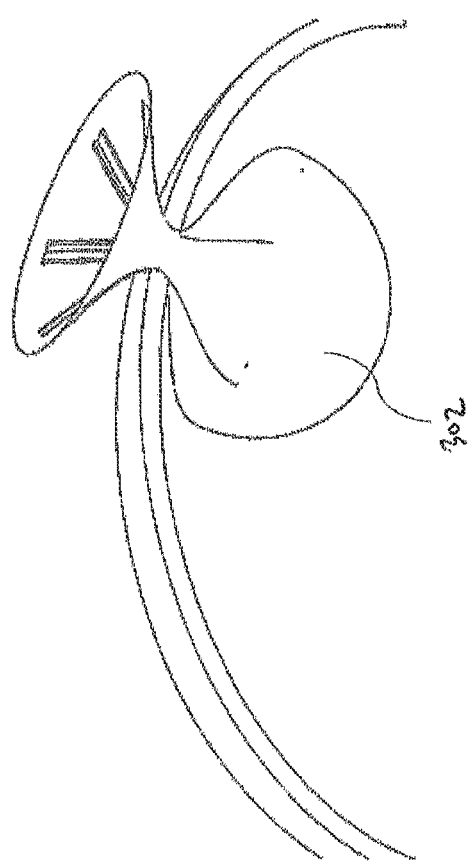

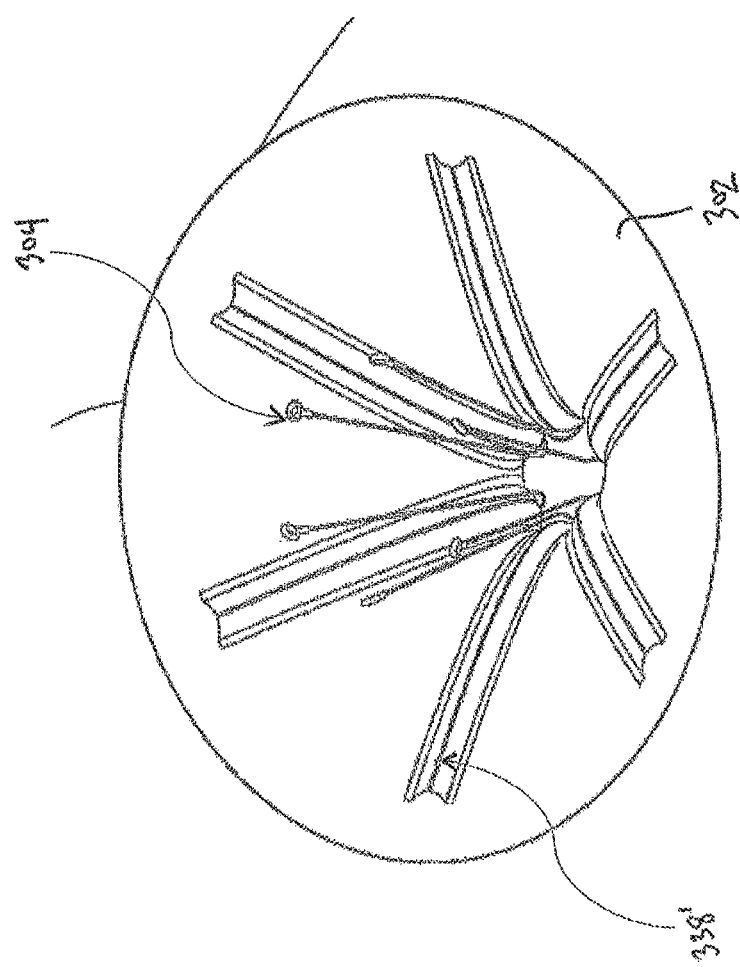

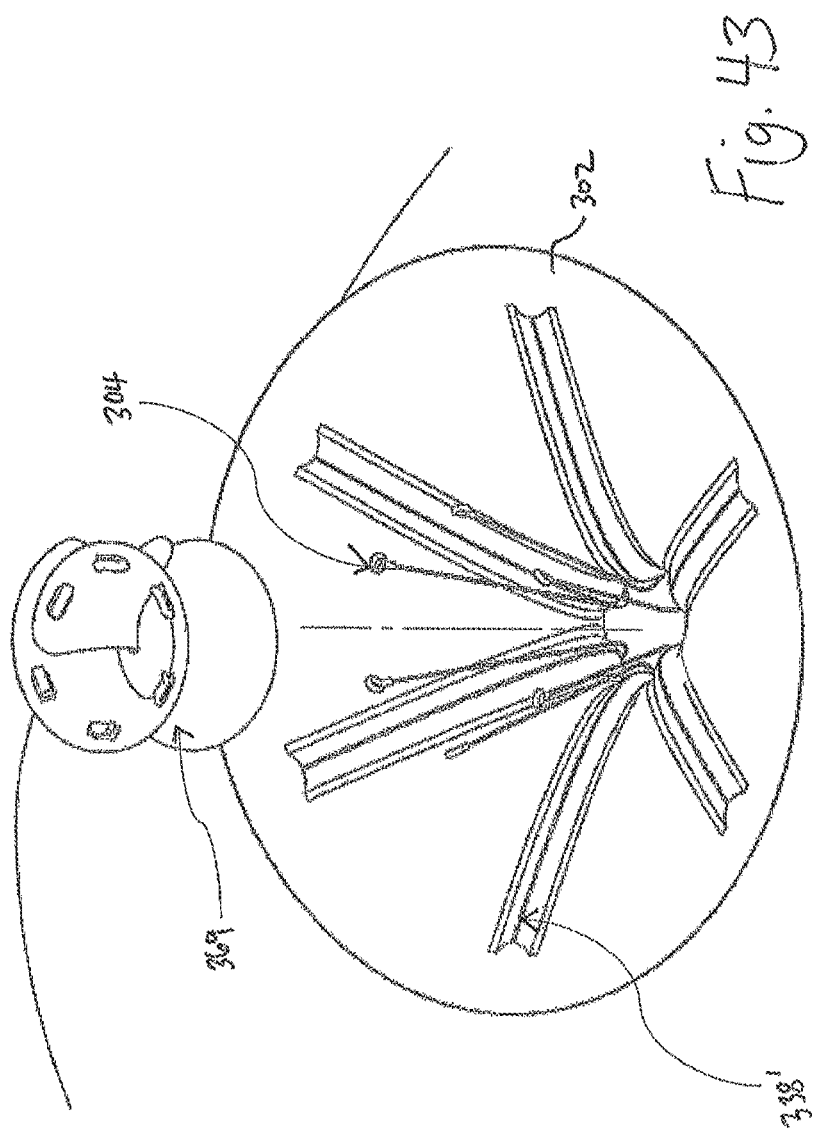

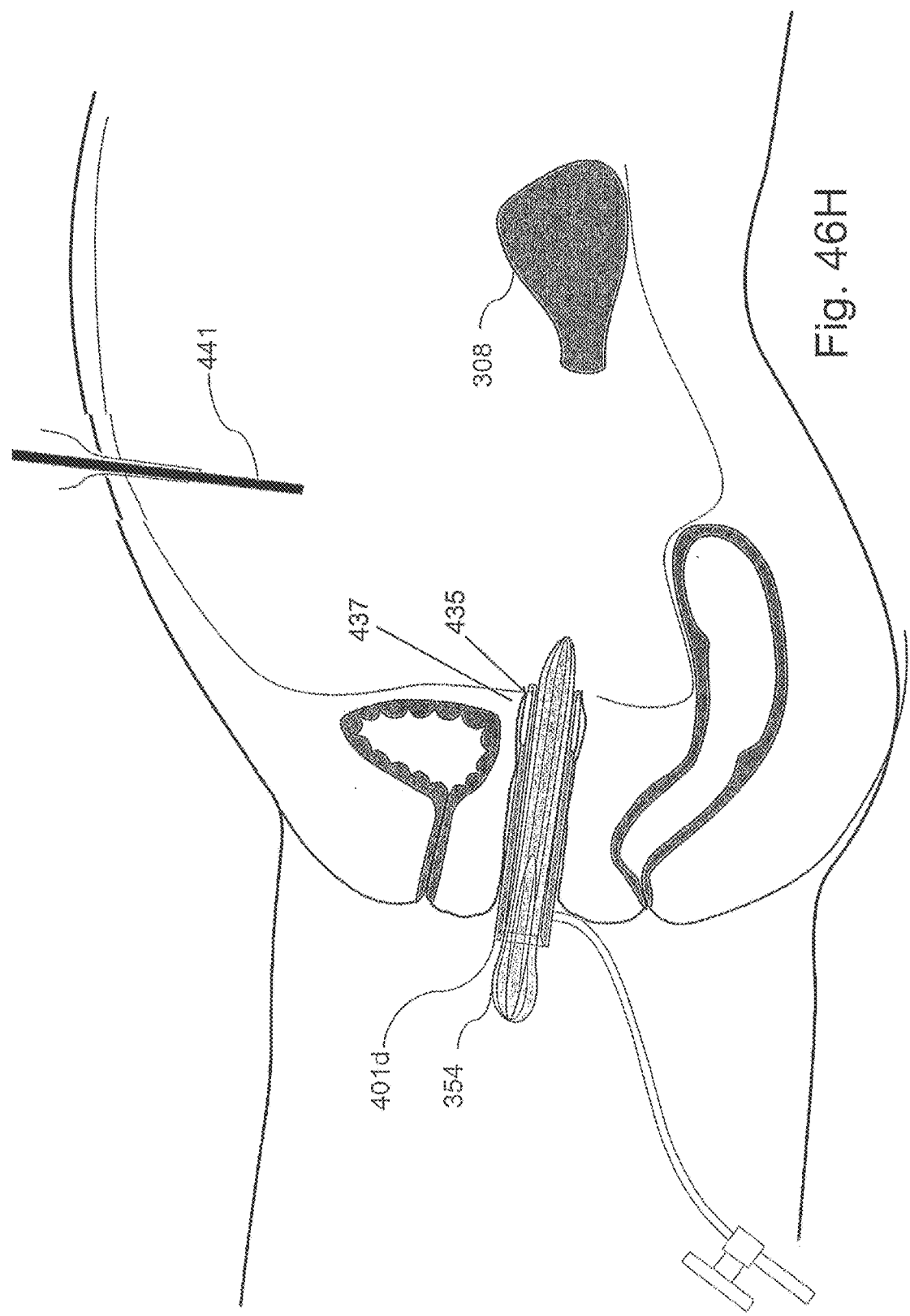

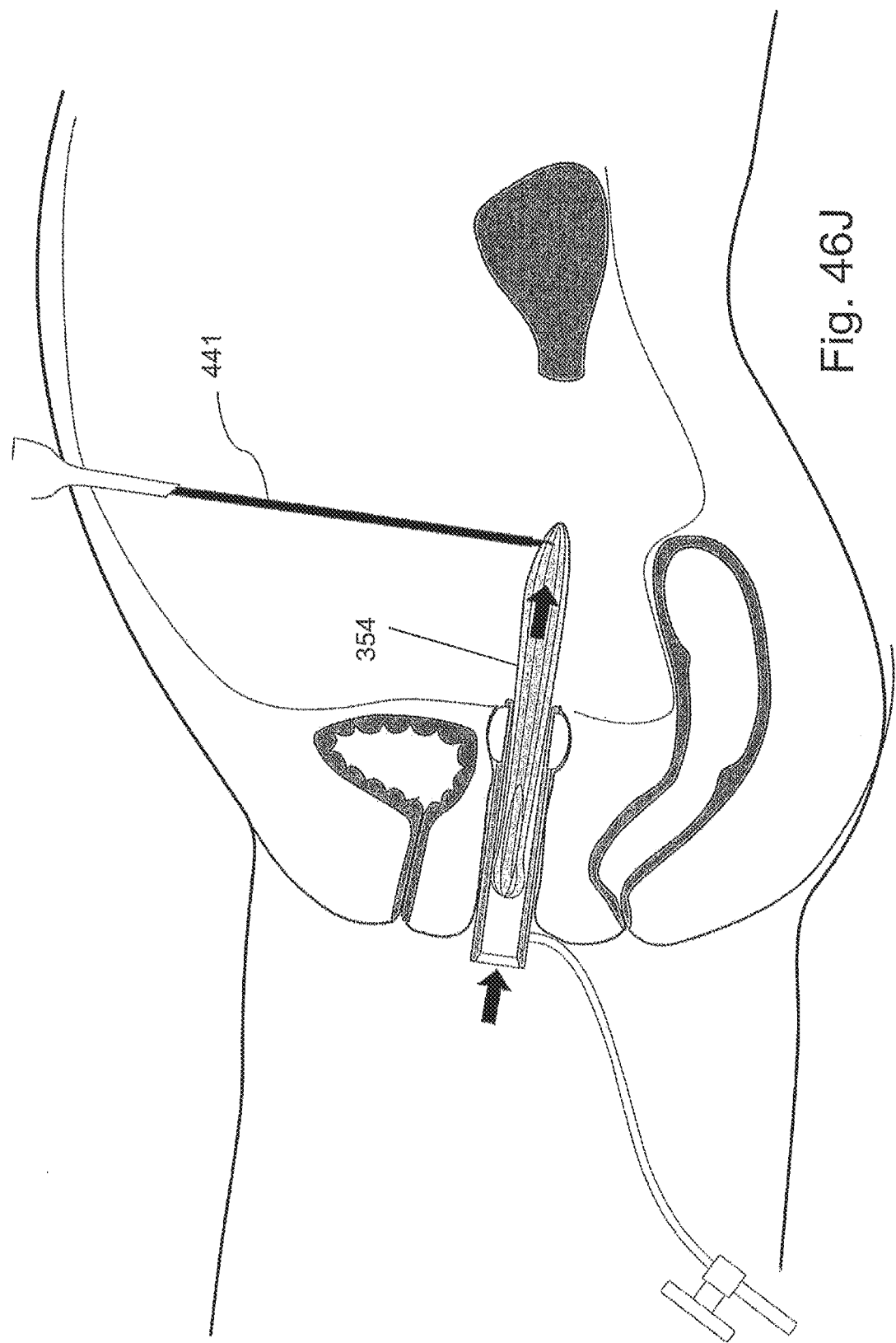

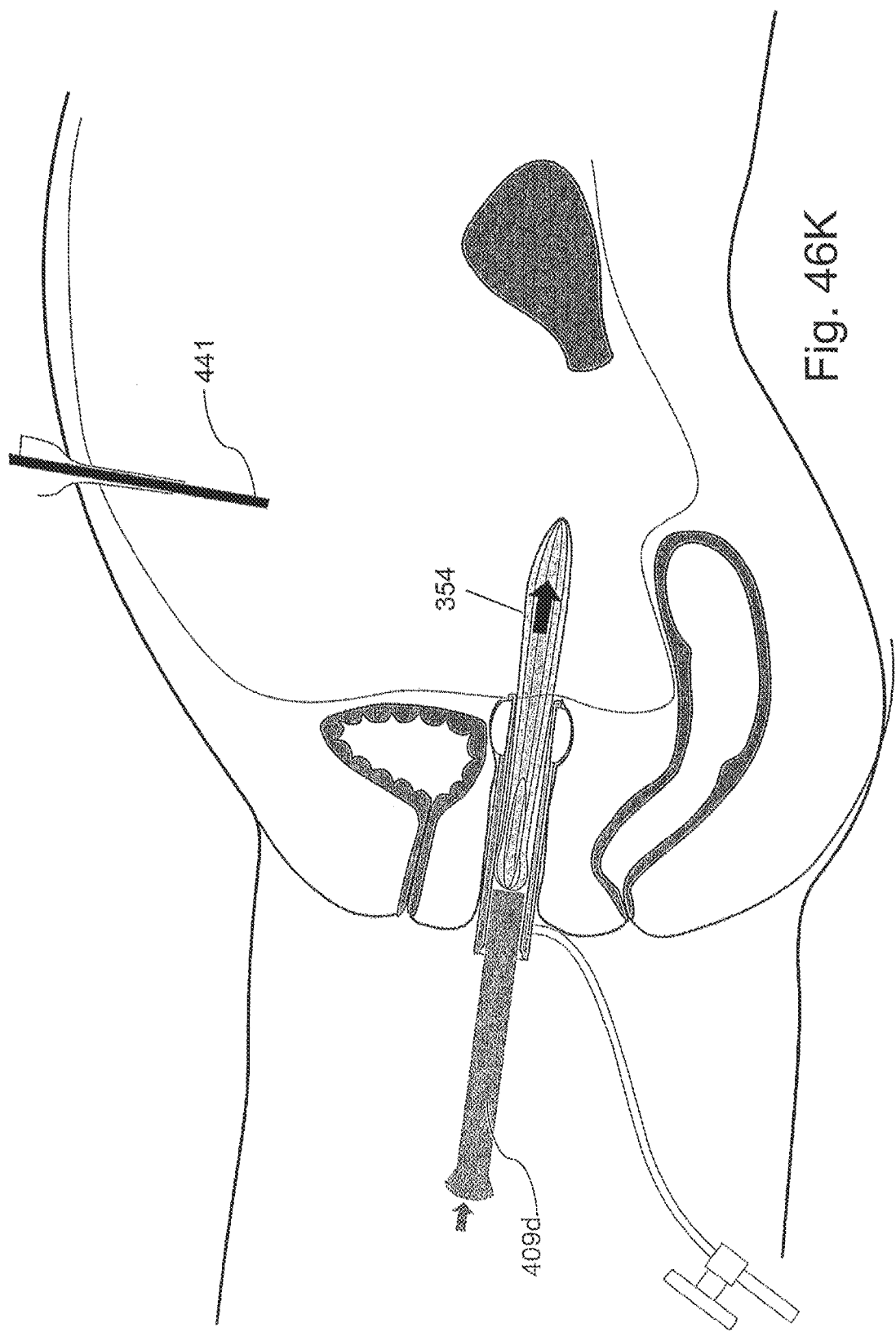

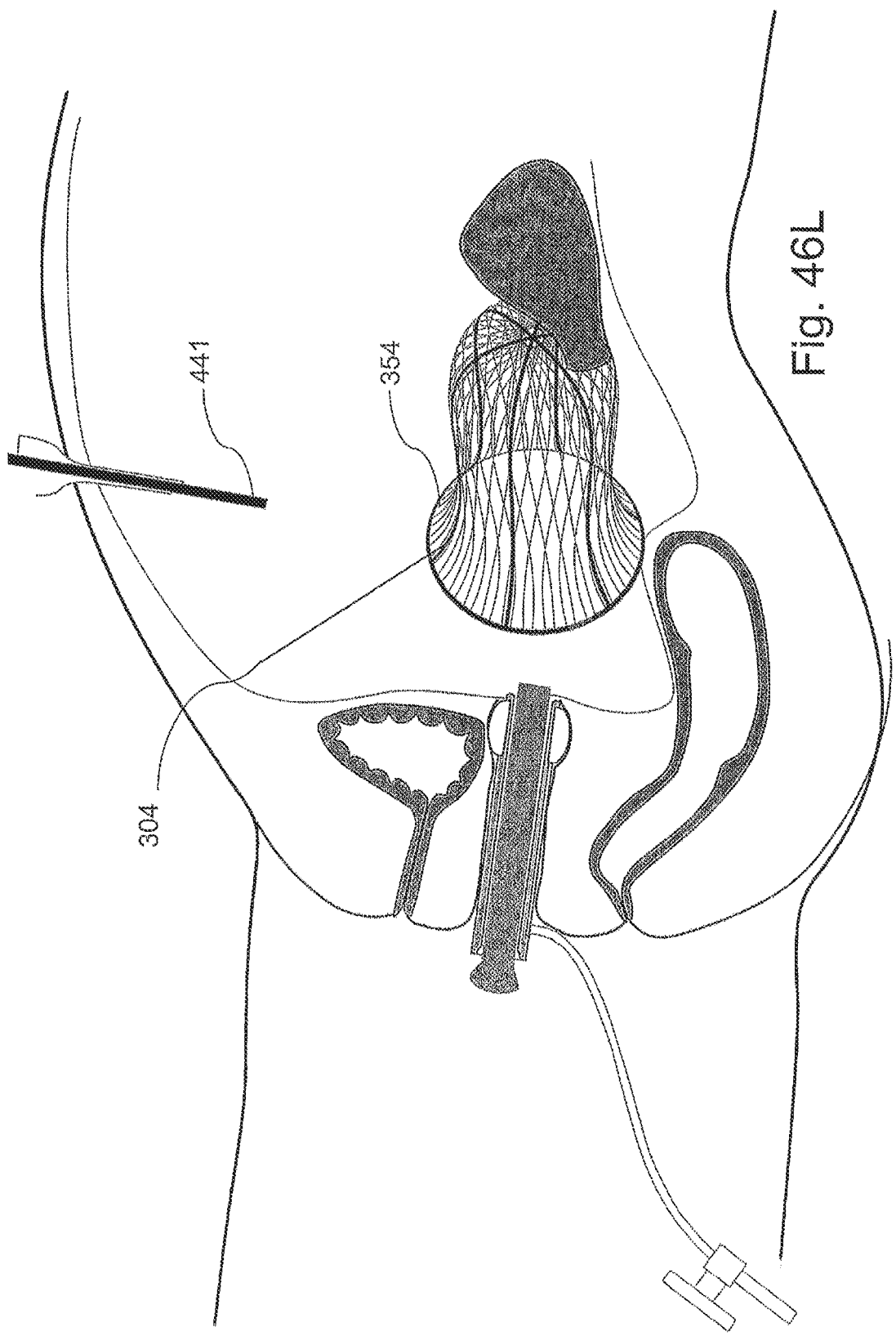

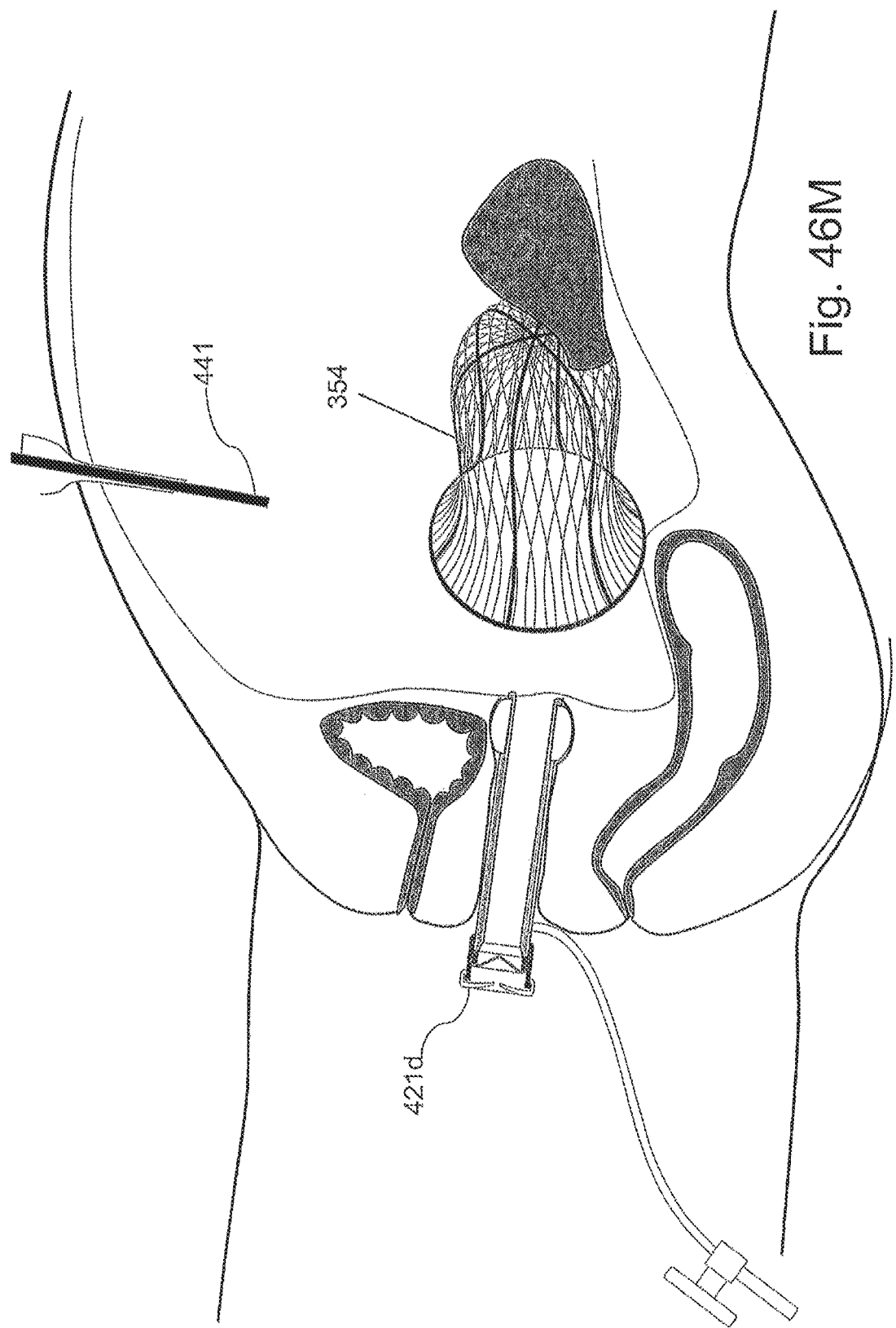

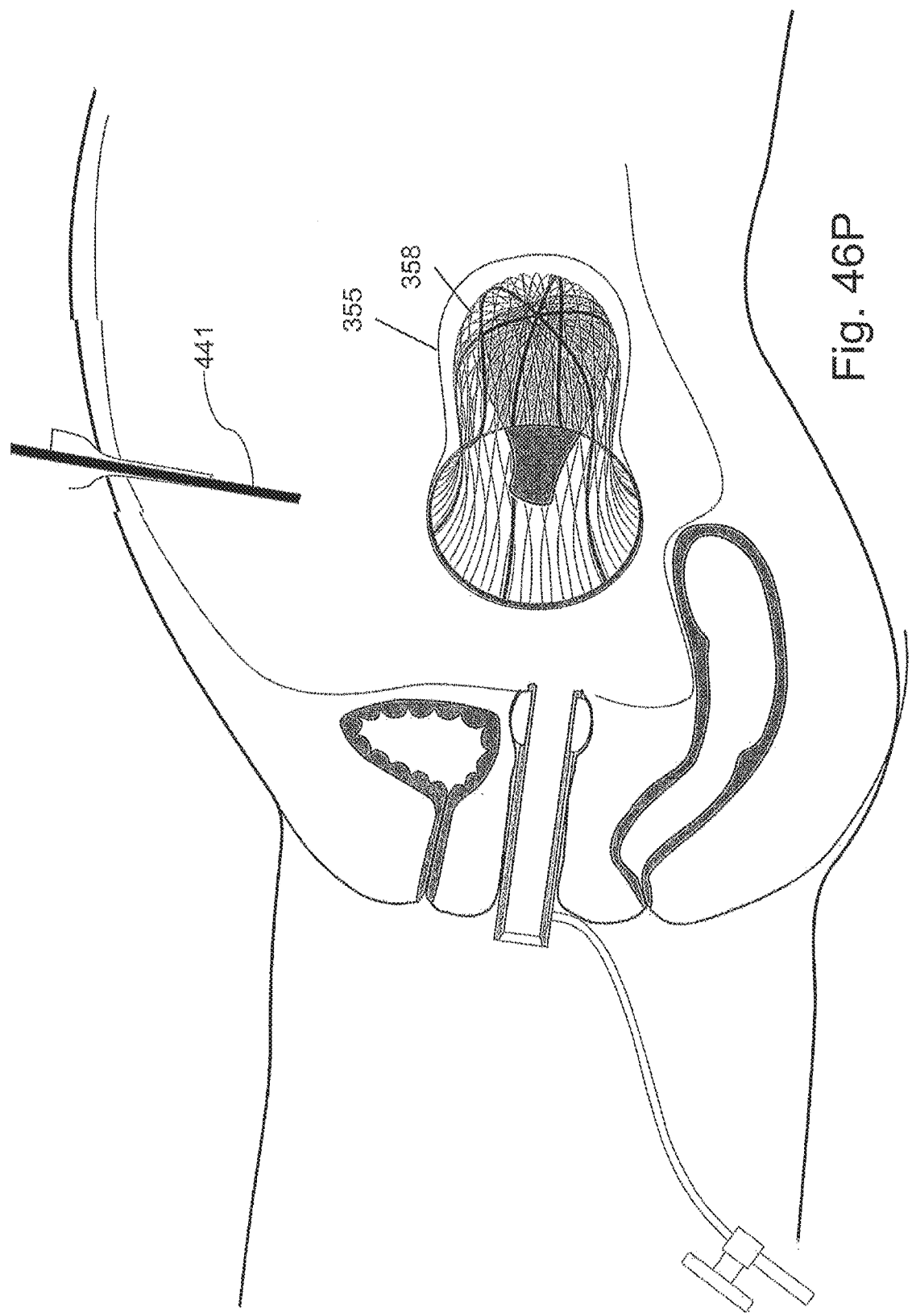

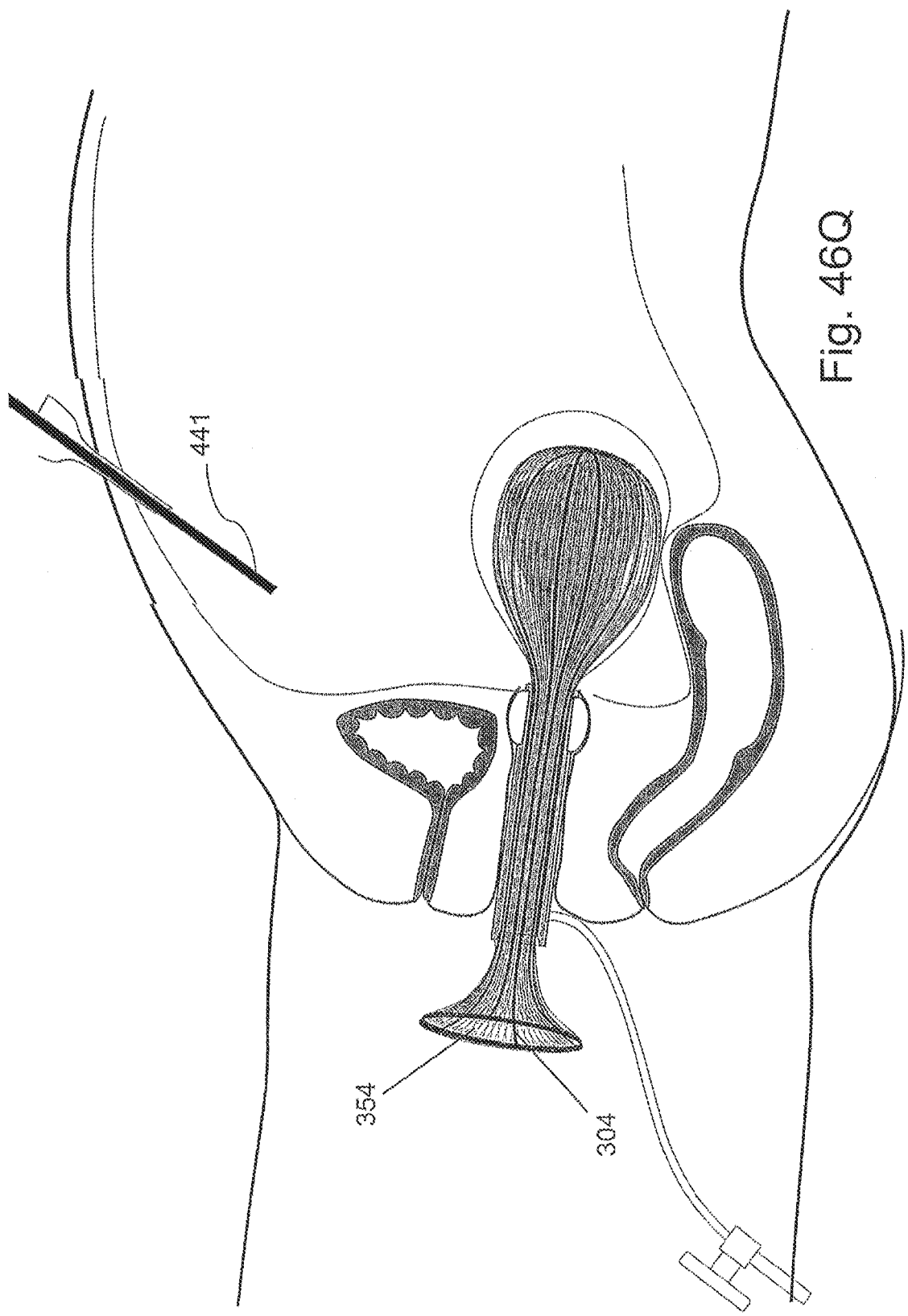

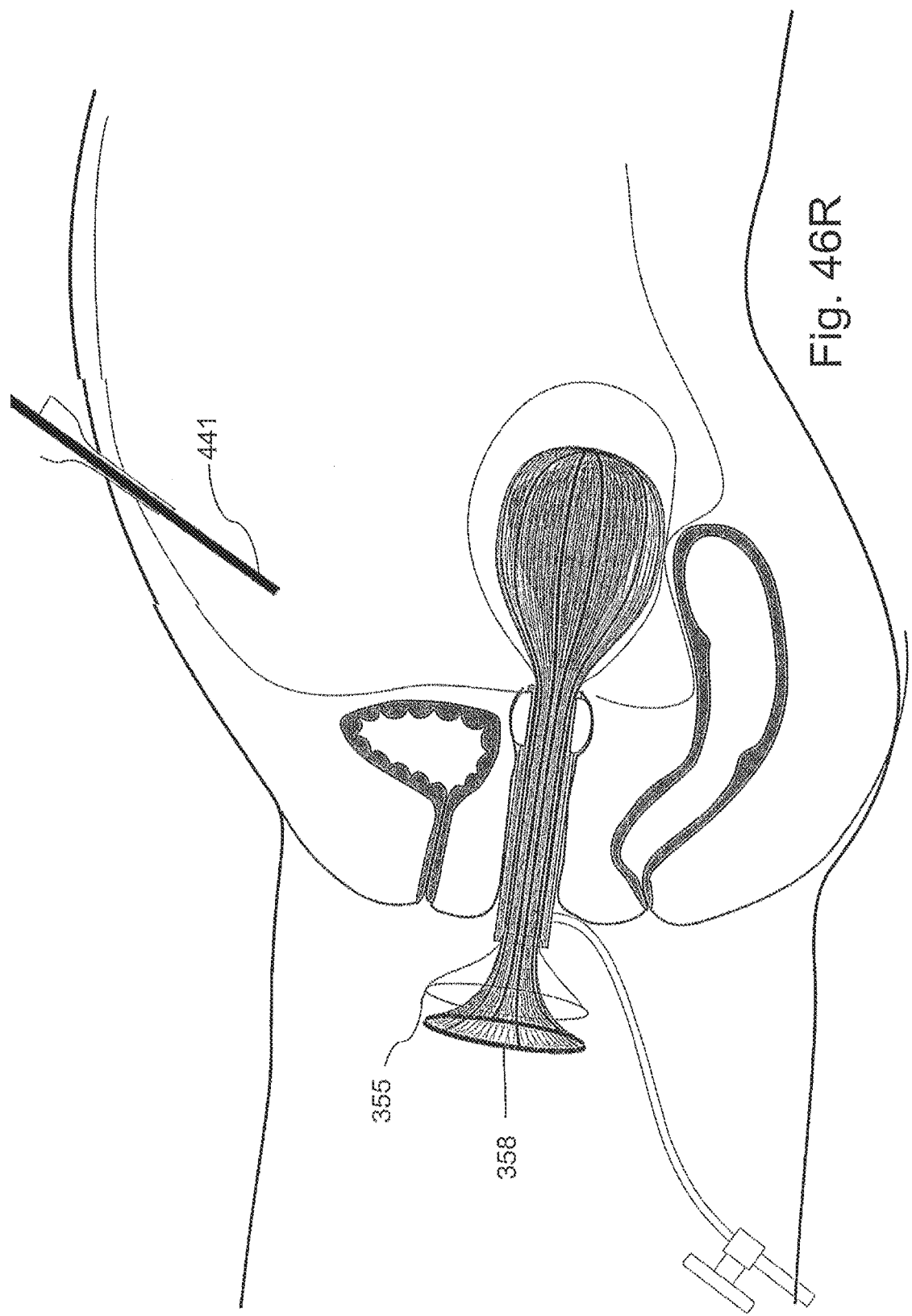

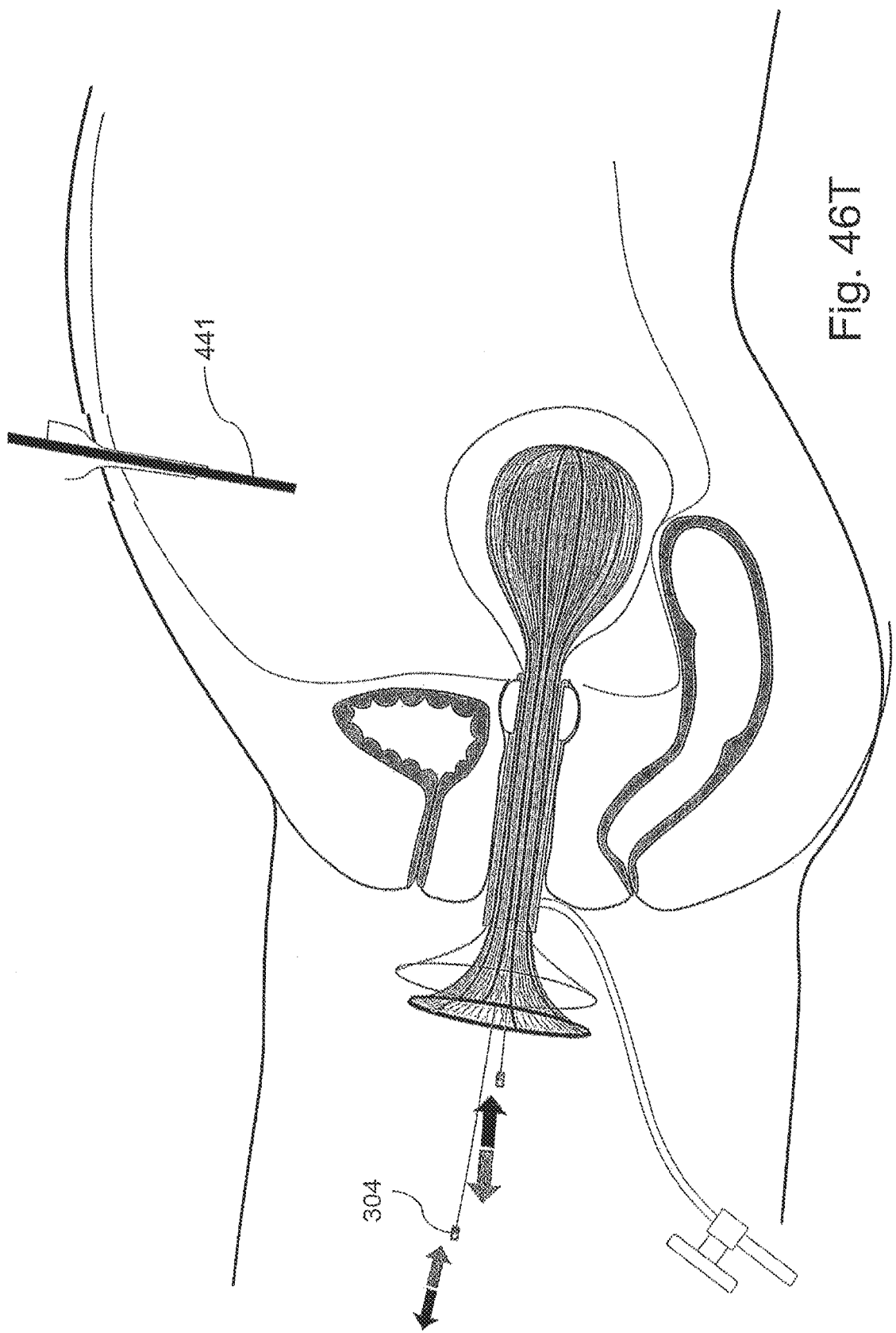

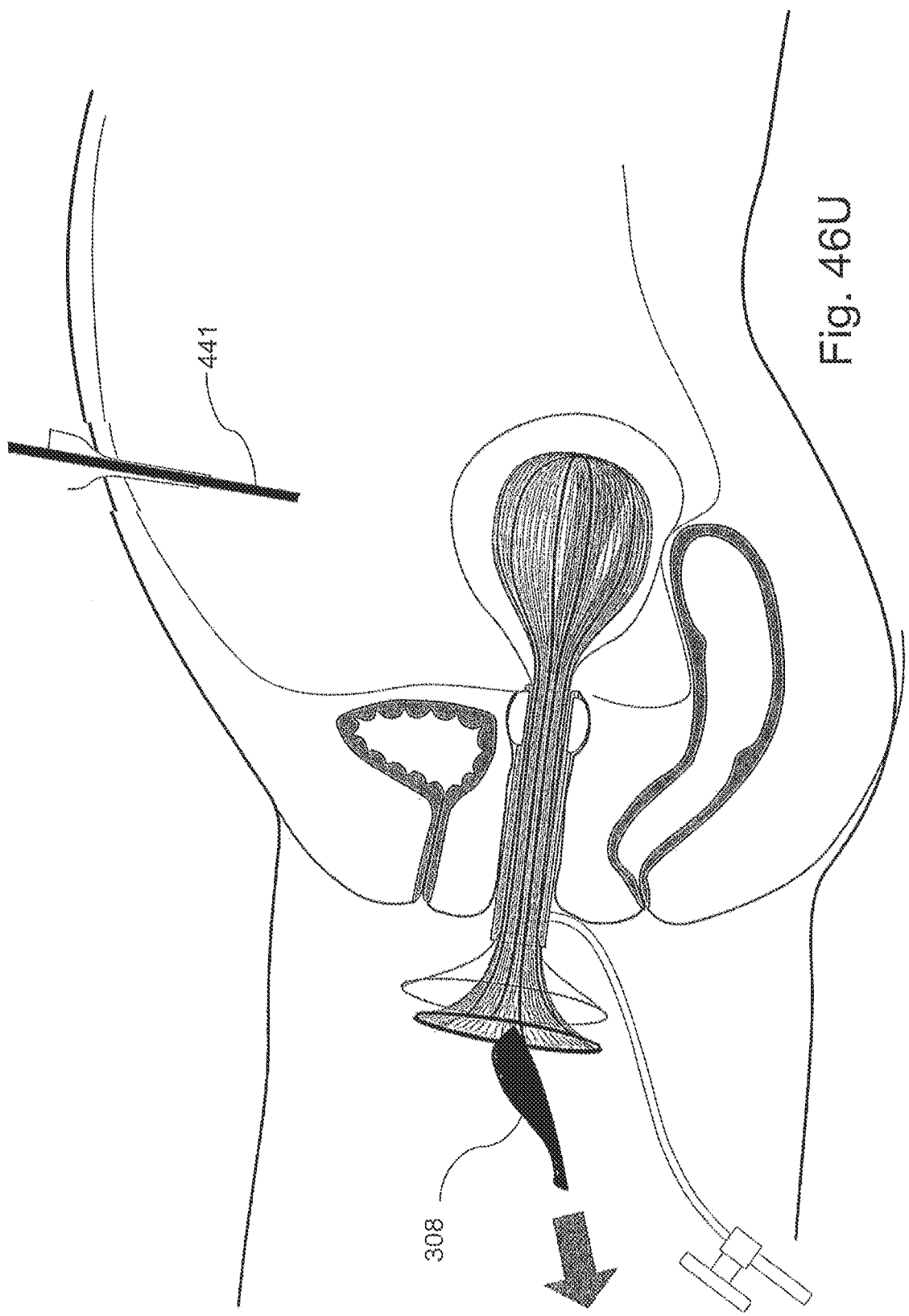

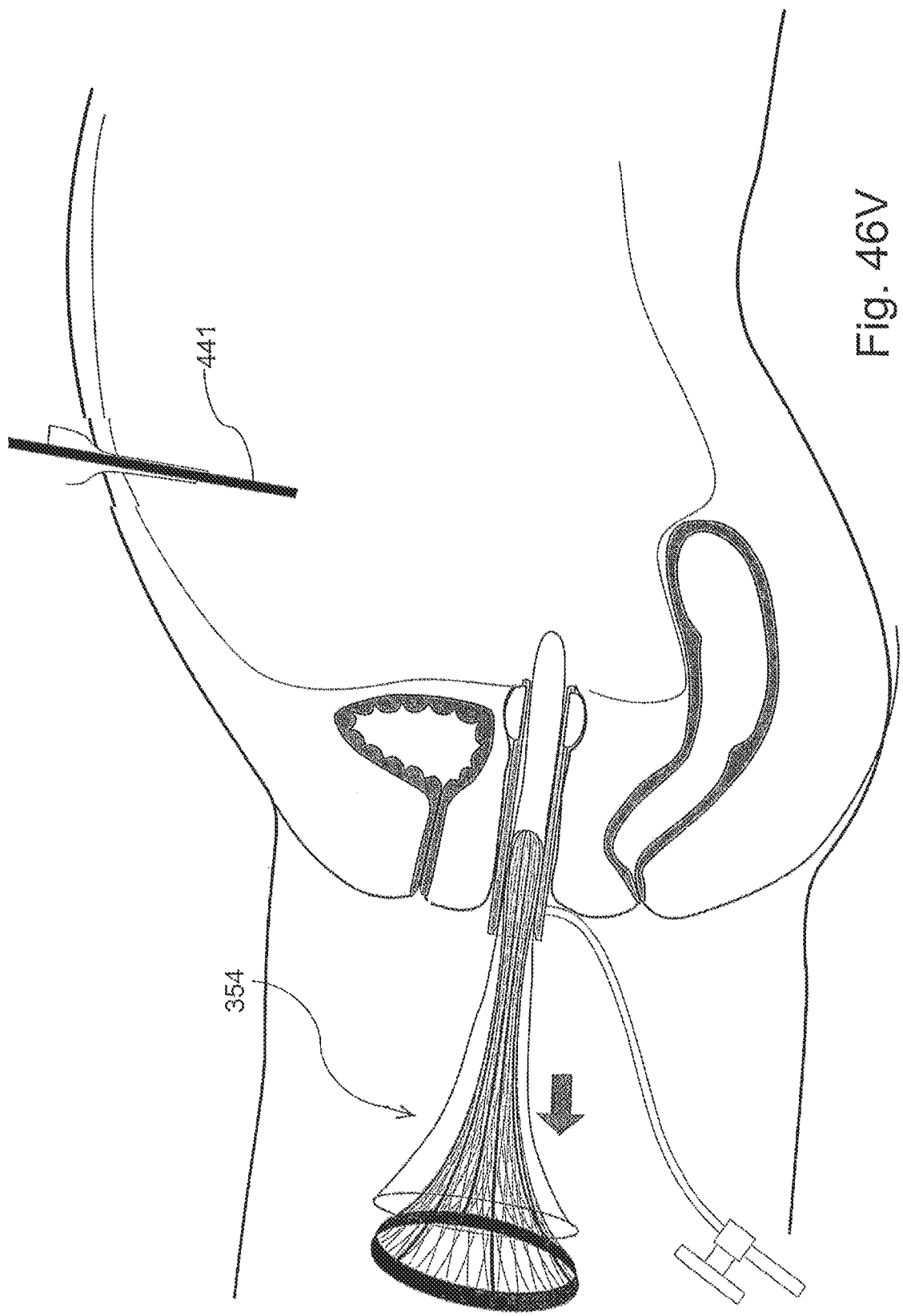

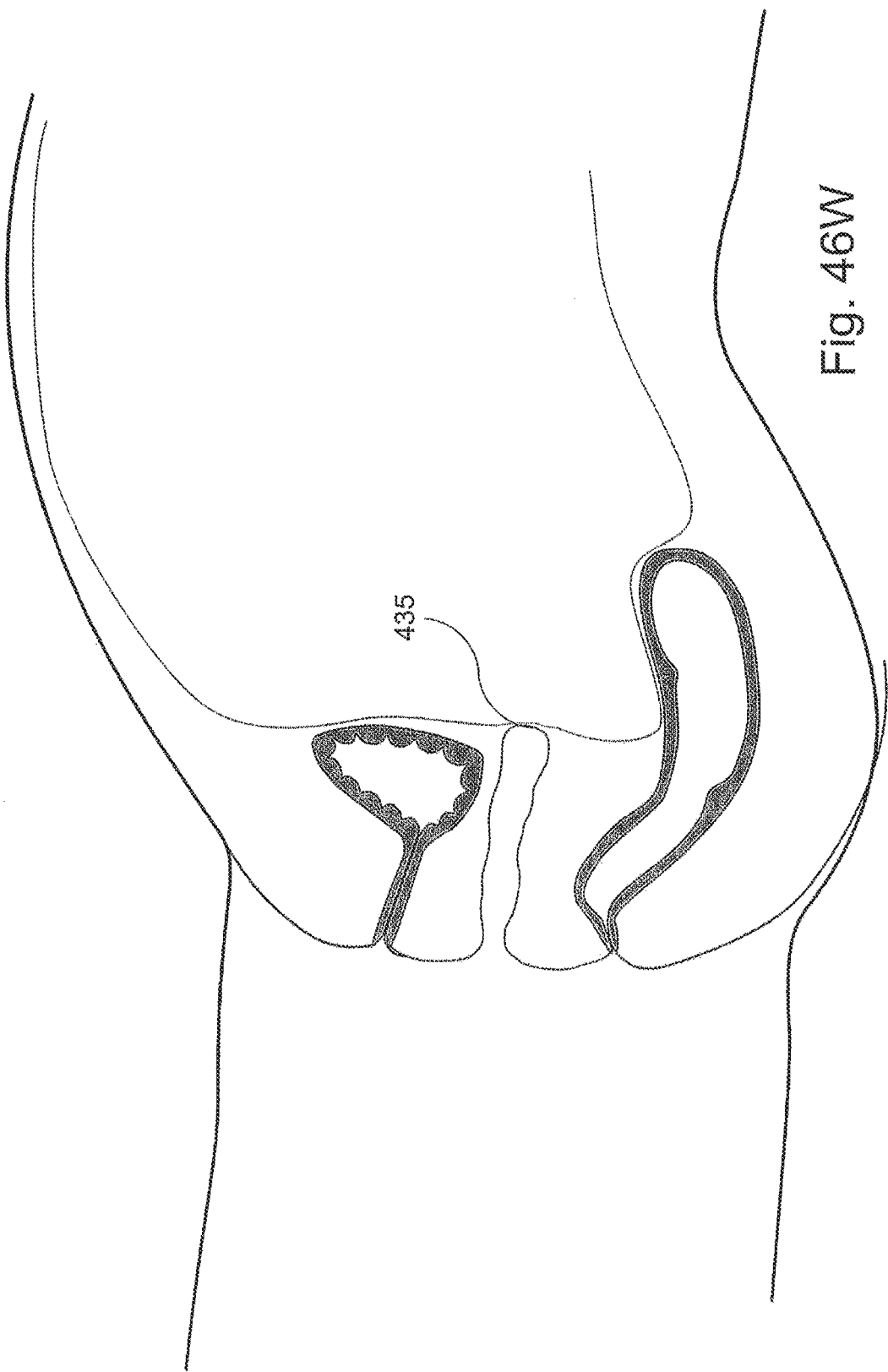

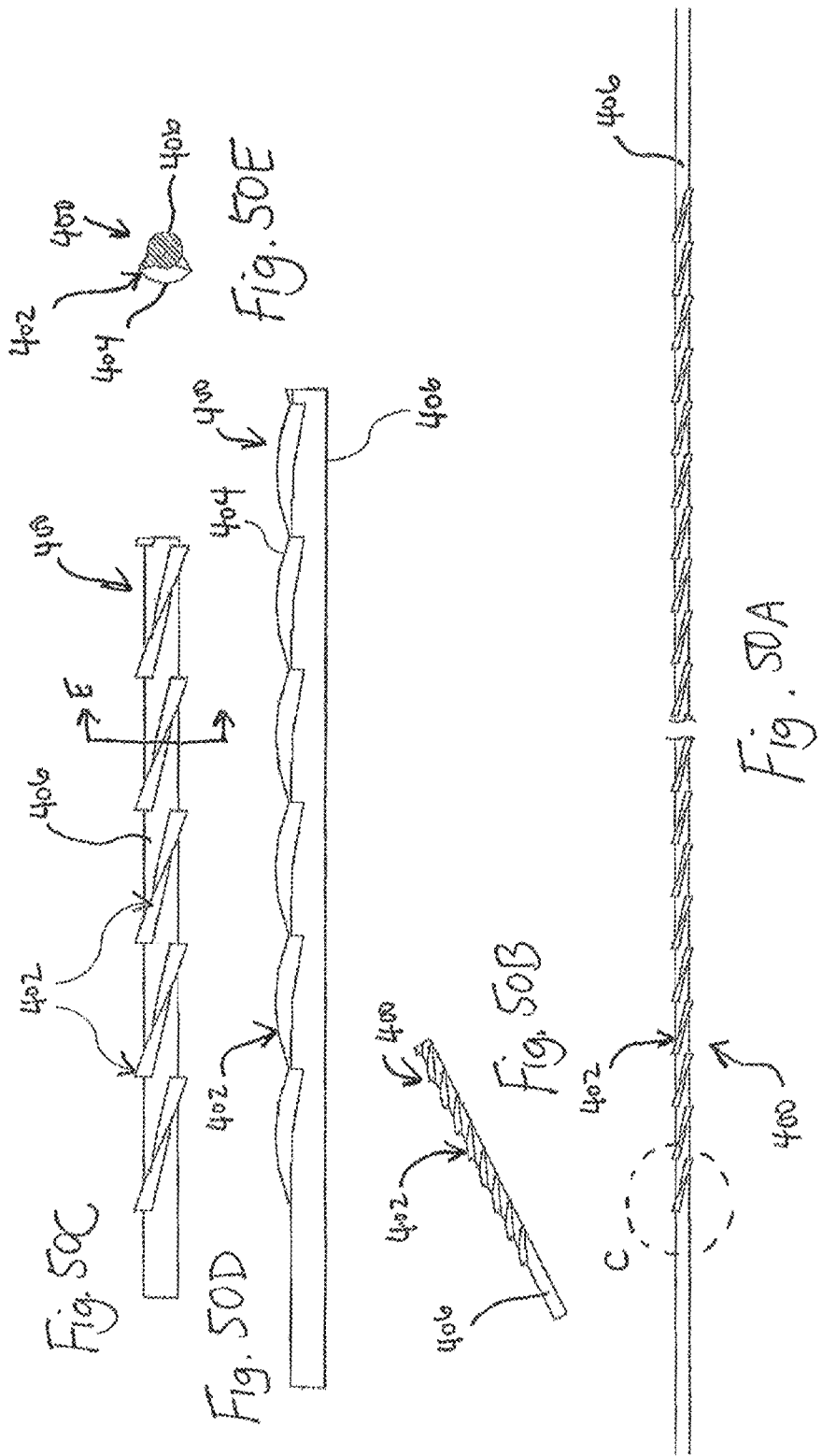

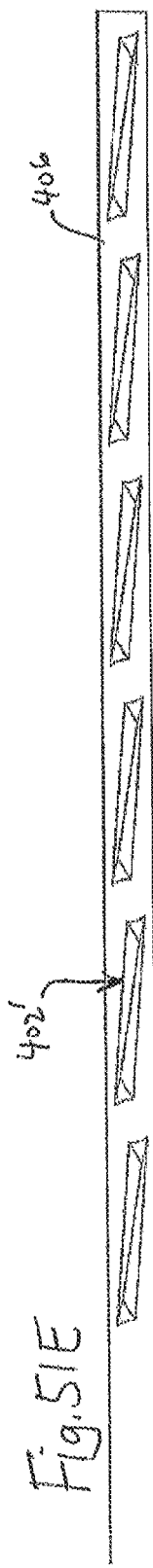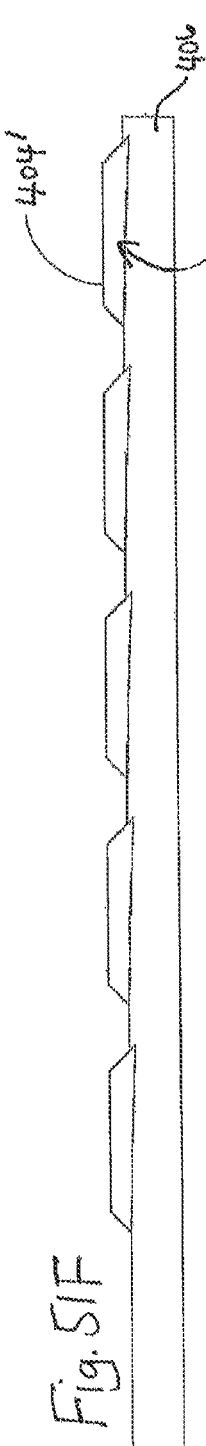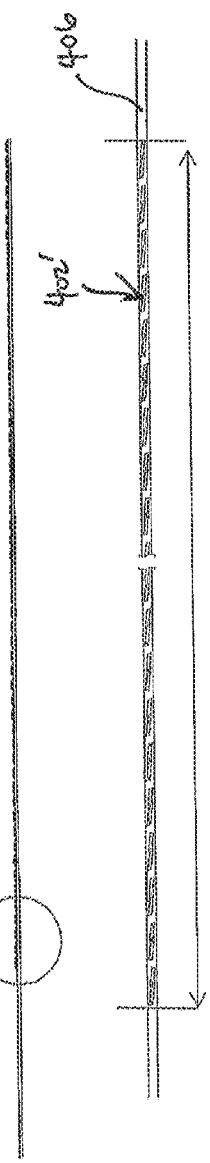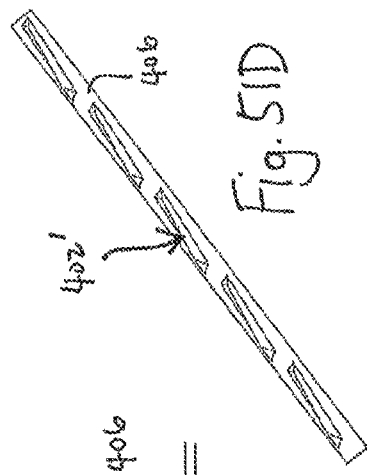

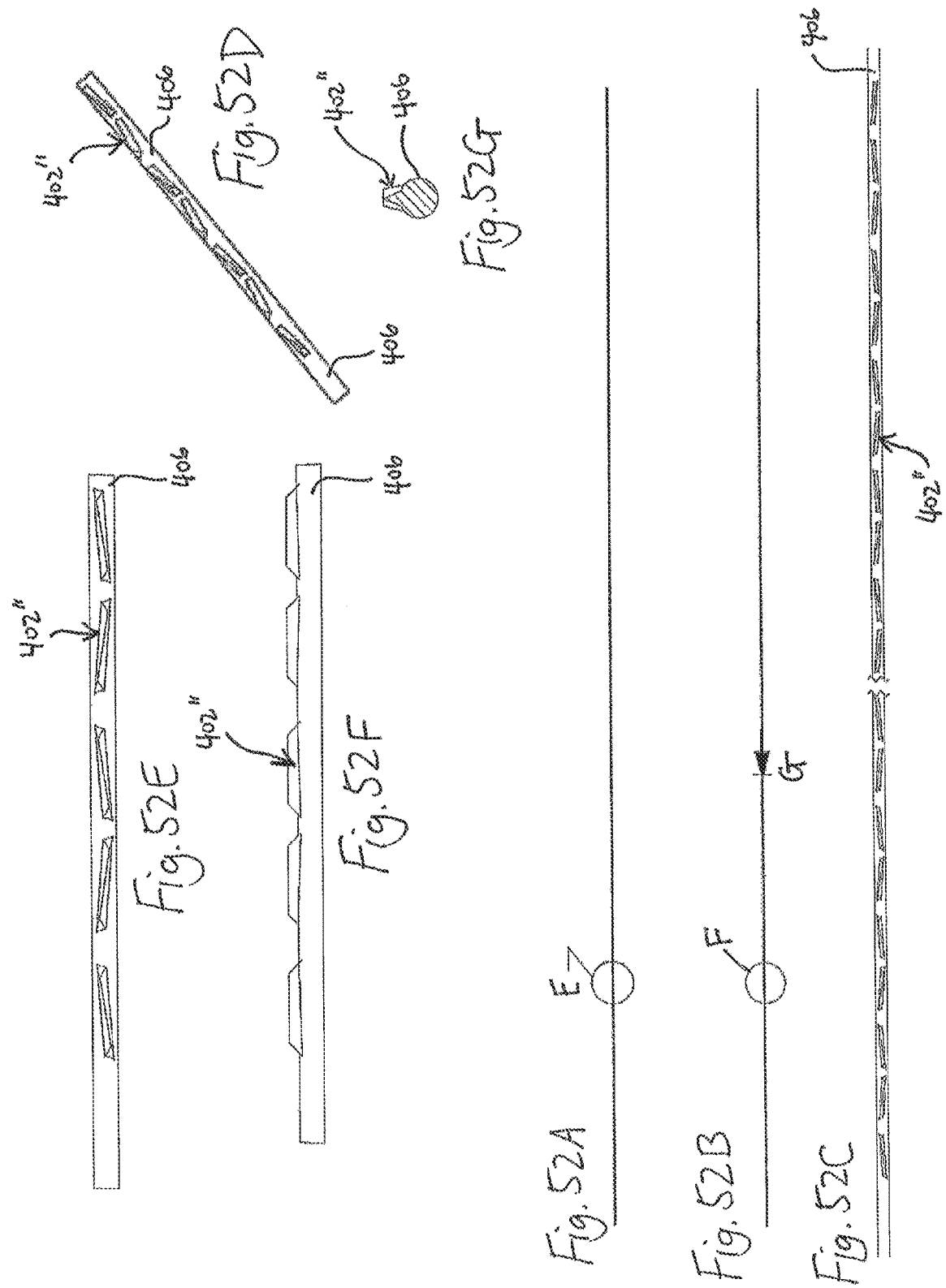

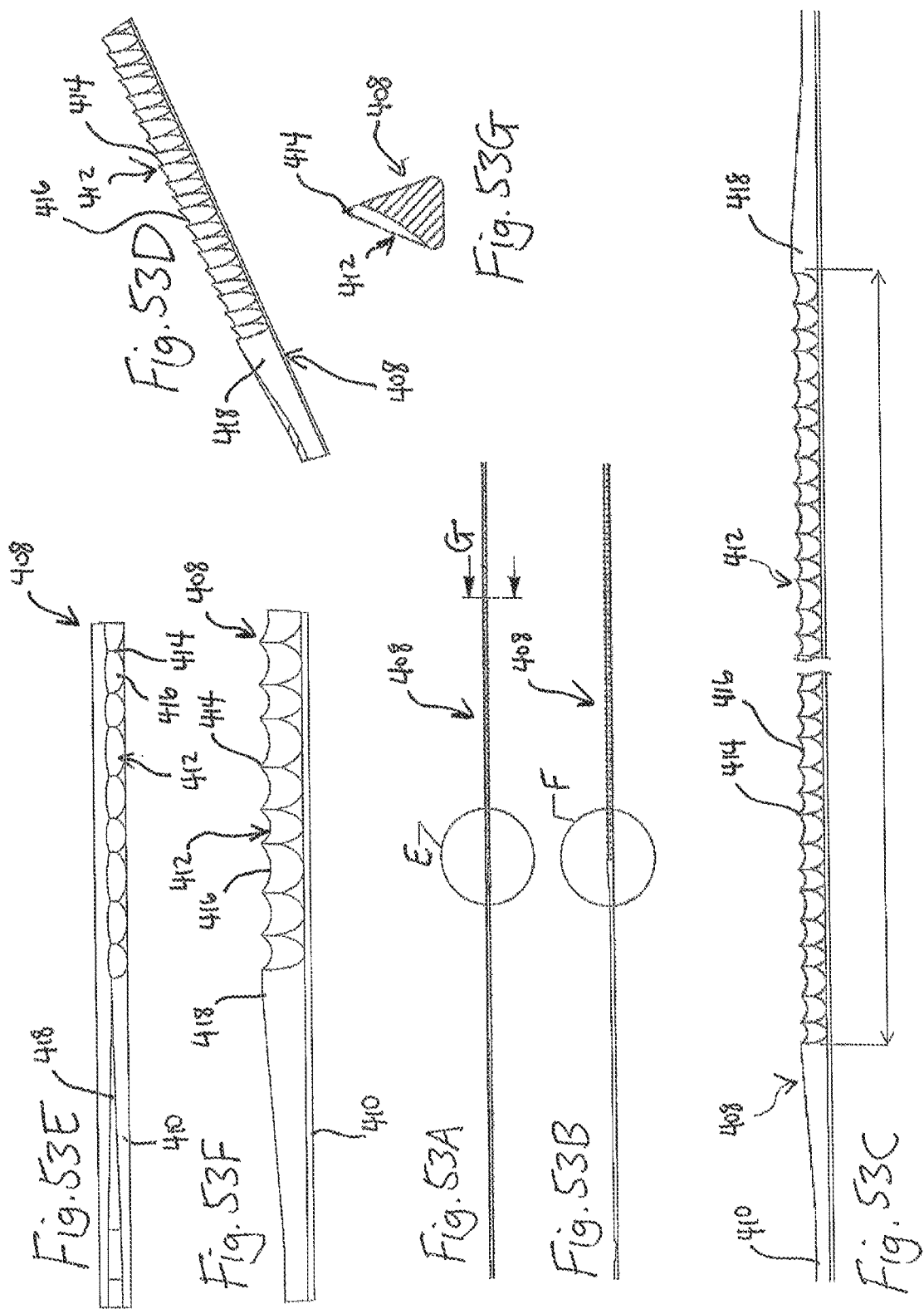

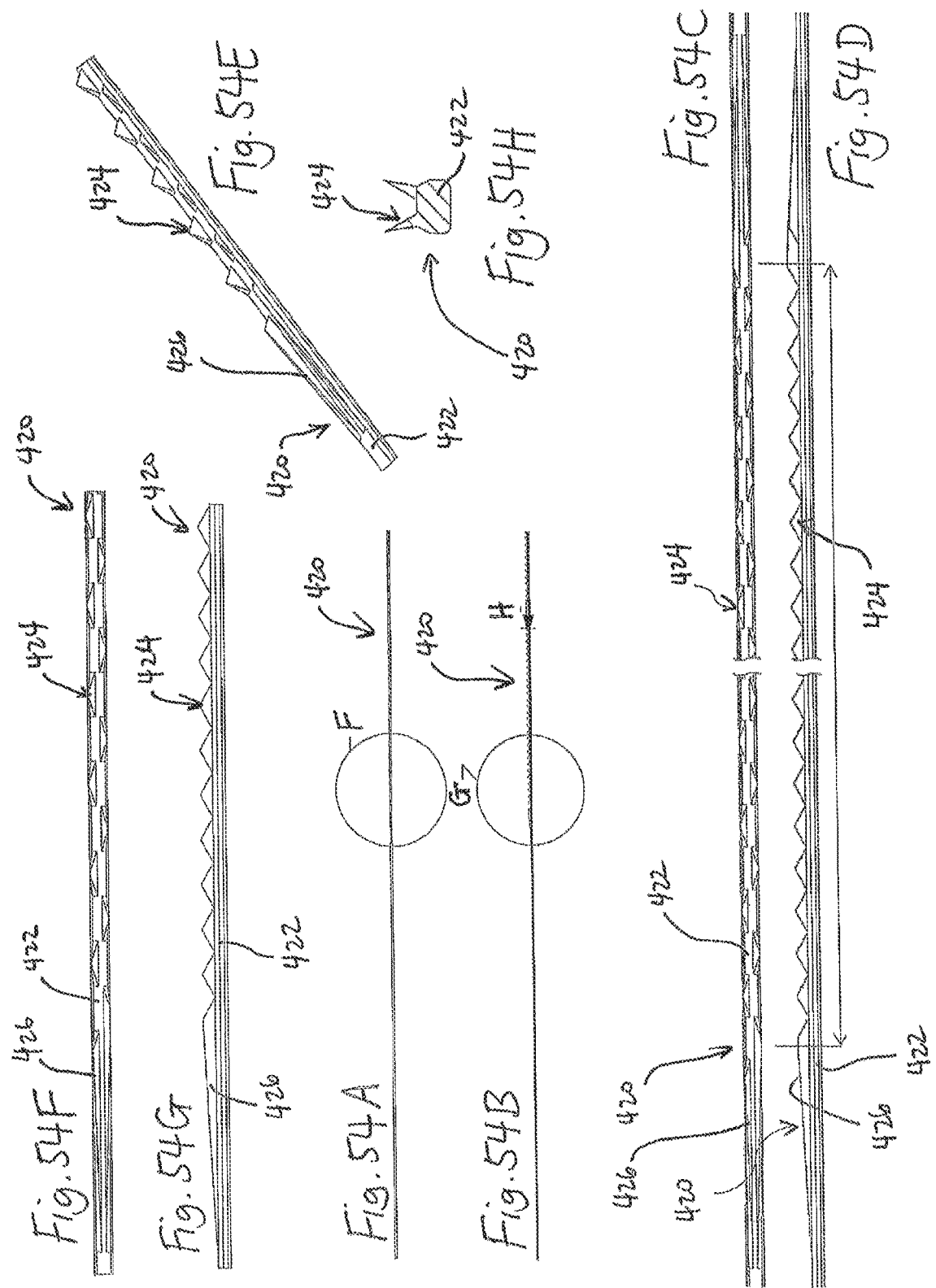

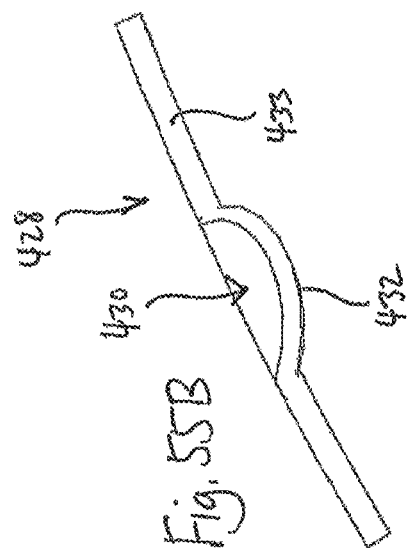
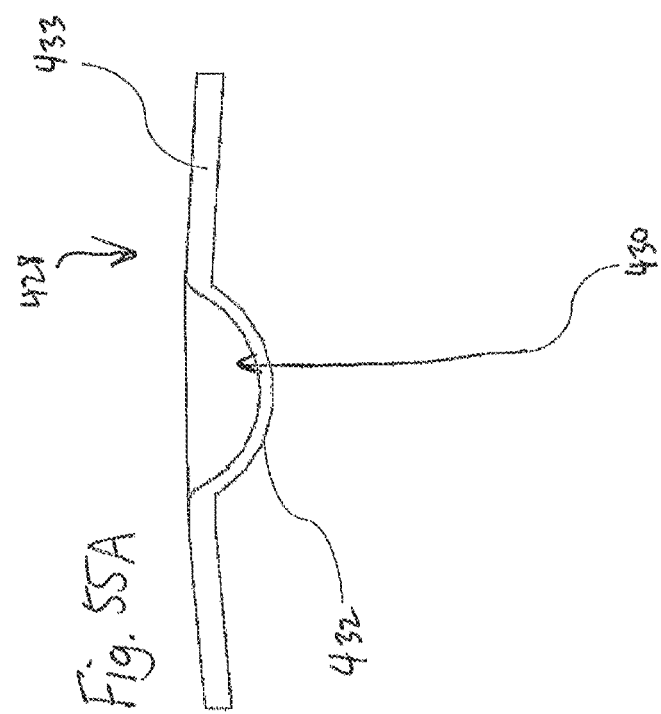

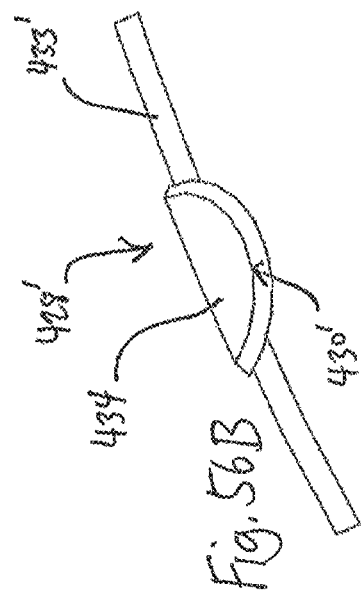
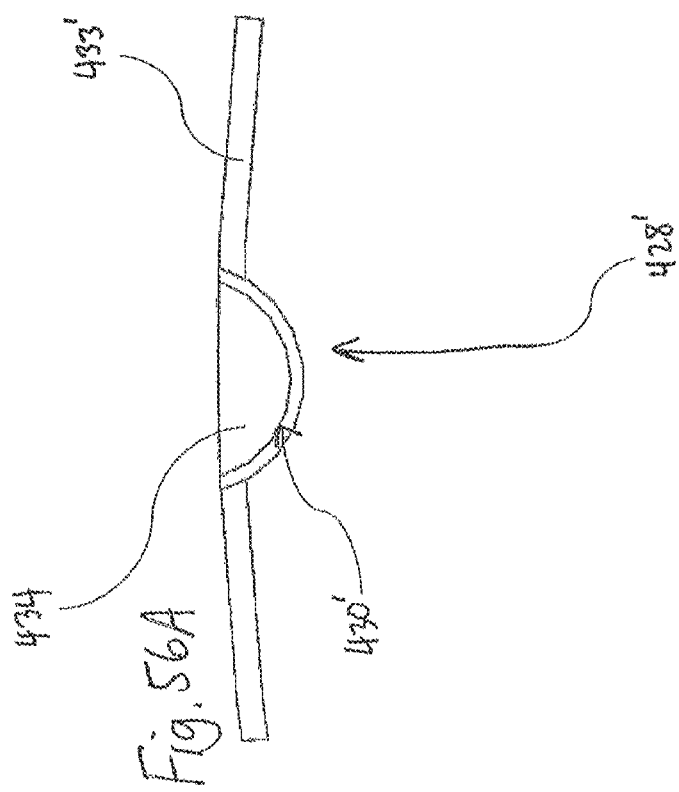

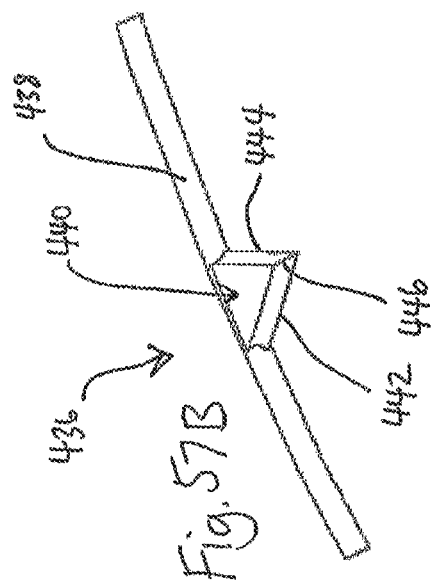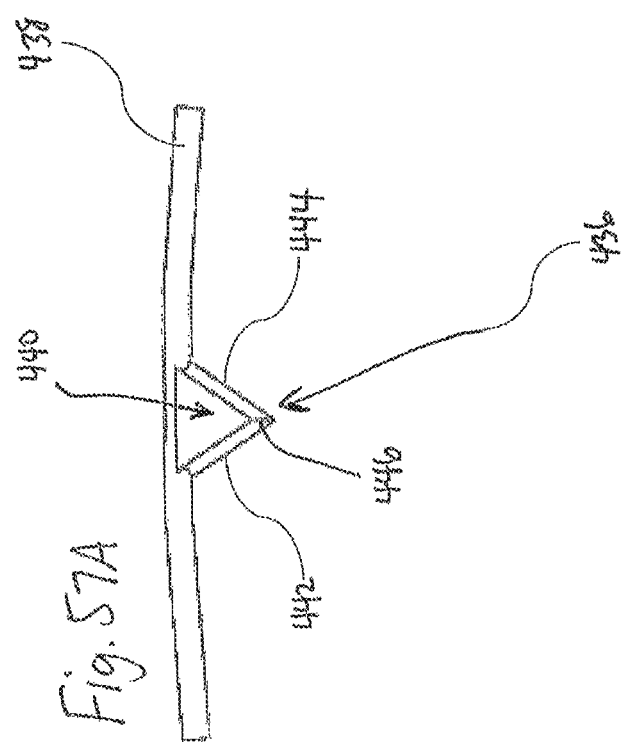

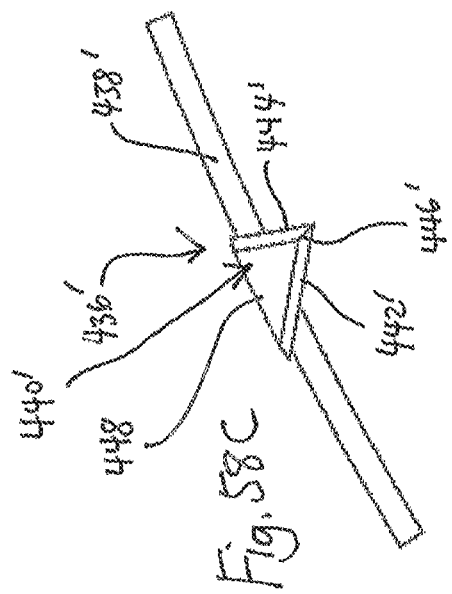
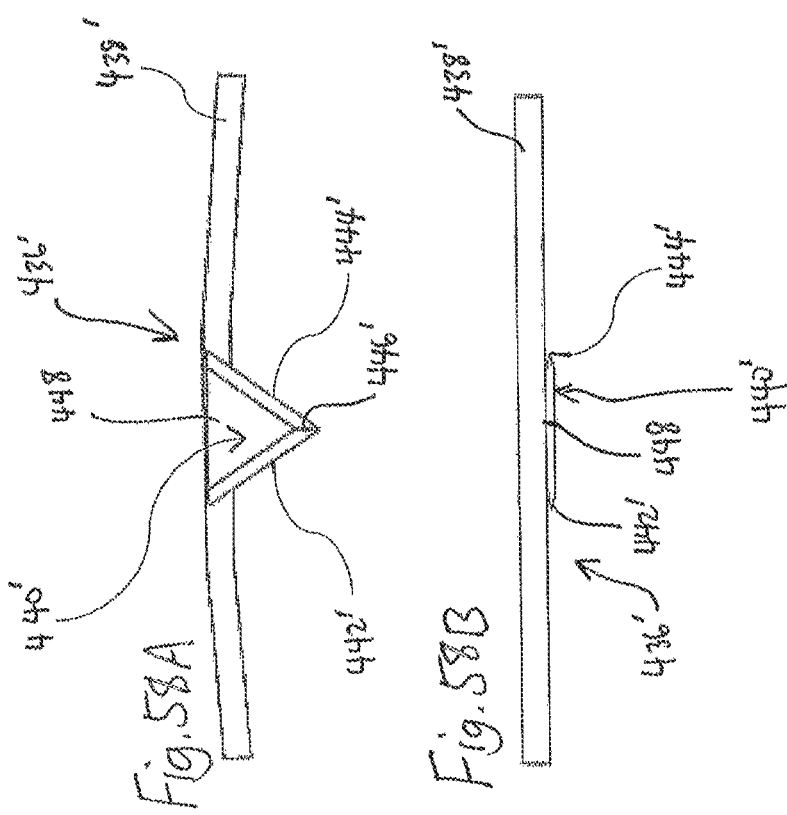

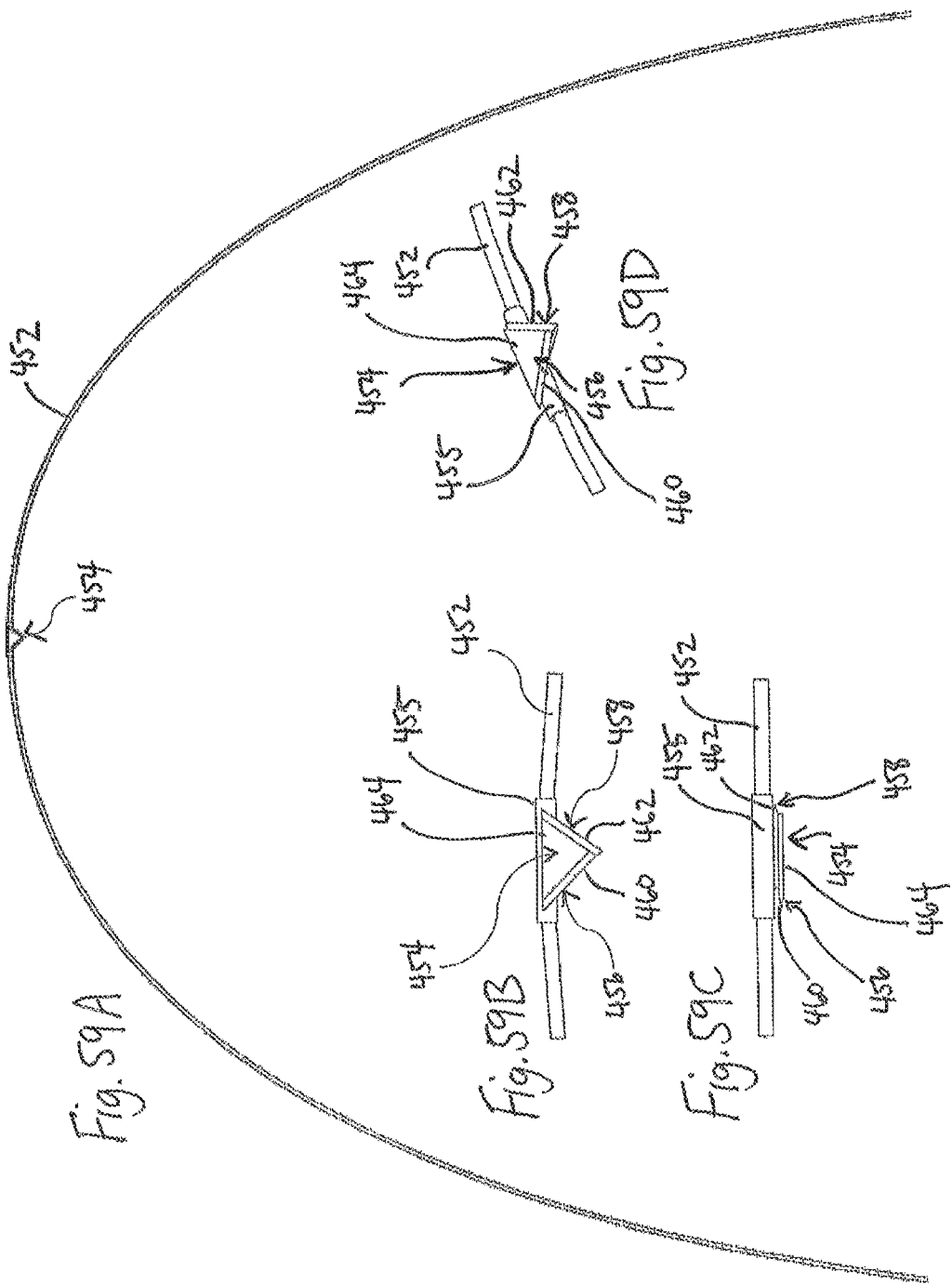

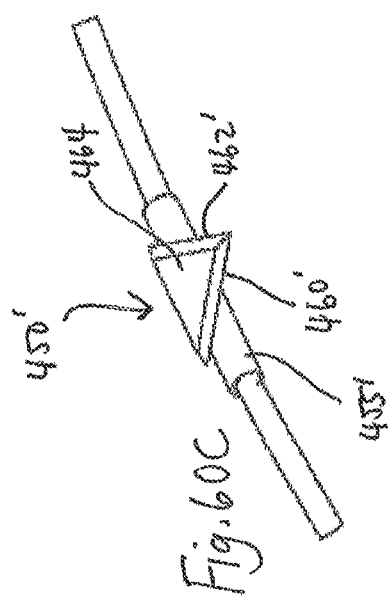
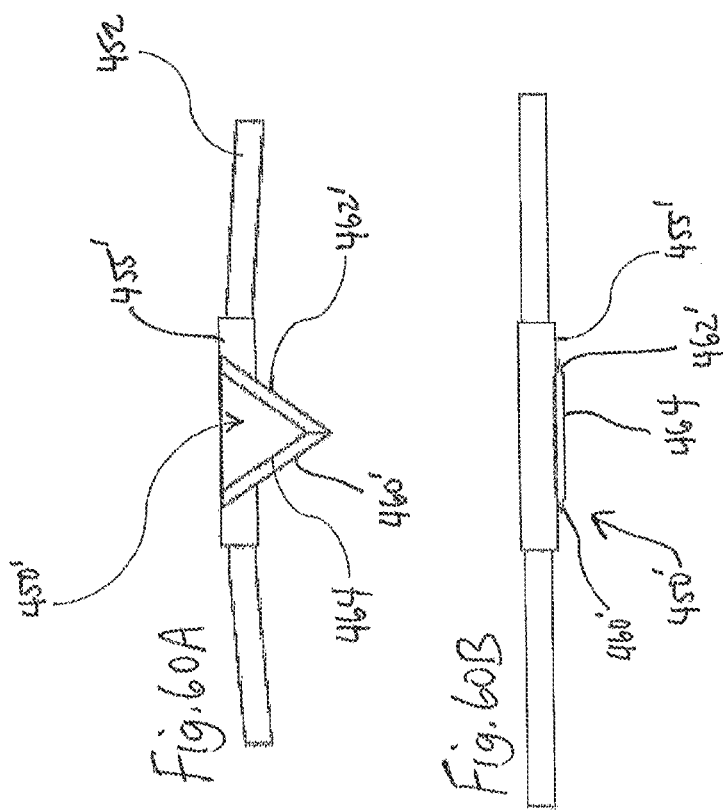

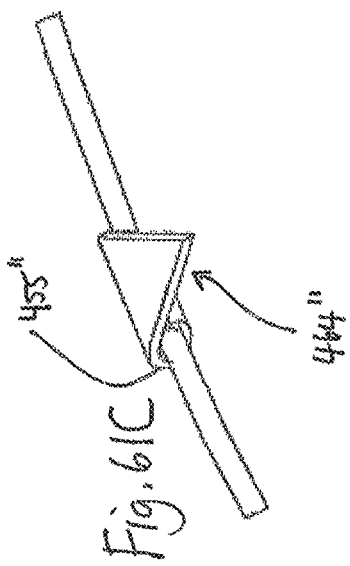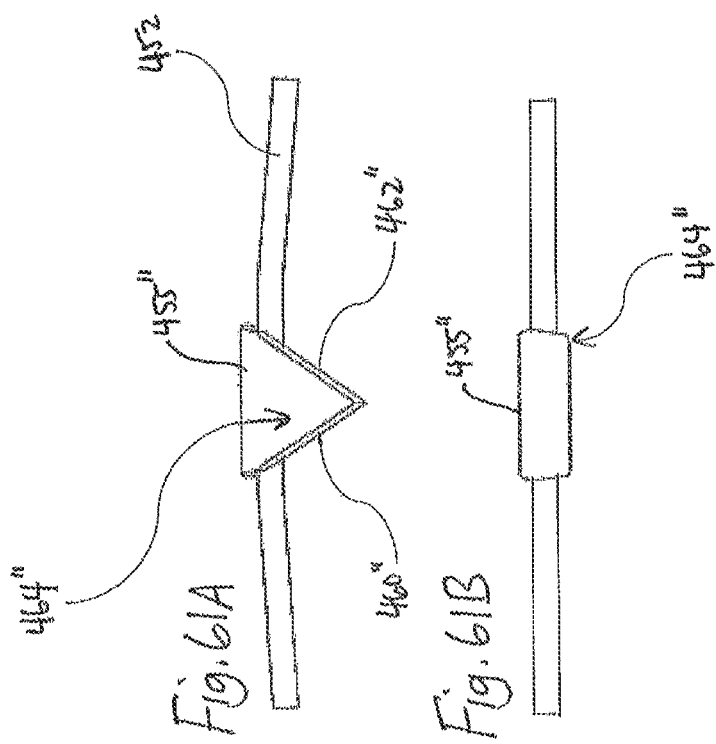

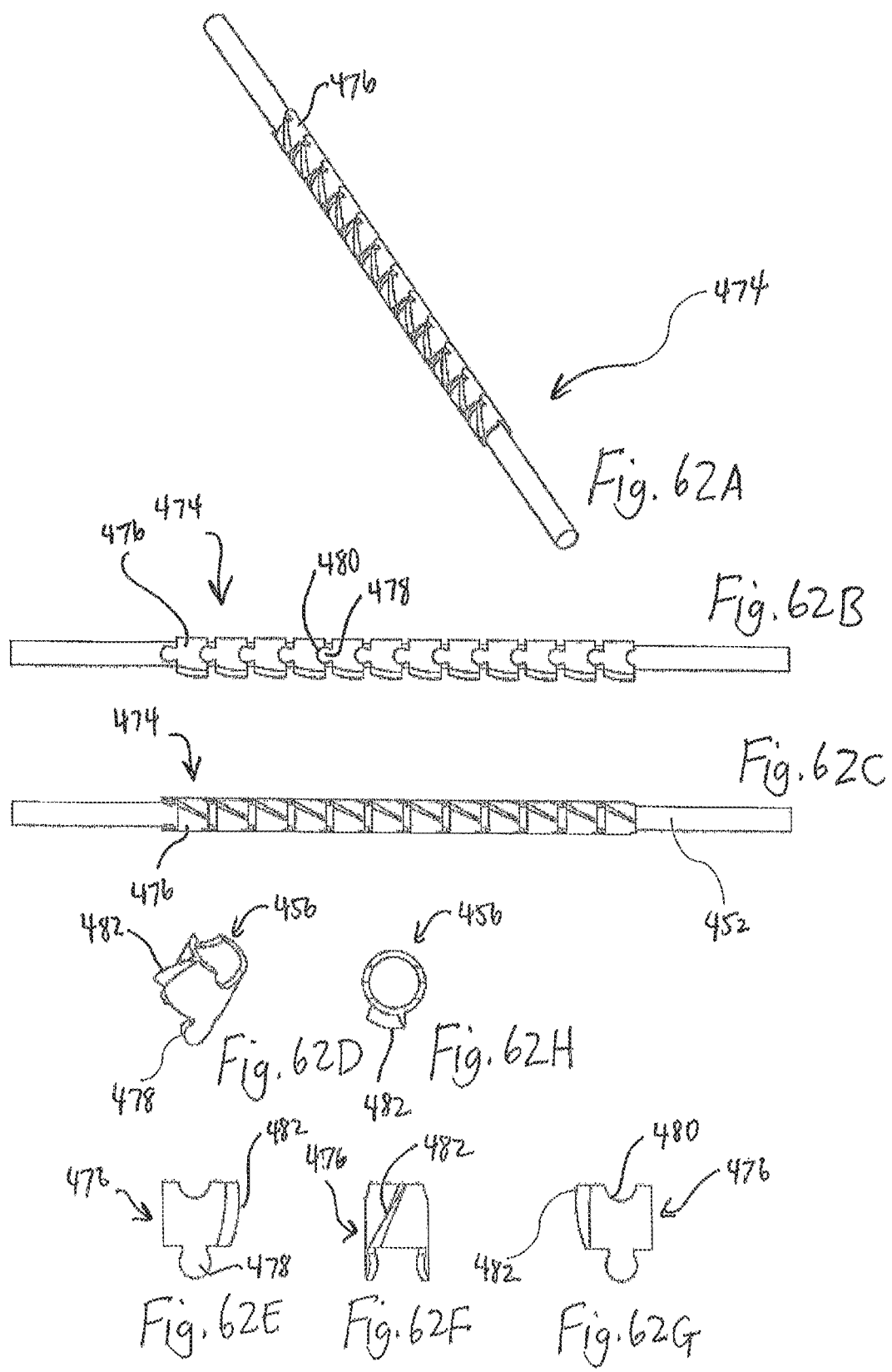

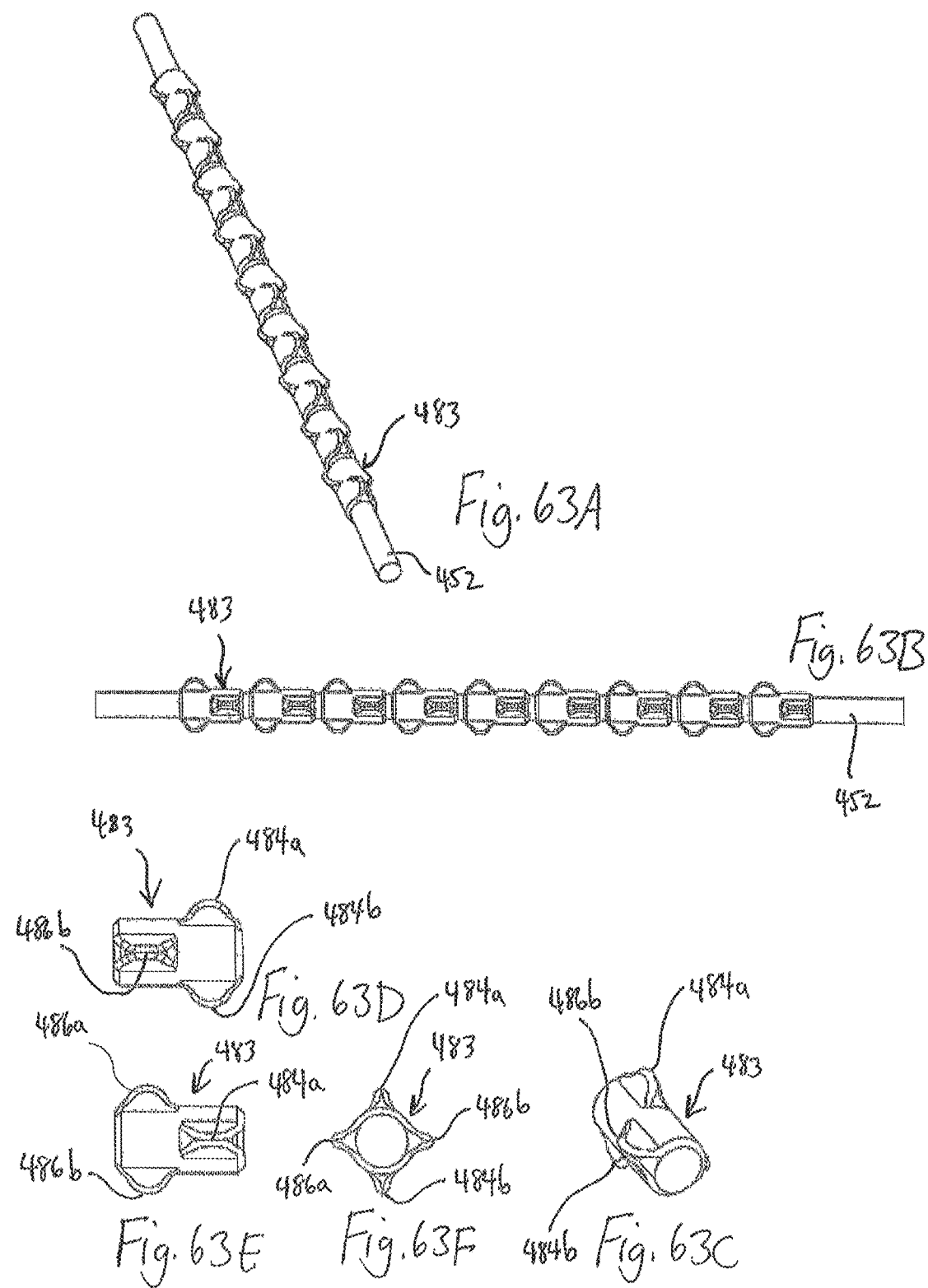

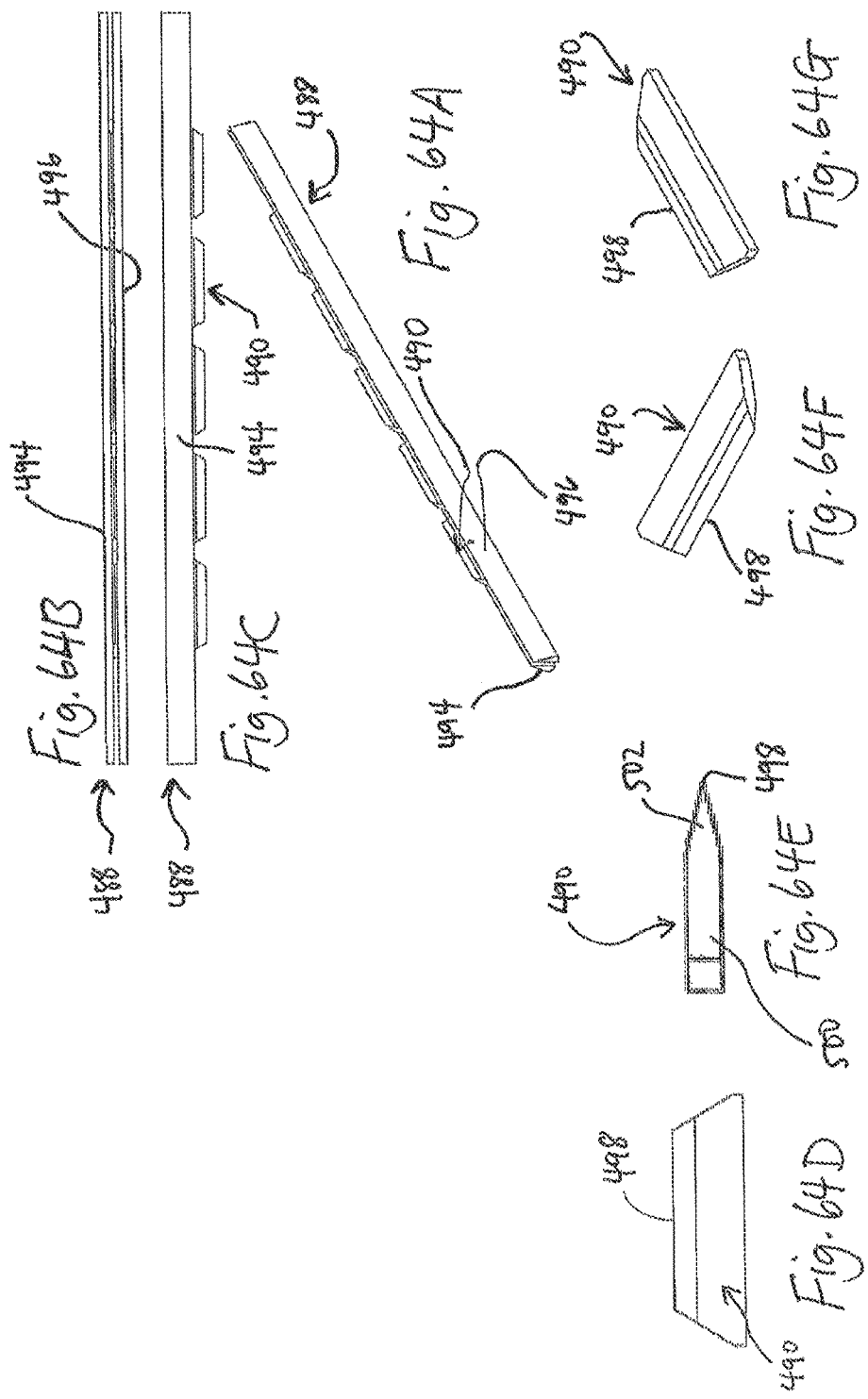

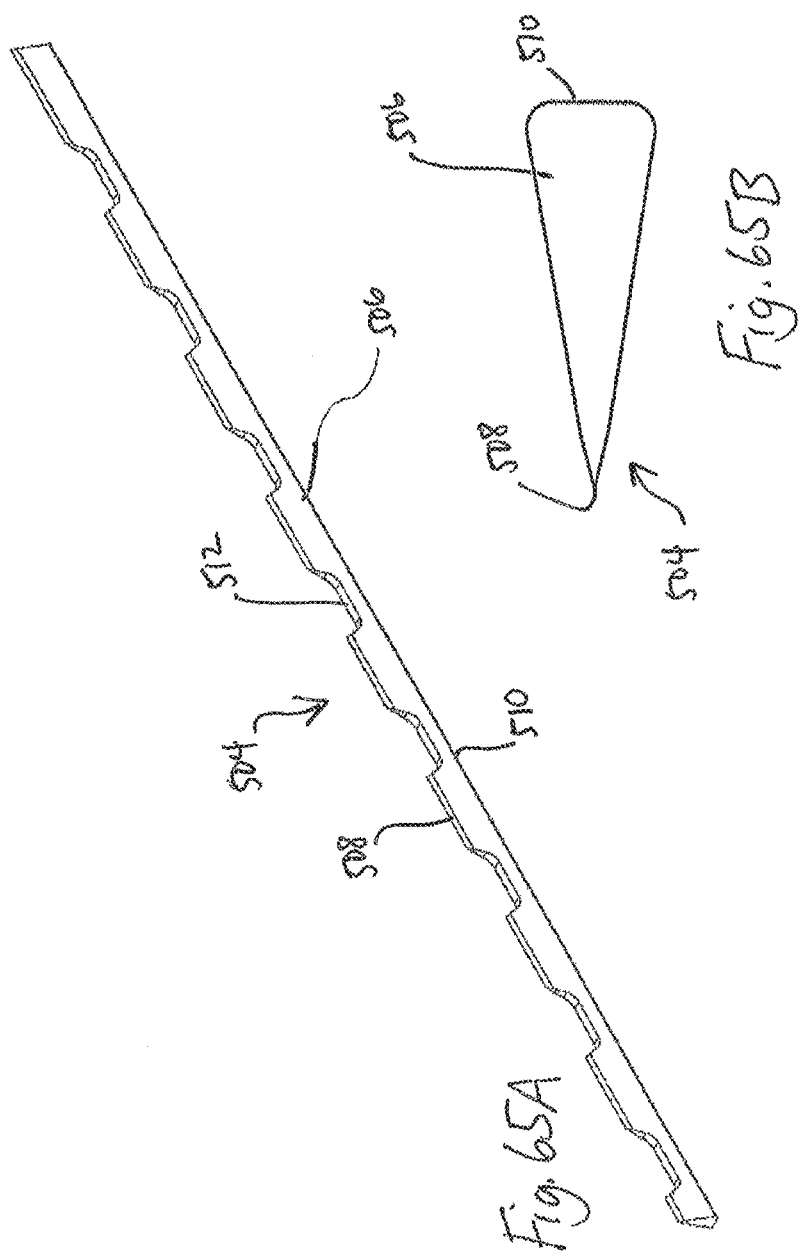

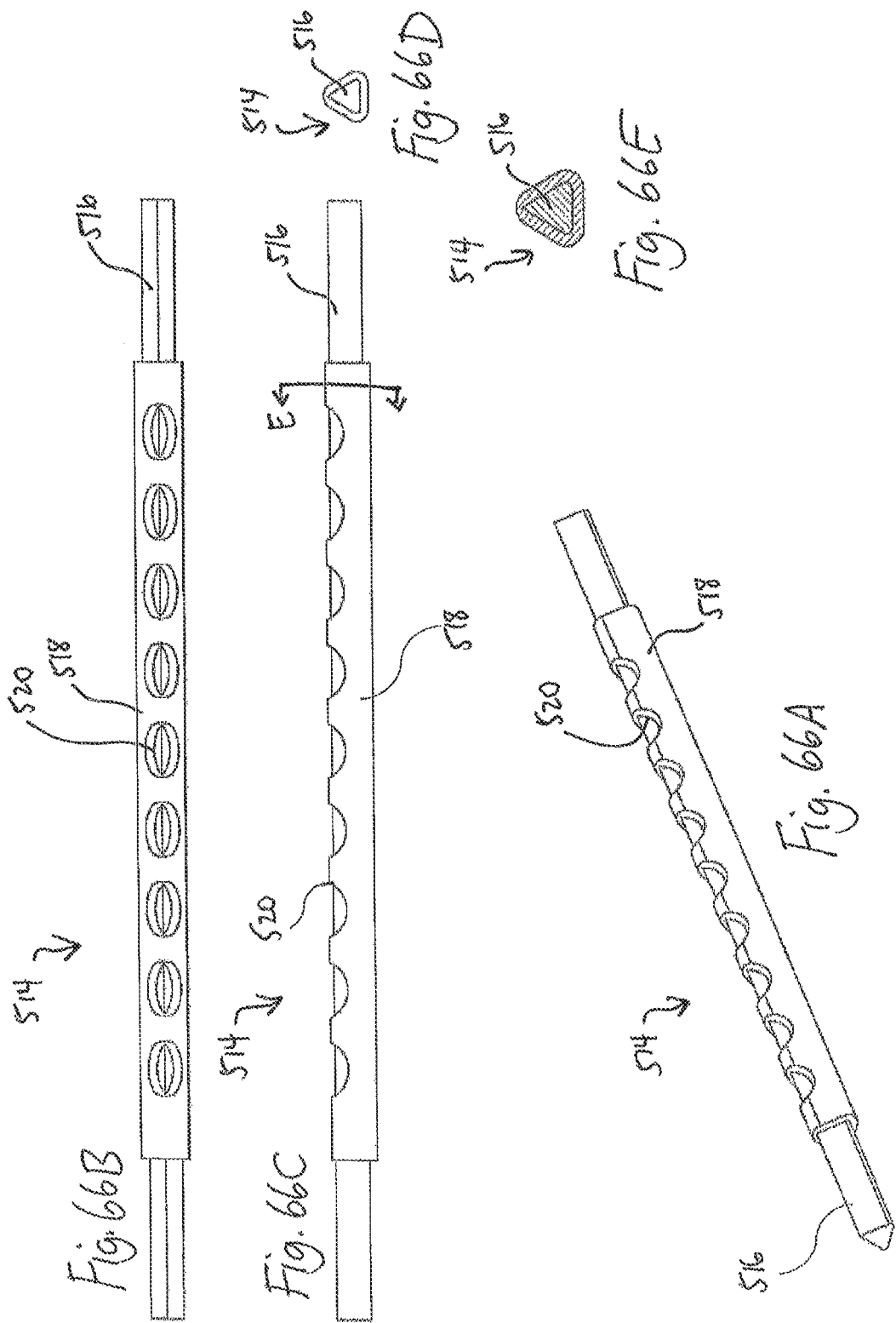

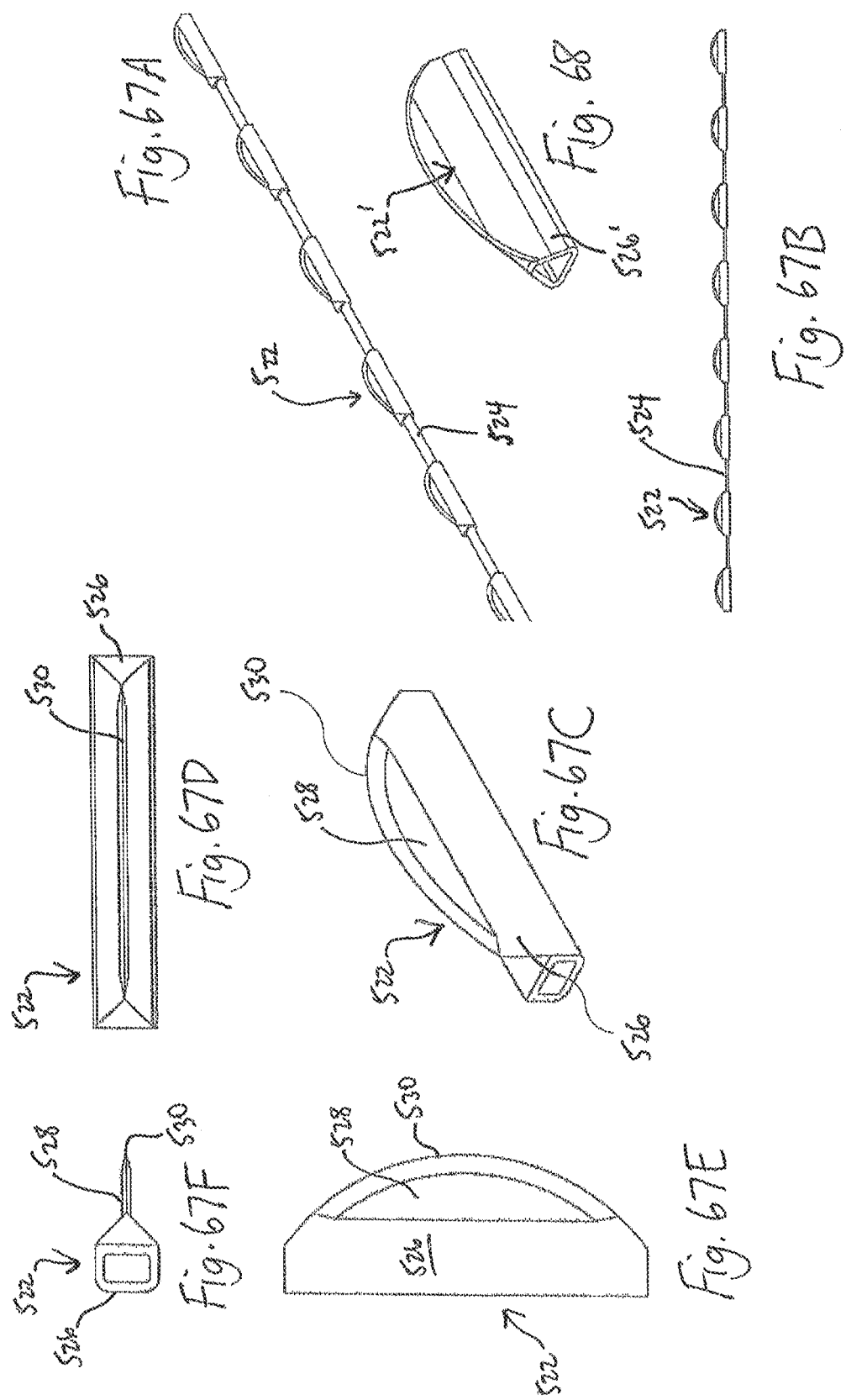

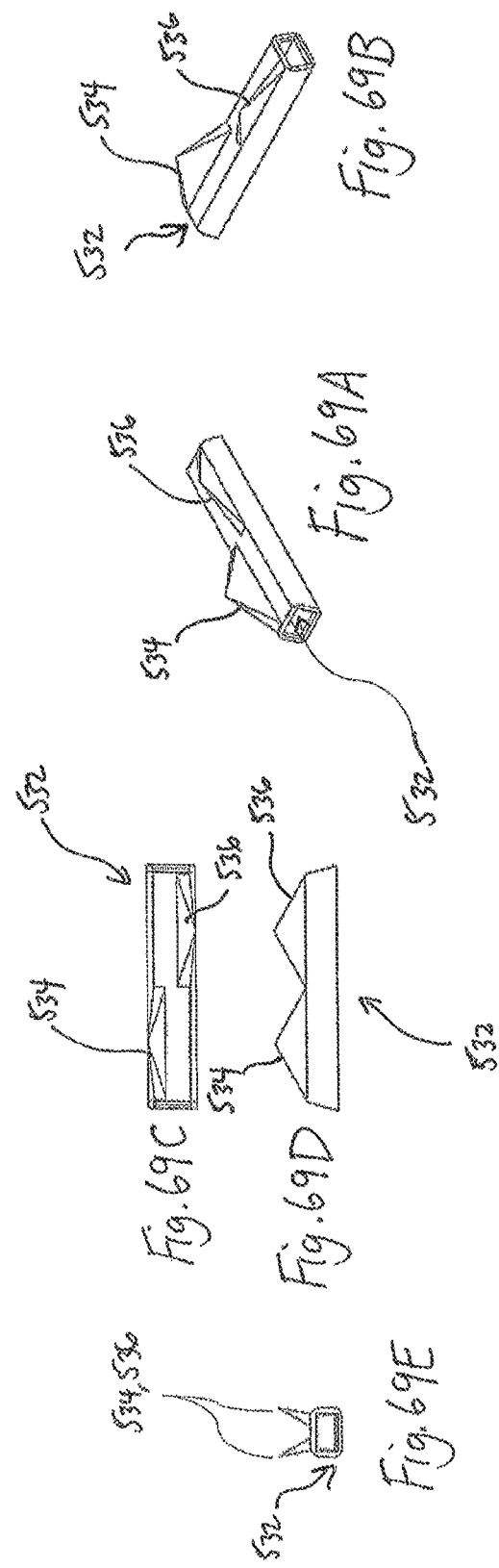

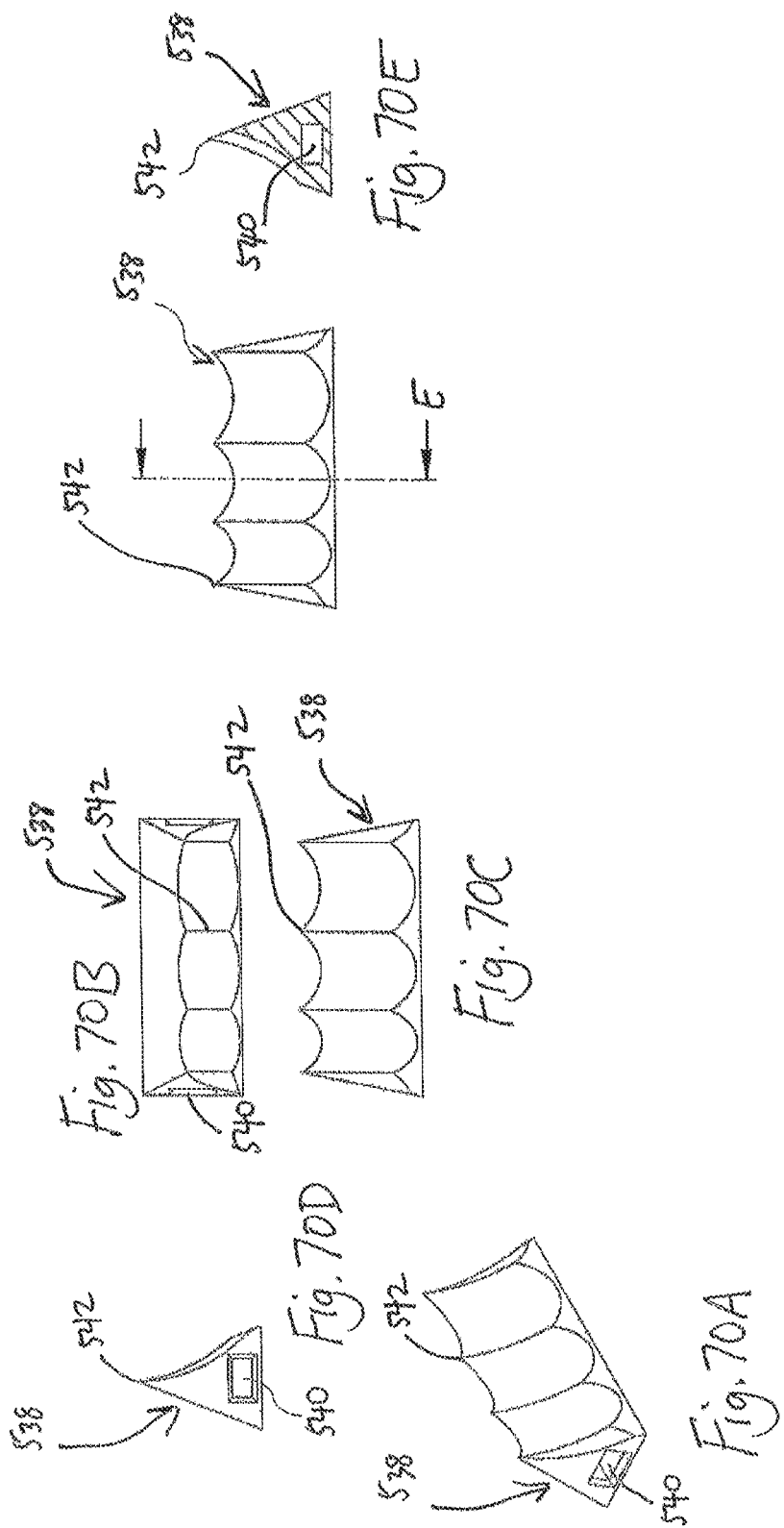

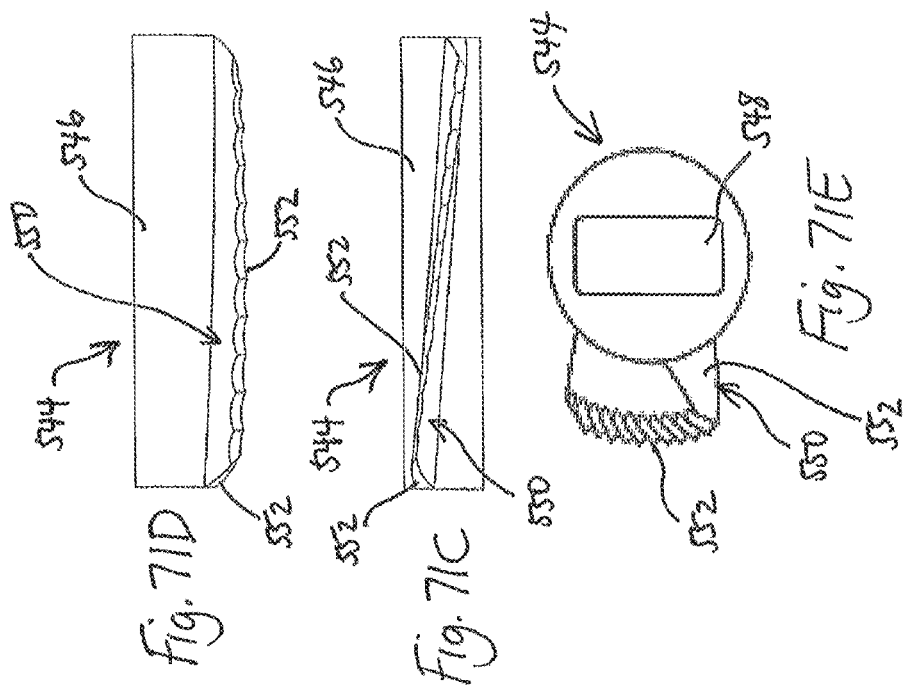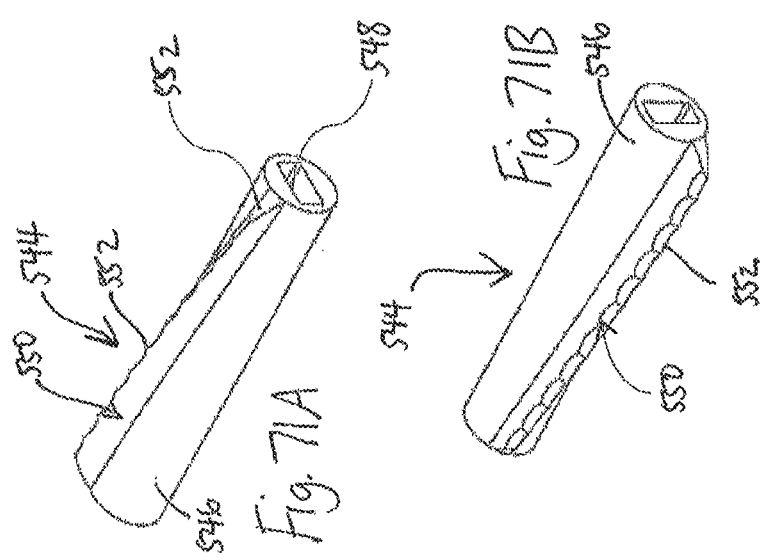

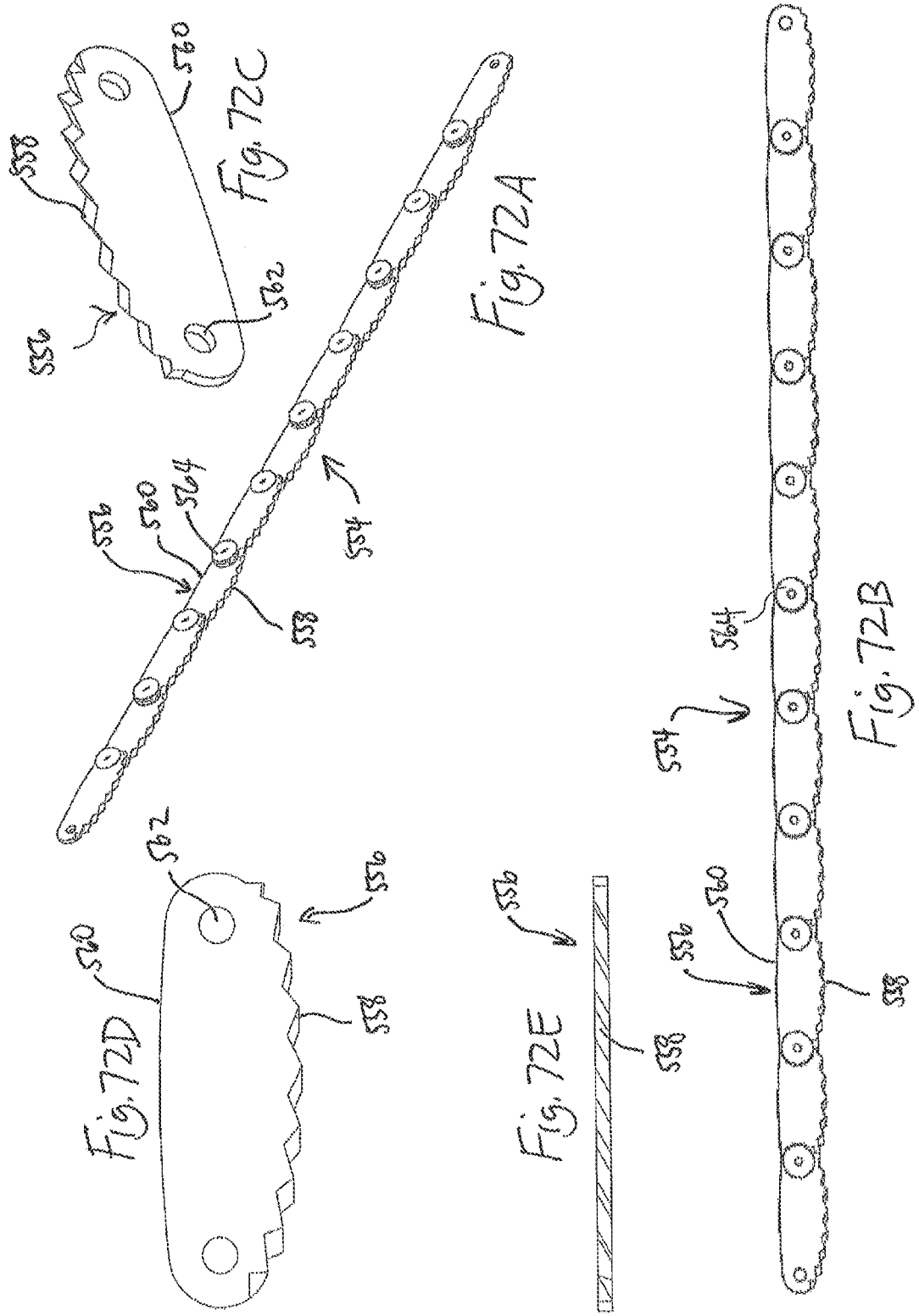

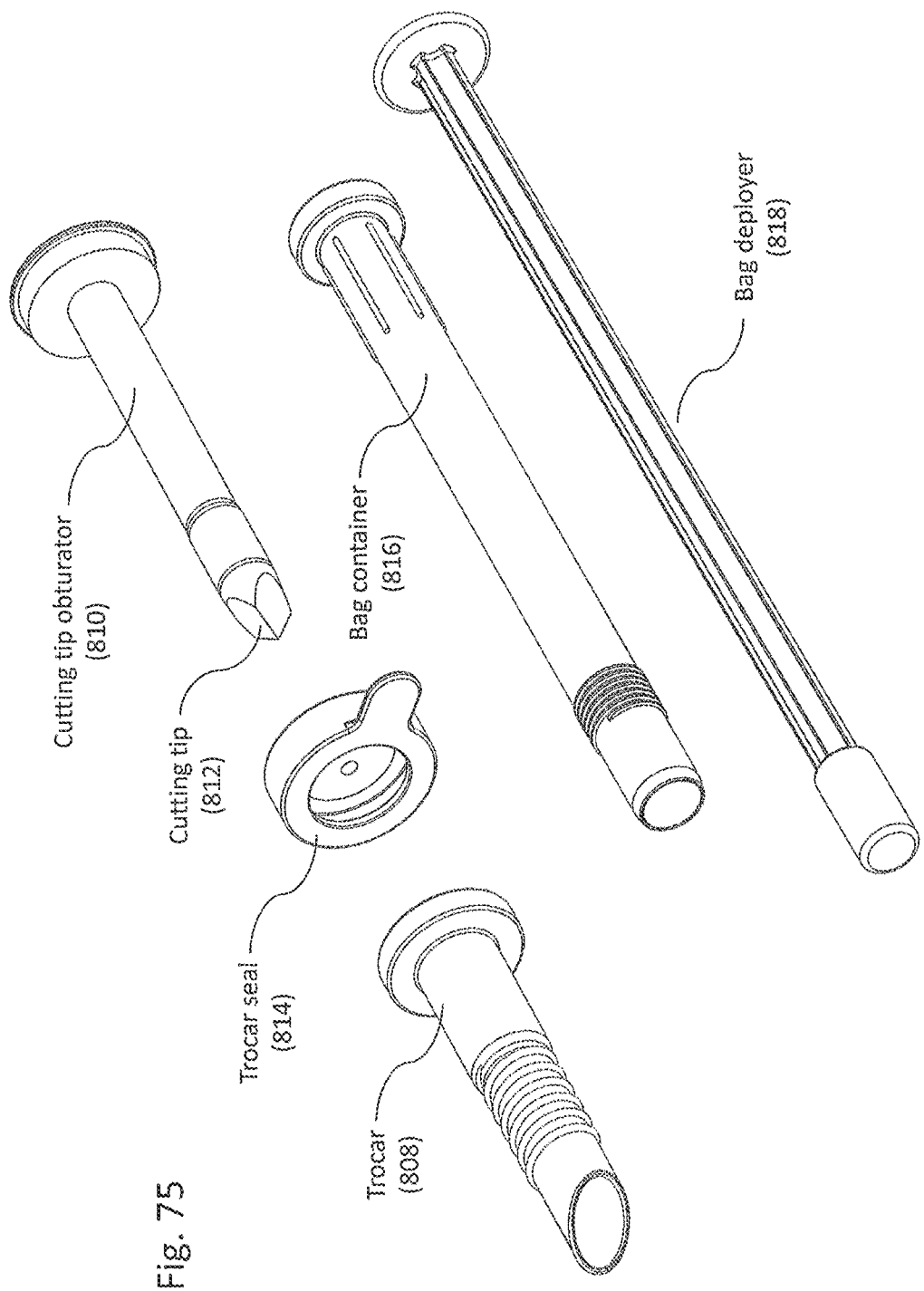

Trocar used for enlarging incision

Trocar used for enlarging incision

Trocar with seal

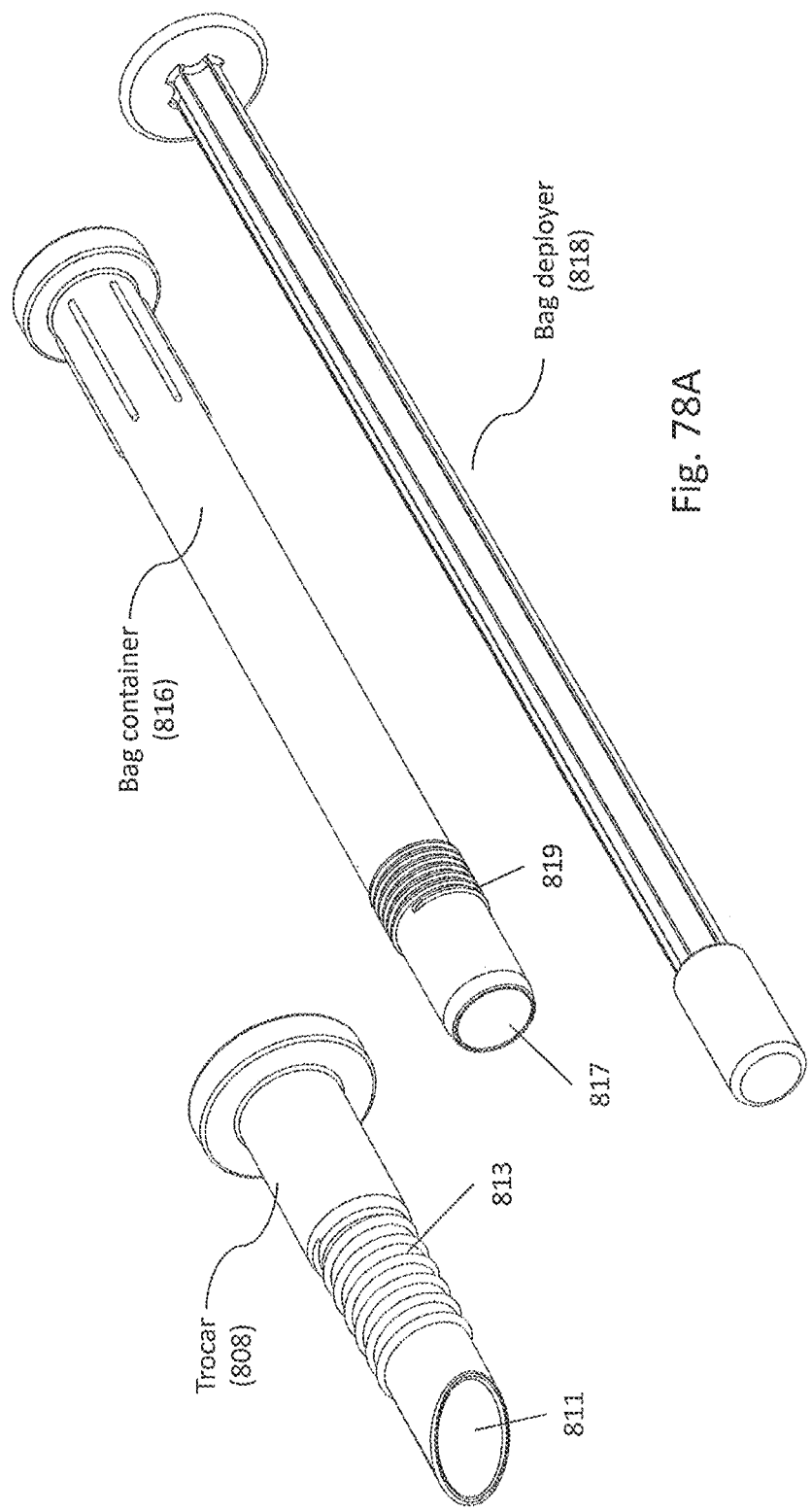

Trocar used for deploying bag

After deployment of the bag

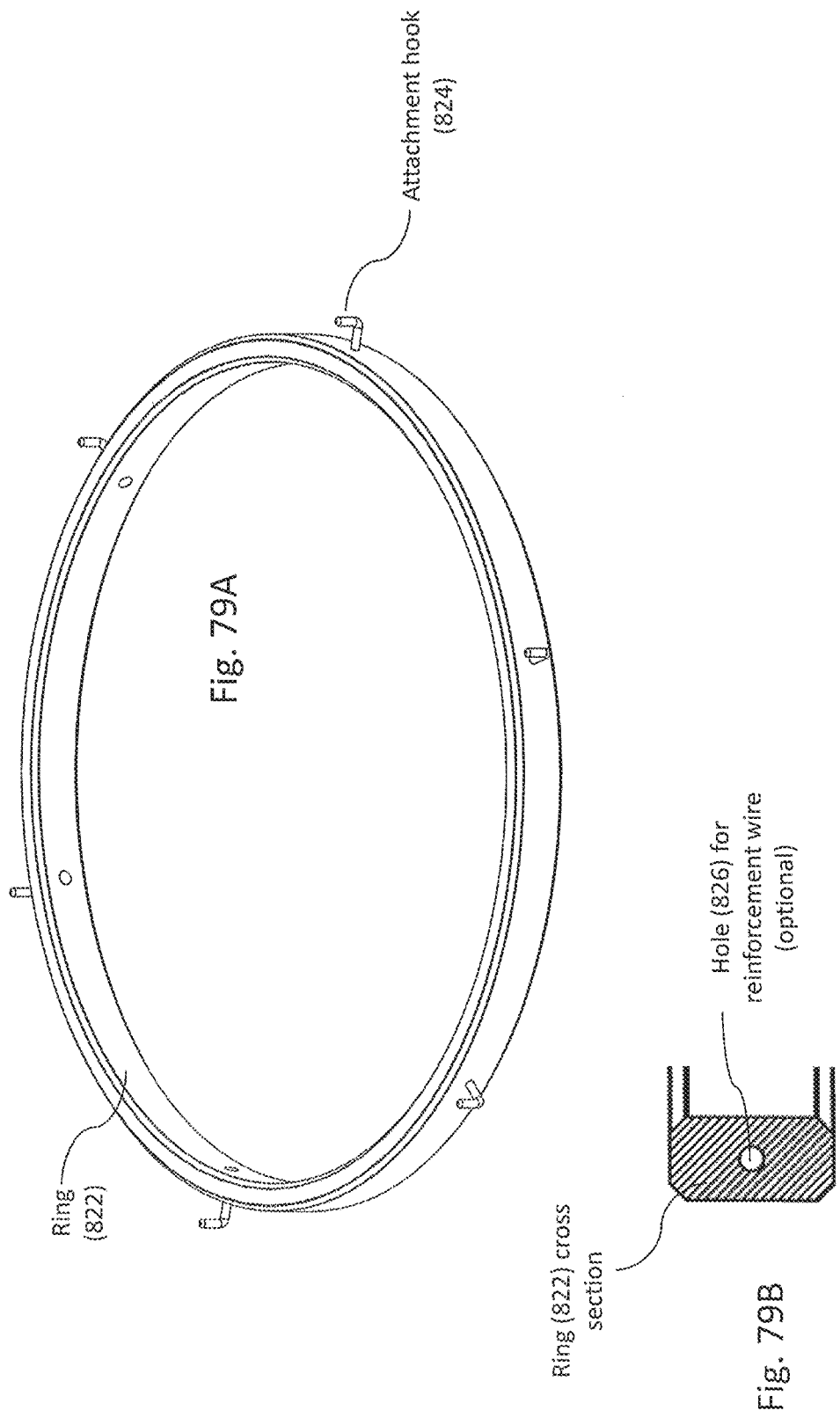

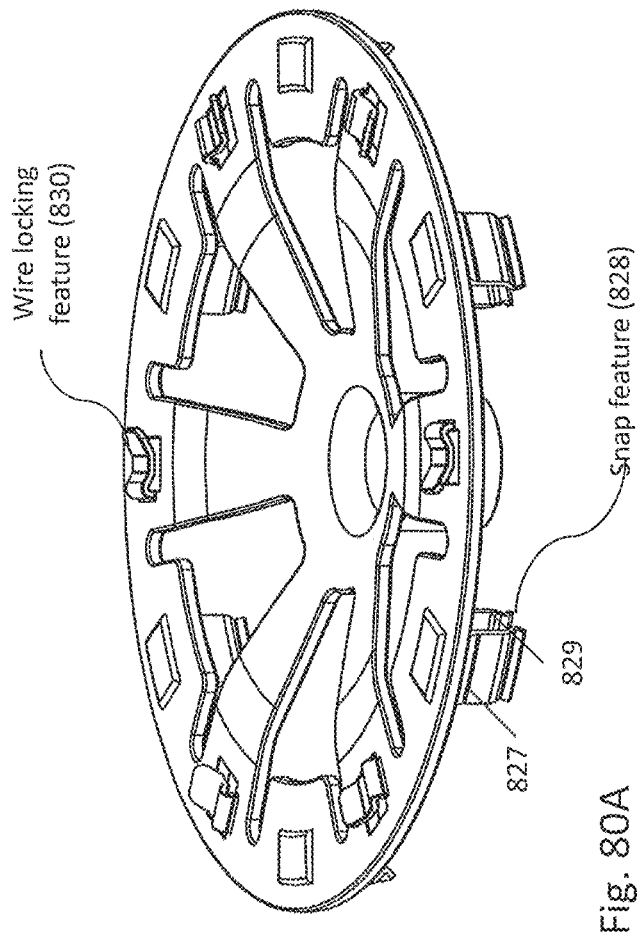

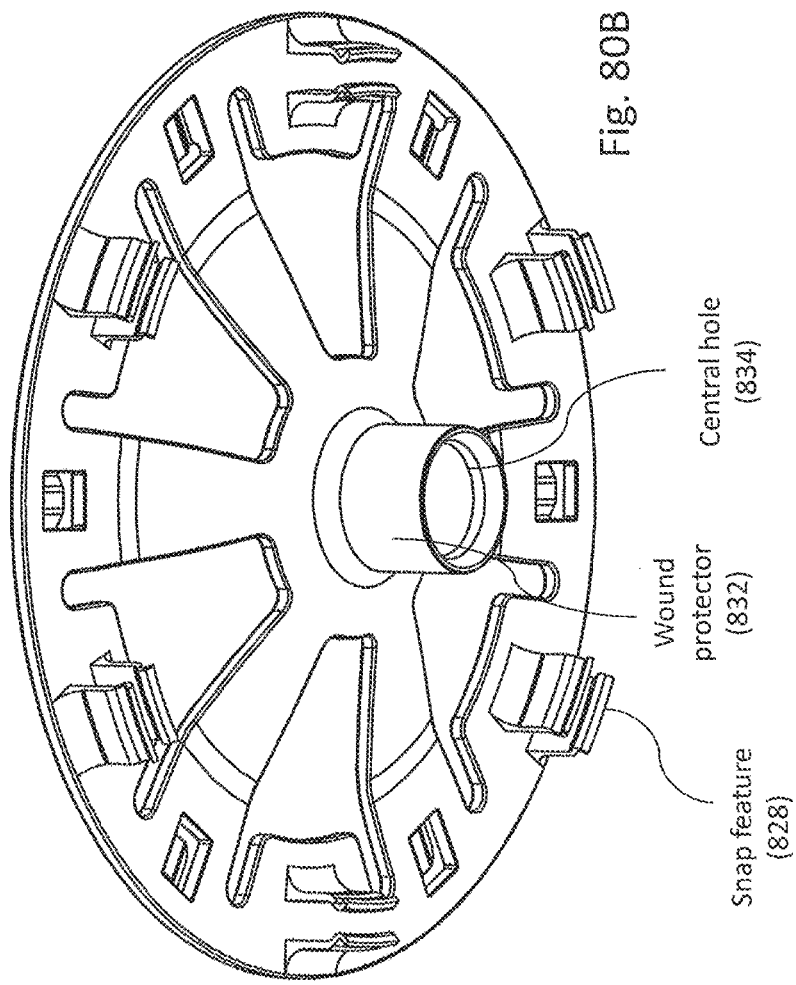

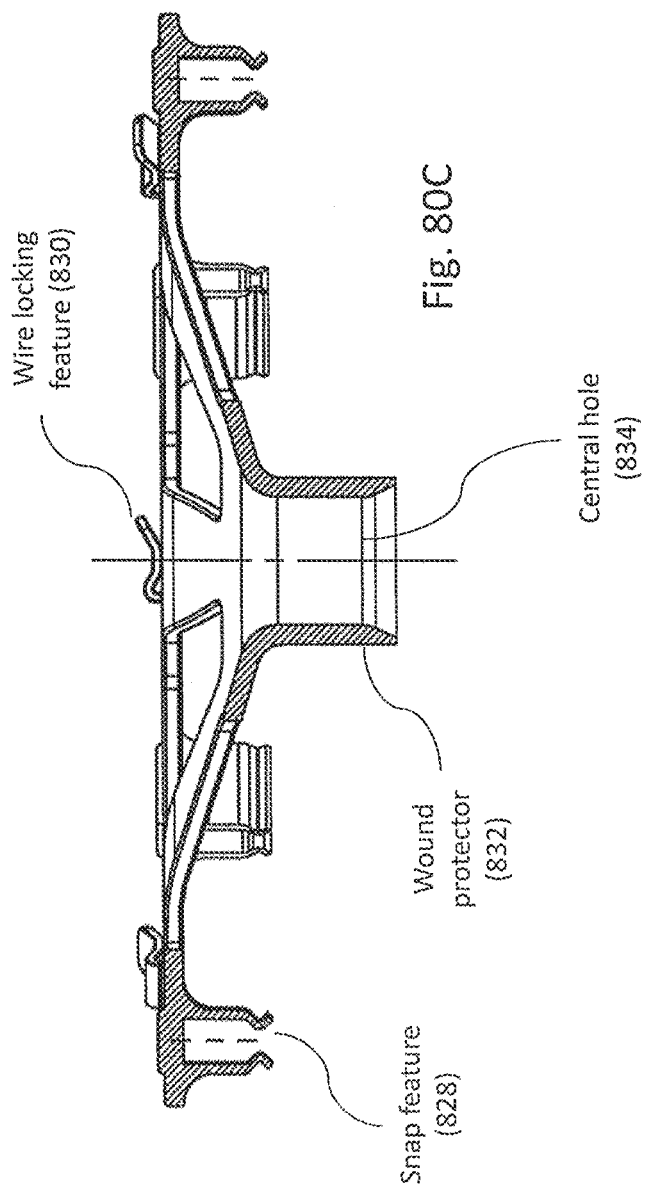

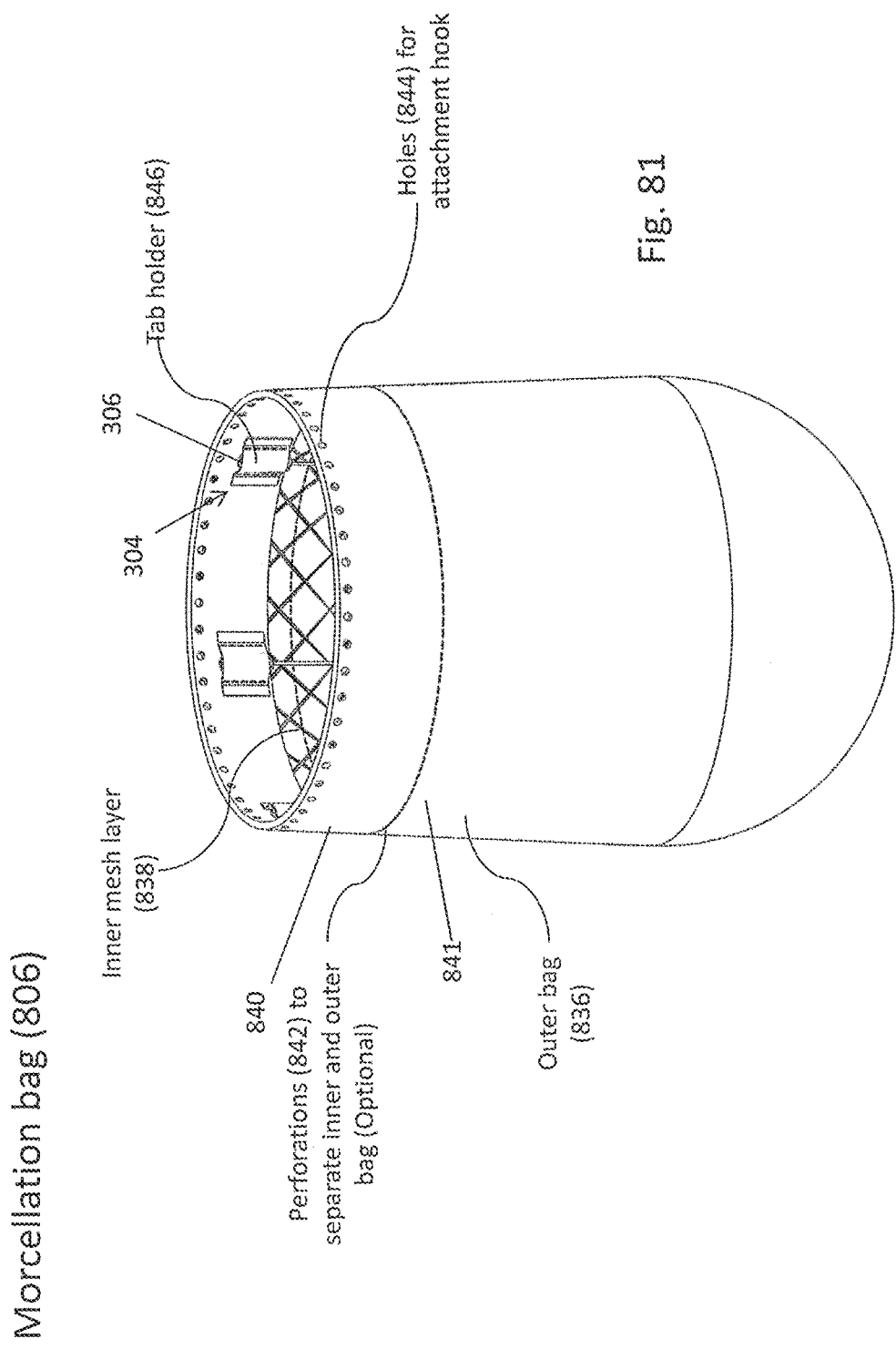

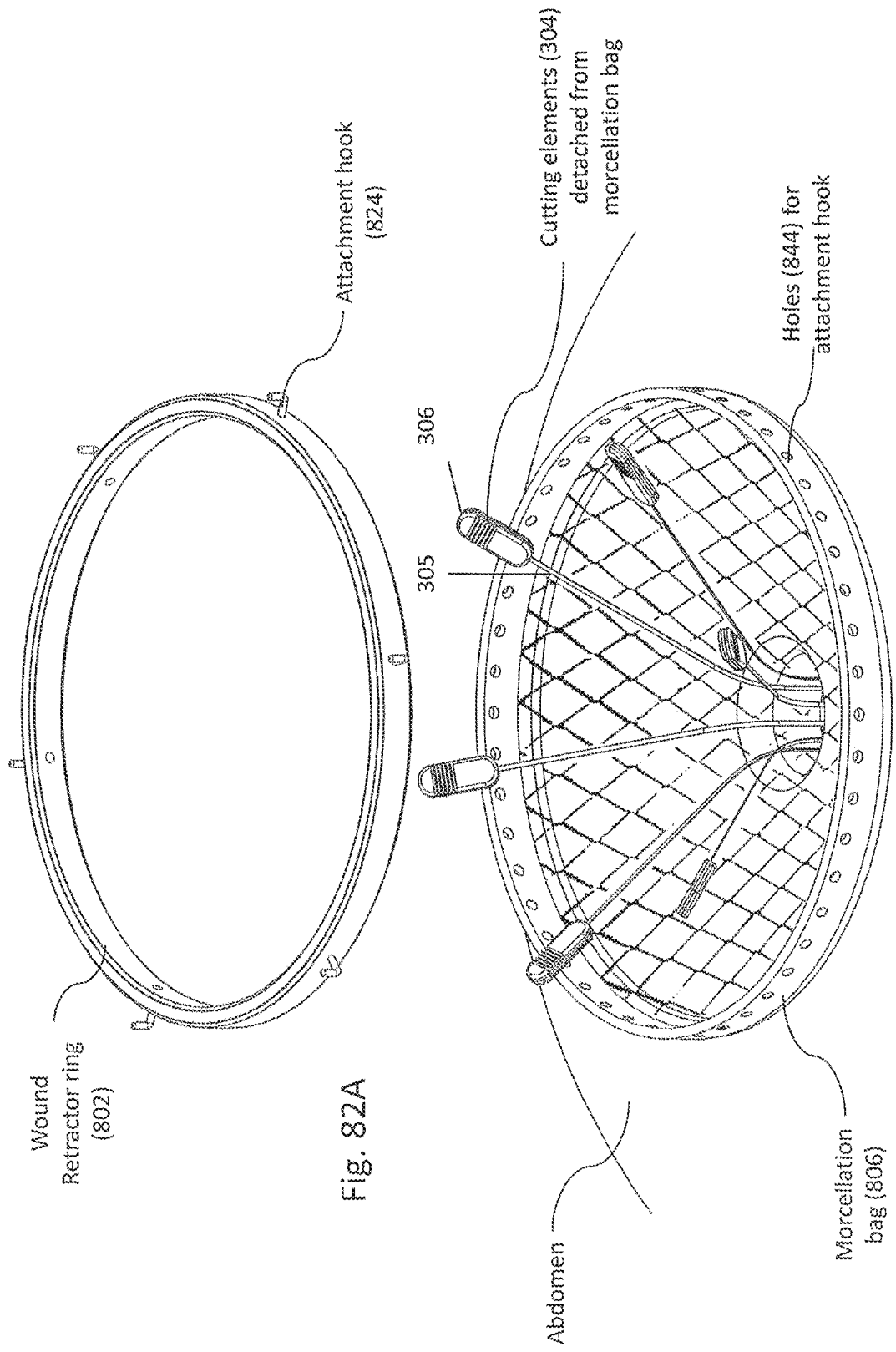

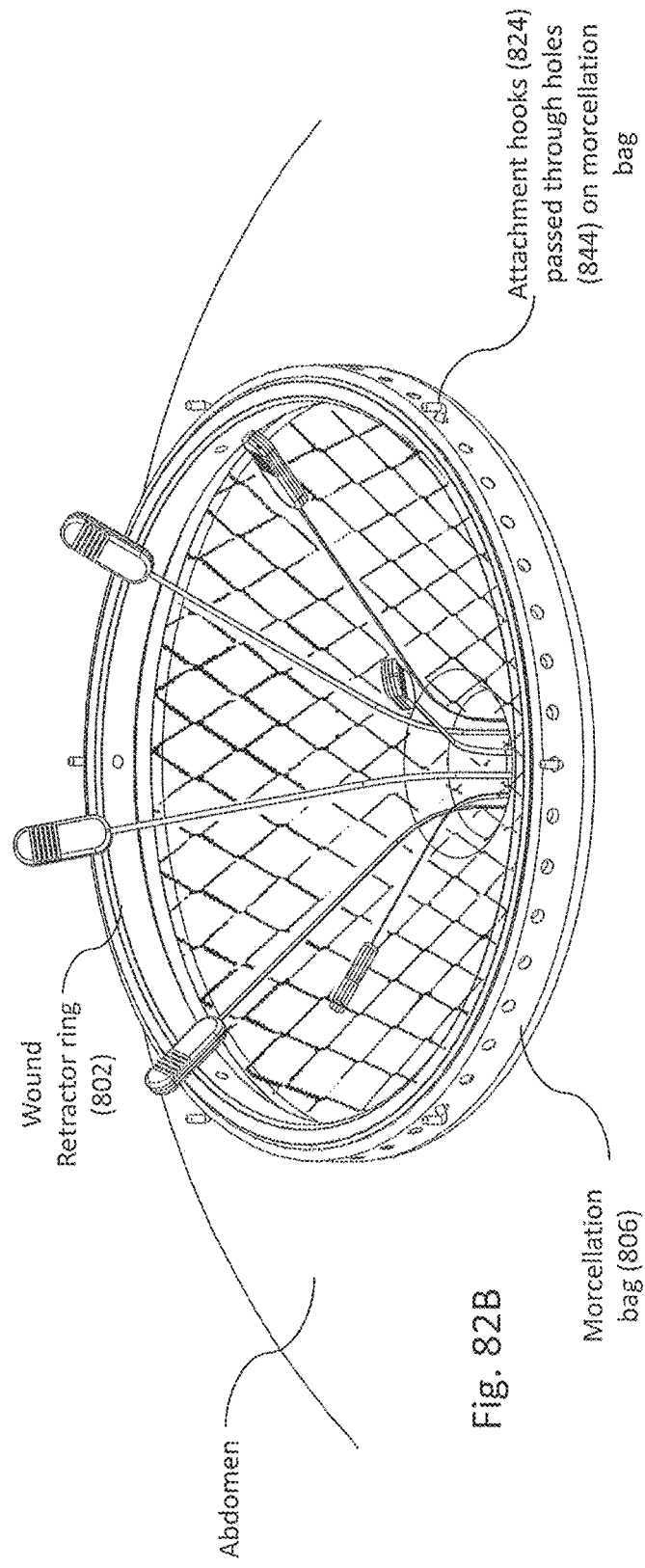

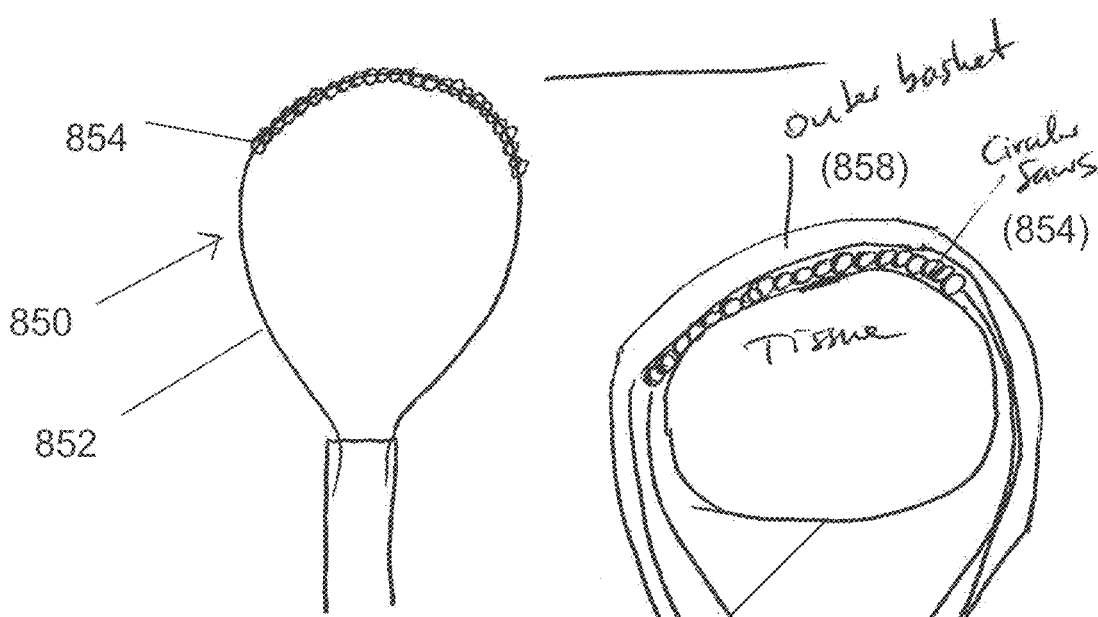
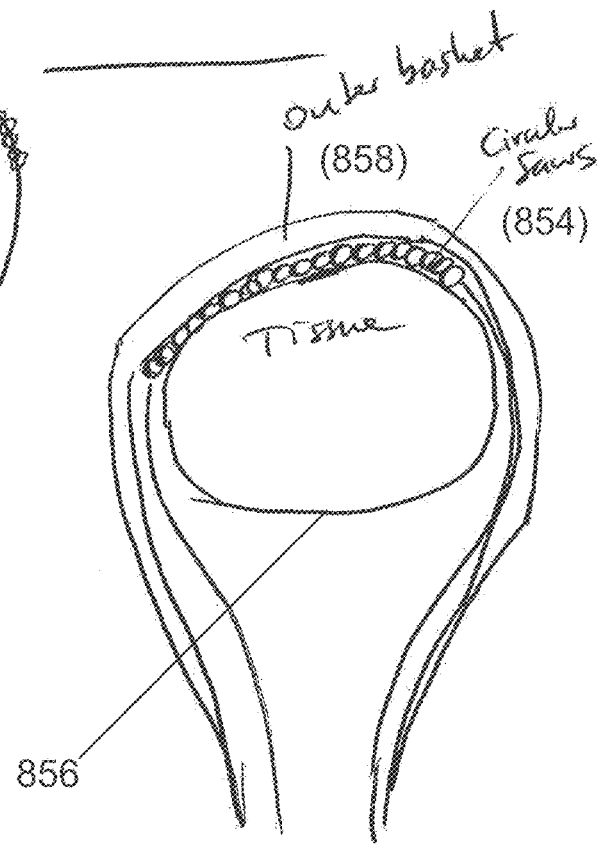
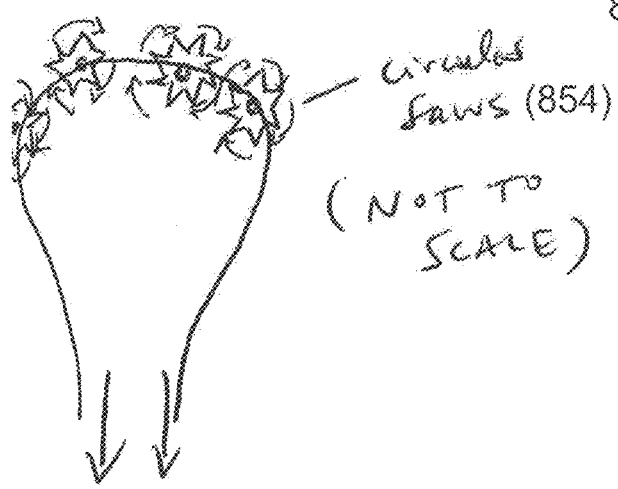
Fig. 83A
Fig. 83B
Fig. 83C

Single Bag Design 880

Fruit Peeler Concept 900

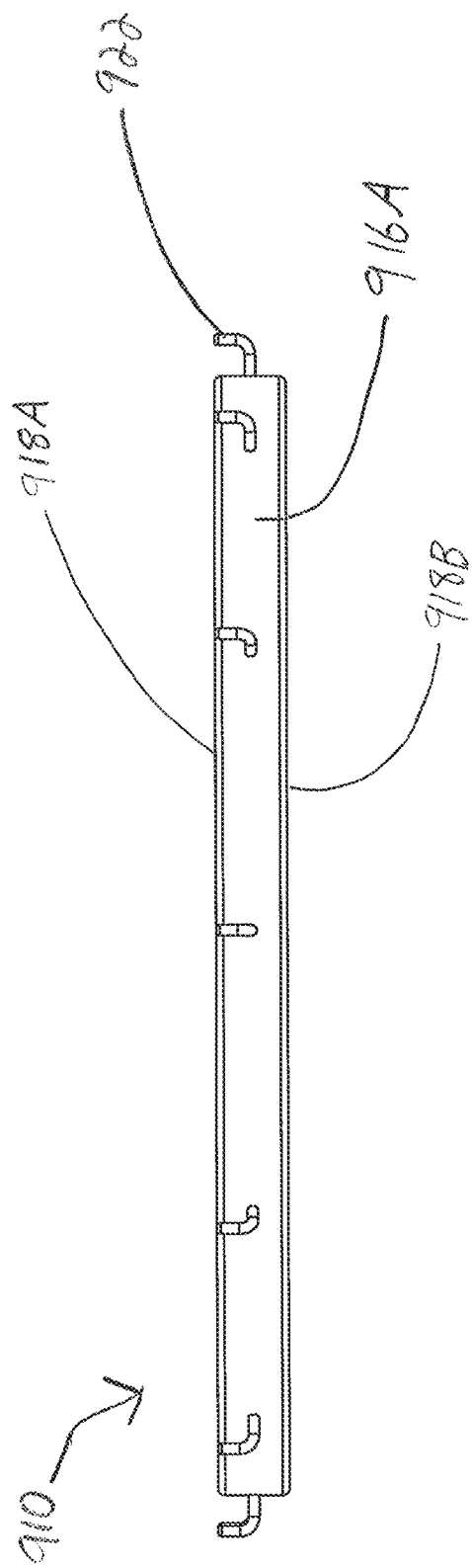

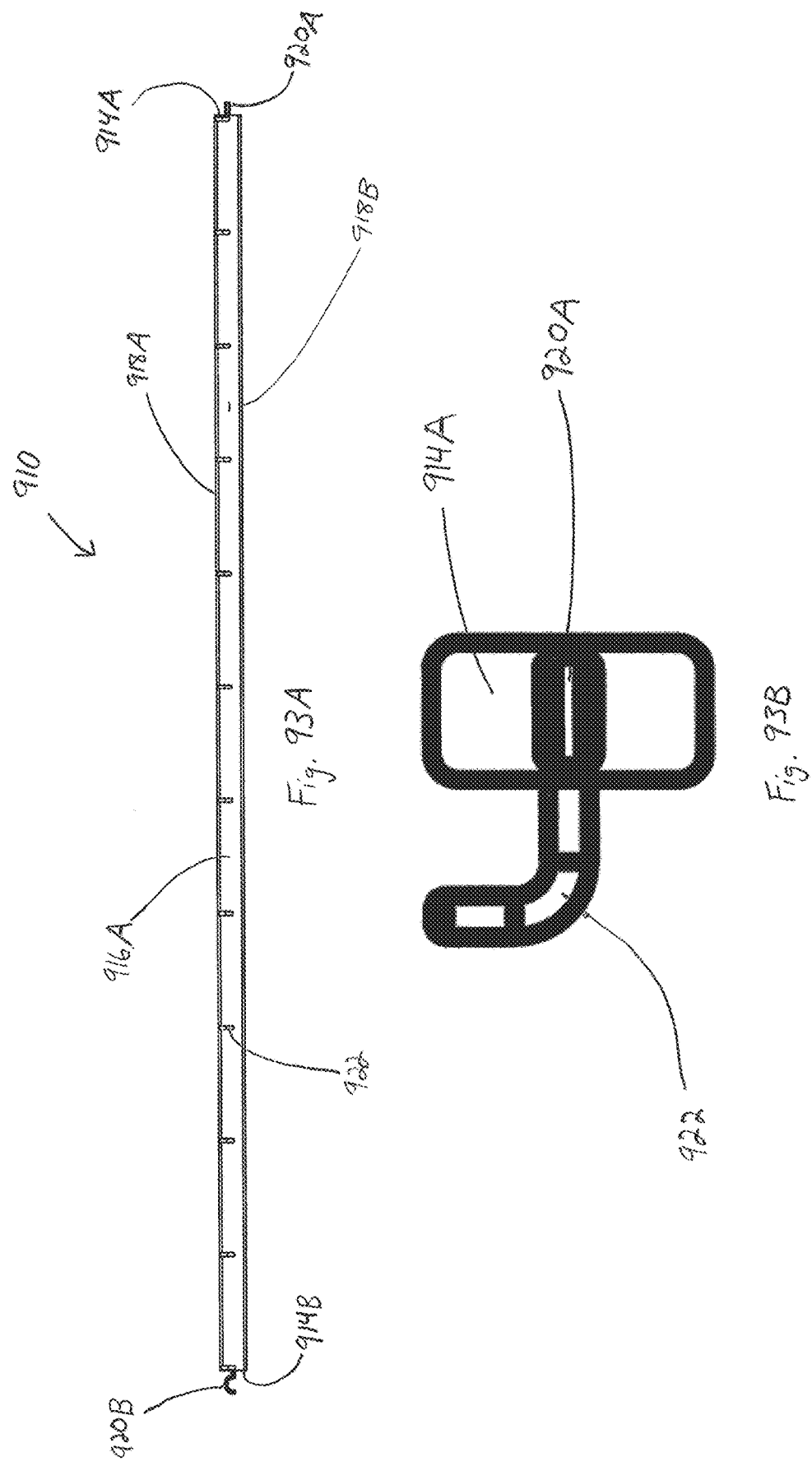

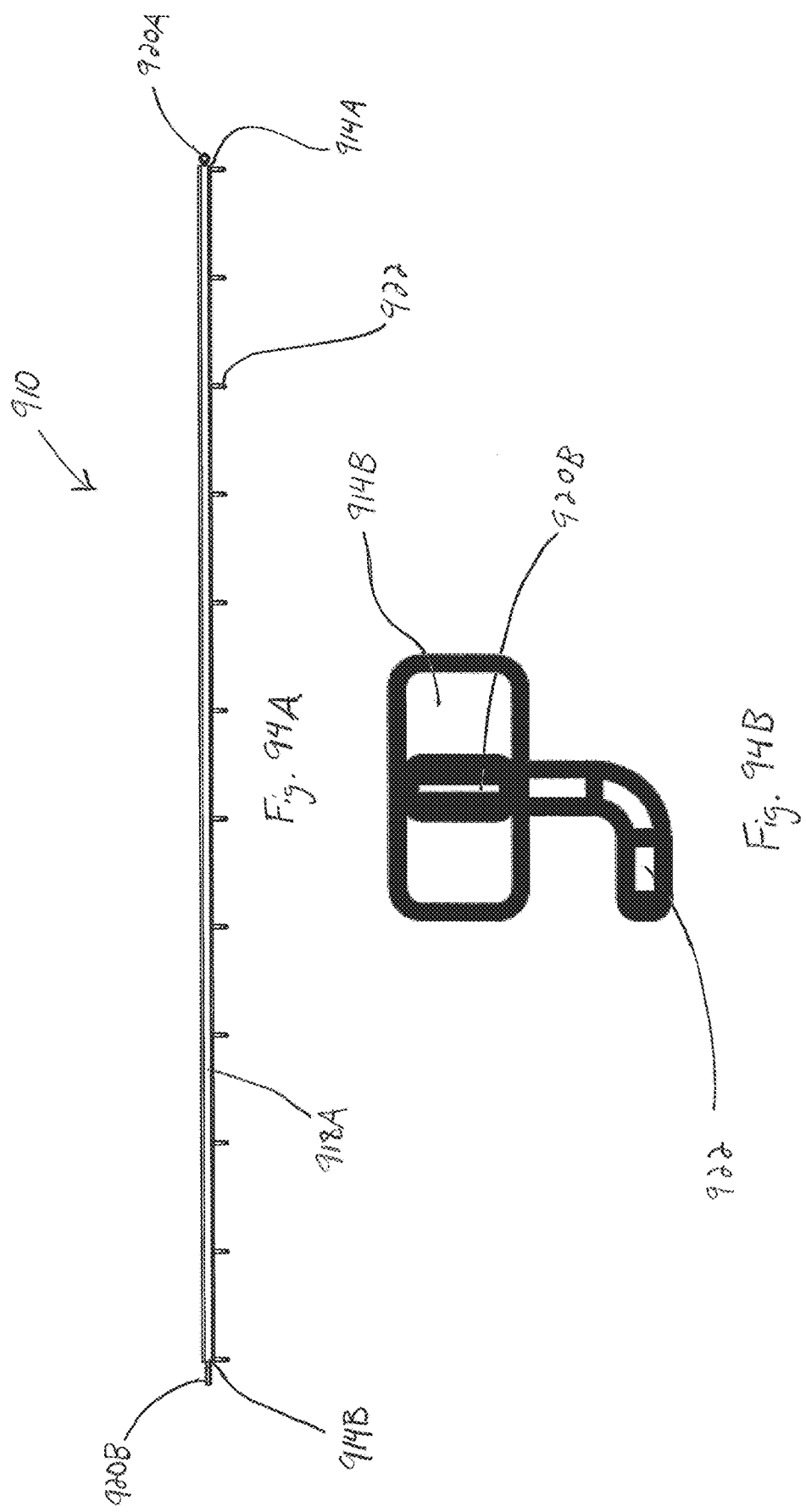

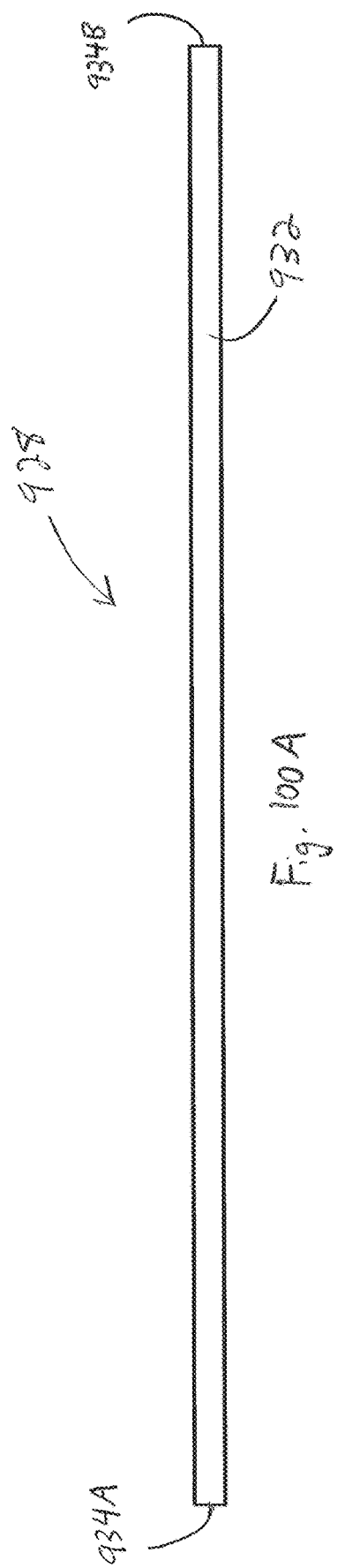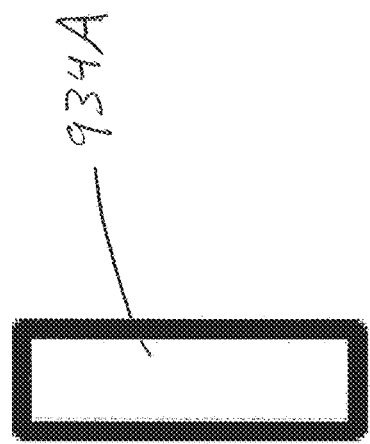
Fig. 100A
Fig. 100B

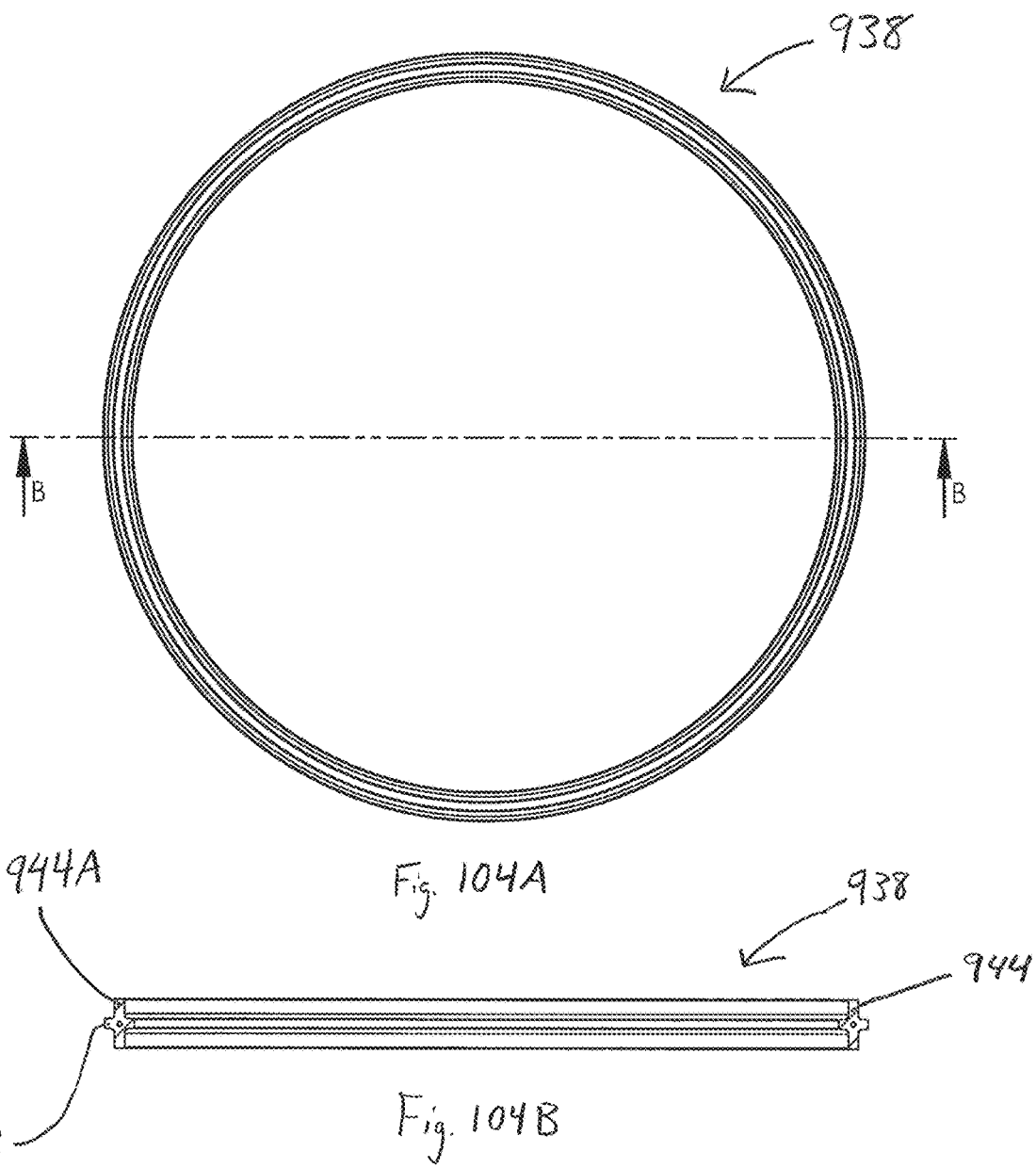

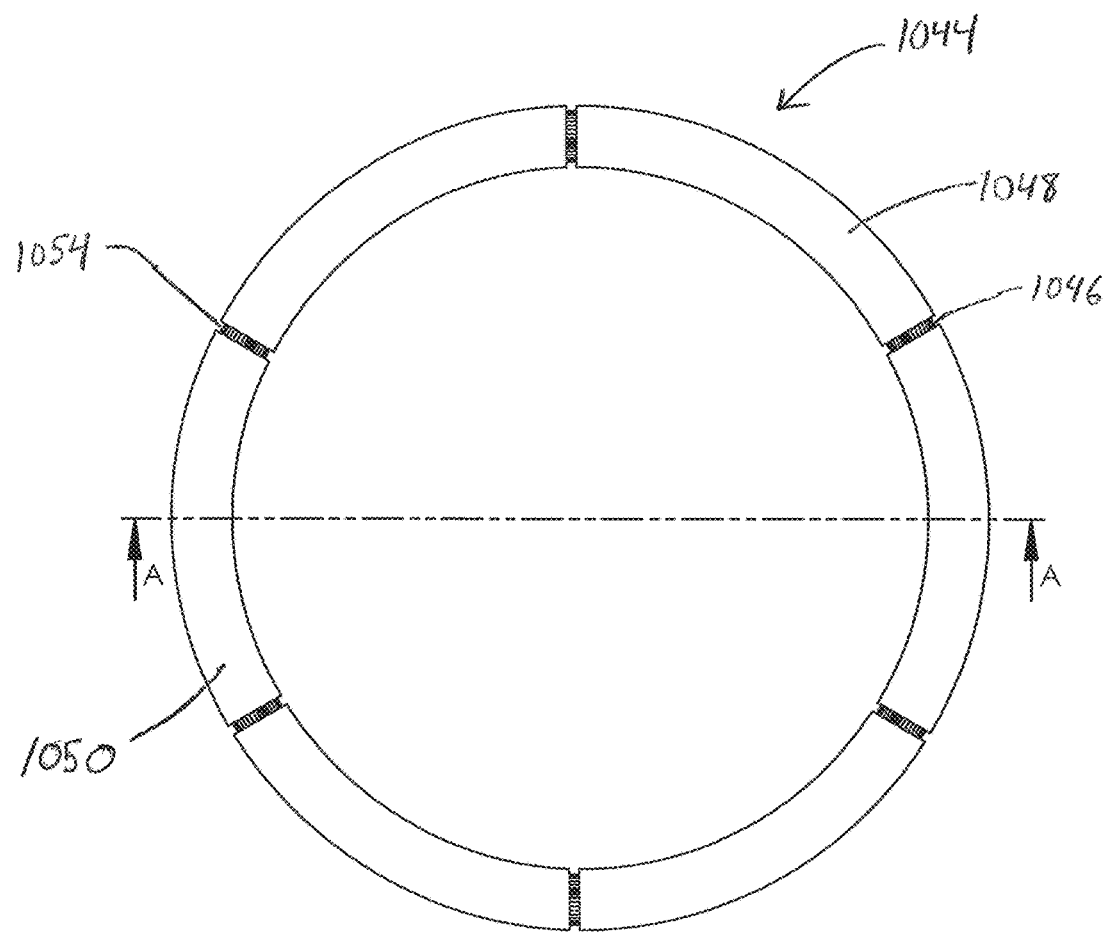
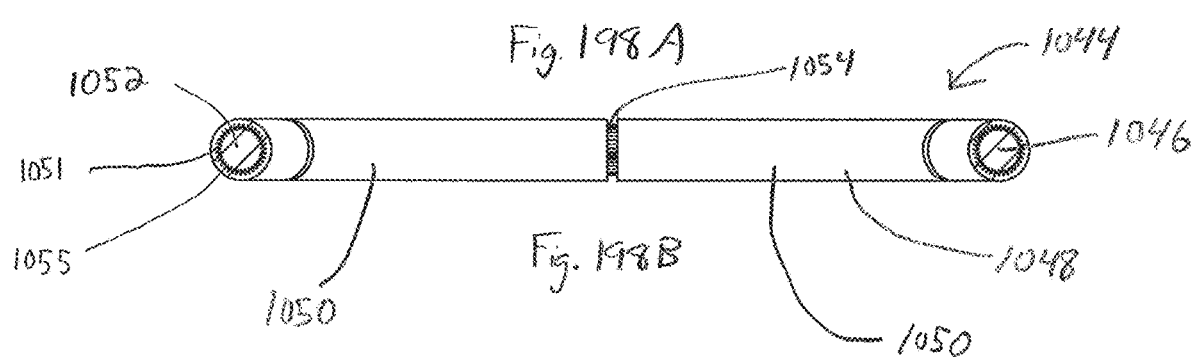

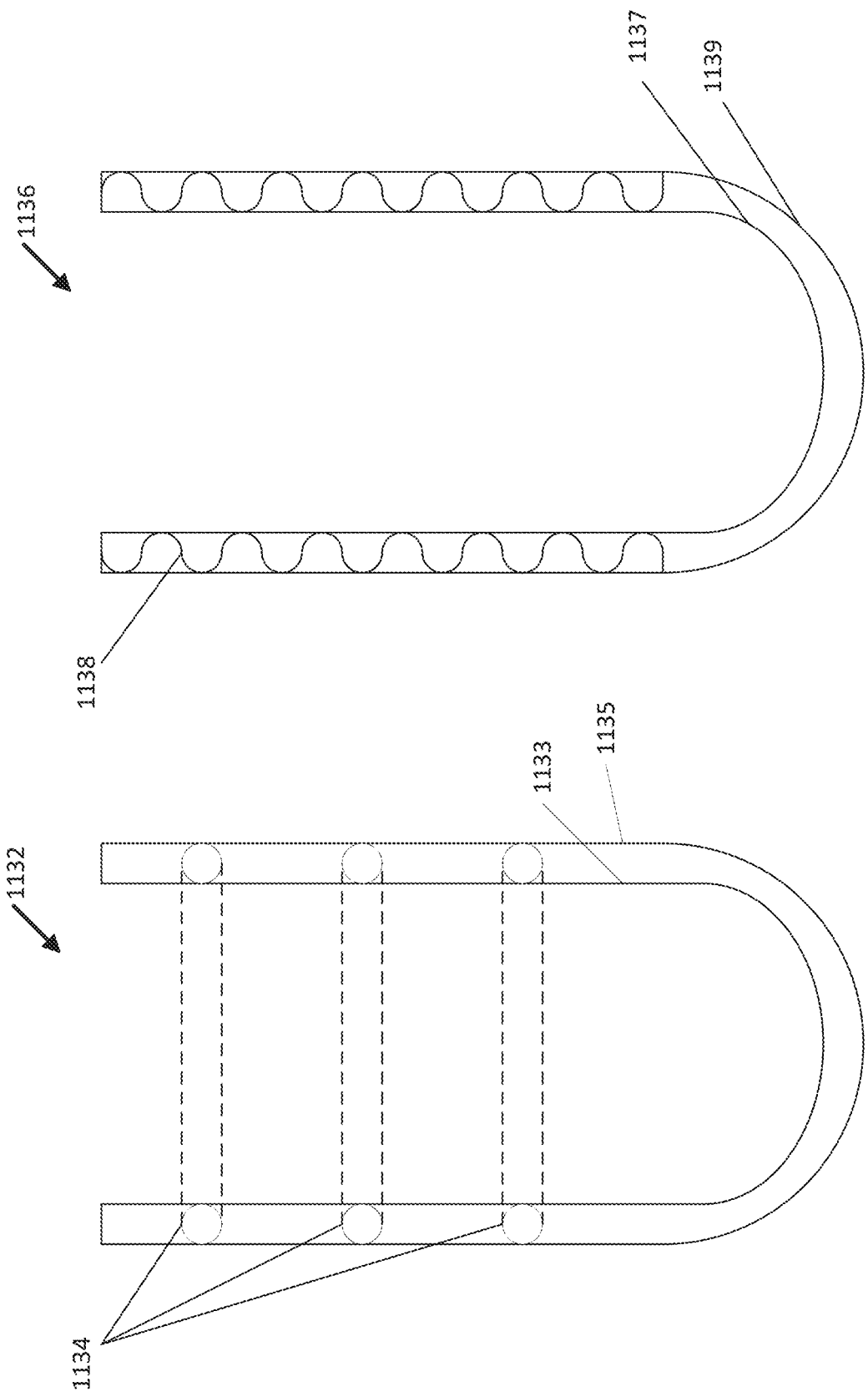

TISSUE EXTRACTION DEVICES AND RELATED METHODS

PRIORITY

The present patent application is a continuation of and claims the benefit of priority to International Patent Application No. PCT/US17/68365, filed Dec. 23, 2017, which in turn claims the benefit of priority to U.S. Provisional Patent Application No. 61/438,916, filed Dec. 23, 2016, U.S. Provisional Patent Application No. 62/470,625, filed Mar. 13, 2017, and U.S. Provisional Patent Application No. 62/569,293, filed Oct. 6, 2017. This patent application is a continuation-in-part of International Patent Application No. PCT/US2016/061595, filed Nov. 11, 2016, which in turn claims the benefit of priority to U.S. Provisional Patent Application No. 62/255,065, filed Nov. 13, 2015, and U.S. Provisional Patent Application No. 62/400,915, filed Sep. 28, 2016. Each of the foregoing patent applications is hereby incorporated by reference herein for any purpose whatsoever.

TECHNICAL FIELD

Various aspects of the present disclosure relate generally to surgical devices and methods. More specifically, the present disclosure relates to tissue extraction devices and related methods for minimally invasive surgery.

BACKGROUND

Conventional tissue extraction devices, such as laparoscopic morcellators, may include a sharp spinning blade for cutting tissue. Such devices may be inefficient and may require prolonged operating times, resulting in increased cost. Such devices also may cause unintended injuries. In some instances, conventional laparoscopic morcellators have the potential to spread occult malignancy, and this may worsen patient prognosis. Improving the design and operation of tissue extraction devices may address one or more of the aforementioned issues.

SUMMARY

Aspects of the present disclosure relate to, among other things, tissue extraction devices and related methods. Each of the aspects disclosed herein may include one or more of the features described in connection with any of the other disclosed aspects.

It may be understood that both the foregoing general description and the following detailed description are exemplary and explanatory only and are not restrictive of the features claimed.

As used herein, the terms "comprises," "comprising," or any other variation thereof, are intended to cover a non-exclusive inclusion such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

The disclosure provides, among other things, embodiments of a kit that in turn includes a bag having a proximal portion and a distal portion, and a retractor ring separate from the bag. The retractor ring can be configured to be coupled to the proximal portion of the bag, and when coupled to the proximal portion of the bag, the retractor ring can be configured to be manipulated from (i) a first orientation, where the retractor ring engages a first region of the proximal portion of the bag, to (ii) a second orientation, where the retractor ring engages a second region of the proximal portion of the bag, the second region being distal to the first region, to pull the distal portion of the bag toward the retractor ring.

In some implementations, the retractor ring can include an inner ring and an outer ring, the inner ring being received in the outer ring. The outer ring can include a plurality of discrete segments. The outer ring can be more flexible than the inner ring. The outer ring can be rotatable relative to the inner ring in a poloidal direction of the retractor ring. The retractor ring can be configured to be coupled to the proximal portion of the bag by clamping the proximal portion of the bag between the inner ring and the outer ring. One of the inner ring and the outer ring can include a protrusion complementary to a recess in the other of the inner ring and the outer ring. The retractor ring can be configured to be coupled to the proximal portion of the bag by at least one of a hook and an adhesive. The proximal portion of the bag can include a channel configured to receive the retractor ring to couple the retractor ring to the proximal portion of the bag.

The disclosure provides, in some aspects, embodiments of a method of applying tension to a distal portion of a bag using a proximal portion of the bag. An illustrative method includes coupling a retractor ring to the proximal portion of the bag, the retractor ring being separate from the bag prior to being coupled to the bag and manipulating the retractor ring from (i) a first orientation, where the retractor ring engages a first region of the proximal portion of the bag, to (ii) a second orientation, where the retractor ring engages a second region of the proximal portion of the bag, the second region being distal to the first region, to pull the distal portion of the bag toward the retractor ring.

In some implementations, manipulating the retractor ring can include rotating at least a portion of the retractor ring in a poloidal direction. Manipulating the retractor ring can include rolling the proximal portion of the bag around the retractor ring. Manipulating the retractor ring can include pulling the proximal portion of the bag proximally relative to the retractor ring.

The disclosure provides embodiments of a tissue extraction device including a bag having an interior and a cutting element extending through the interior of the bag. The cutting element includes a strand, and a cutting member on the strand. The cutting member includes an edge for cutting tissue as the cutting member is drawn across tissue.

In some implementations, the cutting member can include a blade on the strand. The edge can be linear, and/or curved. If desired, the edge can form a partial helix. The cutting member can be one of a plurality of cutting members on the strand, and the edge is one of a plurality of edges of the plurality of cutting members. Each edge of the plurality of edges can be discrete, separated from all other edges of the plurality of edges by a gap.

The tissue extraction device can further include a member coupled to an interior surface of the bag, such that a channel is defined between the member and the interior surface. The cutting element extends through the channel.

The cutting element can include eyelets. The tissue extraction device can further include handles. The handles can be removably coupled to the eyelets.

The tissue extraction device can further include a wound retractor surrounding the cutting element. The wound retractor can include a clip that removably receives a portion of the cutting element. The wound retractor can have a spiral shape.

The bag can include an inner layer and an outer layer. The inner layer can include a mesh. The tissue extraction device can further include a wound retractor surrounding the cutting element. The wound retractor can include a hook for engaging the mesh. A rim of the inner layer can be removably coupled to a rim of the outer layer.

Embodiments are also provided of a method of extracting a tissue specimen from a subject with a tissue extraction device having a bag and a cutting element. The method can include inserting the bag and the cutting element together through an opening in the subject, inserting the tissue specimen into the bag, extracting a proximal portion of the bag, and ends of the cutting element, from the subject, via the opening, holding the ends of the cutting element, and cutting the tissue specimen with the cutting element by moving the cutting element back-and-forth in a sawing motion across the tissue specimen.

The method can further include inserting a wound retractor into the bag and positioning the wound retractor in the opening. The method can further include removably securing the cutting element to the wound retractor. The method can further include retracting the opening by expansion of the wound retractor. The method can further include compressing the tissue specimen between the cutting element and an end of the wound retractor. The method can further include securing the bag to the wound retractor. Securing the bag to the wound retractor can include hooking the bag onto the wound retractor.

The bag can include an inner layer and an outer layer. The method can further include separating the inner layer from the outer layer to tighten the inner layer around the tissue specimen. Separating the inner layer from the outer layer can include breaking a separable connection that removably couples the inner layer to the outer layer.

Cutting the tissue specimen can include moving a cutting member on the cutting element back-and-forth across the tissue specimen. Cutting the tissue specimen can include moving an edge of the cutting member back-and-forth across the tissue specimen.

Inserting the bag and the cutting element through the opening can include penetrating the opening with an introducer, and deploying the bag and the cutting element from the introducer. The cutting element can move from a collapsed configuration to an expanded configuration when the cutting element is deployed from the introducer. The cutting element can move the bag from a collapsed configuration to an expanded configuration when the bag is deployed from the introducer. The introducer can include a tubular elongate member for receiving the bag and the cutting element. The introducer can further include an inflatable securing member for securing the tubular elongate member in the opening.

The tubular elongate member can include a proximal section and a distal section. The proximal section and the distal section can be removably coupled. The proximal section can be uncoupled from the distal section and removed from the subject after the bag and the cutting element are deployed from the introducer. The distal section can remain in the opening as the tissue specimen is inserted into the bag.

The disclosure further provides a method of extracting a tissue specimen from a subject with a tissue extraction device having a bag and a cutting element. The method includes inserting the bag and the cutting element together through an opening in the subject, inserting the tissue specimen into the bag, extracting a proximal portion of the bag, and ends of the cutting element, from the subject, via the opening, separating an inner layer of the bag from an outer layer of the bag, moving the inner layer of the bag relative to the outer layer of the bag to tighten the inner layer of the bag around the tissue specimen, and cutting the tissue specimen with the cutting element.

If desired, the method can further including inserting a wound retractor into the opening. The method can further include securing the inner layer of the bag to the wound retractor to maintain a tightness of the inner layer of the bag around the tissue specimen. The method can still further include compressing the tissue specimen between the inner layer of the bag and an end of the wound retractor. The method can still further include compressing the tissue specimen between the cutting element and an end of the wound retractor. If desired securing the inner layer of the bag to the wound retractor can include bringing the inner layer into engagement with one or more hooks on the wound retractor. Bringing the inner layer of the bag into engagement with the one or more hooks can include sliding the one or more hooks in a radial direction relative to a proximal-facing surface of the wound retractor. The method can still further include inflating a portion of the wound retractor to secure the wound retractor in the opening. The method can still further include adjusting a width of a wound-engaging portion of the wound retractor to retract the opening. If desired, adjusting a width of the wound engaging portion can include moving discrete sections of the wound engaging portion apart from each other.

The disclosure further provides embodiments of an illustrative tissue extraction device that includes a bag having an interior, a strand extending through the interior of the bag, wherein the strand includes a plurality of braided filaments, the braided filaments defining a series of protrusions and recesses for abrading tissue when pulled across the tissue.

The disclosure further provides embodiments of an illustrative tissue extraction device, including only one bag having an interior, a basket in the interior of the bag, a cutting element releasably coupled to the basket, wherein the cutting element includes a cutting edge for cutting tissue as the cutting edge is drawn across tissue. The cutting element can include a plurality of rotatably coupled links that form a chain. The cutting element can include a strand and a plurality of circular saw blades rotatably coupled to the strand. If desired, the circular saw blades can be operatively coupled to a drive mechanism for rotating the circular saw blades relative to the strand.

The disclosure further provides embodiments of a kit for extracting tissue. The kit includes a bag assembly that in turn includes at least one bag and at least one cutting element, an introducer assembly for introducing the bag assembly into a body cavity, a retractor ring configured for coupling to the bag assembly, wherein eversion of the retractor ring rolls a portion of the bag assembly around the retractor ring, a protector disc configured for coupling to the bag assembly and the retractor ring, the protector disc having an opening for receiving the at least one cutting element, and a clip for restraining the at least one cutting element.

The disclosure further provides embodiments of a tissue extraction device, including a bag having and defined by an interior surface, and a cutting element extending through the interior of the bag. The cutting element includes a cutting member having an edge for cutting tissue as the cutting member is drawn across tissue, and a cover movable between a first configuration covering the edge of the cutting member and a second configuration exposing the edge of the cutting member.

The disclosure yet further provides embodiments of a tissue extraction device, including a bag having an interior, and a plurality of cutting elements extending through or along a surface of the bag, wherein the cutting elements have a common end. The cutting elements can be substantially parallel. The cutting elements can have a woven pattern. The tissue extraction device can further include a handle coupled to the common end. If desired, at least one of the cutting elements can transition from a first shape to a second shape upon being released from the interior of the bag. The at least one cutting element can include a shape memory alloy. If desired, the bag can include an inflatable rib. If desired, the bag can include an inner layer and an outer layer separated by an inflatable chamber, and an inflating connection for inflating the inflatable chamber. In some implementations, the inflatable chamber can include an inflatable toroid. In some implementations, the inflatable chamber can include an inflatable corrugation. In some implementations, the inflatable chamber can include a plurality of inflatable cells, wherein at least two of the inflatable cells have a common wall. In some implementations, at least one of the cutting elements can include a barbed suture. In some implementations, at least one of the cutting elements can include a bladed suture. In some implementations, the plurality of cutting elements can be a chain of cutting elements. In some implementations, the chain of cutting elements can include curved cutting elements. In some implementations, each of the curved cutting elements can include a curved cutting edge located on a convex end. In some implementations, the curved edge can face an interior space of the bag.

The disclosure further provides a tissue extraction device including a bag having an interior, and a plurality of strands extending through the interior of the bag, wherein the strands have a common end and each of the strands include a plurality of cutting elements.

If desired, at least one of the cutting elements can transition from a first shape to a second shape upon being released from the interior of the bag. At least one of the cutting elements can include a shape memory alloy. In some implementations, the cutting elements can be configured and arranged to expand such that the cutting elements flare outwardly.

The disclosure further provides embodiments of a tissue extraction device including a first ring including a first component of a ratchet and a channel configured and arranged to receive a second component of the ratchet, wherein the second component is on an arm of a retractor, a second ring removably coupled to the first ring, the second ring including a plurality of retainers positioned at even intervals along the second ring, and a third ring removably coupled to the first ring, the third ring including hooks configured and arranged to receive a bag to be rolled around the third ring.

If desired, the first component of the ratchet can be a pawl positioned in the channel, and the second component of the ratchet is a rack on the arm of the retractor. The retractor can include a blade coupled to the arm. In some implementations, at least a portion of the blade can overlap at least a portion of an adjacent blade.

The disclosure further provides embodiments of a method of extracting tissue. Such methods can include one or more of inserting a bag into the patient via an incision, inserting a tissue specimen into the bag, coupling the edge of the bag to a ring via hooks on the ring, rolling a portion of the bag around the ring, coupling an outer ring to the ring, the outer ring coupled to an inner ring, cutting the tissue specimen with the cutting element, decoupling the inner ring from the outer ring, inserting retractors into the incision, and extracting the cut tissue specimen from the patient.

The method can further include inflating inflatable ribs of the bag prior to cutting the tissue specimen. Inserting the retractors can include coupling the retractors to ratchets of the outer ring, and incrementally retracting the retractors to open the incision such that the cut tissue specimen can pass through a collar formed by the retractors.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIGS. 5A-5D are side and perspective views of tissue extraction devices, in accordance with aspects of the present disclosure.

FIG. 10 is a perspective view of a tissue extraction device, in accordance with aspects of the present disclosure.

FIGS. 11A and 11B are front and side views of a tissue extraction device, in accordance with aspects of the present disclosure.

FIG. 12 is a perspective view of a tissue extraction device, in accordance with aspects of the present disclosure.

FIGS. 16A and 16B are a perspective view and a close-up view, respectively, of a tissue extraction device, in accordance with aspects of the present disclosure.

FIGS. 17A and 17B are side and front views of a tissue extraction device, in accordance with aspects of the present disclosure.

FIGS. 19G and 19H are perspective and semi-transparent side views of the tissue extraction device of FIGS. 19A and 19B, in accordance with aspects of the present disclosure.

FIGS. 25A-25C are perspective, front, and side views of a bag of a tissue extraction device, in accordance with aspects of the present disclosure.

FIGS. 26A-26D are perspective, front, side, and partial section views of a bag of a tissue extraction device, in accordance with aspects of the present disclosure.

FIG. 27 is a partial perspective view of a bag and strands of a tissue extraction device, in accordance with aspects of the present disclosure.

FIGS. 30A-30D are perspective cutaway, front, side, and section views, of a bag of a tissue extraction device, in accordance with aspects of the present disclosure.

FIG. 31 is a section view of a tissue extraction device, in accordance with aspects of the present disclosure.

FIGS. 32A-32G are perspective and close-up perspective views of a tissue extraction device, in accordance with aspects of the present disclosure.

FIGS. 33A-33D are perspective, side, and section views of a wound retractor of a tissue extraction device, in accordance with aspects of the present disclosure.

FIGS. 34A-34D are top, top (with hidden lines shown), section, and close-up section views of a wound retractor of a tissue extraction device, in accordance with aspects of the present disclosure.

FIGS. 35A-35D are perspective views of an introducer for a tissue extraction device, in accordance with aspects of the present disclosure.

FIGS. 35E-35G are side and section views of the introducer of FIGS. 35A-35D, in accordance with aspects of the present disclosure.

FIGS. 36A-36D are perspective views of an introducer for a tissue extraction device, in accordance with aspects of the present disclosure.

FIGS. 36E-36G are side and section views of the introducer of FIGS. 36A-36D, in accordance with aspects of the present disclosure.

FIGS. 37L-37P are perspective and section views of an introducer for a tissue extraction device, in accordance with aspects of the present disclosure.

FIGS. 37Q(i)-37Q(x) are perspective, section, semi-transparent, side, and top views of the introducer of FIGS. 37L-37P, in accordance with aspects of the present disclosure.

FIGS. 37Q(xi)-37Q(xiv) are partial section views of the introducer of FIGS. 37Q(i)-37Q(x) in use, in accordance with aspects of the present disclosure.

FIGS. 38-43 are perspective views showing exemplary introduction, tissue capturing, and tissue extracting steps, in accordance with aspects of the present disclosure.

FIGS. 50A-50E are top, perspective, close-up top, close-up side, and section views of a cutting element, in accordance with aspects of the present disclosure.

FIGS. 51A-51G are top, side, close-up top, perspective, close-up top, close-up side, and section views of a cutting element, in accordance with aspects of the present disclosure.

FIGS. 52A-52G are top, side, close-up top, perspective, close-up top, close-up side, and section views of a cutting element, in accordance with aspects of the present disclosure.

FIGS. 53A-53G are top, side, close-up side, perspective, close-up top, close-up side, and section views of a cutting element, in accordance with aspects of the present disclosure.

FIGS. 54A-54H are top, side, close-up top, close-up side, perspective, close-up top, close-up side, and section views of a cutting element, in accordance with aspects of the present disclosure.

FIGS. 55A and 55B are top and perspective views of a portion of a cutting element, in accordance with aspects of the present disclosure.

FIGS. 56A and 56B are top and perspective views of a portion of a cutting element, in accordance with aspects of the present disclosure.

FIGS. 57A and 57B are top and perspective views of a portion of a cutting element, in accordance with aspects of the present disclosure.

FIGS. 58A-58C are top, side, and perspective views of a portion of a cutting element, in accordance with aspects of the present disclosure.

FIGS. 59A-59D are top, close-up top, side, and perspective views of a portion of a cutting element, in accordance with aspects of the present disclosure.

FIGS. 60A-60C are top, side, and perspective views of a portion of a cutting element, in accordance with aspects of the present disclosure.

FIGS. 61A-61C are top, side, and perspective views of a portion of a cutting element, in accordance with aspects of the present disclosure.

FIGS. 62A-62C are perspective, side, and top views of a portion of a cutting element, in accordance with aspects of the present disclosure.

FIGS. 62D-62H are perspective, side, top, other side, and section views of a bead of the cutting element of FIGS. 62A-62C, in accordance with aspects of the present disclosure.

FIGS. 63A and 63B are perspective and top views of a portion of a cutting element, in accordance with aspects of the present disclosure.

FIGS. 63C-63F are perspective, side, top, and section views of a bead of the cutting element of FIGS. 63A and 63B, in accordance with aspects of the present disclosure.

FIGS. 64A-64C are perspective, top, and side views of a portion of a cutting element, in accordance with aspects of the present disclosure.

FIGS. 64D-64G are front, side, and perspective views of a blade of the cutting element of FIGS. 64A-64C, in accordance with aspects of the present disclosure.

FIGS. 65A and 65B are perspective and section views of a portion of a cutting element, in accordance with aspects of the present disclosure.

FIGS. 66A-66E are perspective, top, side, end, and section views of a portion of a cutting element, in accordance with aspects of the present disclosure.

FIGS. 67A and 67B are perspective and side views of a portion of a cutting element, in accordance with aspects of the present disclosure.

FIGS. 67C-67F are perspective, top, side, and end views of a bead of the cutting element of FIGS. 67A and 67B, in accordance with aspects of the present disclosure.

FIG. 68 is a perspective view of a bead of a cutting element, in accordance with aspects of the present disclosure.

FIGS. 69A-69E are perspective, top, side, and end views of a bead of a cutting element, in accordance with aspects of the present disclosure.

FIGS. 70A-70E are perspective, top, side, end, and section views of a bead of a cutting element, in accordance with aspects of the present disclosure.

FIGS. 71A-71E are perspective, side, top, and end views of a bead of a cutting element, in accordance with aspects of the present disclosure.

FIGS. 72A and 72B are perspective and side views of a portion of a cutting element, in accordance with aspects of the present disclosure.

FIGS. 72C-72E are perspective, side, and top views of a portion of the cutting element of FIGS. 72A and 72B, in accordance with aspects of the present disclosure.

FIG. 75 is a perspective view of an introducer assembly of the kit of FIG. 74, in accordance with aspects of the present disclosure.

FIGS. 78A-78C are perspective views of components of the introducer assembly of FIG. 75, in accordance with aspects of the present disclosure.

FIGS. 79A and 79B are perspective and cross-sectional views of a wound retractor ring of the kit of FIG. 74, in accordance with aspects of the present disclosure.

FIGS. 80A-80C are perspective and cross-sectional views of a protector snap disc of the kit of FIG. 74, in accordance with aspects of the present disclosure.

FIG. 81 is a perspective view of a bag assembly of the kit of FIG. 74, in accordance with aspects of the present disclosure.

FIGS. 82A-82D are perspective views of the bag assembly, wound retractor ring, and protector snap disc in use, in accordance with aspects of the present disclosure.

FIGS. 83A-83C are side views of an exemplary tissue extraction device, in accordance with aspects of the present disclosure.

FIGS. 90 and 91 are top and side views, respectively, of the retractor ring of FIG. 89, in accordance with aspects of the present disclosure.

FIG. 92 is a perspective view of the retractor ring of FIG. 89, in an expanded state, in accordance with aspects of the present disclosure.

FIGS. 93A and 93B are side and front views, respectively, of the retractor ring of FIG. 89, in its expanded state, in accordance with aspects of the present disclosure.

FIGS. 94A and 94B are top and rear views, respectively, of the retractor ring of FIG. 89, in its expanded state, in accordance with aspects of the present disclosure.

FIGS. 100A and 100B are side and front views, respectively, of the retractor ring of FIG. 95, in an expanded state, in accordance with aspects of the present disclosure.

FIGS. 103A, 103B, and 104A are top, side, and bottom views, respectively, of the retractor ring of FIG. 101, in accordance with aspects of the present disclosure.

FIG. 104B is a cross-sectional side view of the retractor ring of FIG. 101, the cross-section being taken along the line B-B in FIG. 104A, in accordance with aspects of the present disclosure.

FIG. 107 is a cross-sectional perspective view of the retractor ring of FIG. 106, in accordance with aspects of the present disclosure.

FIGS. 108A and 108B are top and side views, respectively, of the retractor ring of FIG. 106, in accordance with aspects of the present disclosure.

FIG. 109 is a perspective view of an inner ring of the retractor ring of FIG. 106, in accordance with aspects of the present disclosure.

FIG. 110 is a cross-sectional perspective view of the inner ring of FIG. 109, in accordance with aspects of the present disclosure.

Figure 109:
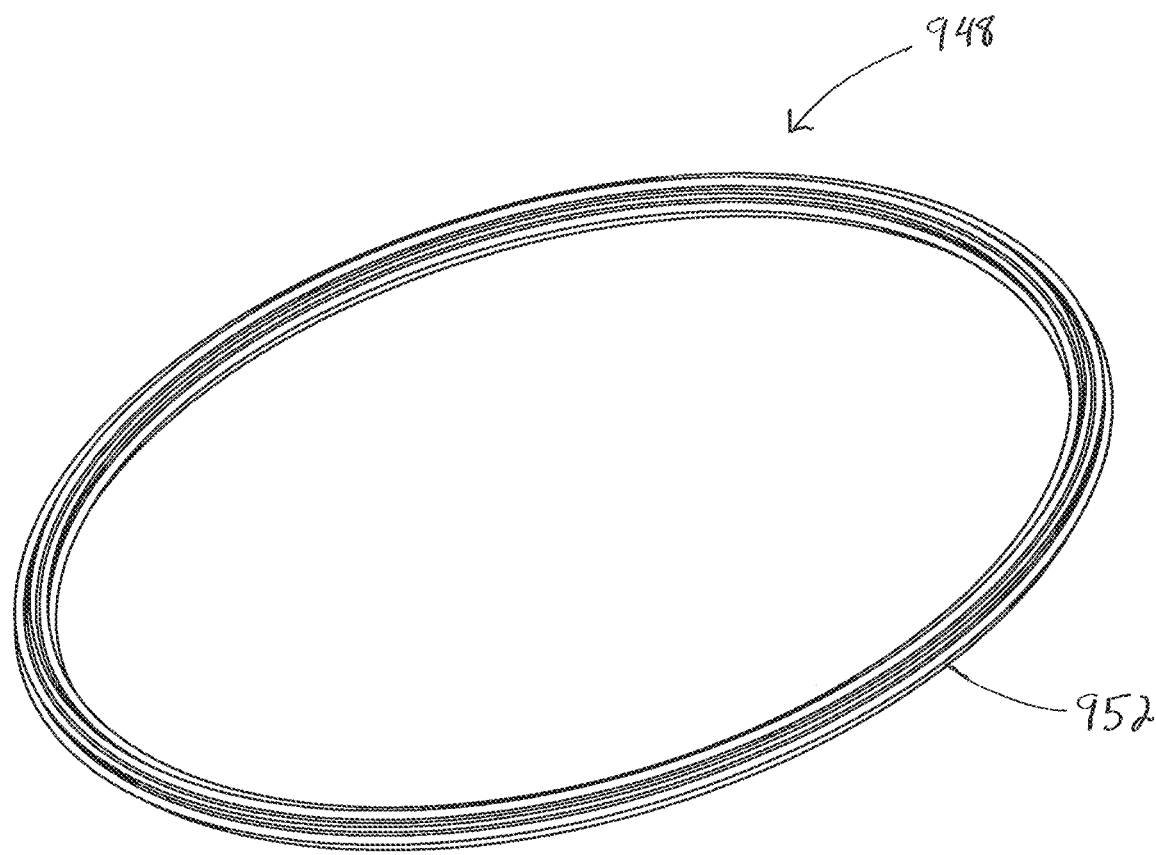
Figure 112A:
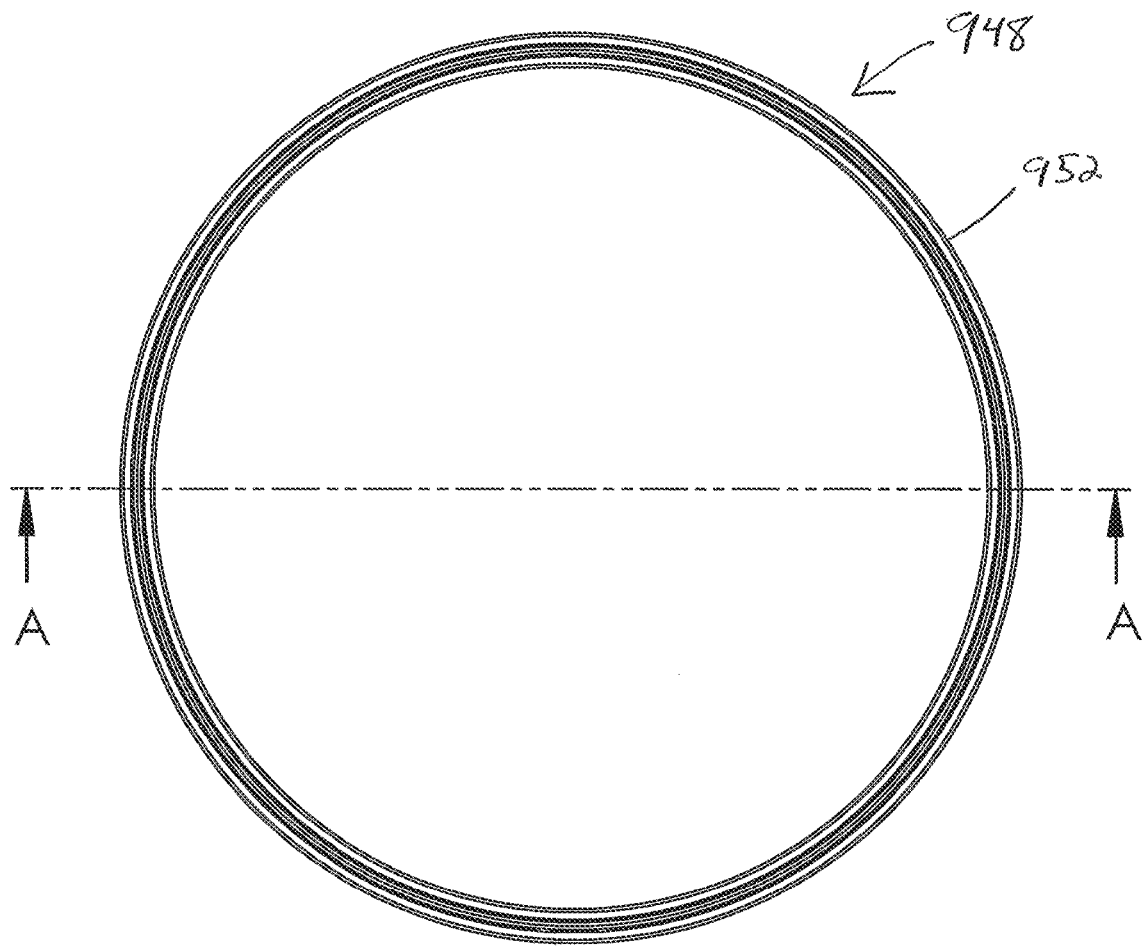
Figure 112B:
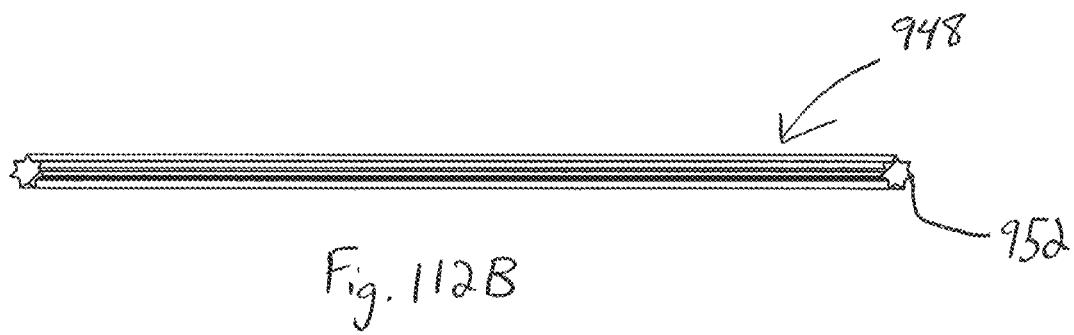

FIGS. 111A, 111B, 112A, and 112B are top, side, bottom, and cross-sectional side views of the inner ring of FIG. 109, in accordance with aspects of the present disclosure. The cross-sectional side view of FIG. 112B is taken along the line A-A in FIG. 112A.

Figure 113:
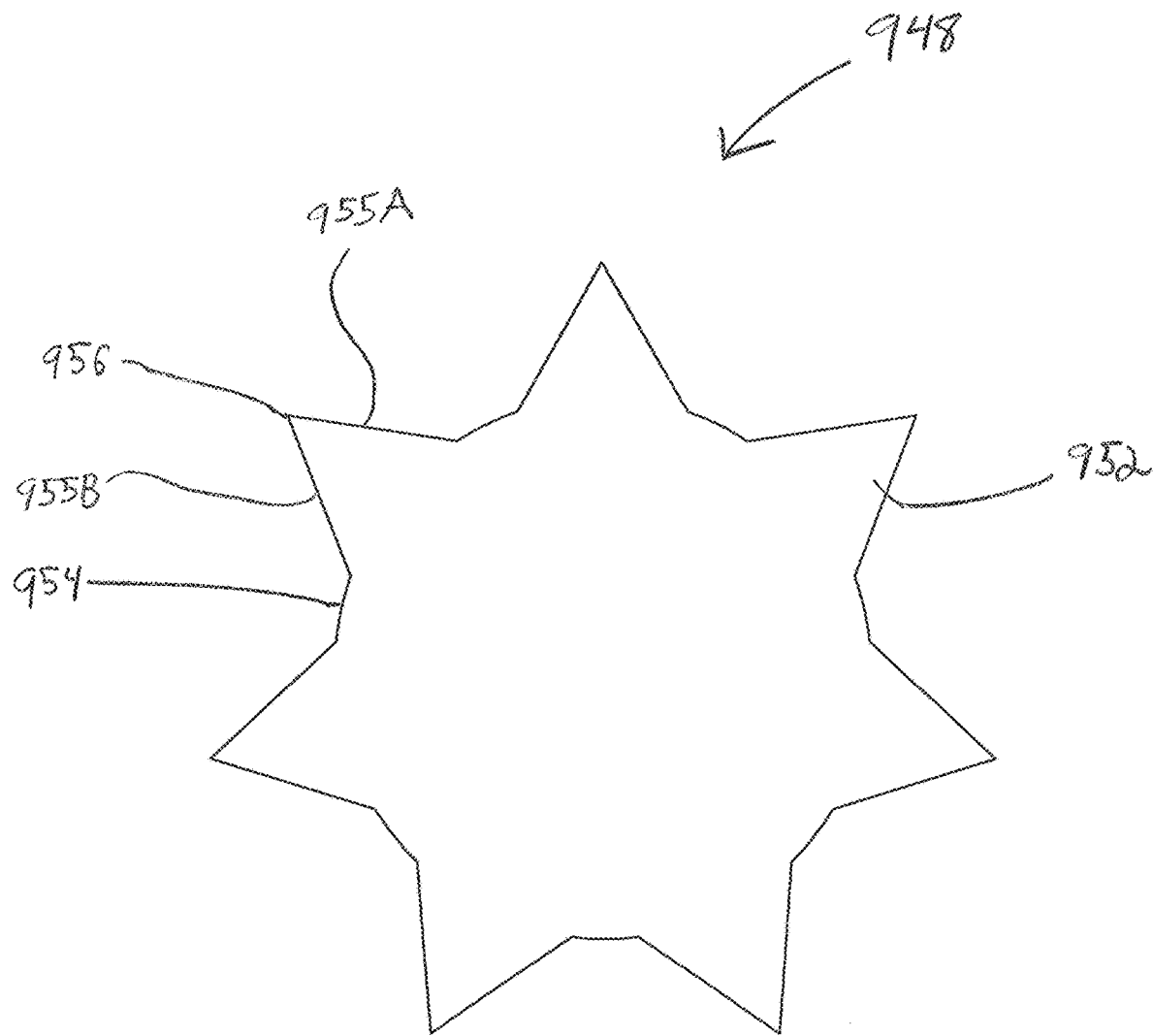

FIG. 113 is a side view of a cross-sectional face of the inner ring of FIG. 109, in accordance with aspects of the present disclosure.

Figure 106:
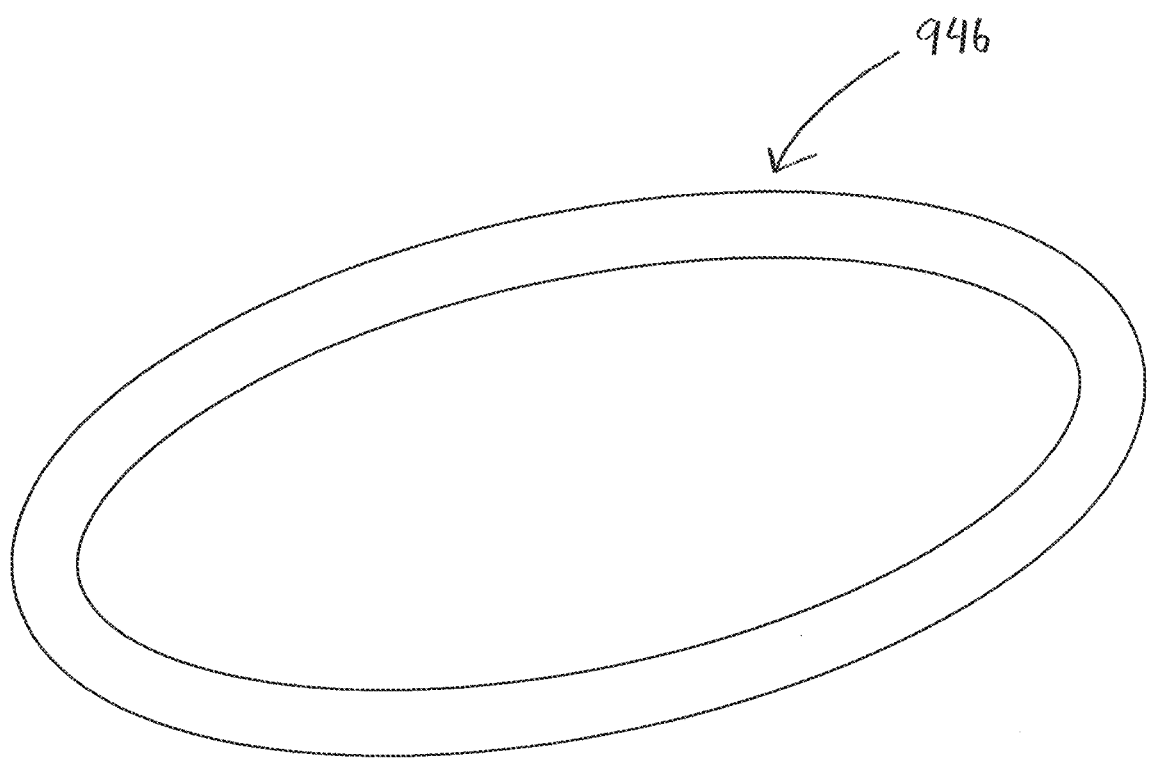
FIG. 106 is a perspective view of another exemplary retractor ring, in accordance with aspects of the present disclosure.
Figure 107:
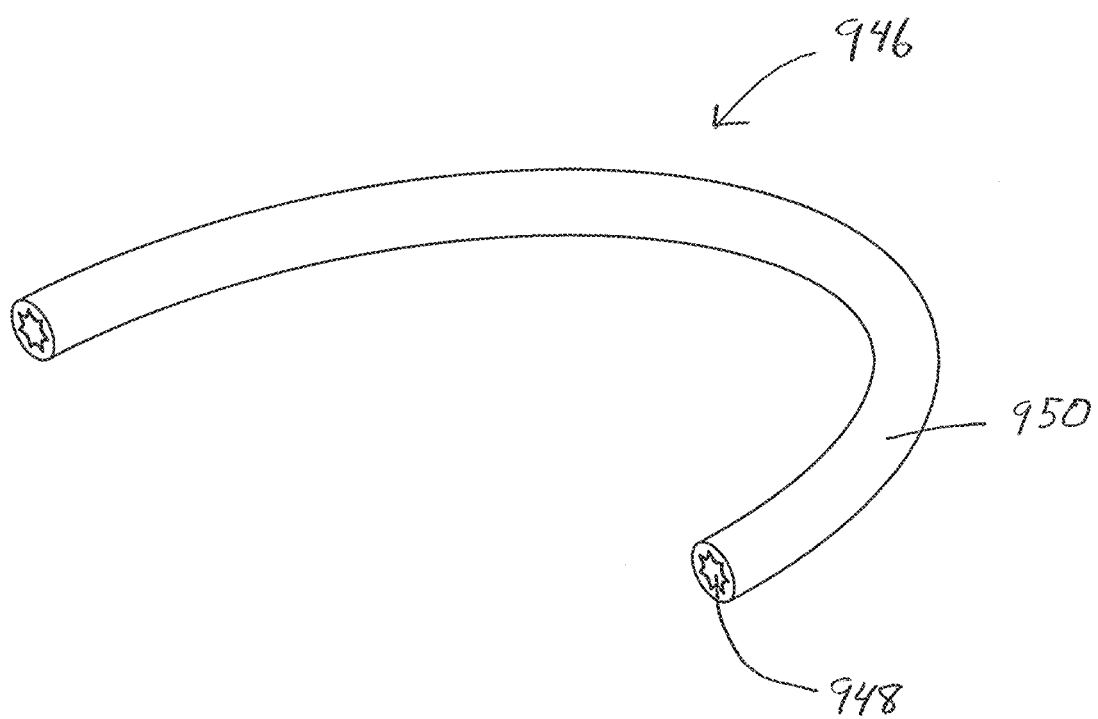
Figure 108A:
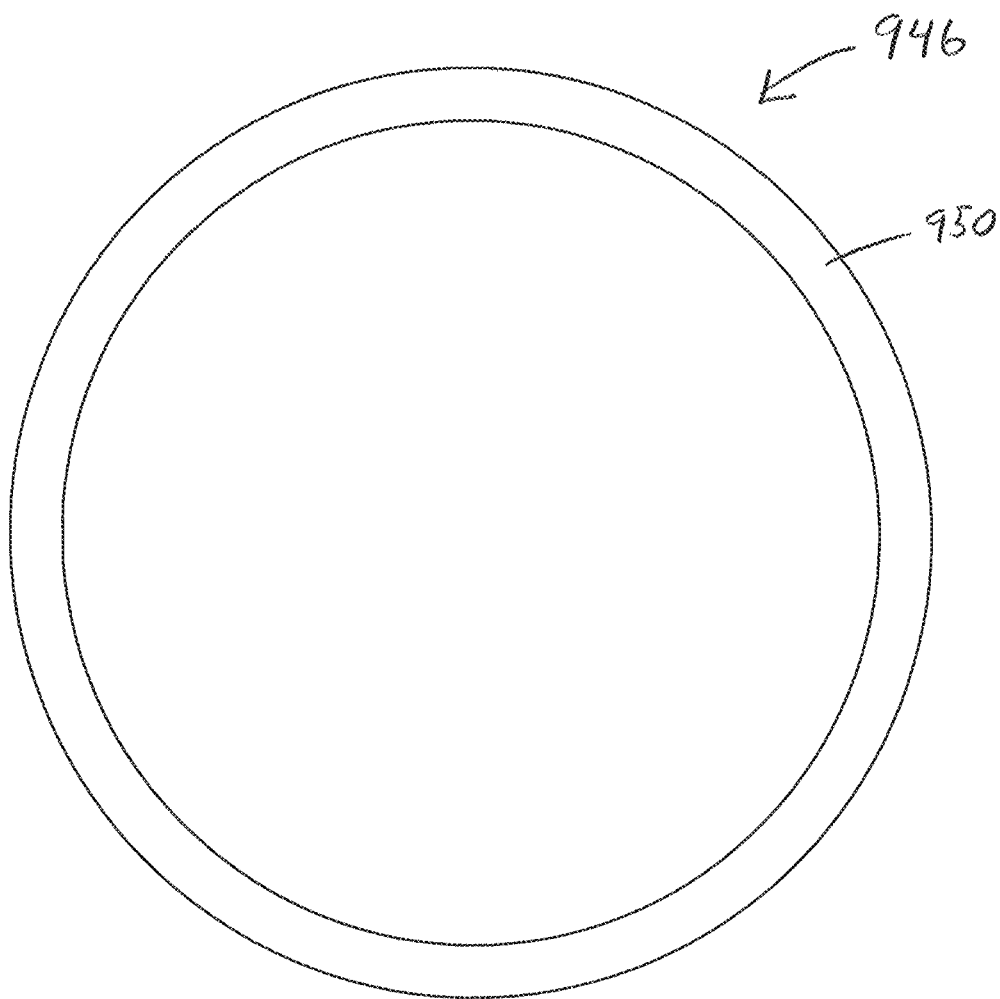
Figure 108B:
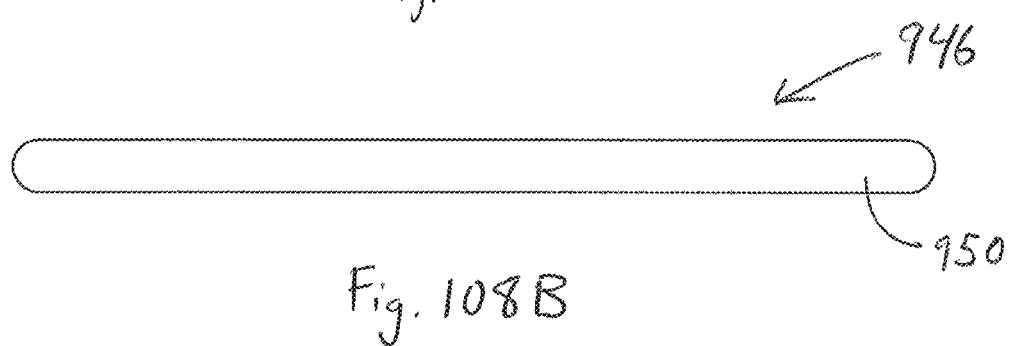
Figure 114:
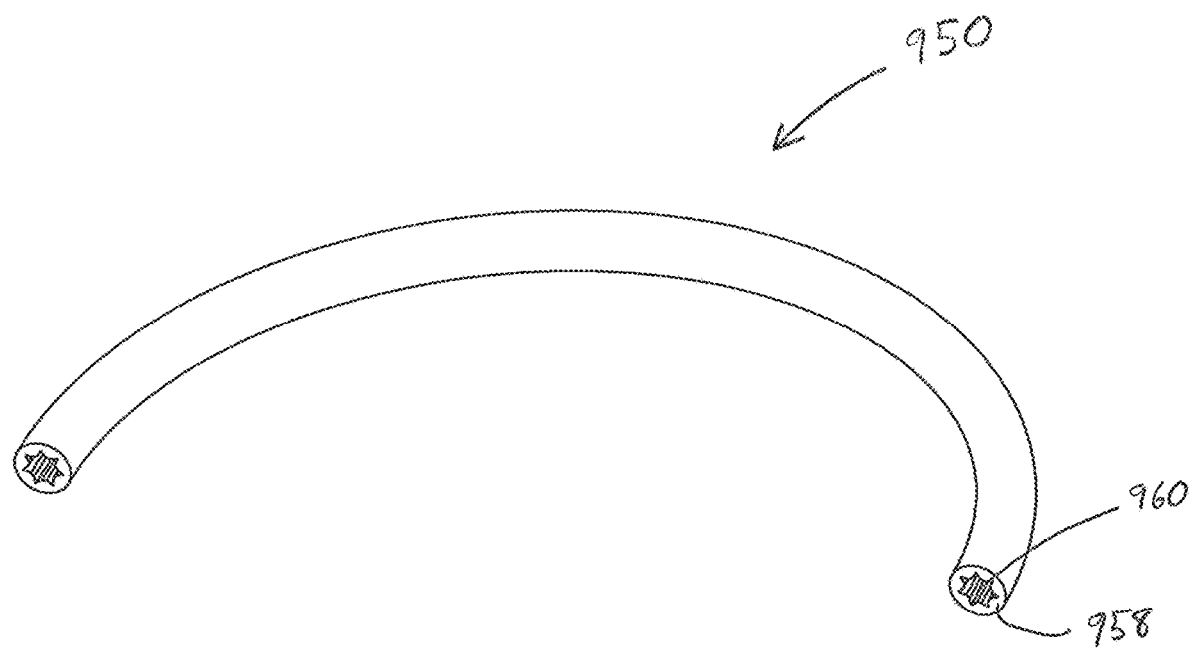

FIG. 114 is a cross-sectional perspective view of an outer ring of the retractor ring of FIG. 106, in accordance with aspects of the present disclosure.

Figure 115A:
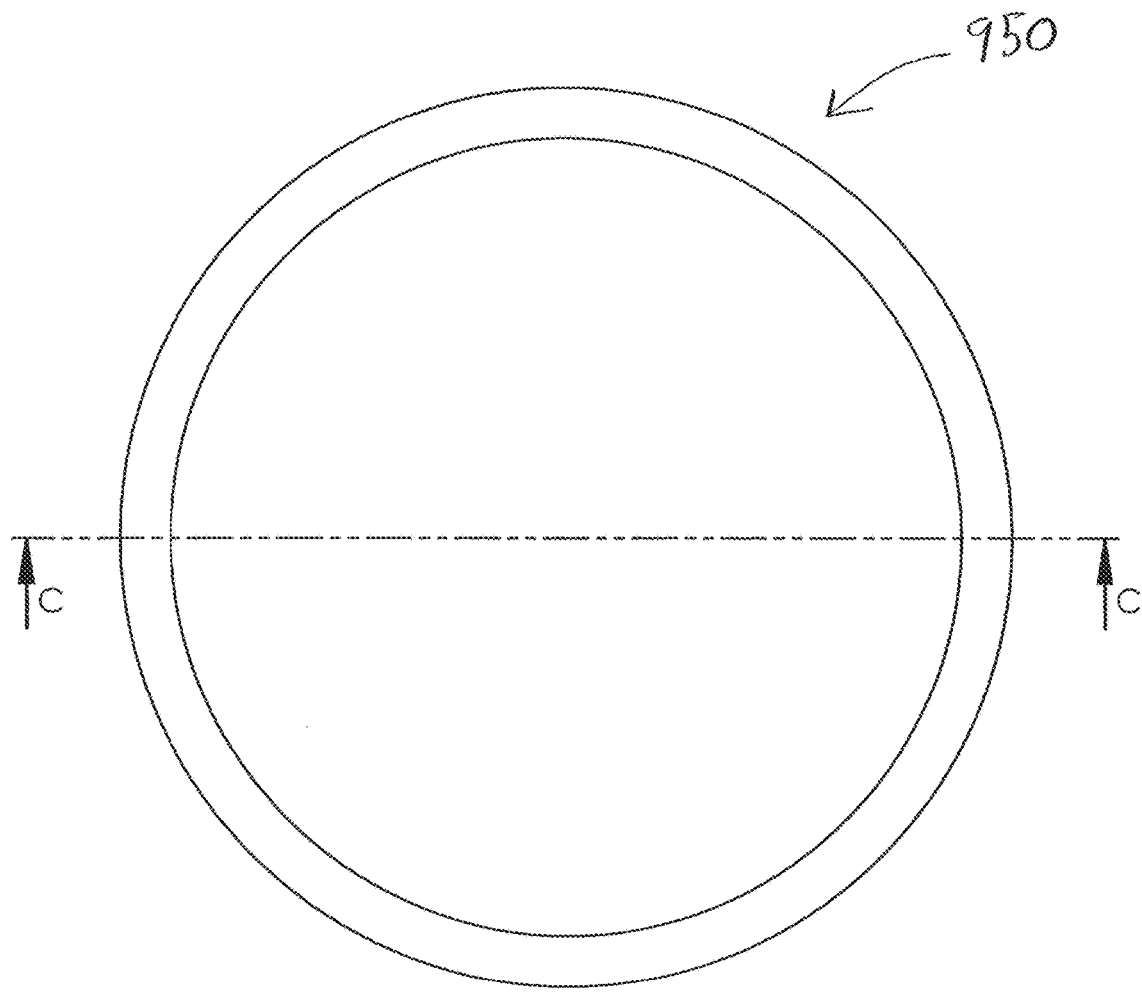
Figure 115B:
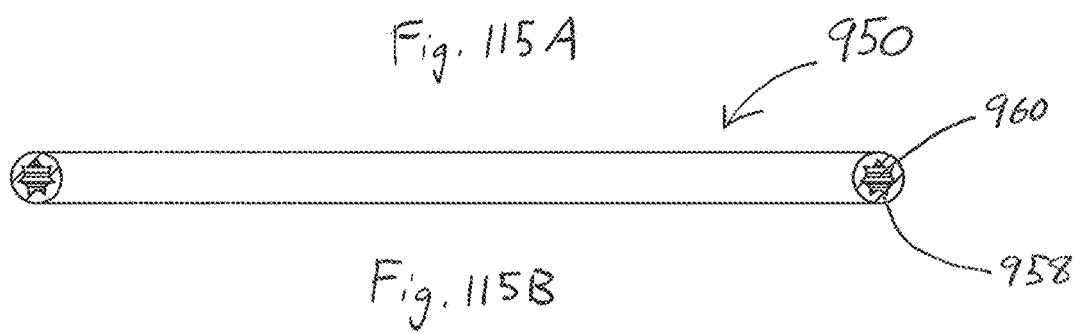

FIGS. 115A and 115B are top and cross-sectional side views, respectively, of the outer ring of FIG. 114, in accordance with aspects of the present disclosure. The cross-sectional side view of FIG. 115B is taken along the line C-C in FIG. 115A.

Figure 116:
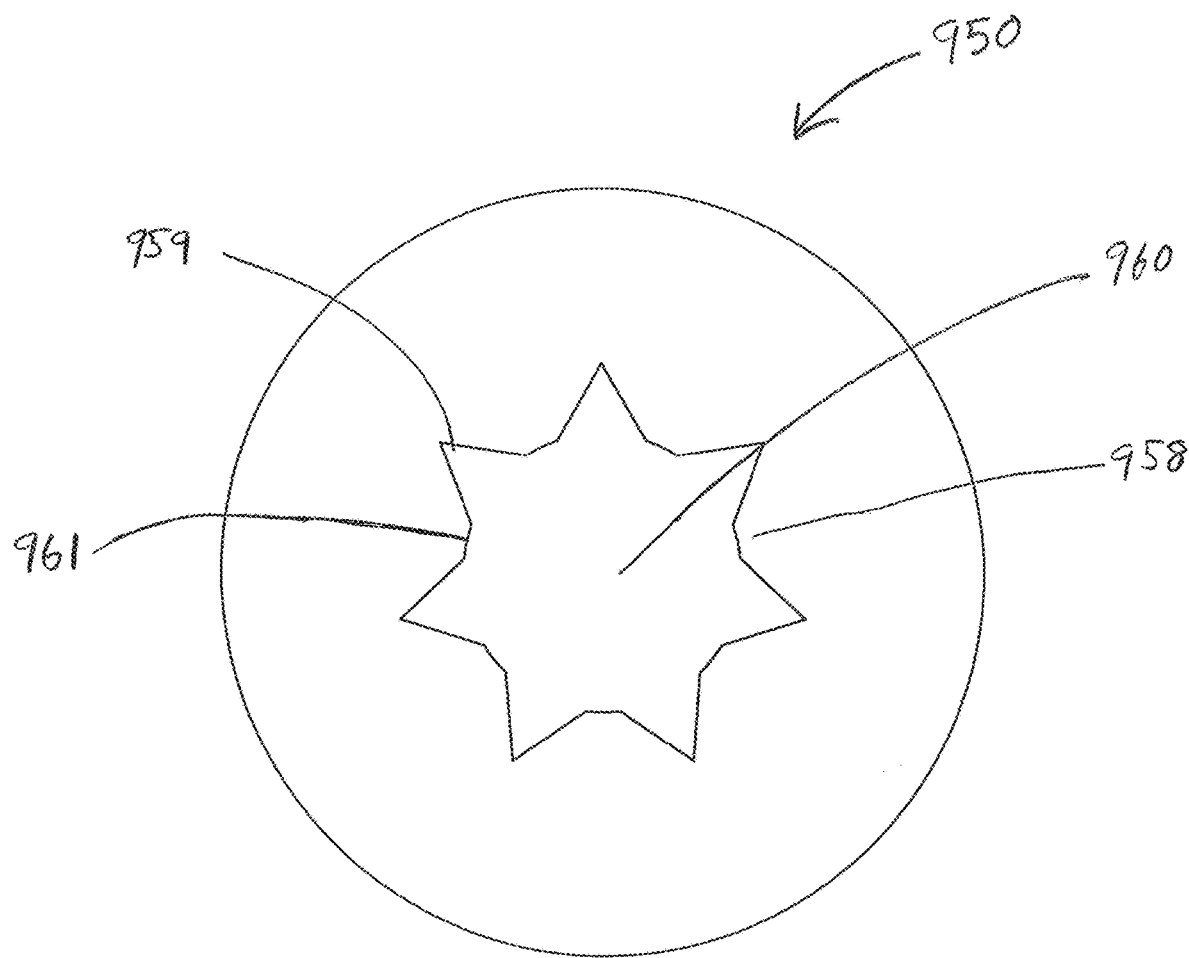

FIG. 116 is a side view of a cross-sectional face of the outer ring of FIG. 114, in accordance with aspects of the present disclosure.

Figure 117:
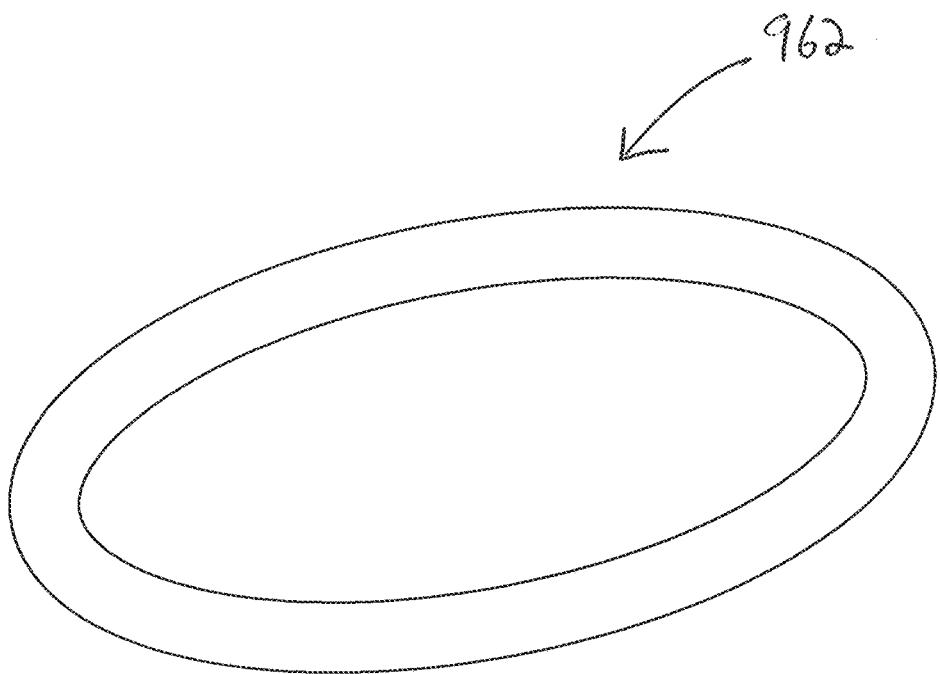

FIG. 117 is a perspective view of another exemplary retractor ring, in accordance with aspects of the present disclosure.

Figure 118:
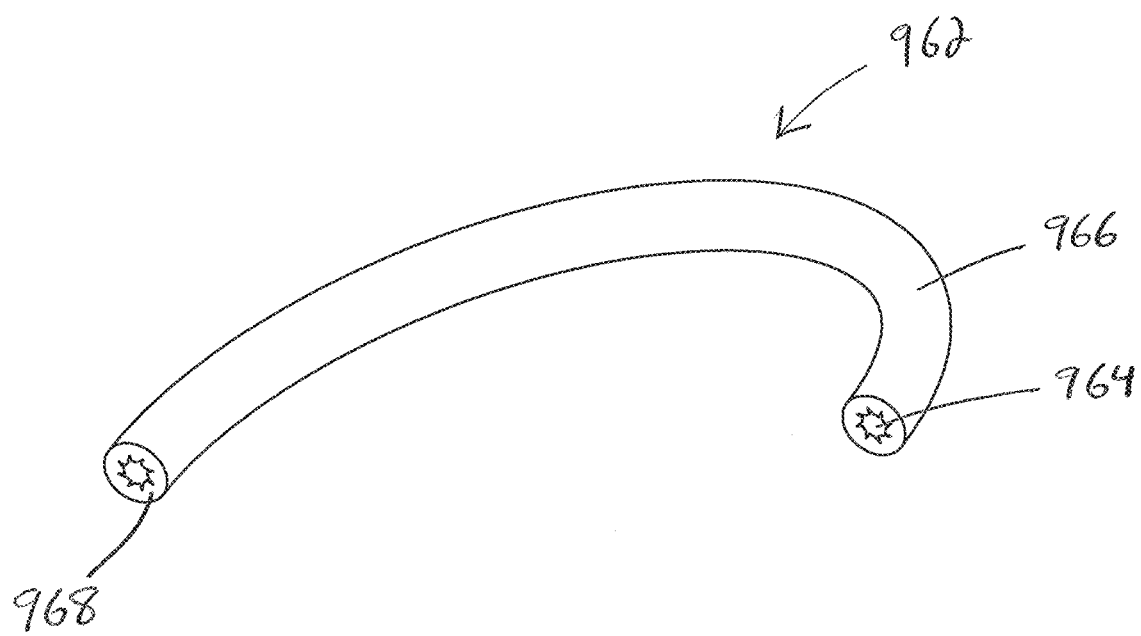

FIG. 118 is a cross-sectional perspective view of the retractor ring of FIG. 117, in accordance with aspects of the present disclosure.

Figure 119A:
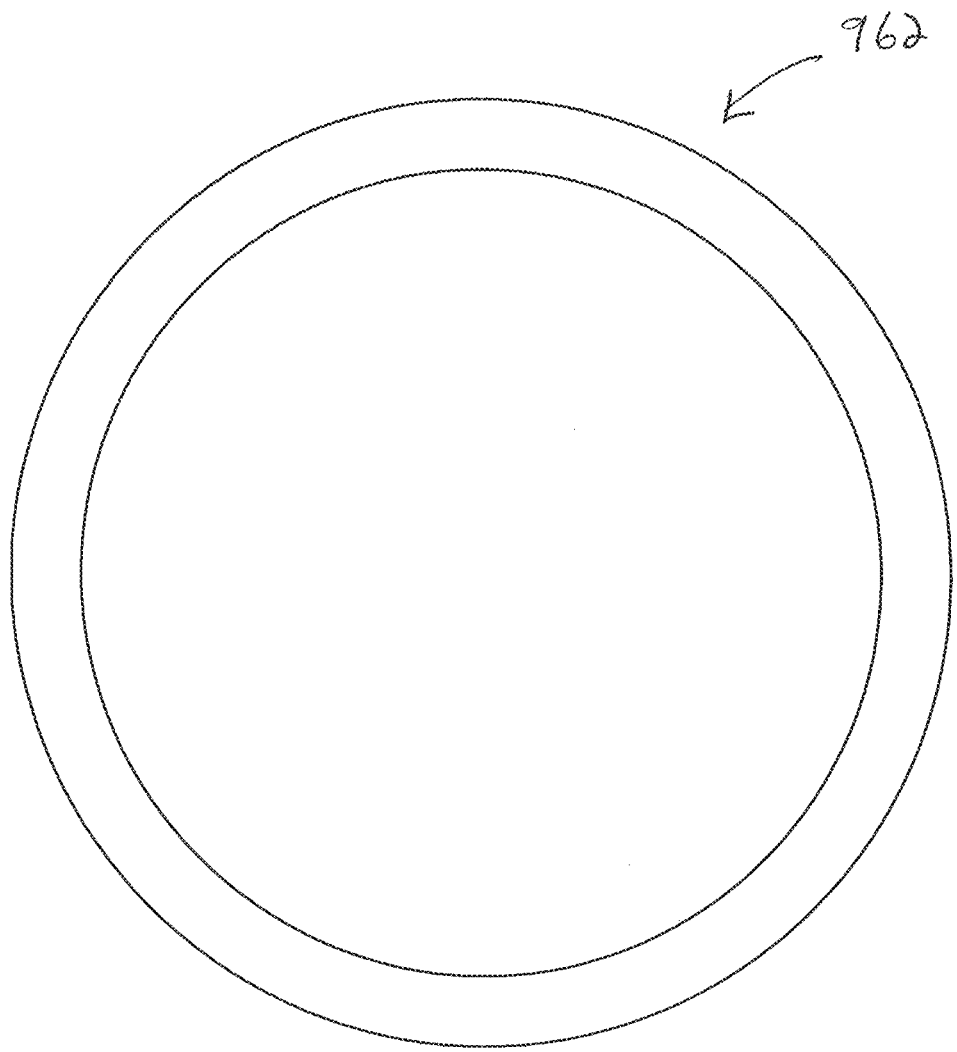
Figure 119B:
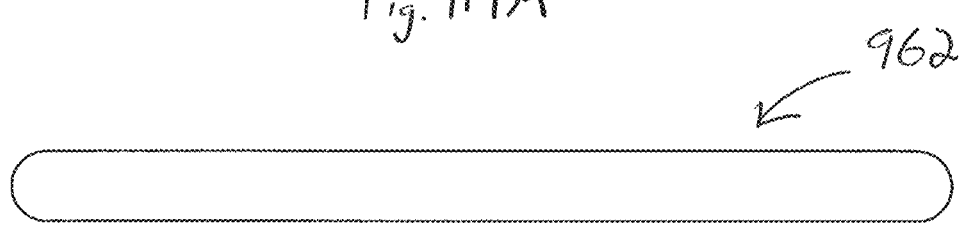

FIGS. 119A and 119B are top and side views, respectively, of the retractor ring of FIG. 117, in accordance with aspects of the present disclosure.

Figure 120A:
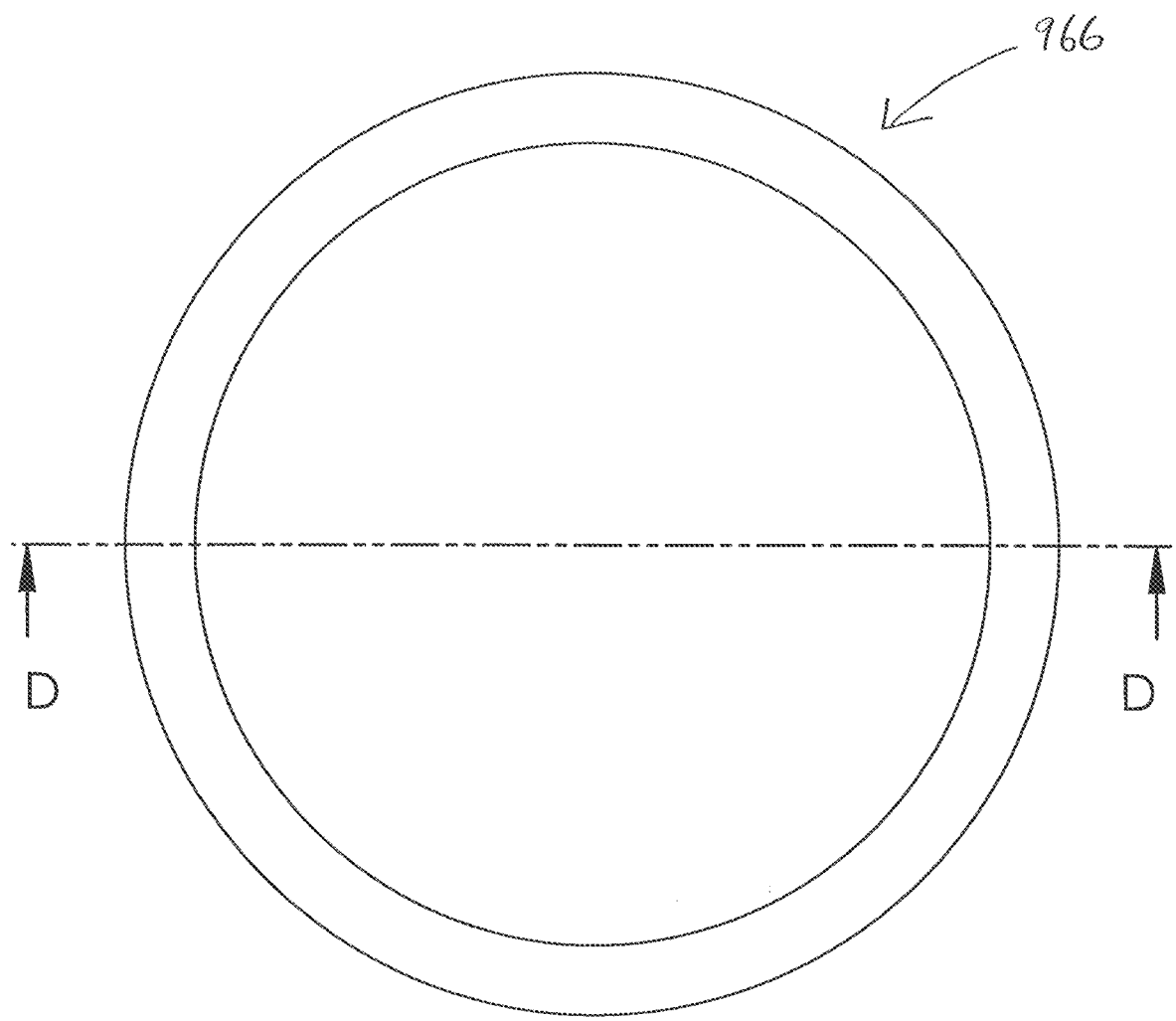
Figure 120B:
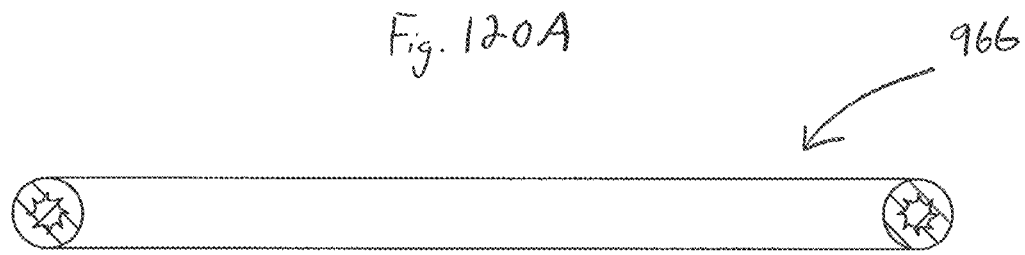

FIGS. 120A and 120B are bottom and cross-sectional side views, respectively, of the retractor ring of FIG. 117, in accordance with aspects of the present disclosure. The cross-sectional side view of FIG. 120B is taken along the line D-D in FIG. 120A.

Figure 121:
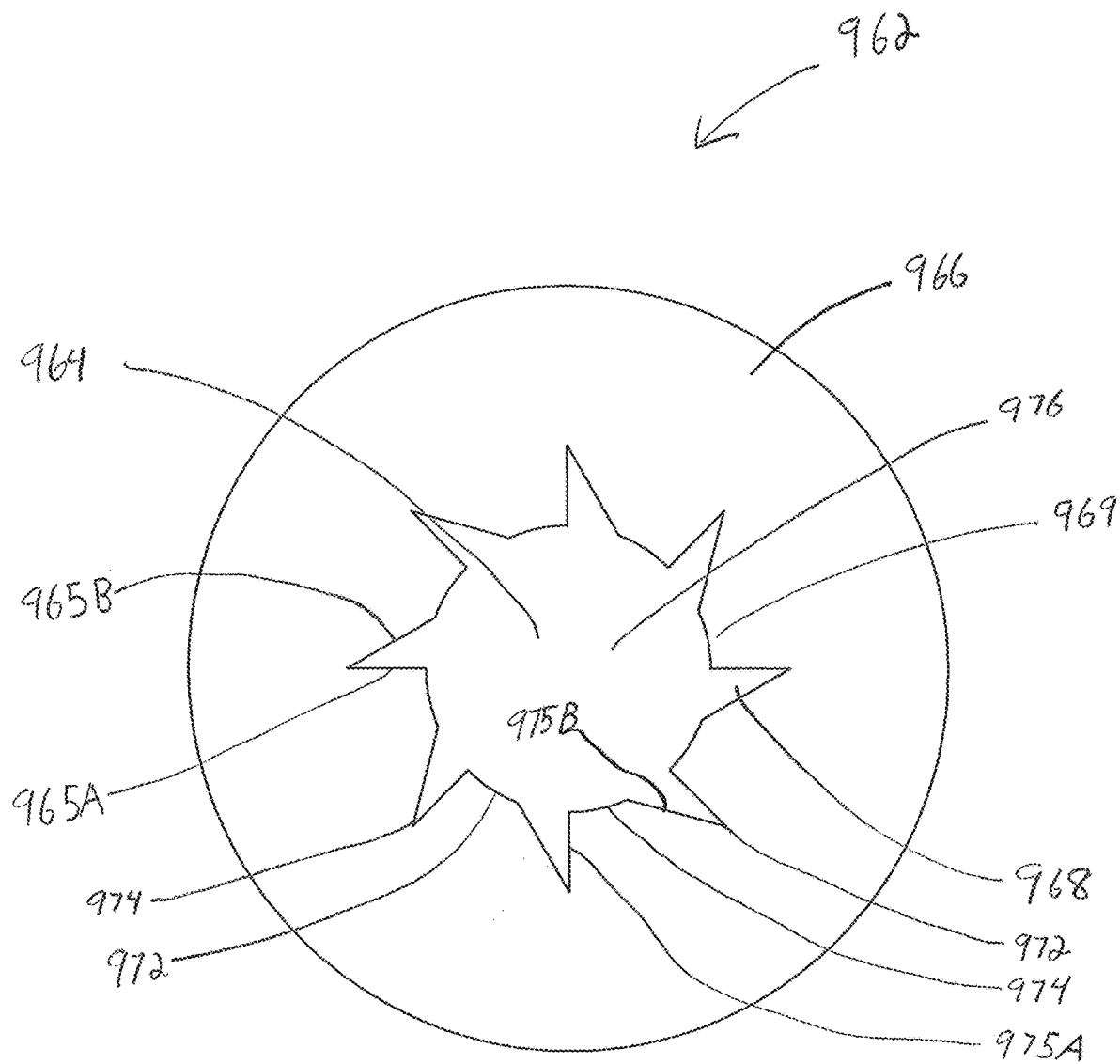

FIG. 121 is a side view of a cross-sectional face of the retractor ring of FIG. 117, in accordance with aspects of the present disclosure.

Figure 122:
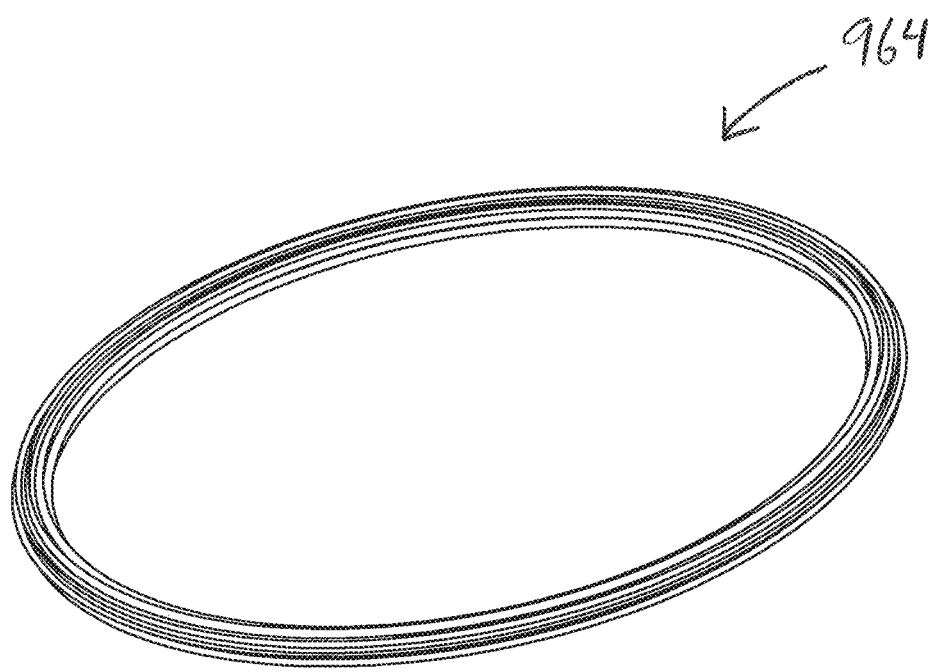
Figure 123:
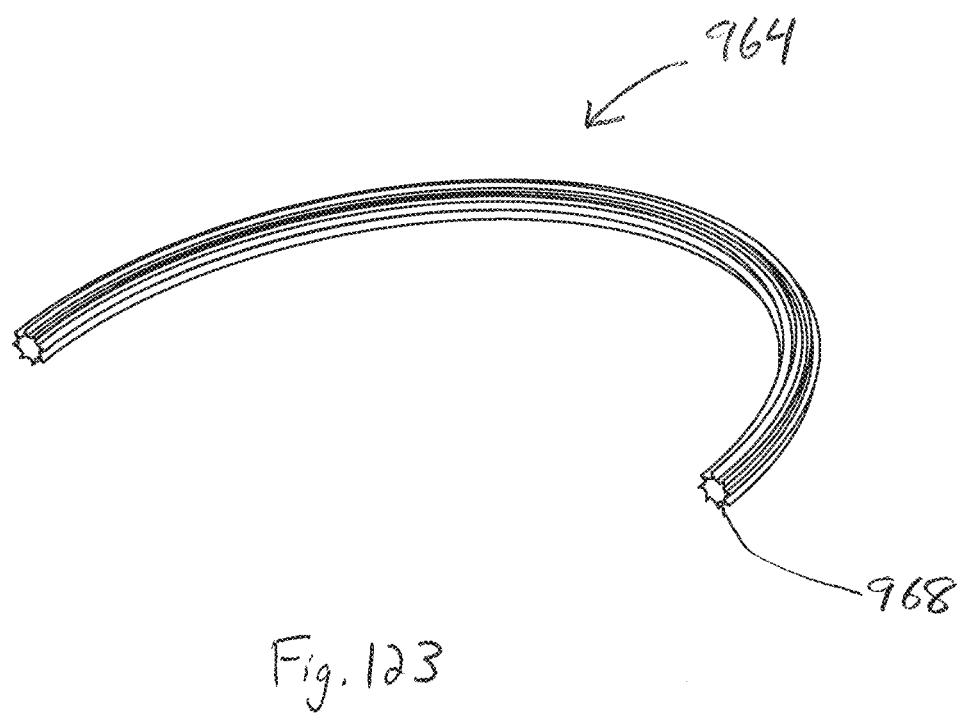
Figure 124A:
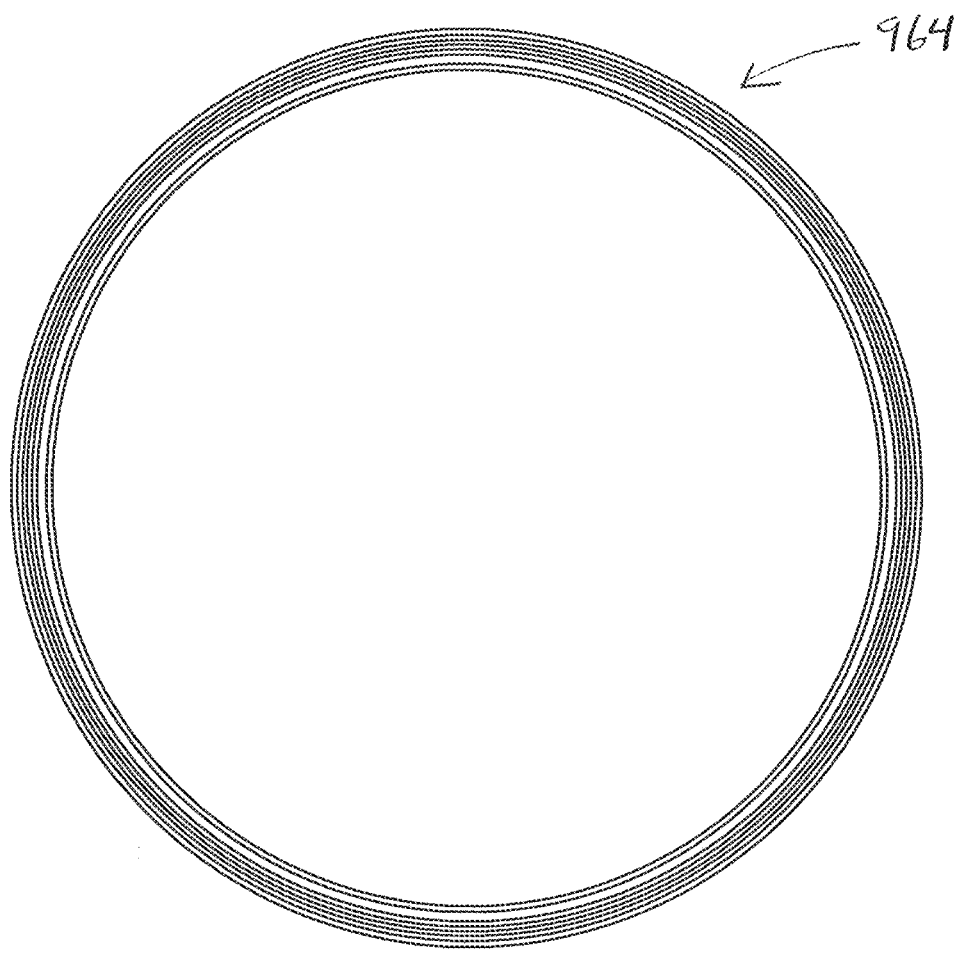
Figure 124B:
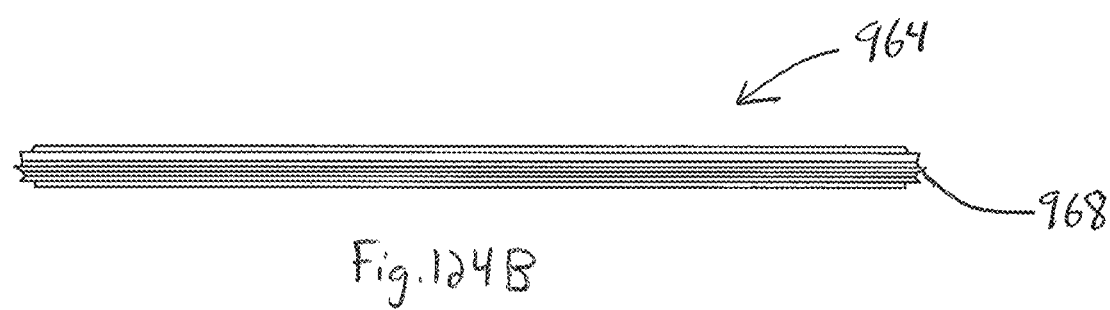

FIGS. 122 and 123 are perspective and cross-sectional perspective views, respectively, of an inner ring of the retractor ring of FIG. 117, in accordance with aspects of the present disclosure.

Figure 125A:
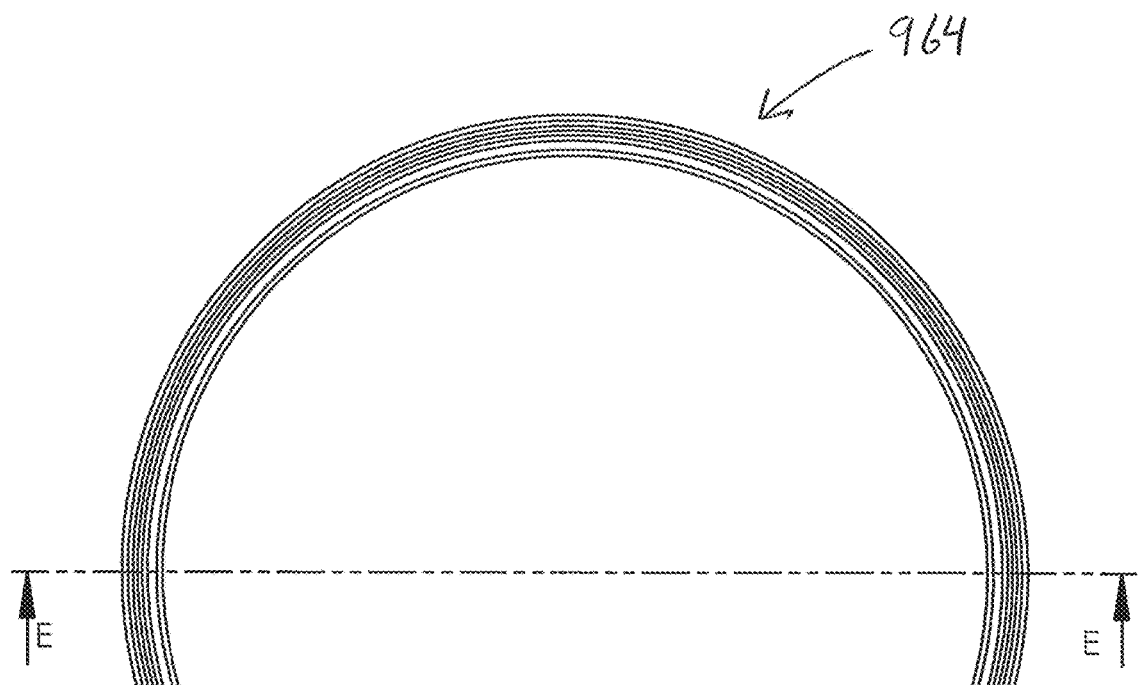
Figure 125B:
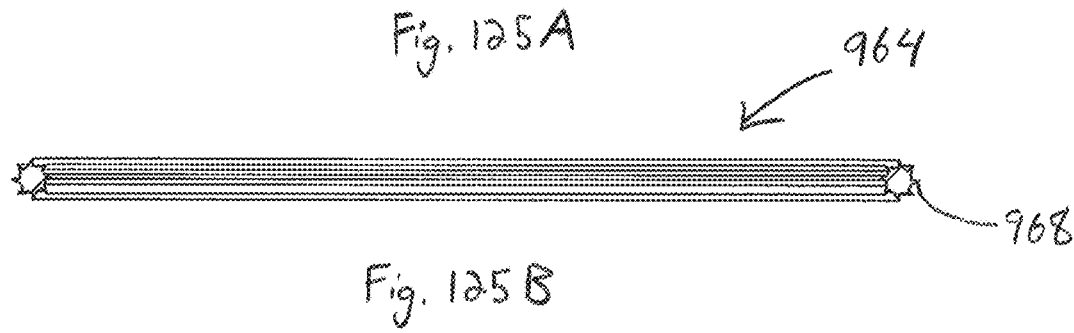

FIGS. 124A, 124B, 125A, and 125B are top, side, bottom, and cross-sectional side views, respectively, of the inner ring of FIG. 122, in accordance with aspects of the present disclosure. The cross-sectional side view of FIG. 125B is taken along the line E-E in FIG. 125A.

Figure 126:
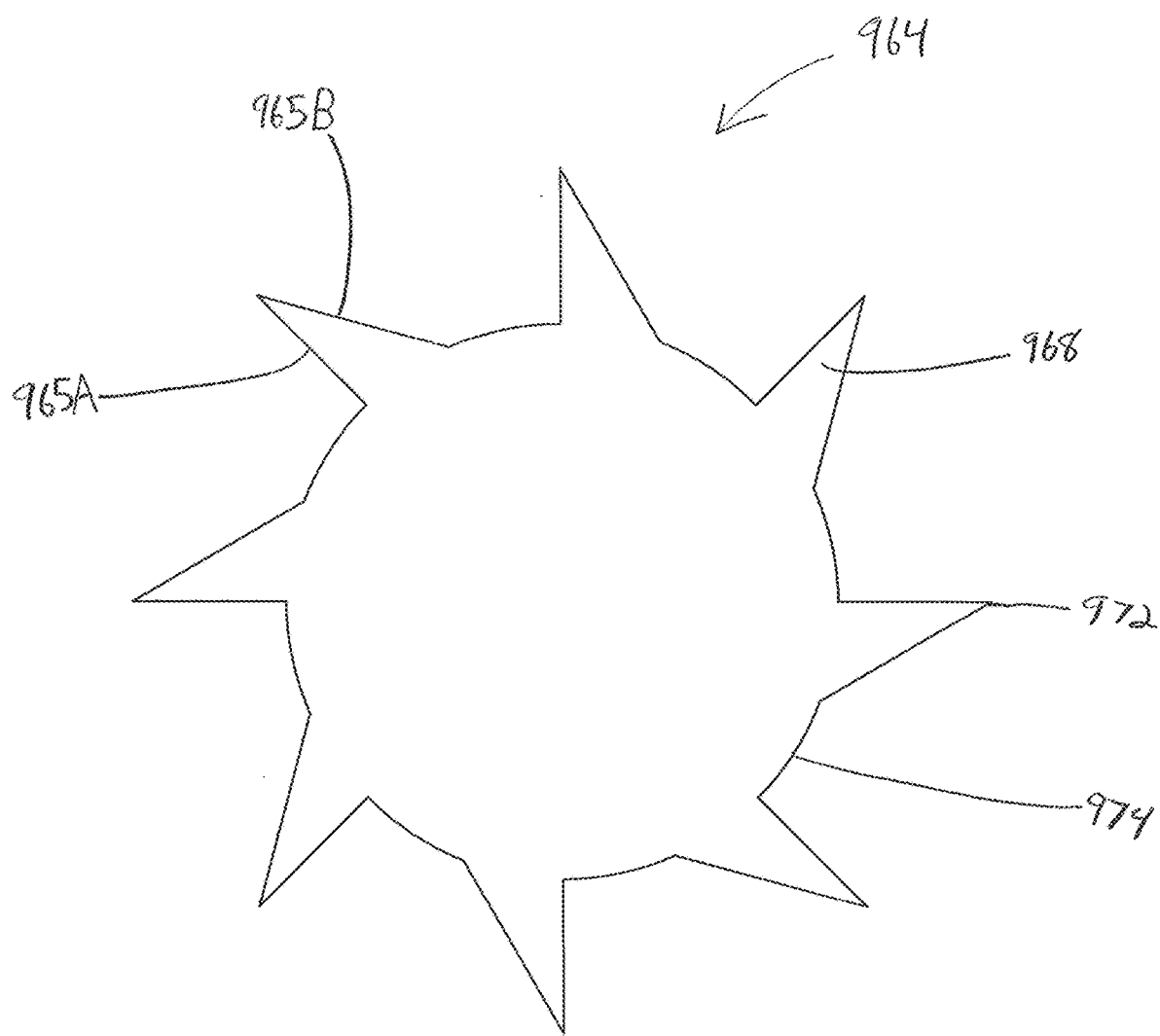

FIG. 126 is a side view of a cross-sectional face of the inner ring of FIG. 122, in accordance with aspects of the present disclosure.

Figure 127:
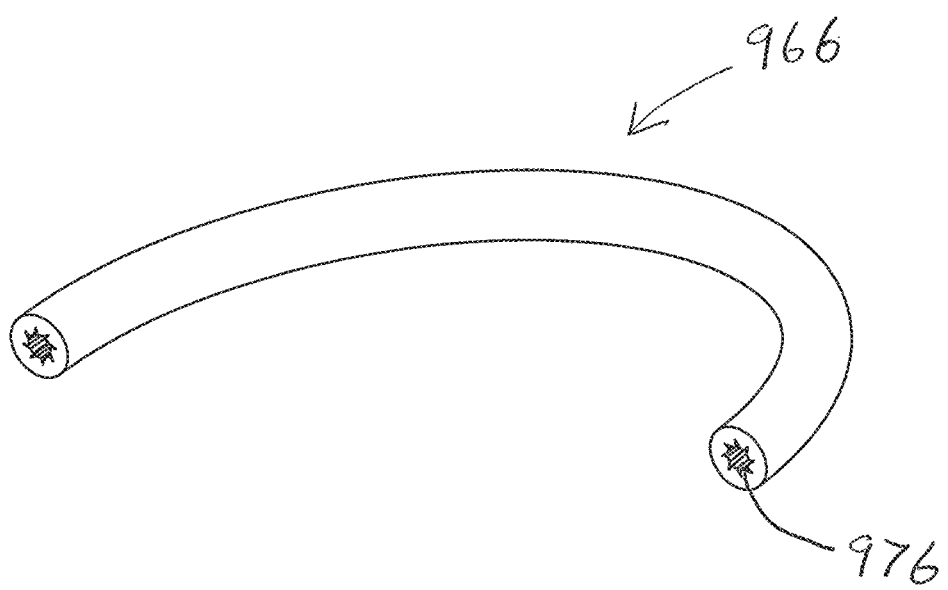
Figure 128:
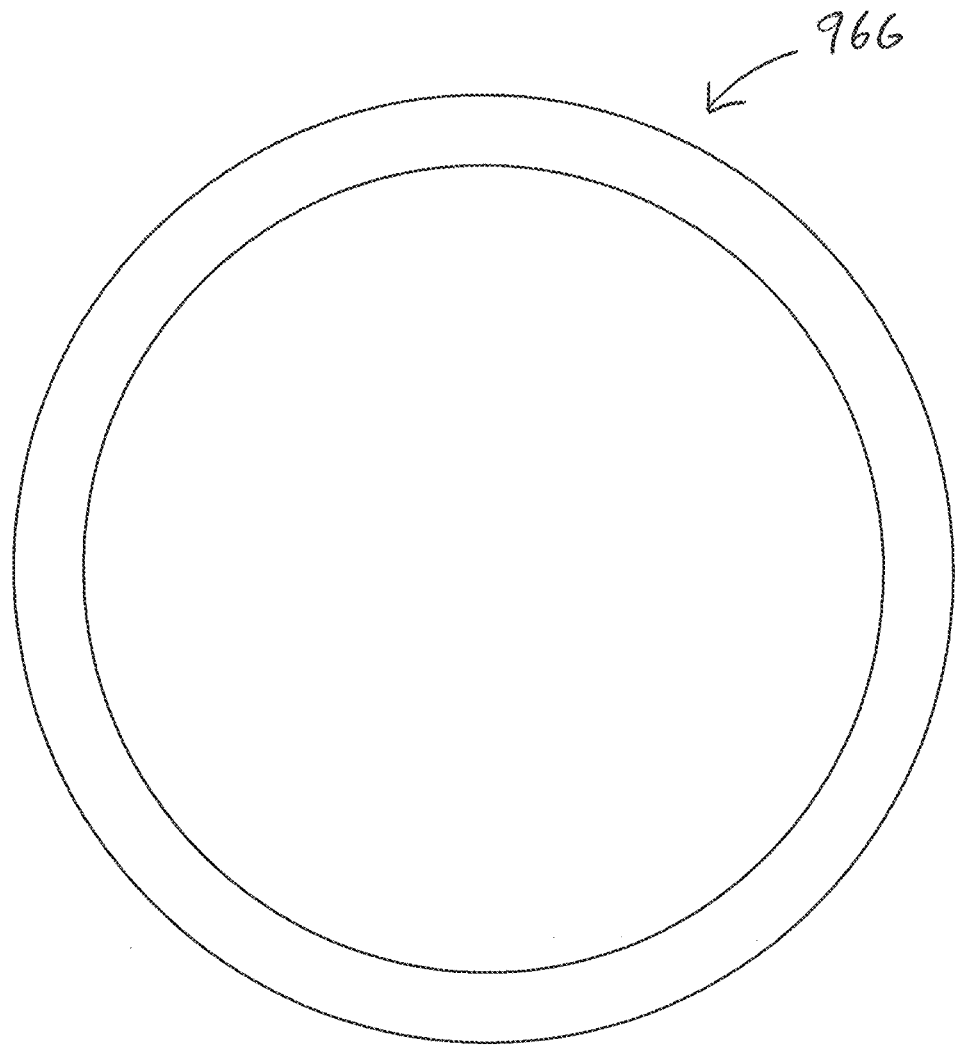
Figure 128:
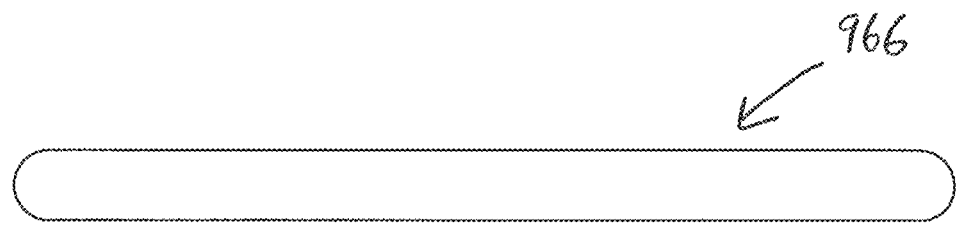

FIG. 127 is a cross-sectional perspective view of an outer ring of the retractor ring of FIG. 117, in accordance with aspects of the present disclosure.

Figure 129A:
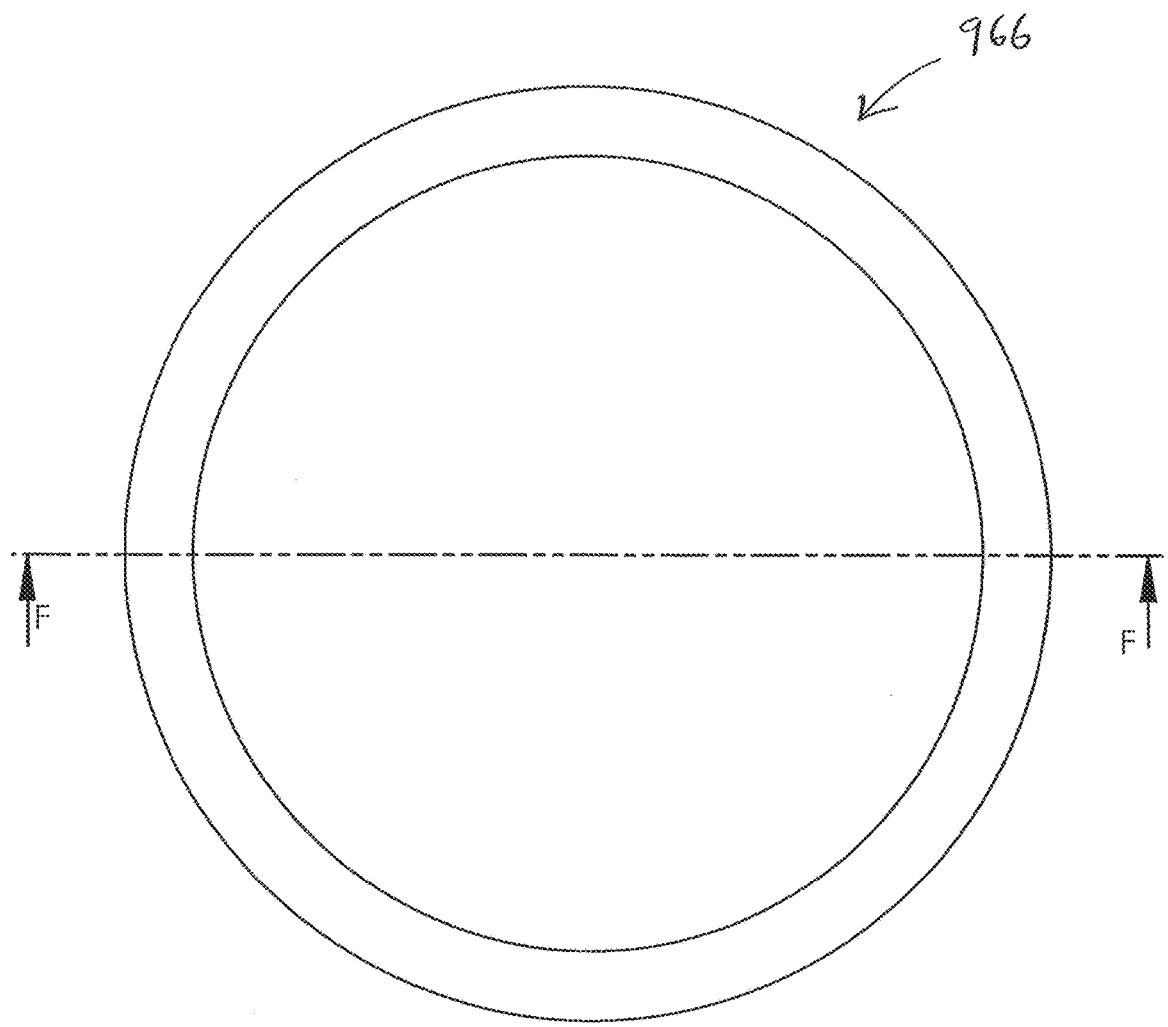
Figure 129B:
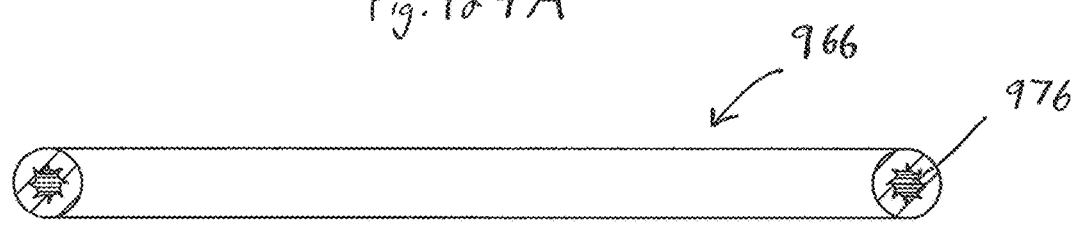

FIGS. 128A, 128B, 129A and 129B are top, side, bottom, and cross-sectional side views, respectively, of the outer ring of FIG. 127, in accordance with aspects of the present disclosure. The cross-sectional side view of FIG. 129B is taken along the line F-F in FIG. 129A.

Figure 130:
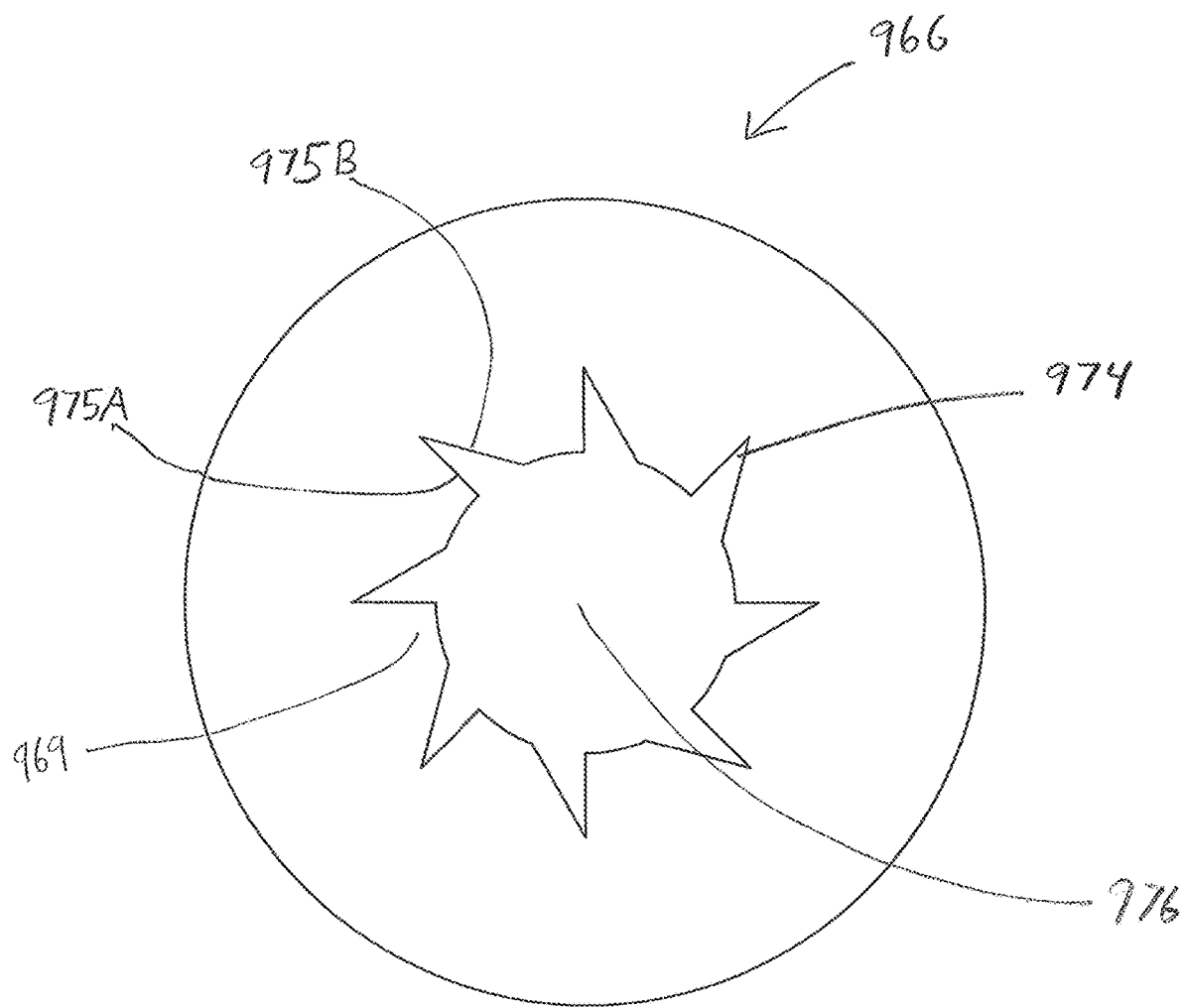

FIG. 130 is a side view of a cross-sectional face of the outer ring of FIG. 127, in accordance with aspects of the present disclosure.

Figure 131A:
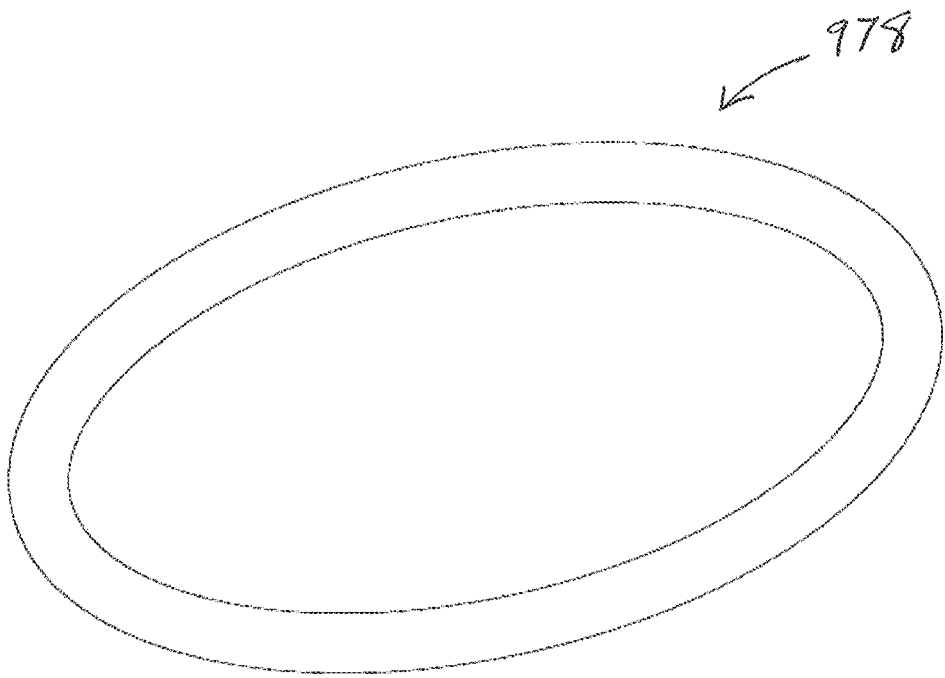

FIG. 131A is a perspective view of another exemplary retractor ring, in accordance with aspects of the present disclosure.

Figure 131B:
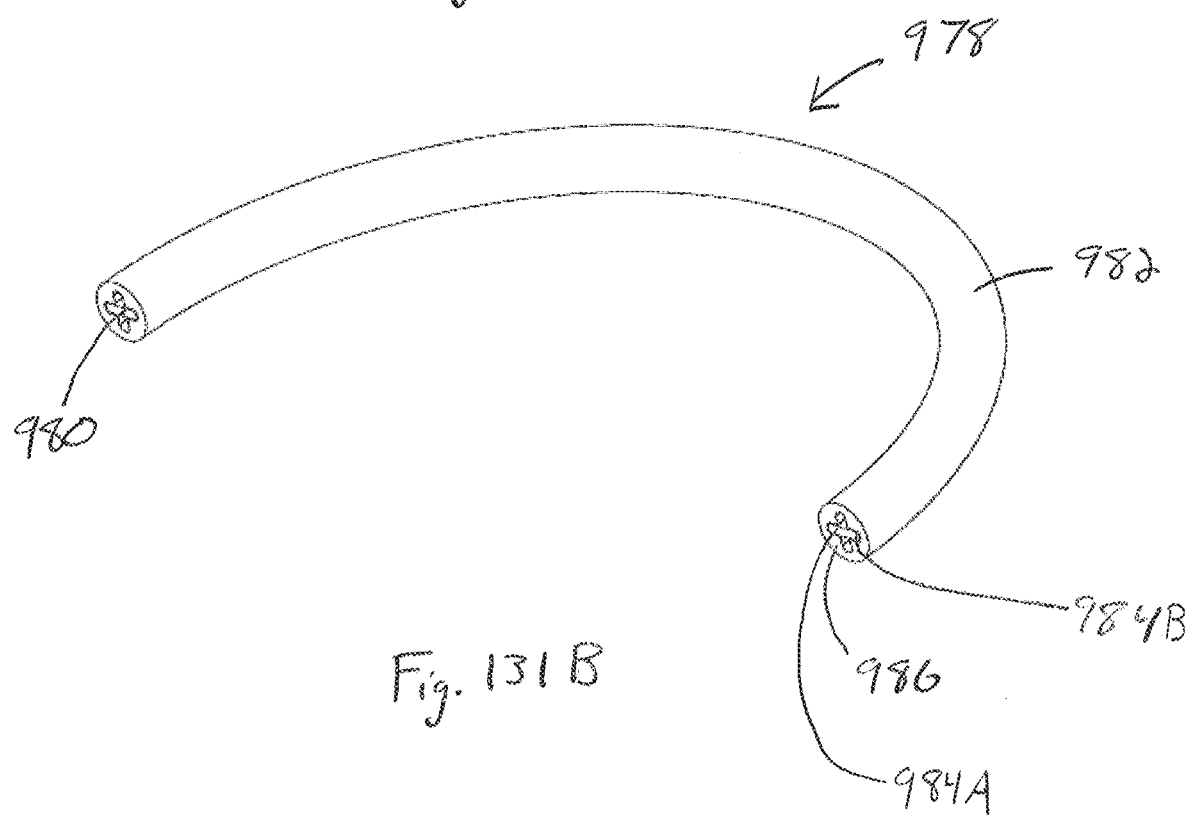

FIG. 131B is a cross-sectional perspective view of the retractor ring of FIG. 131A, in accordance with aspects of the present disclosure.

Figure 132A:
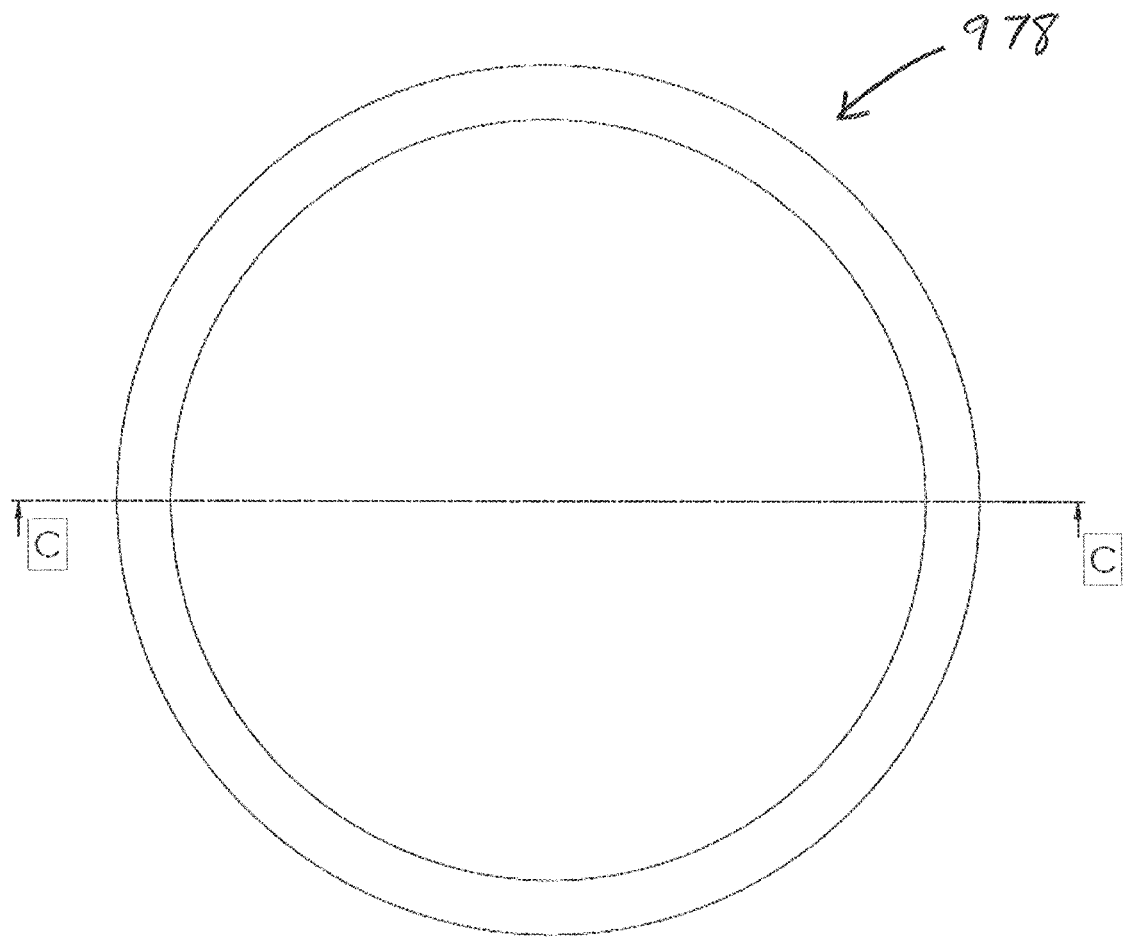
Figure 132B:
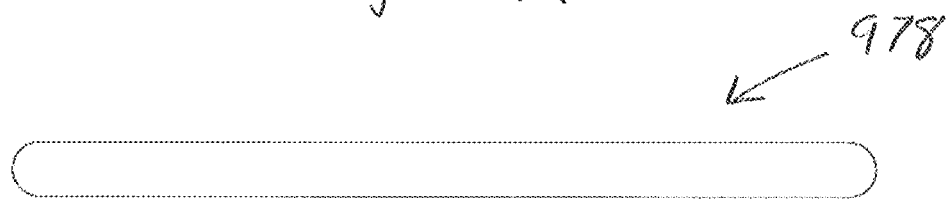
Figure 133:
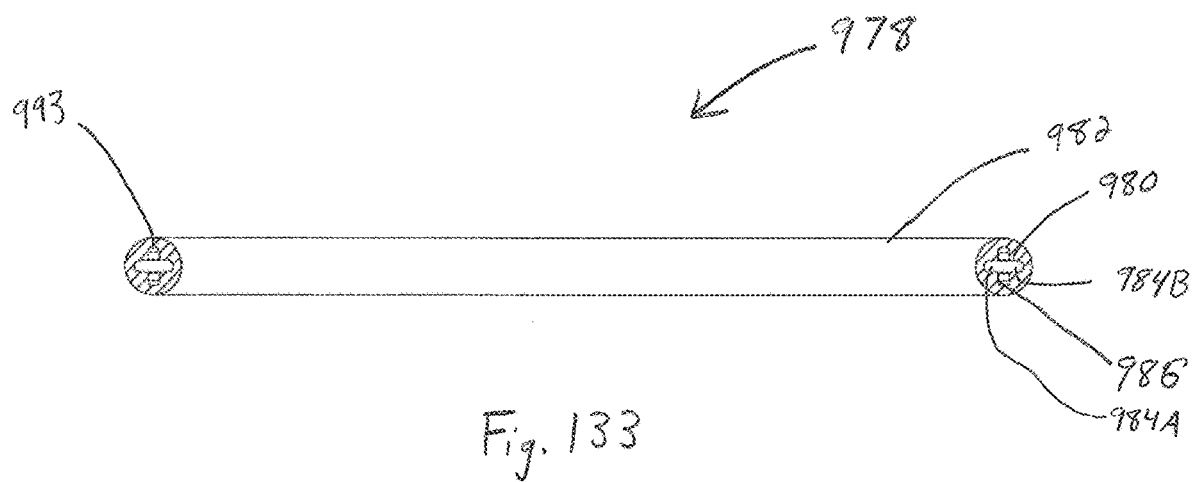

FIGS. 132A, 132B, and 133 are top, side, and cross-sectional side views, respectively, of the retractor ring of FIG. 131A, in accordance with aspects of the present disclosure. The cross-sectional side view of FIG. 133 is taken along the line C-C in FIG. 132A.

Figure 134A:
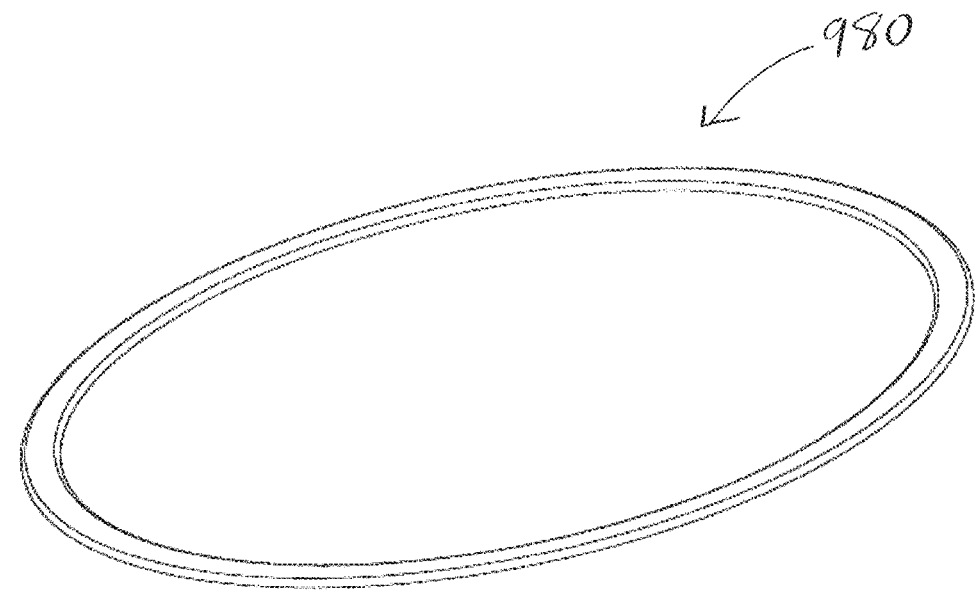
Figure 134B:
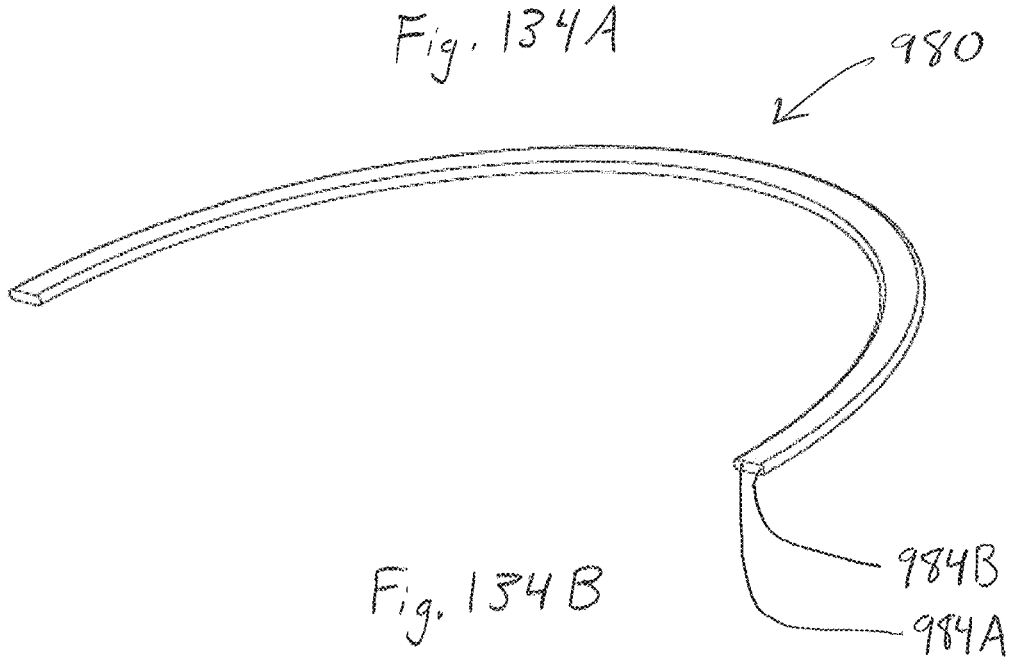
Figure 135A:
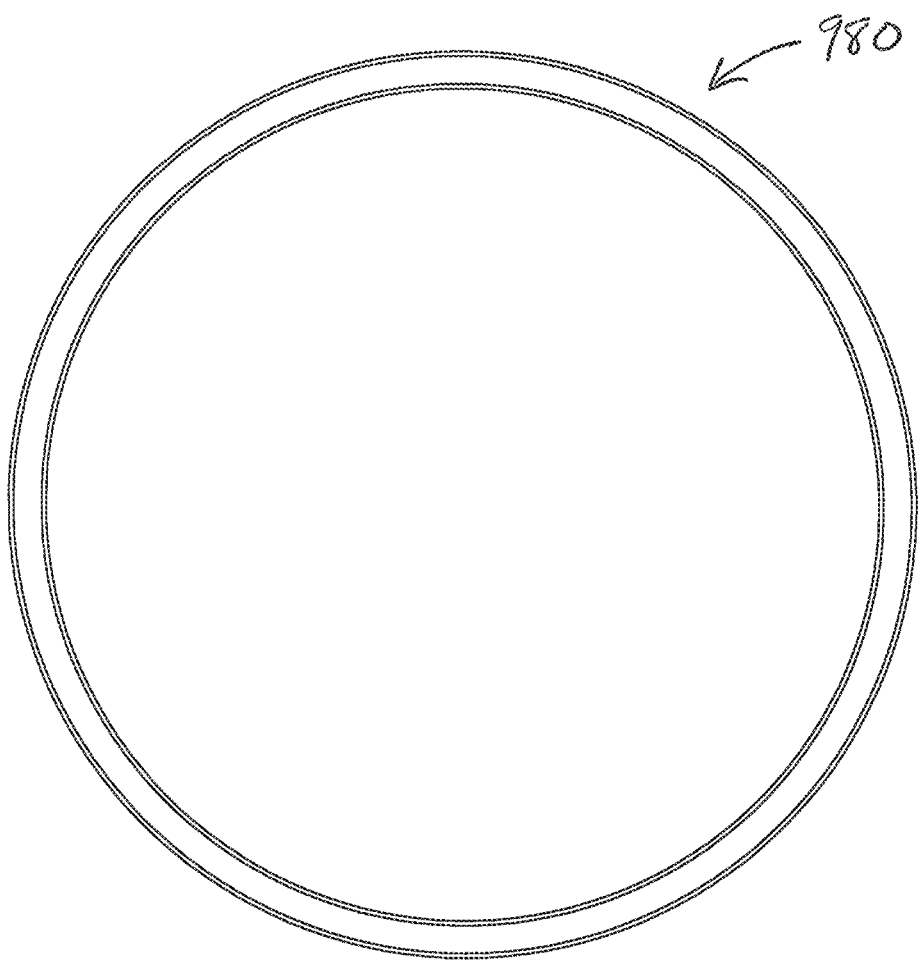
Figure 135B:
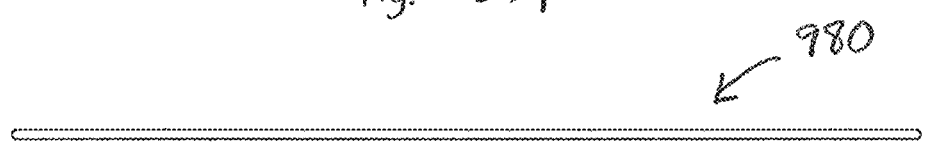

FIGS. 134A and 134B are perspective and cross-sectional perspective views, respectively, of an inner ring of the retractor ring of FIG. 131A, in accordance with aspects of the present disclosure.

Figure 136:
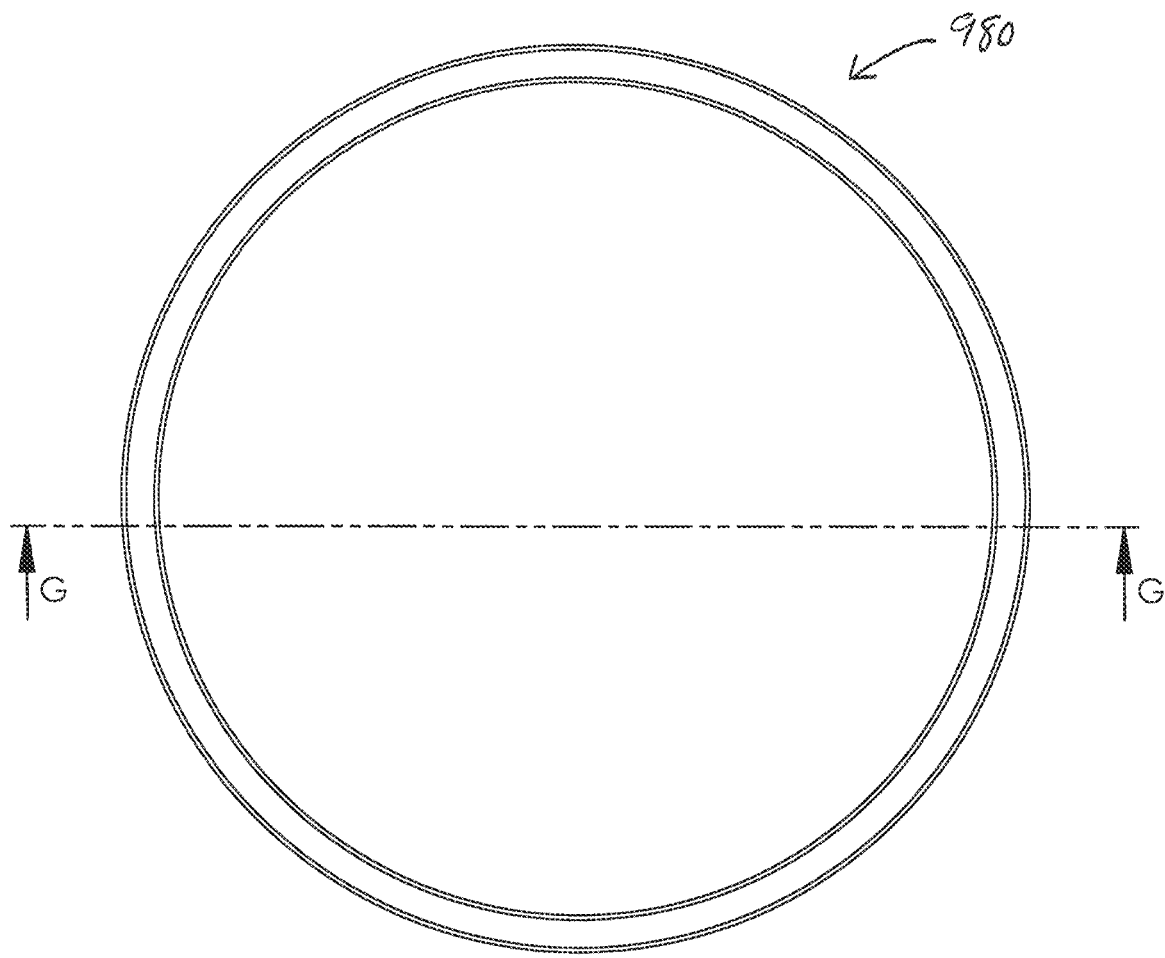
Figure 136:

FIGS. 135A, 135B, 136A, and 136B are top, side, bottom, and cross-sectional side views, respectively, of the inner ring of FIG. 134A, in accordance with aspects of the present disclosure. The cross-sectional side view of FIG. 136B is taken along the line G-G in FIG. 136A.

Figure 137:
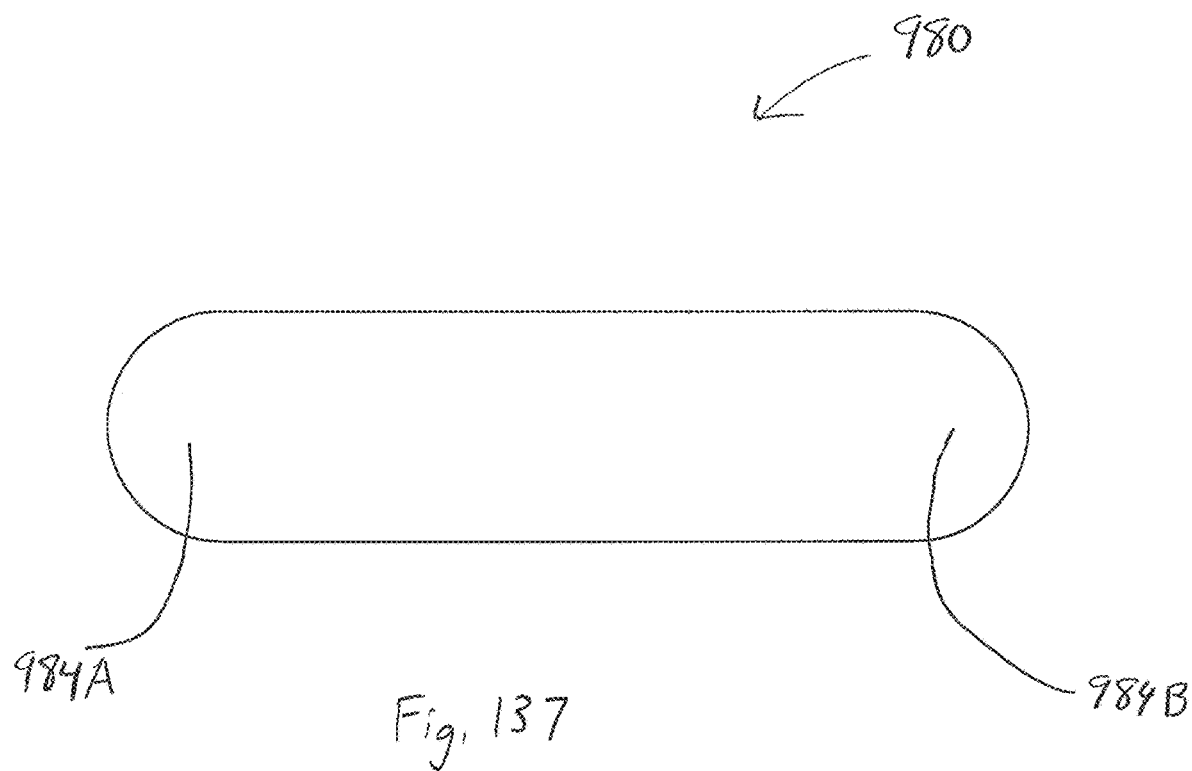

FIG. 137 is a side view of a cross-sectional face of the inner ring of FIG. 134A, in accordance with aspects of the present disclosure.

Figure 138A:
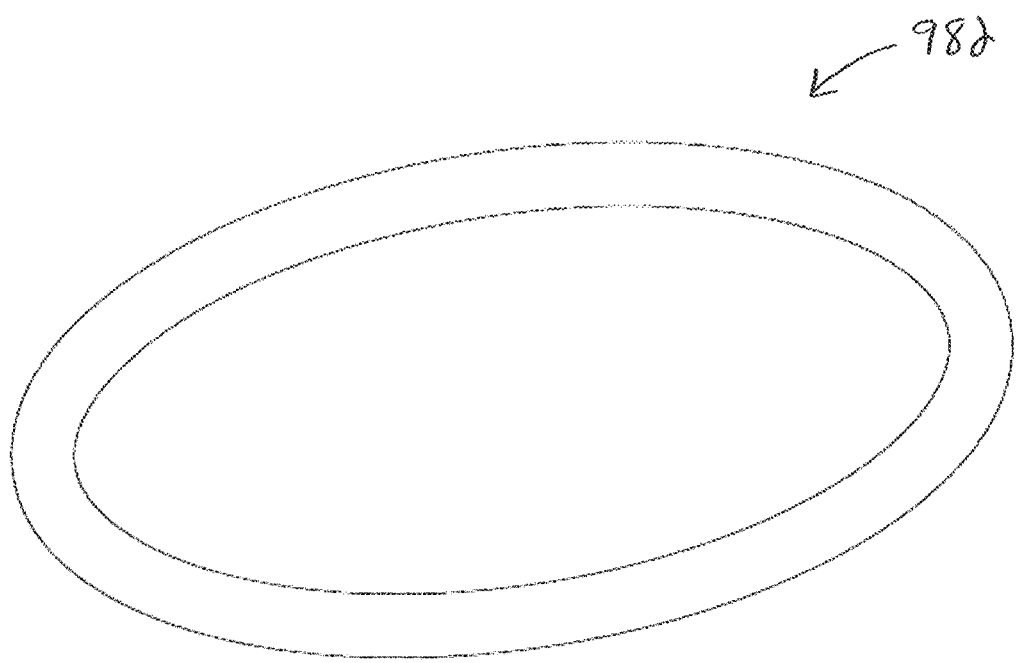
Figure 138B:
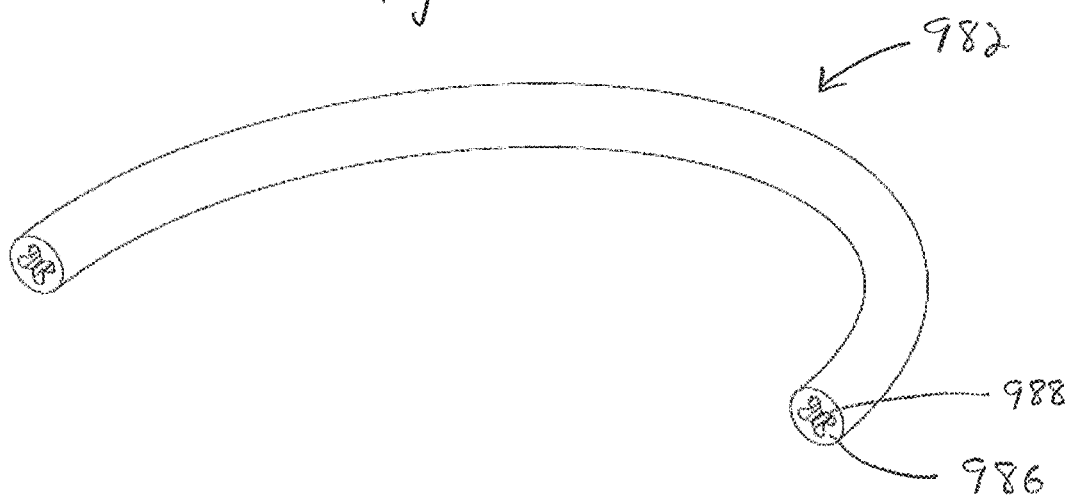

FIGS. 138A and 138B are perspective and cross-sectional perspective views, respectively, of an outer ring of the retractor ring of FIG. 131A, in accordance with aspects of the present disclosure.

Figure 139:
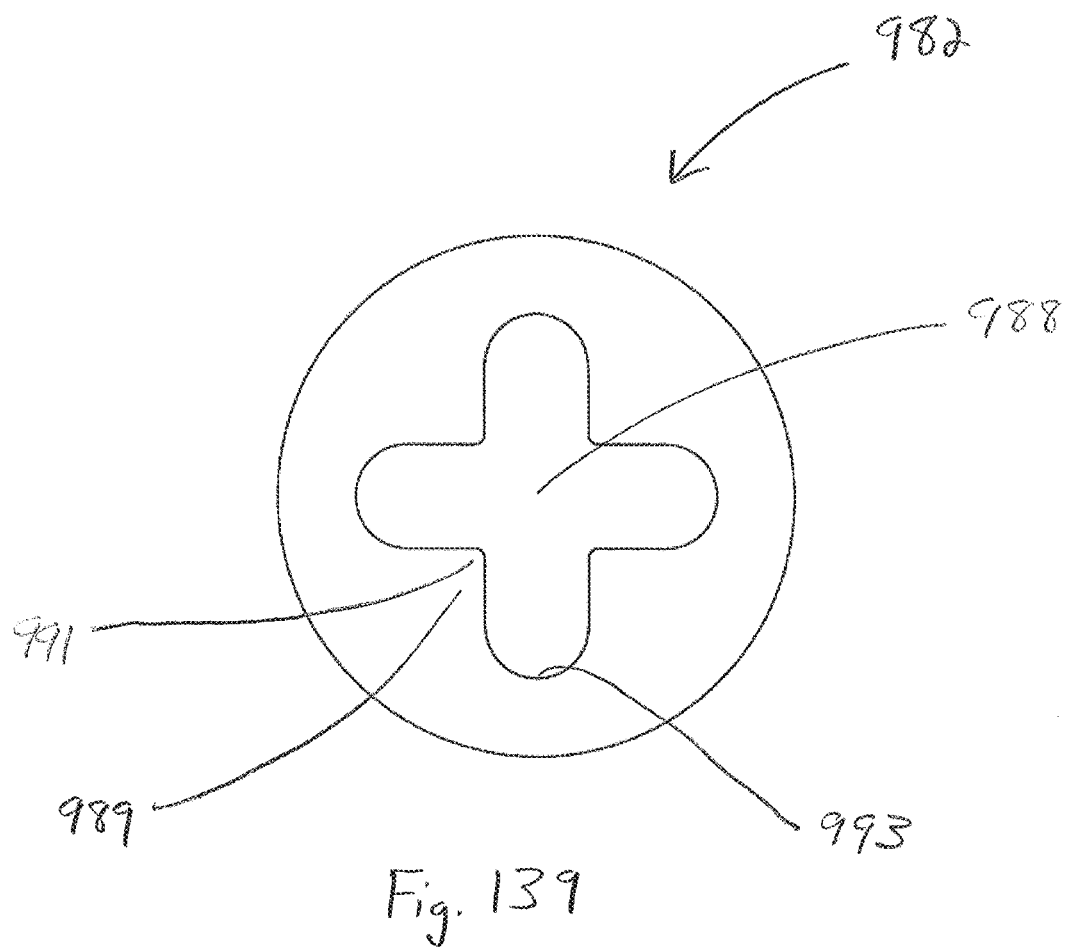

FIG. 139 is a side view of a cross-sectional face of the outer ring of FIG. 138A, in accordance with aspects of the present disclosure.

Figure 140:
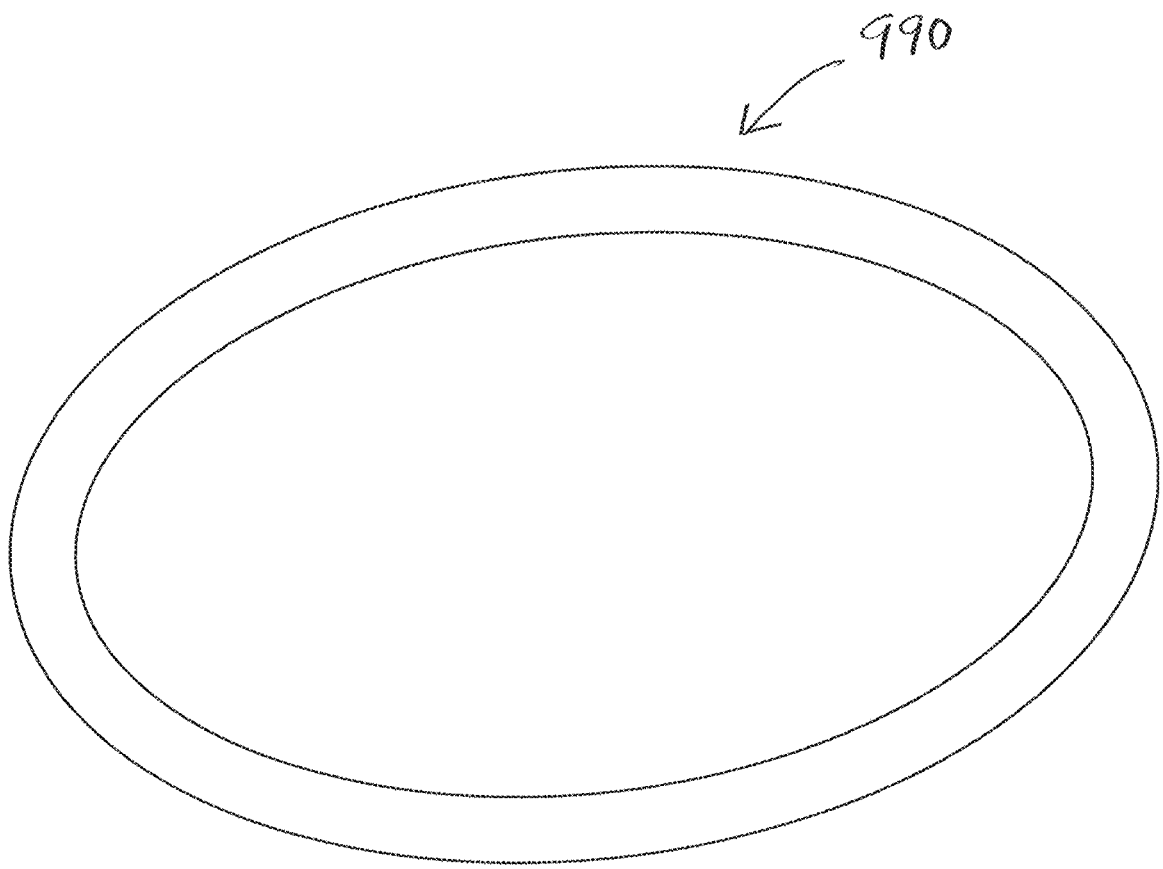

FIG. 140 is a perspective view of another exemplary retractor ring, in accordance with aspects of the present disclosure.

Figure 141:
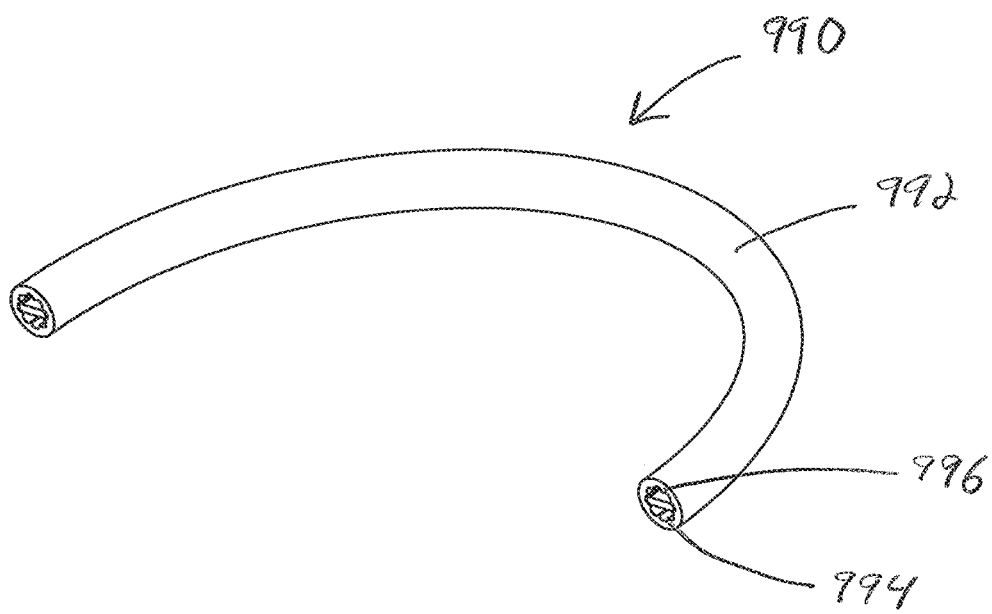

FIG. 141 is a cross-sectional perspective view of the retractor ring of FIG. 140, in accordance with aspects of the present disclosure.

Figure 142A:
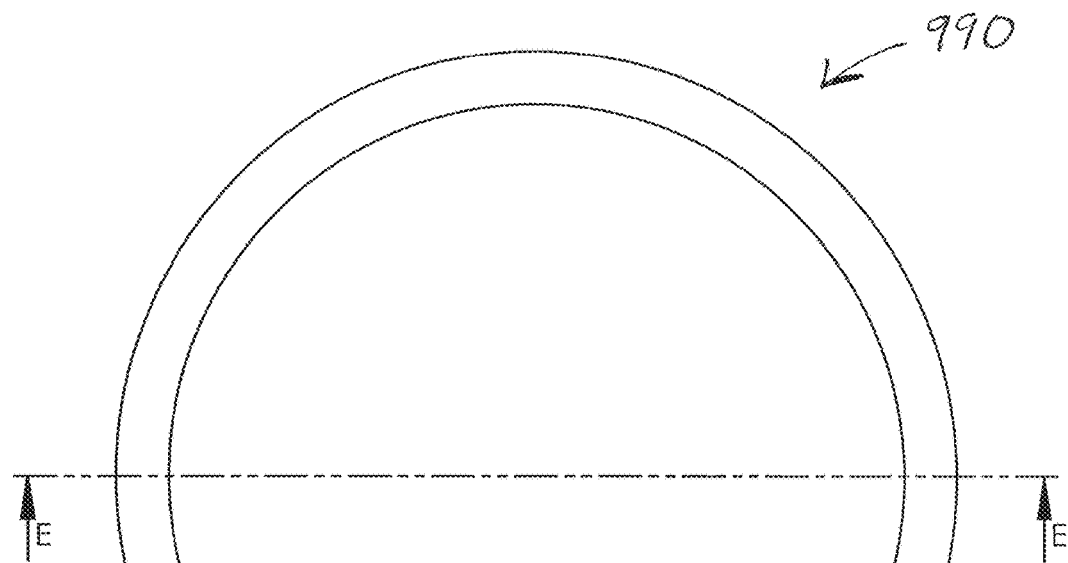
Figure 142B:
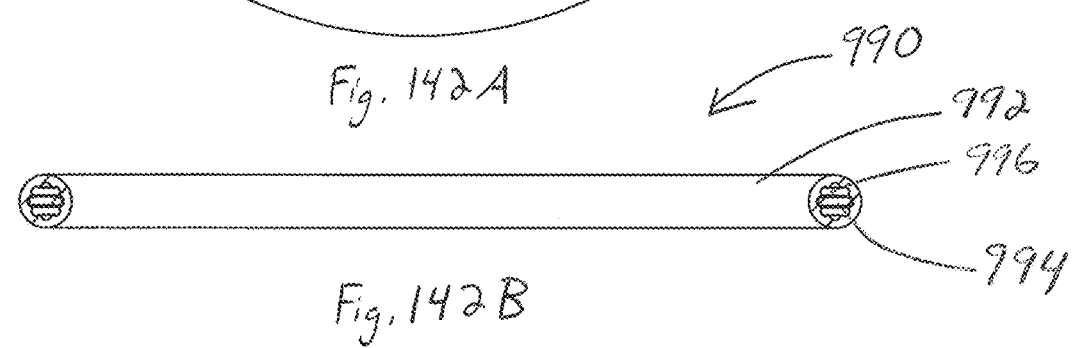

FIGS. 142A and 142B are top and cross-sectional side views, respectively, of the retractor ring of FIG. 140, in accordance with aspects of the present disclosure. The cross-sectional side view of FIG. 142B is taken along the line E-E in FIG. 142A.

Figure 143:
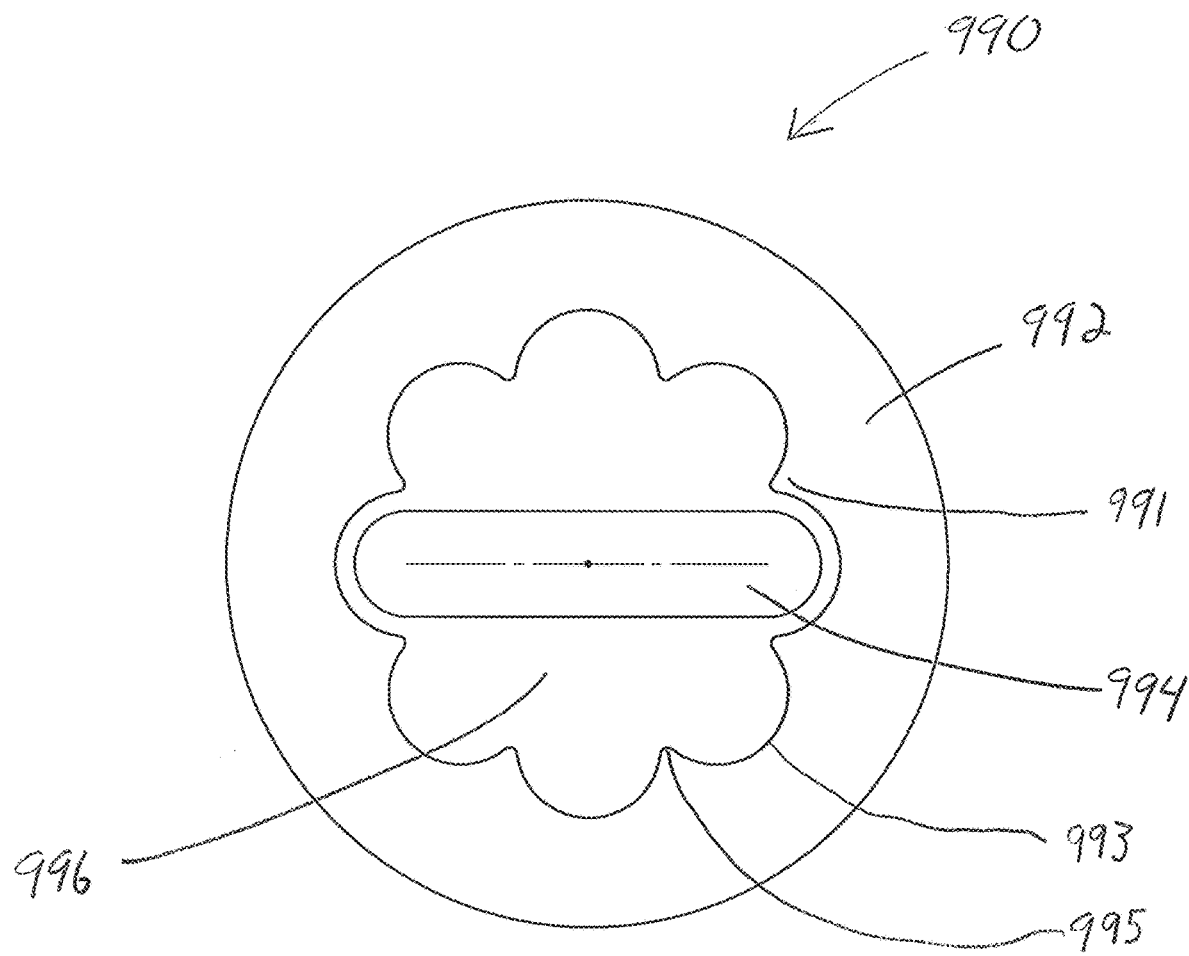

FIG. 143 is a side view of a cross-sectional face of the retractor ring of FIG. 140, in accordance with aspects of the present disclosure.

Figure 144A:
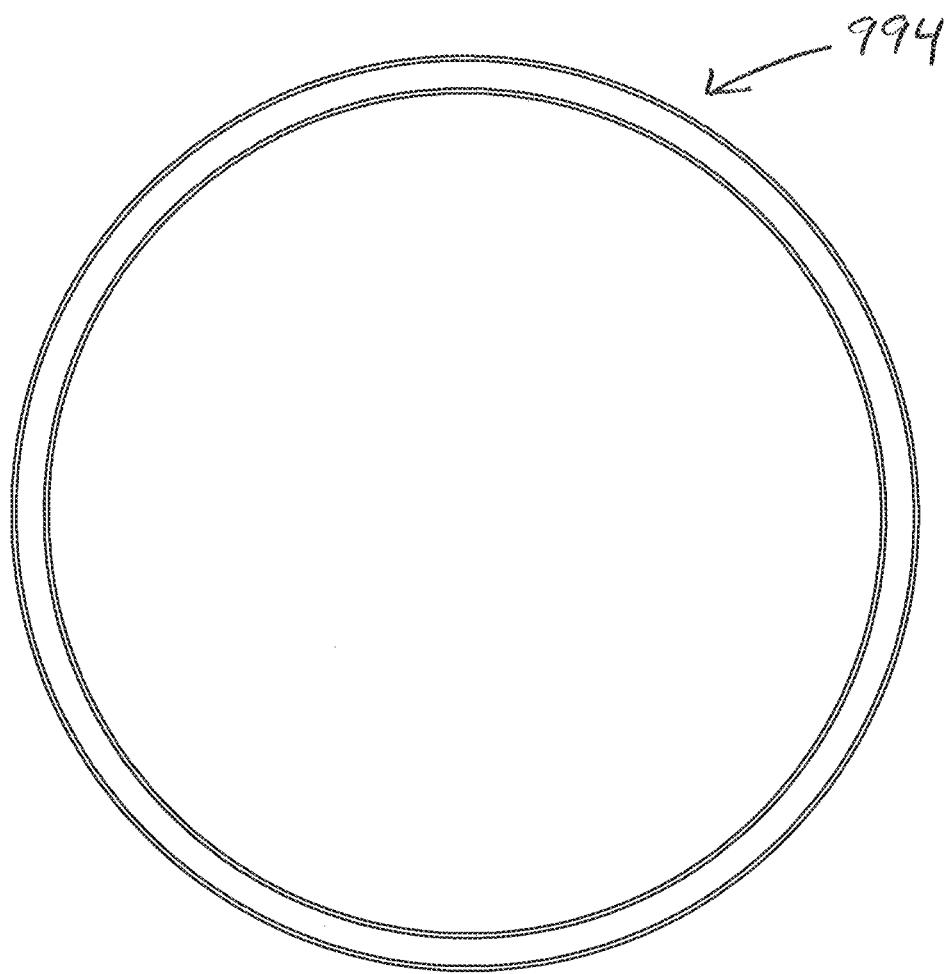
Figure 144B:
Figure 145A:
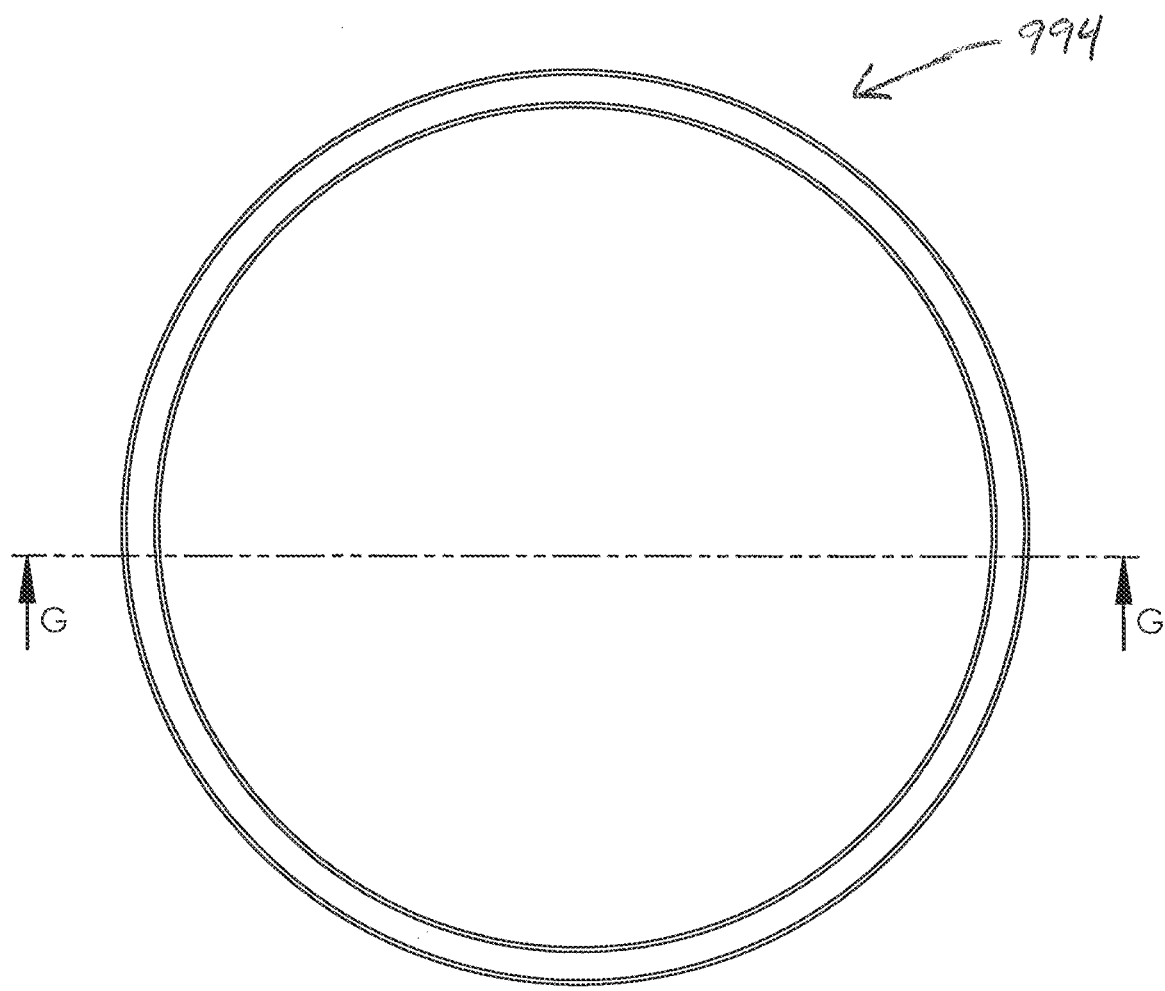
Figure 145B:
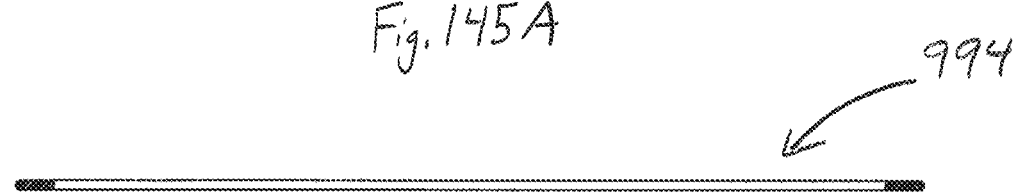

FIGS. 144A, 144B, 145A and 145B are top, side, bottom, and cross-sectional side views, respectively, of an inner ring of the retractor ring of FIG. 140, in accordance with aspects of the present disclosure. The cross-sectional side view of FIG. 145B is taken along the line G-G in FIG. 145A.

Figure 146:
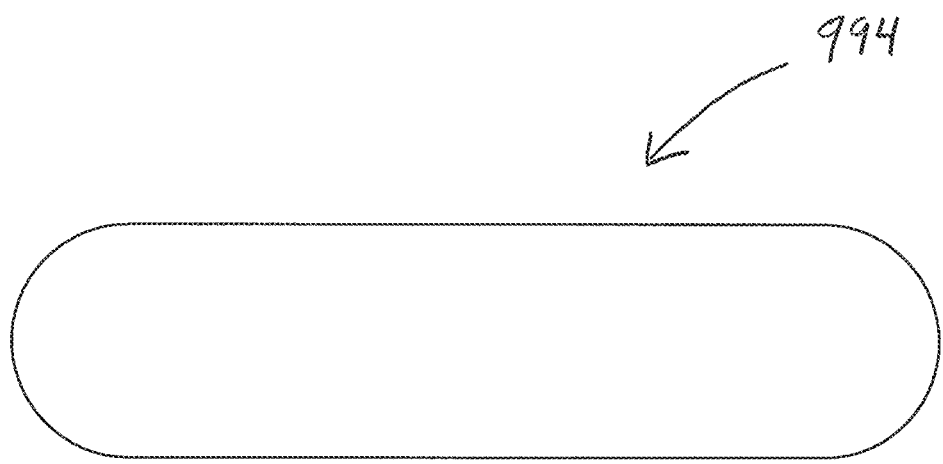

FIG. 146 is a side view of a cross-sectional face of the inner ring of FIG. 144A, in accordance with aspects of the present disclosure.

Figure 147:
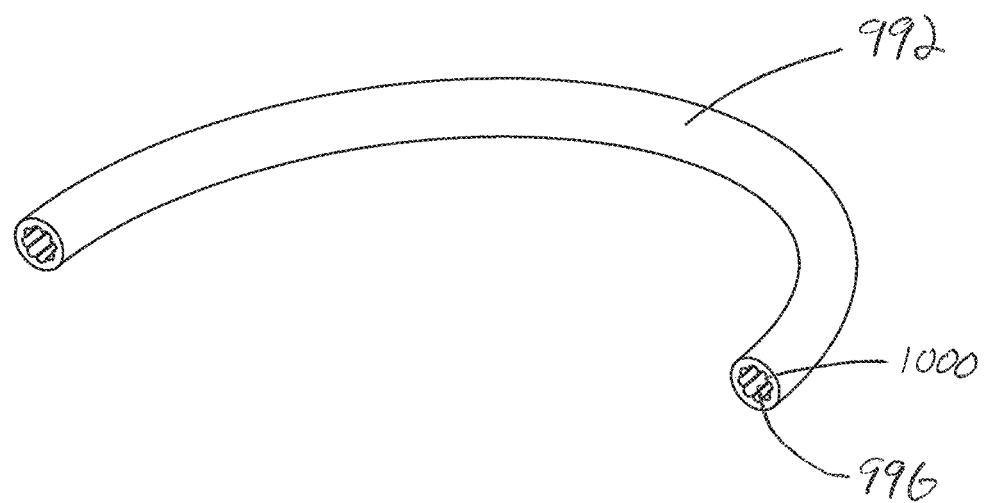
Figure 148A:
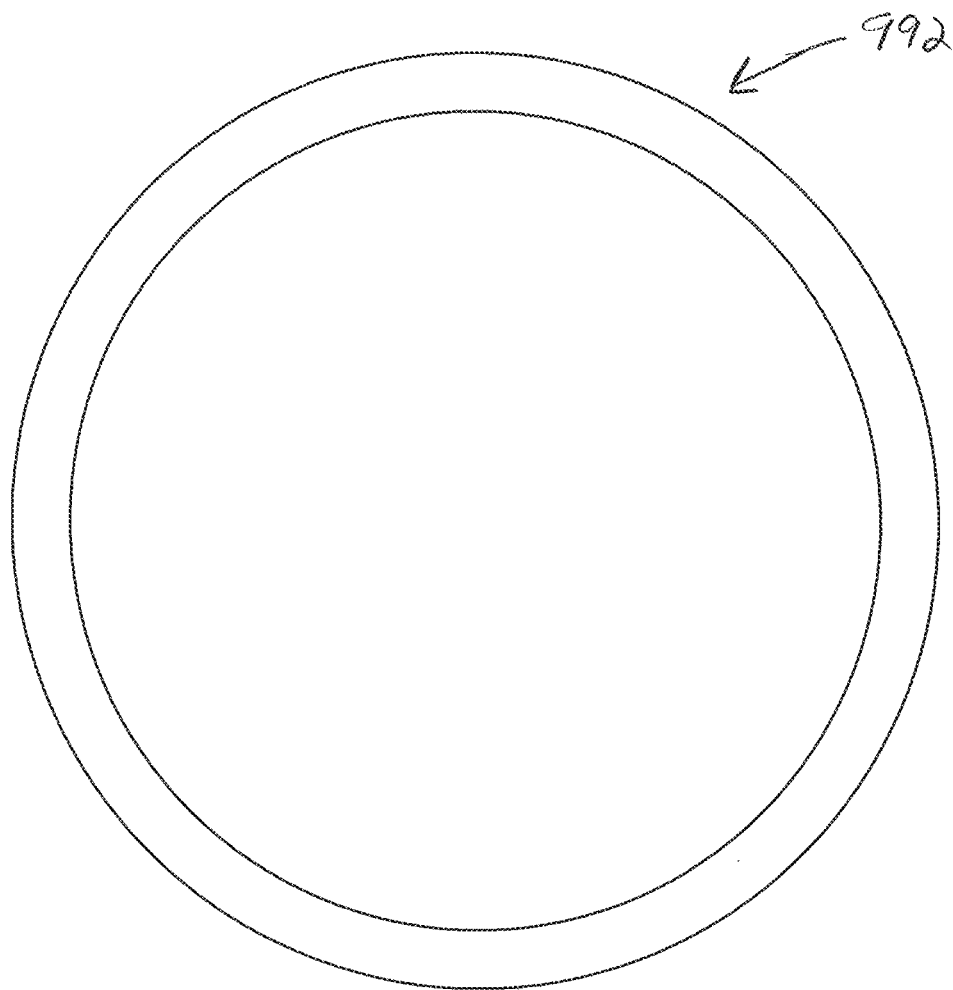
Figure 148B:
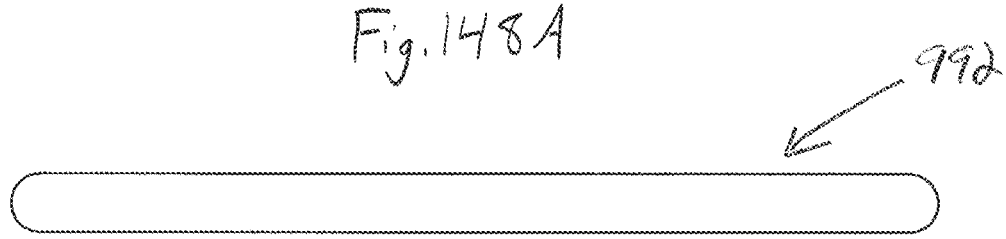

FIG. 147 is a cross-sectional perspective view of an outer ring of the retractor ring of FIG. 140, in accordance with aspects of the present disclosure.

Figure 149A:
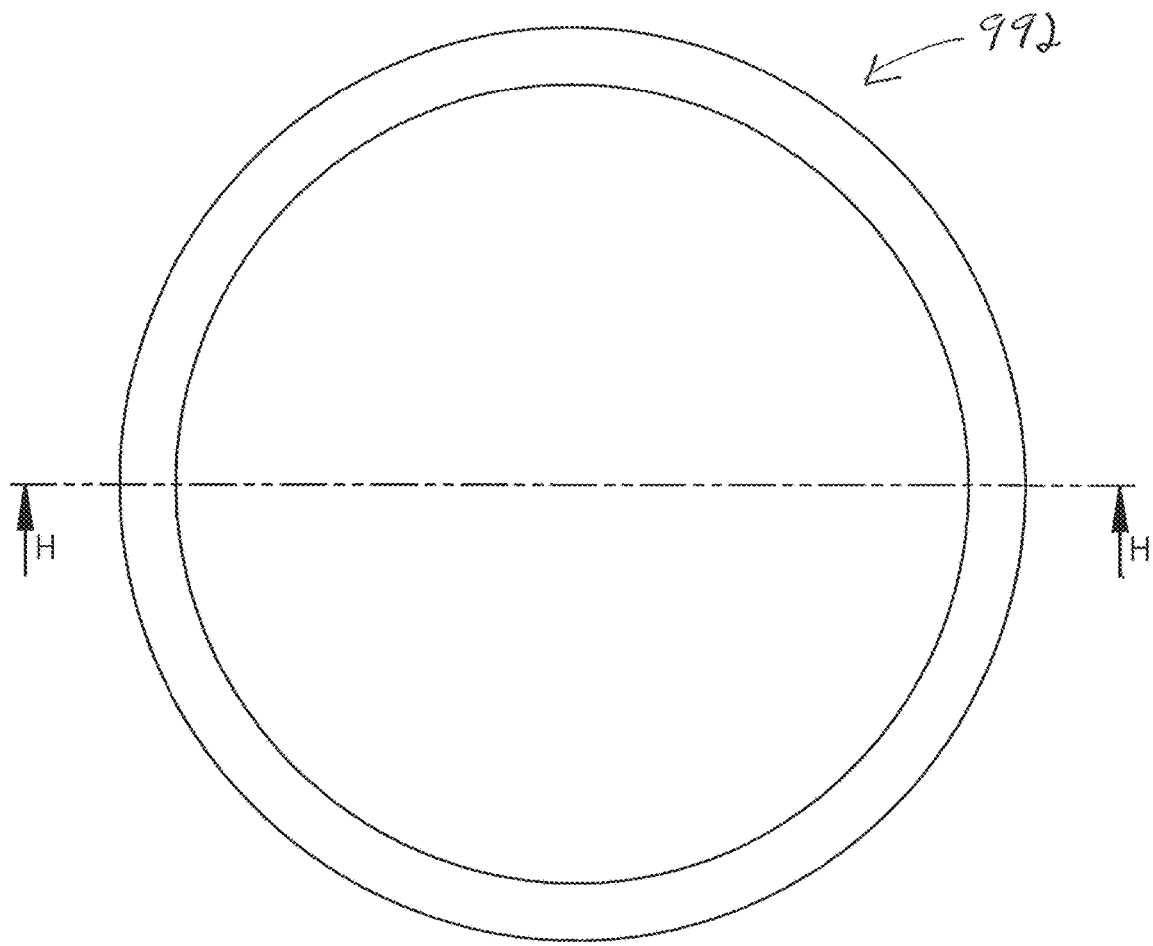
Figure 149B:
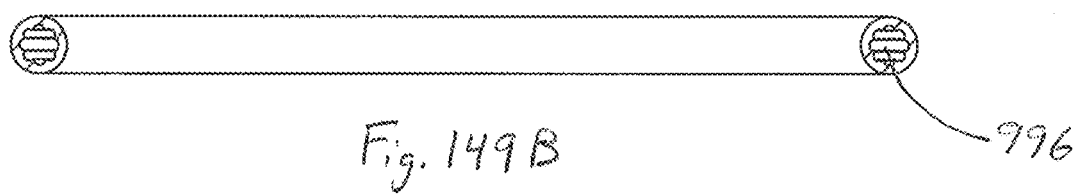

FIGS. 148A, 148B, 149A and 149B are top, side, bottom, and cross-sectional side views, respectively, of the outer ring of FIG. 147, in accordance with aspects of the present disclosure. The cross-sectional side view of FIG. 149B is taken along the line H-H in FIG. 149A.

Figure 150:
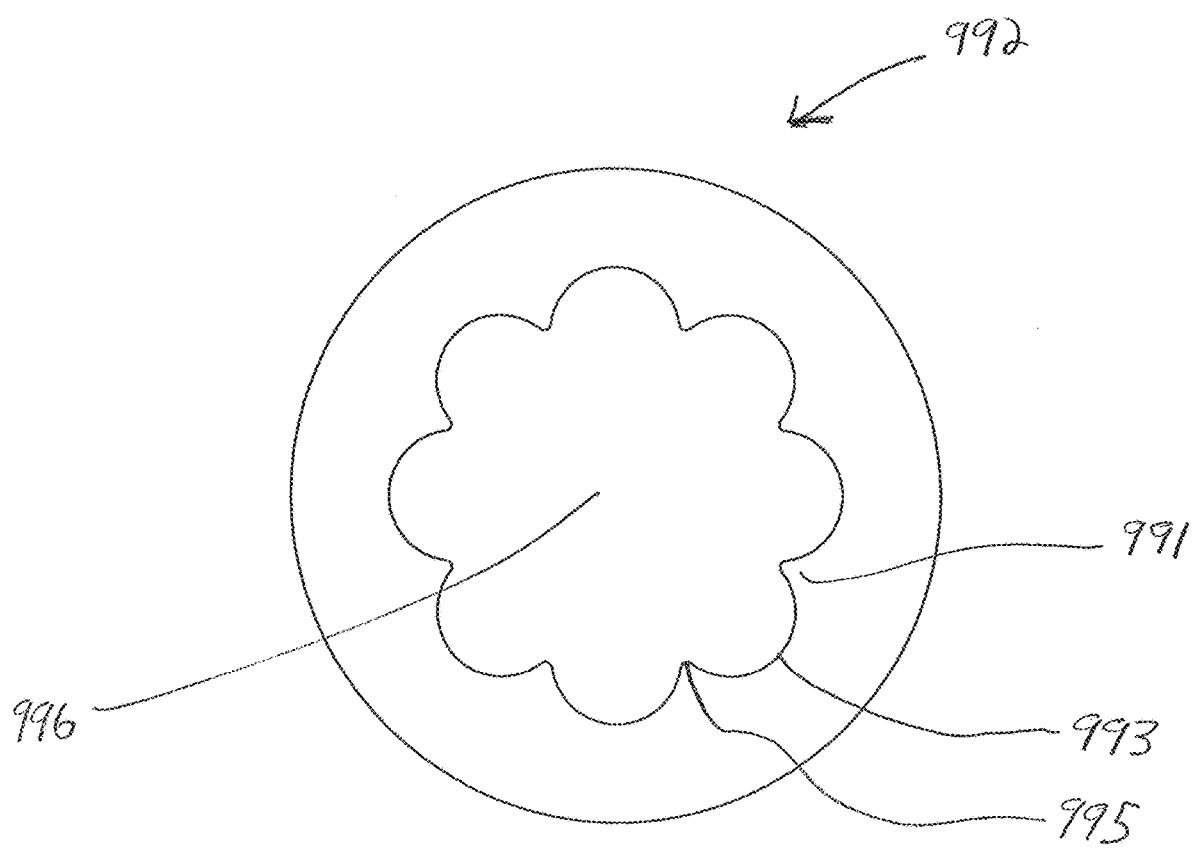

FIG. 150 is a side view of a cross-sectional face of the outer ring of FIG. 147, in accordance with aspects of the present disclosure.

Figure 151:
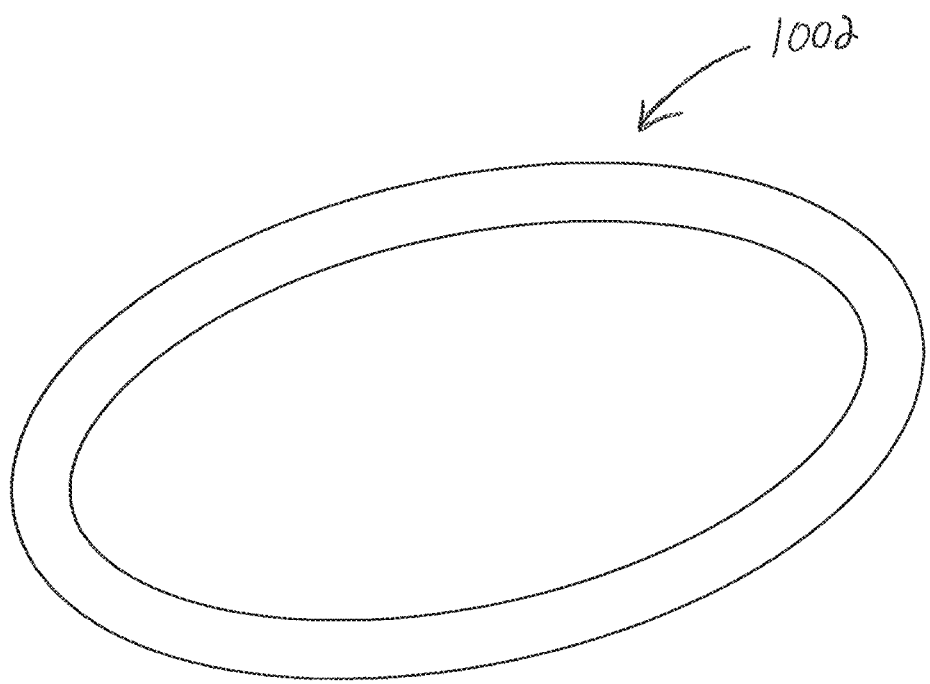

FIG. 151 is a perspective view of another exemplary retractor ring, in accordance with aspects of the present disclosure.

Figure 152:
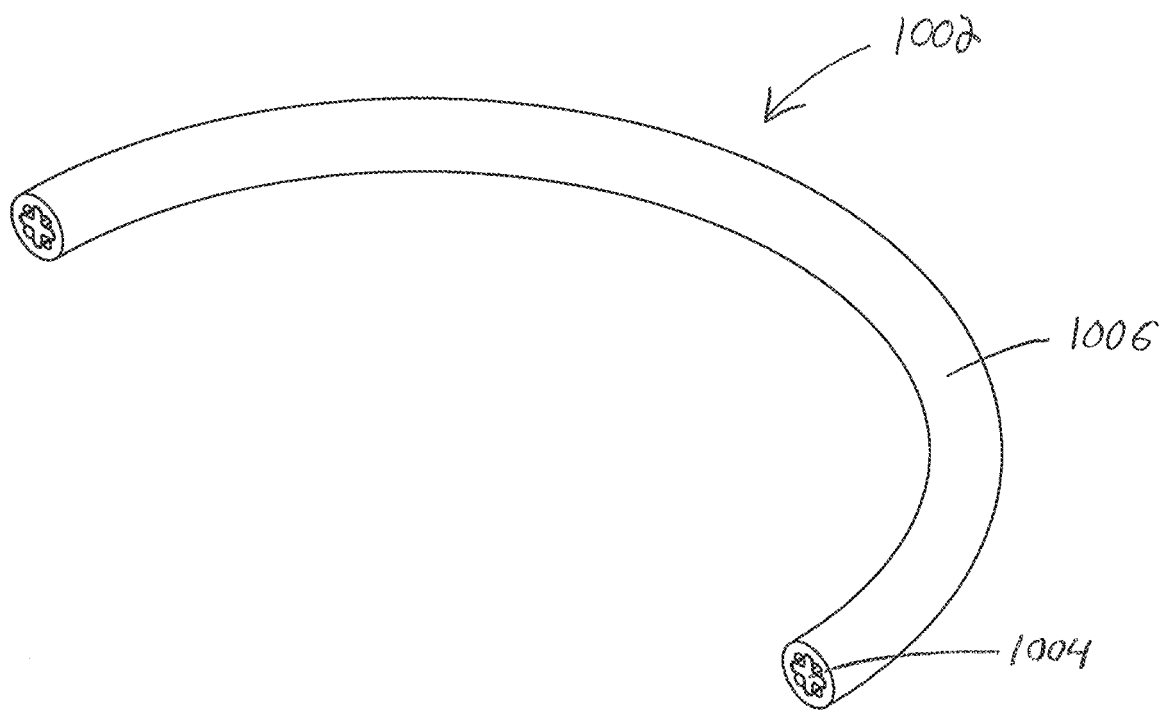

FIG. 152 is a cross-sectional perspective view of the retractor ring of FIG. 151, in accordance with aspects of the present disclosure.

Figure 153A:
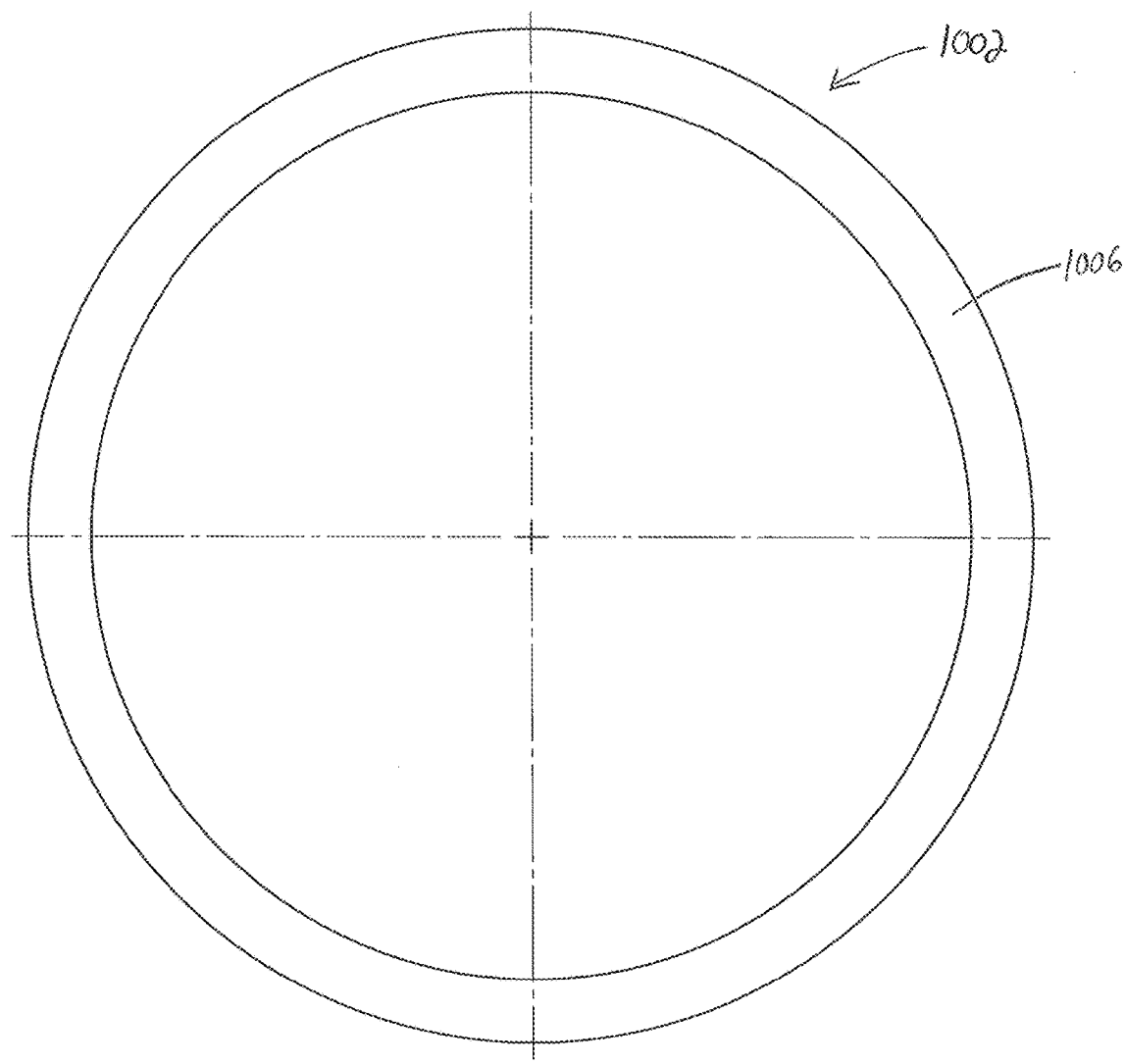
Figure 153B:
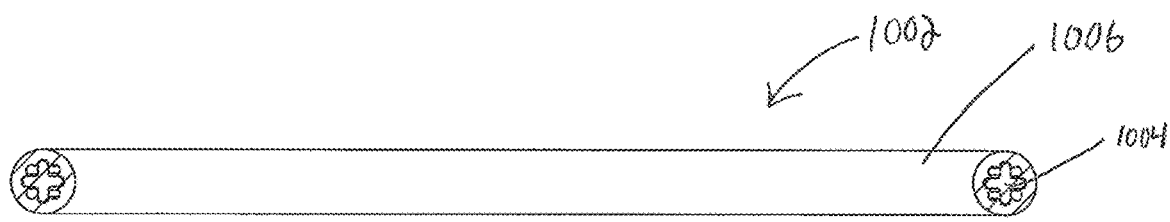
Figure 154A:
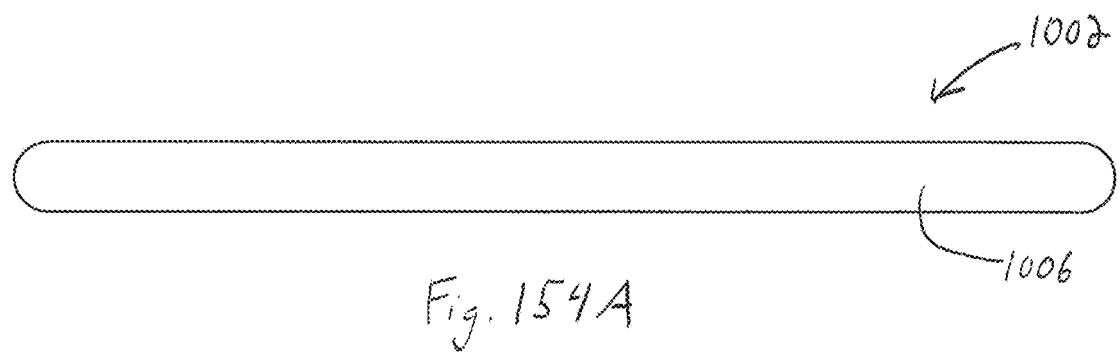

FIGS. 153A, 153B, and 154A are top, cross-sectional side, and side views, respectively, of the retractor ring of FIG. 151, in accordance with aspects of the present disclosure.

Figure 154B:
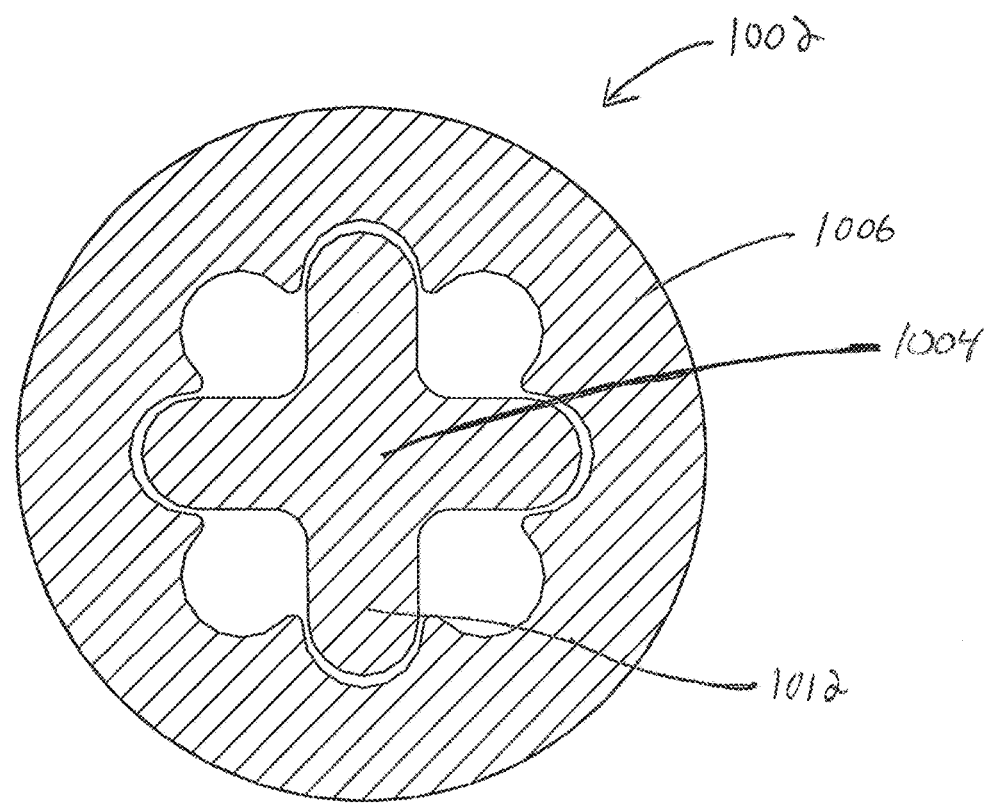

FIG. 154B is a side view of a cross-sectional face of the retractor ring of FIG. 151, in accordance with aspects of the present disclosure.

Figure 155:
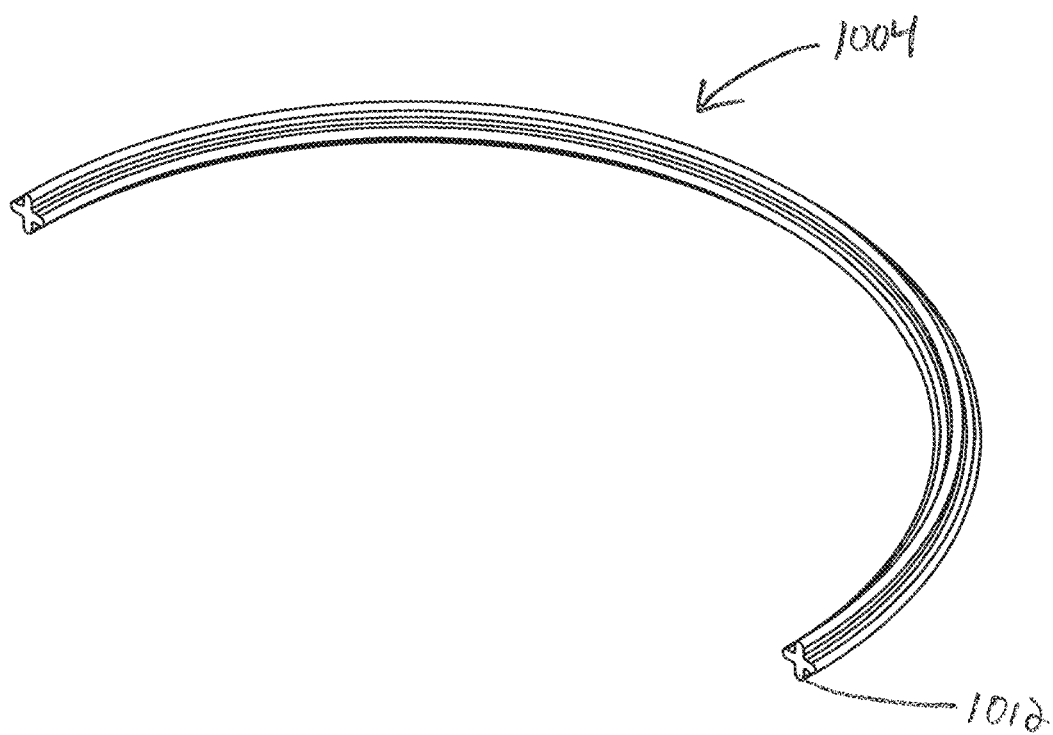

FIG. 155 is a cross-sectional perspective view of an inner ring of the retractor ring of FIG. 151, in accordance with aspects of the present disclosure.

Figure 156:
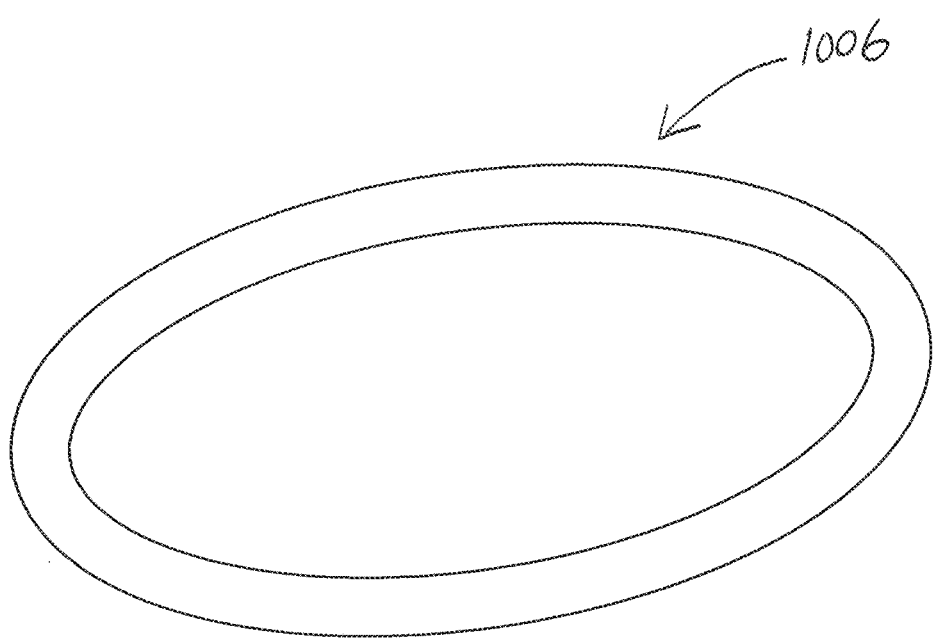
Figure 157:
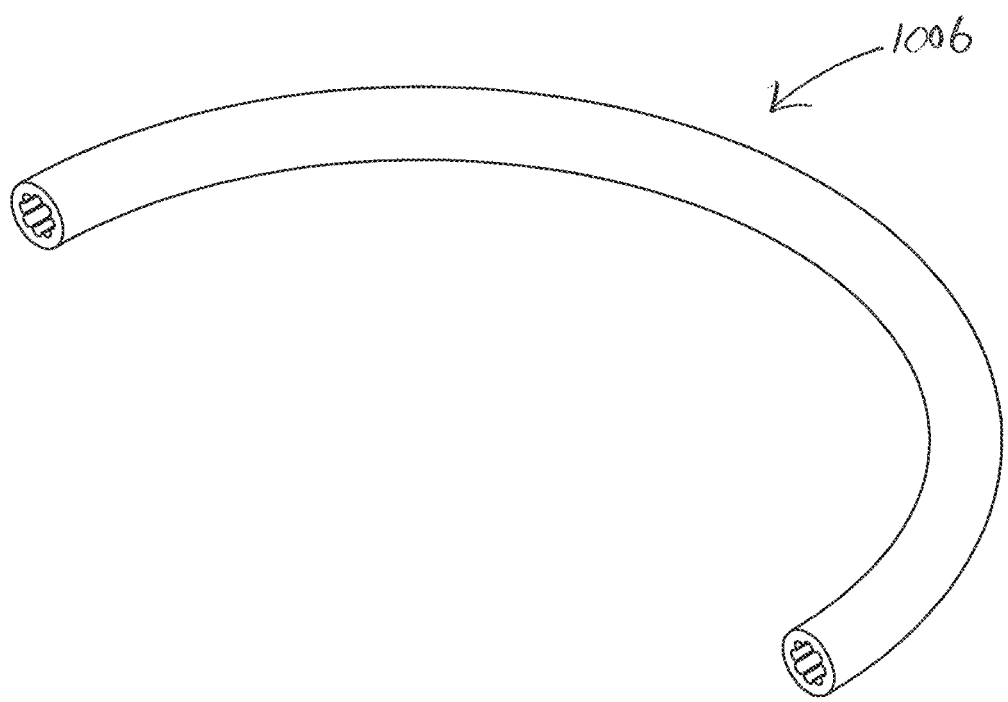

FIGS. 156 and 157 are perspective and cross-sectional perspective views, respectively, of an outer ring of the retractor ring of FIG. 151, in accordance with aspects of the present disclosure.

Figure 158:
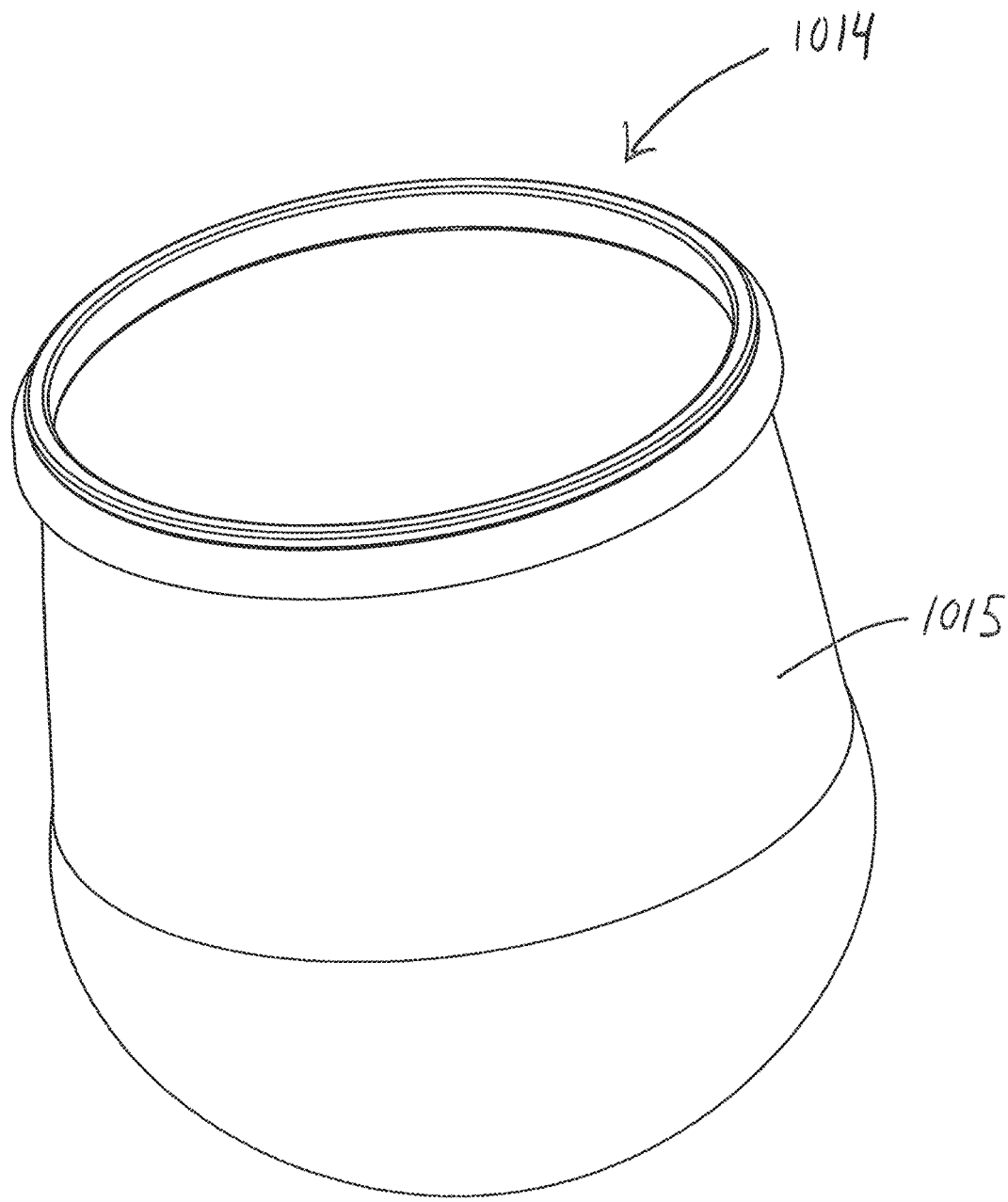
Figure 159:
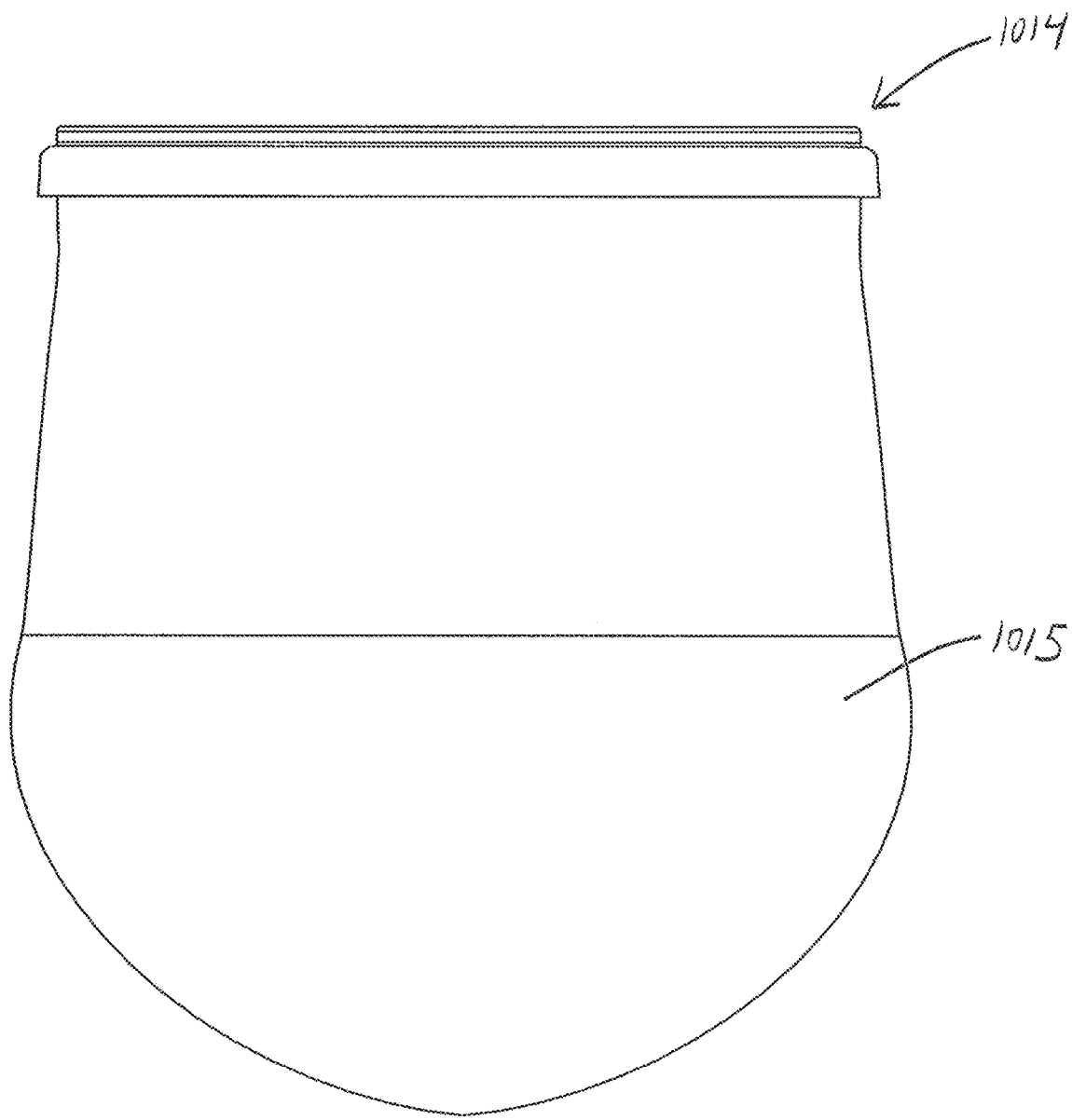

FIGS. 158 and 159 are perspective and side views, respectively, of another exemplary bag assembly, in accordance with aspects of the present disclosure.

Figures 160A, 160B:
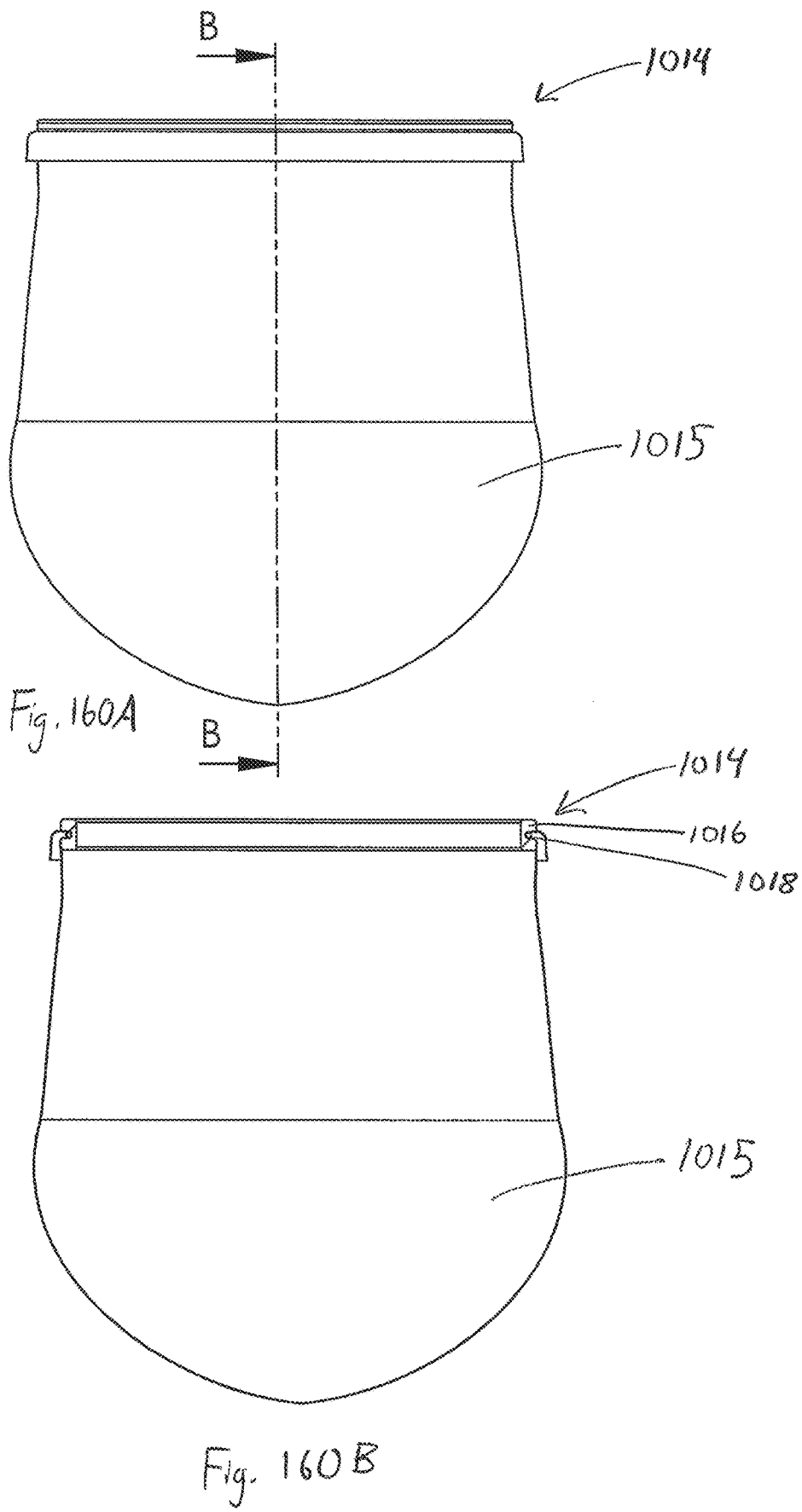

FIGS. 160A and 160B are side and cross-sectional side views, respectively, of the bag assembly of FIG. 158, in accordance with aspects of the present disclosure. The cross-sectional side view of FIG. 160B is taken along the line B-B in FIG. 160A.

Figure 161:
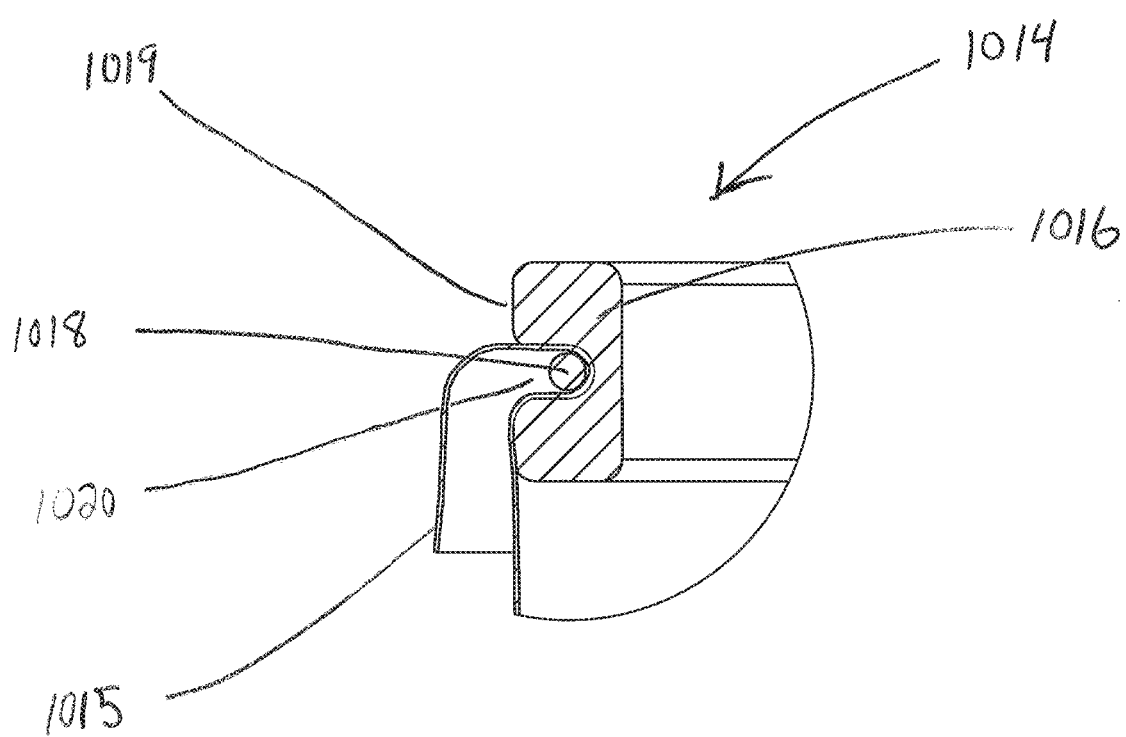

FIG. 161 is a partial cross-sectional side view of the bag assembly of FIG. 158, in accordance with aspects of the present disclosure.

Figure 162:
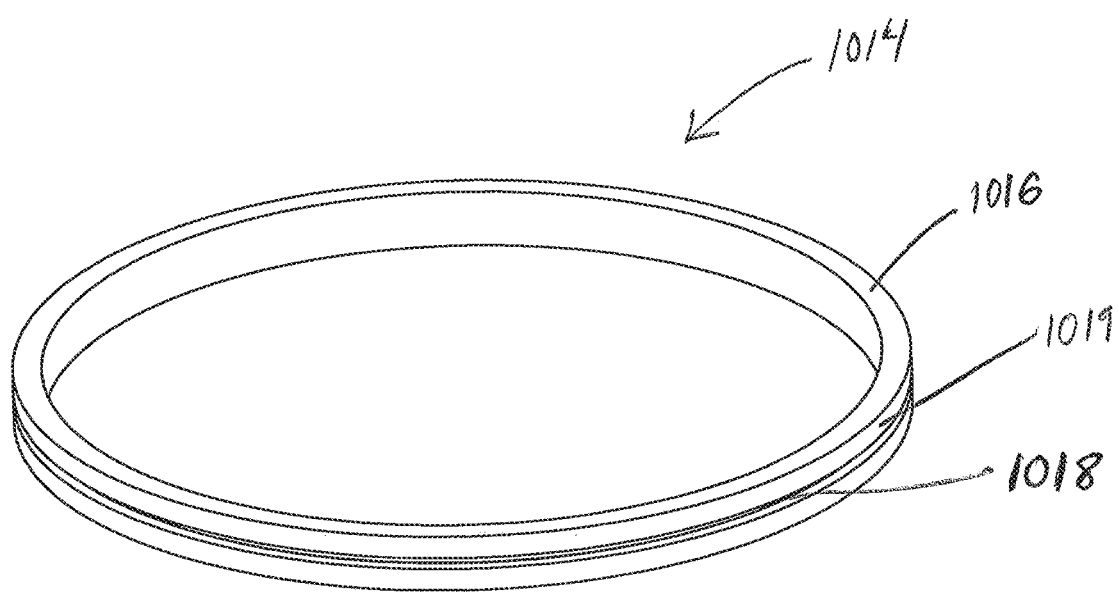
Figure 163:
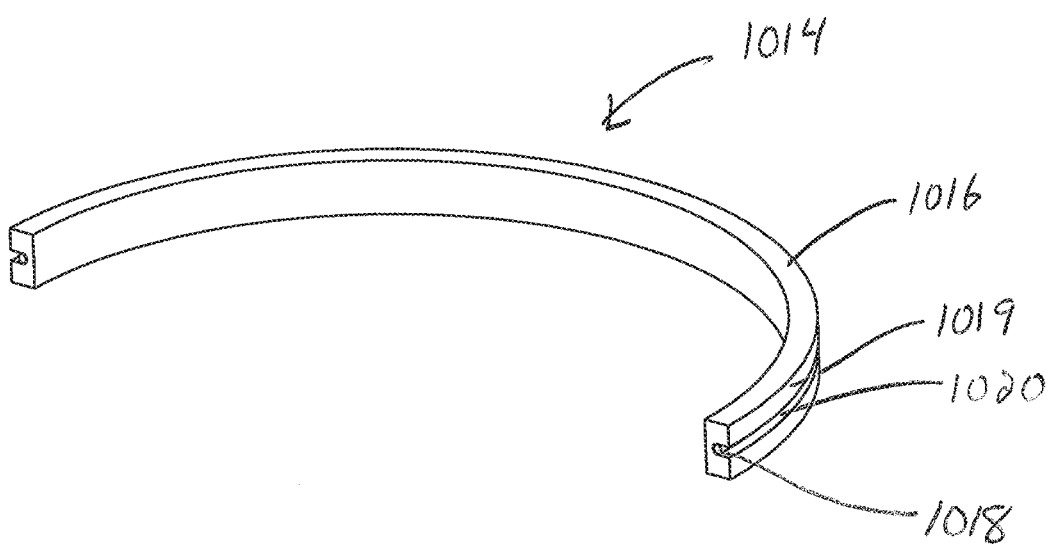
Figure 164A:
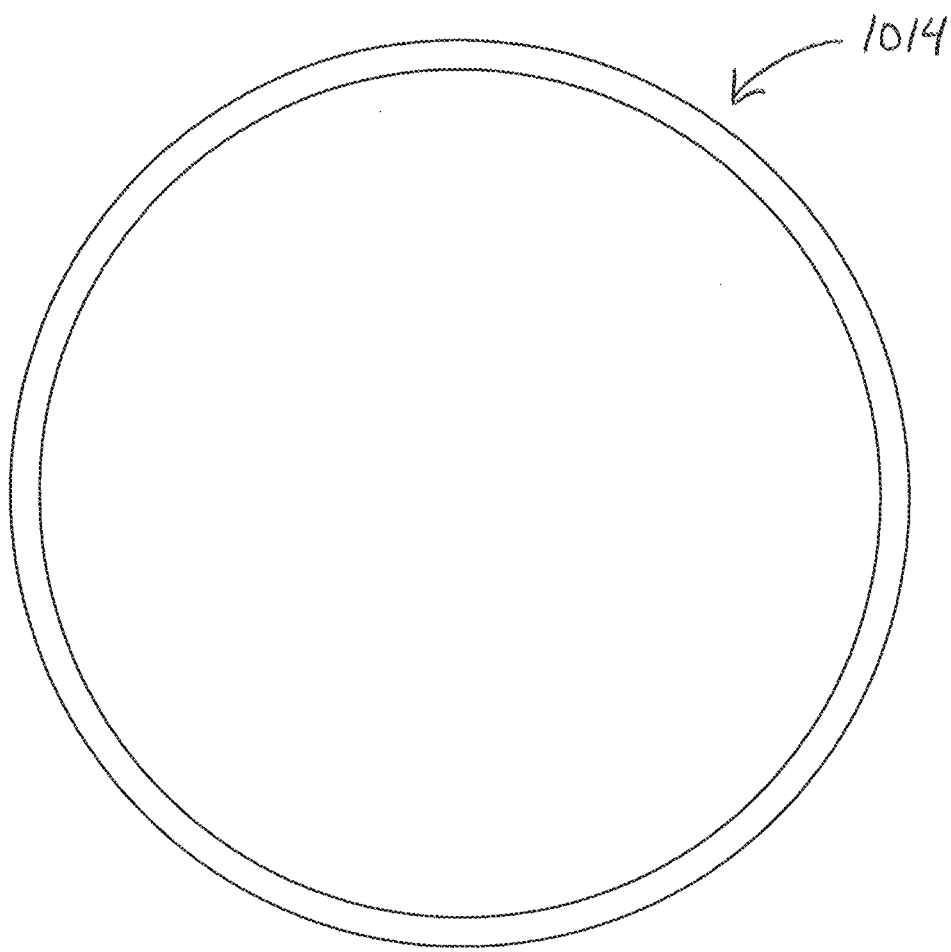
Figure 164B:
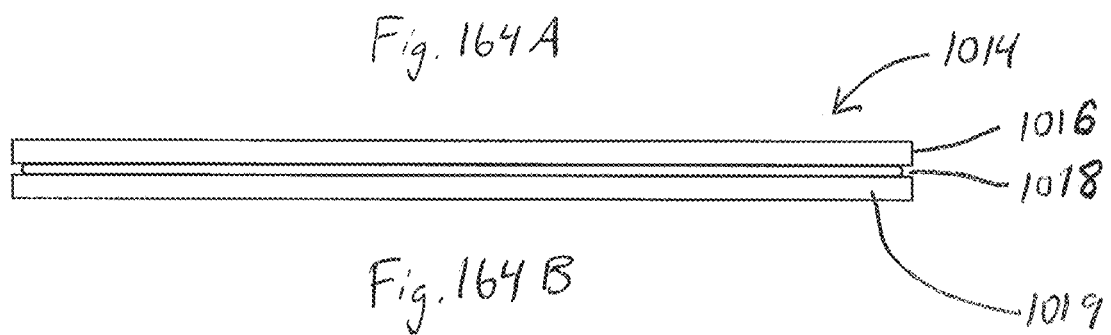

FIGS. 162 and 163 are perspective and cross-sectional perspective views, respectively, of a retractor ring of the bag assembly of FIG. 158, in accordance with aspects of the present disclosure.

Figure 165A:
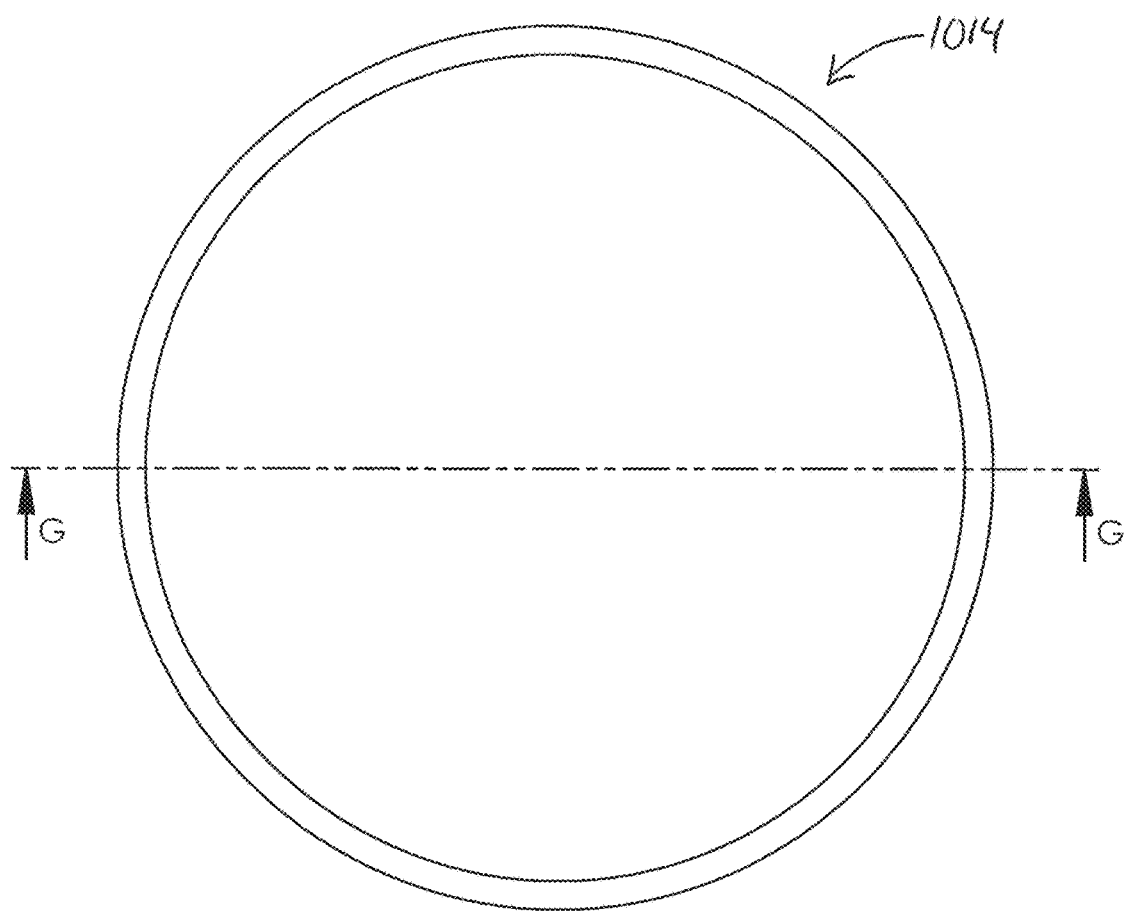
Figure 165B:
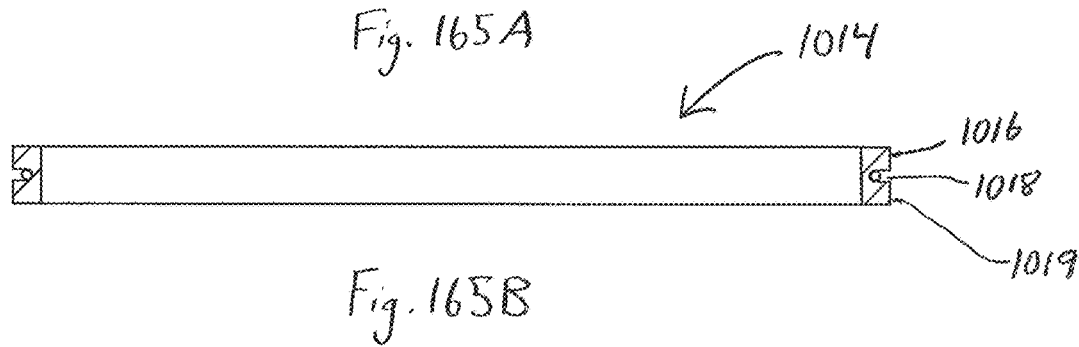

FIGS. 164A, 164B, 165A, and 165B are top, side, bottom, and cross-sectional side views, respectively, of the retractor ring of FIG. 162, in accordance with aspects of the present disclosure. The cross-sectional side view of FIG. 165B is taken along the line G-G in FIG. 165A.

Figure 166:
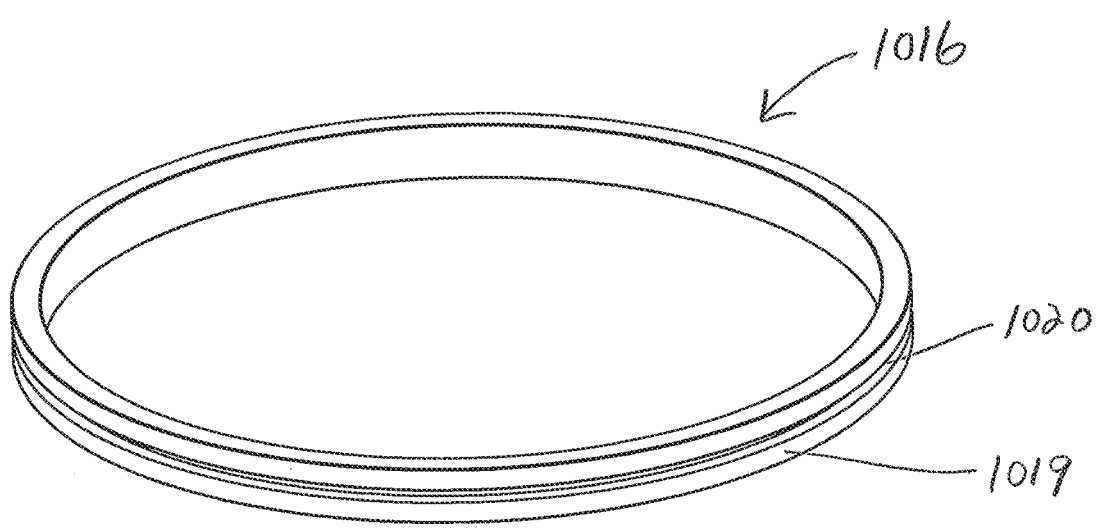
Figure 167A:
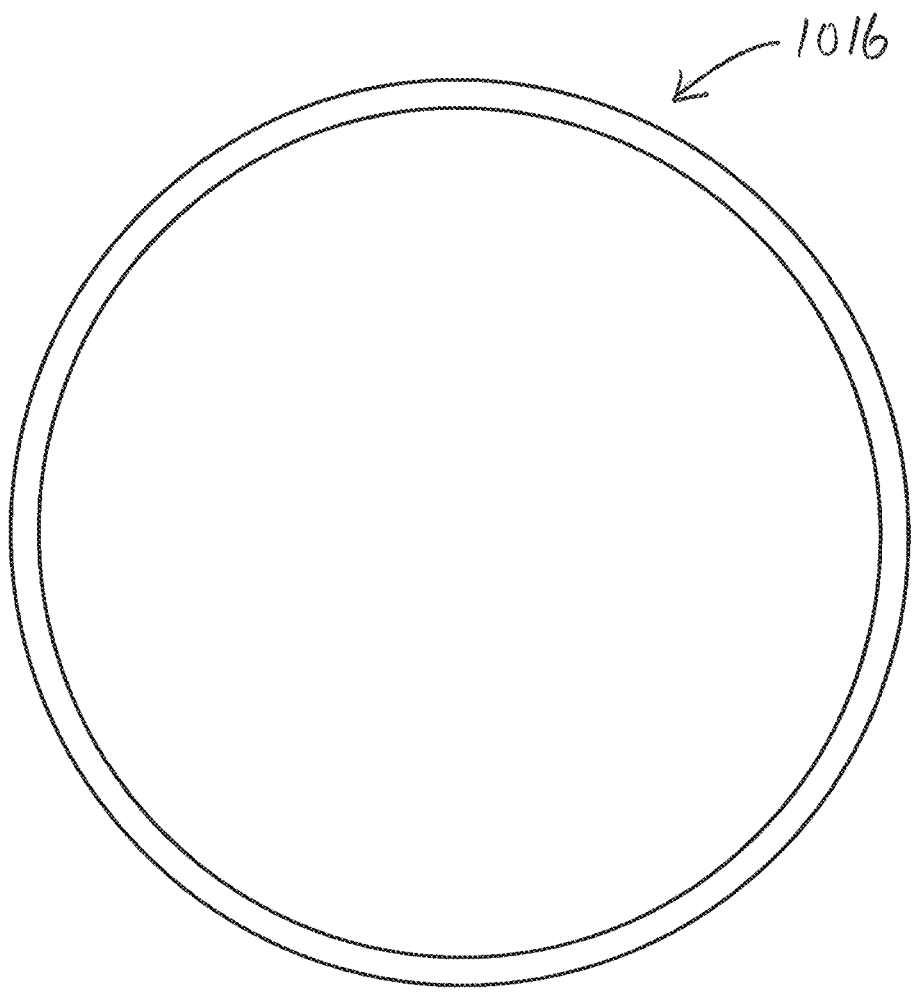
Figure 167B:
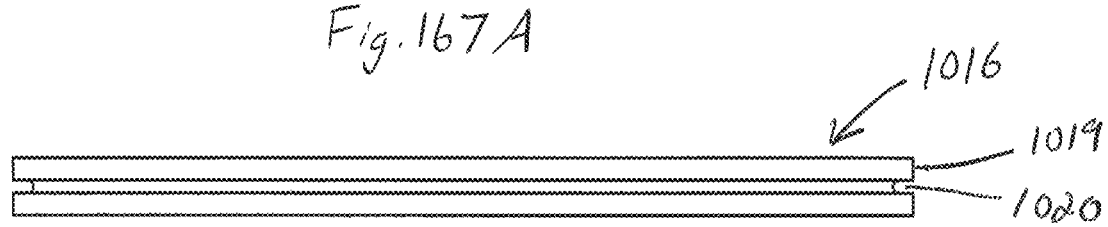

FIG. 166 is a perspective view of an inner ring of the retractor ring of FIG. 162, in accordance with aspects of the present disclosure.

Figure 168A:
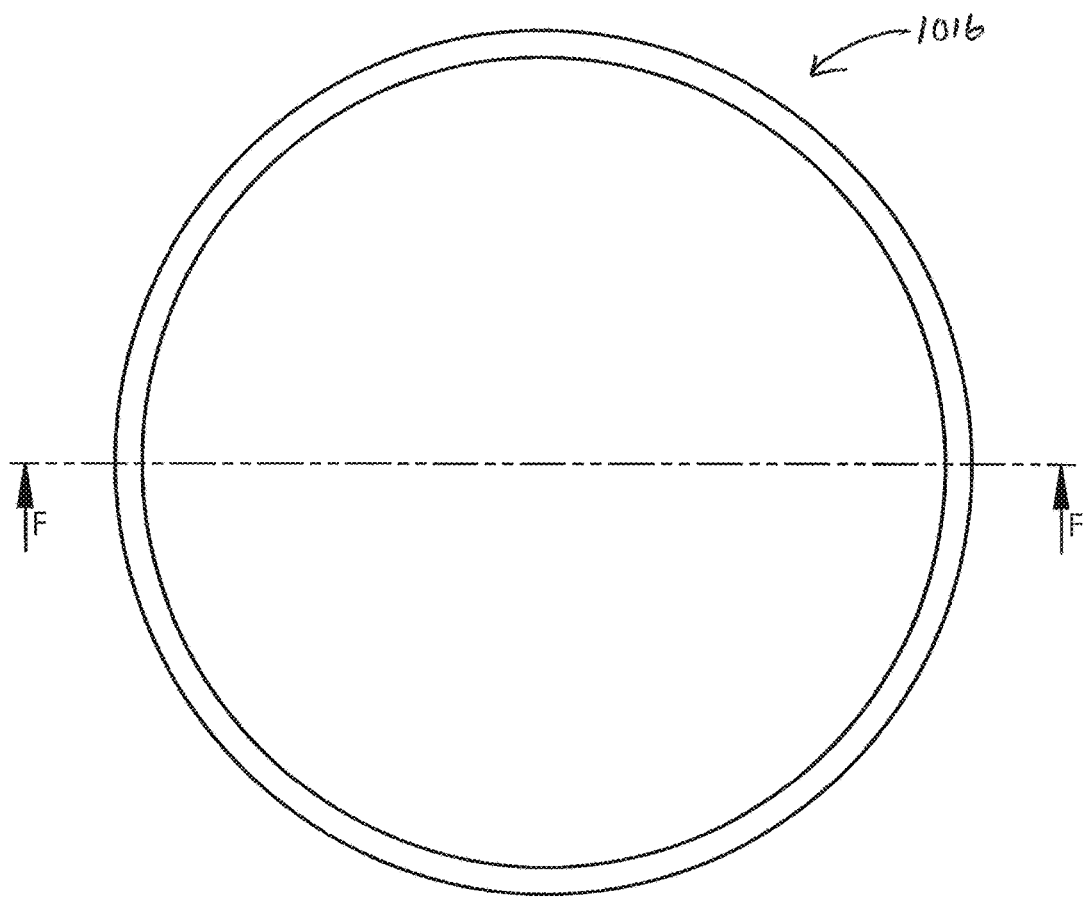
Figure 168B:
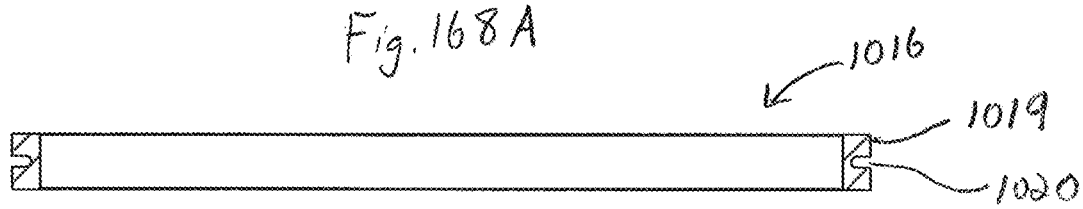

FIGS. 167A, 167B, 168A, and 168B are top, side, bottom, and cross-sectional side views, respectively, of the inner ring of FIG. 166, in accordance with aspects of the present disclosure. The cross-sectional side view of FIG. 168B is taken along the line F-F in FIG. 168A.

Figure 169:
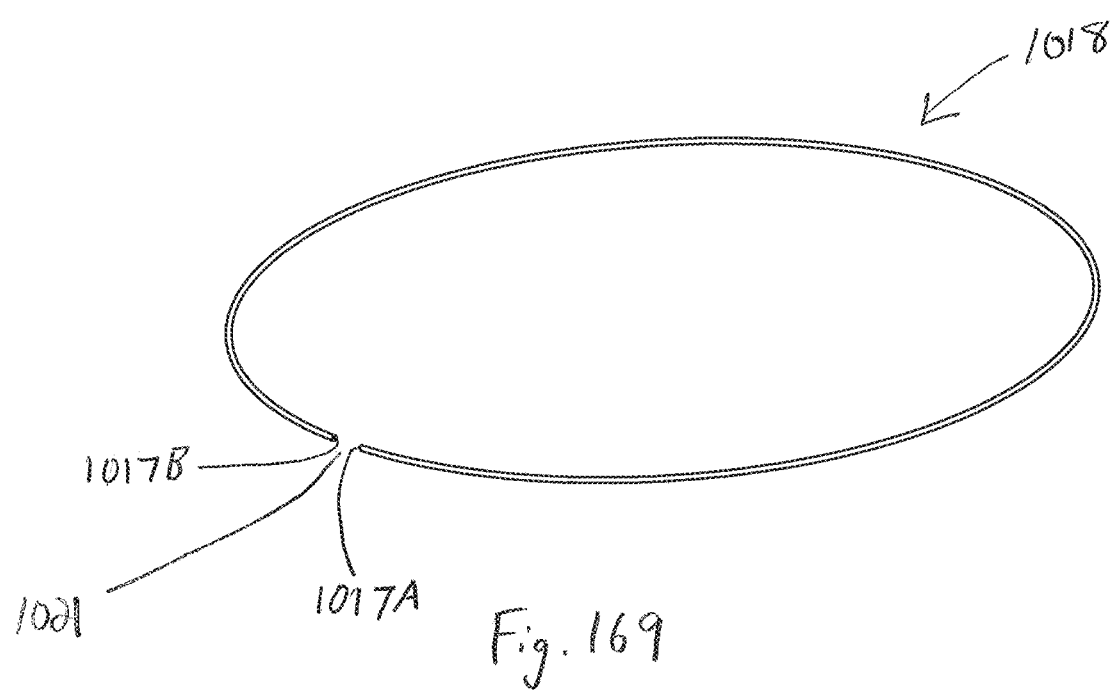

FIG. 169 is a perspective view of an outer ring of the retractor ring of FIG. 162, in accordance with aspects of the present disclosure.

Figure 170A:
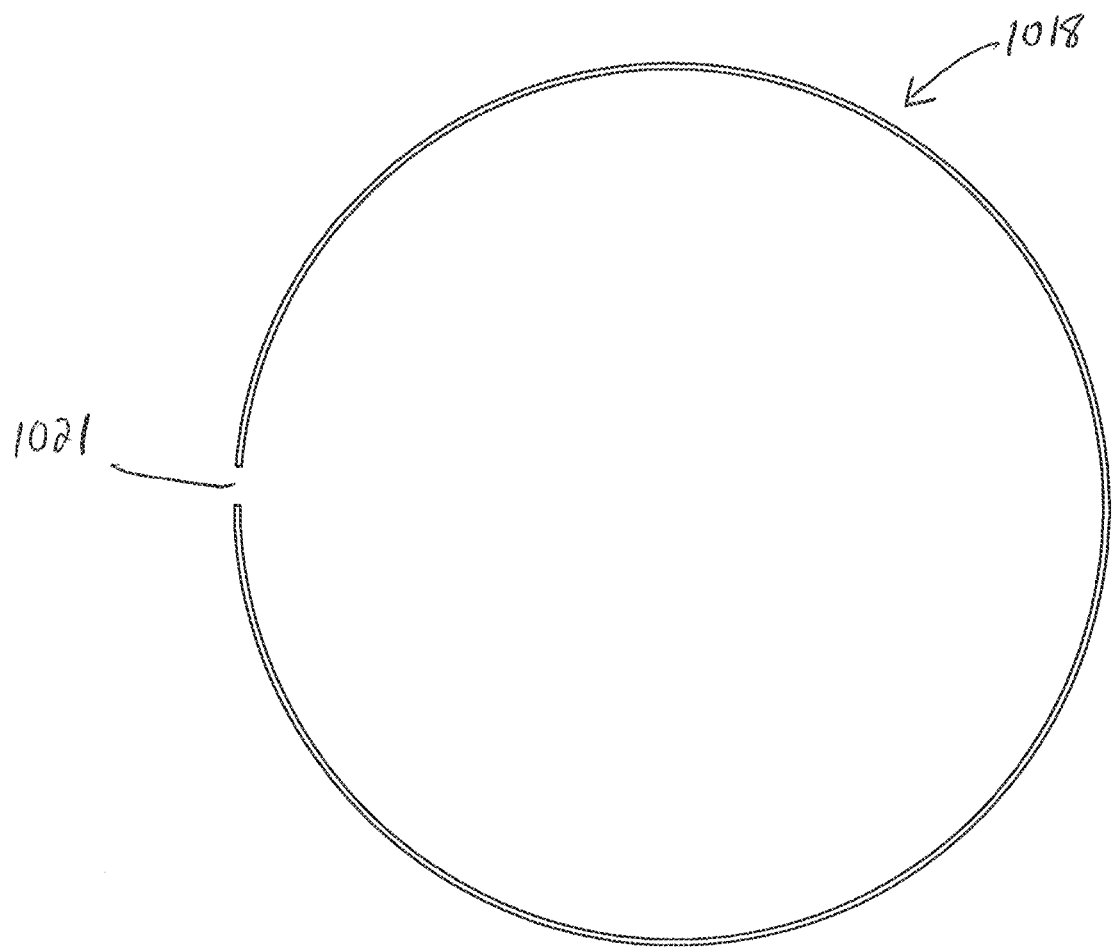
Figure 170B:
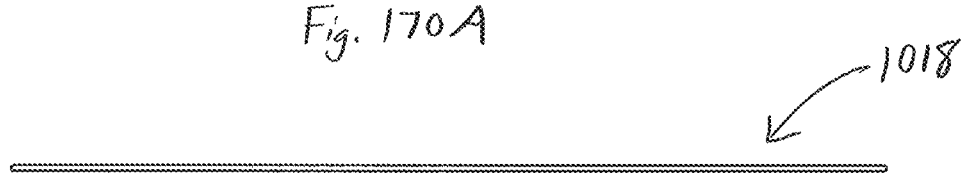

FIGS. 170A and 170B are top and side views, respectively, of the outer ring of FIG. 169, in accordance with aspects of the present disclosure.

Figure 171:
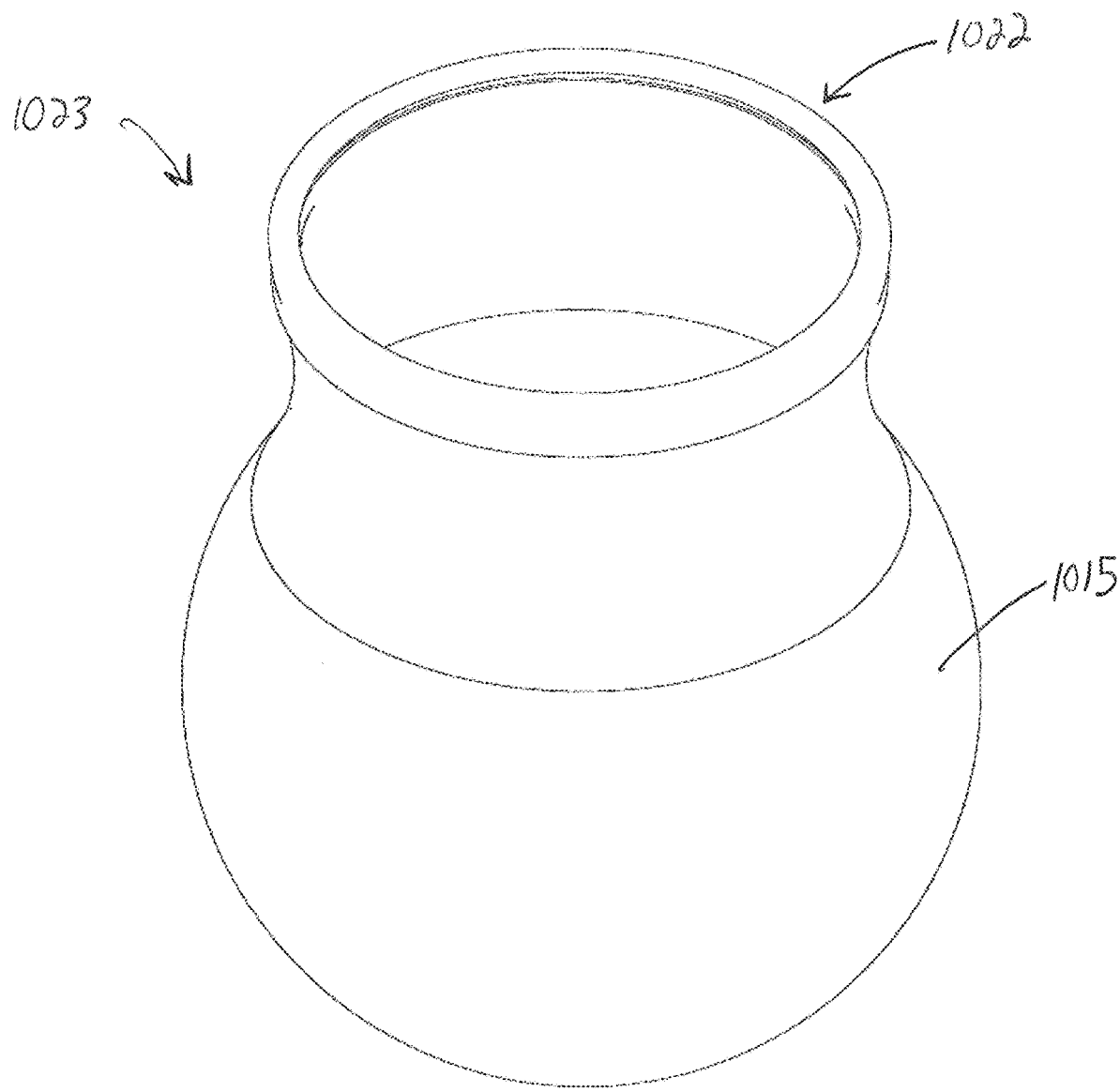

FIG. 171 is a perspective view of another exemplary bag assembly, in accordance with aspects of the present disclosure.

Figure 172:
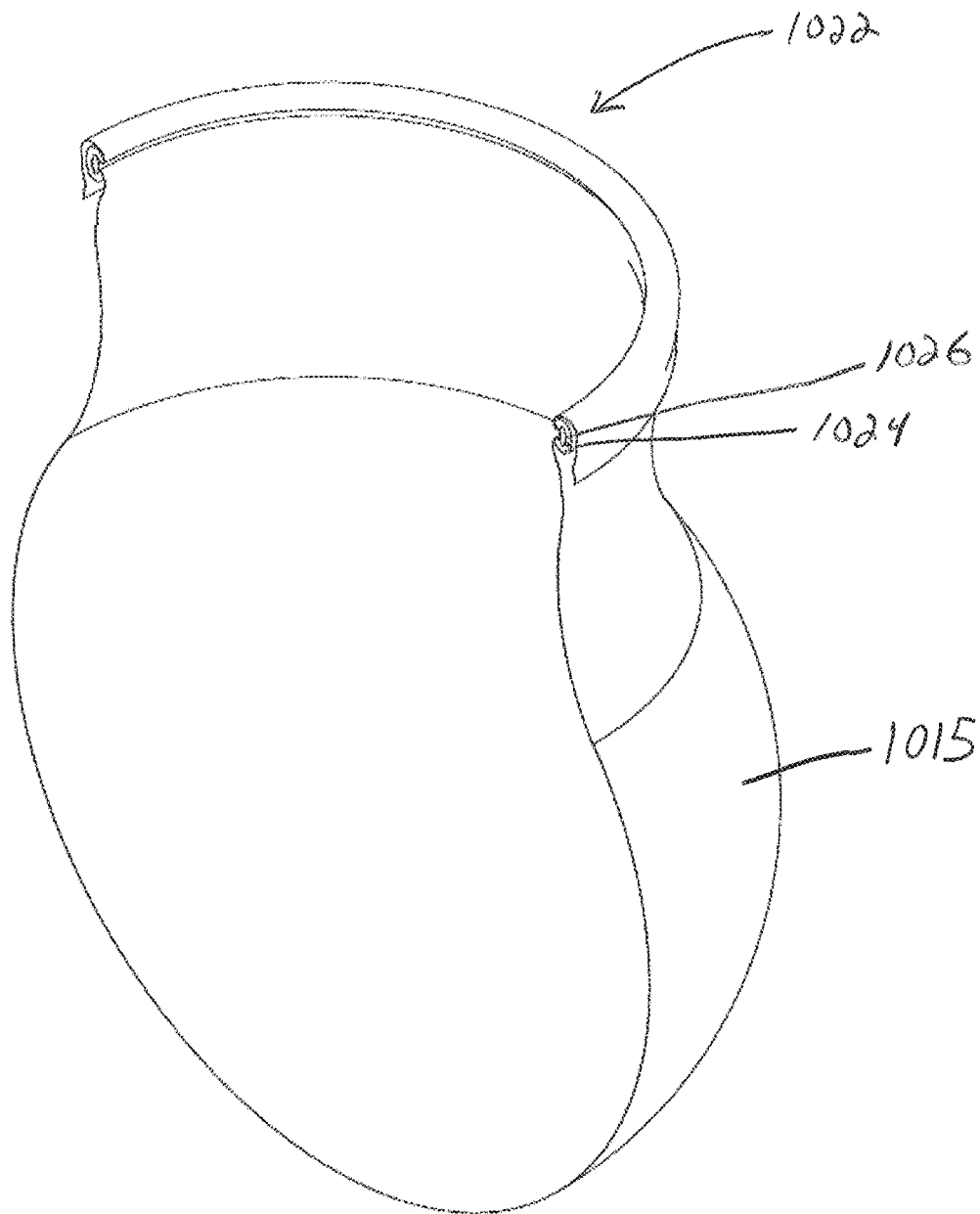

FIG. 172 is a cross-sectional perspective view of the bag assembly of FIG. 171, in accordance with aspects of the present disclosure.

Figure 173:
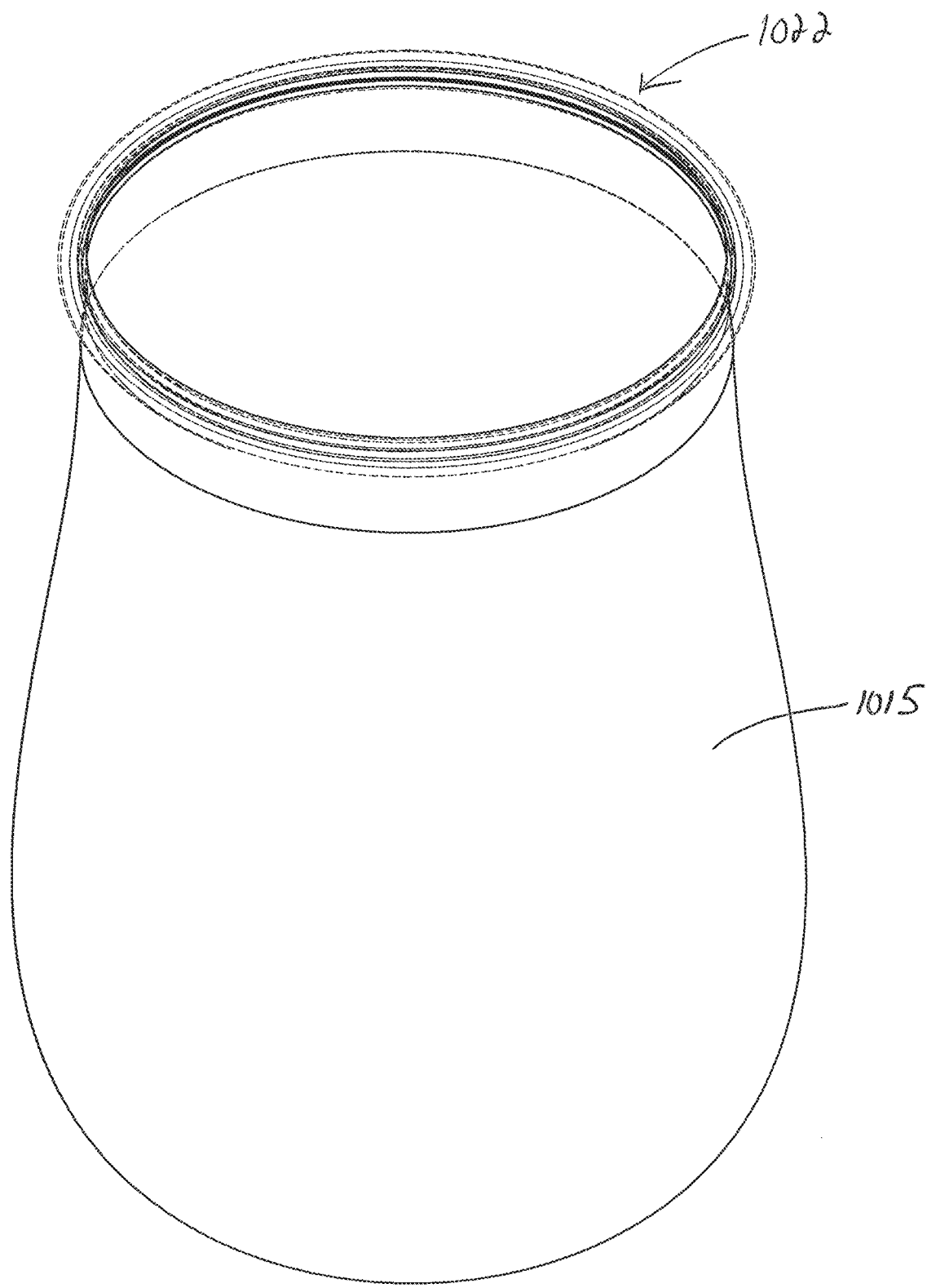

FIG. 173 is a partially-transparent perspective view of the bag assembly of FIG. 171, in accordance with aspects of the present disclosure.

Figure 174:
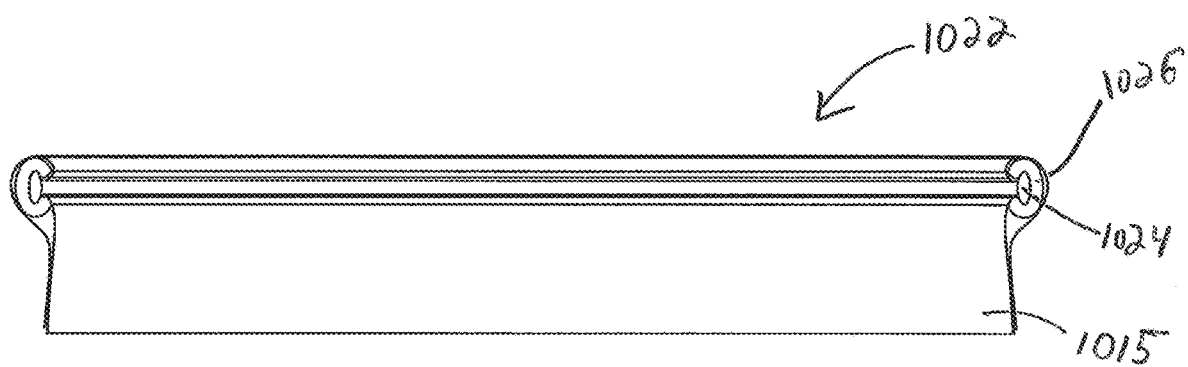

FIG. 174 is a partial cross-sectional side view of the bag assembly of FIG. 171, in accordance with aspects of the present disclosure.

Figure 175:
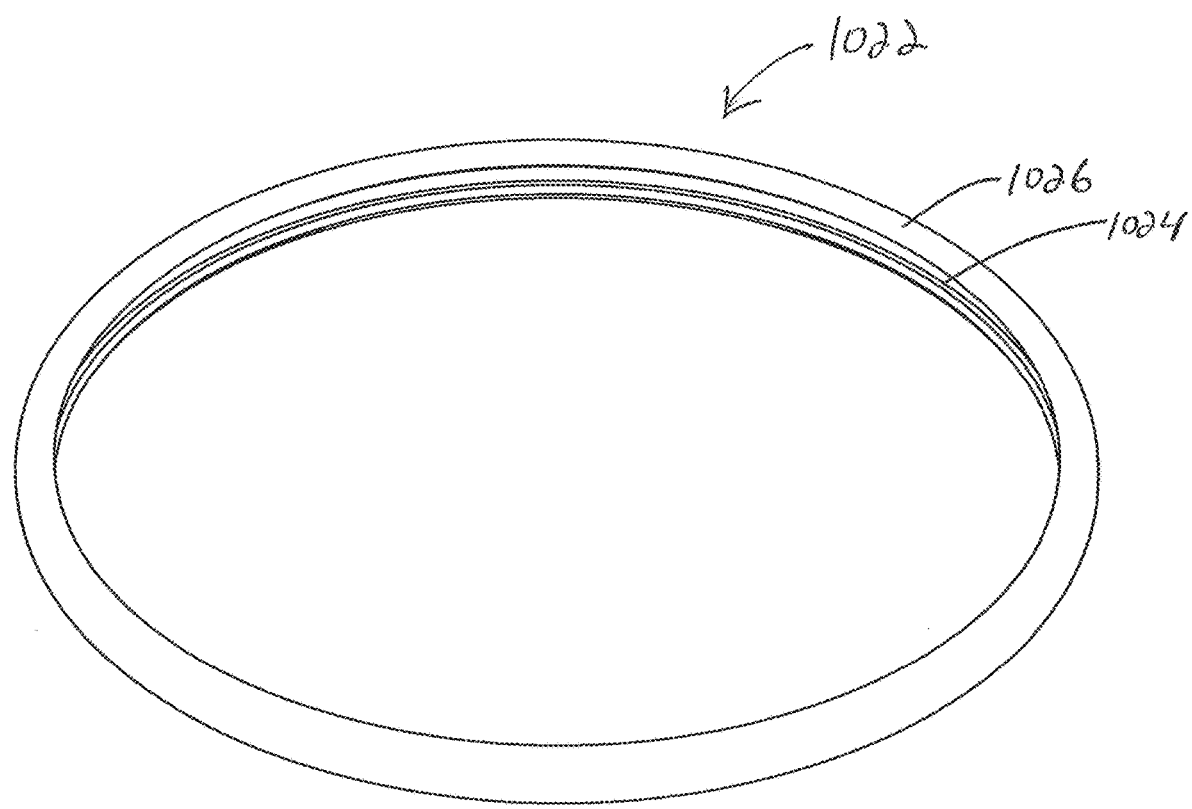
Figure 176:
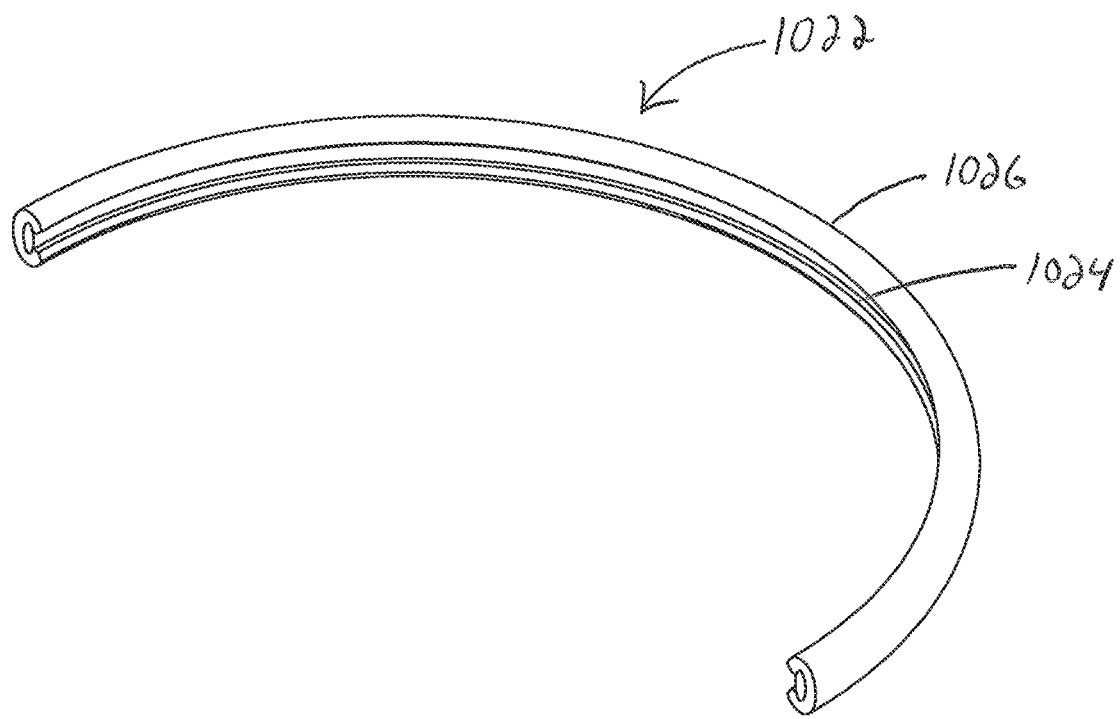

FIGS. 175 and 176 are perspective and cross-sectional perspective views, respectively, of a retractor ring of the bag assembly of FIG. 171, in accordance with aspects of the present disclosure.

Figure 177:
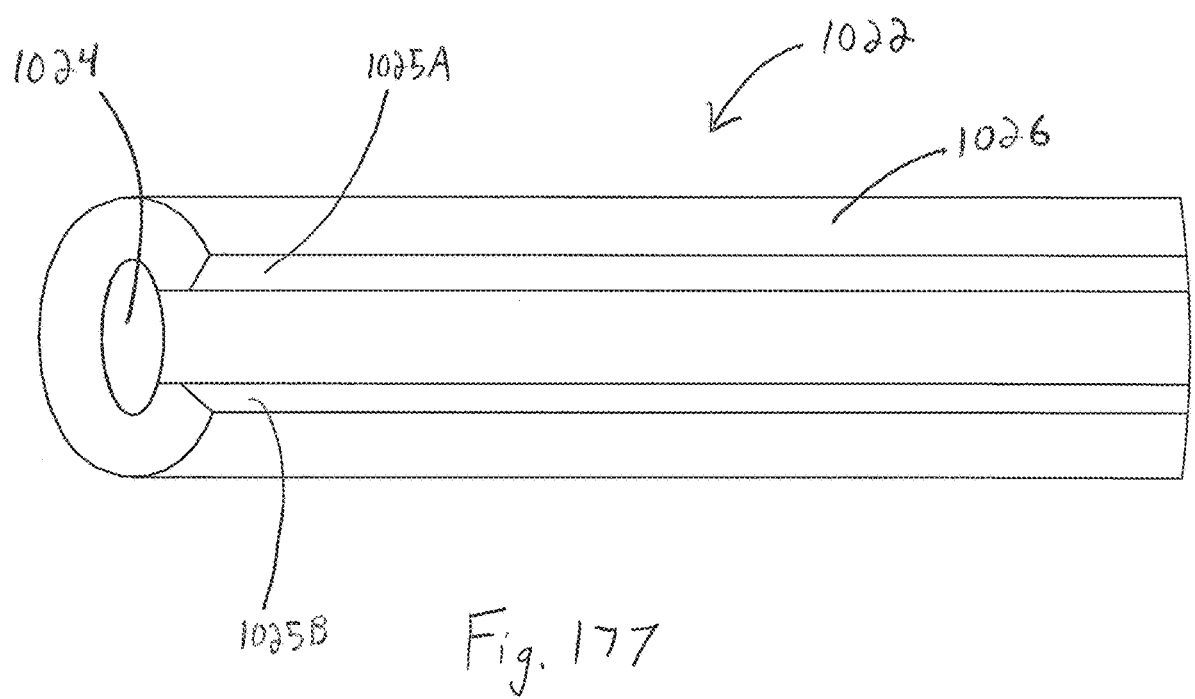

FIG. 177 is a partial cross-sectional side view of the retractor ring of FIG. 175, in accordance with aspects of the present disclosure.

Figure 178:
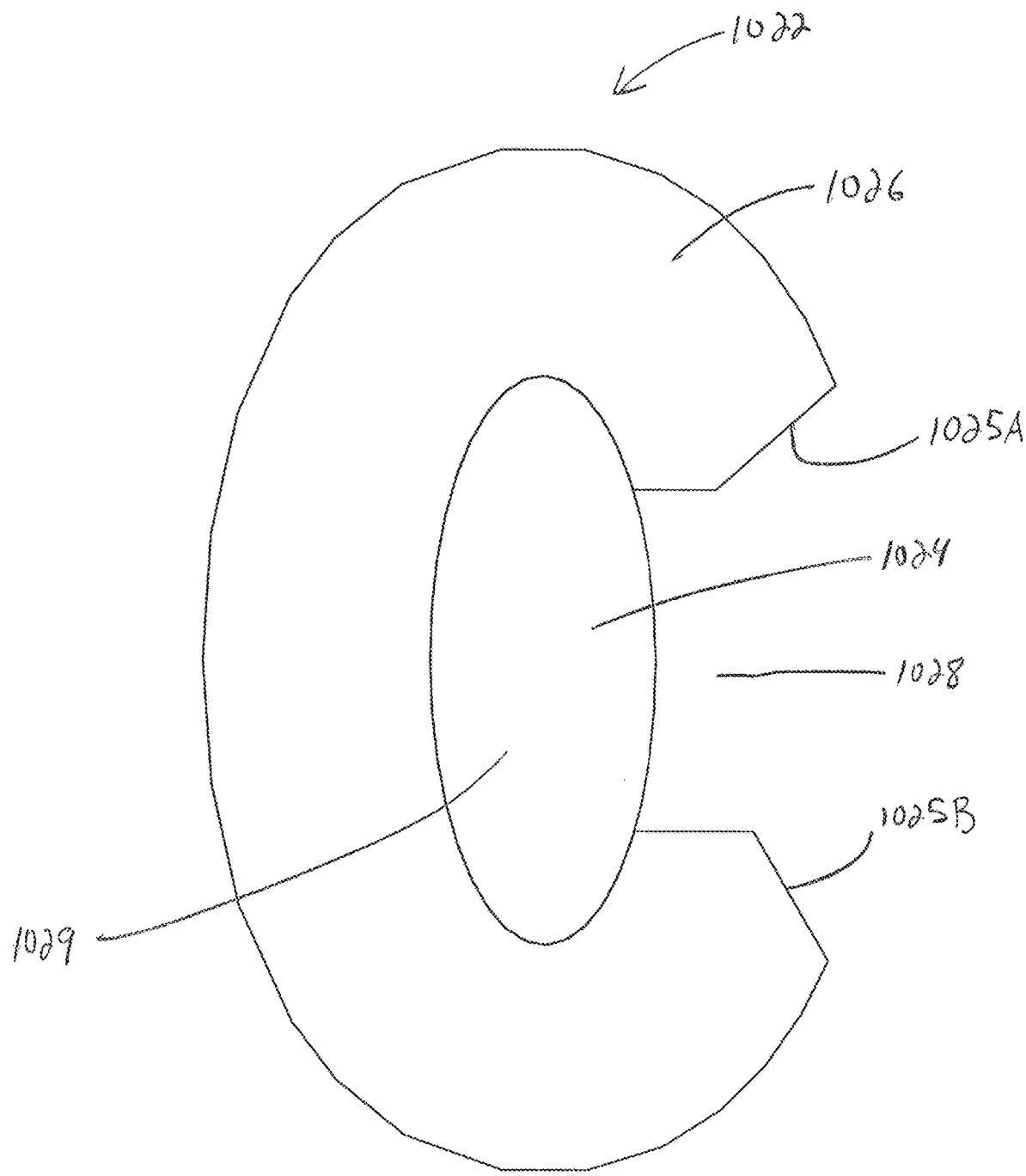

FIG. 178 is a side view of a cross-sectional face of the retractor ring of FIG. 175, in accordance with aspects of the present disclosure.

Figure 179:
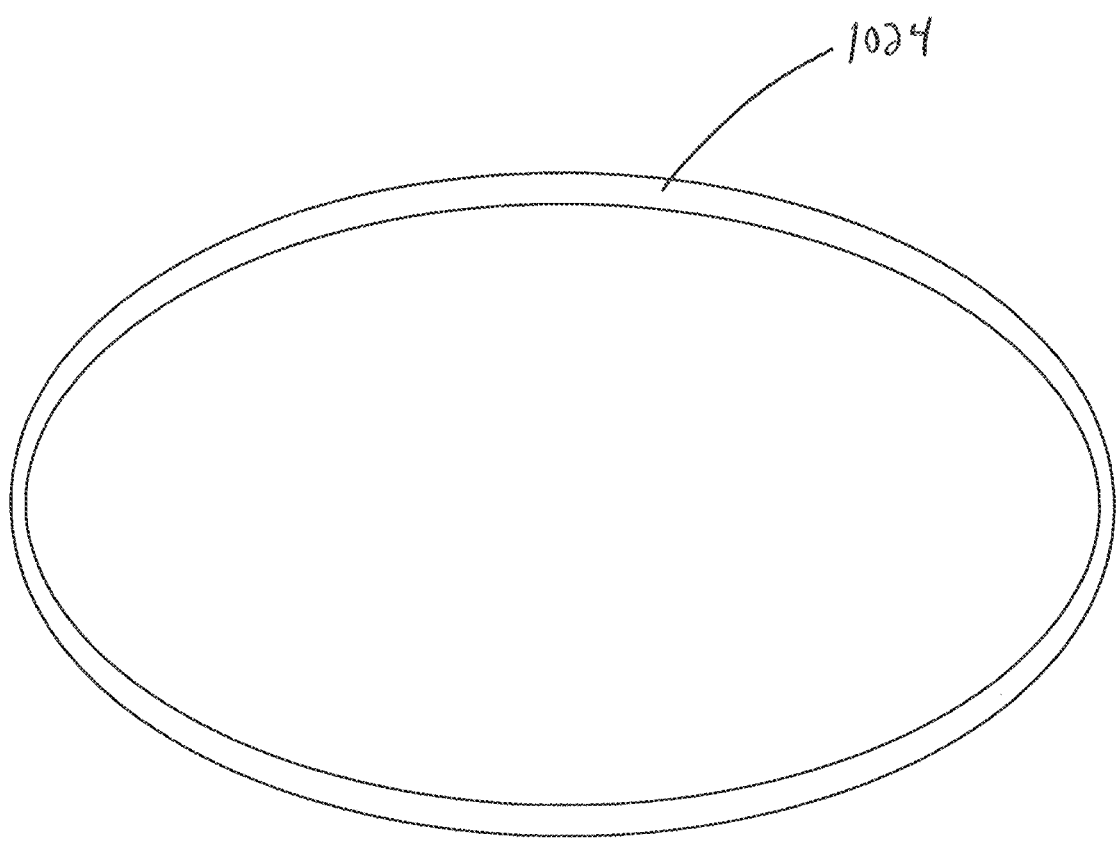
Figure 180:
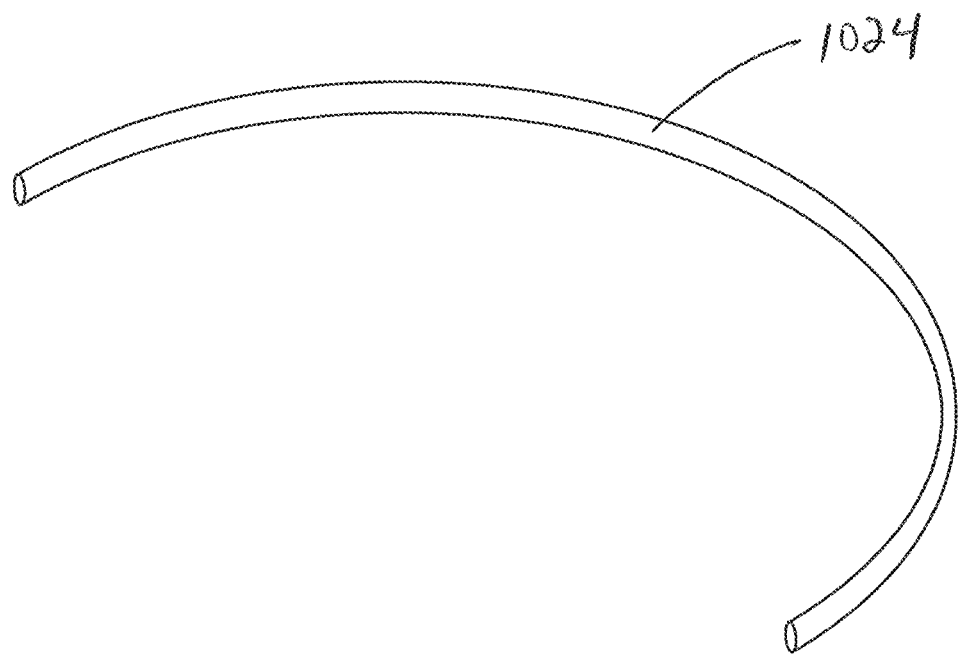

FIGS. 179 and 180 are perspective and cross-sectional perspective views, respectively, of an inner ring of the retractor ring of FIG. 175, in accordance with aspects of the present disclosure.

Figure 181A:
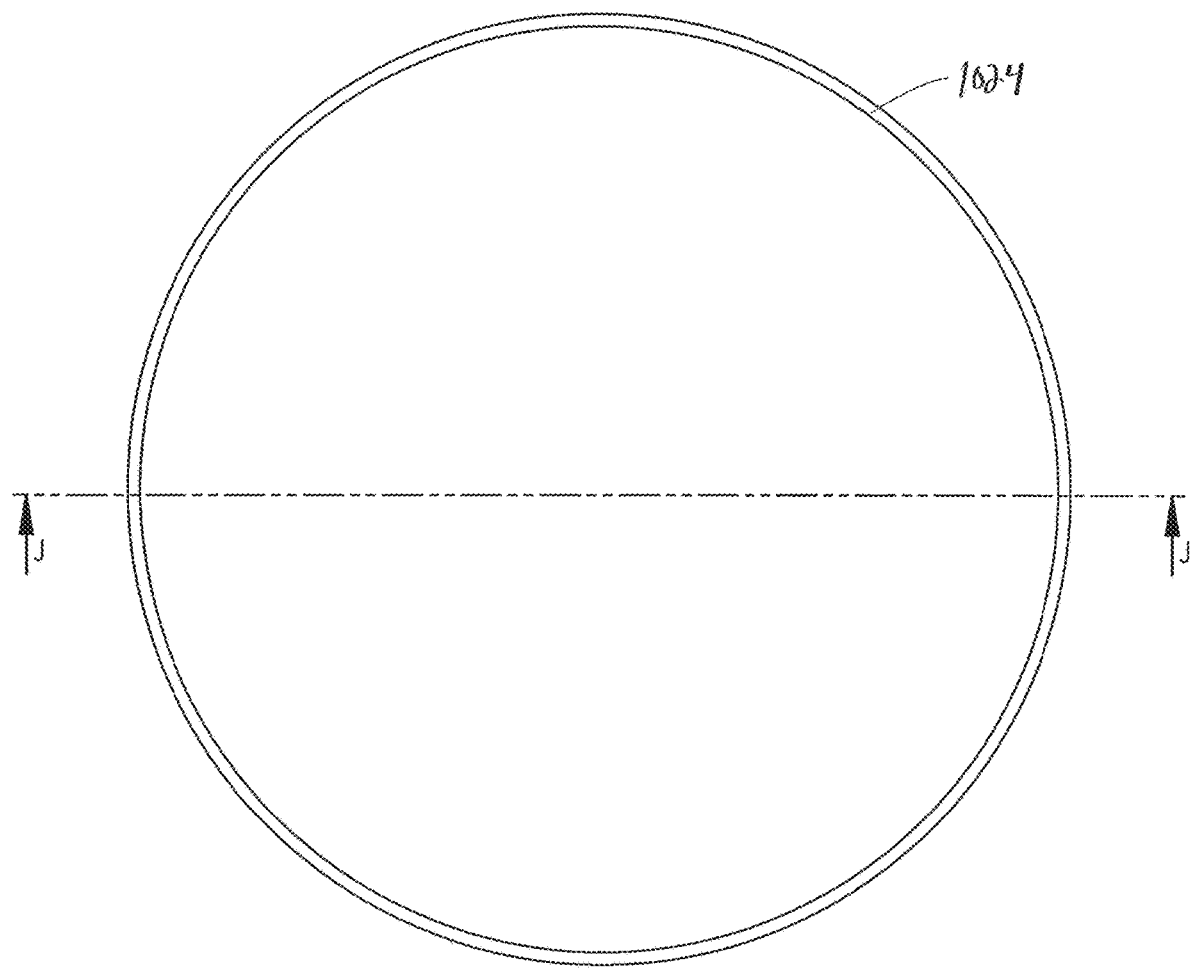
Figure 181B:
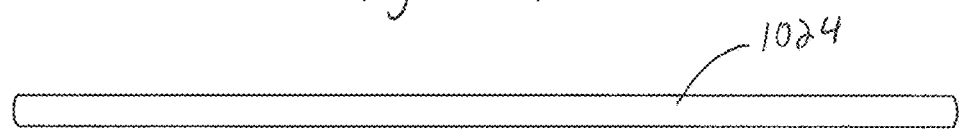
Figure 181C:
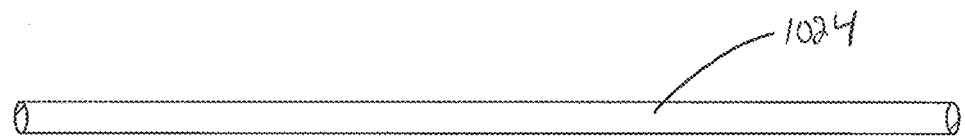

FIGS. 181A, 181B, and 181C are top, side, and cross-sectional side views, respectively, of the inner ring of FIG. 179, in accordance with aspects of the present disclosure. The cross-sectional side view of FIG. 181C is taken along the line J-J in FIG. 181A.

Figure 182:
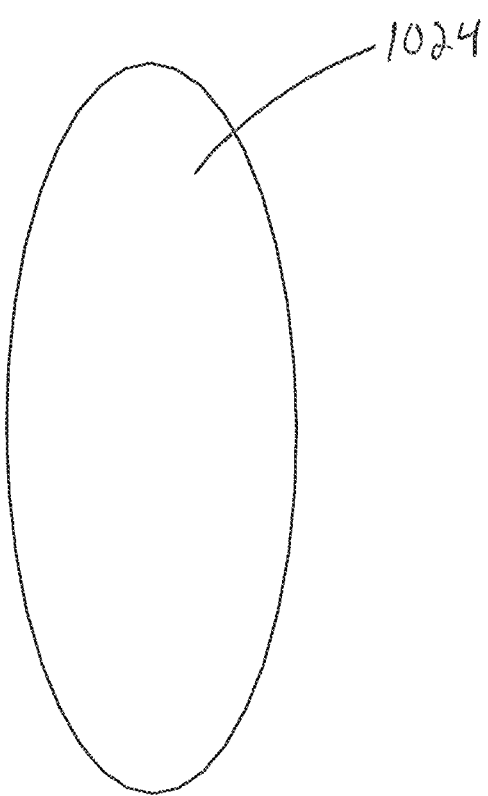

FIG. 182 is a side view of a cross-sectional face of the inner ring of FIG. 179, in accordance with aspects of the present disclosure.

Figure 183:
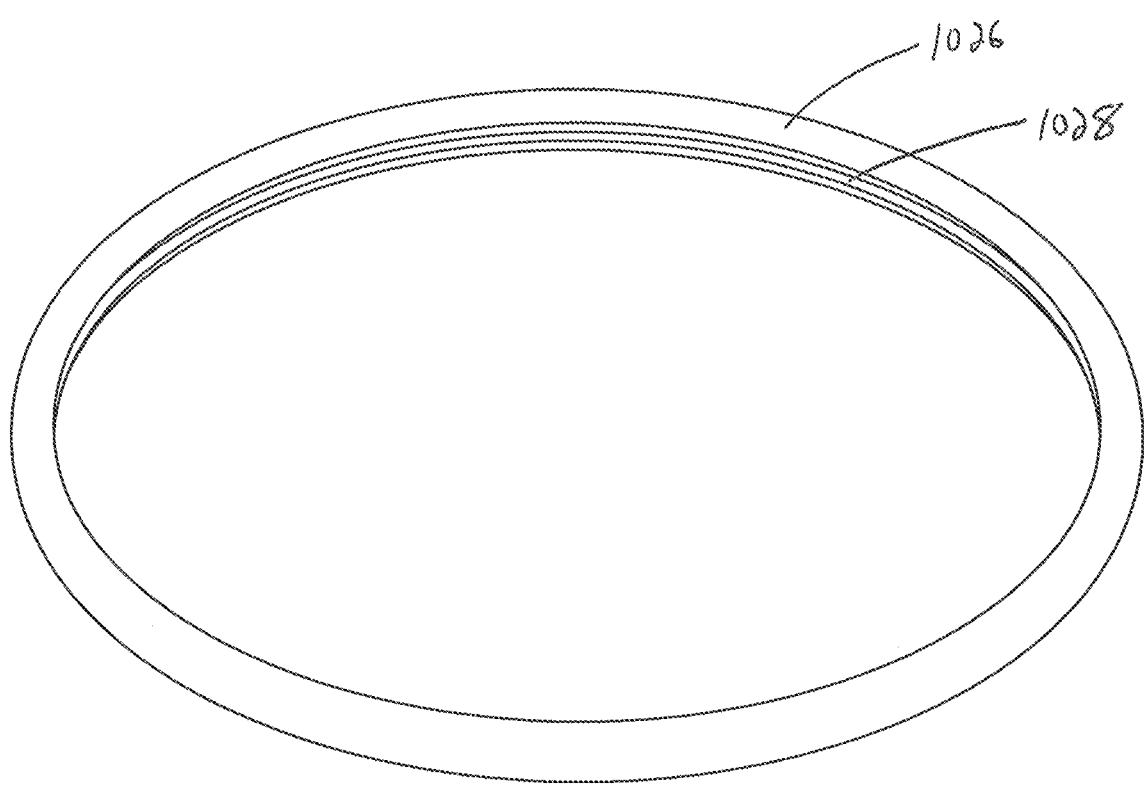
Figure 184:
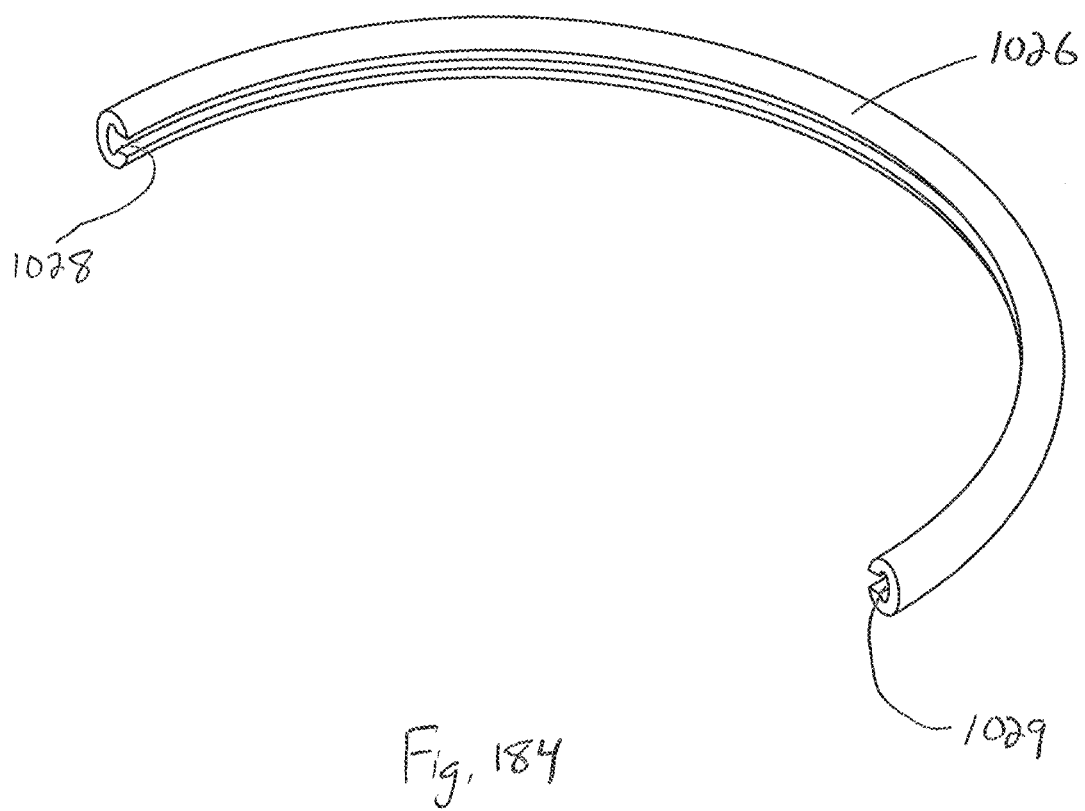

FIGS. 183 and 184 are perspective and cross-sectional perspective views, respectively, of an outer ring of the retractor ring of FIG. 175, in accordance with aspects of the present disclosure.

Figure 185A:
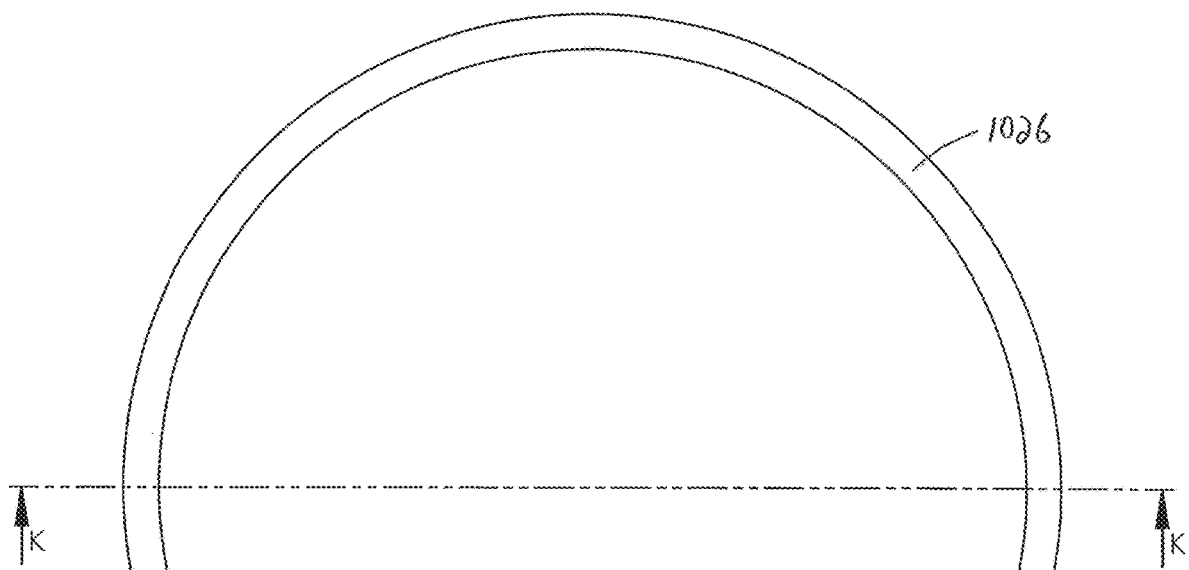
Figure 185B:
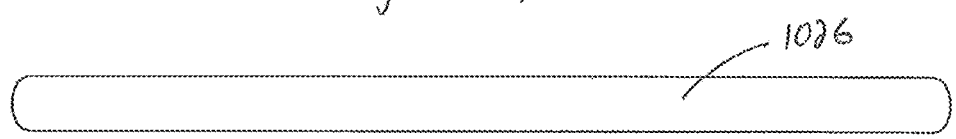
Figure 185C:
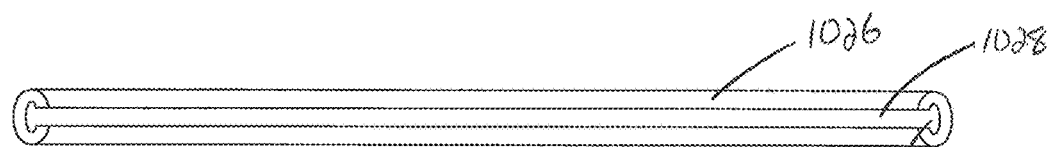

FIGS. 185A, 185B, and 185C are top, side, and cross-sectional side views, respectively, of the outer ring of FIG. 183, in accordance with aspects of the present disclosure. The cross-sectional side view of FIG. 185C is taken along the line K-K in FIG. 185A.

Figure 186:
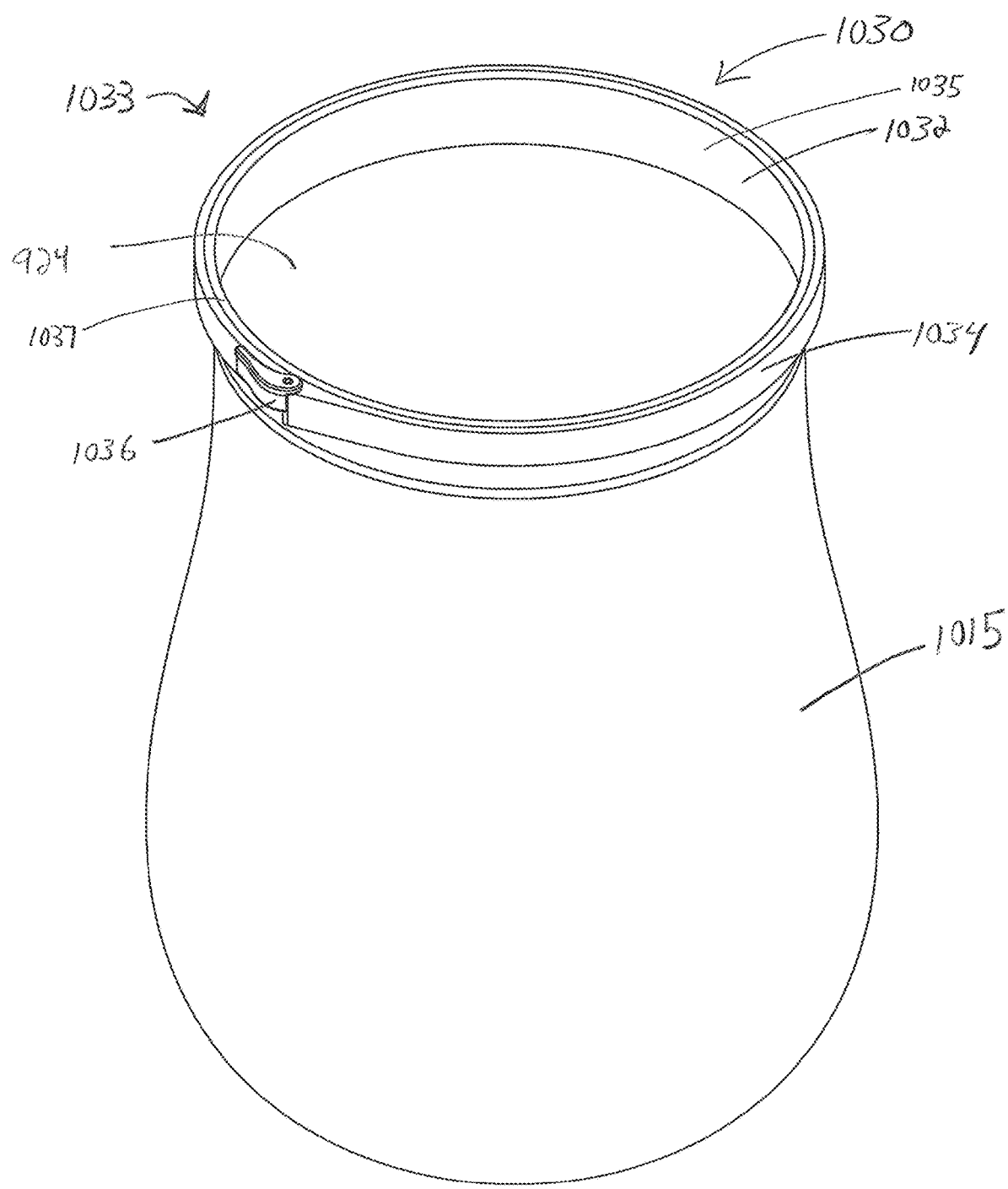

FIG. 186 is a perspective view of another exemplary bag assembly, in accordance with aspects of the present disclosure.

Figure 187:
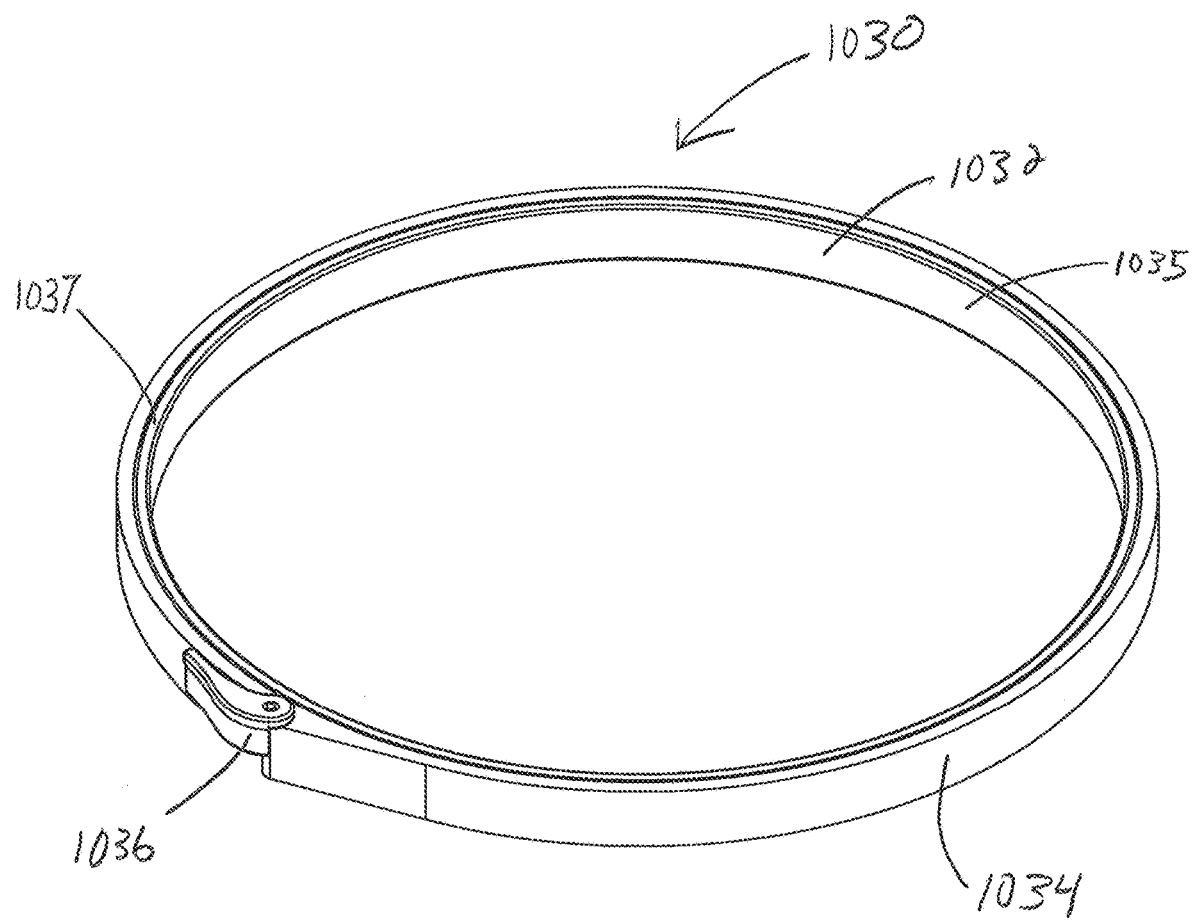

FIG. 187 is a perspective view of a retractor ring of the bag assembly of FIG. 186, in a contracted state, in accordance with aspects of the present disclosure.

Figure 188:
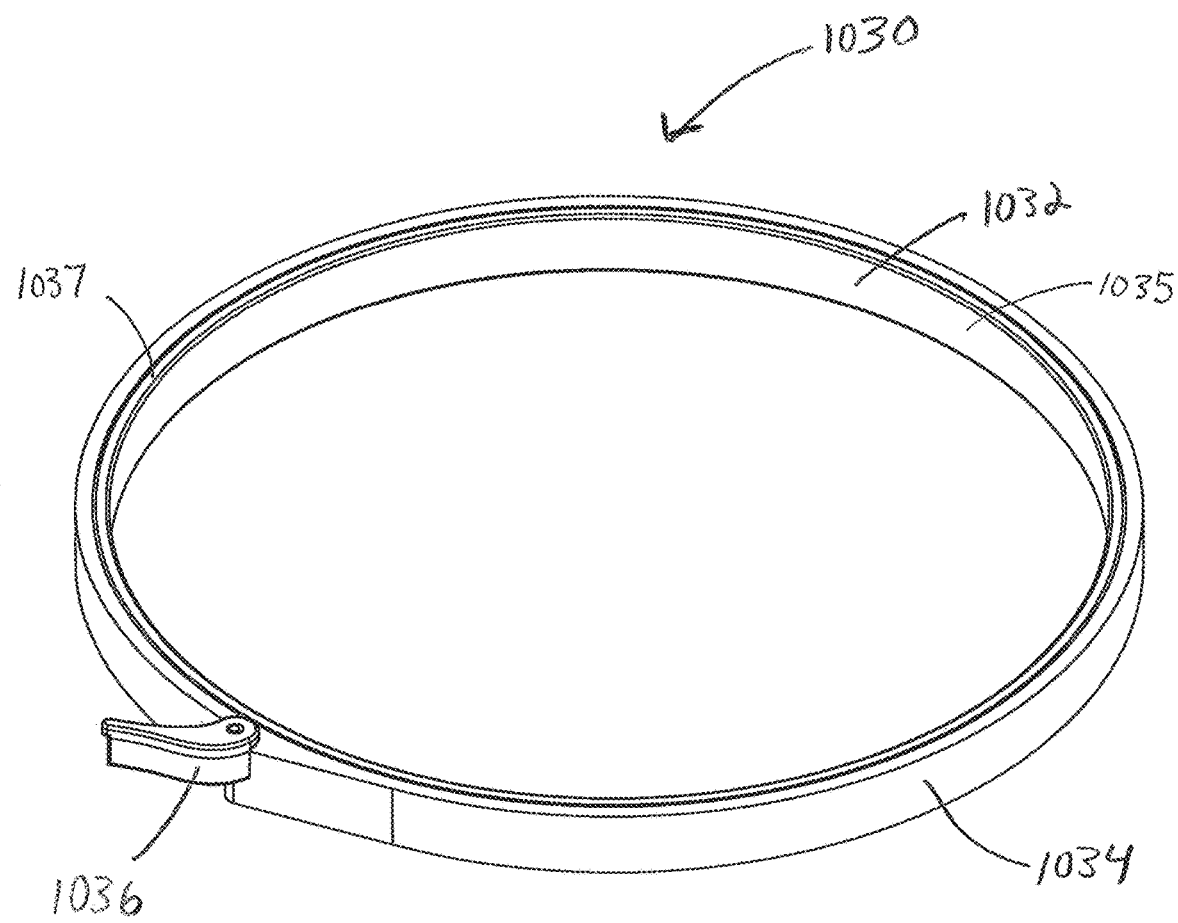

FIG. 188 is another perspective view of the retractor ring of FIG. 186, in an expanded state, in accordance with aspects of the present disclosure.

Figure 189:
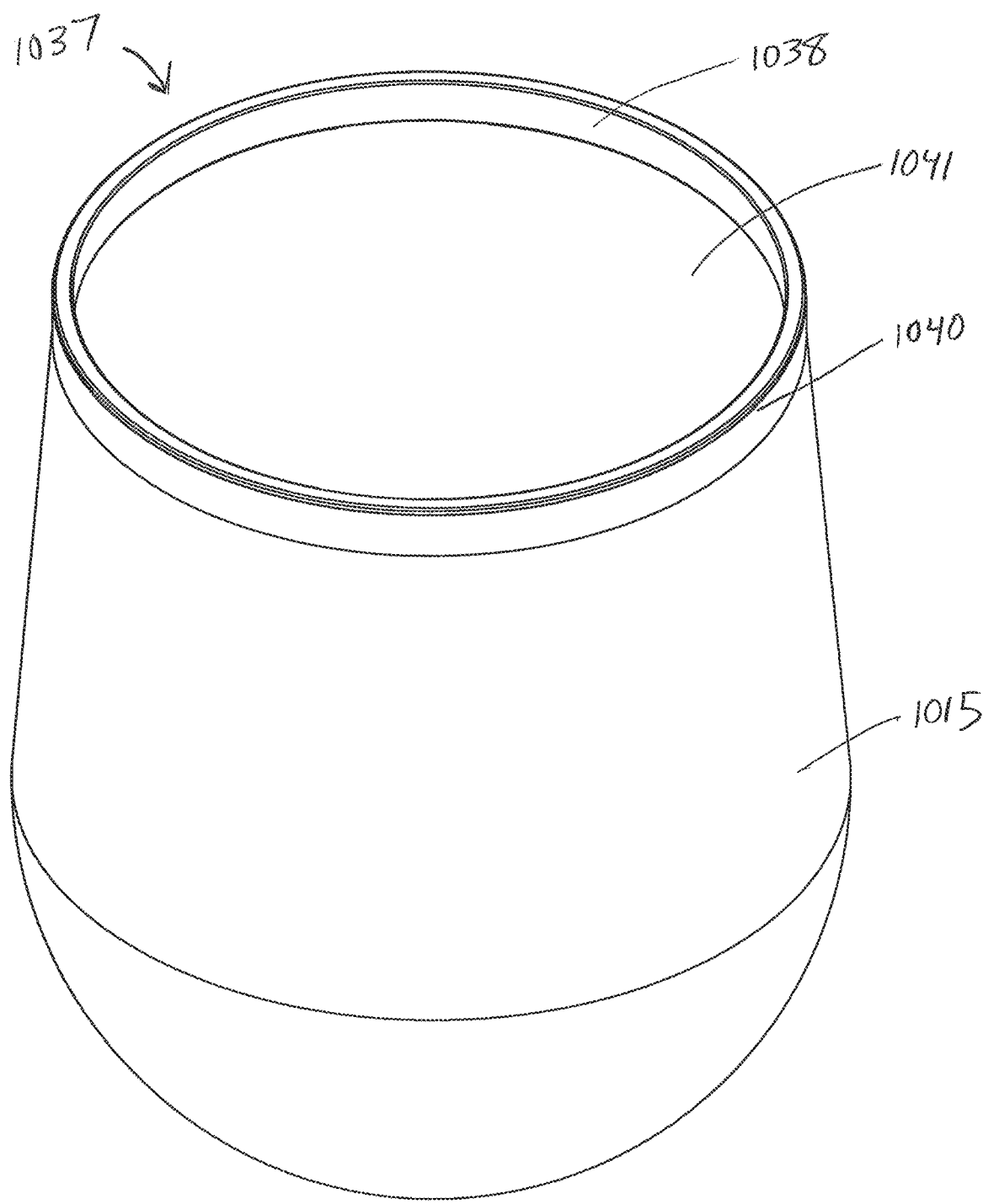

FIG. 189 is a perspective view of another exemplary bag assembly, in accordance with aspects of the present disclosure.

Figure 190:
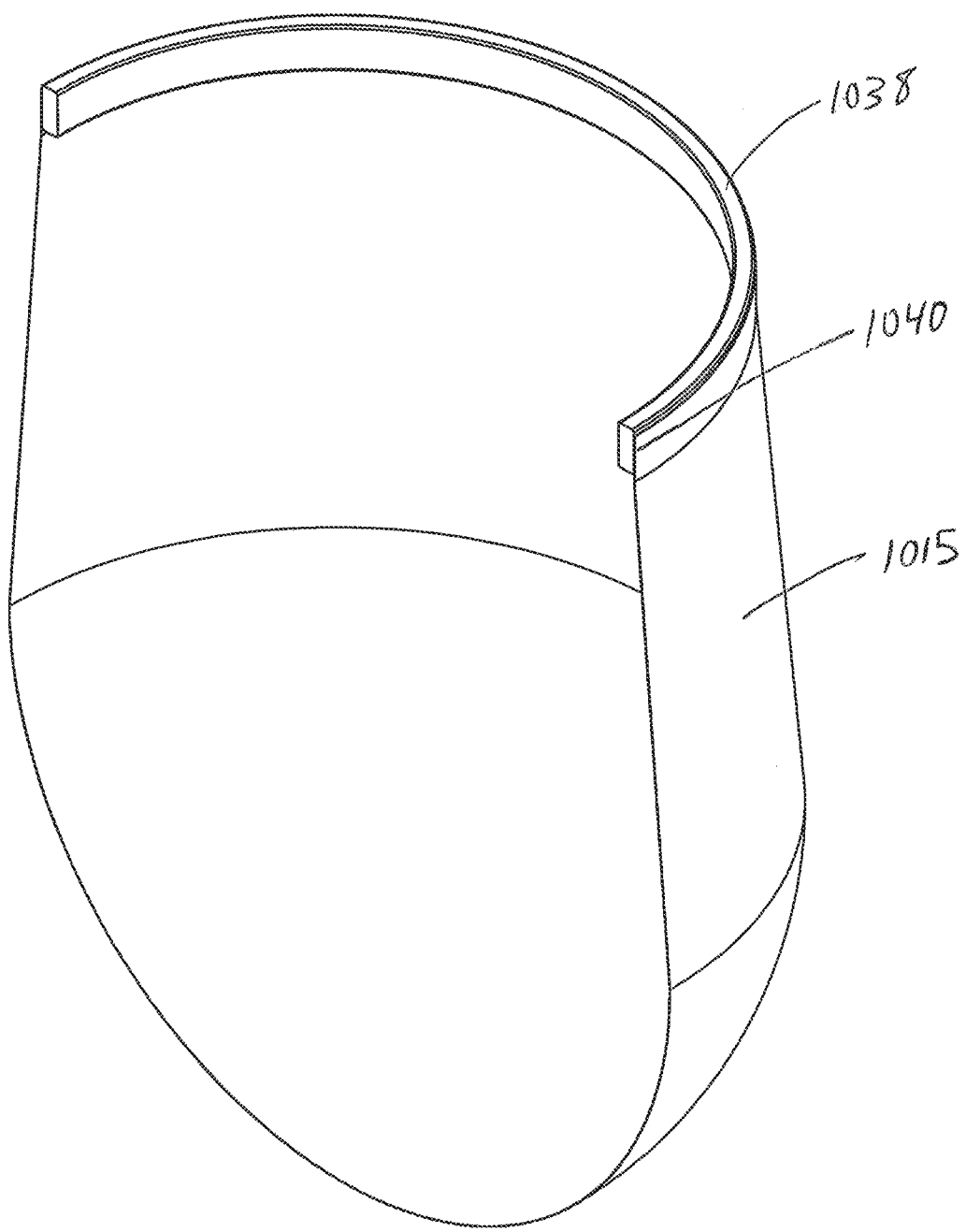

FIG. 190 is a cross-sectional perspective view of the bag assembly of FIG. 189, in accordance with aspects of the present disclosure.

Figure 191:
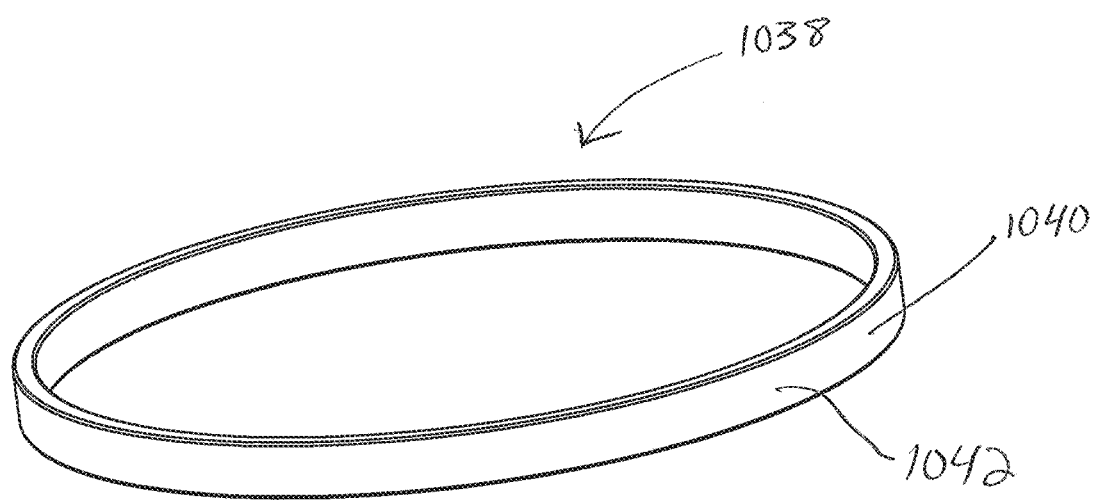

FIG. 191 is a perspective view of a retractor ring of the bag assembly of FIG. 189, in accordance with aspects of the present disclosure.

Figure 192:
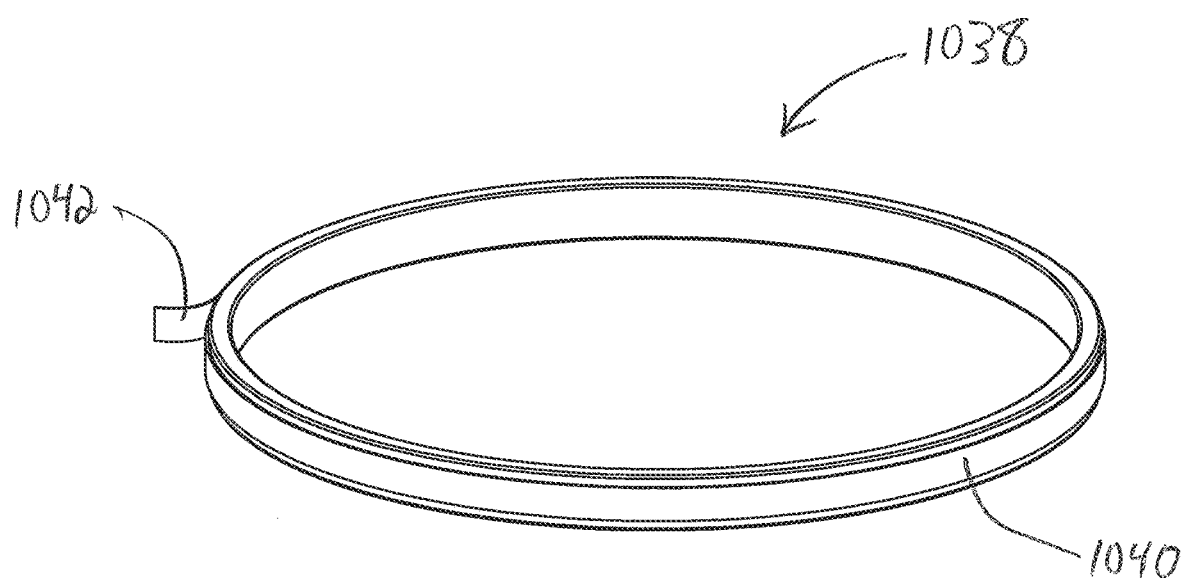

FIG. 192 is another perspective view of the retractor ring of FIG. 189, in accordance with aspects of the present disclosure.

Figure 193A:
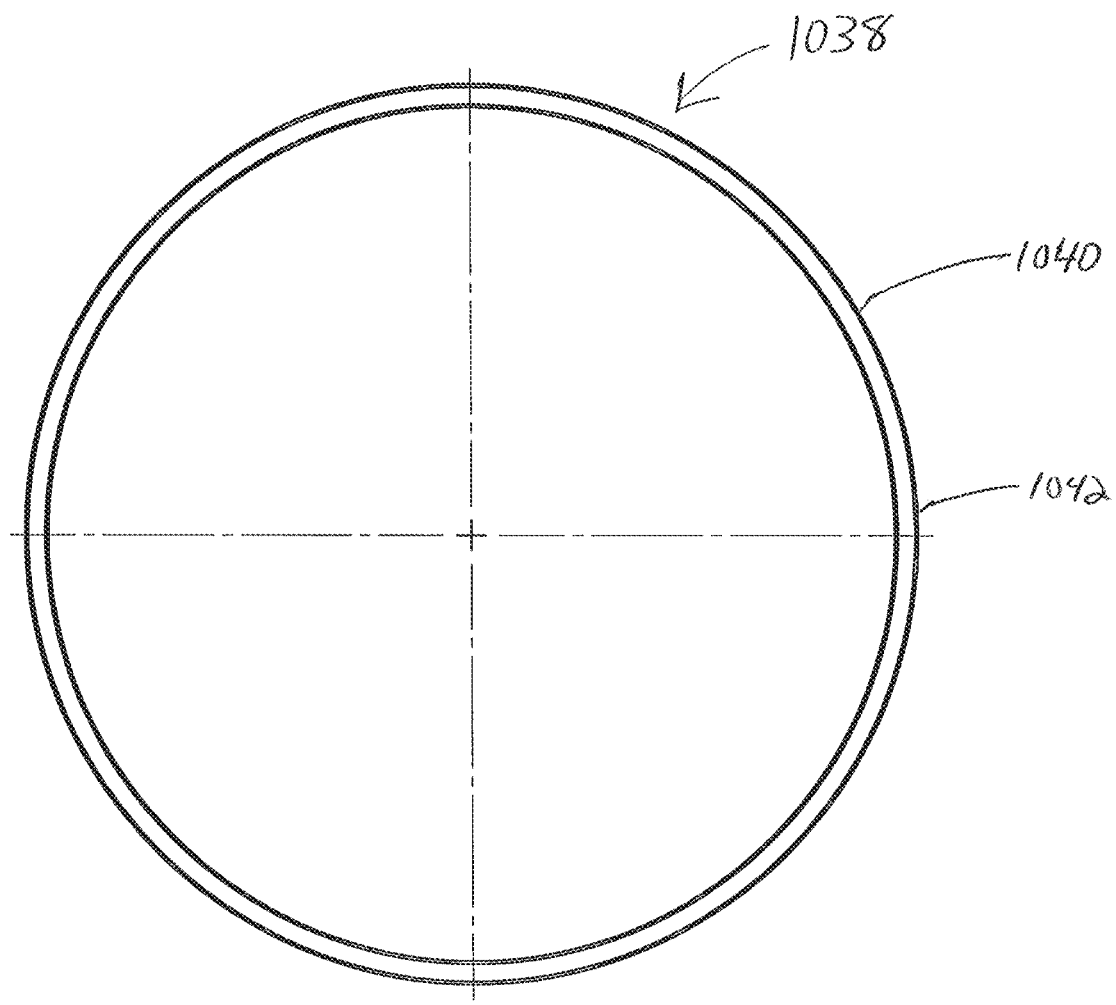
Figure 193B:
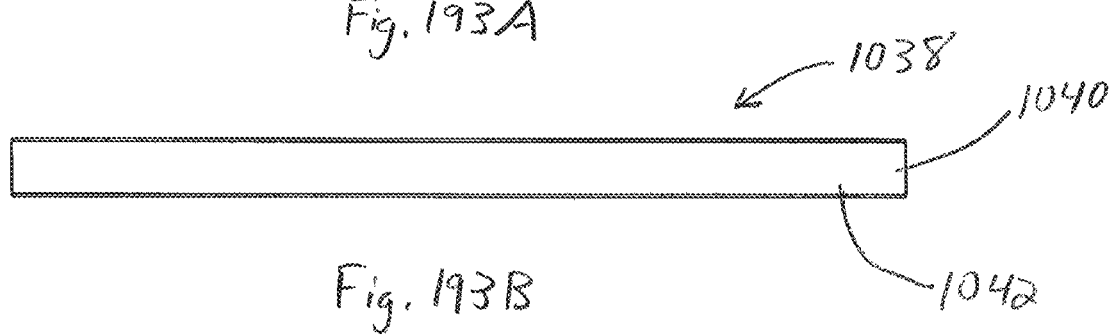

FIGS. 193A and 193B are top and side views, respectively, of the retractor ring of FIG. 189, in accordance with aspects of the present disclosure.

Figure 194A:
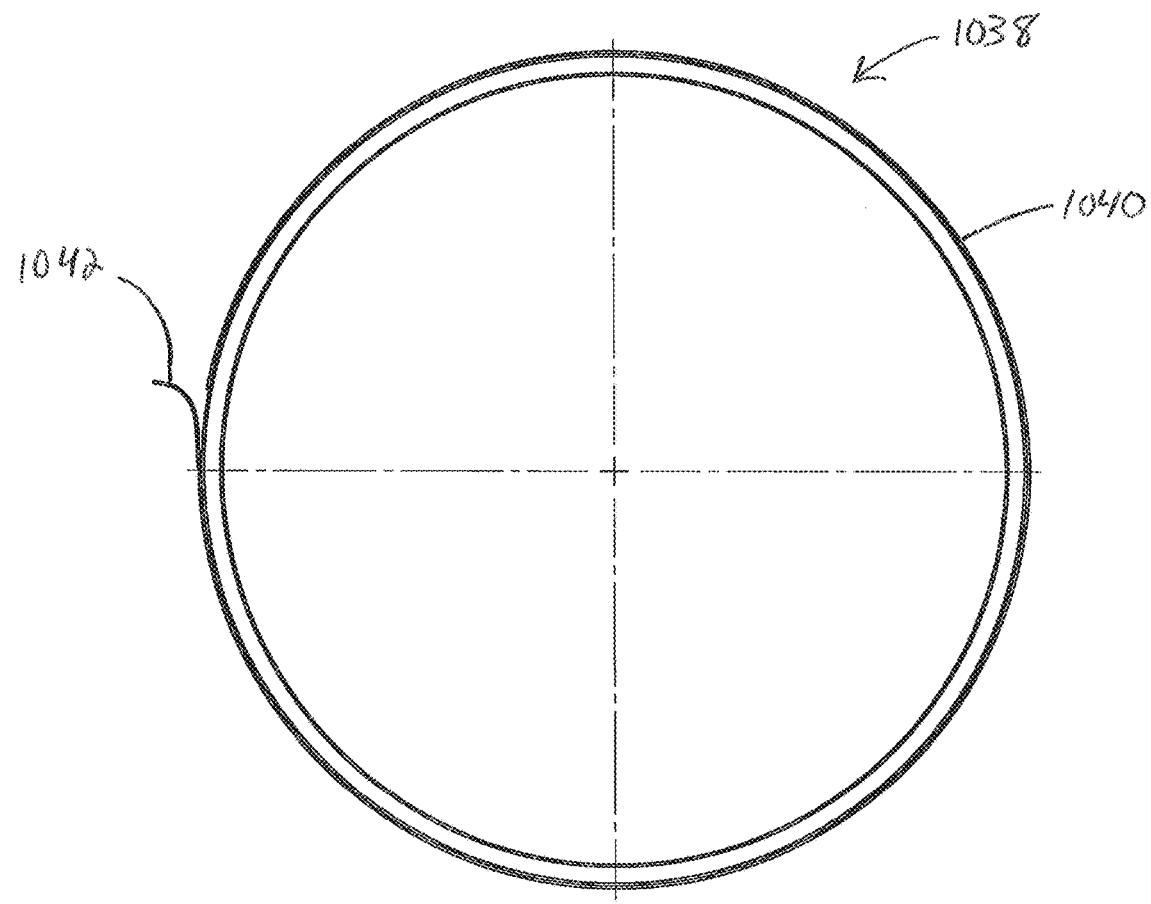
Figure 194B:
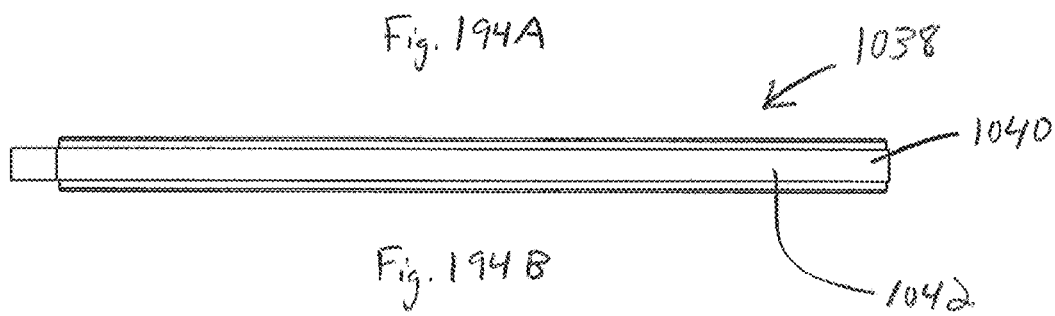

FIGS. 194A and 194B are other top and side views, respectively, of the retractor ring of FIG. 189, in accordance with aspects of the present disclosure.

Figure 195:
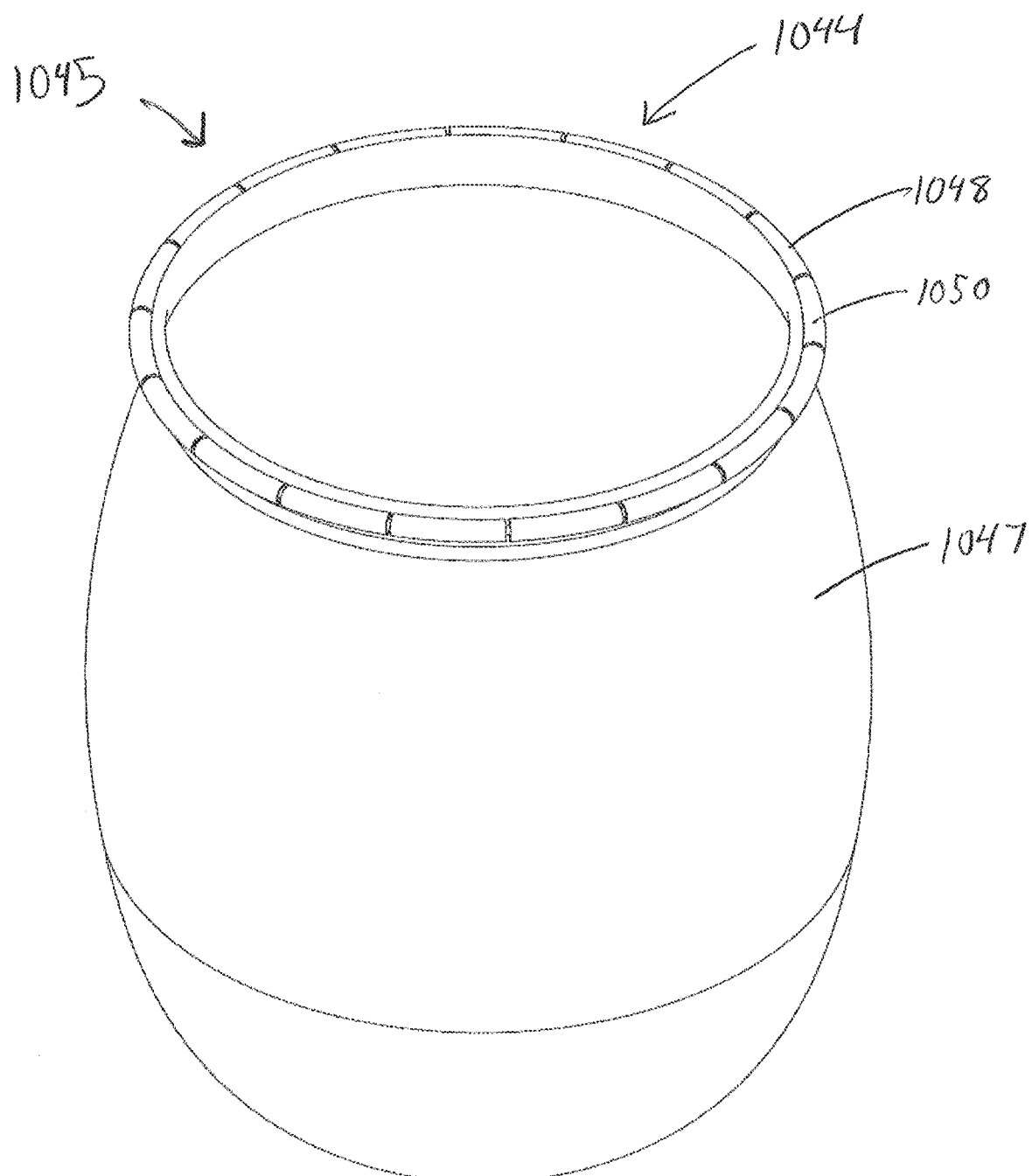

FIG. 195 is a perspective view of another exemplary bag assembly, in accordance with aspects of the present disclosure.

Figure 196:
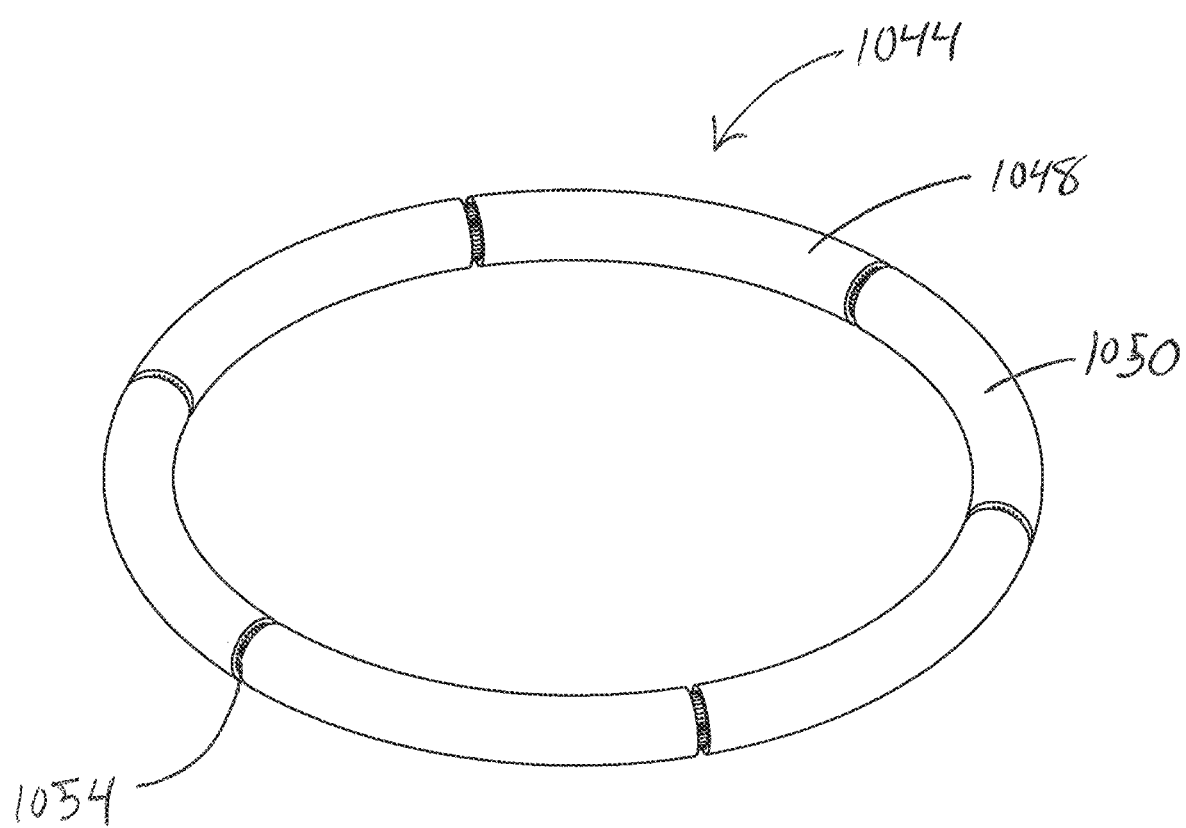

FIG. 196 is a perspective view of a retractor ring of the bag assembly of FIG. 195, in accordance with aspects of the present disclosure.

Figure 197A:
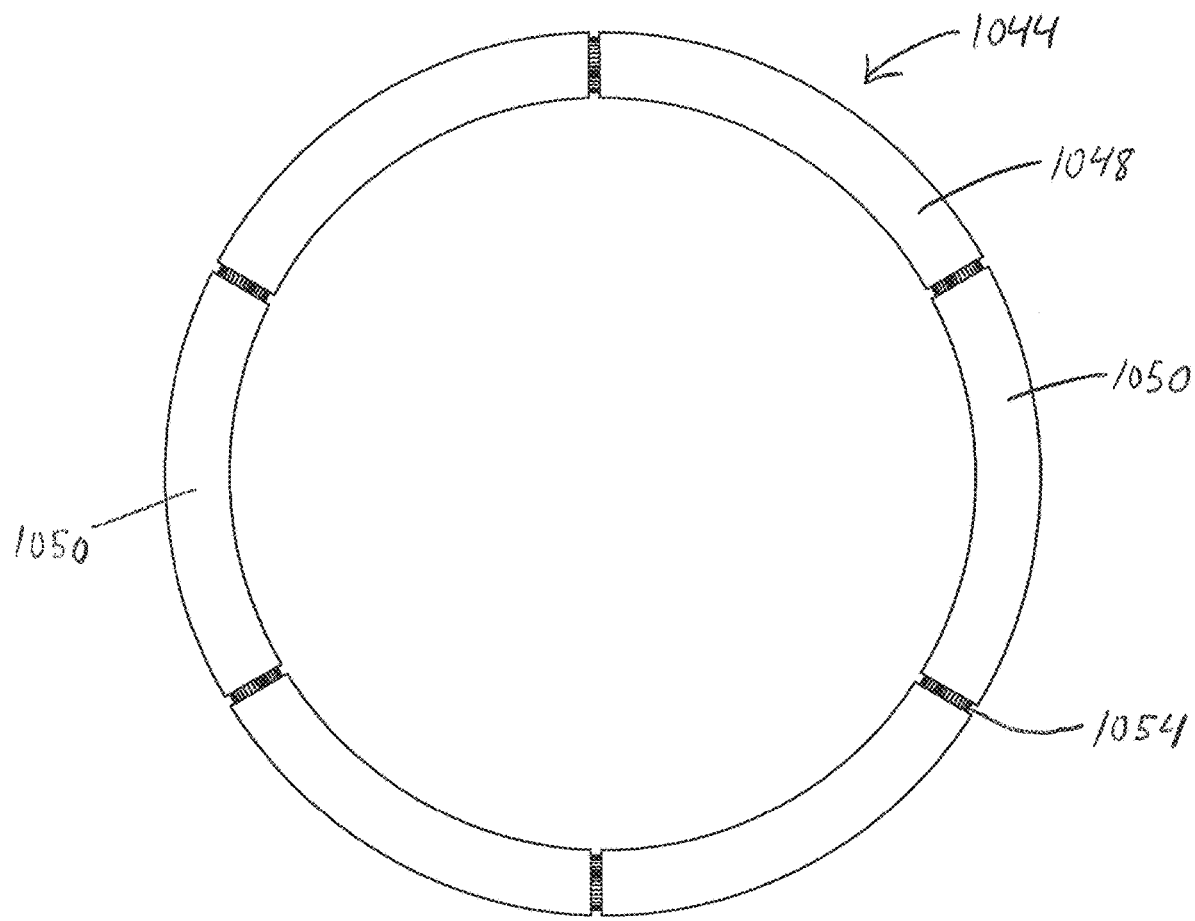
Figure 197B:
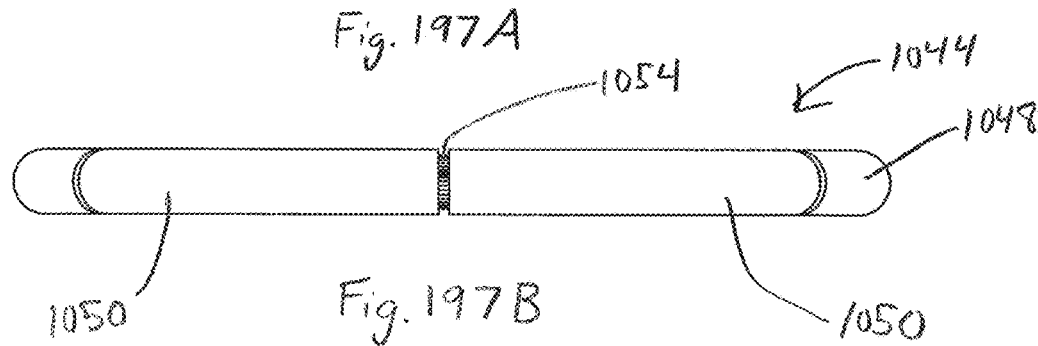

FIGS. 197A and 197B are top and side views, respectively, of the retractor ring of FIG. 196, in accordance with aspects of the present disclosure.

FIGS. 198A and 198B are bottom and cross-sectional side views, respectively, of the retractor ring of FIG. 196, in accordance with aspects of the present disclosure. The cross-sectional side view of FIG. 198B is taken along the line A-A in FIG. 198A.

Figure 199:
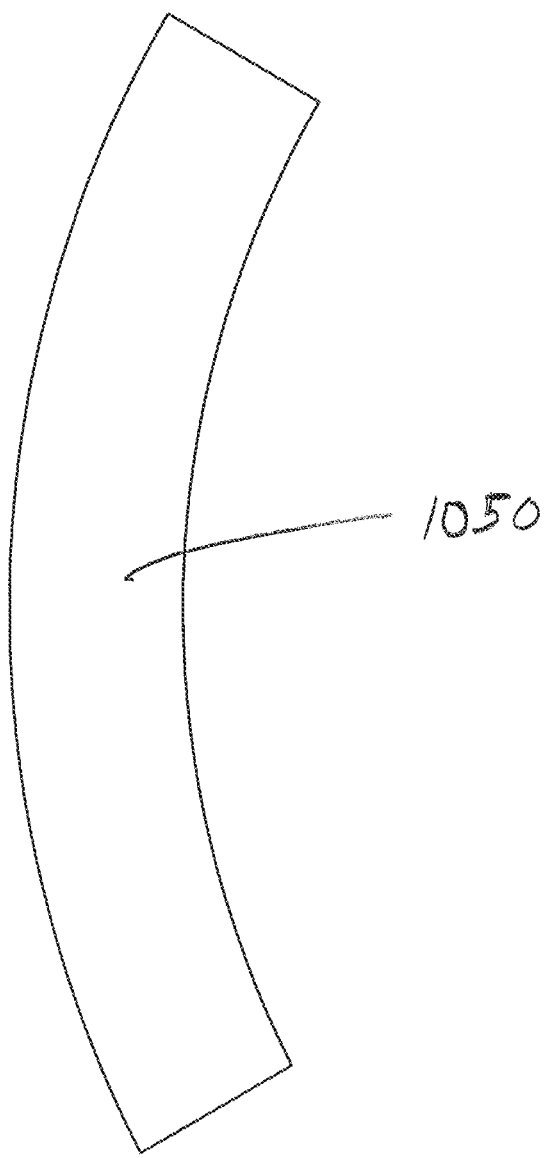
Figure 200:
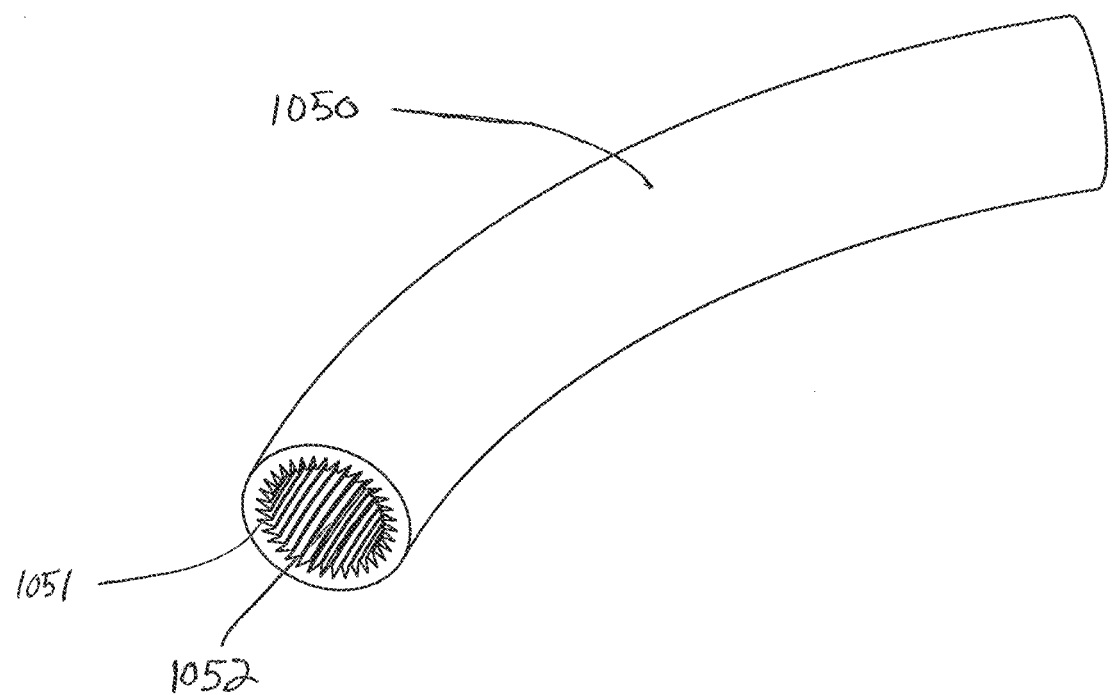

FIGS. 199 and 200 are top and perspective views, respectively, of a section of an outer ring of the retractor ring of FIG. 196, in accordance with aspects of the present disclosure.

Figure 201:
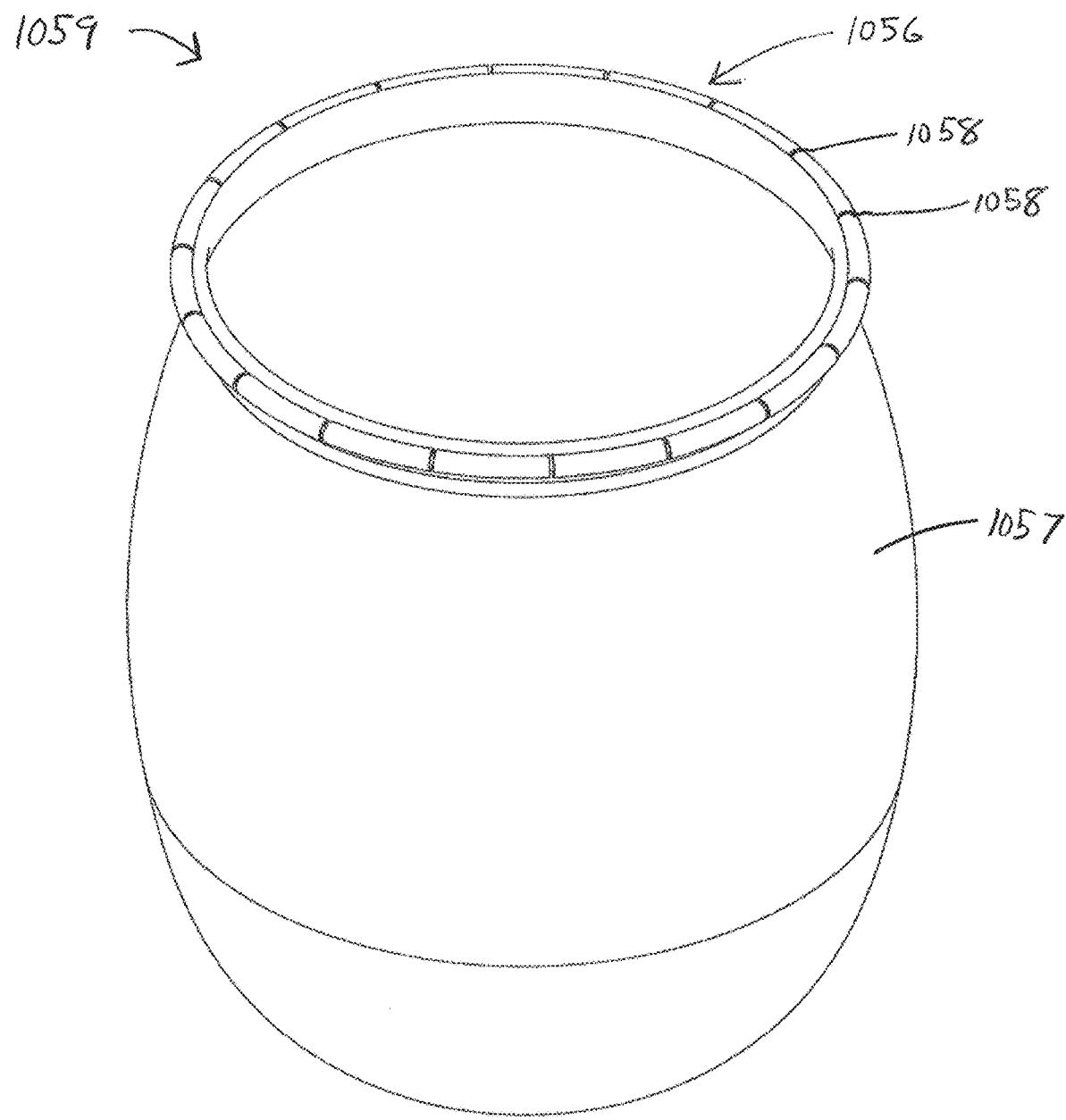

FIG. 201 is a perspective view of another exemplary bag assembly, in accordance with aspects of the present disclosure.

FIG. 202 is a partial top cross-sectional view of the bag assembly of FIG. 201, in accordance with aspects of the present disclosure.

Figure 203A:
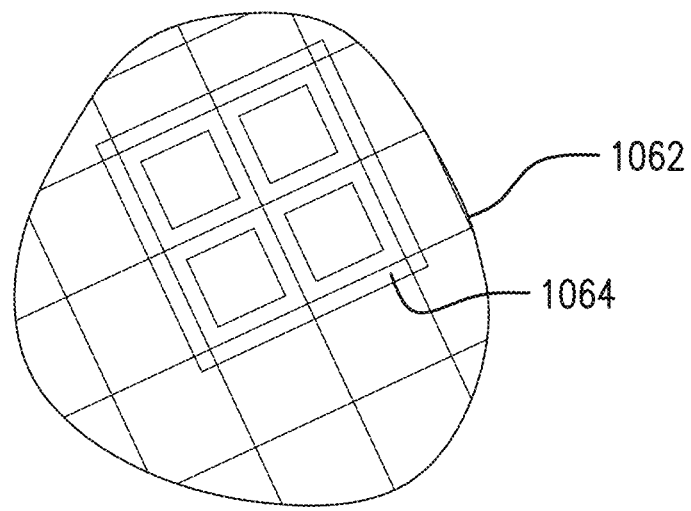

FIG. 203A is a top view of an exemplary mesh bag, in accordance with aspects of the present disclosure.

Figure 203B:
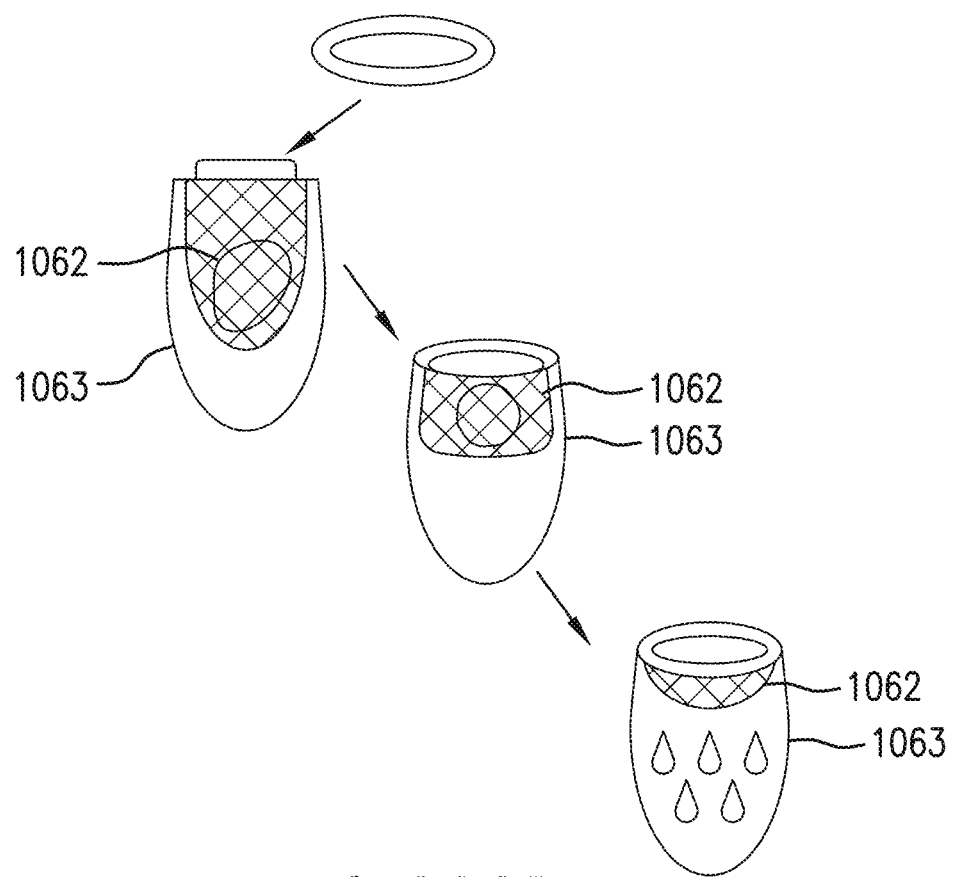

FIG. 203B includes side views of a bag assembly including the mesh bag of FIG. 203A, in accordance with aspects of the present disclosure.

Figure 204A:
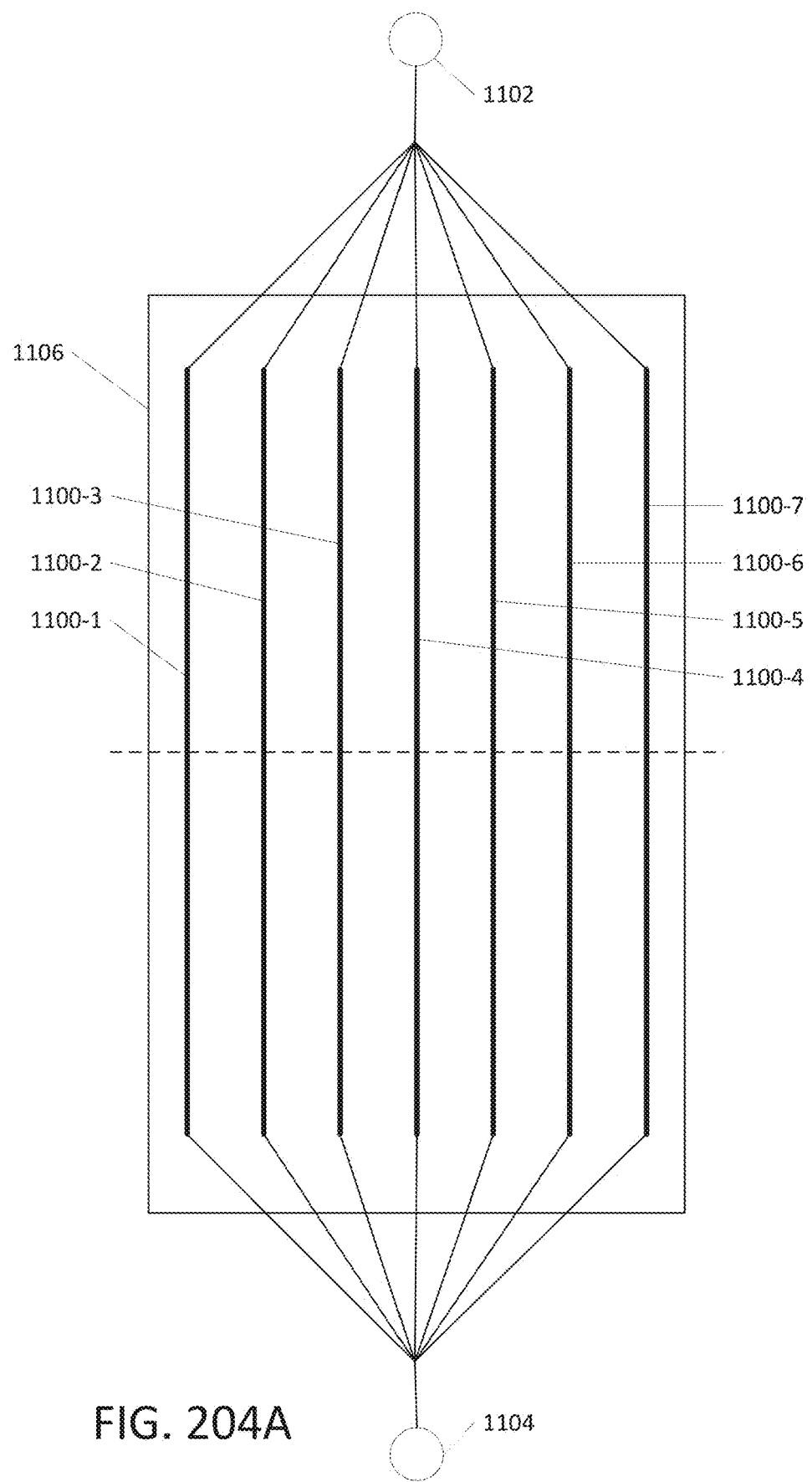
Figure 204B:
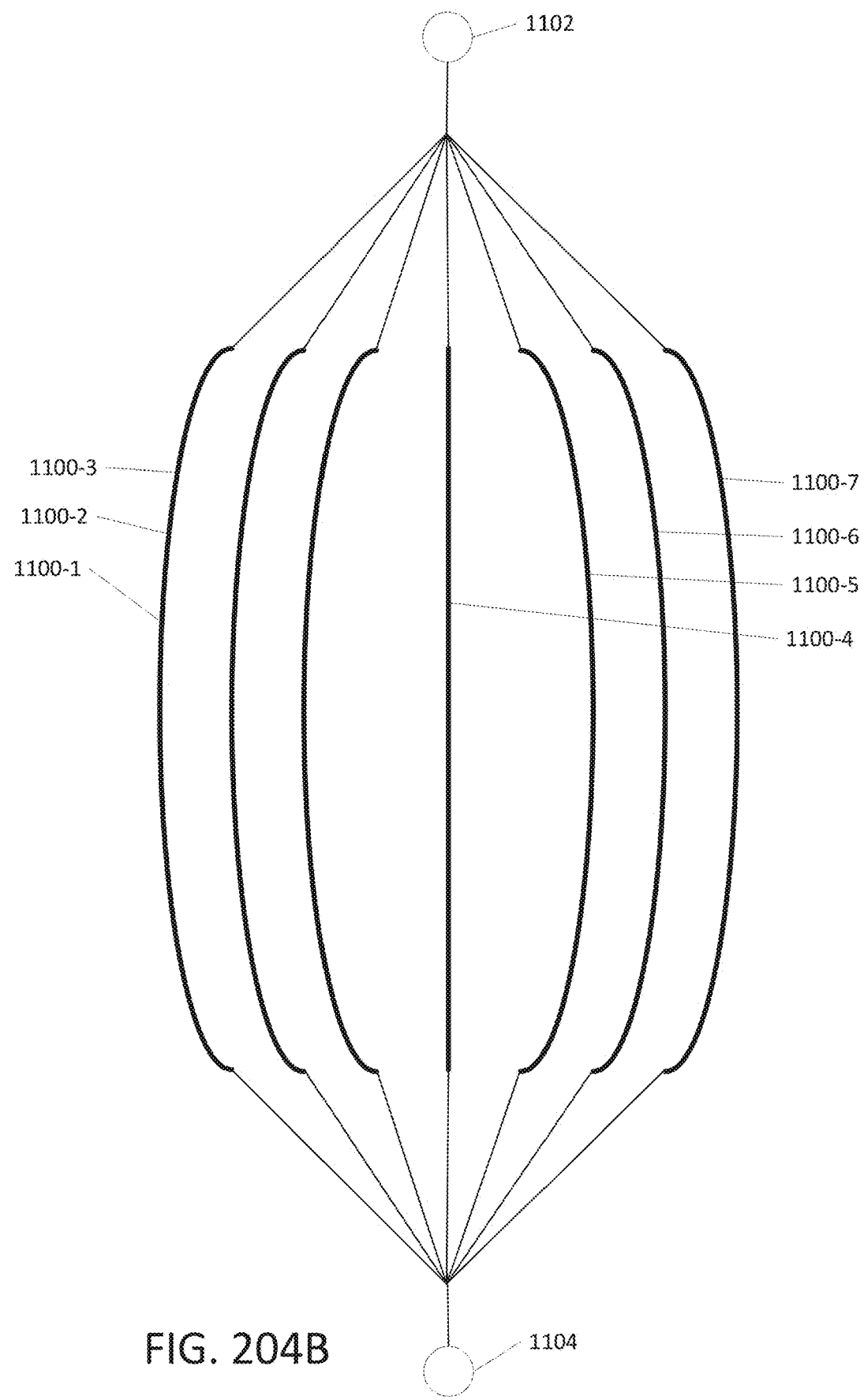

FIGS. 204A and 204B show a plurality of cutting elements having common ends.

Figure 205A:
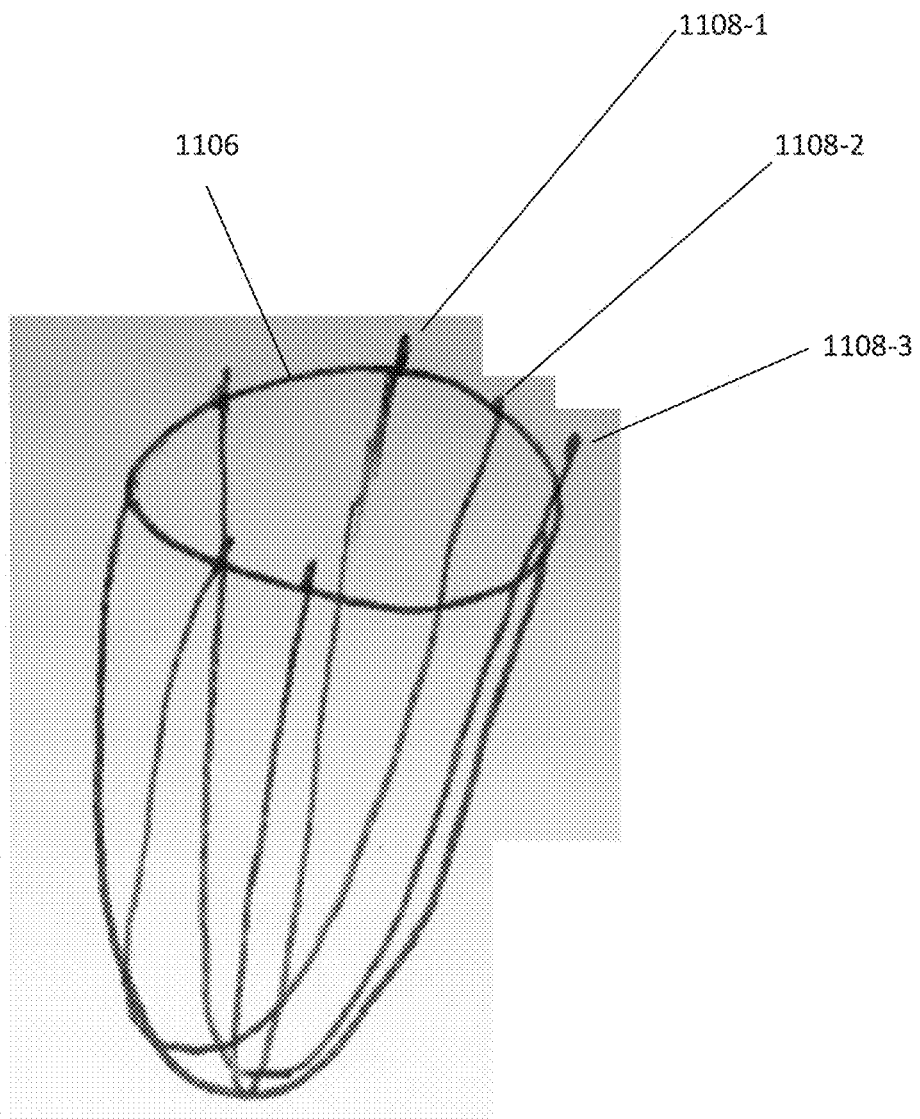

FIG. 205A shows a perspective view of a bag including three strands.

Figure 205B:
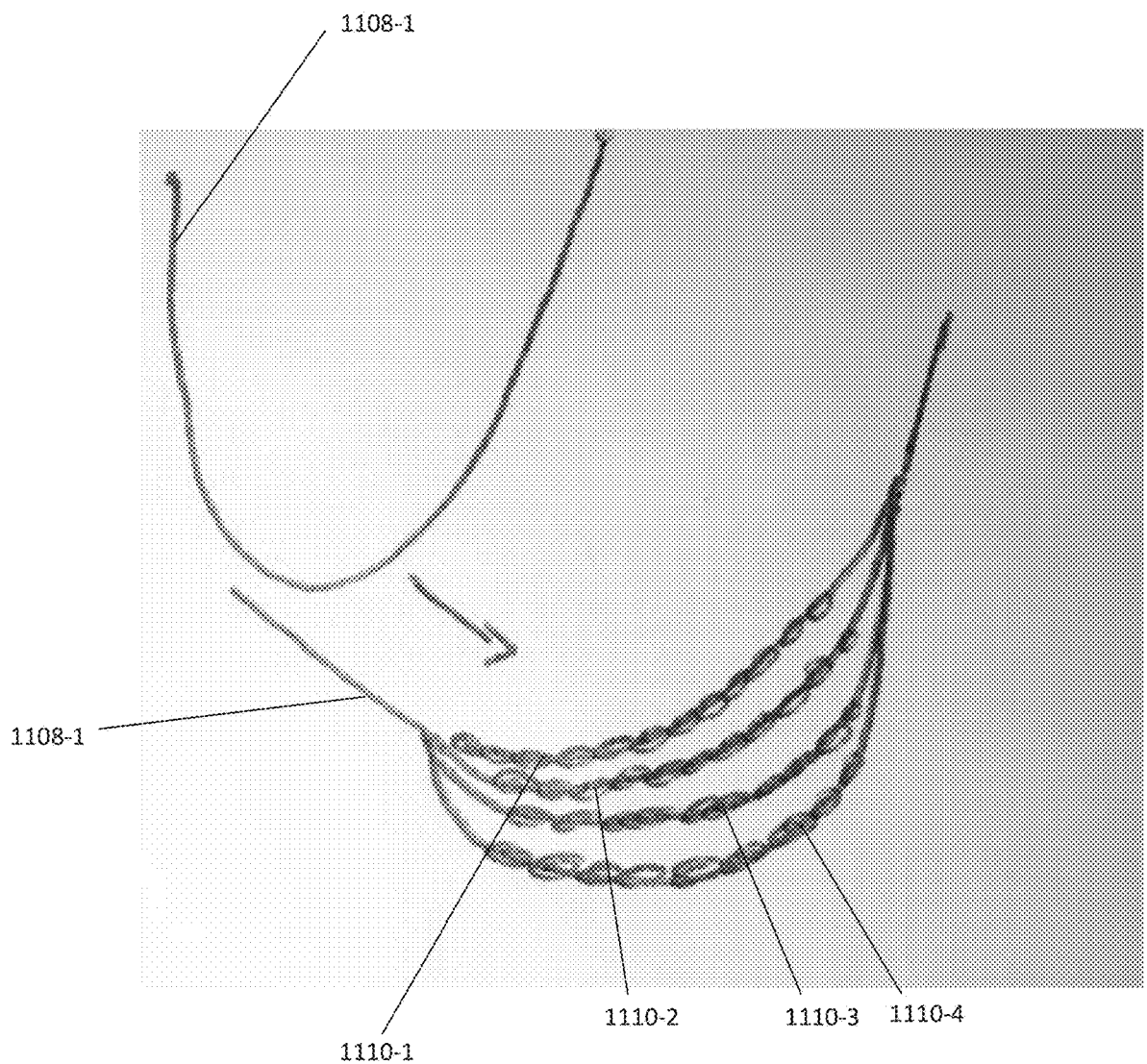

FIG. 205B shows a plurality of cutting elements of a strand in an expanded arrangement.

Figure 205C:
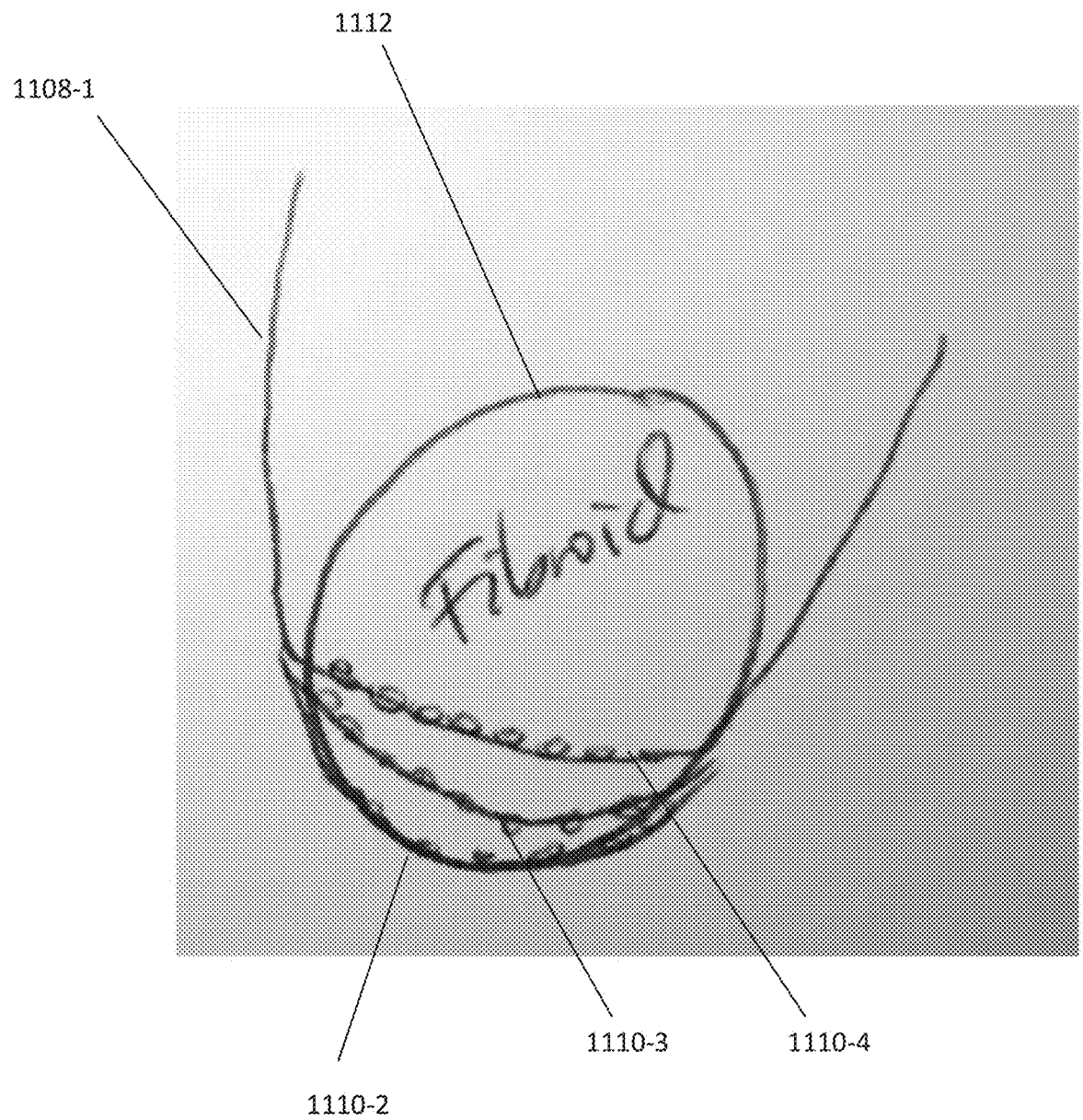

FIG. 205C illustrates the cutting elements of an expanded strand in contact with a tissue specimen.

Figure 206:
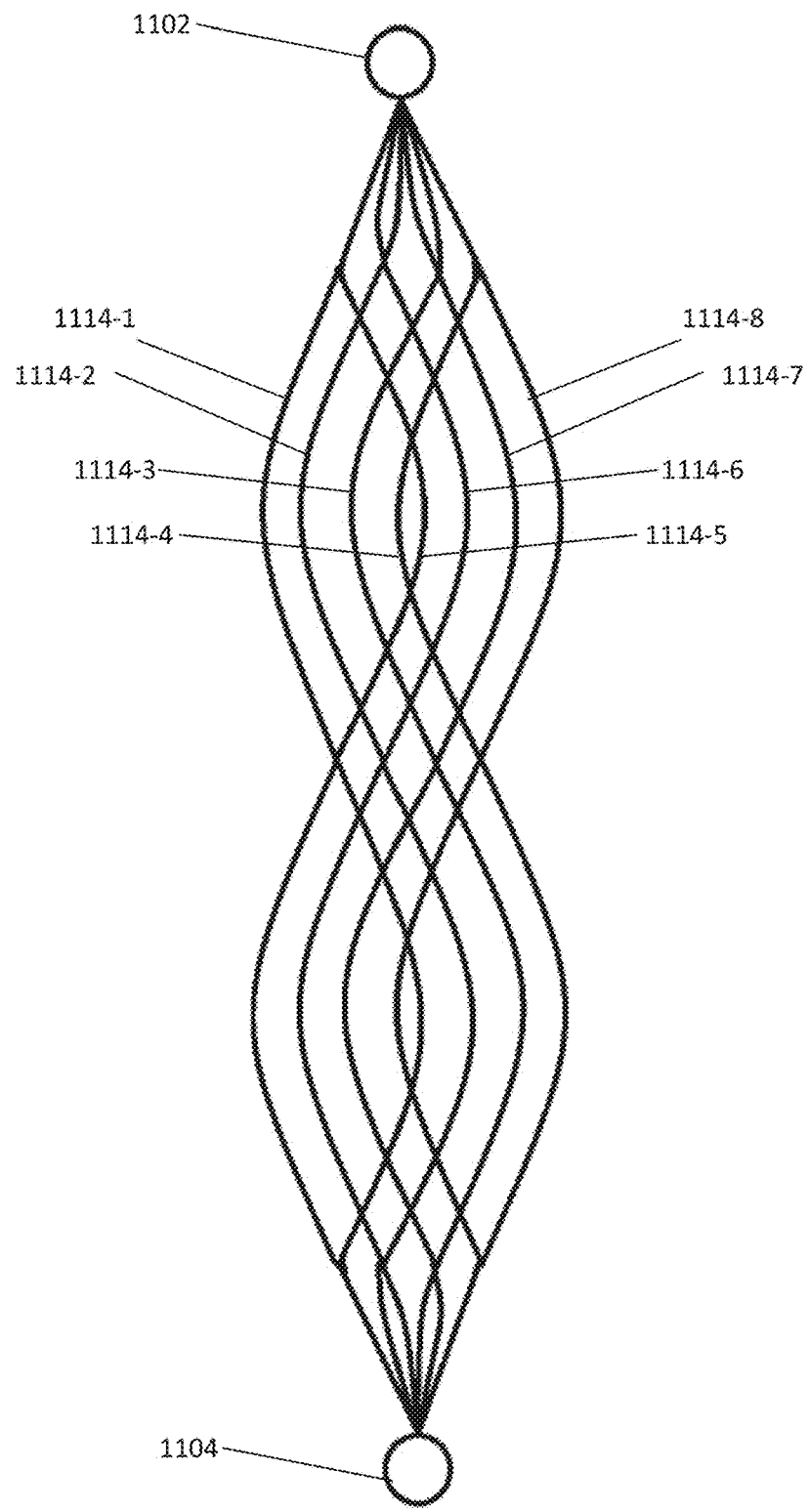

FIG. 206 shows cutting elements having a weaved/woven (crisscrossed) pattern.

Figure 207A:
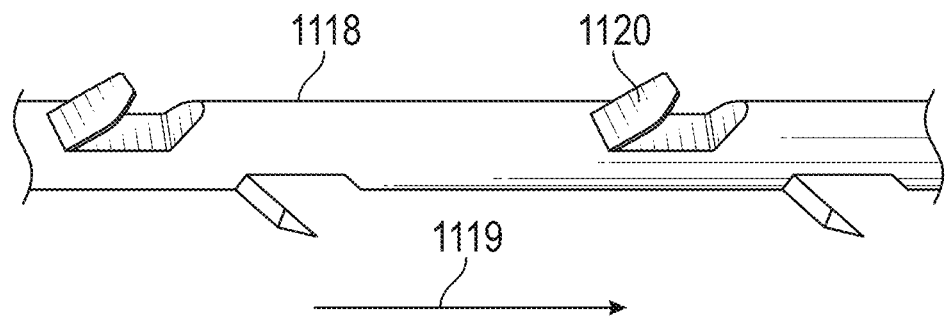

FIG. 207A shows a barbed suture, including a barb, that can serve as a cutting element.

Figure 207B:
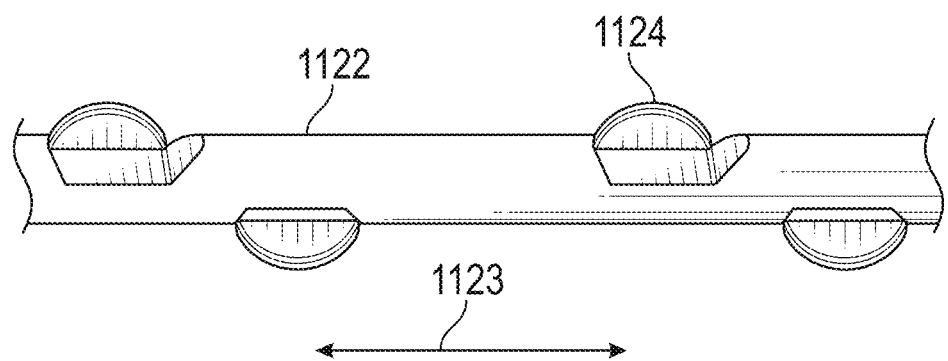

FIG. 207B shows bladed suture, including a blade, that can serve as a cutting element.

Figure 208A:
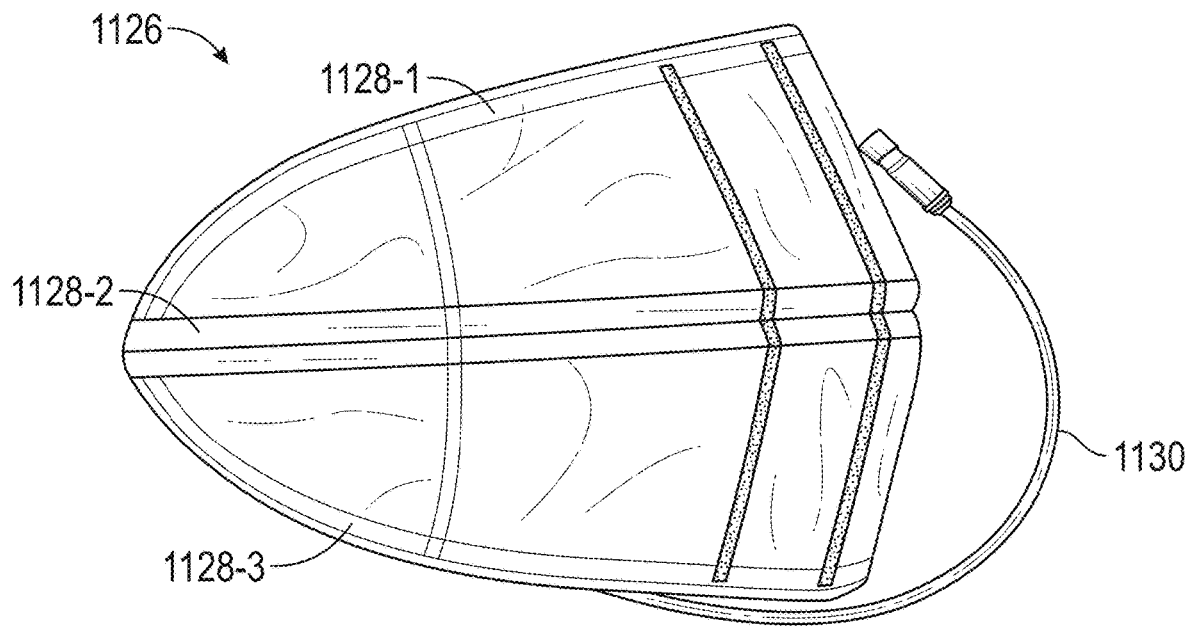

FIG. 208A shows a side view of a bag including inflatable ribs.

Figure 208B:
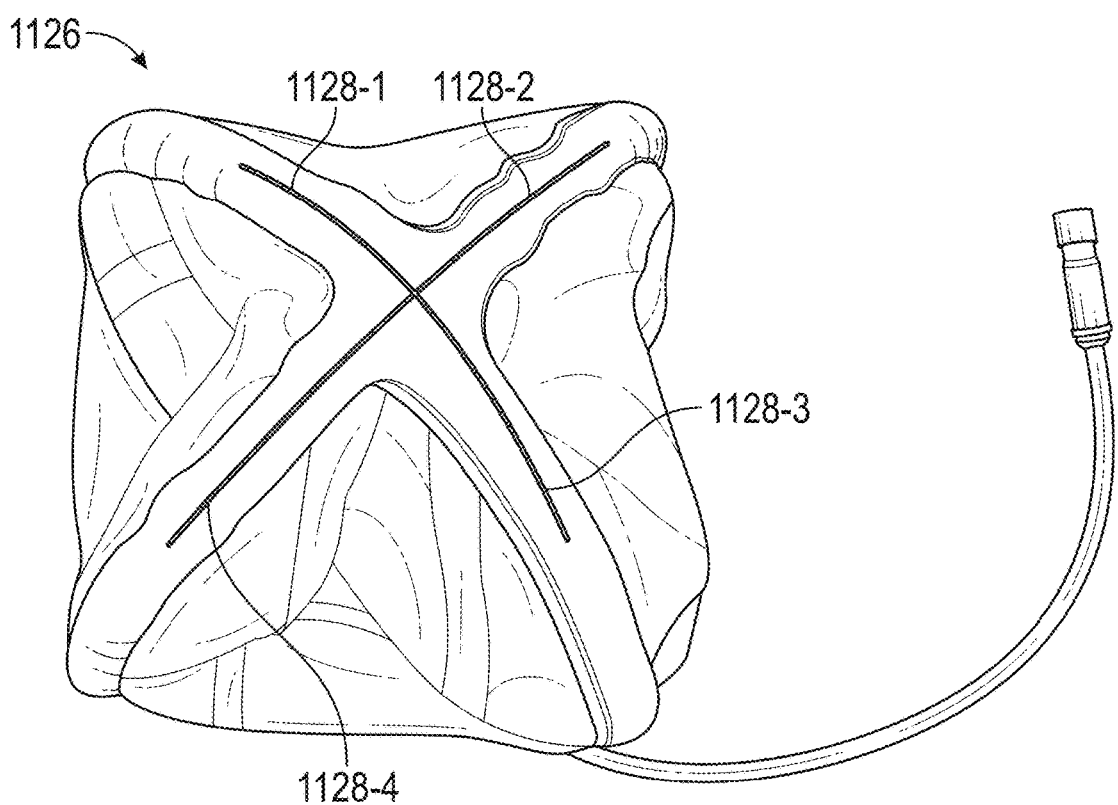

FIG. 208B shows a bottom view of the bag of FIG. 208A including inflated inflatable ribs.

Figure 208C:
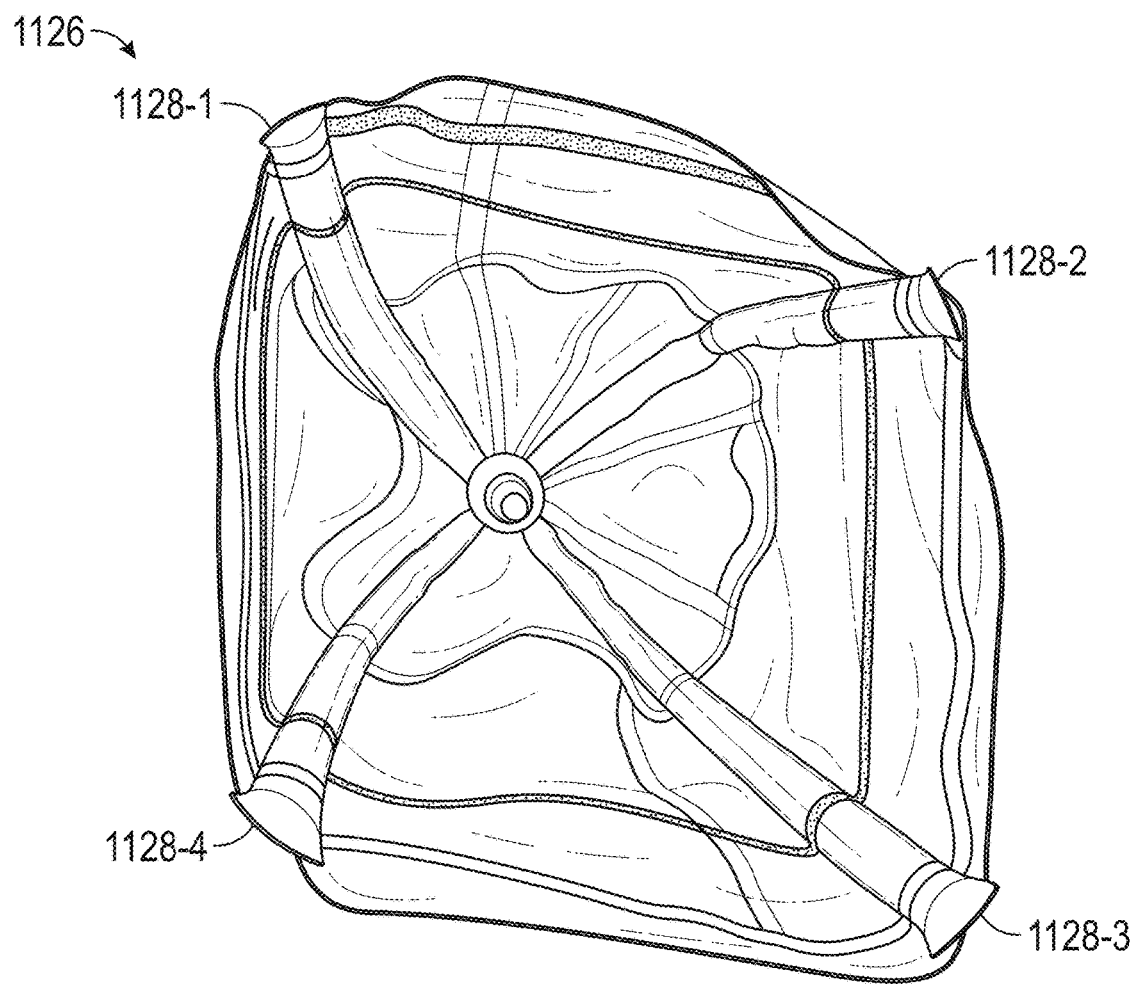

FIG. 208C shows a top view of the bag of FIG. 208A including inflated inflatable ribs.

Figure 208D:
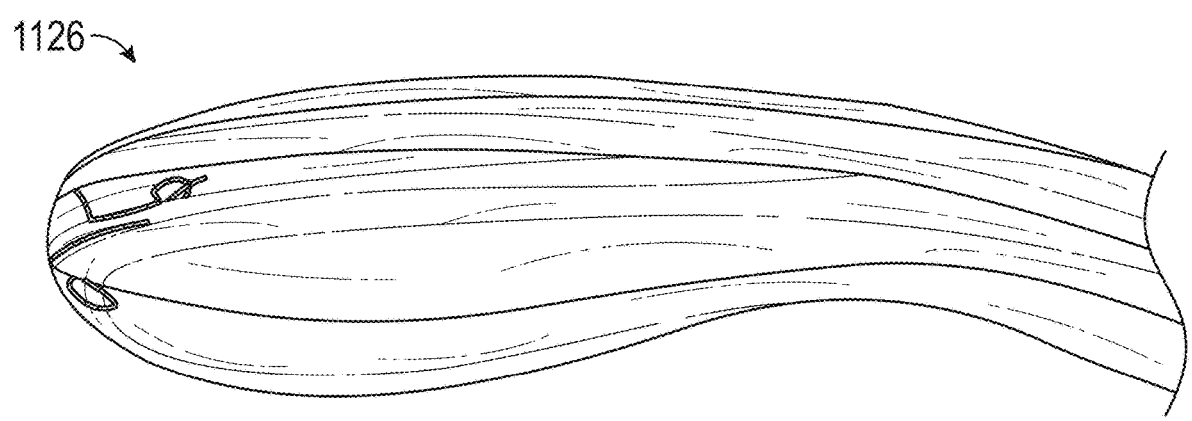

FIG. 208D shows a side view of the bag of FIG. 208A in a compressed state.

FIG. 209 shows a cross-sectional view of a bag including inflatable toroids.

FIG. 210 shows a cross-sectional view of a bag including inflatable corrugation.

Figure 211B:
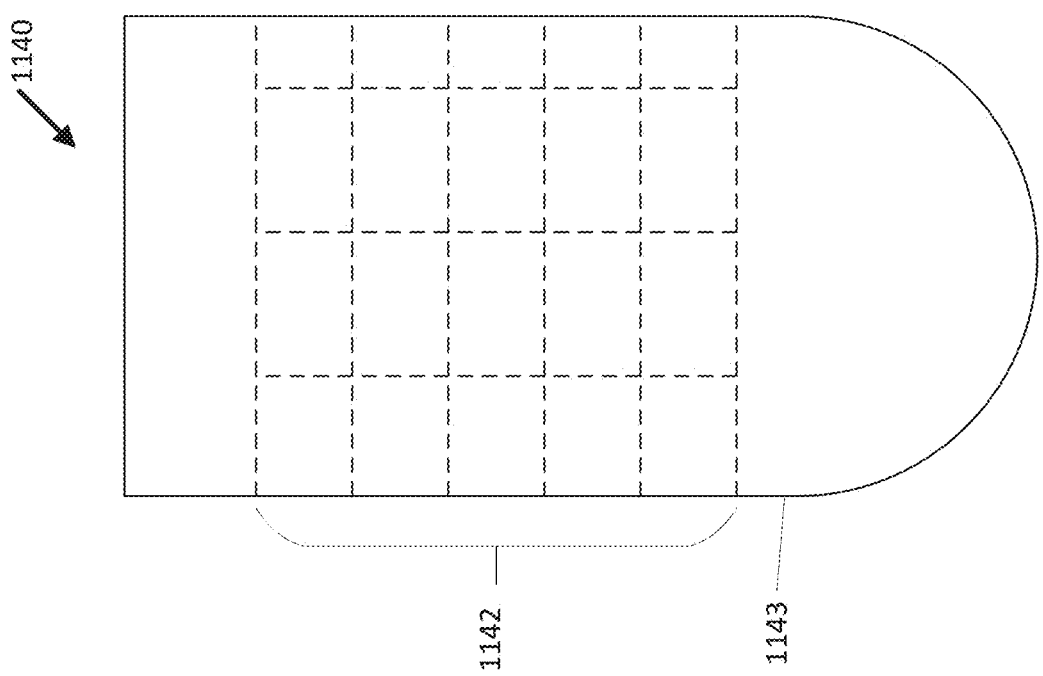
Figure 211A:
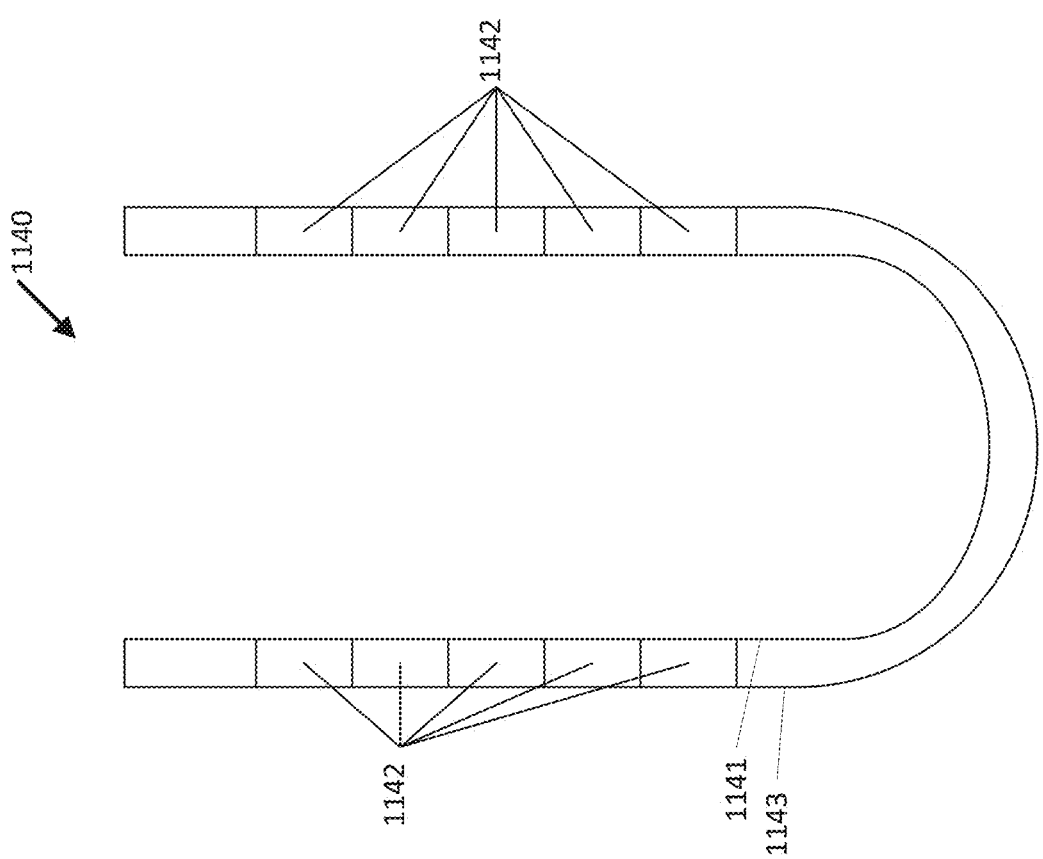

FIG. 211A shows a cross-sectional view of a bag including inflatable cells.

FIG. 211B shows a side view of the bag of FIG. 211B.

Figure 212A:
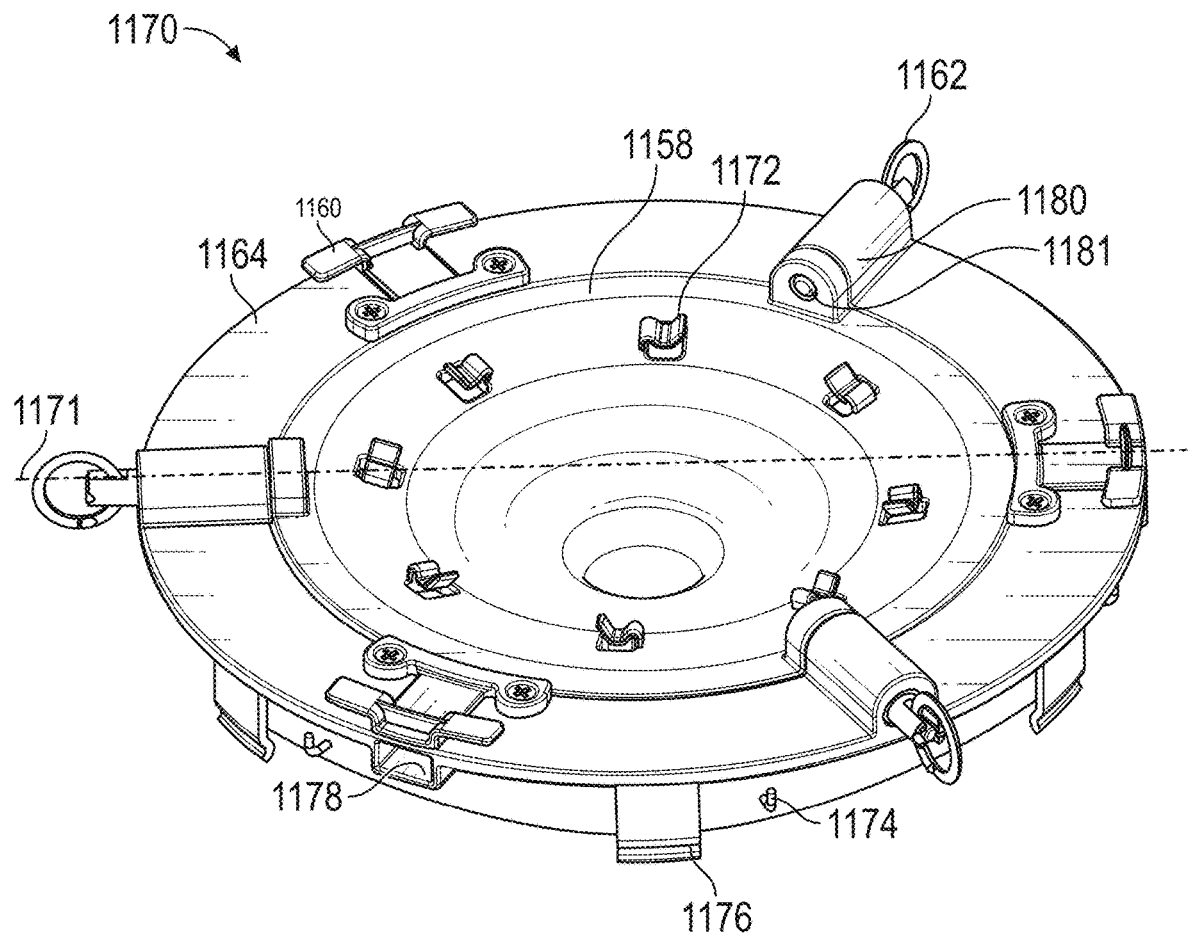

FIG. 212A shows a perspective view of a wound retractor.

Figure 212B:
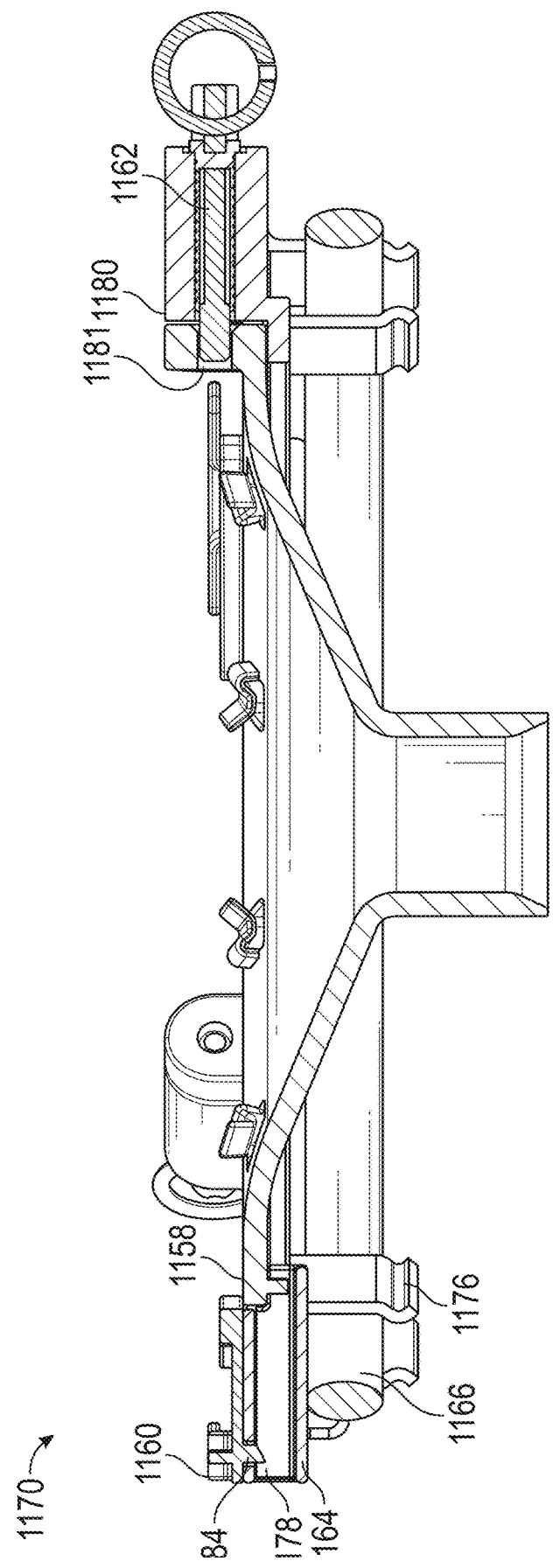

FIG. 212B shows a sectional view of the wound retractor of FIG. 212A.

Figure 212C:
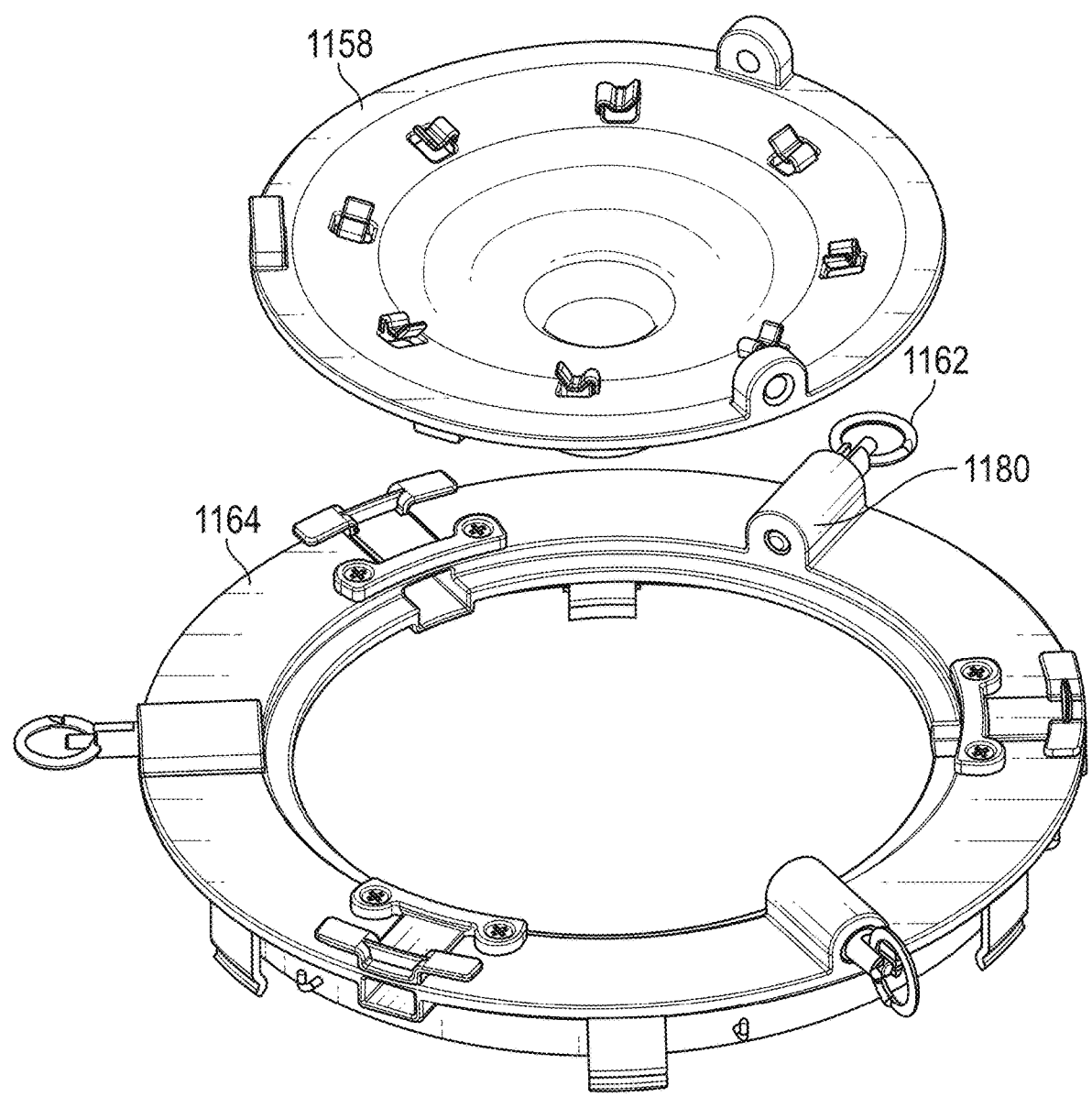

FIG. 212C shows a perspective view of the wound retractor of FIG. 212A with the inner ring removed from the outer ring.

Figure 213A:
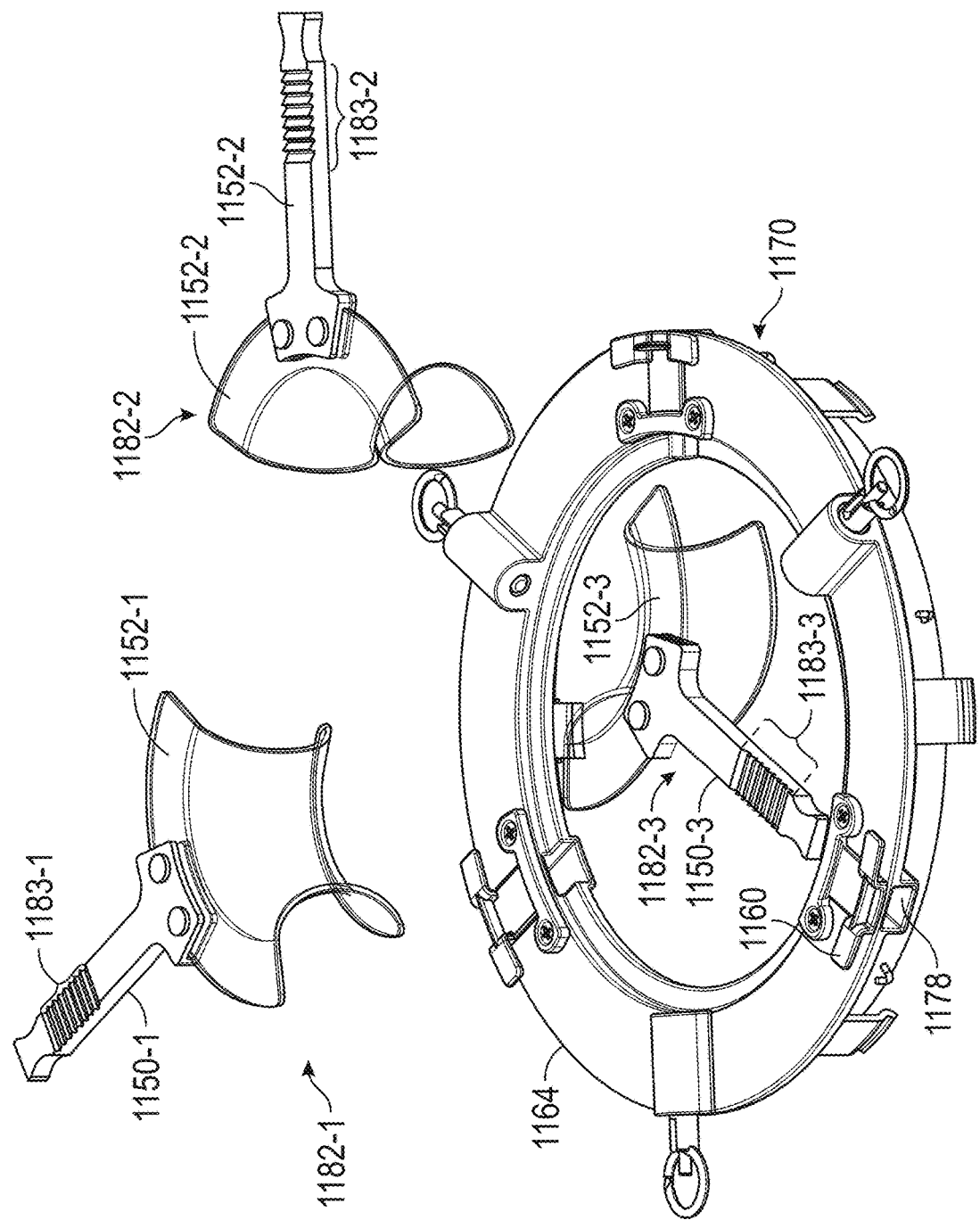

FIG. 213A shows a perspective view of the outer ring of the wound retractor of FIG. 212A and a plurality of retractors.

Figure 213B:
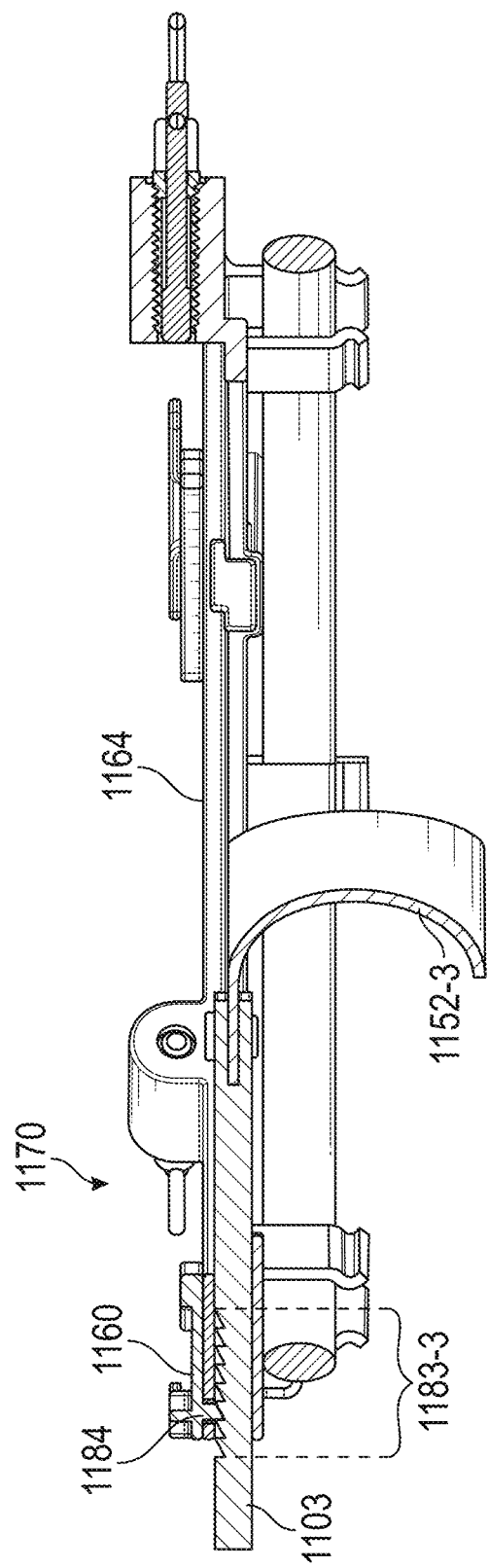

FIG. 213B shows a sectional view of the outer ring of wound retractor of FIG. 212A with a retractor arm positioned within a channel of the outer ring.

Figure 213C:
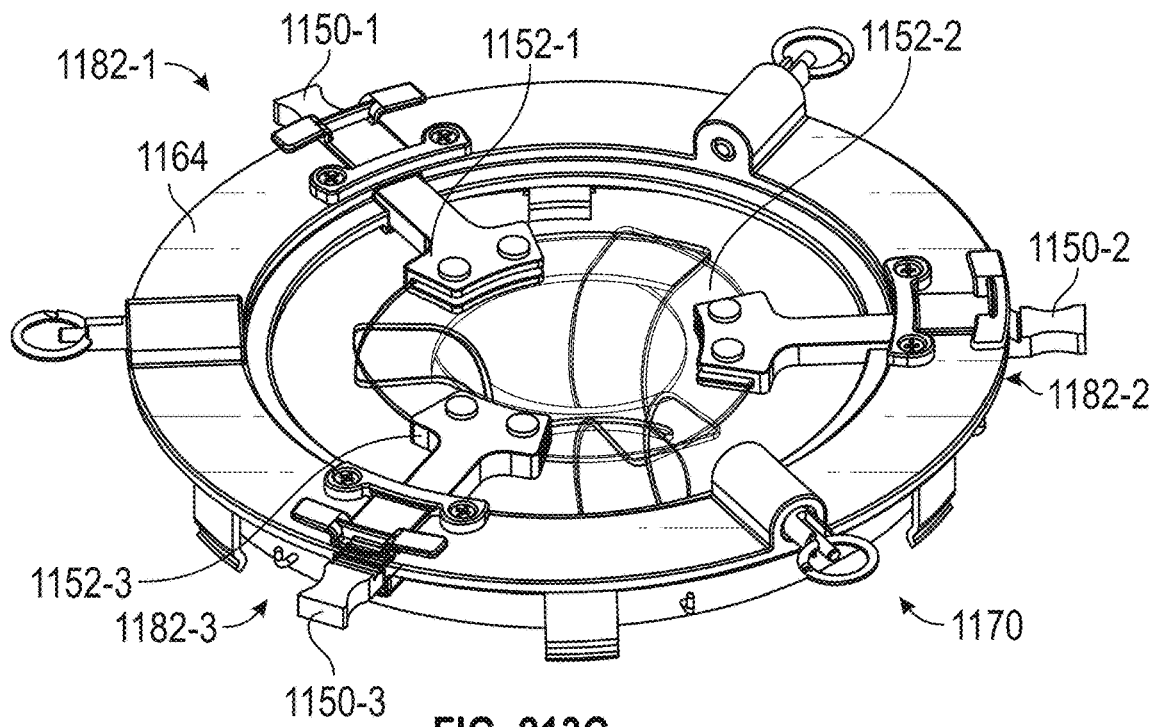

FIG. 213C shows a perspective view of the outer ring of wound retractor of FIG. 212A with retractors positioned within channels of the outer ring.

Figure 213D:
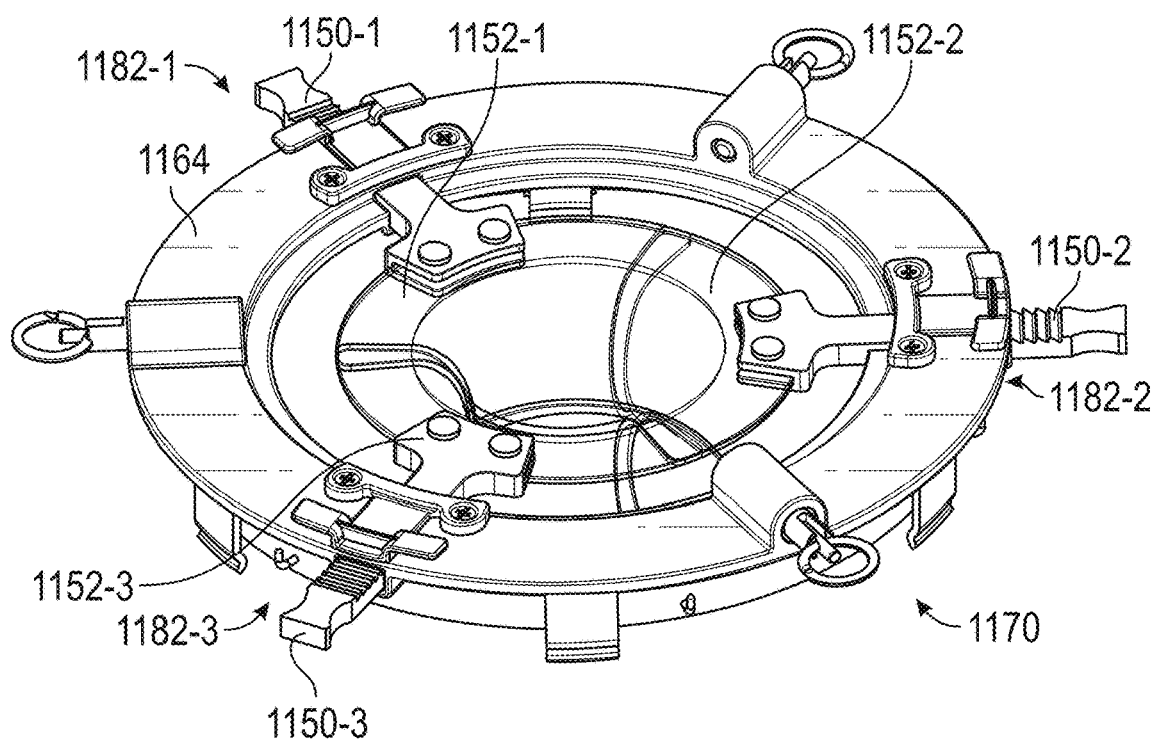

FIG. 213D shows a perspective view of the outer ring of wound retractor of FIG. 212A with retractors positioned within channels of the outer ring.

Figure 214:
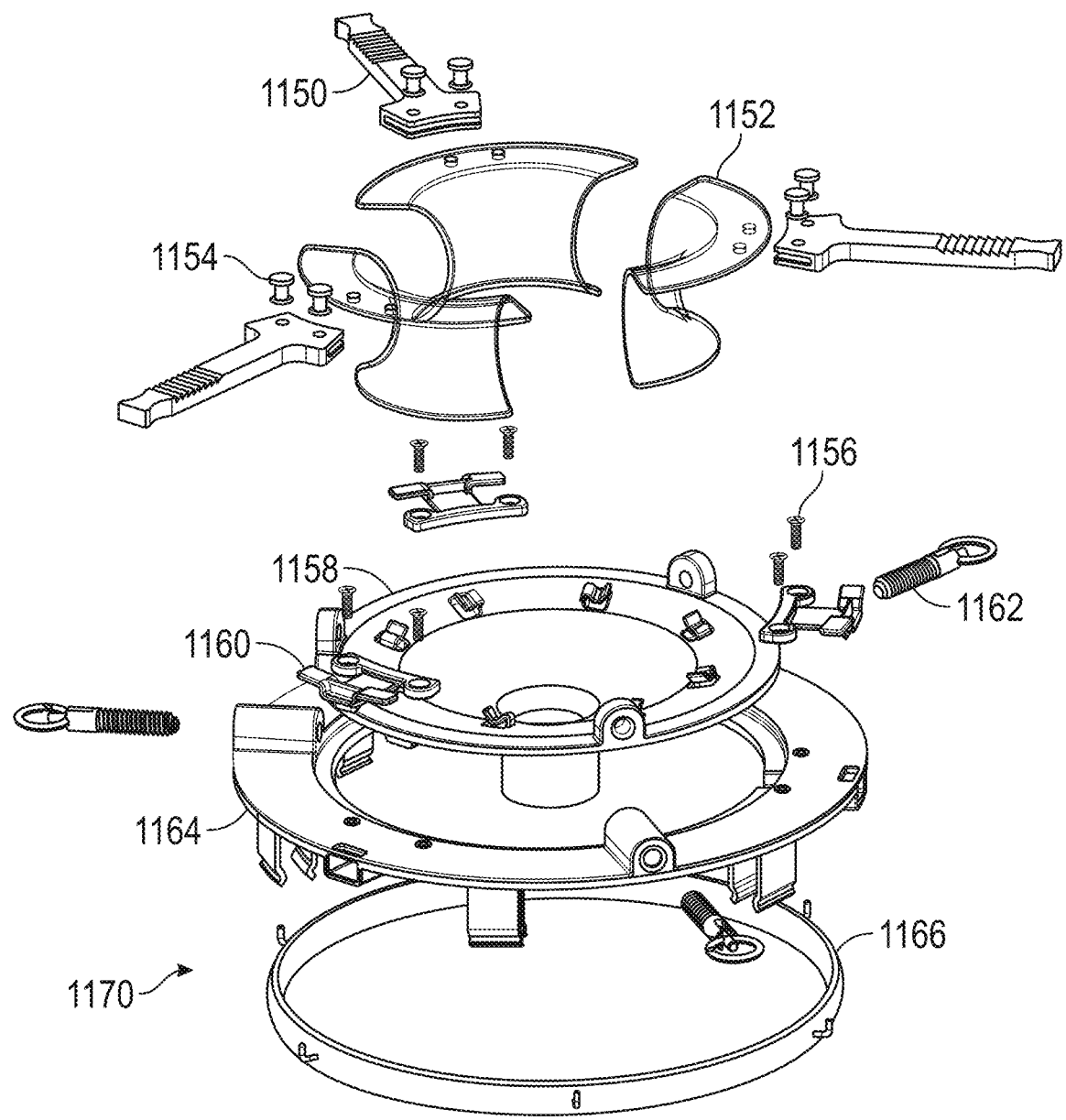

FIG. 214 shows an exploded view of the wound retractor of FIG. 212A.

Figure 215A:
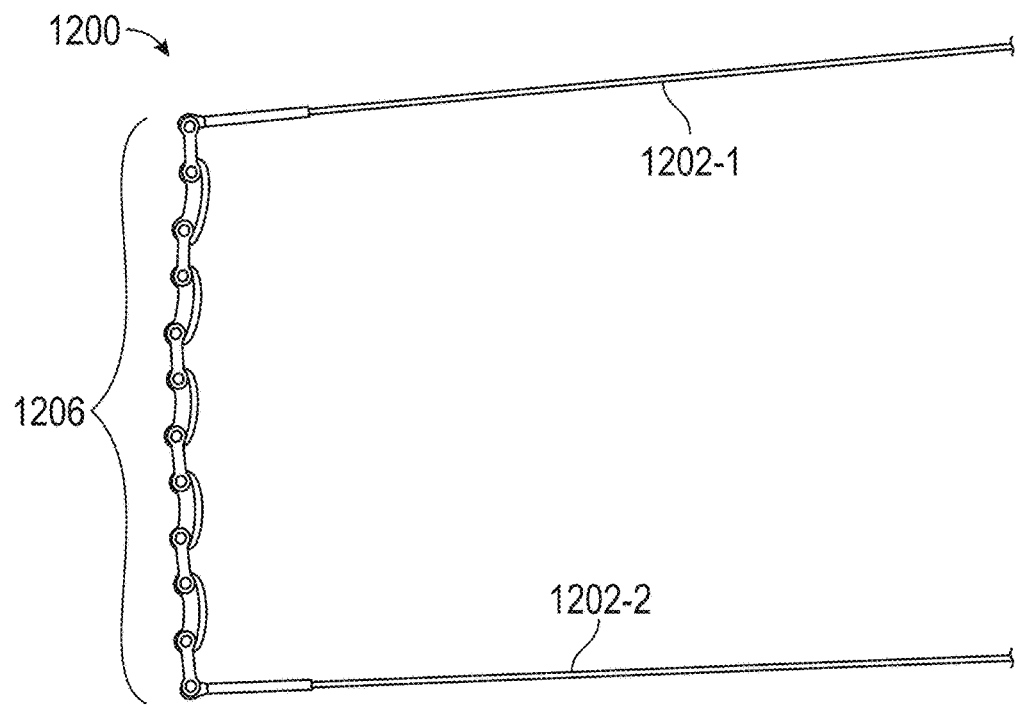

FIG. 215A shows a further illustrative cutter in accordance with the present disclosure.

Figure 215B:
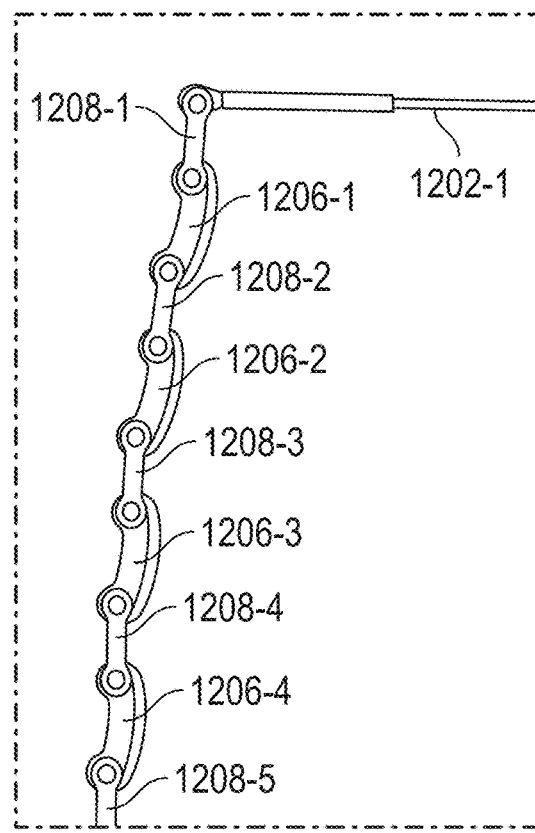
Figure 215C:
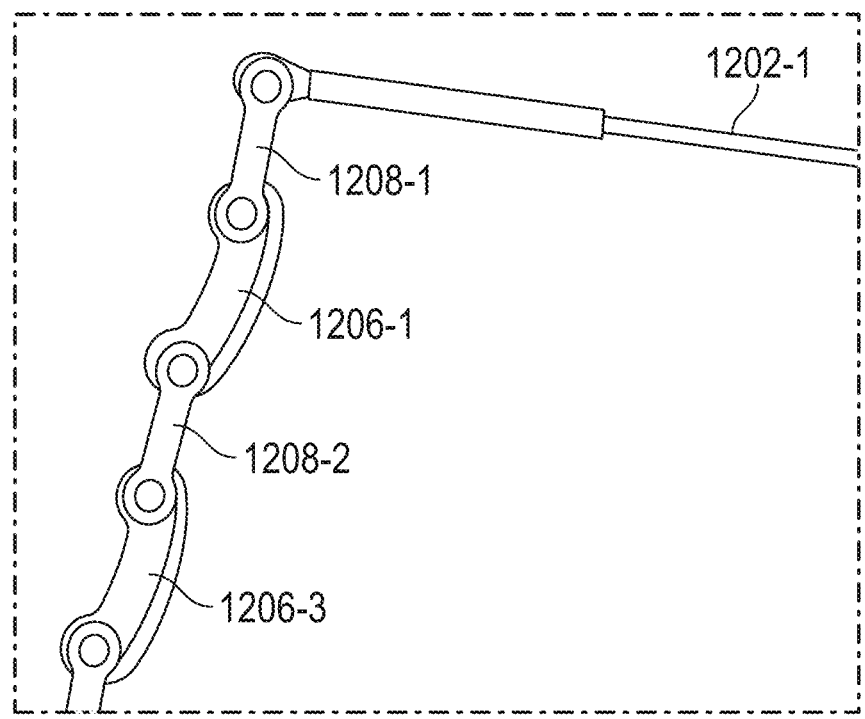

FIGS. 215B and 215C show a portion of the cutter of FIG. 215A.

Figure 215D:
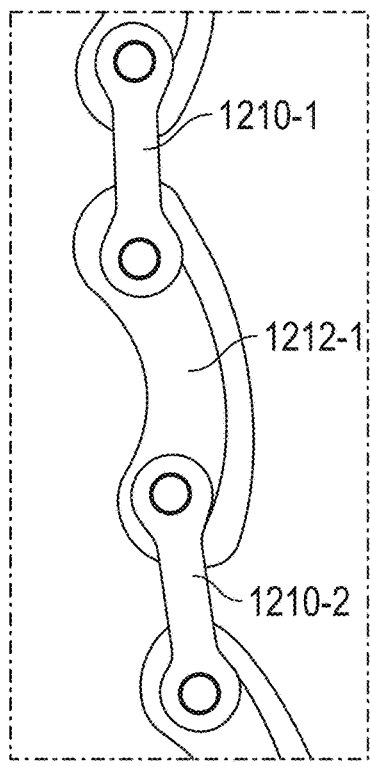
Figure 215E:
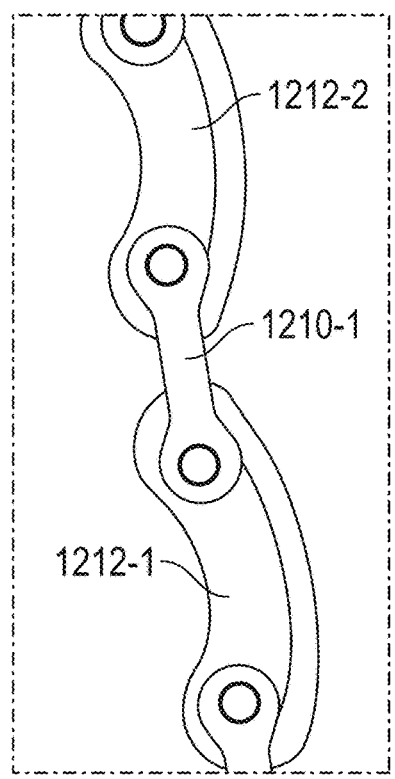

FIGS. 215D and 215E show a portion of a chain of cutting elements.

Figure 215F:
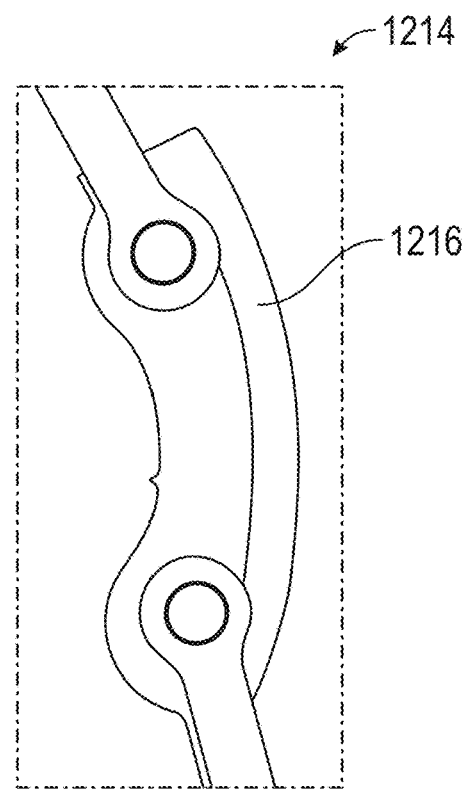

FIG. 215F shows a cutting element in accordance with the present disclosure.

DETAILED DESCRIPTION

The present disclosure is drawn to laparoscopic tissue devices and related methods. Reference now will be made in detail to aspects of the present disclosure, examples of which are illustrated in the accompanying drawings. Wherever possible, the same reference numbers will be used throughout the drawings to refer to the same or like parts. The term "distal" refers to a portion farthest away from a user when introducing a device into a subject. By contrast, the term "proximal" refers to a portion closest to the user when placing the device into the subject. The term "approximately," when used to describe a numerical value, may be anywhere in a range of ±5% from the numerical value.

Figure 1:
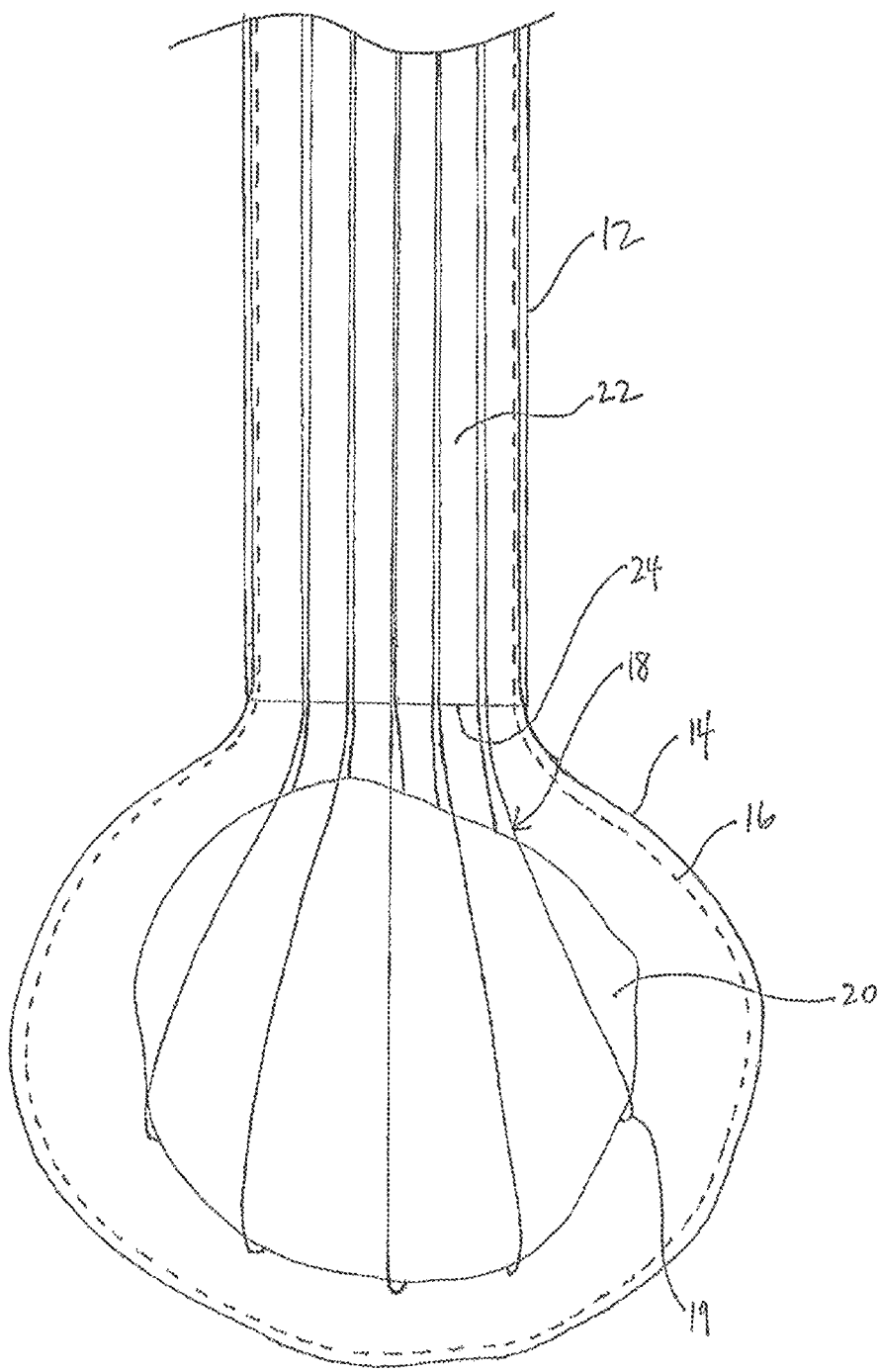
FIG. 1 is a side view of a tissue extraction device, in accordance with aspects of the present disclosure.

FIG. 1 shows an exemplary tissue extraction device 10. Tissue extraction device 10 may include a shaft 12, a bag 14, a liner 16, and one or more strands 18, for performing a procedure on a tissue specimen 20. Aspects of shaft 12, bag 14, liner 16, and strands 18 are described in greater detail below.

Shaft 12 may include a proximal end, a distal end having a distal opening 24, and a lumen 22 extending between the proximal and distal ends. Shaft 12 may be made of plastic, metal, and or any other suitable biocompatible materials. Shaft 12 may have a diameter of about 5 to 50 mm, and may have a length of about 30 to 50 cm.

Strands 18 may extend through lumen 22. Proximal ends of strands 18 may be accessible to a user from the proximal end of shaft 12, and may be manipulated by the user. Distal portions of strands 18 may extend out of distal opening 24, forming loops 19. Strands 18 may include threads, fibers, and/or wires. Strands 18 be made out of polypropylene, steel, Nitinol or any other similar suitable material. It is also contemplated that strands 18 may have an abrasive and/or sharp surface to facilitate cutting of tissue. For example, surfaces of strands 18 that face tissue specimen 20 (e.g., inner surfaces of strands 18) may be abrasive and/or sharp.

Additionally or alternatively, strands 18 may be covered with a coating (not shown) of silicone (or similar material) to prevent strands 18 from tearing bag 14. For example, surfaces of strands 18 that face away from tissue specimen 20 may be coated. It is also contemplated that some of strands 18 may be abrasive and/or sharp, while other strands 18 may be coated. Alternatively, one or more of strands 18 may have alternating coated and uncoated portions along its length.

Loops 19 may surround tissue specimen 20. One or more of the proximal ends of strands 18 may be manipulated by the user to cause loops 19 to cut tissue specimen 20. For example, one of the proximal ends of one of strands 18 may be fixed, or at least held in a fixed position, while the other proximal ends may be movable in a proximal direction to contract loops 19, and in a distal direction to expand loops 19. Additionally or alternatively, both of the proximal ends of each of strands 18 may be movable. For example, the one of the proximal ends may be movable in a reciprocating manner, with one end moving proximally while the other end moves distally, to cause loop 19 to move back-and-forth with a sawing motion across tissue specimen 20. It is also contemplated that both of the proximal ends may be movable proximally or distally together to contract and expand loop 19, respectively.

Combinations of movements of strands 18 are also contemplated. For example, strands 18 may be moved so as to cause loops 19 to contract and reciprocate simultaneously or sequentially. It is also contemplated that strands 18 may move similarly to one another, or alternatively, different strands 18 may undergo different movements. Due to the spaced arrangement of loops 19, spaced cuts may be formed in tissue specimen 20 by loops 19, providing the user with control over the shapes and dimensions of the resulting pieces of tissue specimen 20 that are formed by the cutting.

Bag 14 may be lined by liner 16. Bag 14 may be made out nylon, polyvinyl chloride, or any other suitable material. Bag 14 may be waterproof and may completely enclose tissue specimen 20. For example, an open end 26 of bag 14 may form a seal around the distal end of shaft 12, preventing material from leaking out from within bag 14. Liner 16 may include, for example, a layer of mesh. Liner 16 may be made out of polypropylene or another suitable material. Liner 16 may provide support to tissue specimen 20 during cutting of tissue specimen 20 by strands 18, and/or may assist with extraction of tissue specimen 20. It is contemplated that in one example, liner 16 may be omitted.

In use, bag 14, liner 16, and strands 18 may be deployed from the distal end of shaft 12. Shaft 12 may be introduced via an incision or through an existing orifice (e.g., a subject's vagina). When a target area (e.g., a cavity in the subject's body) is reached, bag 14, liner 16, and strands 18 may be deployed from the distal end of shaft 12. Bag 14 may be opened inside the body cavity. Tissue specimen 20 may be placed into bag 14.

Open end 26 may be pulled out of the incision/orifice, and strands 18 may be inserted into the externalized open end 26 and positioned in bag 14 and around tissue specimen 20. Alternatively, open end 26 may be grasped by a grasping instrument inserted through shaft 12, and may be pulled into shaft 12 and out of the body cavity. The grasping and pulling of open end 26 may take place either prior to or after strands 18 are extended through shaft 12 and inserted into bag 14. Alternatively, open end 26 may be brought into sealing engagement with the distal end of shaft 12 to close bag 14. For example, open end 26 may include a purse-string closure mechanism (not shown) that can be tightened around the distal end of shaft 12.

With bag 14 closed, strands 18 may be actuated by the user to cut tissue specimen 20. For example, one or more of the proximal ends of strands 18 may be pushed or pulled to engage tissue specimen 20. The pushing/pulling force may be applied using the user's hand(s), or with a mechanism (not shown) such as a ratchet or motor. The motor may include two or more pulleys that may pull intermittently in order to move loop 19 with a sawing or back-and-forth motion on tissue specimen 20.

Additionally or alternatively, contraction of loop 19 may cause loop 19 to be brought against and cut into tissue specimen 20. The sawing and/or contracting may cut tissue specimen 20 inside bag 14. Liner 16 may engage tissue specimen 20 during the cutting. Once strands 18 have been actuated, and tissue specimen 20 has been cut to pieces, bag 14 and liner 16 may be pulled out of the subject with the tissue fragments contained inside. Although exemplary tissue extraction devices described below may not be depicted with bag 14 and liner 16, it should be understood that they may be used with bag 14 and liner 16.

Figures 2A, 2B:
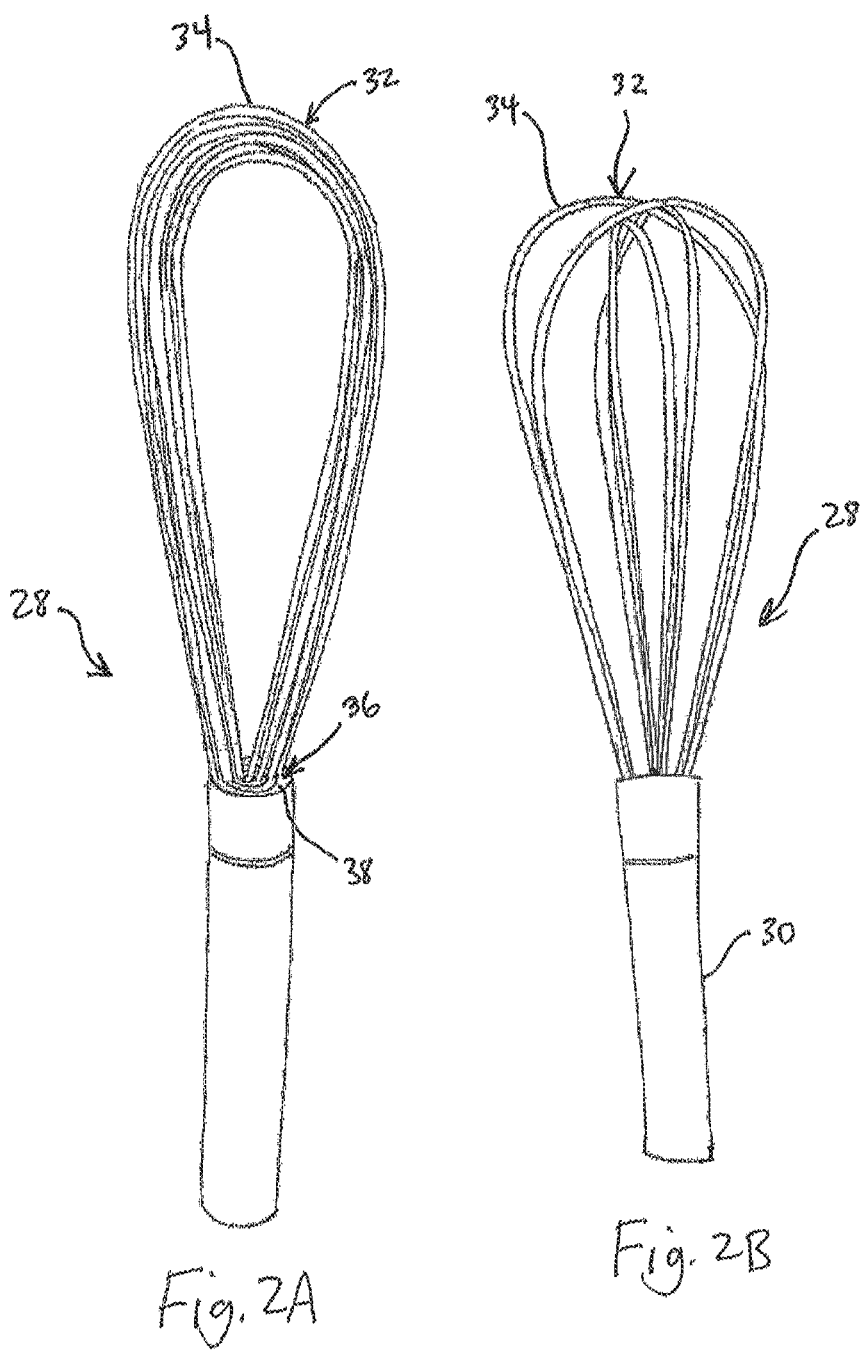
FIGS. 2A and 2B are perspective views of a tissue extraction device, in accordance with aspects of the present disclosure.

FIGS. 2A and 2B show an exemplary tissue extraction device 28. Tissue extraction device 28 may include a shaft 30, and one or more strands 32 forming one or more loops 34, similar to shaft 12, strands 18, and loops 19 (FIG. 1). Proximal portions of strands 32 may include concentrically arranged shafts 36. Each of loops 19 may be connected to the distal end of one of shafts 36. Shafts 36 may extend through shaft 30, and proximal ends of shafts 36 may be accessible to the user. Each of shafts 36 may be rotated individually by the user, or in combination with one or more other shafts 36, about a central longitudinal axis of shaft 30, to rotate loops 34 about the central longitudinal axis.

FIG. 2A shows tissue extraction device 28 with strands 32 deployed from shaft 30, and with loops 34 in a coplanar configuration. Coplanar loops 34 may be positioned against a tissue specimen. FIG. 2B shows tissue extraction device 28 after shafts 36 have been rotated about the central longitudinal axis of shaft 30, to rotate loops 34 so they are no longer coplanar with the other loops 34. During this rotation, loops 34 may surround the tissue specimen on a plurality of sides.

Shafts 36 may be pulled proximally by the user to contract or close loops 34 to cut the tissue specimen. Shafts 36 may be pushed distally by the user to expand loops 34, facilitating the surrounding of tissue specimens by loops 34.

Alternatively, shafts 36 may be omitted. Instead, strands 32 may extend to the proximal end of shaft 30, with proximal portions of each of strands 32 positioned so as to rotate along circular paths to rotate loops 34. The circular paths of strands 32 may be concentric, to reduce or eliminate interference between adjacent strands 32. The proximal portions of strands 32 may be moved proximally or distally to engage a tissue specimen captured therein in a manner similar to strands 18.

Figure 3:
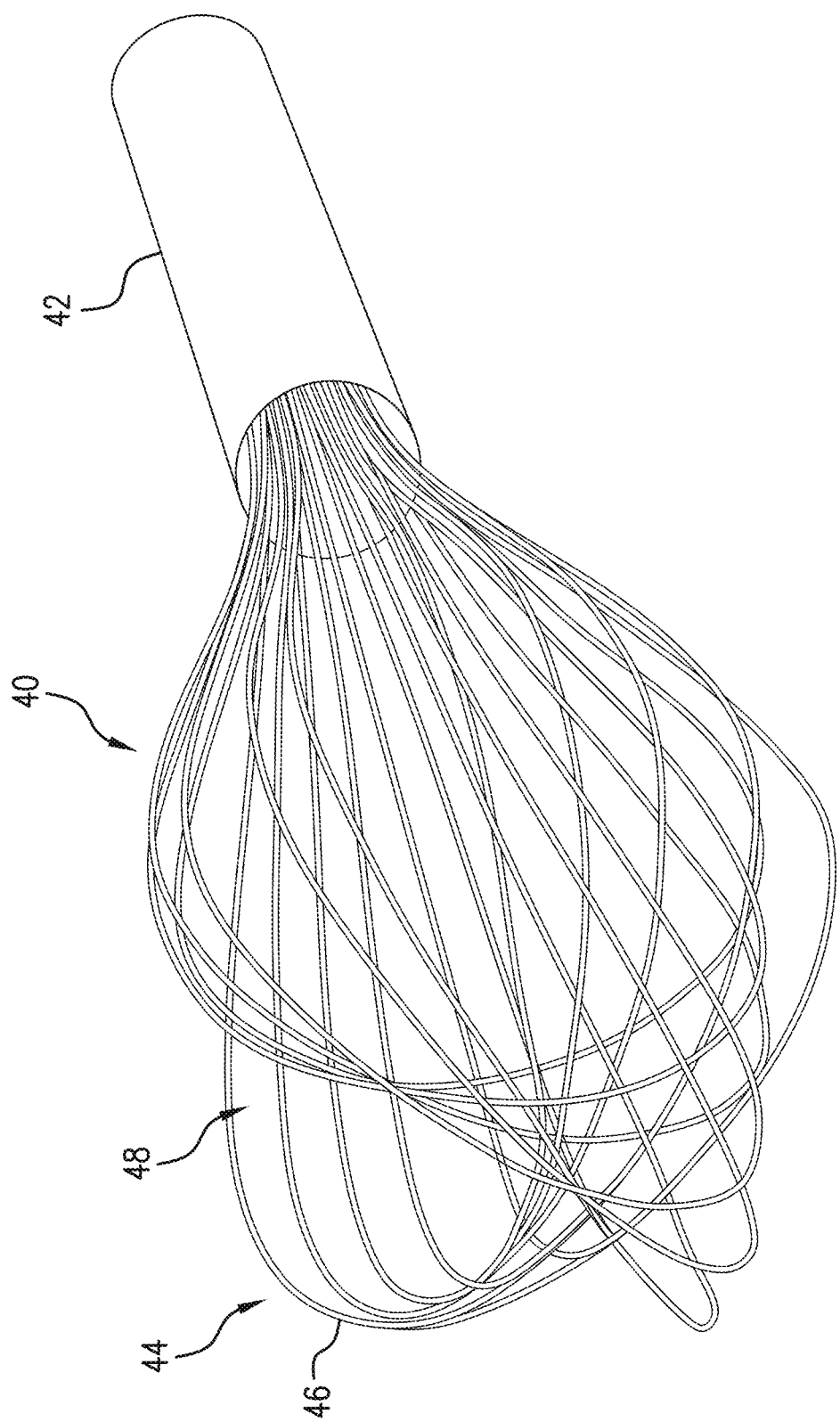
FIG. 3 is a perspective view of a tissue extraction device, in accordance with aspects of the present disclosure.

FIG. 3 shows an exemplary tissue extraction device 40 having a shaft 42, and one or more strands 44 forming one or more loops 46, similar to shaft 12, strands 18, and loops 19 (FIG. 1). Loops 46 are depicted in a partially closed state, in which a gap 48 exists between loops 46. A tissue specimen may be guided through gap 48, where it may be surrounded by loops 46. The size of gap 48 may be decreased to keep the tissue specimen from exiting through gap 48. Loops 46 may be rotated relative to one another to open/close gap 48 in the manner, for example, described with respect to tissue extraction device 28. Additionally or alternatively, loops 46 may be made of a shape memory alloy, such as Nitinol, and shaped such that loops 46 may remain open until they are moved proximally to contract onto the tissue specimen and also to lessen the width of gap 48.

Figure 4D:
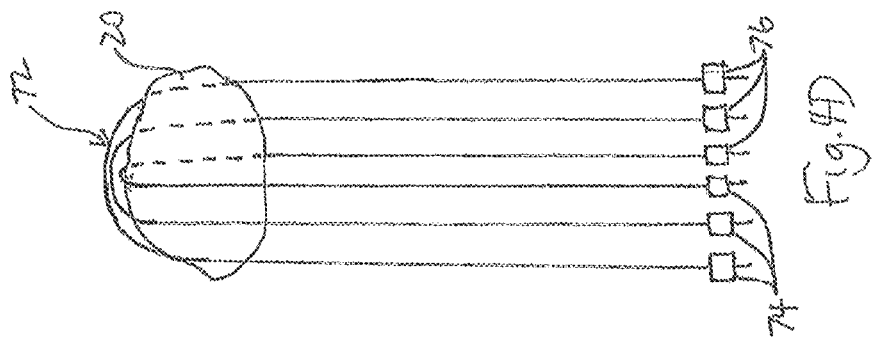
FIGS. 4A-4D are side views of alternative configurations of a portion of a tissue extraction device, in accordance with aspects of the present disclosure.
Figure 4C:
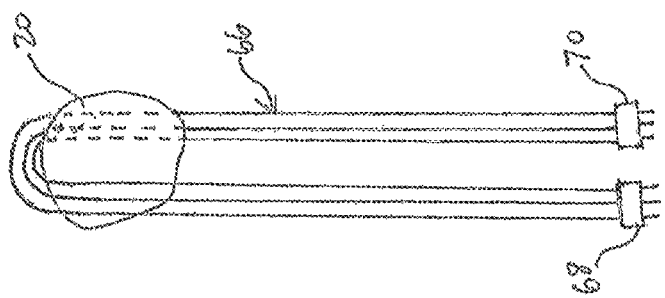
Figure 4B:
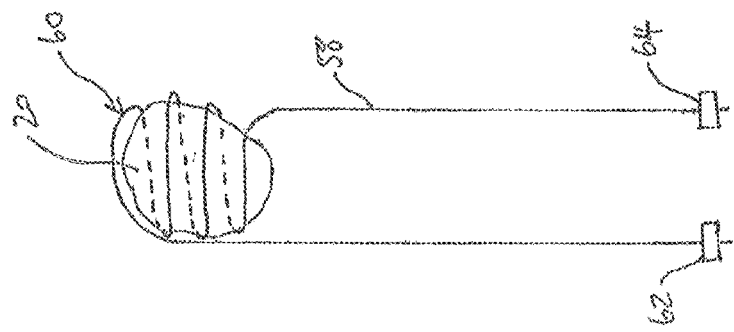
Figure 4A:
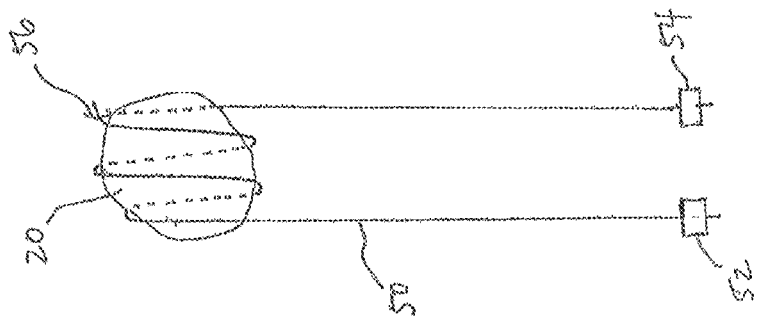

FIGS. 4A-4D show alternative strand configurations using strands similar to strands 18 (FIG. 1). FIG. 4A shows a strand 50 whose proximal ends may be coupled to spools 52, 54. A distal portion 56 of strand 50 may form a spiral for encircling tissue specimen 20. A central longitudinal axis of spiral 46 may extend at an angle relative to the proximal-distal direction. For example, the central longitudinal axis may extend perpendicular to the proximal-distal direction. A shaft (not shown) may surround the portion of strand 50 between spools 52, 54 and spiral 46. The user may pull or rotate one or more of spools 52, 54 to move strand 50 in one direction, and then may pull or rotate one or more of spools 52, 54 to move strand 50 in the opposite direction, to cut tissue specimen 20 with a sawing action. Additionally or alternatively, the user may pull or rotate one of spools 52, 54 while keeping the other spool still, or may pull or rotate both spools 52, 54, to draw spiral 46 into the sheath. Movement of spiral 46 towards and/or into the sheath may cause spiral 46 to close down onto tissue specimen 20, thereby cutting tissue specimen 20. A failsafe mechanism also may be provided. For example, if strand 50 gets stuck during a procedure, one of its proximal ends can be released from spool 52 or spool 54, thereby enabling removal of strand 50 by pulling on the spooled end to entirely remove strand 50 from the proximal end of the shaft. Alternatively, both of the proximal ends of strand 50 may be released from spools 52, 54, allowing removal of strand 50 by pulling on either of its freed ends. While one strand 50 is shown, it should be understood that multiple strands 50 may be provided in one tissue extraction device to help cut tissue specimen 20 into smaller pieces.

FIG. 4B shows a strand 58 having a spiral 60 and ends connected to spools 62, 64, similar to strand 50, spiral 46, and spools 52, 54 (FIG. 4A). Spiral 60 differs from spiral 46 in that a central longitudinal axis of spiral 60 may extend parallel to the proximal-distal direction. While one strand 58 is shown, it should be understood that multiple strands 58 may be provided in one tissue extraction device.

FIG. 4C shows strands 66. Left proximal ends of each of strands 66 may be coupled to a spool 68, while right proximal ends of each of strands 66 may be coupled to a spool 70. Distal portions of strands 66 may loop around tissue specimen 20. Like spools 52, 54 (FIG. 4A), spools 68, 70 may be pushed, pulled, and/or rotated to cause strands 66 to cut tissue specimen 20. While three strands are shown, it should be understood that fewer or more strands may be used depending on the types of cuts/resulting pieces desired by the user.

FIG. 4D shows strands 72. Each of strands 72 may have its own pair of left and right spools. For example, each of the left proximal ends of strands 72 may be coupled to one of the left spools 74, while each of the right proximal ends of the strands 72 may be coupled to one of the right spools 76. Distal portions of strand 72 may loop around tissue specimen 20. Like spools 52, 54 (FIG. 4A), spools 74, 76 may be pushed, pulled, and/or rotated to cause strands 72 to cut tissue specimen 20. Spools 74, 76 may be actuated such that strands 72 move simultaneously to cut tissue specimen 20. Alternatively, spools 74, 76 may be actuated sequentially to cut tissue specimen 20. For example, the proximal-most strand may be pulled before the other strands, or vice-versa.

A motor or series of motors (not shown) may be connected to spools 52, 54, 62, 64, 68, 70, 74, 76 to rotate, push, and/or pull the spools. Alternatively, the spools may be rotated, pushed, and/or pulled by hand, for example by using a handle (not shown) having one or more ratcheting mechanisms. The configurations of the aforementioned strands may be altered based on clinical need. Moreover, different strand configurations may be usable together.

Once the aforementioned strands have been completely pulled through tissue specimen 20, they may be removed from the body cavity. Where bag 14 (FIG. 1) is used, bag 14 may be pulled out of the body cavity through the incision or through the vagina, and along with bag 14, the pieces of tissue specimen 20. Additionally or alternatively, suction apparatus or a small forceps may be used to extract the pieces of tissue specimen 20.

FIGS. 5A and 5B show an exemplary tissue extraction device 78 having a shaft 80 and strands 82 forming loops 84, similar to shaft 12, strands 18, and loops 19 (FIG. 1). FIG. 5A shows loops 84 in a partially deployed state, where proximal portions of loops 84 are constrained by shaft 80. FIGS. 5B-5D show loops 84 in a deployed state. One or more of loops 84 may be biased to deflect away from a central longitudinal axis of shaft 80 when deployed out of shaft 80. In one example, one or more of loops 84 may be made of a shape memory alloy, such as Nitinol, and may bend when exposed to heat from the subject's body. In another example, one or more of loops 84 may be made of spring steel, or some other metal, with a bend formed therein. It is also contemplated that loops 84 may have different sizes when deployed. The difference in size may provide a side having a large opening 86 for receiving a tissue specimen, and another side having a small opening 88 to act as a backstop for the tissue specimen after it passes through the large opening. The difference in size also may contour loops 84 to fit a shape of the tissue specimen. The difference in size also may produce a predetermined pattern of cuts in the tissue specimen that may be desired by the user.

FIGS. 5C and 5D also show loops 84 in their deployed states. FIG. 5C shows a connector 90 coupled to the distal ends of loops 84. FIG. 5D shows an alternative connector 91 that forms a loop that may be coupled to proximal portions and distal ends of one or more of loops 84. Connectors 90, 91 may help keep loops 84 from being bent, pulled, or otherwise deflected in unexpected or undesired ways relative to the other loops 84. Additionally or alternatively, connectors 90, 91 may engage a tissue specimen to produce additional cuts therein. Connectors 90, 91 may be made of strands of material including, for example, threads wrapped around one or more portion of loops 84. Alternatively, loops 90, 91 may be made of the same material as loops 84, and may be fastened to loops 84 or may be integrally formed with loops 84.

FIGS. 6A, 6B, and 7-9 show alternative configurations of exemplary tissue specimen support devices. The tissue specimen support devices may be extended distally out of any of the aforementioned tissue extraction device shafts, such that the tissue specimen support devices may be surrounded by the strands. Alternatively, the strands may be extended out of the tissue specimen support devices, such that the tissue specimen support devices may extend around, or surround the strands.

Figure 6A:
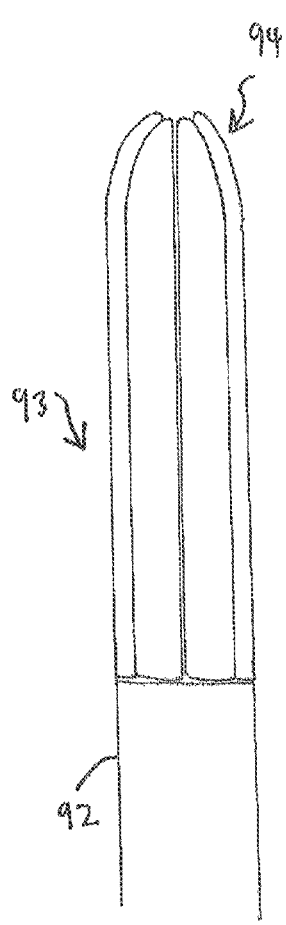
FIGS. 6A, 6B, and 7-9 are perspective views showing alternative configurations of a tissue specimen support device, in accordance with aspects of the present disclosure.
Figure 6B:
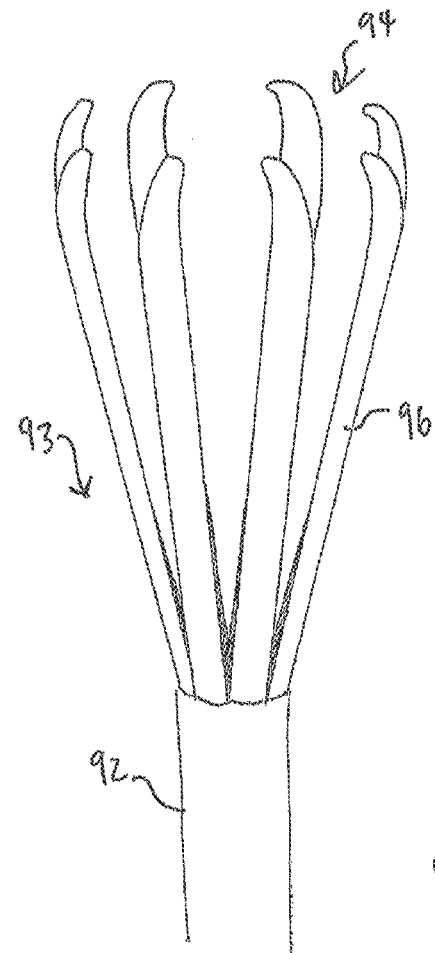

FIGS. 6A and 6B show a tissue specimen support device 93 having a shaft 92 with a support 94 on its distal end. Support 94 may include arms 96 arranged radially around the distal end of shaft 92. FIG. 6A shows support 94 in a delivery configuration, with arms 96 contracted radially inward. Distal tips of arms 96 may be curved such that the distal end of support 94 may be rounded or tapered in the delivery configuration, to facilitate it's insertion through narrow openings/passages. FIG. 6B shows support 94 in a deployed configuration, with arms 96 angled radially outward. Arms 96 may be inherently biased to expand to the deployed configuration in the absence of a constraining force. Thus, arms 96 may be contained within an introducer sheath (not shown), or otherwise secured to one another, during delivery. The sheath or securement may be pulled back or otherwise removed in the body cavity to allow arms 96 to deploy. Any of the shafts of the aforementioned tissue extraction devices may act as the introducer sheath. Alternatively, arms 96 may be made of a shape memory alloy, such as Nitinol, and may expand outward when subjected to the subject's body heat. Alternatively, arms 96 may be moved into the deployed state when the strands are deployed from the distal end of shaft 92 into the space surrounded by arms 96.

When the strands surround a tissue specimen, and the strands are pulled to cut the tissue specimen, the tissue specimen may be pulled by the strands toward the distal end of shaft 92. Due to the relatively small diameter of the distal end of shaft 92, if the tissue specimen is compressed solely against the distal end of shaft 92 by the strands, the tissue specimen may slide off of or around shaft 92 and escape from the grasp of the strands. The chances of escape may increase if the strands are used to saw through the tissue specimen, since the sawing motion may tend to deform and/or move the tissue specimen back-and-forth or side-to-side. This unwanted escape may be prevented by support 94. When the strands pull the tissue specimen towards the distal end of shaft 92, arms 96 of support 94 may engage the tissue specimen, thus supporting a larger surface area of the tissue specimen than the distal end of shaft 92. Moreover, the angling of arms 96 may help keep the tissue specimen centered. Gaps between arms 96 may receive one or more of the strands, allowing for more complete cutting of the tissue specimen while the tissue specimen is held by arms 96.

Figure 8:
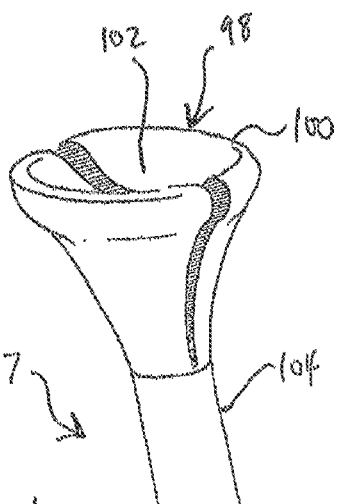
Figure 7:
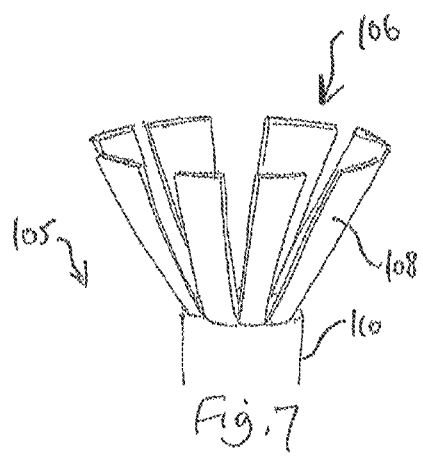
Figure 9:
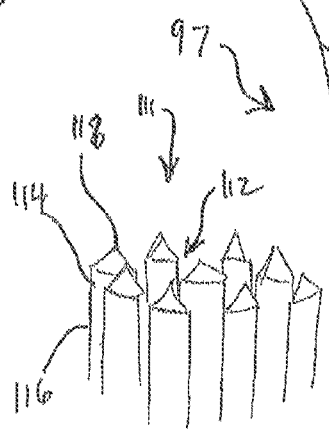

FIGS. 7-9 show alternative tissue specimen support devices. FIG. 7 shows a tissue specimen support device 105 having a support 106 with arms 108, on a distal end of a shaft 110, similar to support 94, arms 96, and shaft 92 (FIGS. 6A, 6B). Arms 108, however, are differently shaped, and may be formed by flat plates. FIG. 8 shows a tissue specimen support device 97 having a support 98 on a distal end of a shaft 104, support 98 having an indentation or recess 102 formed in its distal end for receiving at least a portion of the tissue specimen as the strands bring the tissue specimen toward shaft 104. Support 98 also may include a slot 100 extending therethrough in the proximal-distal direction. Slot 100 may receive one or more of the strands, such that the received strands may be able to cut entirely through the tissue specimen while the tissue specimen is engaged by support 98. FIG. 9 shows a tissue specimen support device 111 having a support 112 with arms 114. Arms 114 may have one or more sharp edges 116. Arms 114 may cut the tissue specimen as the strands urge the tissue specimen against arms 114. Additionally or alternatively, arms 114 may have pointed tips that may penetrate the tissue specimen as the strands draw the tissue specimen towards the shaft (not shown), to help keep the tissue specimen centered.

Additionally or alternatively, gaps/slots between arms 114 may receive one or more of the strands, such that the received strands may be able to cut entirely through the tissue specimen while the tissue specimen is engaged by arms 114.

FIG. 10 shows an exemplary tissue extraction device 120 having a shaft 122 for receiving a coiled strand 124 similar to strand 50 (FIG. 4A). An arrow 126 is indicative of a pulling force exerted on one of the proximal ends of strand 124, in a proximal direction, to cause strand 124 to engage and cut tissue specimen 20.

FIGS. 11A and 11B show an exemplary tissue extraction device 128 having a shaft 130 and strands 132, similar to shaft 12 and strands 18 (FIG. 1). A curved tongue member 134 may be coupled to strands 132. For example, tongue member 134 may be coupled to distal ends of loops 136 formed by strands 132. When deployed from shaft 130, tongue member 134, through its engagement with strands 132, tongue member 134, may maintain a desired positioning of strands 132 relative to each other. For example, tongue member 134 may hold one of loops 136 open such that it is larger than the others, providing a large opening for receiving a tissue specimen. Tongue member 134 may provide a backstop for the tissue specimen after it has entered via the large opening. When strands 132 are pulled to cut the tissue specimen, tongue member 134 may prevent, or at least hinder, the tissue specimen from escaping the grasp of loops 136, by engaging the tissue specimen.

FIG. 12 shows an exemplary tissue extraction device 138 having a shaft 140 and strands 142, similar to shaft 12 and strands 18 (FIG. 1). Strands 142 may form loops 144. Portions of strands 142 extending away from loops 144 may be received in openings 146 in a guide member 148. When deployed from shaft 140, loops 144 may extend from openings 146 in a direction perpendicular to the proximal-distal direction. The user may pull one or more of the proximal ends of strands 18 to close loops 144 around a tissue specimen. Loops 144 may compress the tissue specimen against guide member 148, using guide member 148 as a cutting board on which to cut the tissue specimen.

Figure 13:
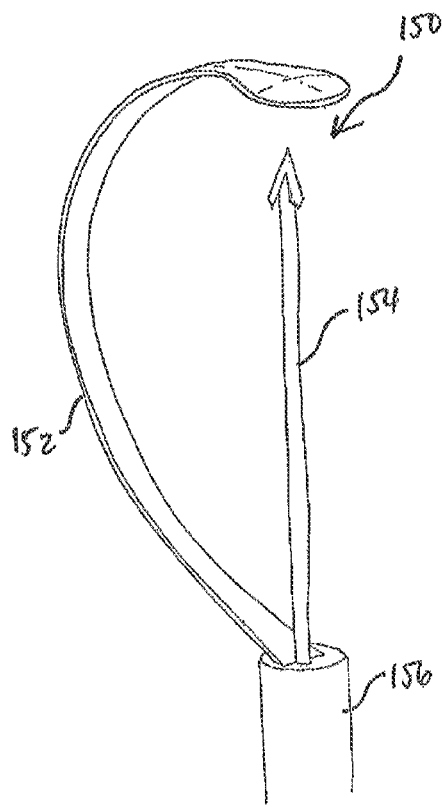
FIG. 13 is a perspective view of a tissue specimen securing mechanism, in accordance with aspects of the present disclosure.

FIG. 13 shows an exemplary tissue specimen securing mechanism 150 that may be used with any of the aforementioned tissue extraction devices. Tissue specimen securing mechanism 150 may be extendable from and retractable into a distal end of a shaft 156. When tissue specimen securing mechanism 150 is deployed, a tongue 152 may be positioned around a portion of the tissue specimen. A barb 154 may be extended out of shaft 156 separately from tongue 152, such that barb 154 may penetrate the tissue specimen as tongue 152 helps to hold the tissue specimen in place. Any of the aforementioned strands may be extended out of the distal end of shaft 156 to surround the secured tissue specimen, and then to cut the secured tissue specimen.

Figure 14:
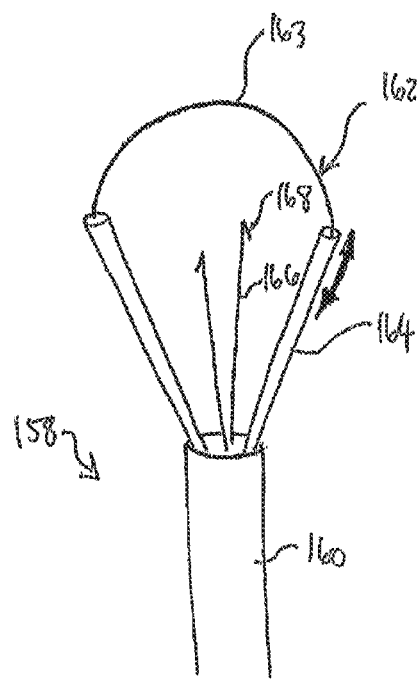
FIG. 14 is a perspective view of a tissue extraction device, in accordance with aspects of the present disclosure.

FIG. 14 shows an exemplary tissue extraction device 158 having a shaft 160 and a strand 162 forming a loop 163, similar to shaft 12, strand 18, and loop 19 (FIG. 1). Portions of strand 162 are shown with a coating 164 thereon. For example, a distal end of strand 162 may be uncoated to assist with cutting a tissue specimen, while proximal portions of strand 162 may be coated to prevent them from damaging bag 14 (FIG. 1). Tissue extraction device 158 also may include one or more reset members 166 that may be extendable out of shaft 160. After strand 162 has been pulled to cut the tissue specimen, the user may want to expand loop 163 to reposition loop 163 to cut another portion of the same tissue specimen, or to make room for receiving a different tissue specimen. The user may attempt to expand loop 163 by moving one of, or both of, the proximal ends of strand 162 in the distal direction. In some instances, however, loop 163 may be trapped in the tissue specimen, or trapped by frictional engagement between loop 163 and the inner surface of shaft 160, thus hindering or preventing the extension and expansion of loop 163. Reset members 166 may be extended from shaft 160 to penetrate the tissue specimen, to hold the tissue specimen at or near the distal end of shaft 160, while the user moves the proximal end(s) of strand 162 distally to free loop 163 from the tissue specimen, thereby allowing loop 163 to expand. Reset members 166 may include barbed ends 168 to help grip the tissue specimen. Barbed ends 168 also may provide reset members 166 with the ability to position the tissue specimen for cutting, similar to barb 154 (FIG. 13). Additionally or alternatively, reset members 166 may engage the tissue specimen and/or loop 163, and force the tissue specimen and/or loop 163 distally, to assist with moving/expanding loop 163. Reset members 166 may include enlarged distal ends (not shown) to provide an adequately-sized contact surface for engaging the tissue specimen and/or loop 163.

Figure 15A:
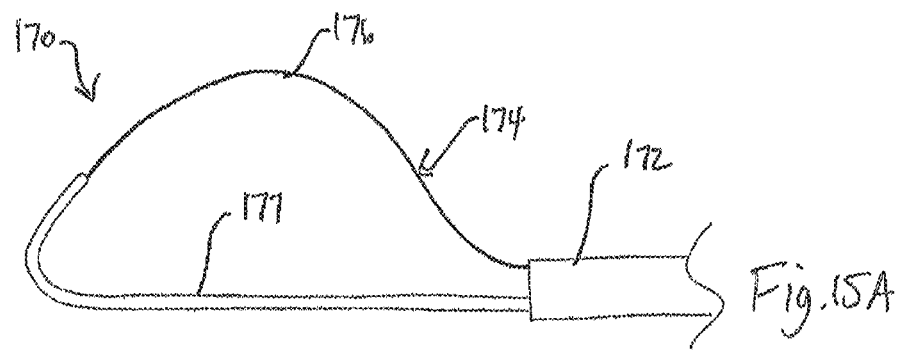
FIGS. 15A-15D are side and top views of a tissue extraction device, in accordance with aspects of the present disclosure.
Figure 15B:
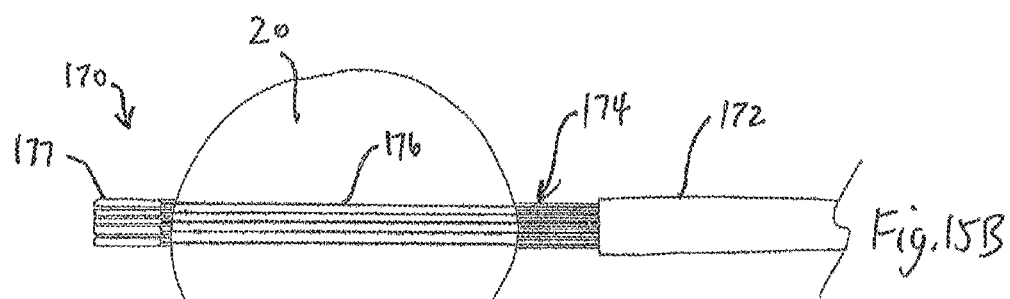
Figure 15C:
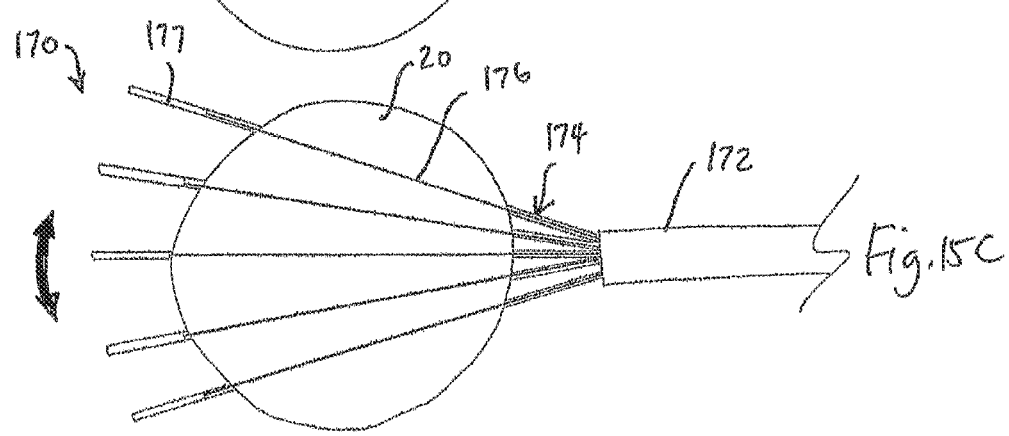
Figure 15D:
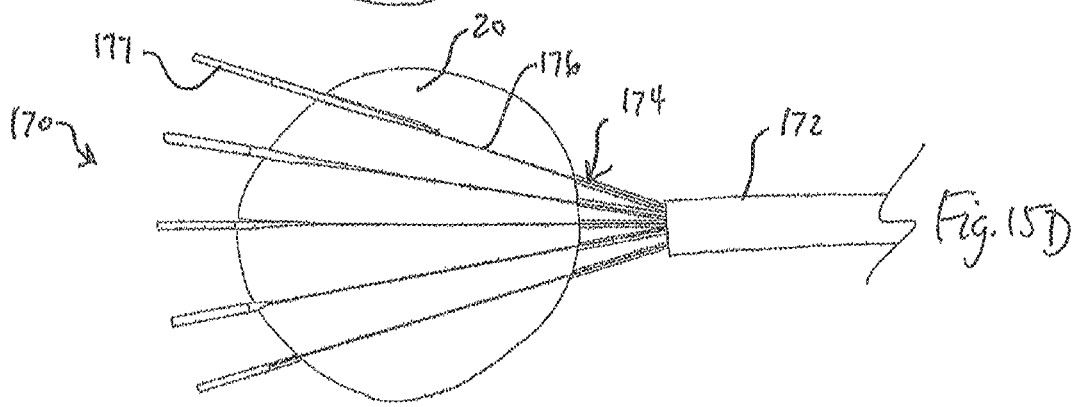

FIGS. 15A-15D show an exemplary tissue extraction device 170 having a shaft 172 and one or more strands 174 forming one or more loops 176, similar to shaft 12, strands 18, and loops 19 (FIG. 1). Portions of strands 174 are shown with a coating 177 thereon. Alternatively, portions of strands 174 may be flattened, thickened, or otherwise widened instead of having coating 176. The thicker/coated portions of strands 174 may have greater stiffness than the thinner/uncoated portions. FIG. 15A shows strand following a curvilinear path when forming loops 176. FIG. 15B shows tissue extraction device 170 in a contracted configuration, with strands 174 adjacent one another and surrounding tissue specimen 20. FIG. 15A shows tissue extraction device 170 in an expanded configuration, with strands 174 fanned out around tissue specimen 20. FIG. 15D shows tissue extraction device 170 during cutting initiated by the user pulling on strands 174. In one example, the proximal ends of strands 174 that are connected to the uncoated/thinner portions of strands 174, may be pulled by the user, while the proximal ends of strands that are connected to the coating/thicker portions of strands 174 may remain fixed. The uncoated/thinner portions of strands 174 may cut into tissue specimen 20. The coated/thicker portions of strands 174 may not cut into tissue specimen 20, but rather, may support tissue specimen 20 to facilitate cutting by the uncoated/thinner portions of strands 174. It is contemplated that the user may initiate the pulling of strands 174 at staggered times, resulting in strands 174 being at different depths within tissue specimen 20 while simultaneously cutting tissue specimen 20, as shown in FIG. 15D. Alternatively, strands 174 may be pulled simultaneously, or sequentially one at a time.

FIGS. 16A and 16B show an exemplary tissue extraction device 178 having a shaft 180 and a strand 182 forming a loop 184, similar to shaft 12, strand 18, and loop 19 (FIG. 1). Tissue extraction device 178 also may include a tissue specimen support device 186, similar to tissue specimen support device 97 (FIG. 8). Tissue extraction device 178 may further include a proximal handle 188, and a motor 190 for pushing and/or pulling strand 182. Motor 190 may, for example, pull one of the proximal ends of strand 182 while the other of the proximal ends of strand 182 remains fixed, thus pulling strand 182 against the tissue specimen and/or across the tissue specimen, thereby cutting the tissue specimen. Motor may push one of the proximal ends of strand 182 distally in preparation for making another cut in the tissue specimen. FIG. 16B shows a close-up view of strand 182. Strand 182, as well as any of the other strands described in this disclosure, may be formed by filaments 192 that are braided in a way that provides surfaces of strand 182 with a series of protrusions and recesses that may be useful for abrading a tissue specimen when pulled against and/or across the tissue specimen. The strand 182 may cut the tissue specimen with any of its sides. Alternatively, strand 182 may be formed by a textured or coated wire with abrasive properties.

FIGS. 17A and 17B show an exemplary tissue extraction device 194 having a shaft 196 and a strand 198 forming a loop 200, similar to shaft 12, strand 18, and loop 19 (FIG. 1). Tissue extraction device 194 also may include a grasping device 202 having opposing movable jaw members 204, 206 for clamping material therebetween. Grasping device 202 may be an alternative to the aforementioned tissue specimen support devices. Jaw members 204, 206 may be opened to receive a tissue specimen as strand 198 is pulled to cut the tissue specimen, and jaw members 204, 206 may be closed to clamp the tissue specimen in place during cutting. Each of jaw members 204, 206 may include a slot 208 therein that may receive a portion of strand 198, so that strand 198 may more fully cut through the tissue specimen even while the tissue specimen is clamped by grasping device 202. Additional strands (not shown) may be received between and/or around jaw members 204,206.

Figure 18:
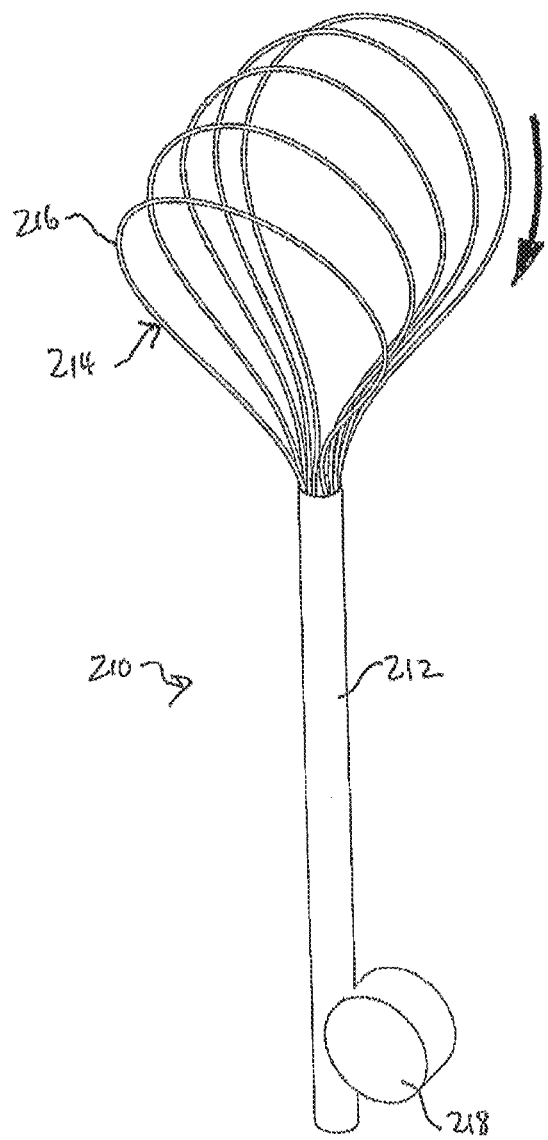
FIG. 18 is a perspective view of a tissue extraction device, in accordance with aspects of the present disclosure.

FIG. 18 shows an exemplary tissue extraction device 210 having a shaft 212 and strands 214 forming loops 216, similar to shaft 12, strands 18, and loops 19 (FIG. 1). Each of strands 214 may have a fixed end or side and an opposing movable end or side. The movable ends or sides may be operatively coupled to an actuator 218 (e.g., a motor, knob, spool, or the like), such that the user may use actuator 218 to pull the movable ends or sides. The pulling may bring strands 214 into engagement with a tissue specimen, and may do so with enough force to cause strands 214 to cut into the tissue specimen.

FIGS. 19A-19J show an exemplary tissue extraction device 220. Tissue extraction device 220 may include a handle assembly 222, an outer tube 224, and an end effector assembly 226. Aspects of handle assembly 222, outer tube 224, and end effector assembly 226 will now be described in detail.

Handle assembly 222 may include a housing 228 that may be gripped by a user. Outer tube 224 may be fixedly coupled to housing 228. Housing 228 may include a first actuator 230 and a second actuator 232 (FIGS. 19C-19H). Actuators 230 and 232 may include linear actuators. For example, first actuator 230 may include a motor 234, a drive shaft 236 (e.g., an externally-threaded shaft), and driven member 238 (e.g., an internally-threaded nut) movably coupled to the drive shaft 236. Motor 234 may rotate drive shaft 236, which may in move driven member 238 along drive shaft 236 in a proximal-distal direction. Motor 234 and drive shaft 236 may be fixed relative to housing 228. Second actuator 232 may be similar to first actuator 230. Second actuator 232, however, may be coupled to driven member 238, such that first actuator 230 may cause longitudinal sliding of second actuator 232 within housing 228 along a proximal-distal direction.

Figure 19A:
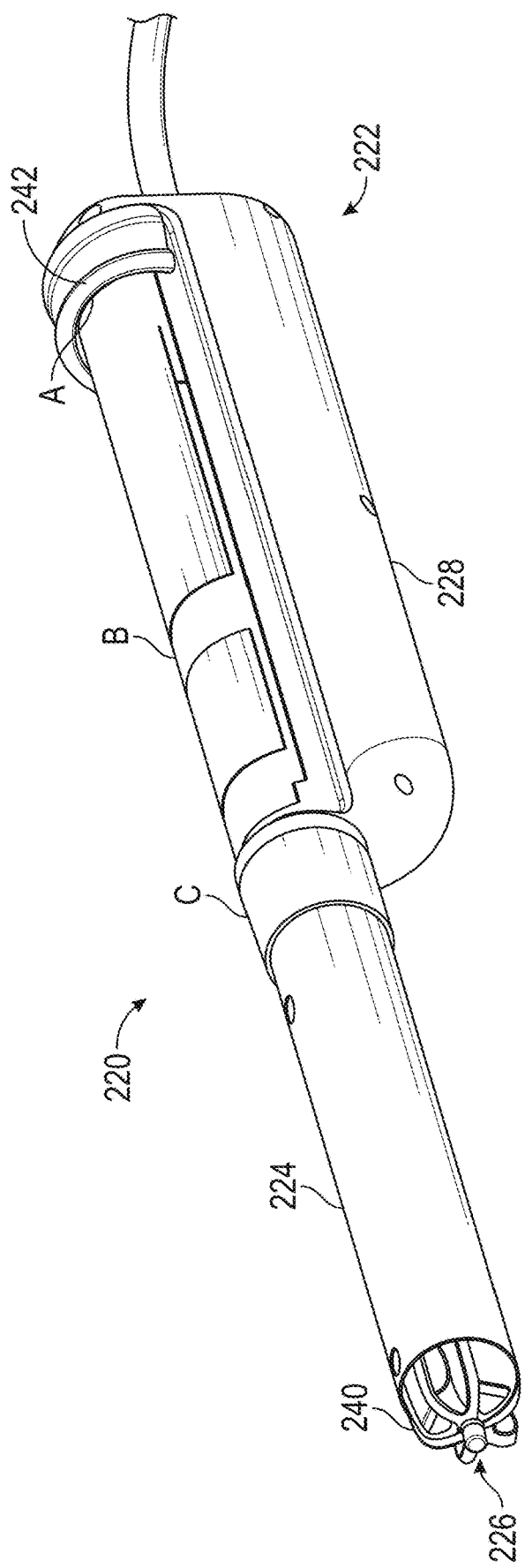
FIGS. 19A and 19B are perspective and side views of a tissue extraction device, in accordance with aspects of the present disclosure.
Figure 19B:
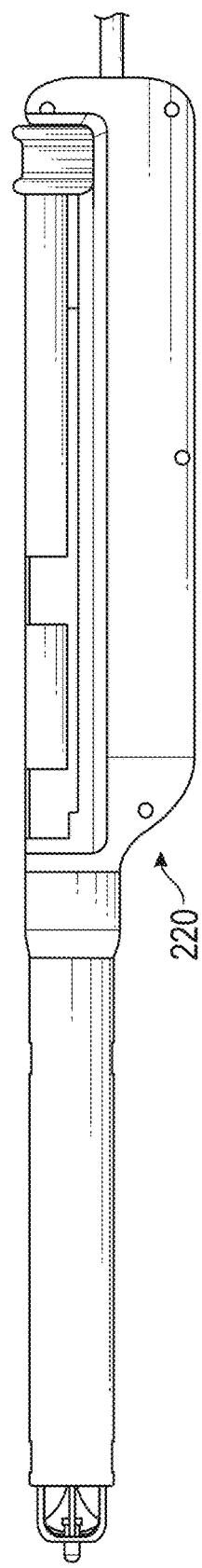
Figure 19C:
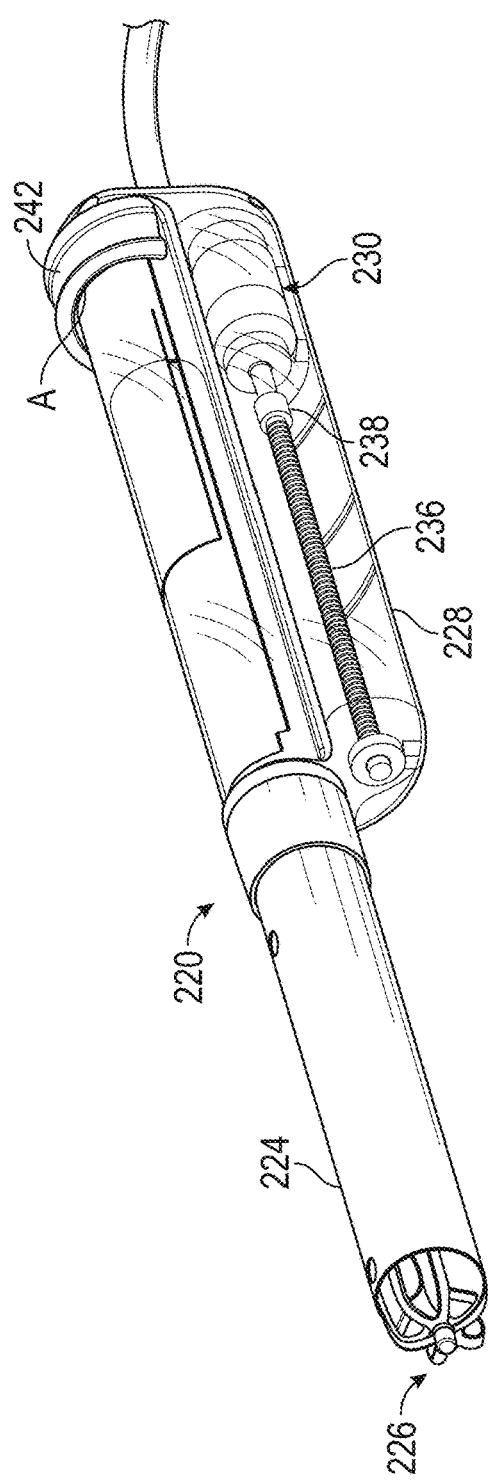
FIGS. 19C and 19D are perspective and semi-transparent side views of the tissue extraction device of FIGS. 19A and 19B, in accordance with aspects of the present disclosure.
Figure 19D:
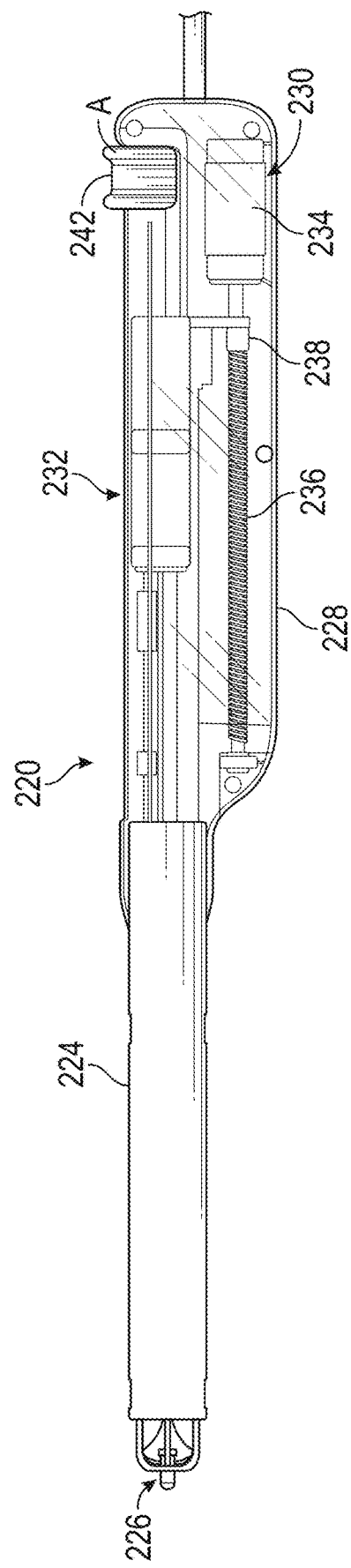
Figure 19E:
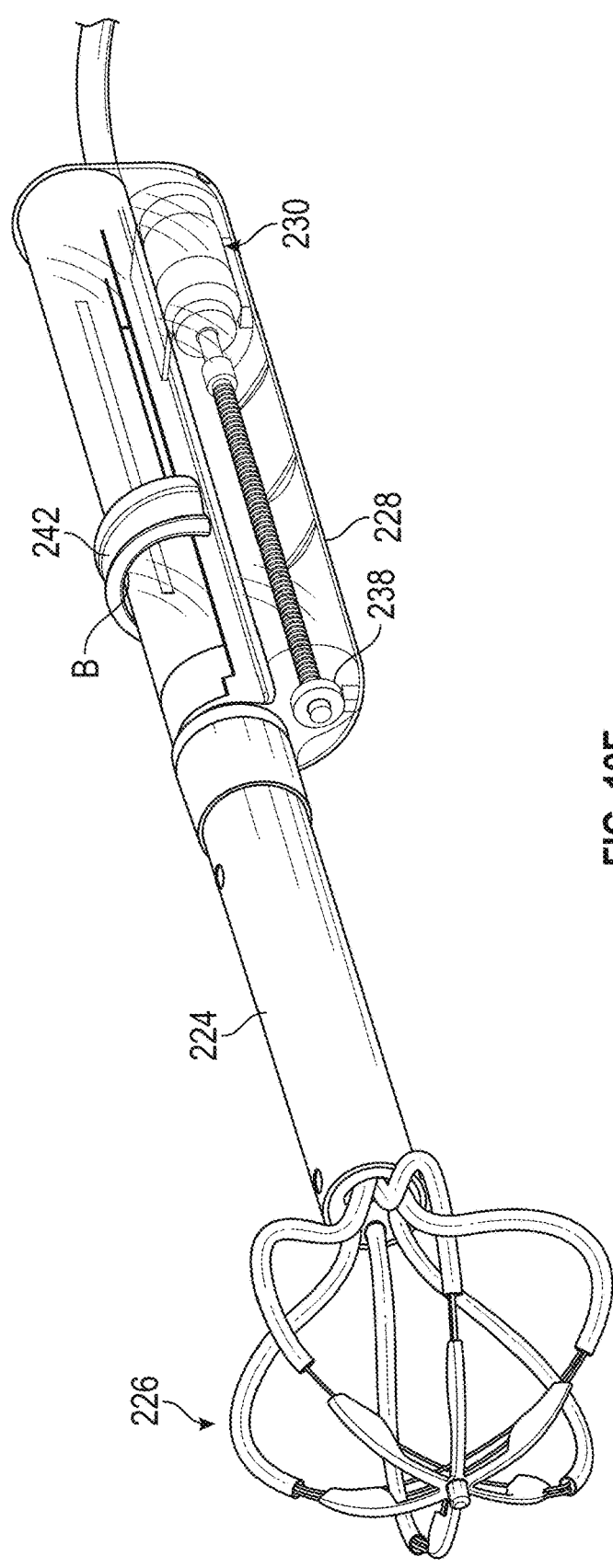
FIGS. 19E and 19F are perspective and semi-transparent side views of the tissue extraction device of FIGS. 19A and 19B, in accordance with aspects of the present disclosure.
Figure 19F:
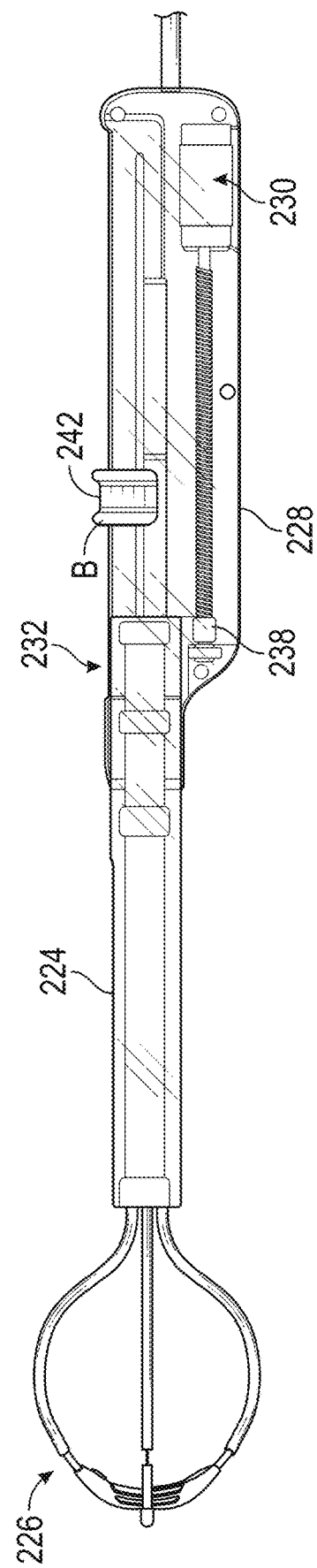

End effector assembly 226 may be coupled to second actuator 232, such that movement of second actuator 232 may move end effector assembly 226. Second actuator 232 may be positioned in various locations along the length of handle 222 and outer tube 224. A slider 242 may be linked to second actuator 232, and may provide a user with an indication of the position of second actuator 232. For example, when slider 242 occupies a position A, it may indicate that second actuator 232 is in an insertion position (FIGS. 19A-19D). With second actuator 232 in the insertion position, end effector assembly 226 may be in a retracted configuration, with a distal end effector 240 received and compressed in a distal end of outer tube 224, to facilitate insertion of the distal end portion of tissue extraction device 220 into a subject. When slider 242 occupies a position B, it may indicate that second actuator 232 is in a deployment position (FIGS. 19E and 19F). As second actuator 232 moves from the insertion position to the deployment position, end effector assembly 226 may be pushed distally, causing end effector 240 to deploy by extending out of the distal end of outer tube 224 and expanding from a radially-compressed configuration to a radially-expanded configuration.

Slider 242 and second actuator 232 may be coupled for movement via a lost motion coupling, such that slider 242 may slide distally from position B to a position C (FIGS. 19G and 19H) while second actuator 232 stays in its deployment position. Slider 242 may be coupled to a portion of end effector assembly 226 such that movement of slider 242 to a position C may expand a side opening of end effector 226 to facilitate the insertion of tissue into end effector 226.

Figure 19I:
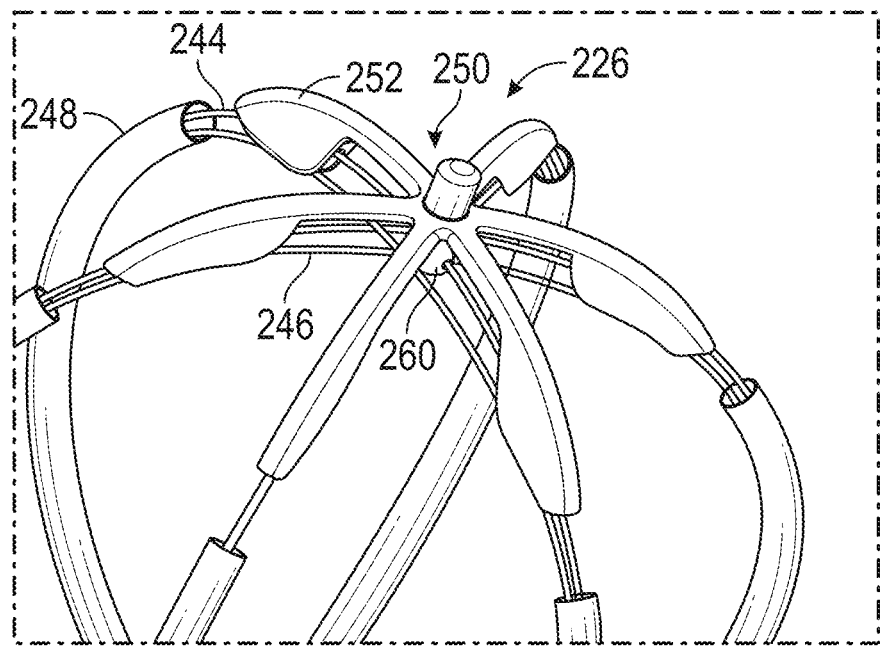
FIGS. 19I and 19J are close-up perspective views of an end effector of the tissue extraction device of FIGS. 19A and 19B, in accordance with aspects of the present disclosure.
Figure 19J:
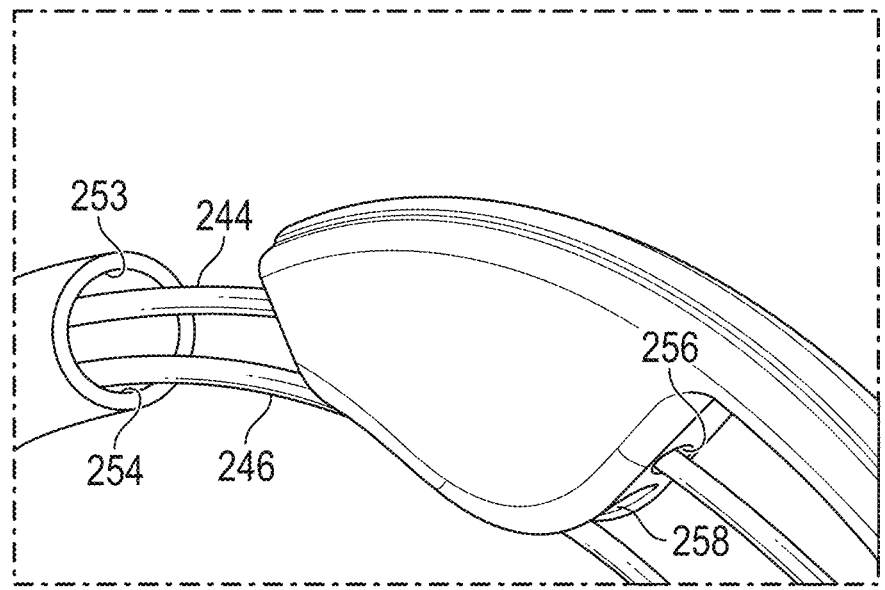

End effector 226 may include one or more support strands 244, one or more cutting strands 246, one or more proximal support arms 248, and a distal support 250 having one or more distal support arms 252 (FIGS. 19I and 19J). Support arm 248 may include a tube or other elongate member having a first lumen 253 and a second lumen 254. First lumen 253 may receive support strand 244. Second lumen 254 may receive cutting strand 246. Support arms 248 and distal support 250 may be arranged to hold strands 244 and 246 in a U-shaped configuration. Distal support 250 may receive distal portions of strands 244 and 246. Strands 244 and 246 may extend outwardly from a center of distal support 250, which may have a star or asterisk-like form. Distal support 250 may include a spacing member 260 (FIG. 19I) that may receive the distal portions of strands 244, to keep strands 244 spaced apart in intervals about end effector 226.

One or more of support arms 252 may include a lumen 256 for support strand 244 and a slot or groove 258 for receiving and holding cutting strand 246. Support strands 244 may be biased to move radially-outwardly in the absence of a constraining force. Thus, support strands 244 may move end effector 226 toward its expanded configuration upon exiting from outer tube 224. This may facilitate insertion of tissue into end effector 226, and into the space defined between cutting strands 246. Support strands 244 may be made, for example, of Nitinol, spring steel, and/or any other suitable material.

Second actuator 232 may be coupled to cutting strands 246 to retract cutting strands 246 proximally, thus freeing the distal portions of cutting strands 246 from slots 258. The wall of support arm 248 extending alongside second lumen 254 may be slit, perforated, or weakened to facilitate freeing of cutting strands 246 from second lumens 254. This allows cutting strands 246 to be tightened onto tissue within end effector 226. A single one of cutting strands 246 may be tightened onto the tissue at a time, or alternatively, more than one of cutting strands 246 may be tightened onto the tissue at the same time. Second actuator 232 also may move cutting strands 246 in a reciprocatory or sawing motion to cut the tissue with cutting strands 246, as described above in the aforementioned examples. It is contemplated that distal support 250 may include a spacing member 260 (FIG. 19I) that may keep cutting strands 246 spaced apart from each other to avoid interference or the inflicting of damage on one cutting strand 246 by another. It is contemplated that cutting strand 246 may be braided similar to strand 182 (FIG. 16B).

Figure 21:
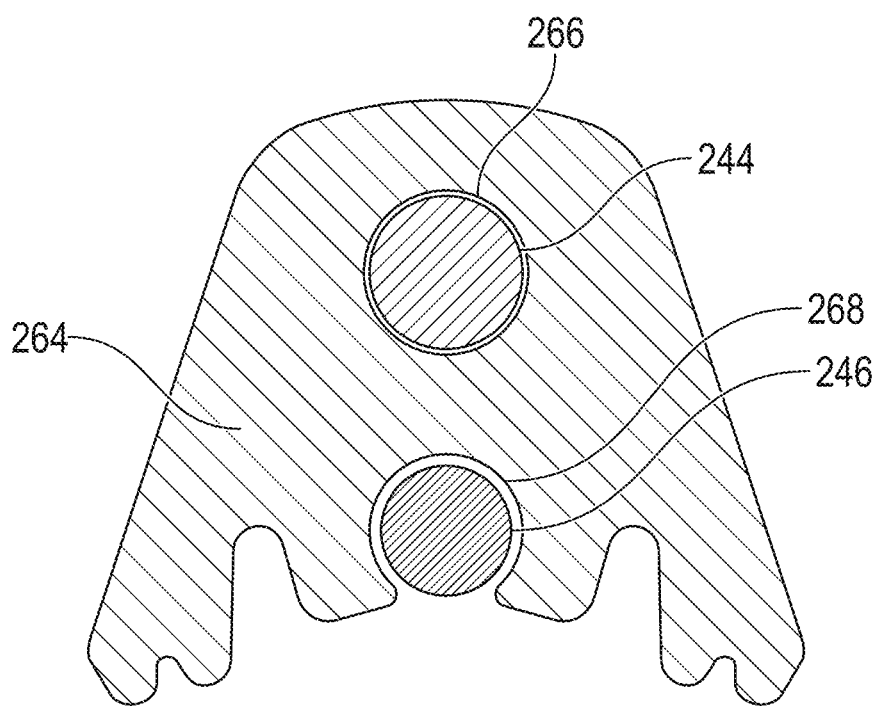
FIG. 21 is a partial section view of the portion of the tissue extraction device of FIG. 20, in accordance with aspects of the present disclosure.
Figure 20D:
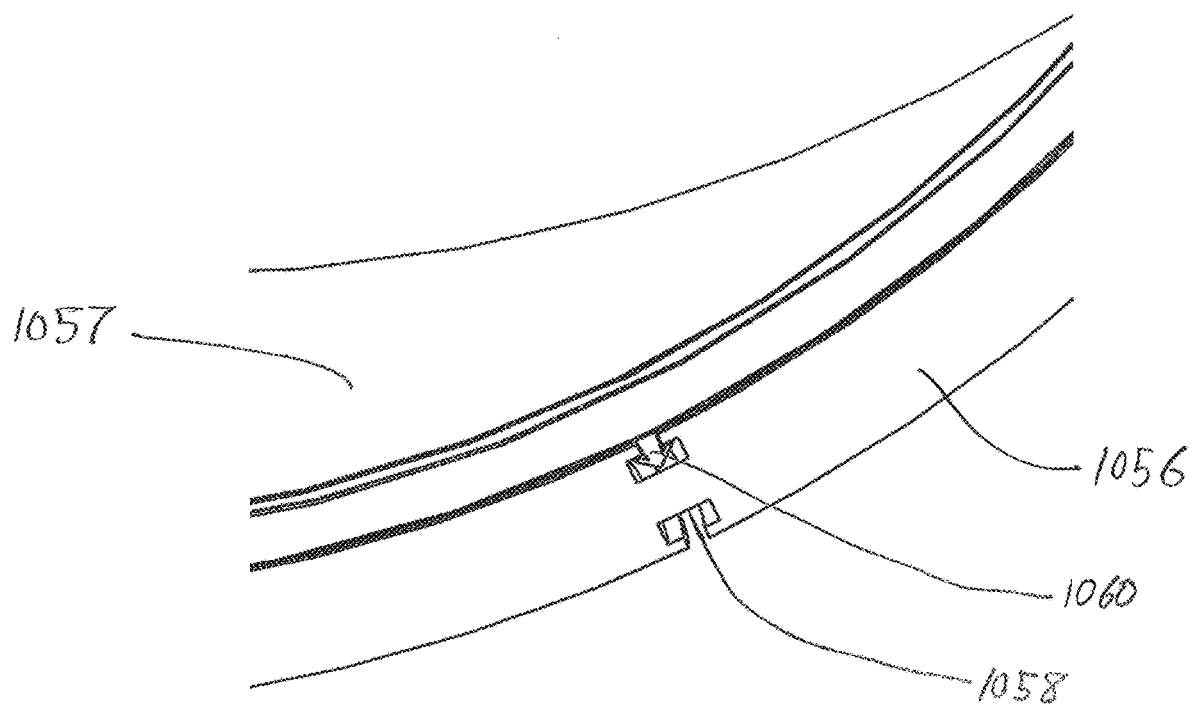
FIG. 20 is a perspective view of a portion of a tissue extraction device in a partially-assembled state, in accordance with aspects of the present disclosure.

FIGS. 20 and 21 show another example of an end effector 262. End effector 262 may include one or more support arms 264 extending proximally from a distal support 266 (FIG. 20). One or more of support arms 264 may include a lumen 266 for support strand 244 and a slot or groove 268 for receiving and holding cutting strand 246 (FIG. 21). Distal support 260 may be similar to distal support 250, and may include a spacing member 270 similar to spacing member 260. End effector 262 also may include another spacing member 272 at a side of end effector 262 opposite that of spacing member 270. Spacing member 272 may include one or more cutouts 274 to position support arms 264 at spaced intervals about end effector 262.

Figure 22A:
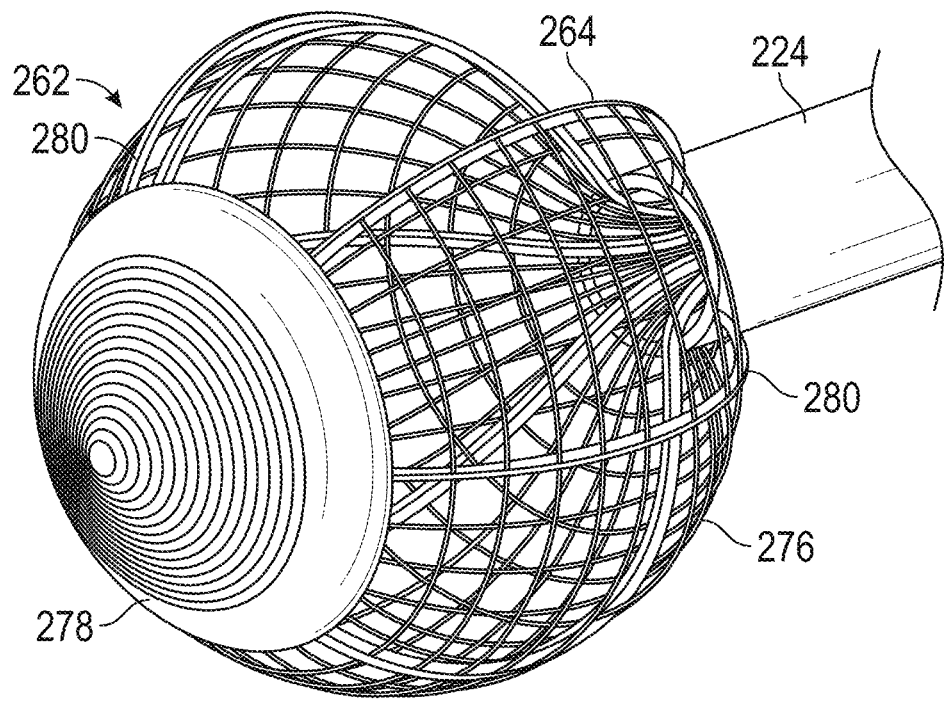
FIGS. 22A and 22B are perspective views of a tissue extraction device, in accordance with aspects of the present disclosure.
Figure 22B:
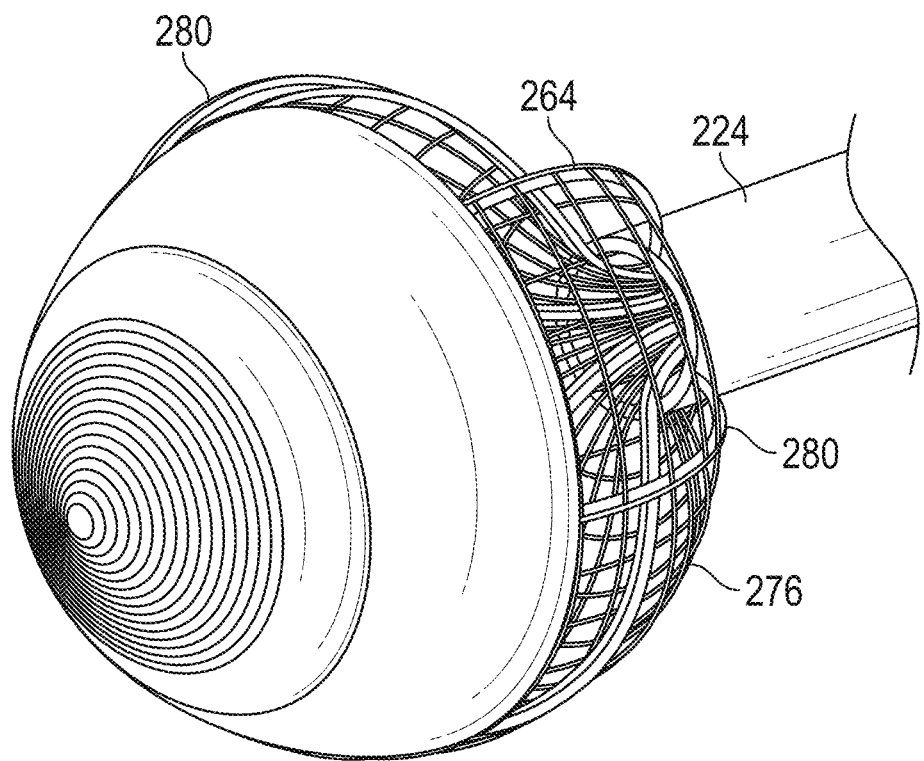

End effector 262 may be retracted into and extended out of the distal end of outer tube 224, and/or otherwise manipulated, using handle assembly 232, in a manner similar to end effector 226. For example, FIGS. 22A and 22B show end effector 262 in an extended or deployed position relative to outer tube 224. End effector 262 may be at least partially surrounded by a mesh 276, supported by support arms 264. Mesh 276 may be omitted between a pair of adjacent support arms 264 to permit insertion of tissue into end effector 262. A bag 278 may be positioned at a distal end of end effector 262. Initially, bag 278 may be concentrically folded or otherwise collapsed (FIG. 22A). A proximal end of bag 278 may be coupled to one or more sutures 280. Suture 280 may extend proximally from bag 278 and into outer tube 224. A proximal end of suture 280 may be pulled by a user to draw bag 278 proximally over support arms 264 and mesh 276 to cover end effector 262 (FIG. 22B), for example, after tissue has been inserted into end effector 262. Bag 278 may be pulled to the distal end of outer tube 224, and/or into outer tube 224, using suture 280. Once bag 278 covers end effector 262, cutting strands 246 may be used to cut the tissue within the confines of bag 278. While end effector 262 is depicted, it should be understood that bag 278 and sutures 280 may be employed with end effector 226 in a similar manner.

Figure 23A:
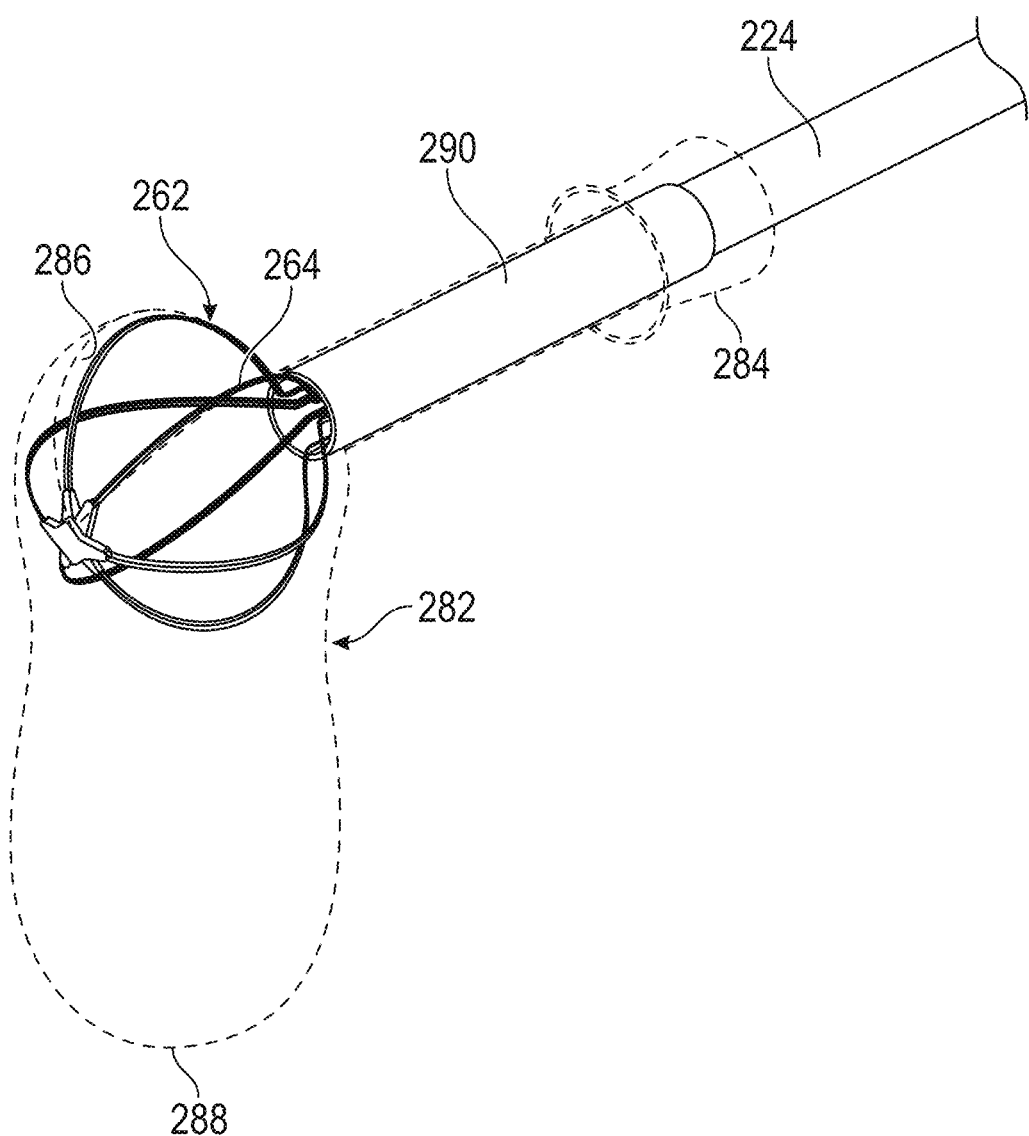
FIGS. 23A and 23B are perspective views of a tissue extraction device, in accordance with aspects of the present disclosure.
Figure 23B:
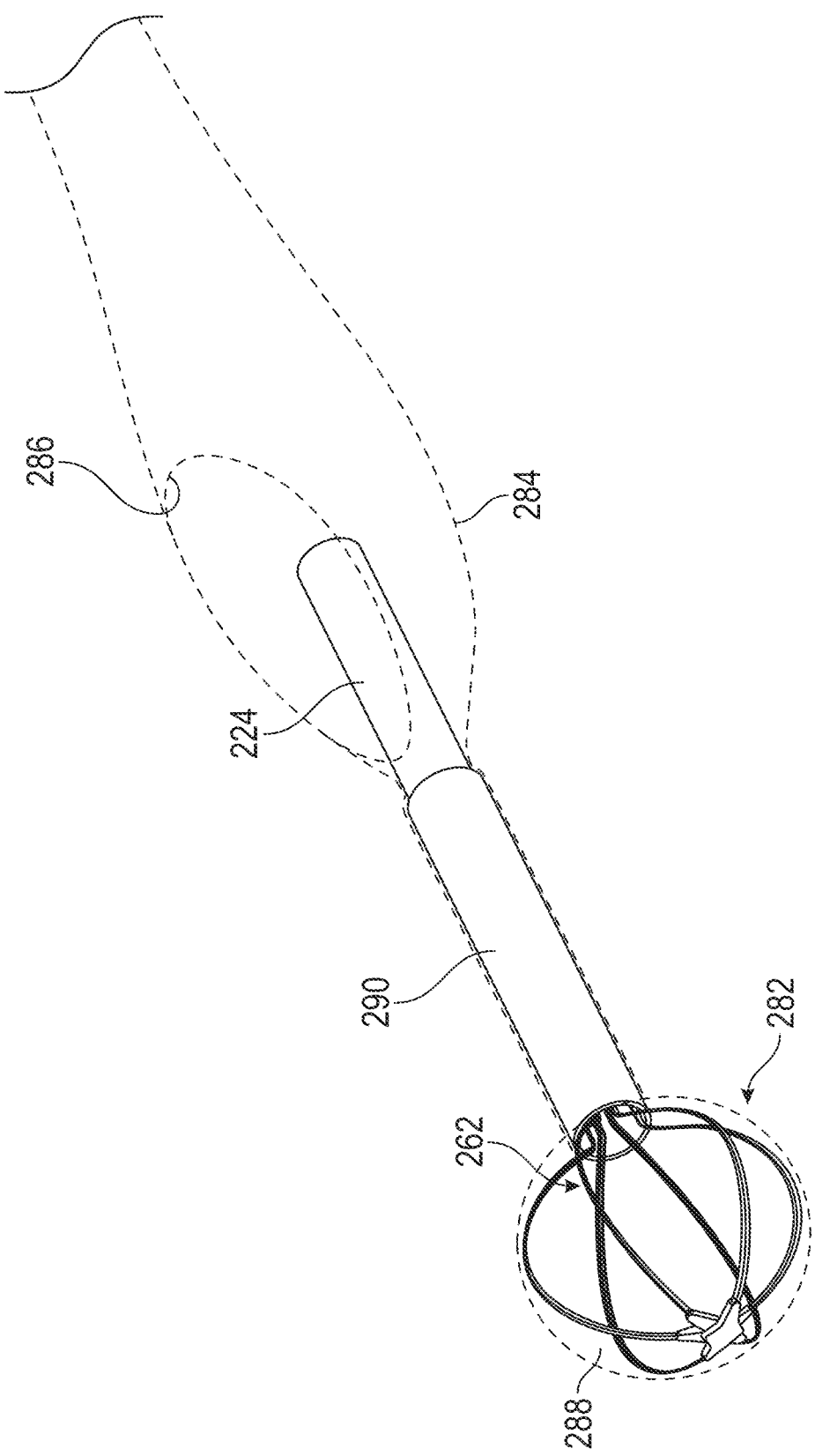

FIGS. 23A and 23B show another example of a bag 282 that may enclose end effector 262. A portion 284 of bag 282 may extend along outer tube 224. For example, portion 284 may extend around outer tube 224. A sheath 290 may be positioned around portion 284 to secure portion 284 on outer tube 224. Portion 284 may be slidable between the outer surface of outer tube 224 and the inner surface of sheath 290. Bag 282 may include an opening 286. Bag 282 also may include a closed end 288.

As shown in FIG. 23A, opening 286 may be positioned along a side of end effector 262, which may allow a user to insert tissue into end effector 262. For example, opening 286 may be positioned to overlap with a gap in mesh 276, and/or between support arms 264 (FIGS. 22A and 22B). After the user inserts tissue into end effector 262, the user may pull portion 284 proximally to retract bag 282 into the space between sheath 290 and outer tube 224. In one example, the portion of bag 282 having opening 286 may be pulled proximally out of sheath 290. This may draw closed end 288 onto end effector 262, and with closed end 288 surrounding end effector 262, procedures may be performed on tissue within the confines of end effector 262 and closed end 288 of bag 282.

Figure 24:
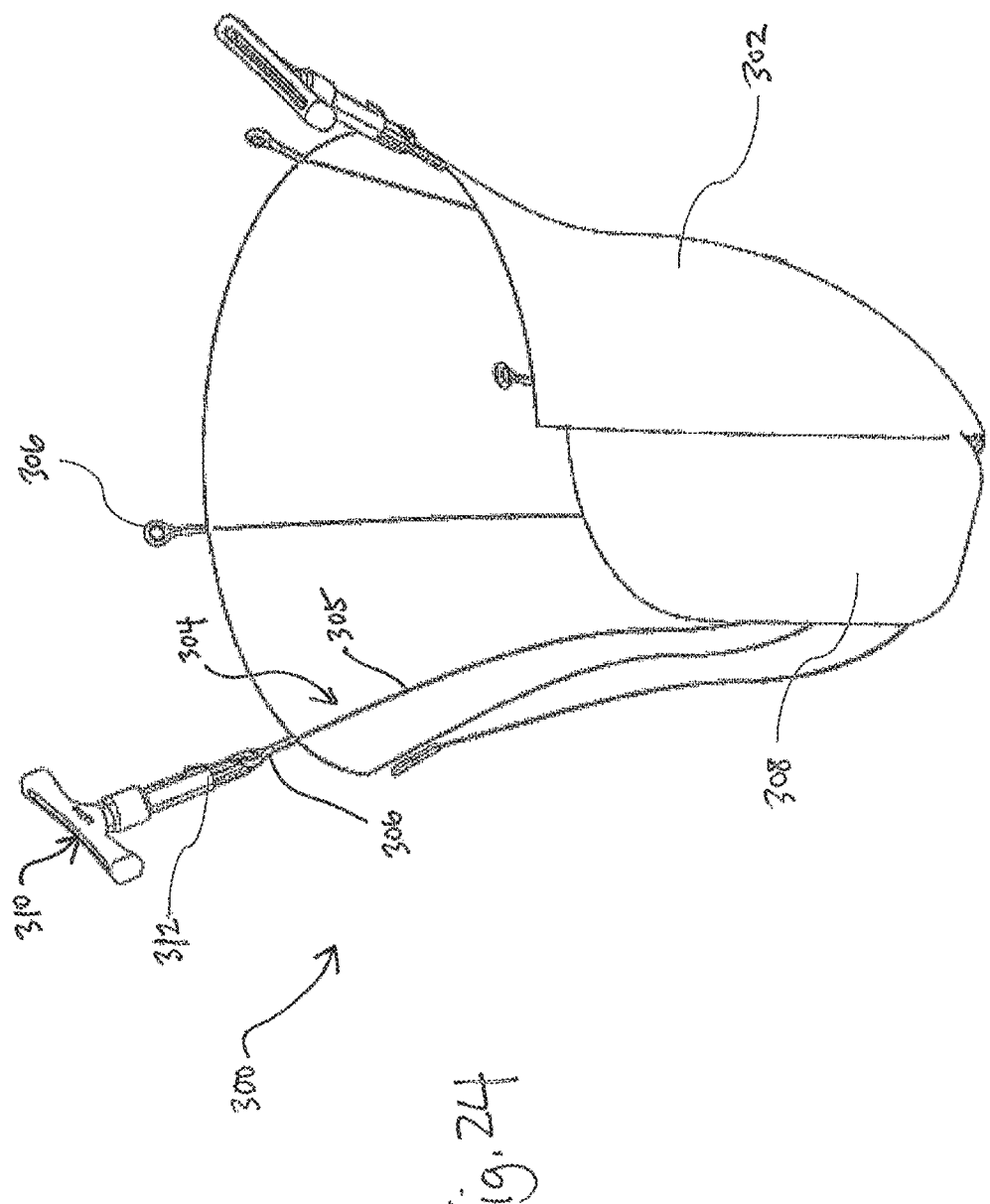
FIG. 24 is perspective view of a tissue extraction device, in accordance with aspects of the present disclosure.

FIG. 24 shows another exemplary tissue extraction device 300. Tissue extraction device 300 may include a bag 302 for receiving a tissue specimen 308, and one or more cutting elements 304 for cutting tissue specimen 308. Cutting element 304 may include a strand (e.g., similar to strand 182 or any of the other strands described in this disclosure, including, for example, cutters 1200) or wire 305 having anchoring ends or elements 306. Tissue extraction device 300 also may include handles 310, each handle 310 including an attachment member or mechanism 312 for attaching handle 310 to one of anchoring elements 306. The elements shown in FIG. 24 may be used with an introducer (FIGS. 35A-35G, 36A-36G, and 37A-37O), a wound retractor (FIGS. 33A-33D, 34A-34D, and 46F-46G), and or a tube (FIGS. 46H-46W). Aspects of tissue extraction device 300 are described in greater detail below.

As shown in FIGS. 25A-25C, bag 302 may have an open end 318 with an opening 320, and a rim 322 surrounding opening 320. Bag also may include a body 324 having a closed end 326 opposite open end 318. Bag 302 may be waterproof or otherwise leak-proof and may enclose tissue specimen 308 within a subject. Body 324 may be flexible and/or tear resistant. For example, body 324 may be made of materials including nylon, polyvinyl chloride, polyurethane, a rip stop nylon woven fabric, low-density polyethylene, and/or any other suitable material.

Bag 302 may take the shape of a subject's body cavity when in use. Additionally or alternatively, bag 302 may have a predefined shape. For example, portions of bag 302 may be wider from a front view (FIG. 25B) than a side view (FIG. 25C), may be deeper or longer than it is wide, and/or may have a curved closed end 326. In one example, open end 318 may be wider than closed end 326. From the front view (FIG. 25B), a portion of body 324 proximate open end 318 may have substantially straight sidewalls, while a portion of body 324 proximate closed end 318 may have curved sidewalls. From the side view (FIG. 25C), bag 302 may have a tapering width that decreases in a direction going from open end 318 to closed end 326. Open end 318, with opening 320, may extend proximally outside of a body cavity while a procedure is performed through an incision (e.g., a mini-laparotomy or laparoscopic procedure through the abdominal wall) or a body orifice (e.g., the vagina), and body 324 and closed end 326 may surround tissue specimen 308 in the subject's body.

A bag 302', similar to bag 302, is shown in FIGS. 26A-26D. Bag 302' may comprise a stiffening element 328 at a rim 322' of an open end 318' of bag 302'. In one example, stiffening element 328 may be annular. Stiffening element 328 may be compressible to a collapsed configuration during insertion of bag 302' into and/or removal of bag 302' from the subject, and may be expandable to an expanded configuration when a compressing force is absent or removed. Stiffening element 328 may bias rim 322' and opening 320' into an expanded configuration to facilitate insertion of tissue specimen 308 into bag 302', and/or facilitate performance of a procedure on tissue specimen 308 within bag 302'.

Stiffening element 328 may be formed of, for example, Nitinol, spring steel, a polymer, and/or any other suitable material. Stiffening element 328 may be secured to the rim 322' via a band 330 formed by an everted portion of a body 324' of bag 302', and/or a piece of material attached to body 324'. Band 330 may trap stiffening element 328 between an interior surface of band 330 and an exterior surface of body 324'. Band 330 may be attached to body 324' by heat-sealing one or more ends of band 330 to body 324', creating a cavity 331 for holding stiffening element 328 (FIG. 26D).

Bag 302 may include one or more interior elements that may removably couple cutting elements 304 to the interior surface of bag 302. While bag 302 is used here as an example, it should be understood that similar interior elements may be provided in any of the other aforementioned bags. FIG. 27 shows one or more frangible, tearable, or otherwise splittable members 332 on the interior surface of bag 302. Splittable member 332 may include a strip of material 334 mounted on the interior surface of the bag 302. One or more cutting elements 304 may be secured to the interior surface of bag 302 by one or more splittable members 332, with splittable members 332 pinning strands 305 against the interior surface.

A user may exert a force on cutting elements 304 to break, tear, or otherwise split splittable members 332. Doing so may free cutting elements 304 to move relative to (e.g., away from) the interior surface of bag 302. In one example, splittable members 332 may include perforations 336 or other forms of weakening to facilitate tearing or splitting. Additionally or alternatively, splittable members 332 may include pre-formed slits (not shown) that may be force open, such that cutting elements 304 may move through the slits and away from the interior surface of bag 302.

It is contemplated that each of cutting elements 304 may be secured to the interior surface of bag 302 by multiple splittable members 332. Short or side edges of splittable members 332 may be coupled to the interior surface of bag 302 by adhesive, heat sealing, or other suitable forms of attachment. Splittable members 332 may be formed, for example, of low-density polyethylene, polyurethane, thermoplastic, and/or other suitable materials.

Figure 28:
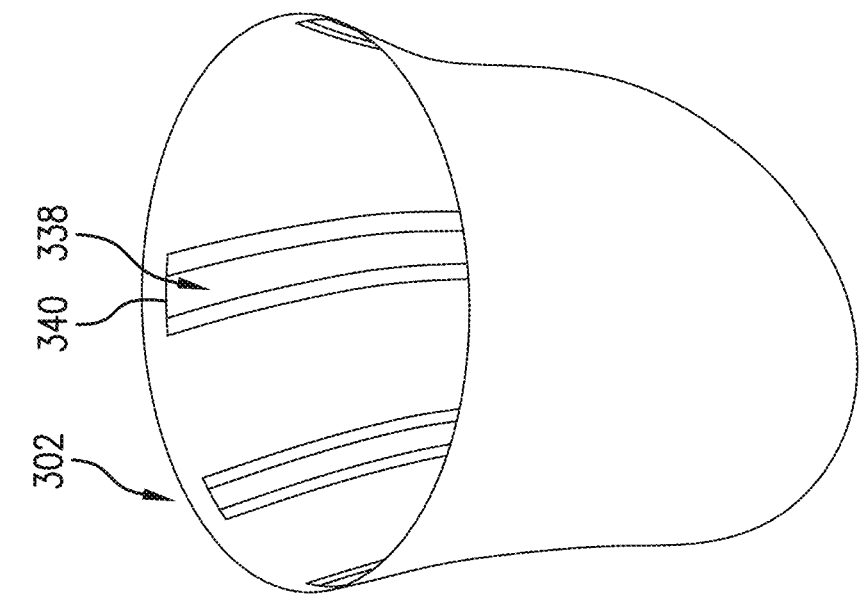
FIG. 28 is a perspective view of a bag of a tissue extraction device, in accordance with aspects of the present disclosure.

Additionally or alternatively, the interior surface of bag 302 (or any of the other aforementioned bags) may include one or more channel sheaths 338 mounted thereon, as shown in FIG. 28, by which one or more of cutting elements 304 may be secured to the interior surface of bag 302. Channel sheath 338 may include one or more pieces of material that may be attached to the interior surface of bag 302. The attachment may be on lateral longitudinal sides of channel sheath 338, such that a channel 340 may be formed between attachment locations for receiving strand 305.

Figure 29A:
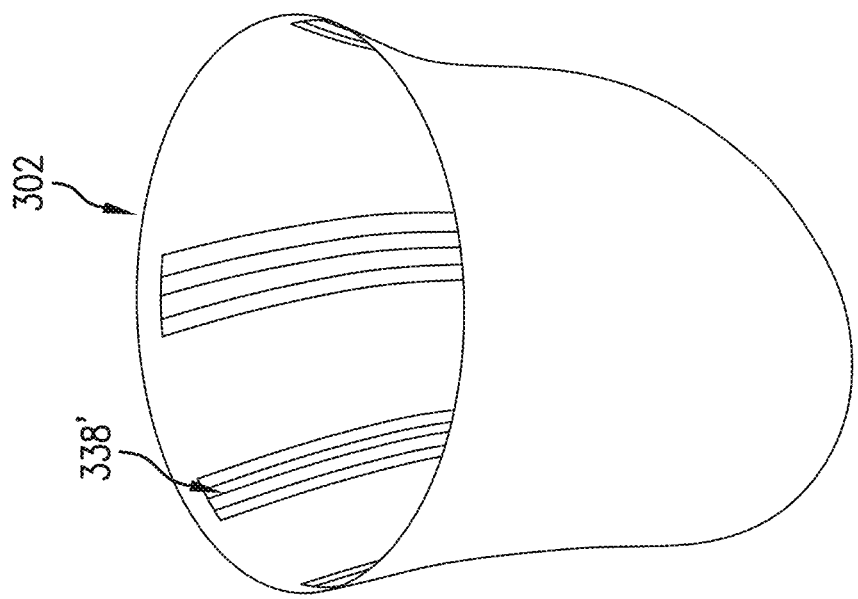
FIGS. 29A-29C are perspective, front, and side views of a bag of a tissue extraction device, in accordance with aspects of the present disclosure.
Figure 29C:
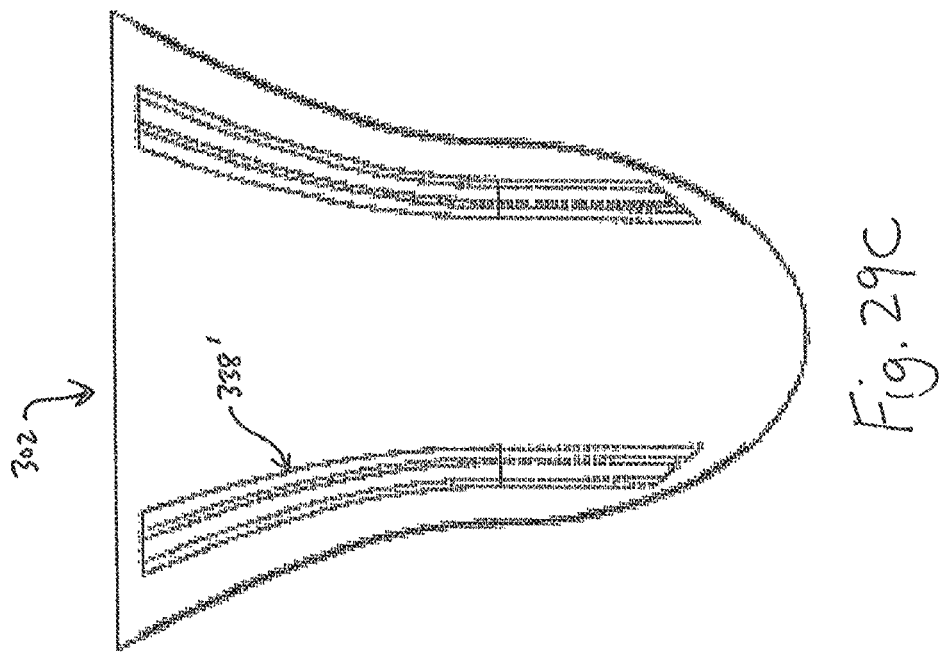
Figure 29B:
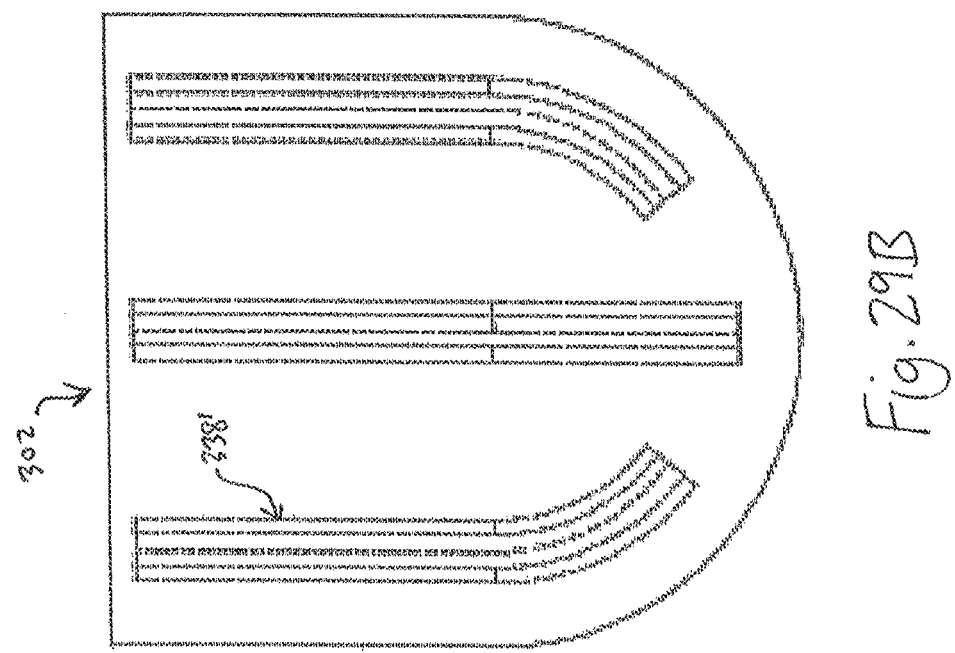
Figure 32B:
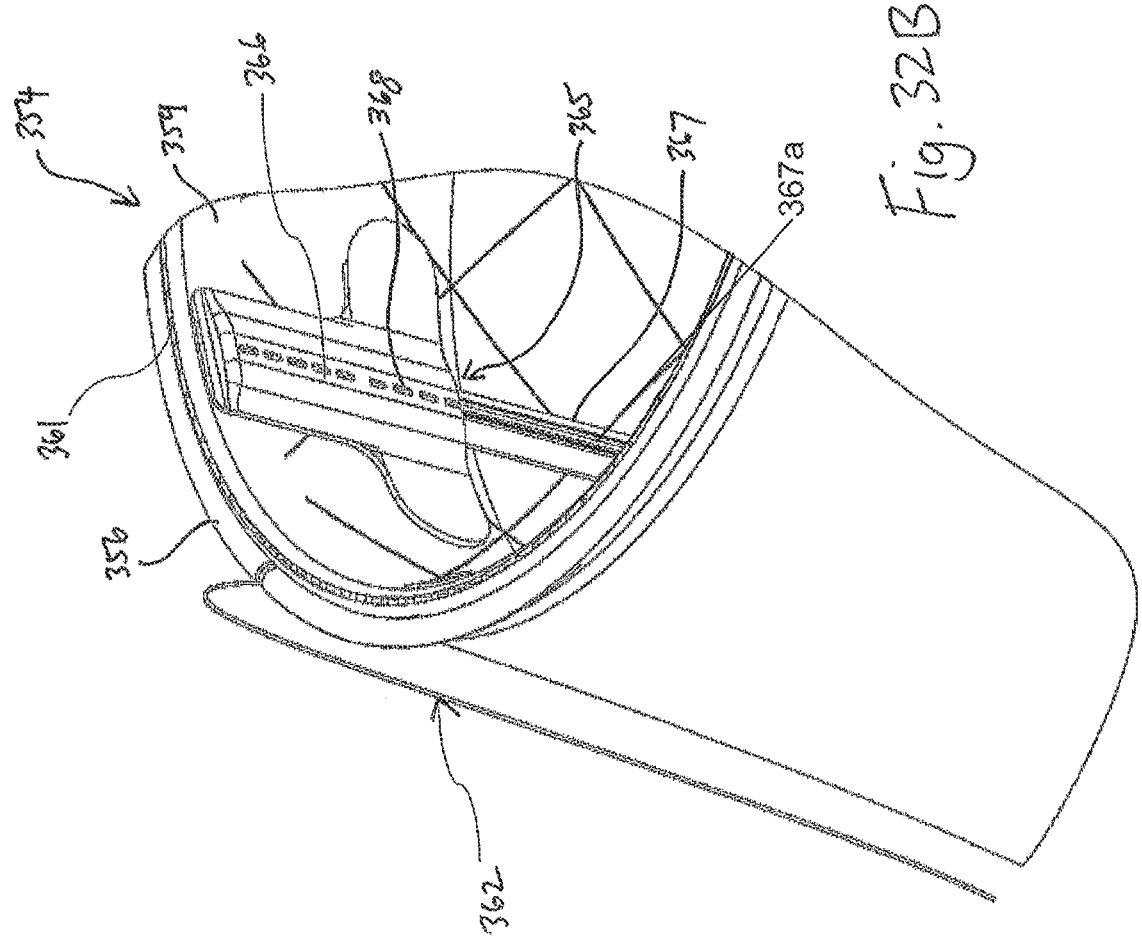
Figure 32D:
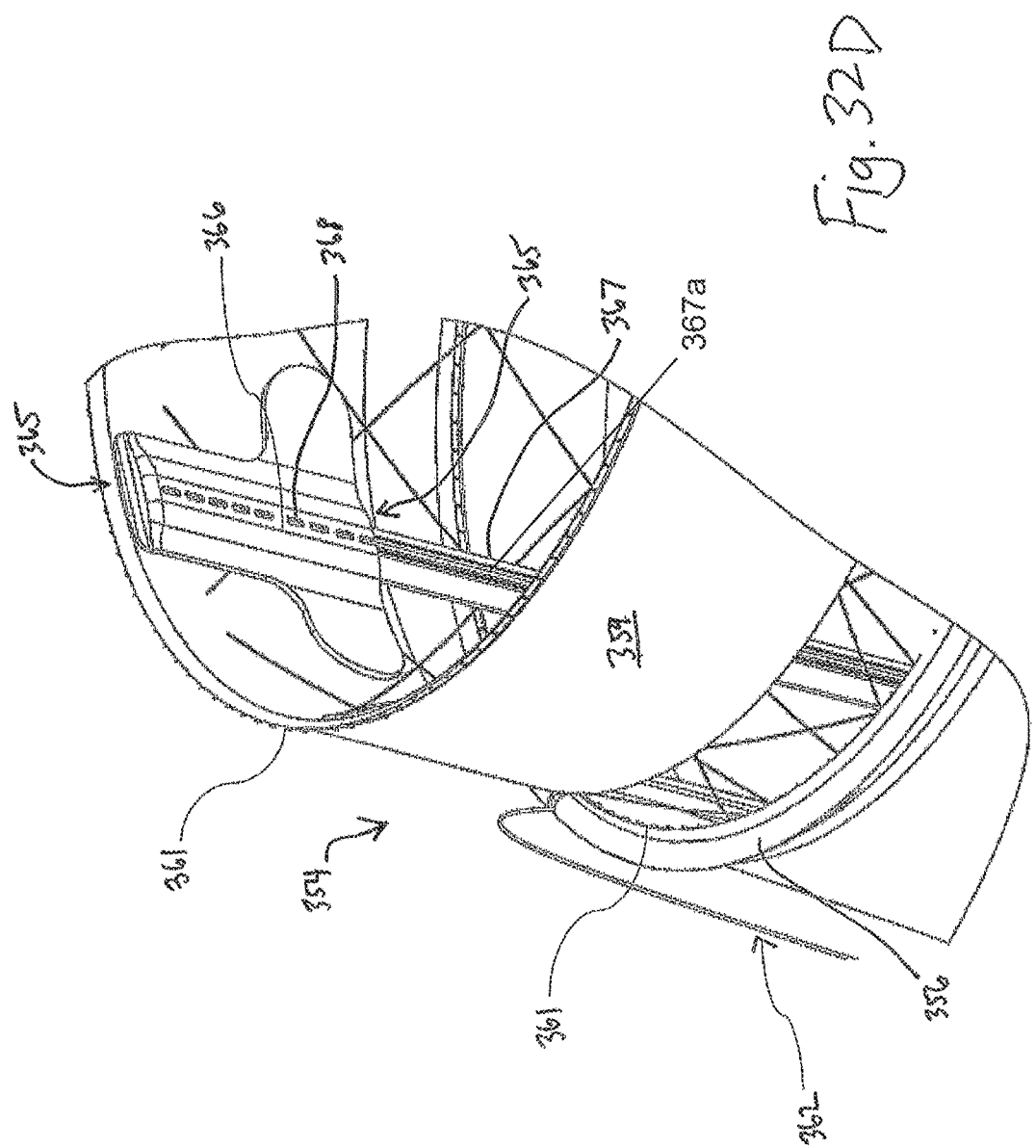
Figure 33D:
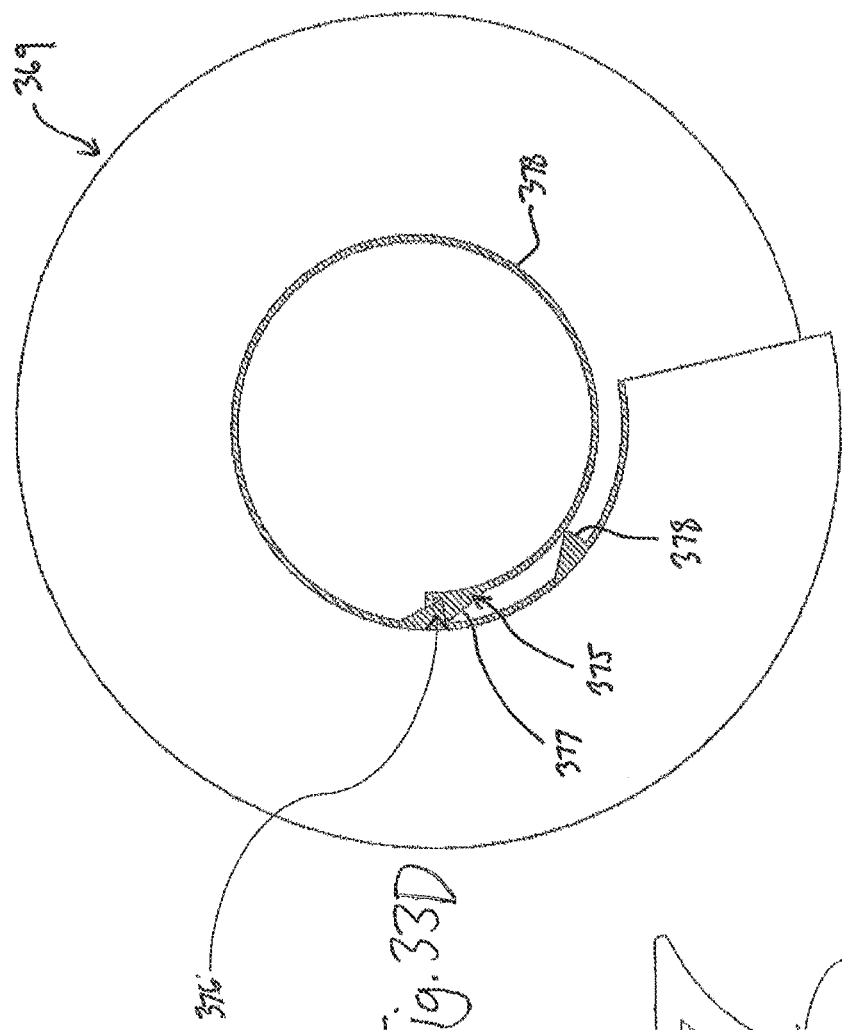
Figure 33C:
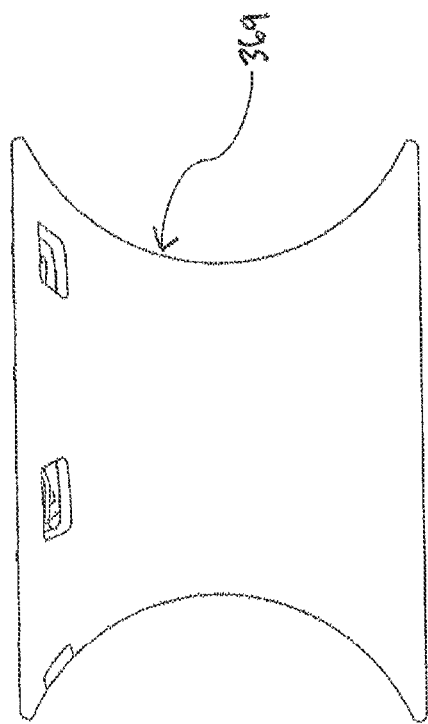

Channel sheath 338 may be coupled to the bag 302 in the same manner as the aforementioned splittable member 332. Channel sheath 338 may have a proximal end at or near open end 318. For example, the proximal end of channel sheath 338 may terminate proximate open end 318, but distal to open end 318. A distal end (not shown) of channel sheath 338 may terminate proximate closed end 326, but proximal to closed end 326. A pair of channel sheaths 338 may be diametrically-opposed, and may secure opposite sides of a single cutting element 304, such that cutting element 304 may have a U-shaped configuration within bag 302. Because channel sheaths 338 may terminate proximal to closed end 326, the distal portion of cutting elements 304 (i.e., the base of the U) may be exposed. Channel sheaths 338 may guide cutting elements 304 to facilitate smooth translational, or otherwise controlled, movements, while allowing the distal portions of cutting elements 304 to engage tissue specimen 308. As shown in FIGS. 29A-29C, a channel sheath 338', similar to channel sheath 338, may be splittable in a manner similar to splittable members 332 (FIG. 27). Channel sheaths 338' may be splittable from their proximal ends to their distal ends.

FIGS. 30A-30D illustrate an exemplary double-layered bag 342 that may include an outer bag or layer 344 and an inner bag or layer 346. Bag 342 may be used in place of any of the aforementioned bags, and vice-versa. A gap 348 may exist between outer layer 344 and inner layer 346. Outer layer 344 and inner layer 346 may be made of materials similar to those used in the construction of bag 302 or any of the other aforementioned bags. Outer layer 344 and inner layer 346 may be formed of a single continuous piece of material, or may be coupled at their proximal ends via adhesive, heat sealing, or the like. It is contemplated that inner layer 346 may include one or more channel sheaths 338 on its interior surface. Additionally or alternatively, inner layer 346 may include any of the other aforementioned interior elements (e.g., splittable member 332 and/or channel sheaths 338') on its interior surface.

A double-layered bag 342' is shown in FIG. 31. Bag 342' may be similar to bag 342. Bag 342' may include an insufflation valve 350 and a tube 352. Air, or any other suitable fluid, may be directed through valve 350, into tube 352, and into a gap 348' between an outer layer 344' and an inner layer 346' of bag 342'. Inner layer 346' may contain tissue specimen 308 and at least one cutting element 304. Outer layer 344' may form an additional barrier between contents of inner layer 346 and the body cavity. With outer layer 344' separated from inner layer 346', a procedure may be carried out on tissue specimen 308 within inner layer 346'. Due to the separation, there may be a reduced risk of puncturing outer layer 344' during performance of the procedure, and thus, a corresponding reduced risk of material from tissue specimen 308 leaking into the subject's body. In one example, inner layer 346' may have a greater stiffness than outer layer 344', such that insufflation pressure in gap 348' may be less able/likely to cause inner layer 346' to collapse around tissue specimen 308, thereby giving the user a better view of tissue specimen 308 and more of a working area; and more able/likely to move outer layer 344' away from inner layer 346' to guard against damaging outer layer 344'.

In another example, a double layered bag 354 is shown in FIGS. 32A-32G. Bag 354 may be used in place of any of the aforementioned bags, and vice-versa. Bag 354 may include an outer layer 355 having an outer neck or rim 356 and an outer body 357. Bag 354 also may include an inner layer 358 having an inner neck or rim 359 and an inner body 360. Inner body 360 may be a mesh or net. In one example, inner body 360 may be made of Nitinol or spring steel, such that inner body 360 may be inherently biased to expand outwardly when deployed from any suitable introducer. Alternatively, inner body 360 may be made of a polymeric material, or woven material, that may exhibit elastic properties. Outer rim 356 may receive inner rim 359 such that outer rim 356 may concentrically surround inner rim 359. Inner rim 359 may extend distally beyond outer rim 356. Outer rim 356 and inner rim 359 may be removably coupled to each other by one or more frangible, tearable, or otherwise separable connections 361 to form a separation line, such that inner rim 359 may be separated from outer rim 356 by pulling rims 356 and 359 away from each other at the separation line (FIGS. 32C-32G). The separation line may be formed at the proximal ends of rims 356 and 359, such that the proximal ends of rims 356 and 359 are, at least initially, flush with each other. One or more gripping members 362 may extend from outer rim 356. Gripping member 362 may include a holding tab, ring, or other enlarged portion 363 and a strand 364. A user may pull gripping member 362 and strand 364 to facilitate withdrawal of the proximal end of bag 354 out of a subject's body. Once the proximal end of bag 354 is outside of the subject's body, rims 356 and 359 may be separated. The separation may help keep inner layer 358 (holding tissue specimen 308) away from outer layer 355 while tissue specimen 308 is being cut by cutting element 304.

One or more splittable members 365 may be provided along the interior of inner layer 358. Splittable member 365 may include an enlarged splittable proximal portion 366, for receiving anchoring element 306 of cutting element 304, and a narrower splittable distal portion 367, for receiving strand 305 of cutting element 304. Splittable member 365 may be similar to, for example, splittable members 332 and 338'. For example, splittable member 365 may split, tear, break, or otherwise separate along a split 368. Split 368 may include perforations, frangible portions, pre-formed slits, and/or any other suitable elements to facilitate splitting. Splittable member 365 may be secured to inner layer 358 using any suitable form of attachment. For example, portion 366 of splittable member 365 may be heat-sealed, adhered, or otherwise attached to the interior surface of inner rim 359.

Distal portion 367 may include, for example, a strip of material (e.g., a flexible polymer) having a groove 367a formed therein. Groove 367a may have a radially-inner open end and a radially-outer closed end. Strand 305 of cutting element may be housed within groove 367a. Additionally or alternatively, any cutting components, such as cutting members, cutting saws, teeth, blades, cutting beads, cutting edges, cutting or abrading tubes, shown in FIGS. 50A-50E, 51A-51G, 52A-52F, 53A-53F, 54A-54H, 55A, 55B, 56A, 56B, 57A, 57B, 58A-58C, 59A-59D, 60A-60C, 61A-61C, 62A-62H, 63A-63F, 64A-64G, 65A, 65B, 66A-66E, 67A-67F, 68, 69A-69E, 70A-70E, 71A-71E, and/or 72A-72E, which may be provided on strand 305, may be housed within groove 367a. Strand 305 and/or the cutting components may be pulled out of groove 367a by the user when cutting is to be performed. Prior to the removal of strand 305 and/or the cutting components from groove 367a, walls of distal portion 367 may shield or cover strand 305 and/or the cutting components. It is also contemplated that one or more regions of distal portion 367 may have a cross-sectional shape similar to that of the cover 566 shown in FIG. 73. Strand 305 and/or the cutting components may be pulled out of groove 367a by exiting through the open end of groove 367a.

It is contemplated that distal portion 367 may be coupled to one or more interior portions of inner layer 358. For example, distal portion 367 may be coupled to inner layer 358 using adhesive, snap-fit engagement, and/or any other suitable form of fastening. Alternatively, mesh portions of inner layer 358 distal to inner rim 359 may be omitted, leaving distal portions 367 to hold the tissue specimen. Additionally or alternatively, all mesh portions of inner layer 358 may be omitted, leaving an inner layer formed by splittable members 365 and inner rim 359.

FIGS. 33A-33D illustrate aspects of a wound retractor 369. Wound retractor 369 is shown in use with bag 302. It should be understood, however, that wound retractor 369 may be used with any of the other aforementioned bags. Wound retractor 369 may be collapsible (radially-inwardly) and expandable (radially-outwardly), and may have overlapping ends 370 and 371. For example, wound retractor 369 may form a spiral that may be selectively radially compressed or radially expanded in order to decrease or increase the diameter of wound retractor 369.

Wound retractor 369 may have an hourglass-shape. Sides of wound retractor 369 may be concave to receive margins of a bodily orifice or incision in a subject, thereby helping to secure wound retractor 369 in position. Wound retractor 369 may be inserted along a portion of bag 302 passing through a bodily orifice or incision to secure bag 302 relative to the bodily orifice opening or incision, ensure a working space 372 remains open during a procedure, and/or protect the margins of the bodily orifice or incision from potentially being injured by cutting elements 304 during performance of the procedure. Wound retractor 369 also may provide a counter force on tissue specimen 308 when the user exerts a pulling force on tissue specimen 308 during cutting with cutting elements 304. Wound retractor 369 may be made of a flexible metal, a flexible and/or elastic polymer, semi-rigid plastic, Nitinol, spring steel, and/or other suitable materials.

Wound retractor 369 may include one or more clips 373 positioned at or near a proximal end of wound retractor 369. Clips 373 may be used to secure cutting elements 304 (FIG. 33B) so cutting elements 304 do not become tangled or otherwise interfere with each other during use, are positioned for easy access by the user, and/or remain selectively maneuverable from outside bag 302. Clip 373 may protrude from an inner surface of wound retractor 369, and may include a cantilevered arm 374 that extends over cutting elements 304. Clip 364 may punched out of the wall of wound retractor 369, or formed in any other suitable manner. Diametrically-opposed pairs of clips 364 may be positioned around wound retractor 369, such that opposing clips 364 may hold opposite end portions of a single U-shaped cutting element 304.

Wound retractor 369 also may include at least one radially-outward facing engagement member 375 and at least one radially-inward facing engagement member 376. Each engagement member 375 and 376 may include a sloped portion 377 and a shoulder 378. The shoulders of engagement members 375 and 376 may engage to releasably set the diameter of wound retractor 369. Moreover, wound retractor 369 may include multiple engagement members 376 to provide multiple diameter settings. Engagement member 375 and engagement member 376 may be positioned at or near a central portion of wound retractor 369. The adjustability of size and/or shape of wound retractor 369 may allow wound retractor 369 to adjustably set the size and/or shape of the bodily orifice or incision of a subject into which wound retractor 369 is inserted.

Radially-outward facing engagement member 375 and radially-inward facing engagement member 376 may be connected to, or may be positioned proximate to, a stiffening element 378 of wound retractor 369. Stiffening element 378 may include, for example, an annular metal member, while other portions of wound retractor 369 may be made of silicone. Engagement members 375 and 376 may be on opposite sides of stiffening element 378, such that the shoulders of engagement member 375 and 376 may engage to releasably lock engagement members 375 and 376. Although engagement members 375 and 376 are depicted as wedge-shaped or triangularly-shaped protrusions, it should be understood that any paired shapes that releasably lock to each other may be used.

Wound retractor 369 may be inherently radially-inwardly biased to move towards a contracted configuration in the absence of an expanding or holding force. Engagement between engagement members 375 and 376 may maintain wound retractor 369 in an expanded configuration. Alternatively, wound retractor 369 may be inherently radially-outwardly biased to move towards an expanded configuration in the absence of a constraining or holding force, in which case the orientation of the sloped and shoulder surfaces of engagement members 375 and engagement members 376 may be reversed.

Another wound retractor 379 is illustrated in FIGS. 34A-34D. Wound retractor 379 may be similar to wound retractor 369. Wound retractor 379 may include at least one extension 380 and at least one aperture 381. Extension 380 may be cylindrical, or any other suitable shape, and may include a protrusion 375 extending from its side (FIG. 34D). Aperture 381 may include a hole or indentation sized/shaped to releasably receive and hold extension 380. Protrusion 375 may facilitate releasable securement of extension 380 in aperture 381 by providing a snap-fit engagement of extension 380 in aperture 381.

Wound retractor 379 may include a plurality of apertures 381 extending along a radial plane that passes through wound retractor 379. Positioning extension 380 in one of apertures 381 may serve to retain the size and/or shape of wound retractor 379, and thus, retain the size and/or shape of the bodily orifice or incision in which wound retractor 379 may be positioned. Moreover, the presence of multiple apertures 381 provides for selective adjustment of a width of wound retractor 379, adjustment of the size and/or shape of the bodily orifice or incision, and/or adjustment of the size and/or shape of working space 372.

Wound retractor 379 also may include at least one holding feature 382 extending radially-outwardly to provide a user with something to grasp or hold for manipulating wound retractor 379. In one example, wound retractor 379 may include two holding features 382 extending proximally and radially-outwardly. One holding feature 382 may extend from an outer end of the spiral formed by wound retractor 379, and the other holding feature 382 may extend from an inner end of the spiral formed by wound retractor 379. Holding feature 382 may be a tab. Extension 380 may be aligned with one of holding features 382, assisting a user with positioning the extension 380 in apertures 381.

Alternatively, a tube (not shown) may be used in a similar manner as the aforementioned wound retractors. For example, the tube may be used in a procedure through an existing bodily orifice (e.g., a subject's vagina), to line the margins of the bodily orifice. In one aspect, the tube may be used to protect the vaginal walls and/or to retract the vaginal walls. The tube may include a hollow elongate device with a diameter large enough to receive any of the aforementioned bags and cutting elements. The shape/size of the tube may differ from the shape size of the aforementioned wound retractors to accommodate the shape/size of the bodily orifice into which the tube is inserted.

Another wound retractor 600 is shown in FIGS. 34E-34K. Wound retractor 600 may be used with any of the bags described in this disclosure, including, for example, bag 354. Wound retractor 600 may include a proximal flange 602. Proximal flange 602 may be annular, with a central opening 603. Wound retractor 600 also may include one or more clips 604 positioned adjacent a radially-outer edge of proximal flange 602. Clips 604 may be spaced from each other at equal intervals. Clips 604 may be similar to clips 373 (FIGS. 33A and 33B), and may help secure strands 305 of cutting elements 304. Additionally or alternatively, wound retractor 600 may include one or more engagement elements or hooks 606 at the radially-outer edge of proximal flange 602. Hooks 606 may be spaced from each other at equal intervals. Hooks 606 may be similar to hooks 345 (FIGS. 46F and 46G), and may engage the mesh or netting forming inner layer 358 of bag 354. Hooks 606 may be positioned between clips 373 to help ensure that when strands 305 are secured in clips 604, hooks 606 may be positioned to engage portions of inner layer 358 between splittable distal portions 367 of splittable members 365.

Figure 34E:
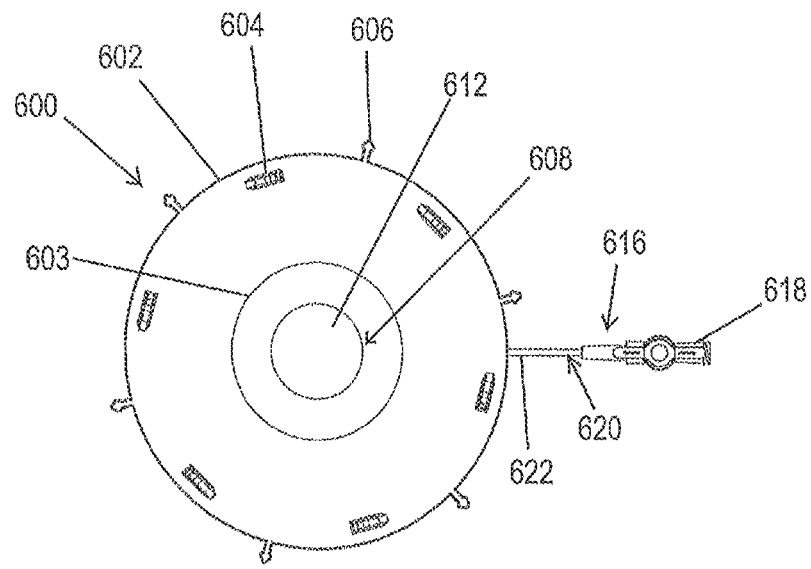
FIGS. 34E-34K are top, perspective, and section views of a wound retractor of a tissue extraction device, in accordance with aspects of the present disclosure.
Figure 34F:
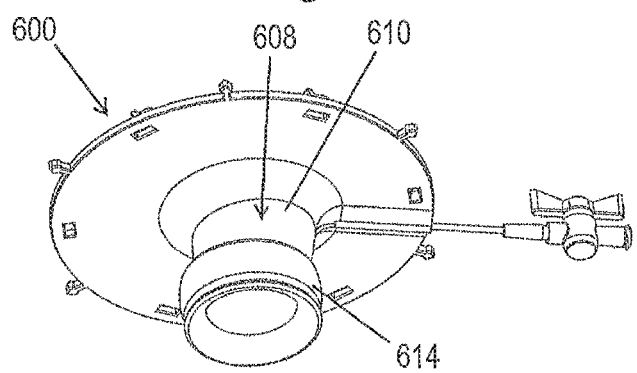
Figure 34G:
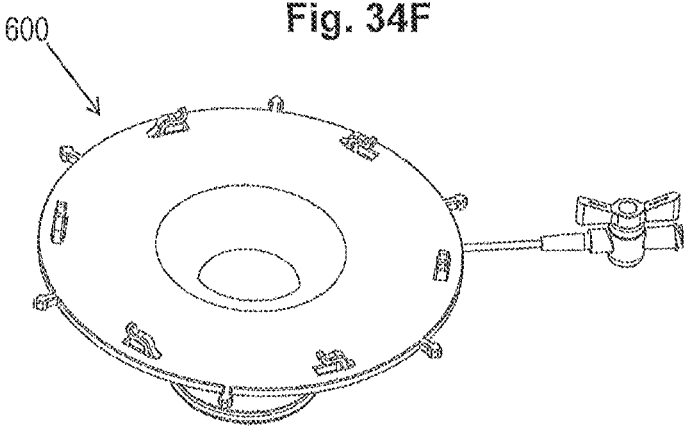
Figure 34H:
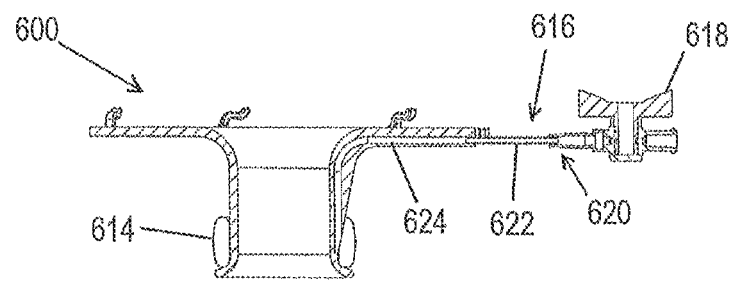
Figure 34I:
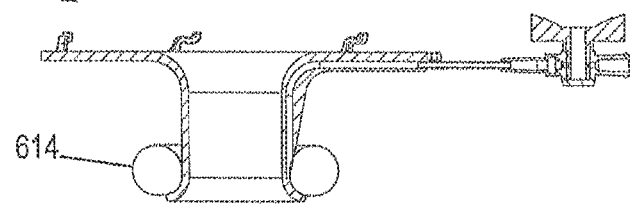
Figure 34J:
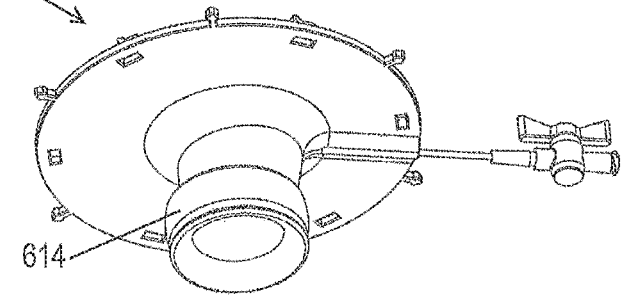
Figure 34K:
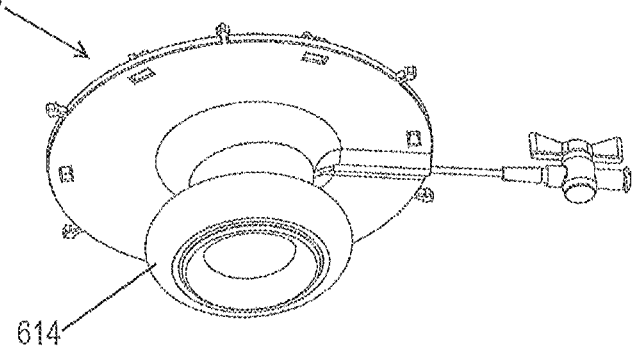

Wound retractor 600 also may include a tubular member 608 extending distally from proximal flange 602. Tubular member 608 may include a wall 610 surrounding a central passage 612. Tubular member 608 may connect proximal flange 602 with a distal inflatable member 614. Distal inflatable member 614 may include, for example, a toroidal balloon. FIGS. 34H and 34J show distal inflatable member 614 in an uninflated state, while FIGS. 34I and 34K shows distal inflatable member 614 in an inflated state. Distal inflatable member 614 may be in the uninflated state to facilitate insertion of wound retractor 600 into a wound opening. Wound retractor 600 may be inserted into a wound opening until distal inflatable member 614 passes through the wound opening, and/or until further insertion is prevented by a proximal end portion of tubular member 608 and/or a distal-facing surface of proximal flange 60. Distal inflatable member 614 may then be inflated to secure wound retractor 600 relative to the wound opening. For example, the inflated distal inflatable member 614 may prevent withdrawal of wound retractor 600 out of the wound opening.

Wound retractor 600 may include an insufflation assembly 616 for inflating and/or deflating distal inflatable member 614. Insufflation assembly 616 may include, for example, an insufflation valve 618 and an insufflation lumen 620. Insufflation valve 618 may move between open and closed positions to control the flow of an insufflation fluid through insufflation lumen 620. Insufflation lumen 620 may include an external tubular portion 622. Insufflation lumen 620 also may include an internal portion 624. Internal portion 624 may include a passage extending through proximal flange 602 and wall 610 of tubular member 608 to distal inflatable member 614.

Figure 34L:
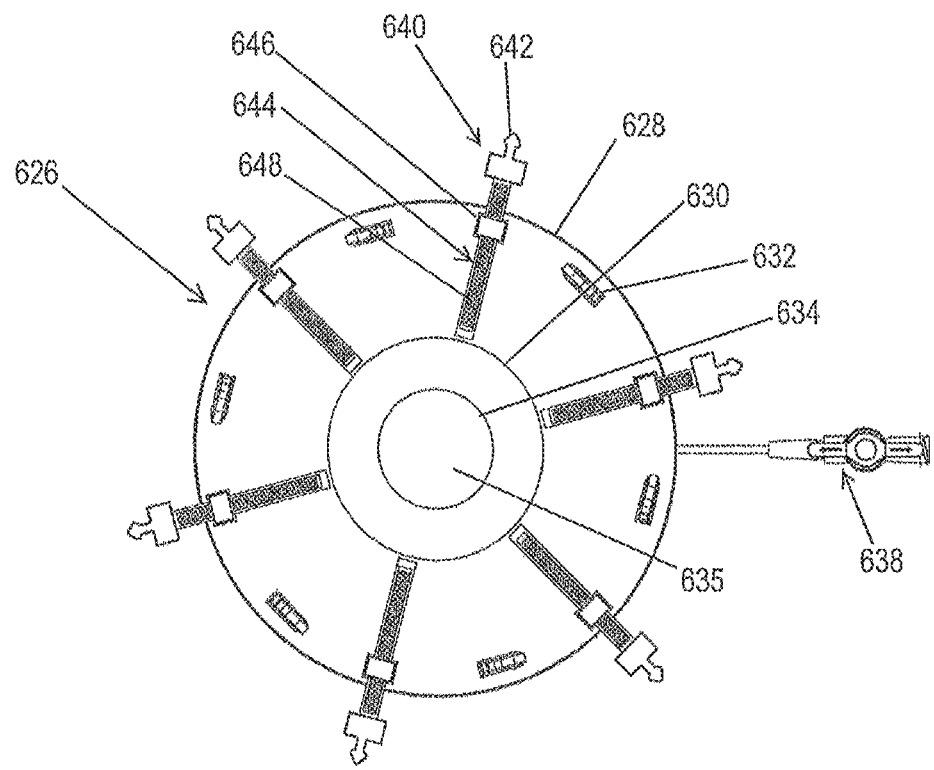
FIGS. 34L and 34M are top and perspective views of a wound retractor of a tissue extraction device, in accordance with aspects of the present disclosure.
Figure 34M:
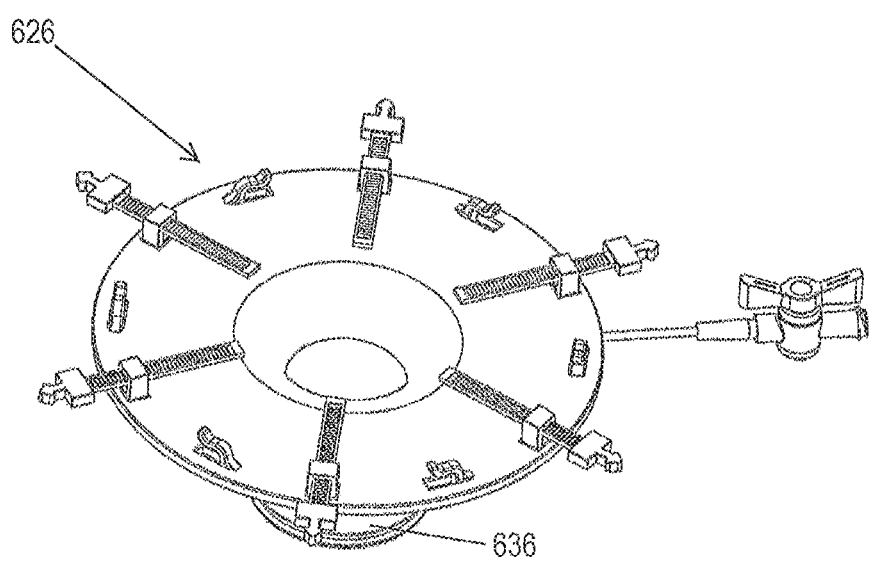
Figure 34N:
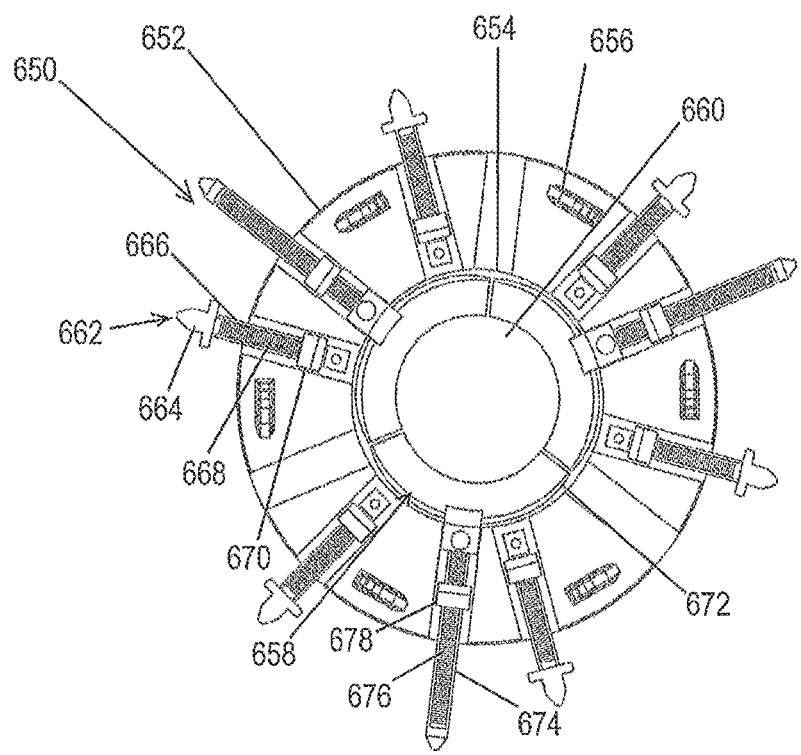
FIGS. 34N-34Q are top and perspective section views of a wound retractor of a tissue extraction device, in accordance with aspects of the present disclosure.
Figure 34O:
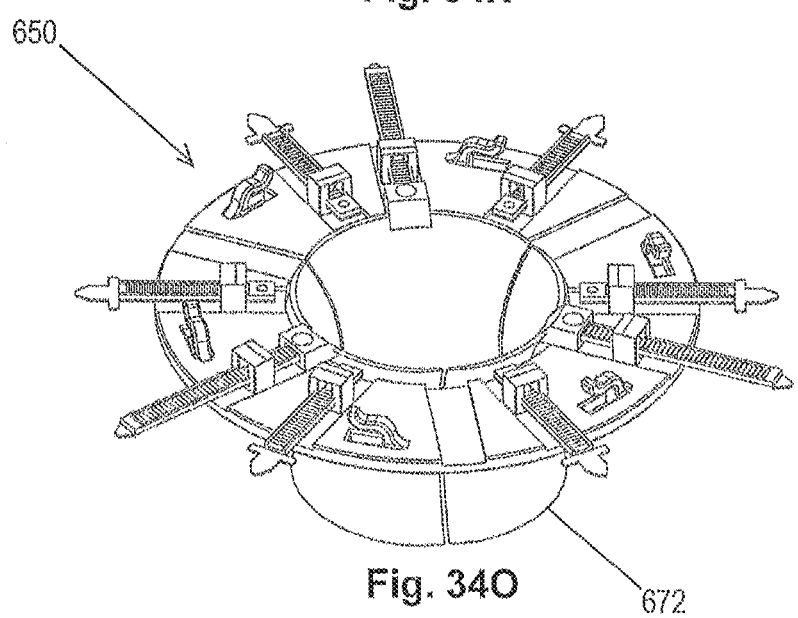

Another wound retractor 626 is shown in FIGS. 34L and 34M. Wound retractor 626 may be similar to wound retractor 600, and may include a proximal flange 628, a central opening 630, one or more clips 632, a tubular member 634, a central passage 635, a distal inflatable member 636, an insufflation assembly 638, and one or more hooks 642. A difference between wound retractor 626 and wound retractor 600 is that wound retractor 626 may include one or more adjustable hook assemblies 640. Adjustable hook assembly 640 may include hook 642, which may be similar to hook 606. Hook 642 may be fixedly coupled to a slidable member 644. Slidable member 644 may be slidable along a proximal-facing surface of proximal flange 628, and may be slidably received by a case or housing 646. Slidable member 644 may include protrusions or teeth 648 on a proximal-facing surface thereof. Housing 646 may include a pawl (not shown) therein that may form a ratchet with teeth 648. A radial position of hook 642 may be adjusted by sliding slidable member 644 along the proximal-facing surface of proximal flange 628 and through housing 646 until the desired radial position is reached. The radial position may be locked or otherwise maintained by engagement between the pawl and one or more of teeth 648. It is contemplated that wound retractor 626 may include a plurality of adjustable hook assemblies 640, with each hook assembly 640 being independently adjustable. This may allow hooks 642 to engage the mesh or netting forming inner layer 358 of bag 354 when used in wound openings of different sizes and/or shapes.

Another wound retractor 650 is shown in FIGS. 34N-34Q. Wound retractor 650 may be similar to wound retractor 626, and may include a proximal flange 652, a central opening 654, one or more clips 656, a tubular member 658, a central passage 660, and one or more adjustable hook assemblies 662. Adjustable hook assembly 662 may include a hook 664, a slidable member 666 with teeth 668, a housing 670, and a pawl (not shown) in housing 670, that may be similar to hook 642, slidable member 644, teeth 648, housing 646, and the pawl of adjustable hook assembly 640. One difference is that hook 664 may have a different shape than hook 642, and/or housing 670 may be positioned more radially-inward along proximal flange 652 than housing 646 on proximal flange 628.

Figure 34P:
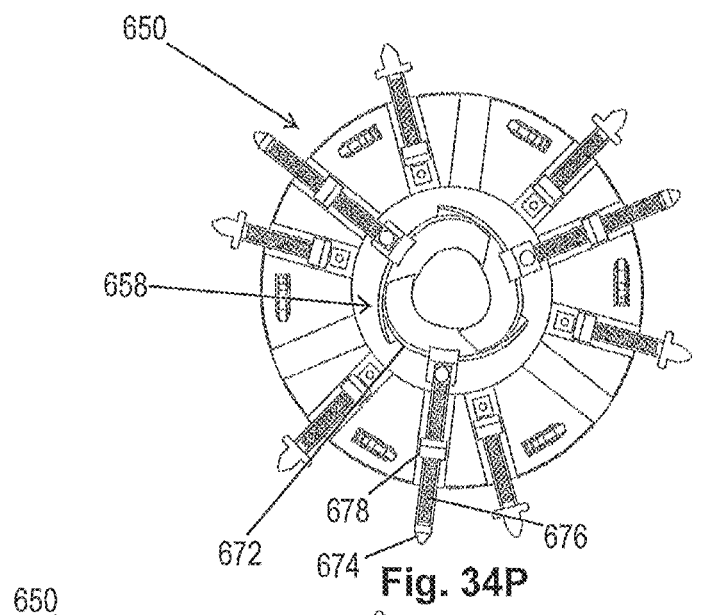
Figure 34Q:
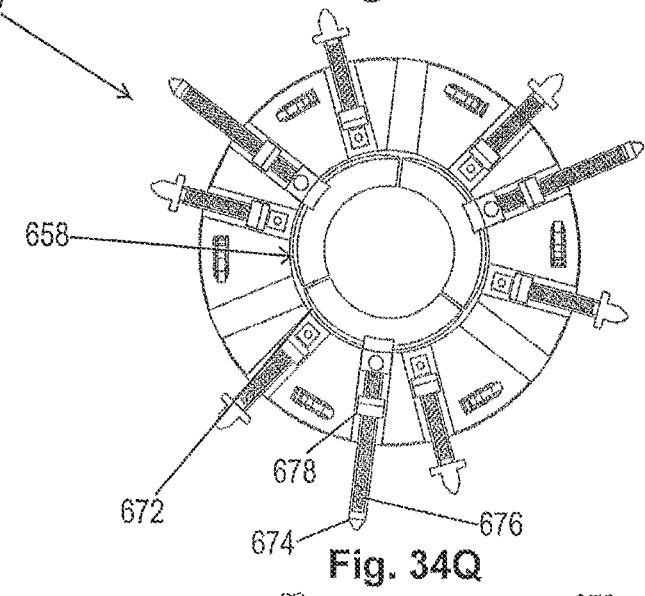
Figure 34R:
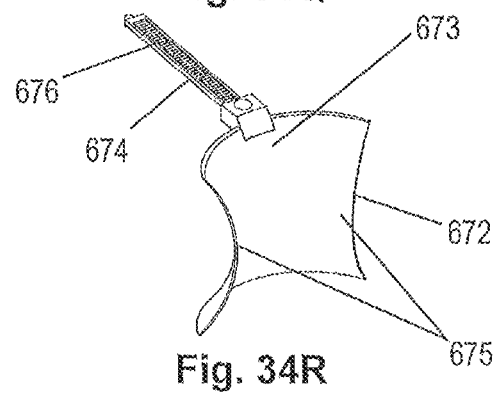
FIG. 34R is a perspective view of a component of the wound retractor of FIGS. 34N-34Q, in accordance with aspects of the present disclosure.

Tubular member 658 may have an adjustable width or diameter. To achieve this, tubular member 658 may include a plurality of petals 672. As shown in FIG. 34R, each petal 672 may include a curved panel defining a portion of tubular member 658. For example, each petal 672 may include two pairs of parallel curved edges, the edges of each pair being perpendicular to the edges of the other pair. Each petal 672 may include a central region 673 that may be thicker than side regions 675 on each side of the central region. Side regions 675 may be more flexible than central region 673.

Each petal 672 may be coupled to a slidable member 674 having teeth 676, similar to slidable member 644 and teeth 648. Slidable member 674 may be slidably received within a housing 678 having a pawl (not shown), similar to housing 672. The pawl and teeth 676 may form a ratchet. To facilitate insertion of wound retractor 650 into a wound opening, tubular member 658 may be held in a collapsed state, as shown in FIG. 34P. In the collapsed state, edge portions of each of petals 672 may overlap with edge portions of adjacent petals 672. For example, side regions 675 of each of petals 672 may overlap with side regions of adjacent petals 672. After tubular member 658 is positioned within the wound opening, petals 672 may be moved radially outwardly by sliding slidable members 674 through housings 678. Petals 672 may be slid radially outwardly until a desired retraction of the wound opening is achieved. The radial position may be locked or otherwise maintained by engagement between the pawls of housings 678 and teeth 648 of slidable members 674. The position of each petal 672 may be independently set/adjusted. FIG. 34Q shows tubular member 658 in an expanded state with petals 672 no longer overlapping each other.

FIGS. 35A-35G illustrate aspects of an exemplary introducer 383. Introducer 383 may be used to introduce any of the aforementioned bags and cutting elements into a body cavity via an incision (e.g., through an abdominal wall) or existing bodily orifice (e.g., a subject's vagina). Introducer 383 may include a hollow elongate member 384 and a pusher or plunger 385. Hollow elongate member 384 may include a grip portion 386, a distal end 387 having a distal opening 388, and a proximal end 390 having a proximal opening 392. Distal end 387 may taper distally to facilitate insertion of elongate member 384 through the incision or bodily orifice. Distal end 387 also may include a plurality of flexible projections 393 that allow for distal end 387 to expand from a narrow, undeployed configuration (FIGS. 35A, 35B, 35E, and 35F), to a wider, deployed configuration (FIGS. 35C, 35D, and 35G). Proximal opening 392 may be flared to facilitate insertion of the bag, cutting elements, and/or pusher 385. Pusher 385 may include a solid elongate member that is configured to slide through hollow elongate member 384 to distally push the contents of hollow elongate member 384 toward and out of distal opening 388. Pusher 385 also may have an enlarged proximal end 394 to facilitate pushing by the user.

Figure 37A:
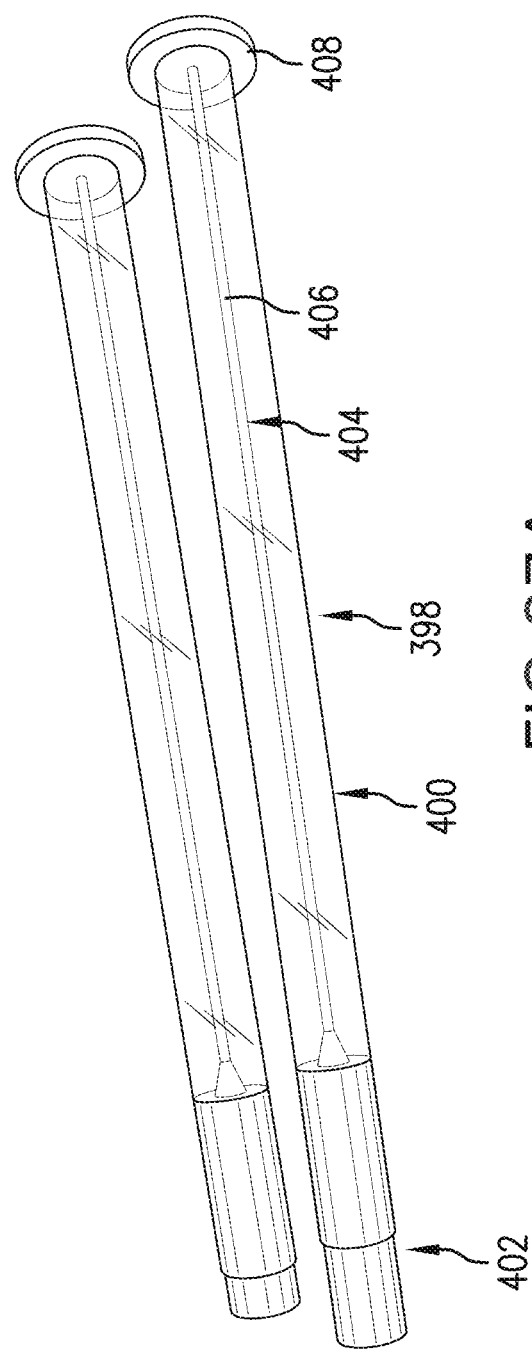
FIG. 37A shows a perspective view of introducers for a tissue extraction device, in accordance with aspects of the present disclosure.
Figure 37B:
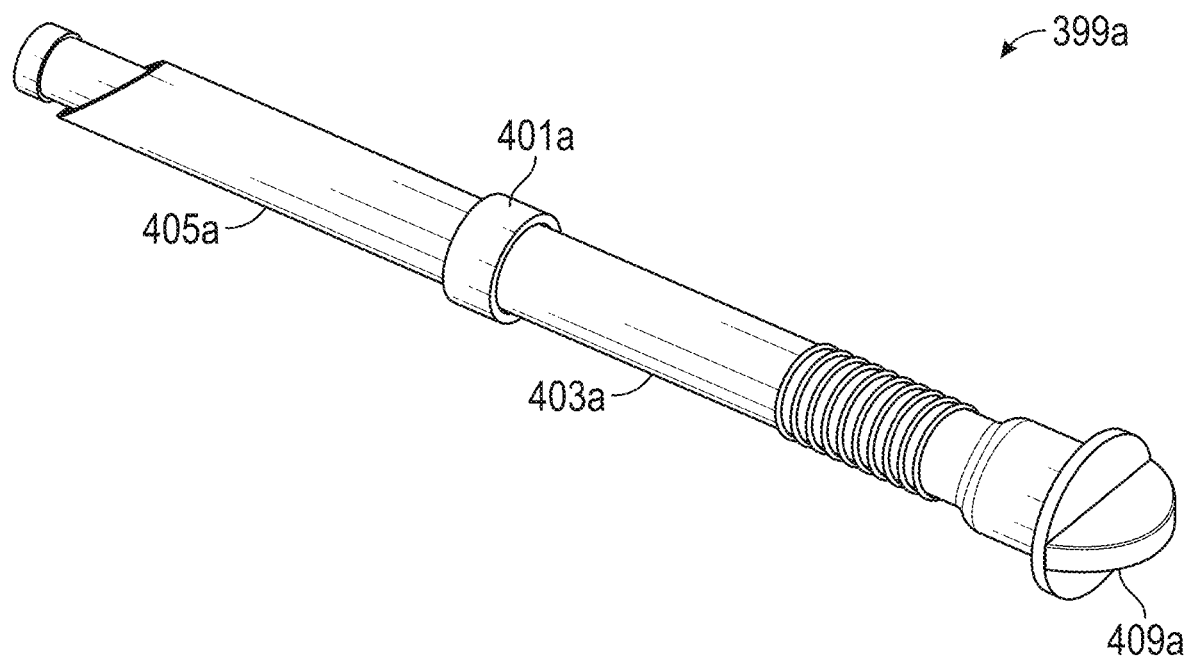
FIGS. 37B-37E are perspective and section views of an introducer for a tissue extraction device, in accordance with aspects of the present disclosure.

FIGS. 33A-34C illustrate another example of an introducer 396 that is similar to the introducer 383, except that introducer 396 may include an elongate member 384', similar to elongate member 384, but having a flat or otherwise blunt tip 397 without flexible projections 393. The absence of flexible projections 393 may allow a bag and cutting elements to be inserted into introducer 396 via openings at either of its ends. FIG. 37A illustrates another exemplary introducer 398 similar to introducers 383 and 396, including an elongate member 400 with an open distal end 402 and a metallic pusher 404. Here, elongate member 400 may be at least partially transparent or see-through. Metallic pusher 404 may include a thin stem 406 with an enlarged distal end 408 to push a bag and cutting elements distally out of elongate member 400.

FIGS. 37B-37E illustrate another example of an introducer 399*a*. Introducer 399*a* may be used to introduce any of the aforementioned bags and cutting elements into a body cavity via an incision or existing bodily orifice. Introducer 399*a* may include a hollow elongate member 401*a*. Hollow elongate member 401*a* may include a proximal section 403*a* and a distal section 405*a*, at least one of which may have a tubular cross-sectional shape. When assembled to each other, proximal section 403*a* and distal section 405*a* may receive any of the aforementioned bags and cutting elements, and may constrain the bags and cutting elements in a collapsed configuration. Hollow elongate member 401*a* may receive a pusher 409*a*, which may be similar to any of the aforementioned pushers. Pusher 409*a* may be inserted into an opening 415*a*, and may slide through hollow elongate member 401*a*, to distally push the contents of hollow elongate member 401*a* toward and out of a distal opening 411*a*. Distal section 405*a* may include a tapered distal end 419*a* to make it easier for the user to insert hollow elongate member 401*a* through the incision or existing bodily orifice of the subject. In one example, distal section 405*a* may have a diameter of approximately 2 cm to approximately 4 cm. For example, distal section 405*a* may have a diameter of approximately 2.5 cm where distal section 405*a* engages tissue.

Figure 37C:
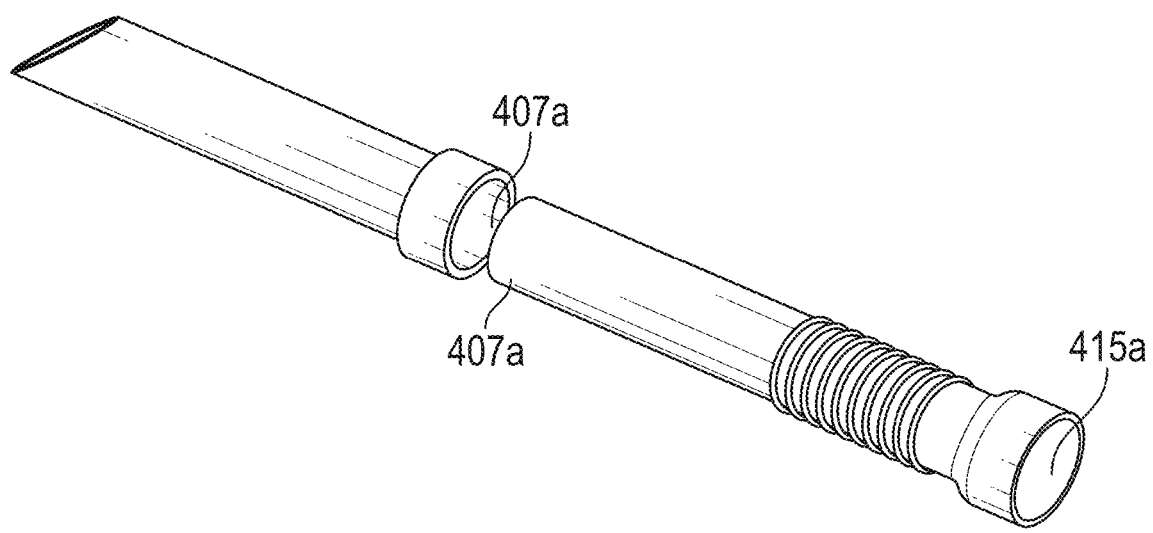
Figure 37D:
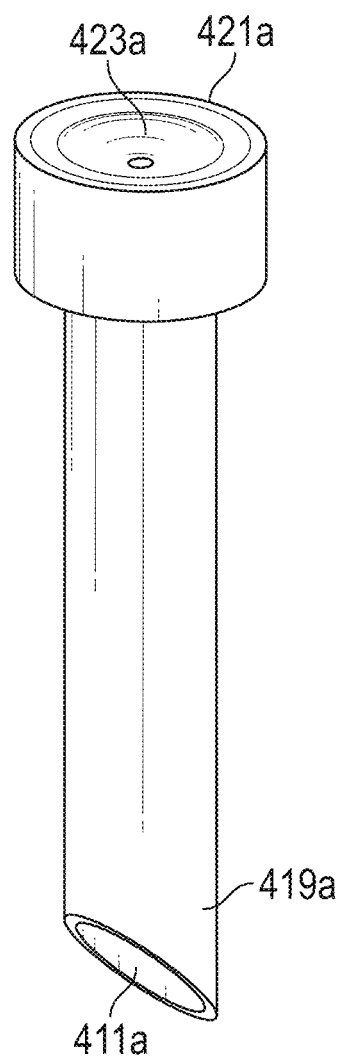
Figure 37E:
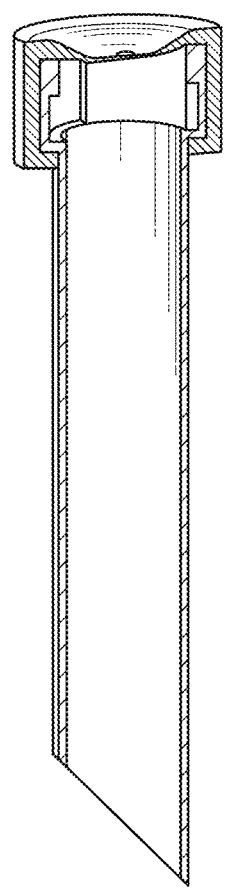
Figure 46A:
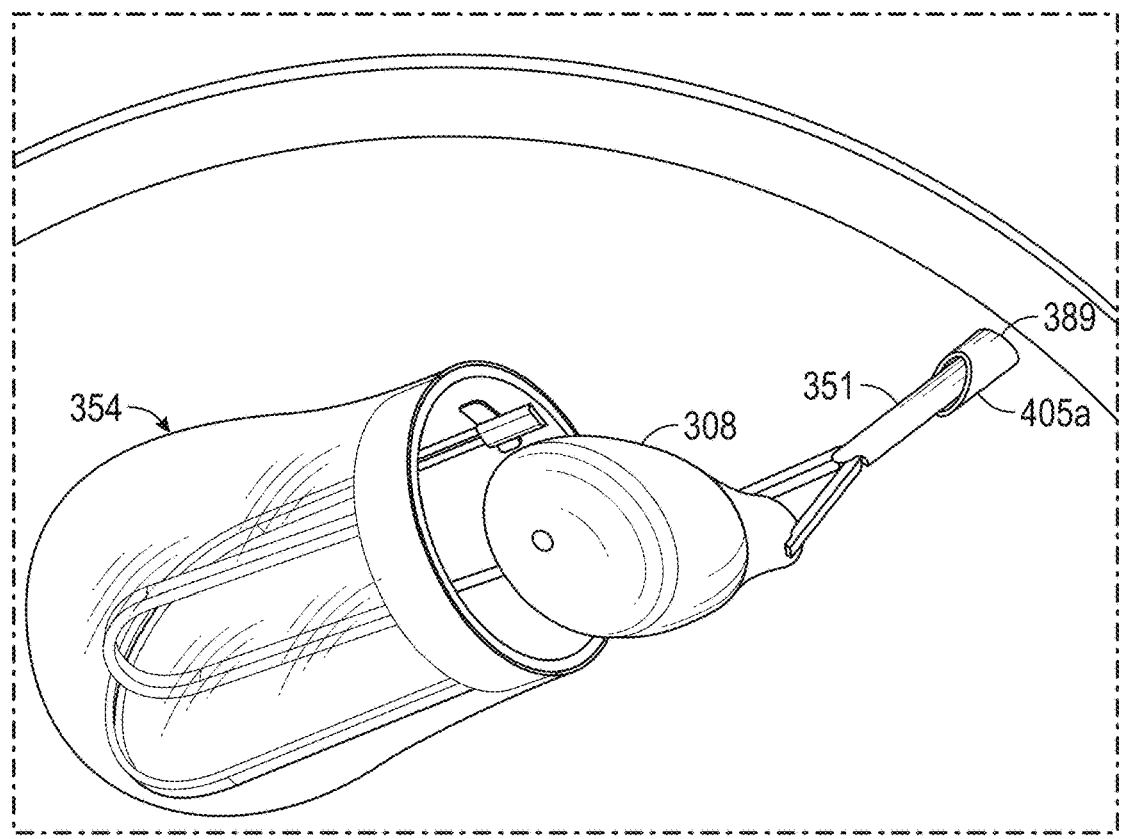
FIGS. 46A-46G are perspective views showing tissue extracting steps, in accordance with aspects of the present disclosure.

Proximal section 403*a* and distal section 405*a* may be removably coupled (FIG. 37B) via a twist lock mechanism 407*a* at a distal end of proximal section 403*a* and a proximal end of distal section 405*a*. Once the bag and cutting elements have been deployed in the body cavity, the user may disengage twist lock mechanism 407*a* to uncouple proximal section 403*a* from distal section 405*a* (FIG. 37C). The user may remove proximal section 403*a* and plunger 409*a* from the subject. Distal section 405*a* may remain in the incision or existing bodily orifice. The subject's body cavity may be insufflated via distal section 405*a*. A cap 421*a* may be used to cover a proximal end of distal section 405*b* to maintain the insufflation pressure in the body cavity. Cap 421*a* may include an opening 423*a* for receiving an instrument (not shown), and forming a seal with an outer surface of the instrument to reduce leakage of the insufflation gas from the body cavity. The instrument may include, for example, a forceps or grasper inserted through distal section 405*b* to manipulate the bag and/or tissue (FIG. 46A).

Figure 37F:
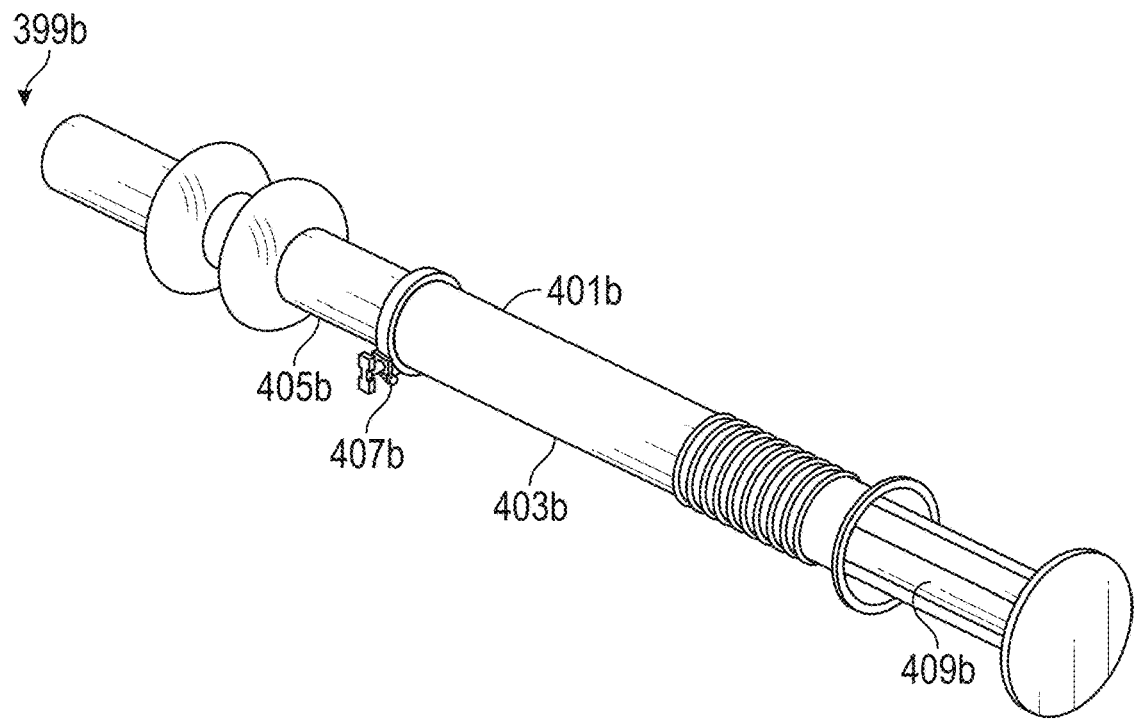
FIGS. 37F-37K are perspective views of an introducer for a tissue extraction device, in accordance with aspects of the present disclosure.
Figure 37G:
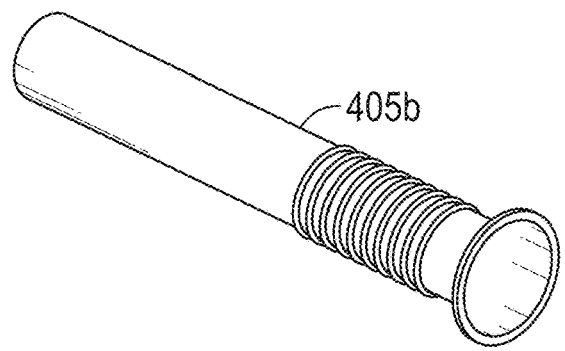
Figure 37H:
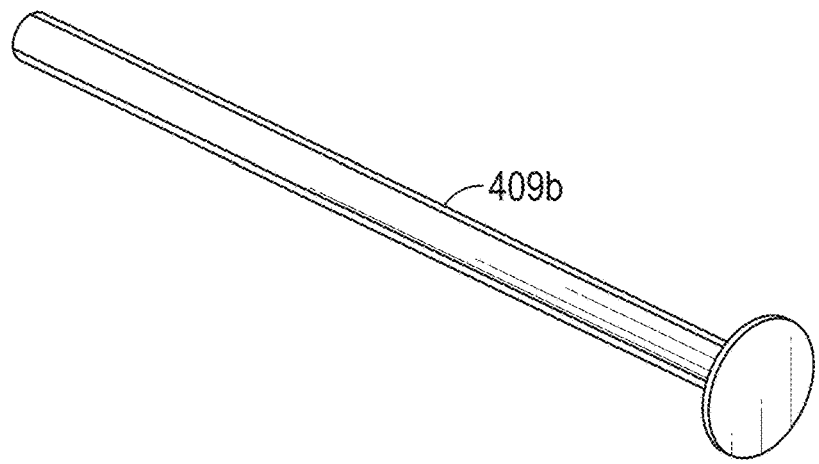
Figure 37I:
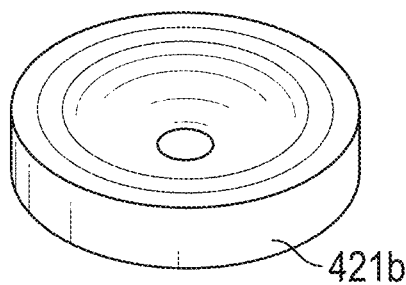
Figure 37J:
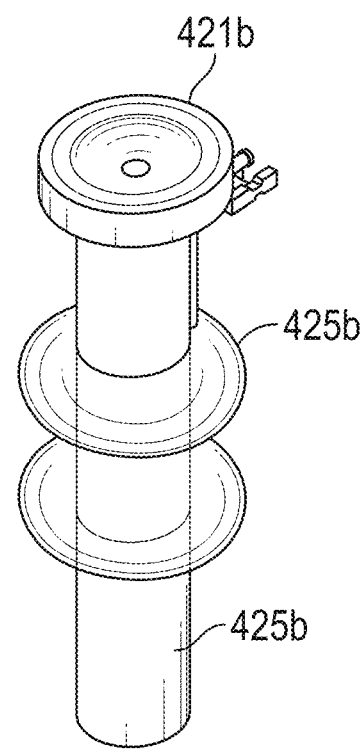

FIGS. 37F-37K illustrate another example of an introducer 399*b*. Introducer 399*b* may be used to introduce any of the aforementioned bags and cutting elements into a body cavity via an incision or existing bodily orifice. Introducer 399*b* may be similar to introducer 399*a*. Introducer 399*b* may include a hollow elongate member 401*b* including a tubular proximal section 403*b* and a tubular distal section 405*b*. Hollow elongate member 401*b* may slidably receive a pusher 409*b* (FIGS. 37F and 37H). Distal section 405*b* may be blunt or flat to reduce the likelihood of a user accidentally damaging tissue during use of introducer 399*b*. In one example, distal section 405*b* may have a diameter of approximately 2 cm to approximately 4 cm. For example, distal section 405*b* may have a diameter of at least approximately 2.5 cm in a region inserted into tissue.

Distal section 405*b* may include a securing member 425*b*. Securing member 425*b* may include a cuff fixedly attached to a radially-outer tubular surface of distal section 405*b*. Securing member 425*b* may include enlarged proximal and distal portions, connected by a narrow intermediate portion. Additionally or alternatively, securing member 425*b* may have an hourglass shape. Securing member 425*b* may be positioned in an incision or aperture in the subject, with its enlarged proximal and distal portions on opposite sides of the incision/orifice. In one example, securing member 425*b* may be inflatable. For example, securing member 425*b* may be inserted into the incision/orifice in a deflated state, to facilitate insertion of securing member 425*b* into the incision/orifice. Securing member 425*b* may then be inflated to enlarge its proximal and distal portions, thereby firmly seating securing member 425*b* and distal section 405*b* in the incision/orifice. An inflation fluid may be introduced into securing member 425*b* via one or more lumens (not shown) extending along or through distal section 405*b*, or distal section 405*b* and proximal section 403*b*. Securing member 425*b* may be deflated to facilitate removal of distal section 405*b* from the incision/orifice.

Figure 37K:
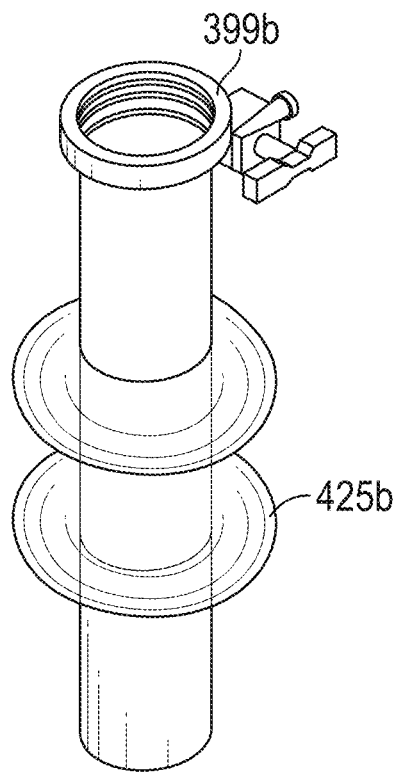

Proximal section 403*b* and distal section 405*b* may be removably coupled (FIG. 37F) via a push-button lock mechanism 407*b*. Once the bag and cutting elements have been deployed in the body cavity, the user may actuate push-button lock mechanism 407*b* to uncouple proximal section 403*b* from distal section 405*b* (FIGS. 37G and 37K). Distal section 405*b* may remain in the incision or existing bodily orifice, secured there with the help of securing member 425*b*. The subject's body cavity may be insufflated via distal section 405*b*. A cap 421*b* (FIGS. 37I and 37J), similar to cap 421*a*, may be used to cover a proximal end of distal section 405*b* to maintain the insufflation pressure in the body cavity, and to sealingly receiving an instrument, for example a forceps or grasper used to manipulate the bag and/or tissue (not shown). Engagement between securing member 425*b* and the incision/orifice also may help maintain the insufflation pressure in the body cavity.

Figure 37L:
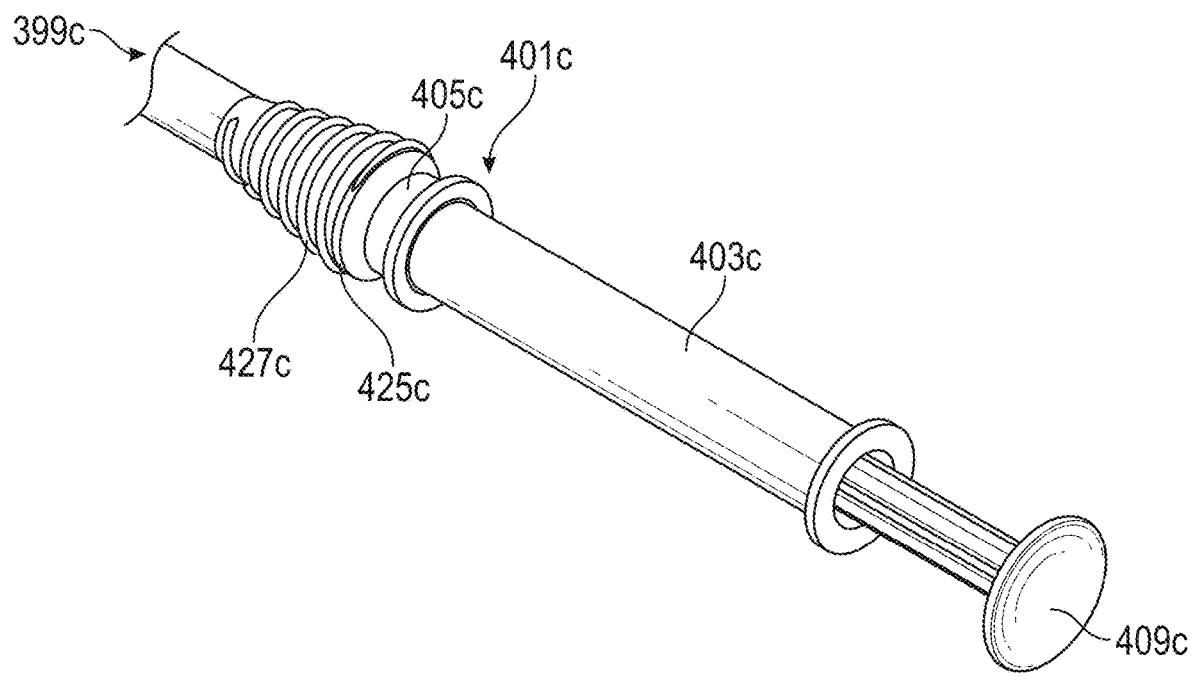

FIGS. 37L-37P illustrate another example of an introducer 399*c*. Introducer 399*c* may be used to introduce any of the aforementioned bags and cutting elements into a body cavity via an incision or existing bodily orifice. Introducer 399c may be similar to introducer 399a and/or introducer 399b. Introducer 399c may include a hollow elongate member 401c including a tubular proximal section 403c and a tubular distal section 405c (FIG. 37L). Hollow elongate member 401c may slidably receive a pusher 409c. Distal section 405c may include a tapered distal end 419c to make it easier for the user to insert hollow elongate member 401c through the incision or existing bodily orifice of the subject. In one example, distal section 405c may have a diameter of approximately 2 cm to approximately 4 cm. For example, distal section 405c may have a diameter of approximately 2.5 cm in a region distal to a securing member 425c.

Distal section 405c may include securing member 425c. Securing member 425c may include an enlarged, tapered region at a proximal portion of distal section 405c. Securing member 425c may include external threading 427c for screwing distal section 405c into an incision or aperture in the subject, thereby securing distal section 405c in position relative to the incision/orifice via engagement between external threading 427c and tissue surrounding the incision/orifice. Securing member 425c may be screwed out of the incision/orifice when it is no longer needed.

Proximal section 403c and distal section 405c may be removably coupled (FIG. 37L) via a threaded connection 407c. For example, a proximal end of distal section 405c may include internal threading 429c for receiving/engaging external threading (not shown) at a distal end of proximal section 403c. Once the bag and cutting elements have been deployed in the body cavity, the user may screw proximal section 403c out of distal section 405b. Distal section 405b may remain in the incision or existing bodily orifice, secured there with the help of external threading 427c. The subject's body cavity may be insufflated via distal section 405c. A cap 421c (FIGS. 37N-37P), similar to cap 421a and/or cap 421b, may be used to cover a proximal end of distal section 405c to maintain the insufflation pressure in the body cavity, and to sealingly receiving an instrument, for example a forceps or grasper used to manipulate the bag and/or tissue (not shown). Engagement between external threading 427c and the incision/orifice also may help maintain insufflation pressure in the body cavity.

FIGS. 37Q(i)-37Q(x) also illustrate aspects of introducer 399c. Distal section 405c may include an annular shoulder 680. Annular shoulder 680 may engage a distal end 682 of proximal section 403c to stop proximal section 403c from being further inserted into distal section 405c. For example, annular shoulder 680 may engage distal end 682 to prevent external threading 684 of proximal section 403c from passing through and exiting from internal threading 429c (FIG. 37Q(ii)) of distal section 405c.

As shown in at least FIGS. 37Q(i), 37Q(vii), and 37Q(viii), proximal section 403c may include gripping elements 686 on a proximal end portion thereof. Gripping elements 686 may be held by the user when inserting proximal section 403c into distal section 405c, which may entail sliding proximal section 403c into distal section 405c and/or rotating proximal section 403c relative to distal section 405c. Proximal section 403c may be transparent for visibility therethrough during deployment of any of the aforementioned bags, which may be housed in a lumen 694 (FIG. 37Q(viii)) of proximal section 403c.

As shown in at least FIGS. 37Q(ix) and 37Q(x), pusher 409c may include an enlarged proximal portion 688, a ribbed shaft 690, and an enlarged distal portion 692. As shown in FIG. 37Q(i), when proximal section 403c is fully inserted into distal section 405c, and pusher 409c is fully inserted into proximal section 403c, enlarged distal portion 692 may protrude distally from tapered distal end 419c. Enlarged distal portion 692 may terminate at a flat distal end face 693 (FIG. 37Q(x)). As shown in at least FIGS. 37Q(iii)-37Q(vi), cap 421c may include a grip or tab 696 on its periphery. The user may hold tab 696 to facilitate placement of cap 421c onto a collar 698 (FIG. 37Q(ii)) at the proximal end of distal section 405c, and/or removal of cap 421c from collar 698. Cap 421c may be made of an elastomeric material having a port 700 (FIG. 37Q(v)) through which an endoscope or any other suitable instrument may be inserted. Cap 421c may help maintain insufflation pressure in the body cavity after the bag is deployed. For example, cap 421c may include a valve system, such as a lip seal, for sealingly engaging an outer surface of the endoscope while maintaining insufflation pressure in the body cavity. It is also contemplated that the valve system may include an additional seal or seals to maintain insufflation pressure even if the endoscope is not inserted into cap 421c.

FIGS. 37Q(xi)-37Q(xiv) show introducer 399c in use. FIG. 37Q(xi) shows distal section 405c in a wound opening 702 in tissue 704, proximal section 403c in distal section 405c, and pusher 409c in proximal section 403c. FIG. 37Q(xii) shows the same view of introducer 399c as FIG. 37Q(xi), but in FIG. 37Q(xii) a bag 706 is depicted, while in FIG. 37Q(xi) bag 706 is not shown so that more of introducer 399c is visible. After bag 706 has been deployed, proximal section 403c and pusher 409c may be removed from distal section 405c. Distal section 405c may remain in wound opening 702, as shown in FIG. 37Q(xiii). Cap 421c may be coupled to distal section 405c to maintain insufflation pressure in the body cavity. FIG. 37Q(xiv) shows an endoscope 708 inserted through port 700 of cap 421c. Cap 421c may sealingly engage the outer surface of endoscope 708 at port 700.

The distal sections of introducers 399a, 399b, 399c, and 399d, which may remain in the incision/orifice after deployment of the bag and cutting elements, may be removed after tissue specimen 308 has been inserted into the bag. Removal of the distal section may create space in the incision/orifice to facilitate withdrawal of the proximal end portions of the bag and cutting elements in a subsequent step of a procedure. Alternatively, the distal section may remain in the incision/orifice, and the proximal end portions of the bag and cutting elements may be withdrawn from the incision/orifice by pulling them around the distal section and sliding them proximally between the distal section and the tissue forming the incision/orifice. Alternatively, the distal section may remain in the incision/orifice, and the proximal end portions of the bag and cutting elements may be withdrawn from the incision/orifice by pulling them through the distal section. A transvaginal approach is described below, and it should be understood that aspects of that approach may be applicable to steps performed using introducers 399a, 399b, 399c, and 399d, and vice-versa.

FIGS. 38-45B illustrate steps for positioning tissue extraction device 300 (or any of the other aforementioned tissue extraction devices) proximate to tissue specimen 308 and performing a procedure on tissue specimen 308. In one example, elongate member 384 of introducer 383 (or the elongate member of any of the other introducers described above), loaded with bag 302 (or any of the aforementioned bags) and cutting elements 304, may be inserted into a subject (FIG. 38). The introduction may be either through an incision or existing bodily orifice 389. After insertion, distal opening 388 may be positioned at a surgical site and/or proximate a tissue specimen (not shown).

As shown in FIG. 39, actuating pusher 385 may push bag 302 and cutting elements 304 in bag 302 out of distal opening 388 and into the target area. Pusher 385 may push bag 302 and cutting elements 304 (hidden from view in FIG. 39) entirely out of hollow elongate member 384. As bag 302 and cutting elements 304 exit from distal opening 388, cutting elements 304 may move from their collapsed delivery configuration to their expanded deployed configuration. Additionally or alternatively, stiffening element 328 (not shown in FIG. 40) may move from its collapsed delivery configuration to its expanded deployed configuration (FIG. 40), to open the open end of bag 302 to facilitate insertion of tissue specimen 308 into bag.

When the user uses any of introducers 399a, 399b, and 399c, the distal sections of each of the introducers may be positioned in, and in some instances secured in, incision/orifice 389. Proximal sections and plungers of each of the introducers may be removed. The body cavity may be insufflated via the distal sections. After insufflation, the distal sections may be capped to maintain the insufflation pressure in the body cavity. Instruments (e.g., forceps, graspers, and/or any other suitable instruments) may be inserted into the body cavity through the caps and distal sections. Forceps 410 may be used to maneuver tissue specimen 308 into bag 302, or alternatively maneuver bag 302 to surround tissue specimen 308, as illustrated in FIG. 40. Forceps 410 may be used to pull the open end of bag 302 out of the incision or bodily orifice such that the open end is positioned outside of the subject (FIG. 41).

In one example, bag 302 may include splittable sheaths 338' on the interior surface of bag 302. Cutting elements 304 may be removably mounted to the interior surface of bag 302 by channel sheaths 338'. As shown in FIG. 42, proximal portions of cutting elements 304 may be positioned outside the incision or bodily orifice with the open end of bag 302. Cutting elements 304 may be exposed from channel sheaths 338' by, for example, pulling cutting elements 304 away from the interior surface of bag 302 to split channel sheaths 338'.

Figure 44B:
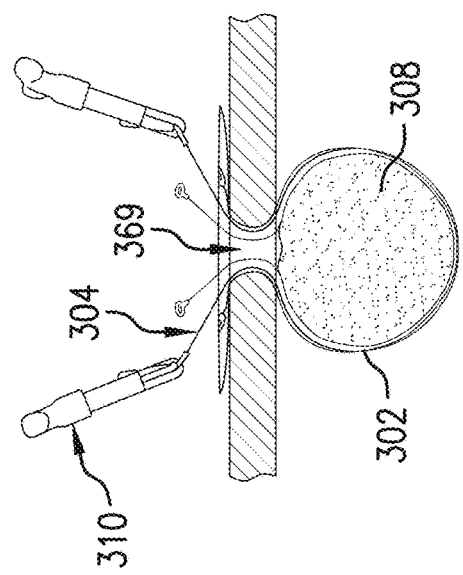
FIGS. 44A and 44B are perspective and side views showing tissue extracting steps, in accordance with aspects of the present disclosure.
Figure 44A:
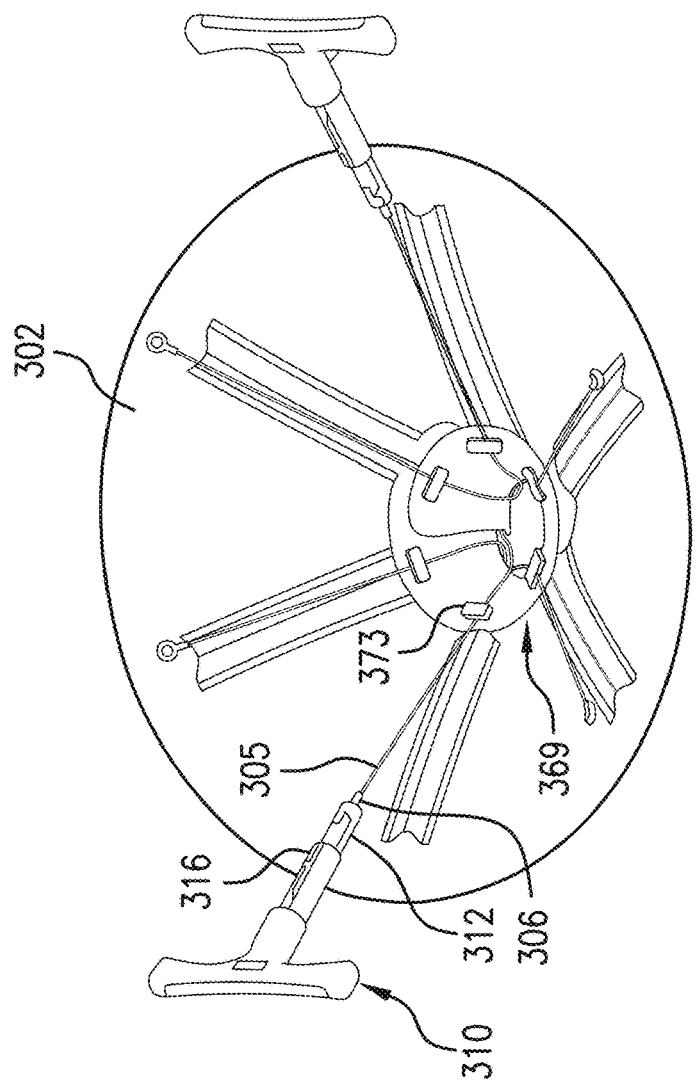

Wound retractor 369 may be inserted through the incision or bodily orifice (FIGS. 43, 44A, and 44B). Wound retractor 369 may be compressed to fit the distal portion of wound retractor 369 through the incision or bodily orifice. Once inserted, wound retractor 369 may expand to a desired size, and the size may be set by the interaction of engagement members 375 and 376. Securing the size of wound retractor 369 may serve to retract the incision or bodily orifice, and/or stabilize bag 302 relative to the incision or bodily orifice. The freed cutting elements 304 may be inserted through wound retractor 369, and/or wound retractor 369 may be unrolled to receive cutting elements 304 and rolled back into a spiral after receipt. Strands 305 may slide into clips 373 of wound retractor 369, which may serve to secure and/or position cutting elements 304 (FIGS. 44A, 44B, 45A, and 45B). The open end bag 302 may be trimmed or pulled back to better expose cutting elements 304.

Handles 310 may be attached to one or more anchoring ends 306 via hooks 312 (FIGS. 44A, 44B, 45A, and 45B). Handles 310 may be shaped to allow a user to easily control, manipulate, and maneuver anchoring ends 306, and thus strands 305. Anchoring element 306 may include a lug or eyelet attached to end of strand 305, a circular loop of strand 305, or any other suitable shape or element that may be removably secured to hook 312 of handle 310.

Figure 47B:
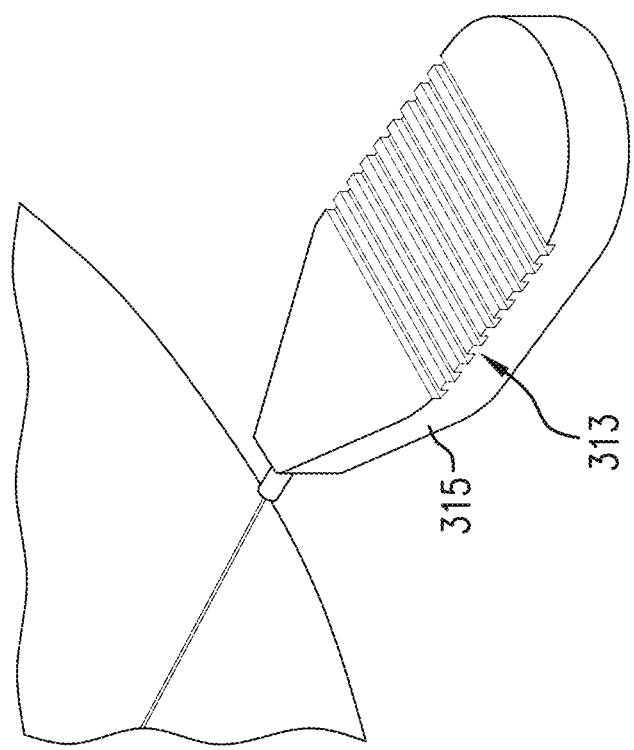
FIG. 47B is a perspective view of a handle of a tissue extraction device, mounted on the portion of the cutting element of FIG. 47A, in accordance with aspects of the present disclosure.
Figure 47A:
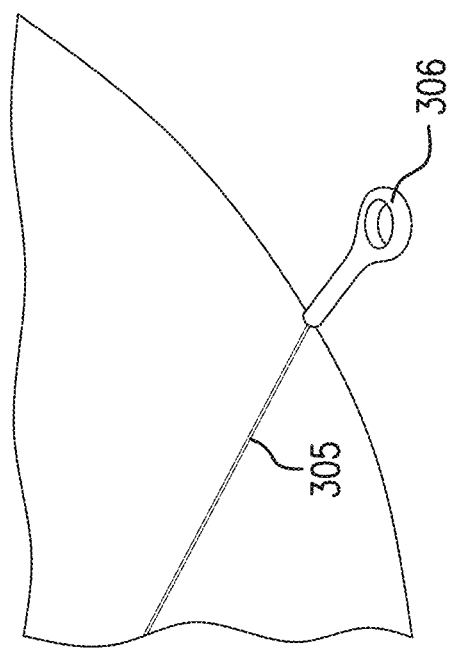
FIG. 47A is a perspective view of a portion of a cutting element of a tissue extraction device, in accordance with aspects of the present disclosure.
Figure 48:
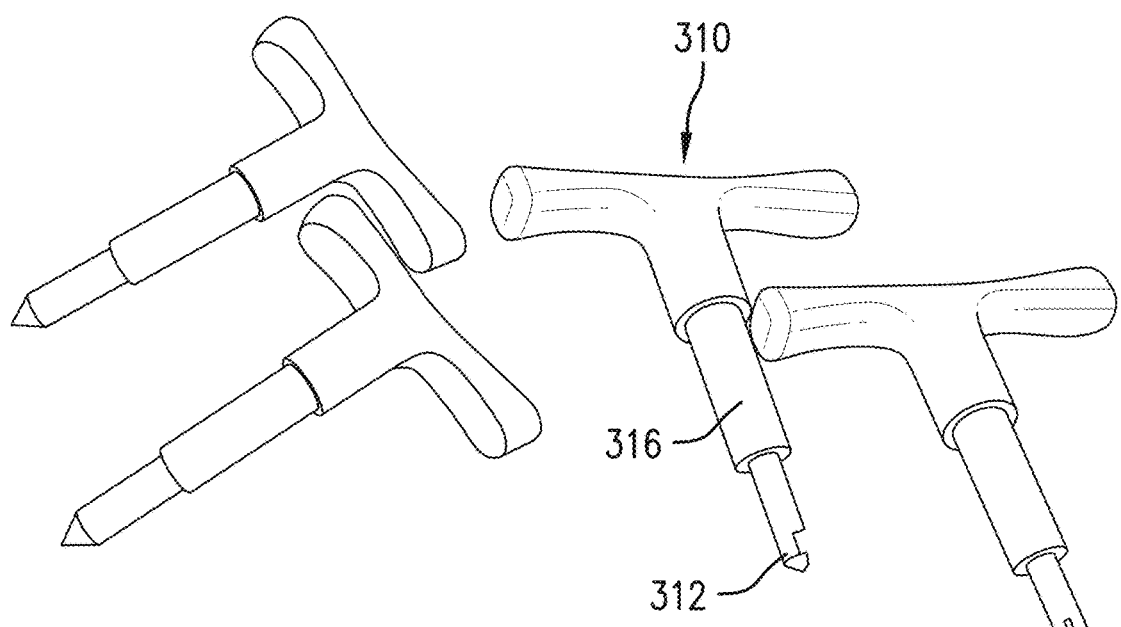
FIG. 48 is a perspective view of handles of a tissue extraction device, in accordance with aspects of the present disclosure.
Figure 49:
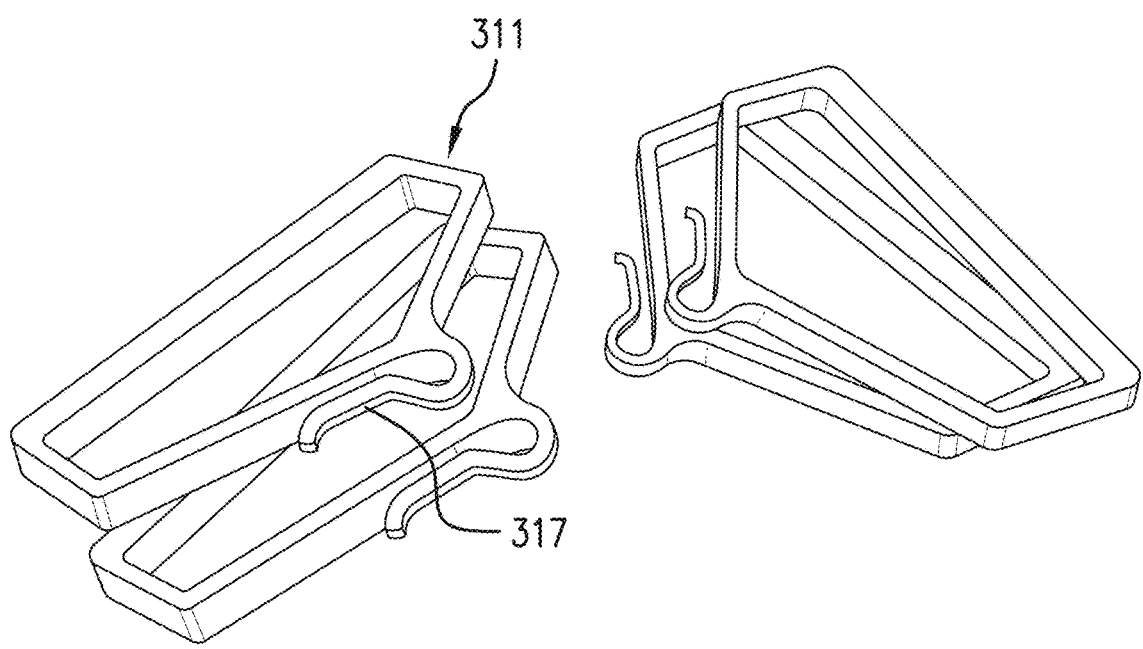
FIG. 49 is a perspective view of handles of a tissue extraction device, in accordance with aspects of the present disclosure.

Handle 310 may have a T-shaped configuration for gripping by a user (FIG. 48). Alternatively, a handle may be used that may include a D-shaped loop 311 (FIG. 49), or a flat handle or tab 313 that may snap onto anchoring element 306 (FIGS. 47A and 47B). Handle 313 may include, for example, a slot 315 for slidably receiving anchoring element 306, which may help reduce twisting of strand 305 during pulling. Handle 310 may have a switch 413 to open and close hook 312. Handle 311 may include a bent clip-hook 317 (FIG. 49). The aforementioned handles may include any another element that may couple to anchoring element 306.

Figure 45B:
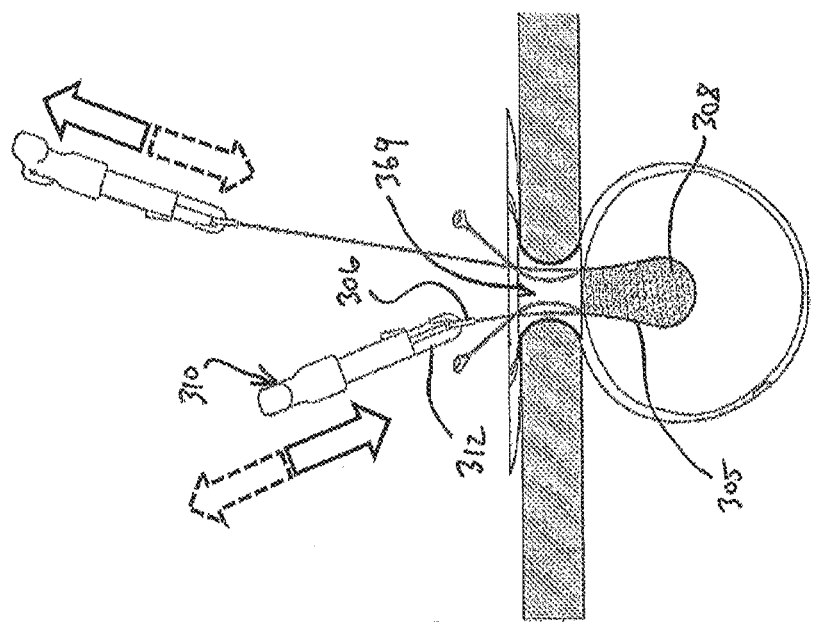
FIGS. 45A and 45B are perspective and side views showing tissue extracting steps, in accordance with aspects of the present disclosure.
Figure 45A:
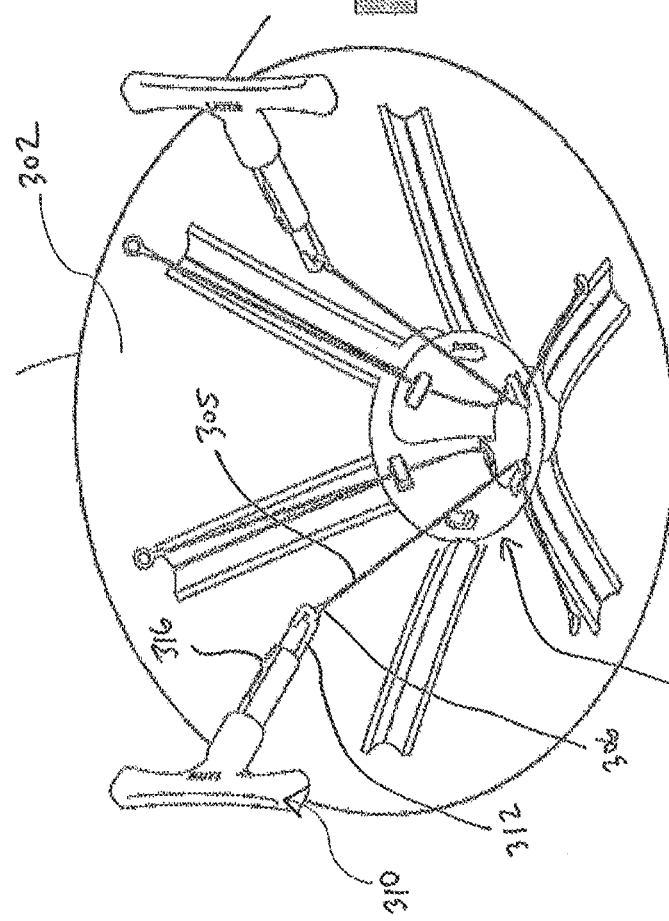

In one example, two handles 310 may be attached to anchoring ends 306 at the opposite ends of one cutting element 304, with cutting element 304 looping around tissue specimen 308 (FIGS. 44A, 44B, 45A, and 45B). One cutting element 304 may be removed from clips 373 in wound retractor 369, while other cutting elements 304 may remain in clips 373 and secured to wound retractor 369 (FIGS. 45A and 45B). Handles 310 may be used to move cutting elements 304 to cut tissue specimen 308. For example, cutting may be achieved via proximally pulling on handles 310 in an alternating manner, thus imparting a sawing motion to strand 305, and causing strand 305 to cut tissue specimen 308 (FIG. 45B). During sawing, one end of cutting element 304 may move proximally while the other end of the cutting element 304 may move distally. This movement may be reversed and repeated to cause the cutting element 304 to move back-and-forth about and against tissue specimen 308. The exertion of a proximally-directed force on tissue specimen 308 by cutting element 304 may compress a portion of tissue specimen against the distal end of wound retractor 369, thereby increasing the force exerted against tissue specimen 308 by proximal pulling of cutting element 304. It should be understood that both ends of cutting element 304 may be pulled proximally using handles 310 to compress tissue specimen 308 against wound retractor 369 before and/or during sawing. The proximal pulling may facilitate movement of cutting element 304 further through tissue specimen 308 after each cut into tissue specimen 308, such that a point on strand 305 may follow a zig-zag path through tissue specimen 308.

The sawing motion may be repeated with other cutting elements 304. This may be accomplished by removing handles 310 from the first cutting element 304, hooking handles 310 onto a different cutting element 304, releasing cutting element 304 from its clip 364, and sawing tissue specimen 308. In one example, the first cutting element 304 may saw completely through tissue specimen 308, and may be removed from bag 302 before another cutting element 304 is used to saw tissue specimen 308. In another example, the first cutting element 304 may be used to saw partially through tissue specimen 308, sawing with first cutting element 304 may cease, a second cutting element 304 may be used to saw tissue specimen 308 until second cutting element 304 approaches or reaches the depth of the first cutting element 304, and so on for any other cutting elements 304. The process may then be repeated to cut deeper into tissue specimen 308, and repeated again until all cutting elements 304 have cut through tissue specimen 308.

Cutting elements 304 may be moved one at a time, or two or more cutting elements 304 may be moved simultaneously. Cutting elements 304 may be color coded, or identified in some other way, to specify an order of use and/or removal. Because the U-shaped portions of cutting elements 304 may overlap at the closed end 326 of bag 302, a user may use and/or remove the cutting elements 304 in a certain order, for example, with the proximal most cutting element 304 being used and/or removed first. This process may be repeated until the tissue specimen 308 is cut into small enough pieces that bag 302 containing the tissue specimen 308 may be removed from the incision or bodily orifice. Additionally or alternatively, a user also may remove fragments of tissue specimen 308 from bag 302 using a grasper, forceps, or other retrieval device. The wound retractor 369 may be removed, and the entire bag 302 and its contents may be removed from the incision or orifice, ensuring that the tissue specimen 308 does not escape the bag 302. It is also contemplated that the sawing motion may be performed by attaching anchoring ends 306 of cutting elements 304 to a motor or other powered actuator (not shown) instead of manually-operated handles 310. For example, anchoring ends 306 may be attached to handle assembly 222.

Figure 46B:
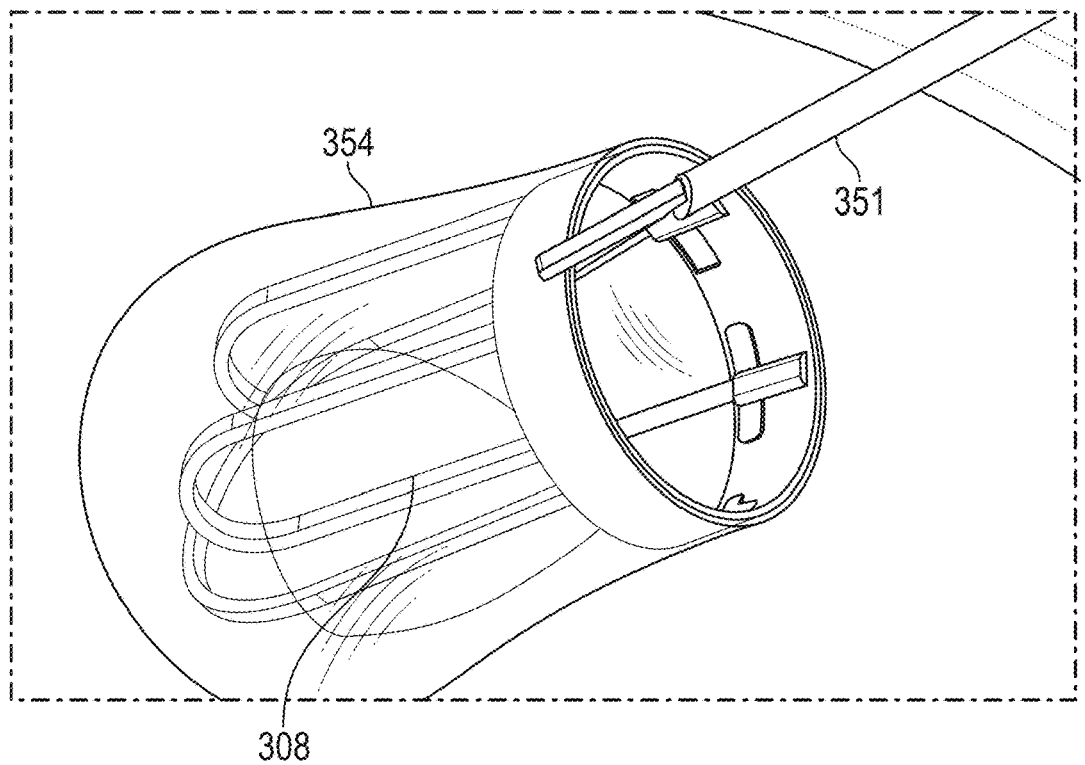
Figure 46C:
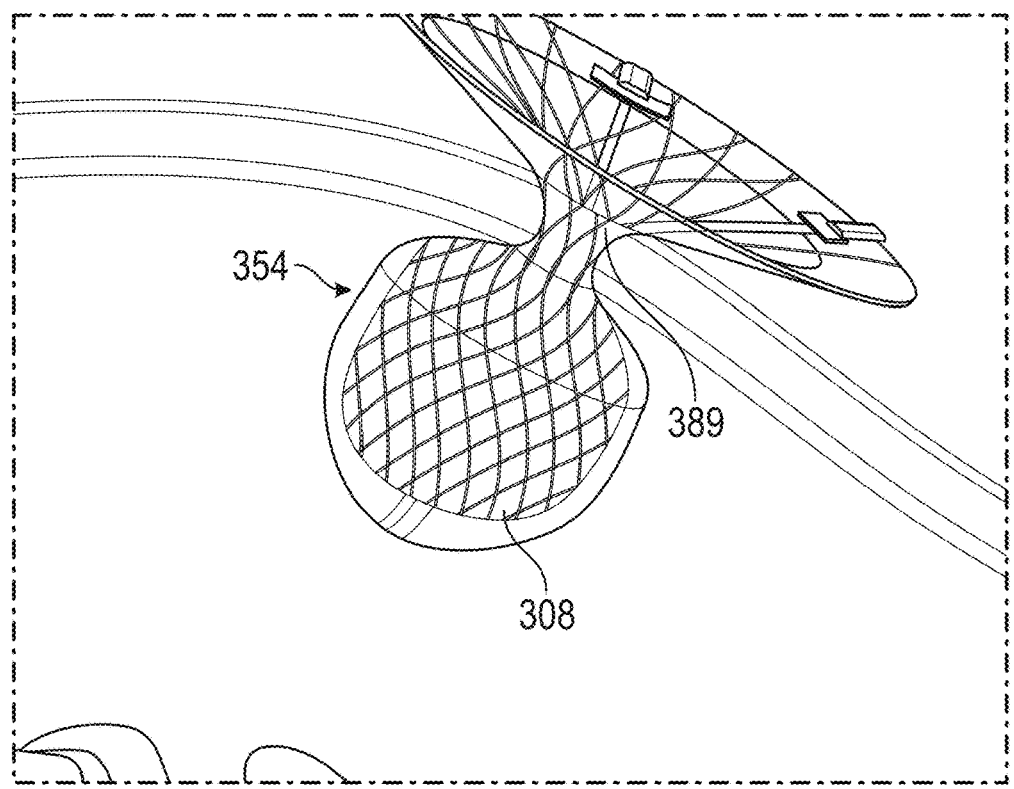
Figure 46D:
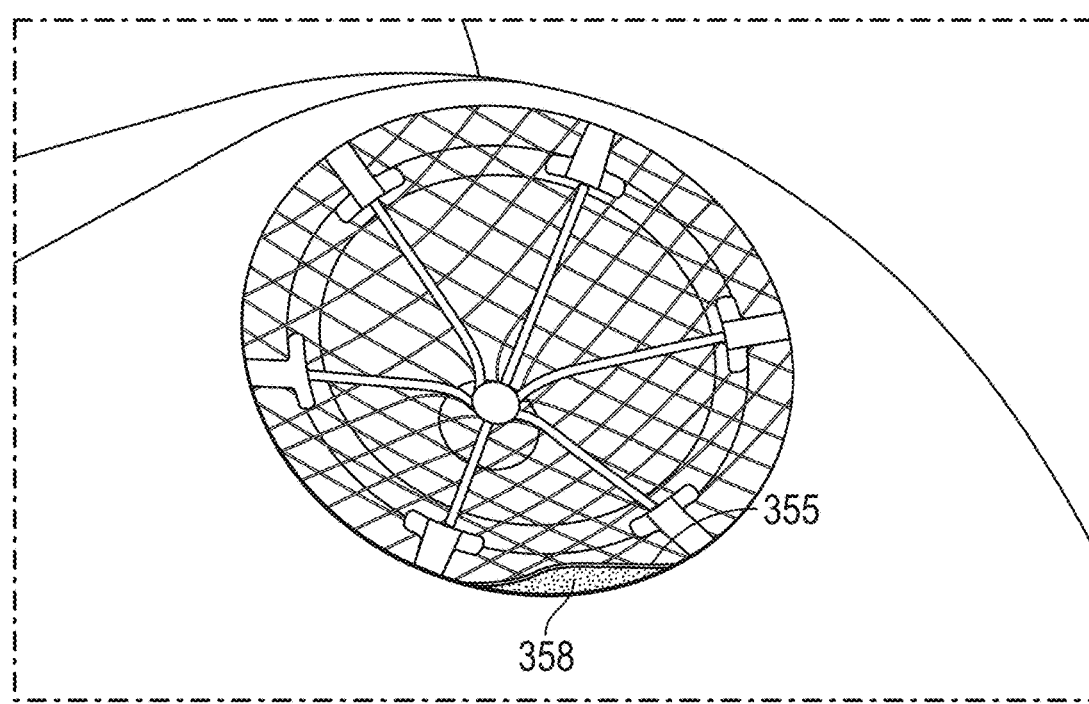
Figure 46E:
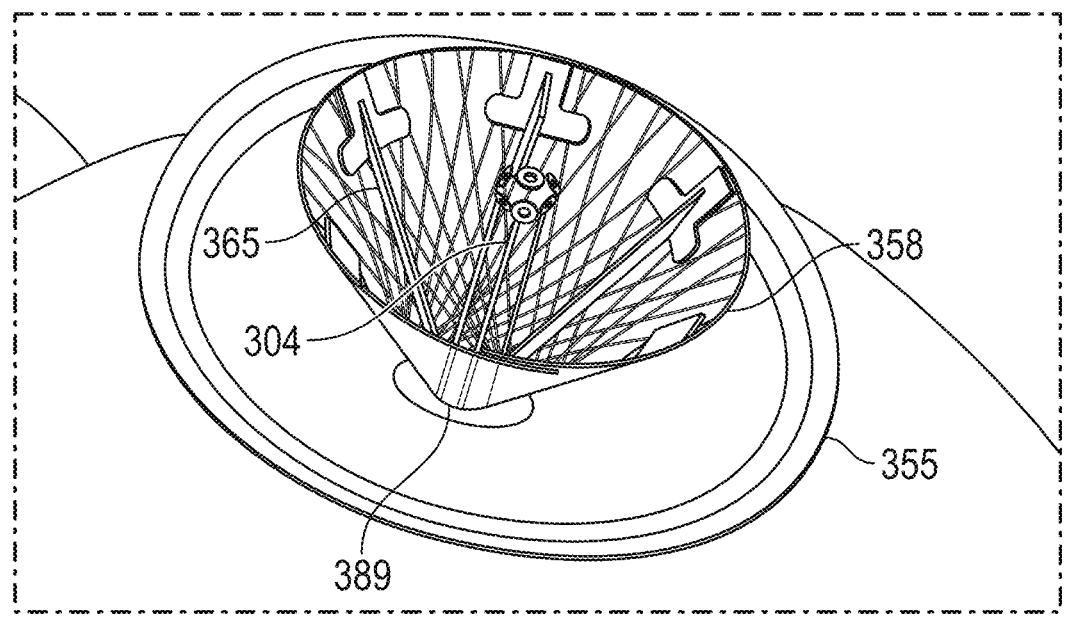
Figure 46F:
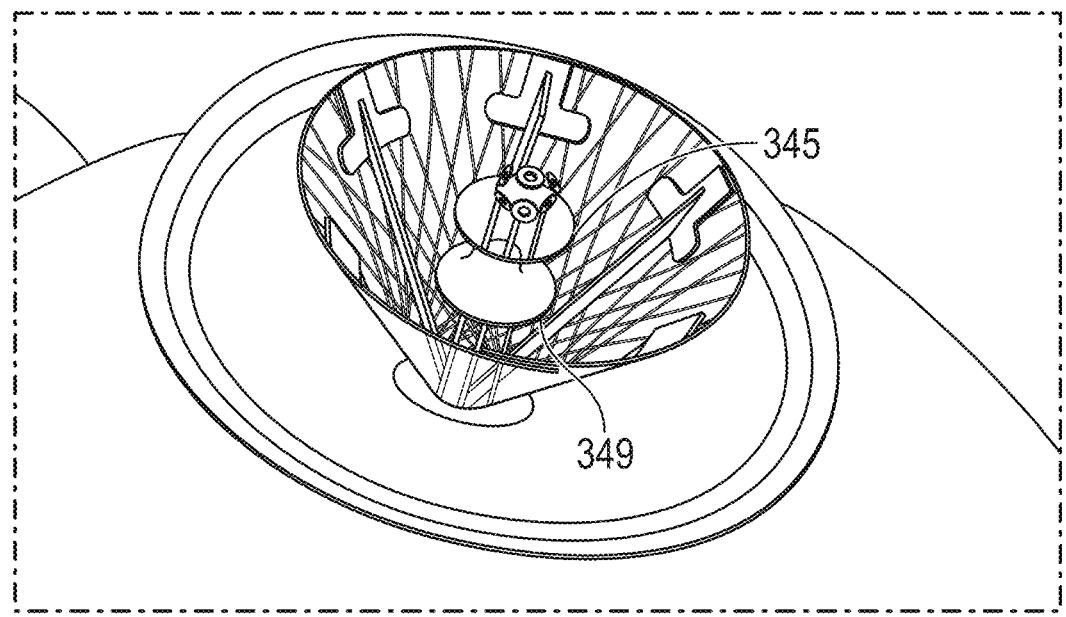

Steps similar to those described above may be employed when using the other aforementioned bags. Additional or alternative steps also are contemplated. For example, with double-layered bag 342', a user may inflate gap 348 between outer layer 344' and inner layer 346' via insufflation valve 350 and tube 352 prior to sawing. As another example, FIGS. 46A-46G illustrate steps for positioning bag 354 proximate to tissue specimen 308 and performing a procedure on tissue specimen 308. A user may deploy bag 354 into a subject's body cavity, via an incision or orifice 389, using any of the aforementioned introducers. Once bag 354 has been deployed, the user may insert tissue specimen 308 into bag 354 (FIG. 46A). Using an instrument 351, such as a forceps or grasper, the user may pull a proximal end portion of bag 354 out of the incision/orifice 389 (FIGS. 46B-46D). For example, the user may grasp bag 354 at outer rim 356 and inner rim 359 using instrument 351, and pull instrument 351 proximally. Additionally or alternatively, the user may pull bag 354 by grasping gripping members 362 and strands 364 and pulling them proximally. The user may separate inner layer 358 from outer layer 355, and may pull inner layer 358 proximally such that inner body 360 firmly secures (e.g., exerts a compressive force on) tissue specimen 308 (FIGS. 46D and 46E). Inner body 360 also may be in tension due to the exerted forces.

In another embodiment, where the mesh portions of inner layer 358 are omitted, the user may draw splittable members 365 (FIG. 32B) proximally to firmly secure tissue specimen 308. Splittable members 365 may form a basket around tissue specimen 308. In such an embodiment, splittable members 365 may be directly adjacent outer layer 355. Interior-facing surfaces of splittable members 365 may be textured (e.g., roughened, covered by teeth or other protrusions, and/or provided with grooves or other indentations) to help them grip onto tissue. Splittable members 365 may be interconnected by one or more sutures (not shown) to help position splittable members 365 relative to each other. It is contemplated that splittable members 365 may be made of strips of polymeric material, while sutures may be made of relatively thinner strands of wire or thread material.

Figure 46G:
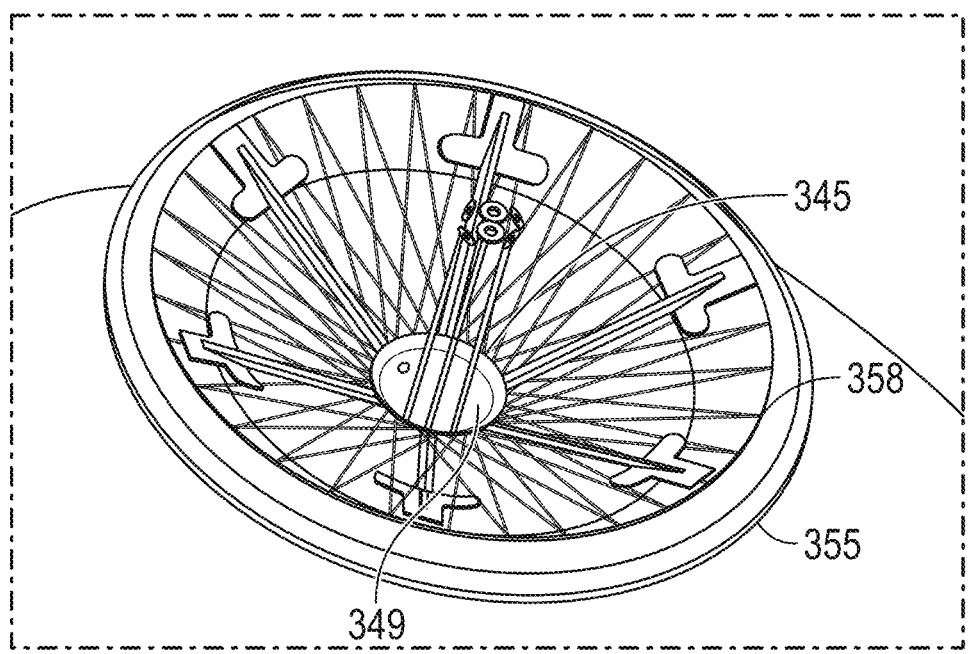

The user may free cutting elements 304 from splittable members 365 (FIG. 46E), and may slide a wound retractor 349 over cutting elements 304 (FIG. 46F) and into incision/orifice 389 (FIG. 46G), such that wound retractor 349 may provide a barrier between cutting elements 304 and inner layer 358. Wound retractor 349 may be similar to wound retractor 369 and/or wound retractor 379. Wound retractor 349 may be expanded such that wound retractor 349 may be firmly seated in incision/orifice 389. At its proximal end, wound retractor 349 may include one or more hooks 345. Hooks 345 may engage the mesh or netting forming inner layer 358. The user may pull inner layer 358 proximally to cause inner layer 358 to forcefully engage tissue specimen 308. The force of engagement may be enhanced as tissue specimen 308 is compressed against the distal portion of wound retractor 349 by inner layer 358. The user may secure hooks 345 to inner layer 358, thereby stabilizing inner layer 358 relative to wound retractor 349 and incision/orifice 389, and maintaining the forceful engagement of inner layer 358 and/or wound retractor 349 with tissue specimen 308 (FIG. 46G). The forceful engagement of tissue specimen 308 may facilitate cutting of tissue specimen 308 by, for example, reducing or eliminating movement of tissue specimen 308 as it is being cut by cutting elements 304. It is also contemplated that inner layer 358 may be released from one or more of hooks 345, inner layer 358 may be pulled proximally to increase the force of engagement between inner layer 358 and tissue specimen 308, and inner layer 358 may be secured to one or more of hooks 345 to maintain the enhanced engagement.

As an alternative, inner layer 358 and cutting elements 304 may be inserted through wound retractor 349, and wound retractor may be seated within incision/orifice 389 between inner layer 358 and outer layer 355. In such an example, inner layer 358 still may be secured to hooks 345 for tightening inner layer 358 about tissue specimen 308.

As yet another example, FIGS. 46H-46W illustrate steps for positioning any of the aforementioned bags and cutting elements in a subject's body cavity, e.g., within the abdomen, by introducing the bag(s) and cutting element(s) into the body cavity via an elongate body orifice of the subject, e.g., via the vagina. In one example bag 354 and cutting elements 304 may be inserted into an introducer 399d, and may be held in a collapsed, delivery configuration by introducer 399d (FIG. 46H). Introducer 399d may be similar to the aforementioned introducers. Introducer 399d may include a tubular elongate member 401d. A distal end of tubular elongate member 401d may be blunt or flat to reduce the likelihood of a user accidentally damaging tissue during use of introducer 399d, or may be pointed or sharp to pierce tissue. In one example, elongate member 401d may have a diameter of approximately 2 cm to approximately 4 cm. For example, elongate member 401d may have a diameter of approximately 2.5 cm where it engages tissue.

In use, tubular elongate member 401d may be inserted into the vagina, and through a wound opening 435 formed in the vaginal cuff 437 (at a top of the vagina). Bag 354 and cutting elements 304 may be deployed into the abdomen after being pushed through tubular elongate member 401d by a pusher 409d (similar to any of the aforementioned pushers) (FIG. 46K), and/or being pulled through by a gasper 439 (FIG. 46J). A camera 441 may be inserted into the abdomen through the incision to provide visualization of the interior of the abdomen.

Tubular elongate member 401d may include a securing member 425d. Securing member 425d may include a toroidal member at a distal portion of tubular elongate member 401d. Securing member 425d may be positioned just distal to the vaginal cuff 437. Securing member 425d may engage the vaginal cuff 437 to secure tubular elongate member 401d in position within the vagina (e.g., to prevent unintended withdrawal of tubular elongate member 401d from the vagina during cutting of tissue specimen 308), and/or to maintain pneumoperitoneum in the abdomen after insufflating the abdomen (which may be carried out via tubular elongate member 401d).

Figure 46I:
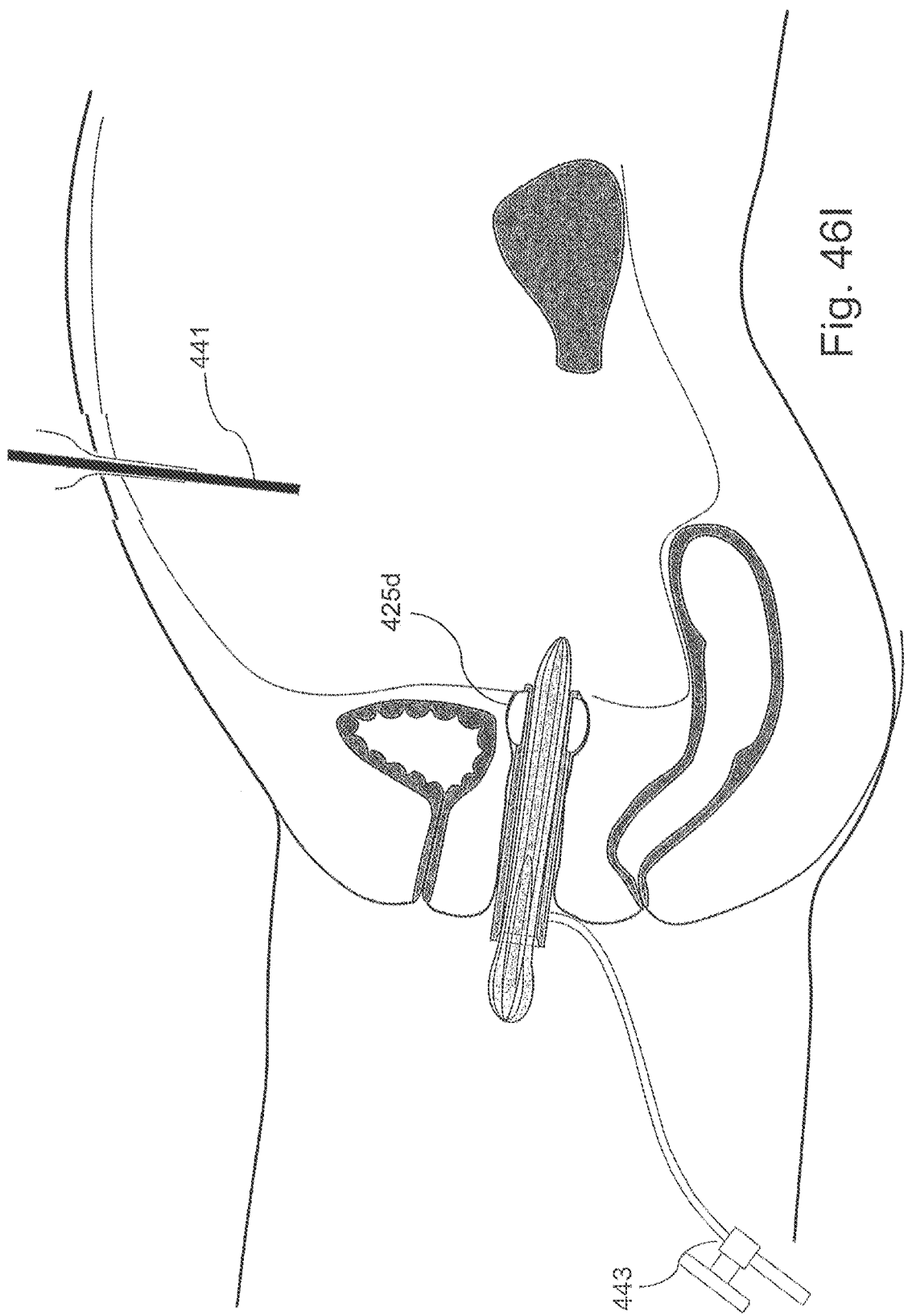
FIGS. 46H-46W are perspective views showing tissue extracting steps, in accordance with aspects of the present disclosure.

In one example, securing member 425d may be inflatable, similar to a balloon. Securing member 425d may be inserted into the vagina in a deflated state (FIG. 46H). Securing member 425d then may be inflated to expand at the vaginal cuff 437 (FIG. 46I), by introducing an inflation fluid into securing member 425d via a valve and lumen assembly 443 extending along or through tubular elongate member 401*d*. Securing member 425*d* may be deflated to facilitate removal of tubular elongate member 401*d* from the vagina.

In one example, after being deployed, bag 354 and cutting elements 304 may be drawn around and onto the outer surface of tubular elongate member 401*d*. Alternatively, tubular elongate member 401*d* may be withdrawn from the vagina after deploying bag 354 and cutting elements 304 in the abdomen, proximal ends of bag 354 and cutting elements 304 may be extracted through the vagina after tissue specimen 308 has been inserted into the bag 354, and tubular elongate member 401*d* may be inserted back into the vagina. Tubular elongate member 401*d*, like the aforementioned wound retractors, may surround the cutting elements and form a protective barrier between cutting elements 304 and bag 354, thereby protecting bag 354 and/or vaginal tissue during cutting. Tubular elongate member 401*d* may include one or more hooks (not shown), similar to hooks 345, for securing inner layer 358 to tubular elongate member 401*d*.

Figure 46N:
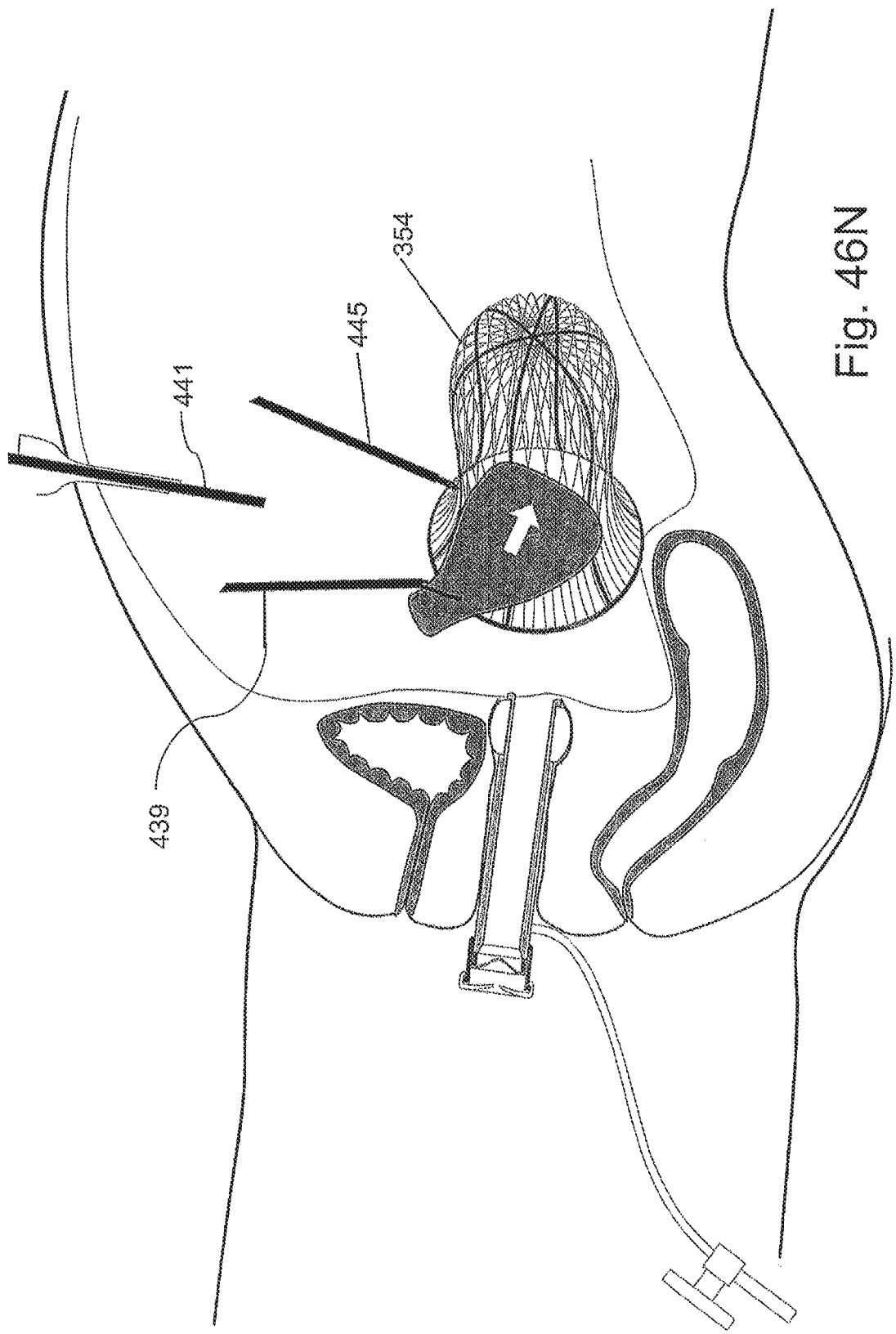
Figure 460:
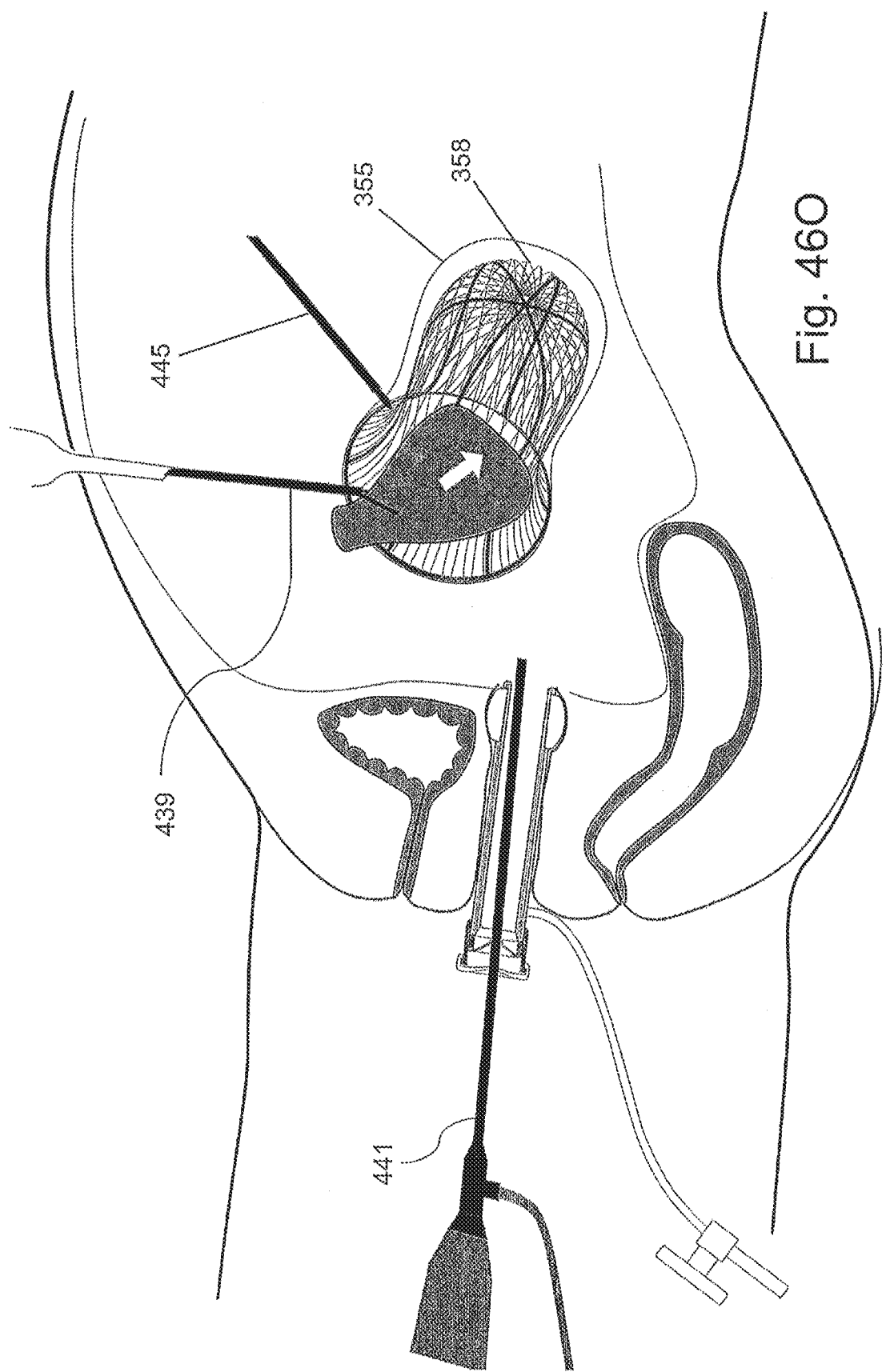

Alternatively, tubular elongate member 401*d* may remain in the vagina after deployment of bag 354 and cutting elements 304. In such an example, securing member 425*d* may be inflated at the vaginal cuff any time before, during, or after deployment of bag 354 and cutting elements 304. Once deployed, bag 354 and cutting elements 304 may move to an expanded configuration (FIG. 46L). A cap 421*d*, similar to any of the aforementioned caps, may be applied onto tubular elongate member 401*d* to maintain insufflation pressure in the abdomen (FIG. 46M). Tissue specimen 308 may be inserted into bag 354 using graspers 439 and 445. Camera 441 may be positioned through an incision in the abdomen (FIG. 46N) or through cap 421*d* and tubular elongate member 401*d* (FIG. 46O), to provide visualization during insertion of tissue into bag 354.

Figure 46S:
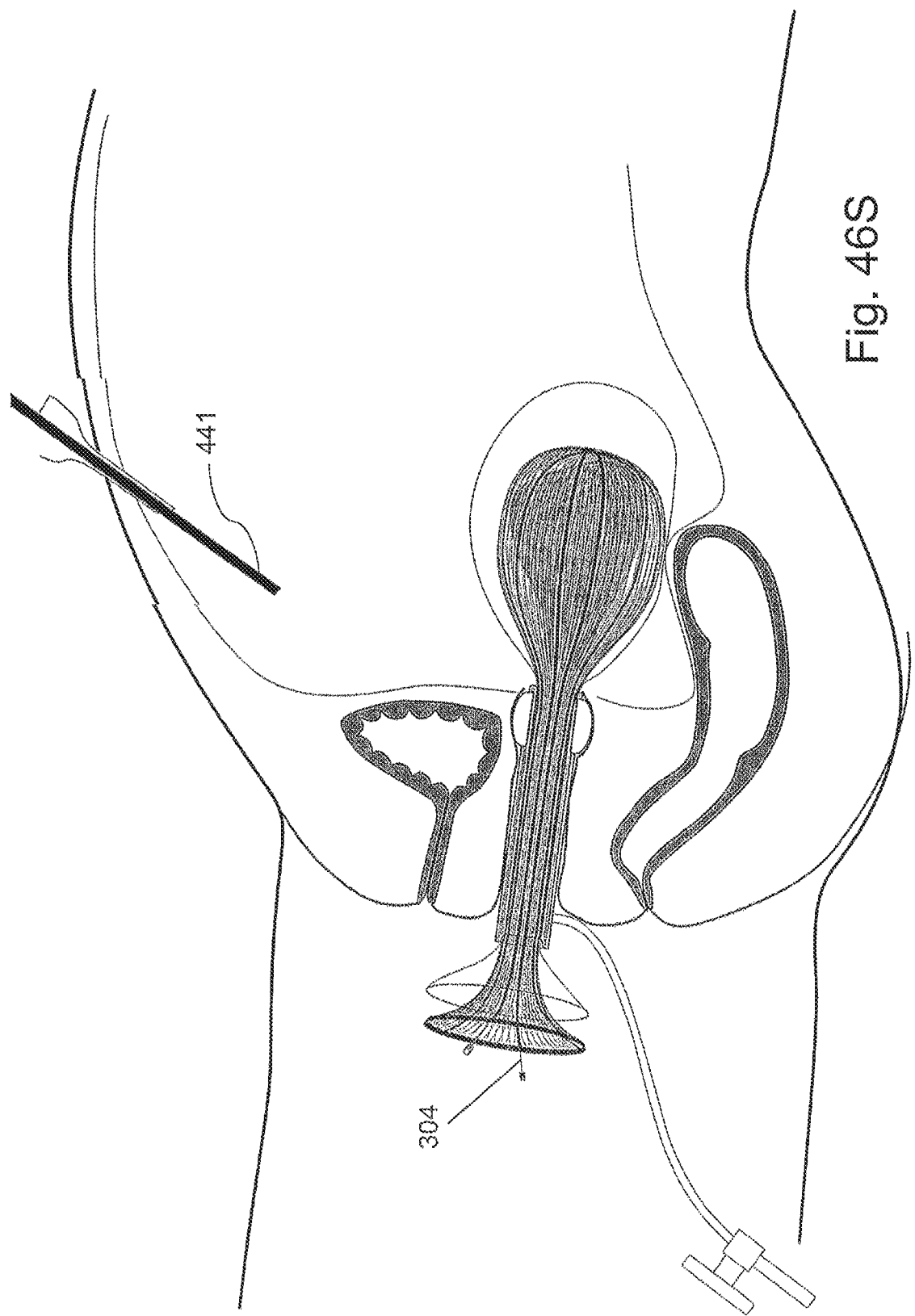

After tissue specimen 308 is inserted into bag 354, cap 421*d* may be removed (FIG. 46P), and proximal ends of bag 354 and cutting elements 304 may be extracted from the abdomen and vagina through the interior of tubular elongate member 401*d* (FIG. 46Q). Inner layer 358 and outer layer 355 may be separated, and the proximal end portion of inner layer 358 may be pulled outwardly from the vagina to tighten inner layer 358 around tissue specimen 308 (FIG. 46R). Inner layer 358 may be secured to hooks (not shown) on a proximal end of tubular elongate member 401*d*, the hooks being similar to hooks 345 of wound retractor 349. Cutting elements 304 may be disengaged/exposed from inner layer 358 (FIG. 46S) and used to cut tissue specimen 308 with the aforementioned sawing motion (FIG. 46T). Tubular elongate member 401*d* may form a protective barrier between bag 354 and cutting elements 304, and the vaginal tissue.

Cutting elements 304 may be extracted after being used. Cut pieces of tissue specimen 308 may be extracted via tubular elongate member 401*d* (FIG. 46U). Once all of the cut pieces have been extracted, bag 354 and tubular elongate member 401*d* may be extracted (FIG. 46V). Securing member 425*d* may be deflated to facilitate extraction of tubular elongate member 401*d*. Finally, wound opening 437 at the vaginal cuff may be surgically closed.

In any of the foregoing examples, the strands of the cutting elements may have blades or other cutting members disposed thereon. The blades or cutting members may be disposed on the strands such that they extend away from the interior surface of the bag (e.g., toward the tissue specimen during performance of a procedure). The side from which the blades or cutting members extend may be referred to as a cutting side of the cutting element. Opposite the cutting side, the cutting element may include a smooth side that may face or abut the interior surface of the bag. Having the blades or cutting members along the cutting side and not smooth side may reduce the likelihood that the blades or cutting members may damage the bag during insertion of the bag and the cutting elements into the target area, and/or during cutting of the tissue specimen.

The blade or cutting members may be disposed along the entire length of the strand, or may only be disposed on an effective cutting length of the strand. The effective cutting length may include a portion of the strand proximate the closed end of the bag. For example, the effective cutting length may extend along the base of a U-shaped strand, and at least partially up the legs of the U-shaped strand.

In one example, shown in FIGS. 50A-50E, a cutting element 400 may include a linear array of partially helical cutting members 402. Cutting member 402 may include a curved cutting edge 404. Curved cutting edges 404 may be disposed on only one side (e.g., a cutting side) of a strand 406. Cutting members 402 may be integral with strand 406 or may be assembled onto or inserted into strand 406. In another example shown in FIGS. 51A-51G, partially helical cutting members 402' may have straight cutting edges 404'. In yet another example shown in FIGS. 52A-52F, partially helical cutting members 402" may alternate in direction along the effective cutting length of strand 406, forming a zig-zag pattern. Strand 406 may include a wire-like member or braided filaments similar to filaments 192 of strand 182.

In another example shown in FIGS. 53A-53F, a cutting element 408 may include a strand 410 and a cutting saw 412 with a linear array of cutting teeth 414. Teeth 414 may have sharp points, and concave or indented regions 416 may lie between the sharp points. Cutting saw 412 may have varying distances between teeth 414, as well as varying heights or widths of teeth 414. Cutting saw 412 also may have a smooth portion 418 beside its effective cutting length. Smooth portion 418 may allow for a smooth entry of tissue specimen 308 onto the effective cutting length, thereby reducing the initial force needed to move the effective cutting length across tissue specimen 308. Cutting saw 412 may be integral with strand 408, or may be mounted on or attached to strand 408. Cutting saw 412 may have a triangular cross-sectional profile (FIG. 53G).

In another example shown in FIGS. 54A-54H, a cutting element 420 may include a strand 422 having a zig-zag, staggered cutting pattern of teeth 424 over its effective cutting length, and a smooth entry section 426. Teeth 424 may be arranged in two parallel rows extending longitudinally along strand 422, with teeth 424 in one row being positioned beside gaps between teeth 424 of the other row. While identical teeth 424 are depicted, it is contemplated that teeth 424 may have different orientations (e.g., may lie at different angles relative to the surface of strand 422) and/or profiles. Teeth 424 may be integral with strand 422 or may be mounted or attached to strand 422.

As shown in FIGS. 55A and 55B, a cutting element 428 may feature a cutting blade 430. Cutting blade 430 may have a half-moon or semicircular shape, defining a cutting edge 432, with an arc that extends longitudinally along and radially away from a strand 433. Cutting blade 430 may be integral with strand 433 or securely connected to strand 433. For example, as shown in FIGS. 56A and 56B, a cutting element 428', similar to cutting element 428, may include a cutting blade 430' attached to a strand 433' by a securing joint 434. Securing joint 434 may be formed by welding, brazing, and/or any other suitable form of attachment.

Strand 433 and/or strand 433' may include a wire-like member or braided filaments similar to filaments 192 of strand 182 (FIG. 16B).

As shown in FIGS. 57A and 57B, a cutting element 436 may include a strand 438 having a cutting blade 440 thereon. Cutting blade 440 may have a triangular shape, and may include a first cutting edge 442 and a second cutting edge 444 that meet at a point 446. Cutting blade 440 may be integral with strand 438. In another example shown in FIGS. 58A-58C, a cutting element 436', similar to cutting element 436, may include a cutting blade 440' with cutting edges 442' and 444' and a point 446'. Cutting blade 440' may be attached to a strand 438' by a securing joint 448. Strand 438 and/or strand 438' may include a wire-like member or braided filaments similar to filaments 192 of strand 182 (FIG. 16B).

In a further variation, a cutting element 450 may include a strand 452, a tubular holding element 454 surrounding strand 452, and a cutting blade 454 attached to a tubular holding element 455 (FIGS. 59A-59D). Cutting blade 454 may include a first triangular blade 456, and a second triangular blade 458 on top of and secured to first triangular blade 456. First triangular blade 456 and second triangular blade 458 may be offset to define first and second cutting edges 460 and 462. A securing joint 464 may secure first and second triangular blades 456 and 458, and may secure cutting blades 456 and 458 to tubular holding element 454. It is contemplated that strand 452 may include a wire-like member or braided filaments similar to filaments 192 of strand 182 (FIG. 16B).

In another example shown in FIGS. 60A-60C, a cutting element 450', similar to cutting element 450, may include a single triangular cutting blade 464 with two cutting edges 460' and 462'. Cutting blade 464 may be mounted on a tubular holding element 455' that may surround strand 452. In another example shown in FIGS. 61A-61C, a cutting element 450", similar to cutting element 450', may include a cutting blade 464" having cutting edges 460" and 462", with cutting blade 464" being formed with an integral tubular portion 455". Tubular portion 455" may be securely coupled to strand 452, and may extend over and at least partially surround strand 452.

In another example, a cutting element 474 may include cutting beads 476 mounted on strand 452 (FIGS. 62A-62H). Cutting beads 476 may have a hollow annular cross-section, such that they may be slid onto strand 452. When a plurality of cutting beads 476 are mounted on strand 452 to form an effective cutting length, adjacent beads 476 may be joined by rotatable joints. An exemplary rotatable joint may include one or more rounded protrusions 478 of one bead 476 movably received in one or more rounded recesses 480 of an adjacent beads 476. This may allow beads 476 to rotate or pivot relative to each other to accommodate bending of strand 452. Each cutting bead 476 also may have a partially helical cutting edge 482. Cutting edges 482 of adjacent cutting beads 476 may be aligned along the cutting side of the effective cutting length of cutting element 474. In another example shown in FIGS. 63A-63F, cutting beads 483 may include pairs of diametrically-opposed cutting edges 484a, 484b, 486a, and 486b. Cutting edges 484a and 484b may be offset by 90 degrees from cutting edges 486a and 486b.

In another example shown in FIGS. 64A-64G, a cutting element 488 may include at least one blade 490 secured between two strands 494 and 496. Blade 490 may have a width that tapers going toward a cutting edge 498. For example, in a section or end view, blade 461 may have a base 500 with a constant width, and a triangular tip 502 (FIG. 64E). Additionally or alternatively, blade 461 may have a trapezoidal shape. Alternatively, a strand (not shown) may include one or more slots or grooves along its length for receiving one or more blades 490. Blade 490 may be brazed, welded, or otherwise attached to the strand or strands 494 and 496.

In another example, a cutting element 504 may include a strand 506 having a triangular cross-sectional shape terminating on one side with a cutting edge 508, and terminating on the other side with a flat surface 510 (FIGS. 65A and 65B). Cutting element 504 also may include cutouts 512 on a cutting side to allow tissue to enter cutouts 472, thereby positioning the tissue for cutting by cutting edges 508 when strand 466 is moved, as well as to ensure that cutting edges 508 do not interfere with each other even when cutting element 504 is bent. It is contemplated that strand 506 may include a wire-like member or braided filaments similar to filaments 192 of strand 182 (FIG. 16B).

In a further example, a cutting element 514 may include a strand 516, and a tissue cutting or abrading tube 518 surrounding strand 516 (FIGS. 66A-66E). Tube 518 may have a cross-sectional shape corresponding to a cross-sectional shape of strand 516. For example, when strand 516 has a triangular cross-sectional shape, tube 518 also may have a triangular cross-sectional shape. Tube 518 may include one or more edged apertures 520 to form a cutting and/or abrasive side. Apertures 520 may be circular or another suitable shape. It is contemplated that strand 516 may include a wire-like member or braided filaments similar to filaments 192 of strand 182 (FIG. 16B).

In another example shown in FIGS. 67A-67F, multiple cutting tubes 522 may surround a strand 524. Tubes 522 may have a body 526, and a blade 528 extending from body 526. Blade 528 may have an arced or curved cutting edge 530. A plurality of tubes 522 may be positioned along strand 524 and may be spaced apart such that strand 524 may bend without tubes 522 interfering with each other. Body 526 may have a rectangular cross-sectional shape when strand 524 has a similar shape, or may have any other suitable cross-sectional shape depending on the cross-sectional shape of strand 524. For example, a body 526' of a tube 522' may have a triangular cross-sectional shape to match a strand 524' having a similar cross-sectional shape. In another example, a tube 532 may include staggered teeth 534 and 536, which may be curved, triangular, pyramidal, or any other suitable shape (FIGS. 69A-69E). It is contemplated that strand 524 may include a wire-like member or braided filaments similar to filaments 192 of strand 182 (FIG. 16B).

In another example shown in FIGS. 70A-70E, a tube 538 may include a through-hole 540 for receiving a strand. The cross-sectional shape of through-hole 540 may match the cross-sectional shape of the strand. It is contemplated that the strand may include a wire-like member or braided filaments similar to filaments 192 of strand 182 (FIG. 16B). Tube 538 may have teeth 542 similar to teeth 414 (FIGS. 53A-53G).

In a further example shown in FIGS. 71A-71E, a tube 544 may include a cylindrical core or body 546 with a through-hole 548, and a blade 550 having a cutting edge 552. Cutting edge 552 may be toothed/serrated. Blade 550 may be angled across core 546. For example, blade 550 may be partially helical. Tube 544 may have a smooth entry chamfer 552 at one end or both ends. It is contemplated that a strand, formed of a wire-like member or braided filaments similar to filaments 192 of strand 182 (FIG. 16B), may be received in through-hole 548.

In the aforementioned examples the tubes may be coupled to strands through welding, brazing, adhesive attachment, and/or other suitable coupling methods. Also in the aforementioned examples, the strands may have a non-circular cross-sectional shapes for a number of reasons. For example, the use of non-circular cross-sectional shapes may reduce the likelihood of the strands rotating or twisting when in use. Additionally or alternatively, the use of non-circular cross-sectional shapes may facilitate bending of the strands in one or more directions and/or discourage bending of the strands in one or more directions. Additionally or alternatively, using non-circular cross-sectional shapes may help maintain the cutting sides of the cutting elements pointed away from the interior surface of the bag, and/or maintain the smooth sides of the cutting elements pointed toward the interior surface of the bag. The aforementioned tubes may have corresponding cross-sectional shapes so they are securely mounted on their strands. It is also contemplated that a single tube may be provided on a single strand, or a plurality of tubes may be provided on a single strand. The plurality of tubes on the single strand may be of the same type, or may be a combination of any of the aforementioned strands.

In a further aspect illustrated in FIGS. 72A-72E, a cutting element 554 may be at least partially formed of a plurality of saw elements or links 556. Each element link 556 may include a jagged or toothed side 558 (corresponding to the cutting side of cutting element 554) and an opposite smooth side 560. Links 556 may have holes 562 formed thereon. Links 556 may be arranged such that holes 562 of one link 556 may overlap holes 562 of adjacent links 556, allowing adjacent links 556 to be pivotally joined together by rivets 564 inserted through holes 562. A plurality of linked links 556 may form a chain. The chain may be connected at its ends to strands (not shown). The strands may be removably connected to handles, such that the chain may be manipulated from outside of a bag to cut a tissue specimen. Alternatively, the chain may be directly connected to the handles for sawing the tissue specimen.

In one exemplary manner of cutting the tissue specimen, the chain may saw through the tissue specimen by being drawn across a surface of the specimen in a back-and-forth sawing motion (see, e.g., FIG. 45B). Additionally or alternatively, the chain may be coupled to an external drive, for example a motor or manual crank (not shown), that may drive/rotate the chain in a single direction across the surface of the specimen to cut through the specimen. When utilizing the sawing motion and/or the rotating motion to cut, simultaneous pulling of the chain in the proximal direction may facilitate cutting through the specimen.

Figure 86:
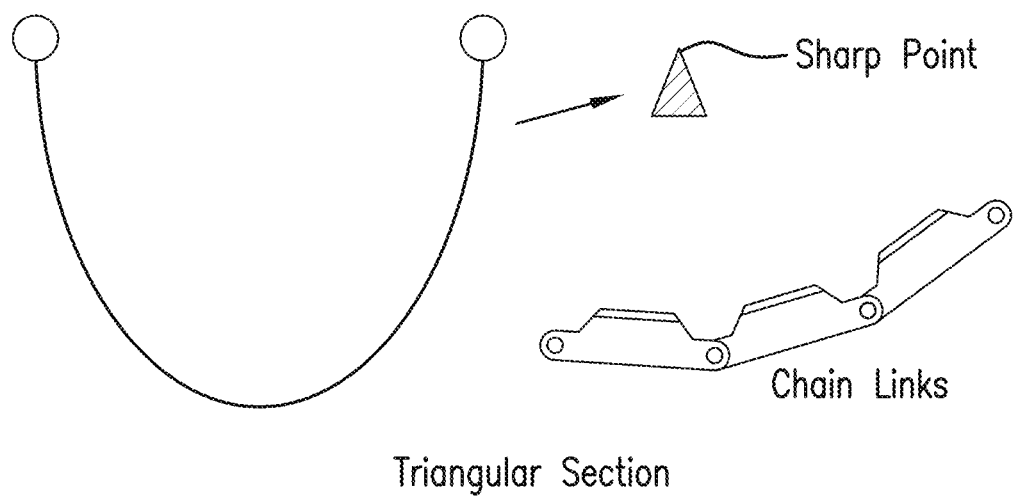
FIG. 86 is a side view of an exemplary cutting element, in accordance with aspects of the present disclosure.

FIG. 86 shows additional or alternative aspects that may be utilized with respect to the aforementioned cutting elements. For example, it is contemplated that one or more of the aforementioned strands and/or cutting members/components may terminate at a sharp point for cutting tissue. This may apply, for example, to versions of the cutting elements include strands, similar to strand 305. This also may apply to cutting elements formed by one or more sections that include interconnected chain links.

Figure 73:
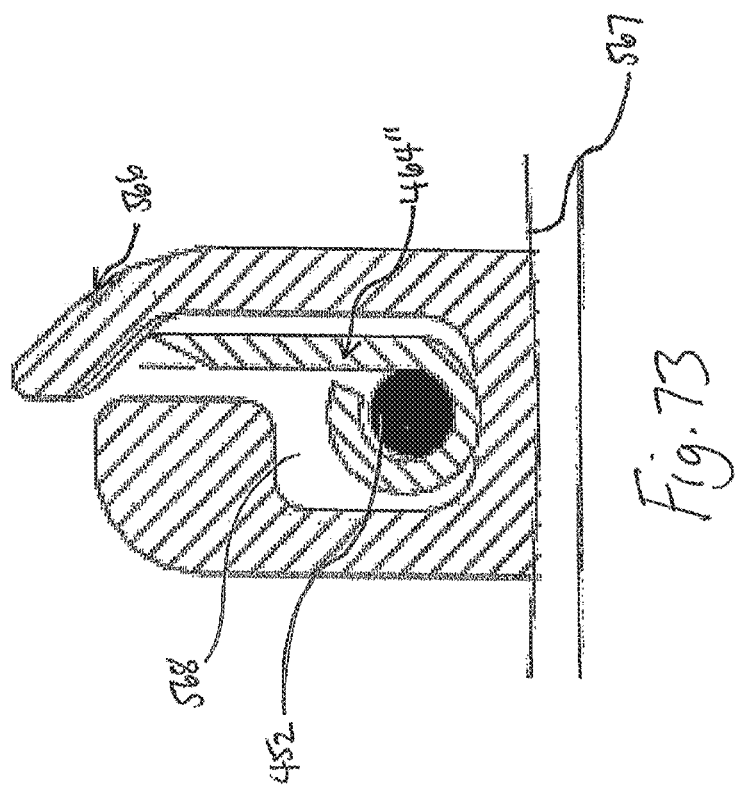
FIG. 73 is a section view of a portion of a cutting element, a cover, and a bag, in accordance with aspects of the present disclosure.

As illustrated in FIGS. 27 and 73, a cover 566 may be provided to receive any of the aforementioned blade structures and cutting members. The bottom surface of cover 566 may be affixed to an interior surface 567 of a bag. Cover 566 may include a cavity or slot 568 for slidably receiving the blade structures and cutting members. Cover 566 may extend over the cutting edges of the blade structures and cutting members to keep the cutting edges from contacting other components. For example, when cutting elements are inside an introducer with strands and a bag, cover 566 may keep the cutting edges of any blade structures or cutting members from damaging the bag, each other, and/or the strands. Additionally or alternatively, covers 566 may aid in positioning the blade structures and cutting members on the interior surface of the bag so as to avoid interference between the blade structures or cutting members. The blade structures and cutting members may be deployed from cover 566 by being slid laterally out of slot 568 (into or out of the page in FIG. 73).

In any of the aforementioned examples, the strands may be constructed of wires and/or cables. The strands may be made out of steel, Nitinol or any other similar suitable materials. Further, the various blade structures and cutting members discussed in the aforementioned examples may be made of ceramic, stainless steel, titanium, and/or any other suitable material.

It is contemplated that one tissue extraction device may include different types of cutting elements. For example, one tissue extraction device may include cutting elements with different blade structures and/or cutting members. Additionally or alternatively, one cutting element may include different blade structures and/or cutting members. Cutting elements also may include a single type of blade structure and/or cutting member, but with blade structures and/or cutting members varying in dimensions. It is also contemplated that any of the cutting elements described above may be used in any of the tissue extraction devices described above. Also, aspects of any of the cutting elements described above may be used in combination with aspects of any of the other cutting elements described above.

Figure 74:
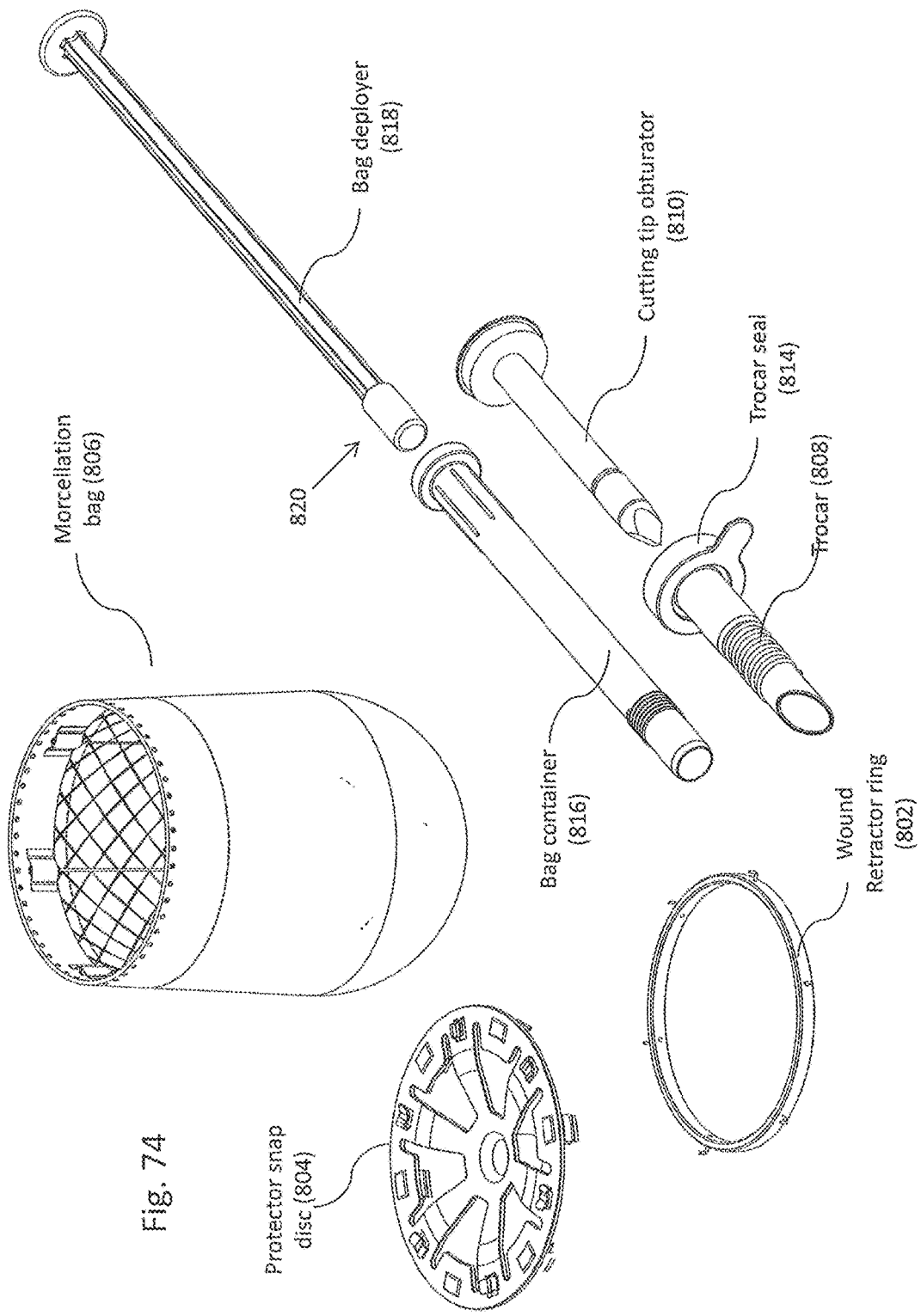
FIG. 74 is a perspective view of a kit, in accordance with aspects of the present disclosure.
Figure 76A:
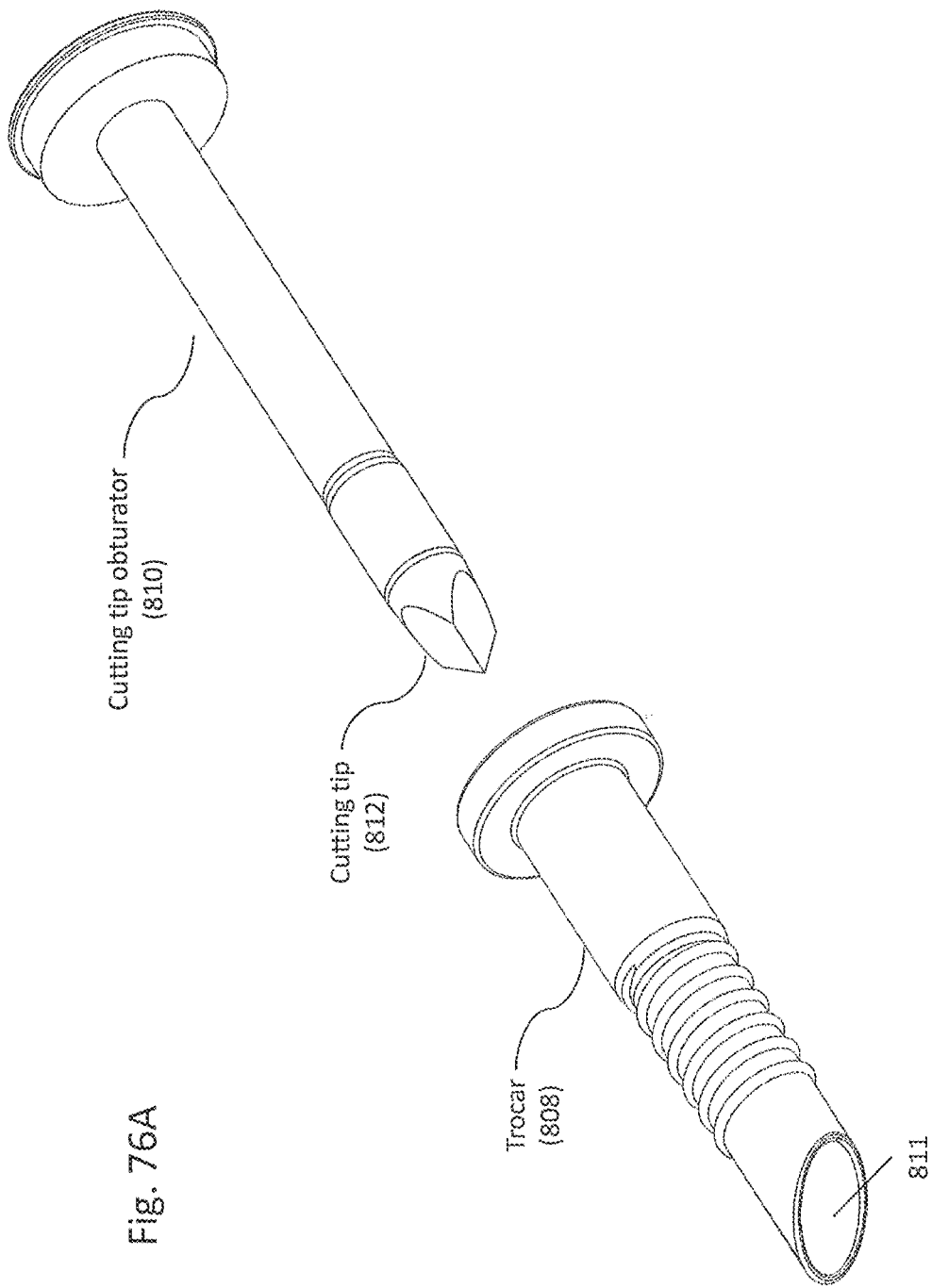
FIGS. 76A and 76B are perspective views of components of the introducer assembly of FIG. 75, in accordance with aspects of the present disclosure.
Figure 76B:
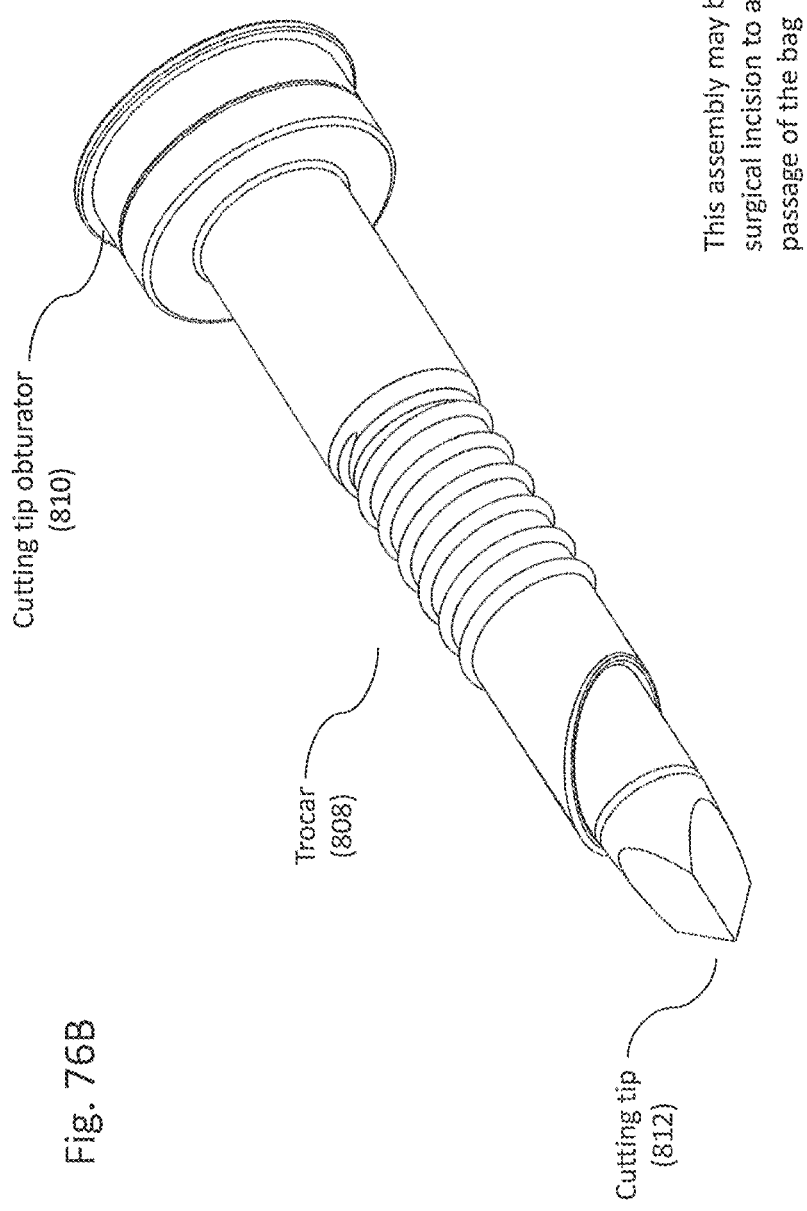

FIG. 74 shows components of a manual tissue morcellation kit 800. Kit 800 may include, for example, a wound retractor ring 802, a protector snap disc 804, a morcellation bag 806, and an introducer assembly 820. Each of these components will be described in greater detail in the paragraphs below, with reference being made to FIGS. 75, 76A, 76B, 77A, 77B, 78A-78C, 79A, 79B, 80A-80C, 81, and 82A-82D. It is contemplated, however, that any of the components of kit 800 may be swapped out for similar components (e.g., bags, introducers, and/or wound retractors) shown in figures preceding FIG. 74. It also is contemplated that components shown in figures preceding FIG. 74 may be combined to form another version of a kit similar to kit 800. FIG. 75 shows a disassembled view of introducer assembly 820. Introducer assembly 820 may include, for example, a trocar 808, an obturator 810 having a cutting tip 812, a trocar seal 814, a bag container 816, and a bag deployer 818. FIGS. 76A and 76B show trocar 808 and obturator 810 in assembled and disassembled states, respectively. Trocar 808 may have the same features as distal section 405c of introducer 399c (FIG. 37M), except external threading 813 on trocar 808 may not be on an enlarged, tapered region, but rather, may be on a straight, tubular region. Alternatively, an enlarged, tapered region may be included. Obturator 810 may be inserted into a passage 811 in trocar 808. When obturator 810 is fully inserted into trocar 808, cutting tip 812 may at least partially protrude from a distal end of trocar 808. In use, the user may grasp the assembled trocar 808 and obturator 810, and force cutting tip 812 through tissue, or force cutting tip 812 through an incision already made in tissue. This may create a sufficiently-sized wound opening in the tissue for trocar 808 to pass through. In one example, trocar 808 may have a diameter of approximately 2 cm to approximately 4 cm. For example, trocar 808 may have a diameter of approximately 2.5 cm in a region where it engages tissue.

Figure 77B:
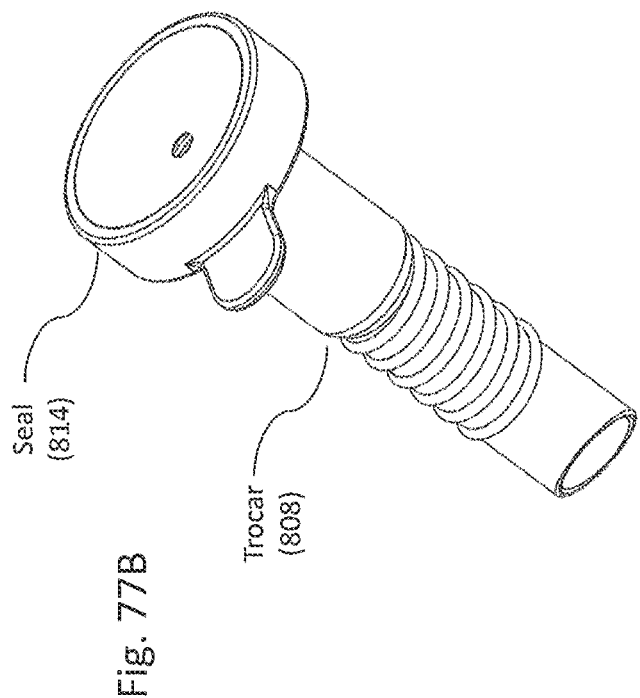
FIGS. 77A and 77B are perspective views of components of the introducer assembly of FIG. 75, in accordance with aspects of the present disclosure.
Figure 77A:
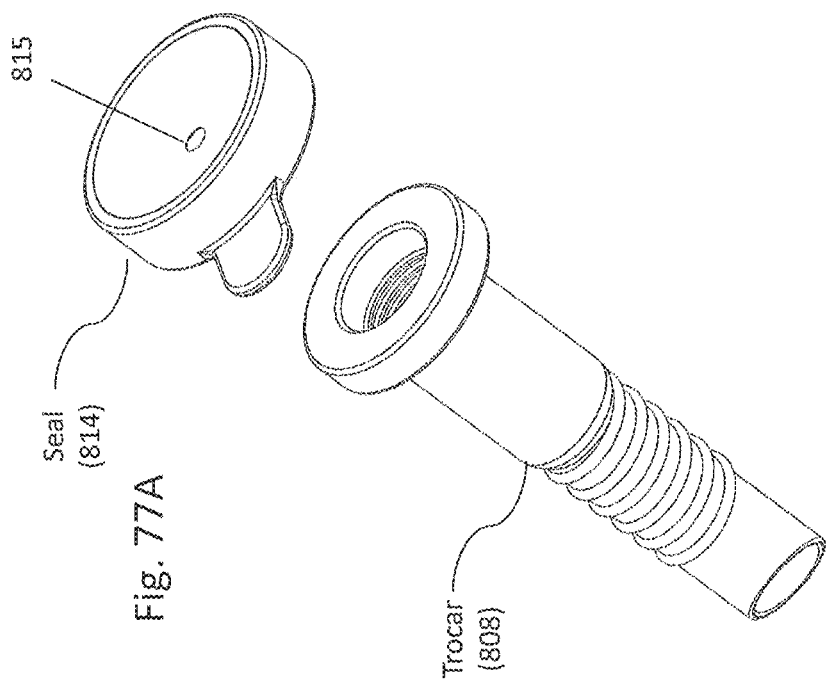

FIGS. 77A and 77B show trocar 808 and a cap or seal 814 in assembled and disassembled states, respectively. Cap 814 may have the same features as cap 421c (FIG. 37Q(v)). Cap 814 may cover a proximal end of trocar 808. Cap 814 may include an opening 815 for receiving an instrument (not shown), and for forming a seal with an outer surface of the instrument.

Figure 78B:
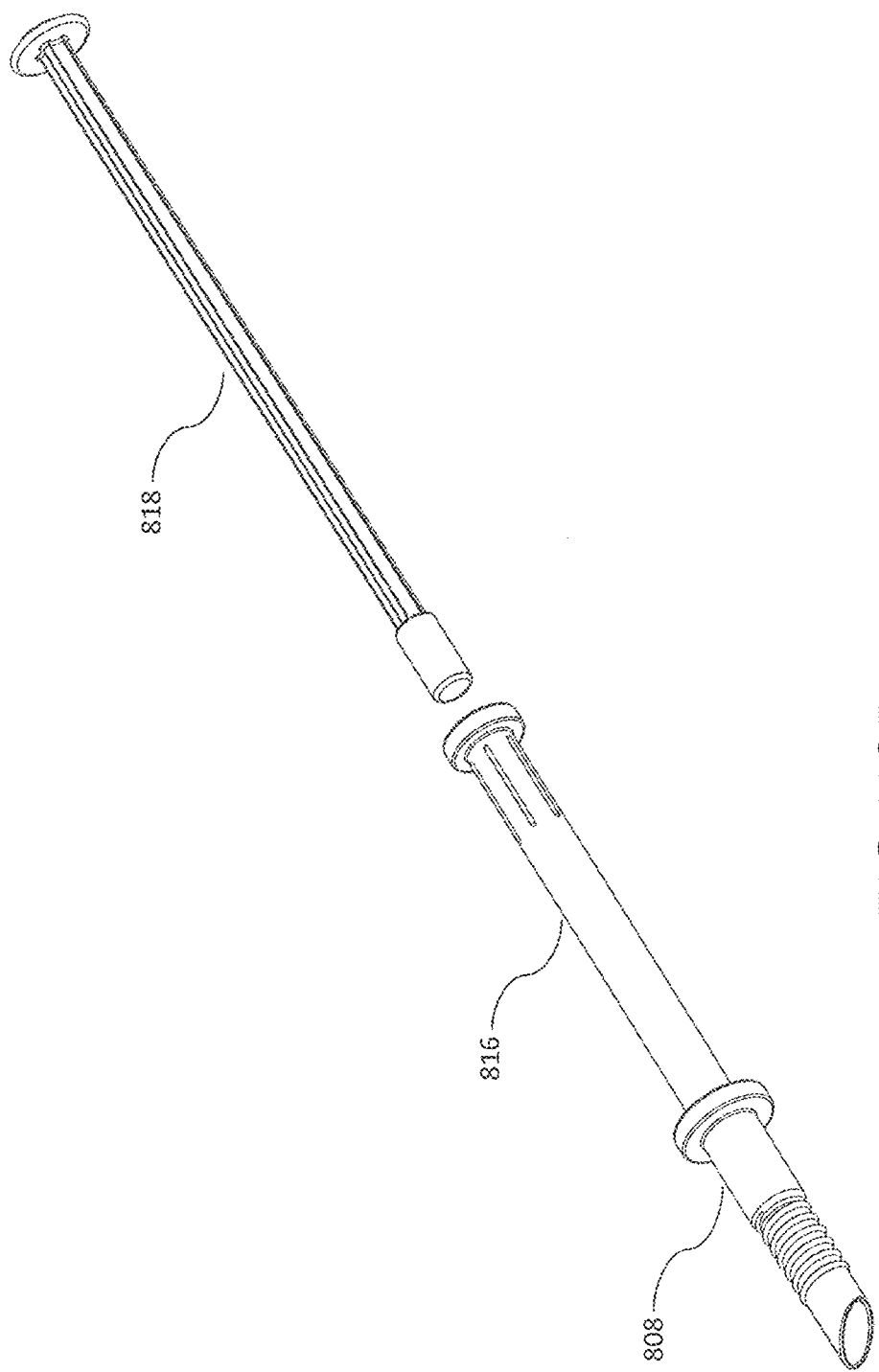
Figure 78C:
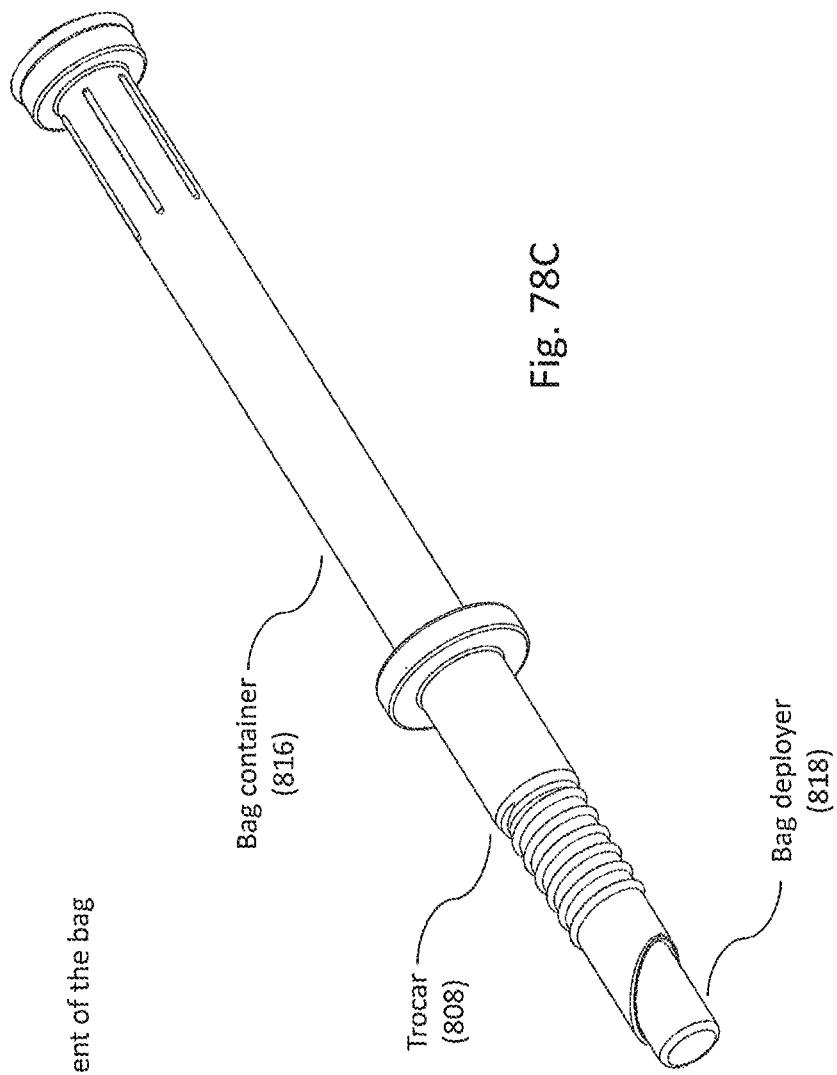

FIGS. 78A-78C show trocar 808, bag container 816, and bag deployer 818 in disassembled, partially-assembled, and fully-assembled states, respectively. Bag container 816 may have the same features as proximal section 403c of introducer 399c (FIG. 37Q(vii)), and may house bag 806 for delivery into the subject. Bag container 816 may be coupled to trocar 808 in the same manner that proximal section 403c may be coupled to distal section 405c (FIG. 37Q(i)) (e.g., may threaded engagement). Bag deployer 818 may have the same features as pusher 409c (FIG. 37Q(ix)), and may be used to push bag 806 out of bag container 816.

FIGS. 79A and 79B show wound retractor ring 802. Wound retractor ring 802 may include a ring body 822 and one or more attachment hooks 824. Ring body 822 may include a hole or passage extending therethrough for receiving a reinforcement wire (not shown). Wound retractor ring 802 may be everted by the user. FIG. 79A shows a first stable configuration of wound retractor ring 802. A second stable configuration of wound retractor ring 802 may be achieved by everting wound retractor ring 802 until attachment hooks 824 face radially-inward. Wound retractor ring 802 may be everted/flipped between its first and second stable configurations. When wound retractor ring 802 is in between its stable configurations, internal forces in wound retractor ring 802 may bias wound retractor ring 802 toward one of its stable configurations. In another example of a tissue extraction device, wherein inner layer 838 is omitted, wound retractor ring 802 may be coupled to outer layer 836 to retract outer layer 836.

FIGS. 80A-80C show protector snap disc 804. Protector snap disc 804 may include one or more snap features 828. Snap feature 828 may include, for example, opposing arms 827 and 829. Arms 827 and 829 may be forced against ring 822 of wound retractor ring 802, causing arms 827 and 829 to move from their rest configuration (FIG. 80A) to a spread-apart configuration (not shown). When arms 827 and 829 fully receive and move beyond ring 822, arms 827 and 829 may move back toward their rest configuration, thereby coupling protector snap disc 804 to wound retractor ring 802. The reverse movement may be used to uncouple protector snap disc 804 from wound retractor ring 802.

Protector snap disc 804 also may include one or more wire locking features 830 similar to clips 373 (FIG. 33A), for securing cutting elements (not shown), such as cutting elements 304, to protector snap disc 804. Protector snap disc 804 also may include a wound protector 832 having a central hole 834 running therethrough (FIG. 80B). The cutting elements may be directed through central hole 834. When the user cuts tissue in bag 806 with the strands, wound protector 832 may ensure a working space remains open during a procedure, and/or protect the margins of the bodily orifice or incision from potentially being injured by the cutting elements.

FIG. 81 shows bag 806. Bag 806 may include an outer layer 836 and an inner layer 838. Outer layer 836 may be similar to outer layer 355 of bag 354 (FIG. 32A). Inner layer 838 may be similar to inner layer 358 of bag 354. A proximal portion 840 of inner layer 838 may be coupled to a proximal portion 841 of outer layer 336. Proximal portion 840 and proximal portion 841 may be joined by a perforated section 842, allowing the user to separate outer layer 836 from inner layer 838 by tearing apart proximal portion 840 and proximal portion 841 at perforated section 842. In one example, proximal portions 840 and 841 may be made of the same material.

A proximal end of proximal portion 840 may include one or more holes 844 for receiving one or more attachment hooks 844 (FIG. 79A), for securing wound retractor ring 802 to inner layer 838. Once secured, everting wound retractor ring 802 may roll proximal portion 840 around wound retractor ring 802, thereby shortening an axial extent of inner layer 838 by drawing a distal end of inner layer 838 toward a proximal end of inner layer 838. The amount of shortening may be determined by the number of times wound retractor ring 802 is everted.

A proximal end of proximal portion 840 may include one or more tab holders 846. Tab holders 846 may secure anchoring elements 306 of cutting elements 304 to an interior surface of proximal portion 840. The user may release anchoring elements 306 from tab holders 846 by sliding anchoring elements 306 distally out from between tab holders 846 and the interior surface of proximal portion 840. Alternatively, inner layer 838 may include splittable members 365, including distal portion 367, for securing cutting elements 304.

FIG. 82A shows bag 806 extending partially into the subject's abdomen and partially out of the subject's abdomen. At this stage, a tissue specimen may already be contained in bag 806 within the abdomen. Optionally, at this stage, inner layer 838 may be separated from outer layer 836. Anchoring elements 306 are freed from tab holders 846 (not shown here, but shown in FIG. 81). Wound retractor ring 802 is positioned for coupling to proximal portion 840.

In FIG. 82B, attachment hooks 824 are placed in holes 844 to attach wound retractor ring 802 to proximal portion 840. Optionally, at this stage, inner layer 838 may be separated from outer layer 836. The user may evert/flip wound retractor ring 802 one or more times to induce tension on inner layer 838, so that inner layer 838 pulls the tissue specimen away from outer layer 836, and firmly holds onto the tissue specimen in preparation for cutting. Wound retractor ring 802 may stay in one of its stable configurations, thereby maintaining inner layer 838 in the tensioned state when the user releases wound retractor ring 802 after eversion/flipping.

Figure 82C:
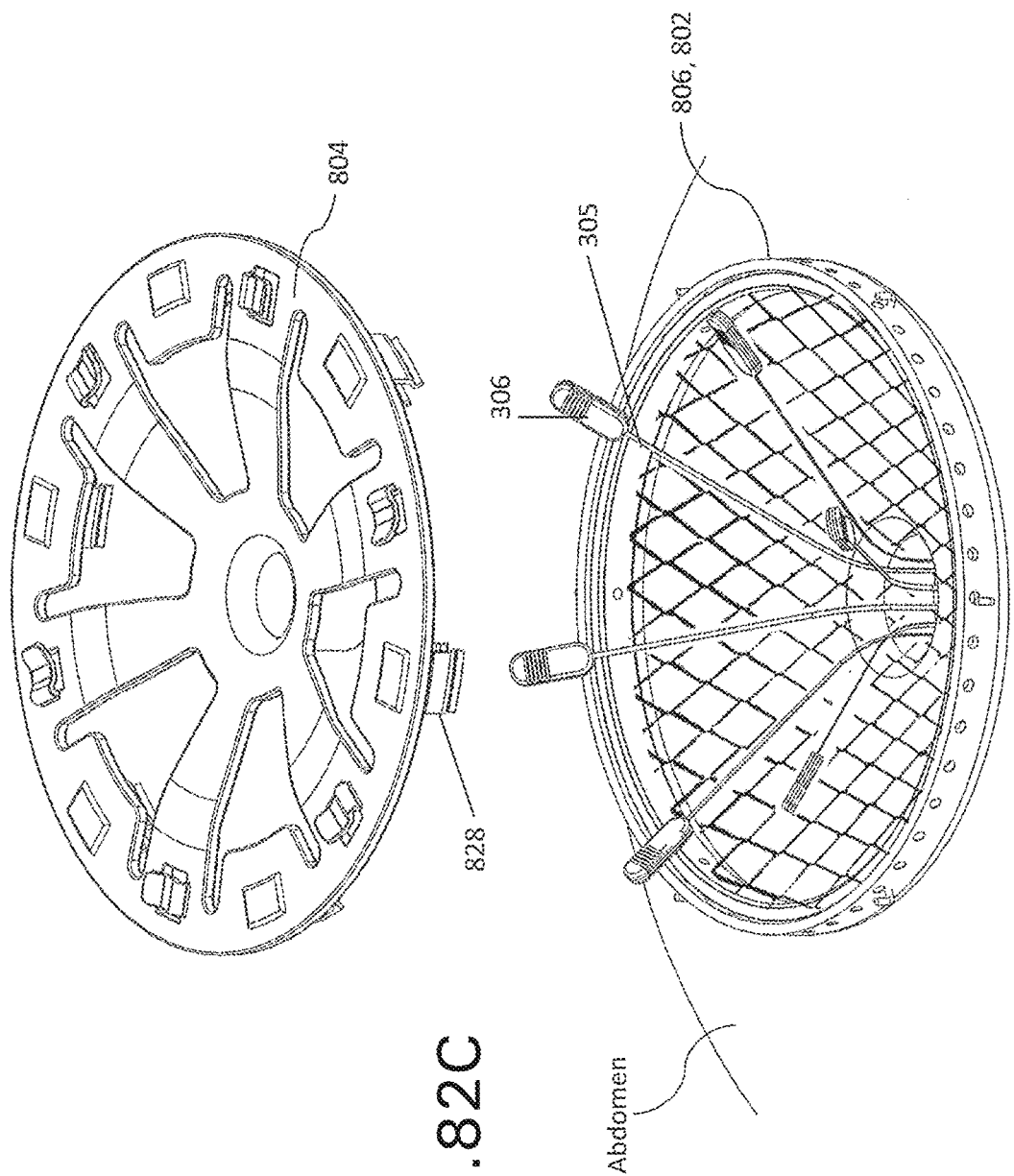
Figure 82D:
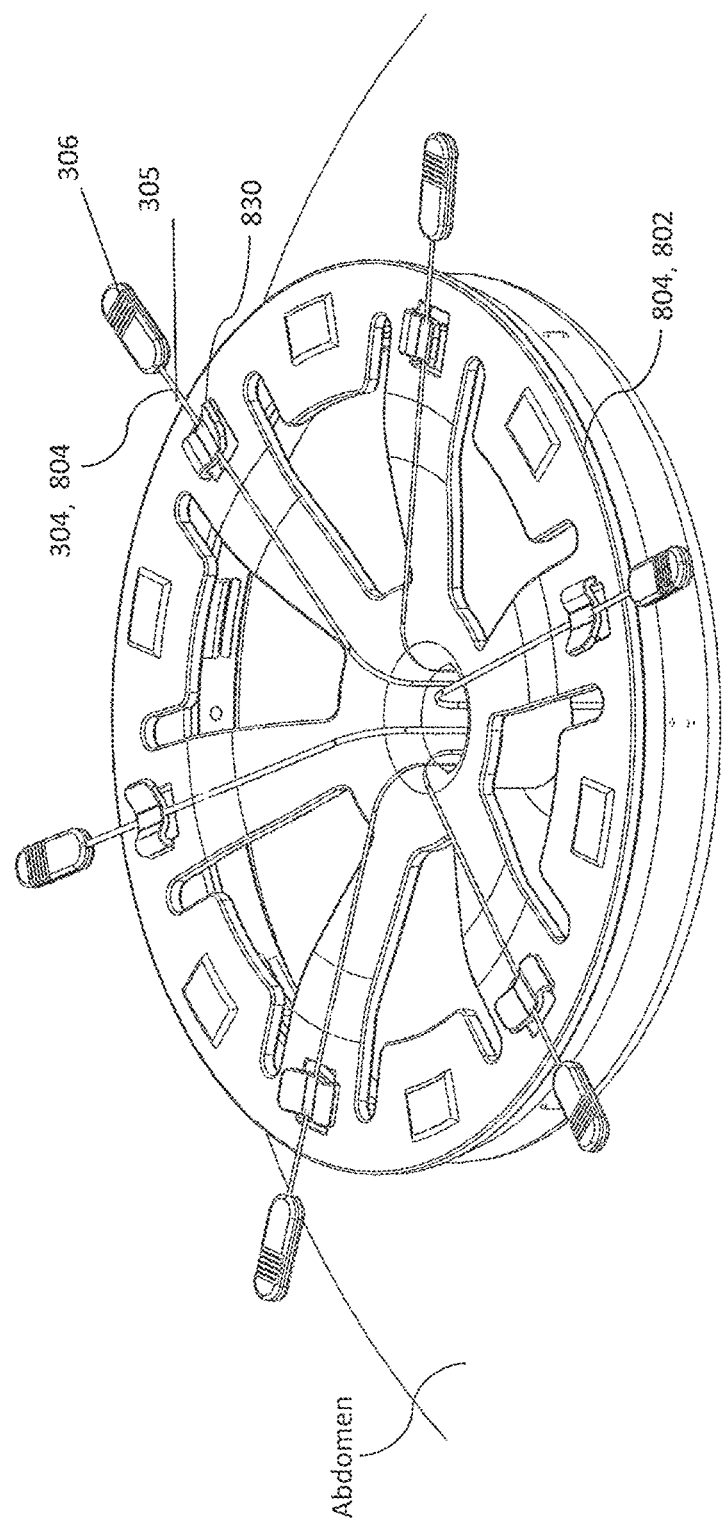

In FIG. 82C, protector snap disc 804 is positioned for coupling to wound retractor ring 802 and bag 806. The user guides strands 305 and anchoring elements 306 of cutting elements 304 through central hole 834, and brings snap features 828 into engagement with wound retractor ring 802 (and portions of inner layer 838 wrapped around wound retractor ring 802). FIG. 82D shows protector snap disc 804 secured to wound retractor ring 802 and bag 806. The user may then move strands 305 of cutting elements 304 into wire locking features 830, serving to secure and/or position cutting elements 304 in preparation for cutting the tissue specimen. The user may release one or more of cutting elements 304 at a time to cut the tissue specimen in a manner similar to that which is shown in FIGS. 44A, 44B, 45A, and 45B.

FIGS. 83A-83C show aspects of a cutting element 850. Cutting element 850 may include a strand 852, which may be similar to strand 305. One or more circular saw blades 854 may be rotatably mounted on strand 305 at, for example, a central portion of strand 305 that may engage a tissue specimen. Saw blades 854 may be operatively coupled to a drive assembly (not shown) (e.g., an external motor) that may cause blades 854 to rotate to cut through tissue 856. The drive assembly may be operatively coupled to blades 854 may a gear assembly, drive chain, and/or any other suitable mechanical connection. Cutting element 850 also may be pulled against tissue 856 while blades 854 spin to further facilitate cutting through tissue 856. FIG. 83C shows that cutting elements 850 may be positioned within a basket 858. Basket 858 may be formed by circumferentially-spaced arms, such as splittable members 365 (FIG. 32A). Splittable members 365 may house cutting elements 850 prior to cutting elements 850 being released to engage tissue 856. Splittable members 365 may be pulled against tissue 856 to hold tissue 856 during cutting.

Figure 84A:
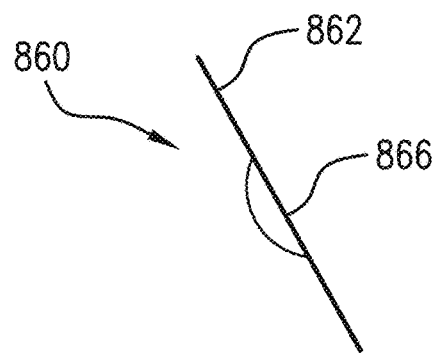
FIGS. 84A-84C are side views of an exemplary cutting element, in accordance with aspects of the present disclosure.
Figure 84B:
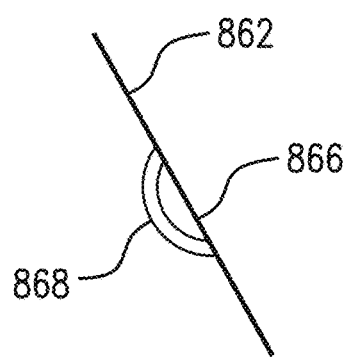
Figure 84C:
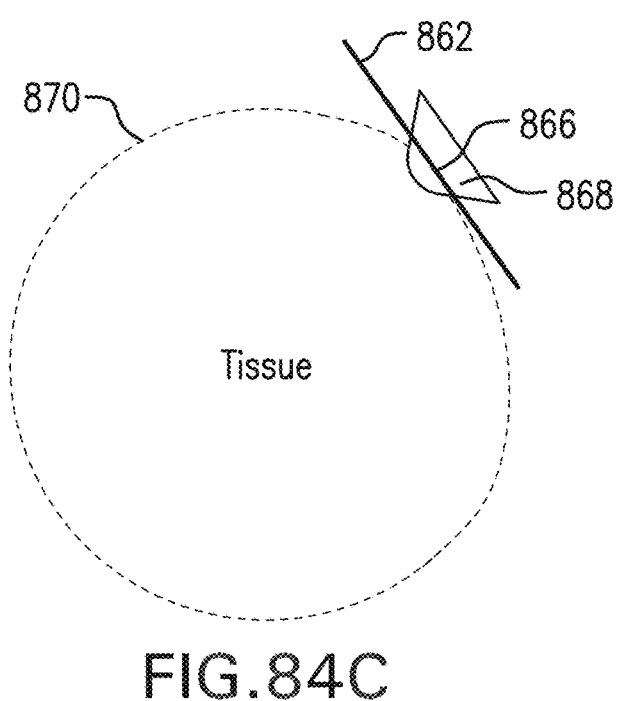

FIGS. 84A-84C show aspects of a cutting element 860. Cutting element 860 may include a strand 862 and a cutting member or component 864 similar to any of the aforementioned cutting components. In one example, cutting member 864 may include a cutting blade 866. Cutting element 860 also may include a blade cover 868. Blade cover 868 may cover cutting blade 866 (FIG. 84B). When cutting element 860 is pulled against tissue 870 (FIG. 84C), blade cover 868 may bend, shift, or otherwise deflect to expose cutting blade 866. When blade cover 868 is not being forced against tissue 870, it may move back into its covering position. Thus, cutting blade 866 may be automatically exposed when cutting tissue 870, and may be automatically covered when not cutting tissue 870.

Figure 85:
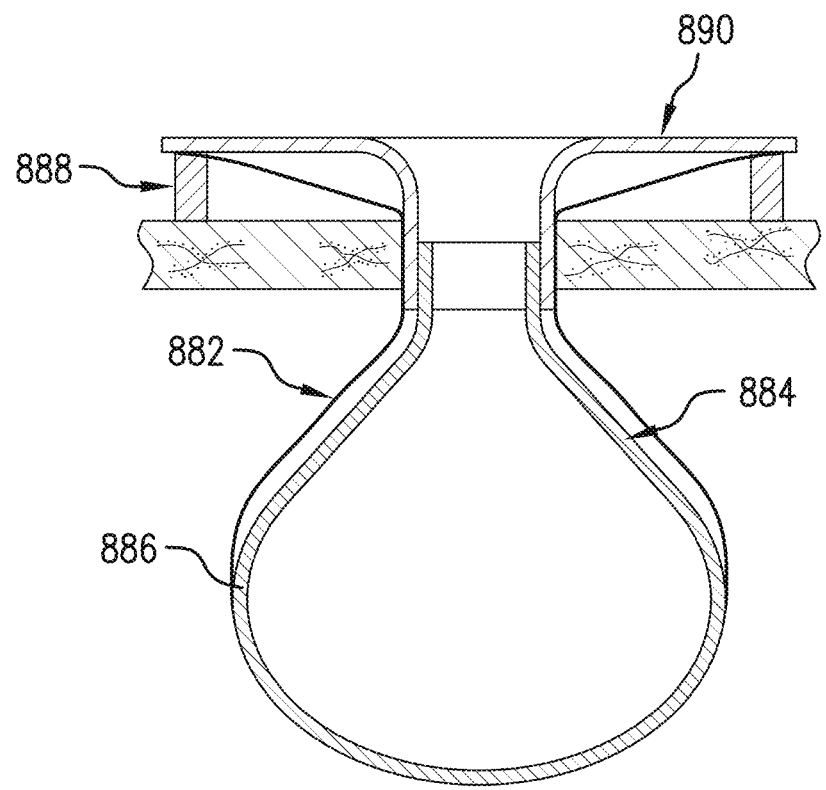
FIG. 85 is a side view of an exemplary tissue extraction device, in accordance with aspects of the present disclosure.

FIG. 85 shows a tissue extraction device 880 including an outer layer or bag 882 (e.g., similar to outer layer 355 in FIG. 32A or an outer layer 836 in FIG. 81 and a basket 884 formed by a plurality of circumferentially-spaced arms 886 (e.g., similar to splittable members 365 (see, e.g., FIG. 32A)), and no inner layer made of mesh. Basket 884 may cover one or more cutting elements, such as any of the aforementioned cutting elements. A tissue specimen may be placed into bag 882, and basket 884 may be pulled up. Additionally or alternatively, bag 882 may be rolled on a ring 888 (e.g., similar to retractor ring 802 (FIG. 79A)) to hold the tissue steady. The inner surfaces of arms 886 may be textured (e.g., roughened, covered by protrusions, and/or covered by indentations) to help hold the tissue in place. Optionally, arms 886 may be connected by slim sutures (not shown) to help compress the tissue and/or maintain positioning of arms 886. It is also contemplated that a protector 890 (e.g., similar to protector snap disc 804 (FIG. 80A)) may be coupled to ring 888 and/or bag 882.

Figure 87:
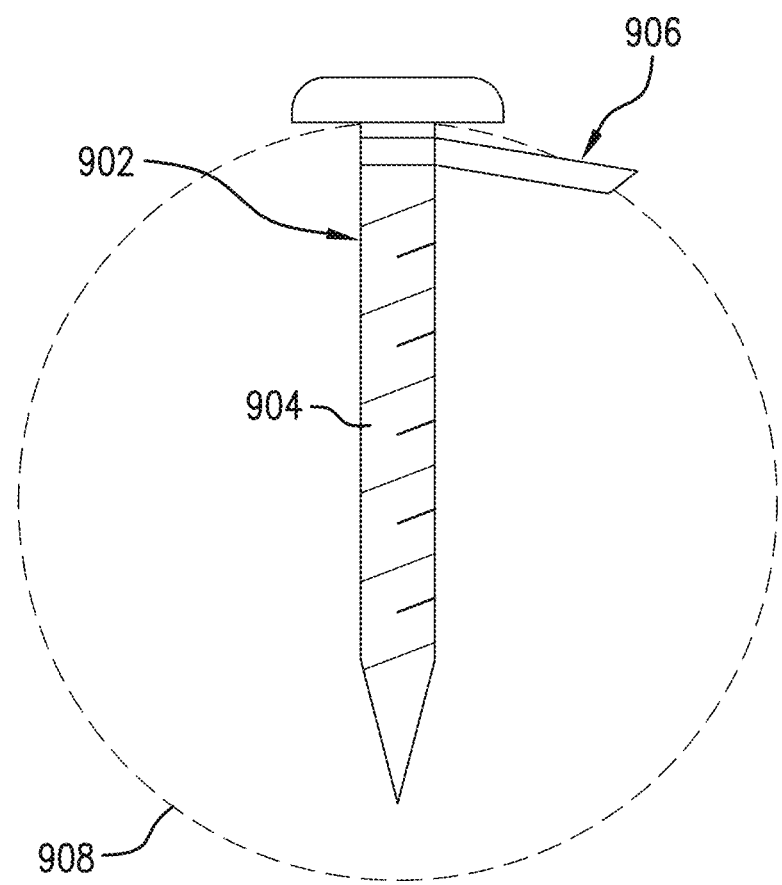
FIG. 87 is a side view of an exemplary cutting element, in accordance with aspects of the present disclosure.
Figure 88:
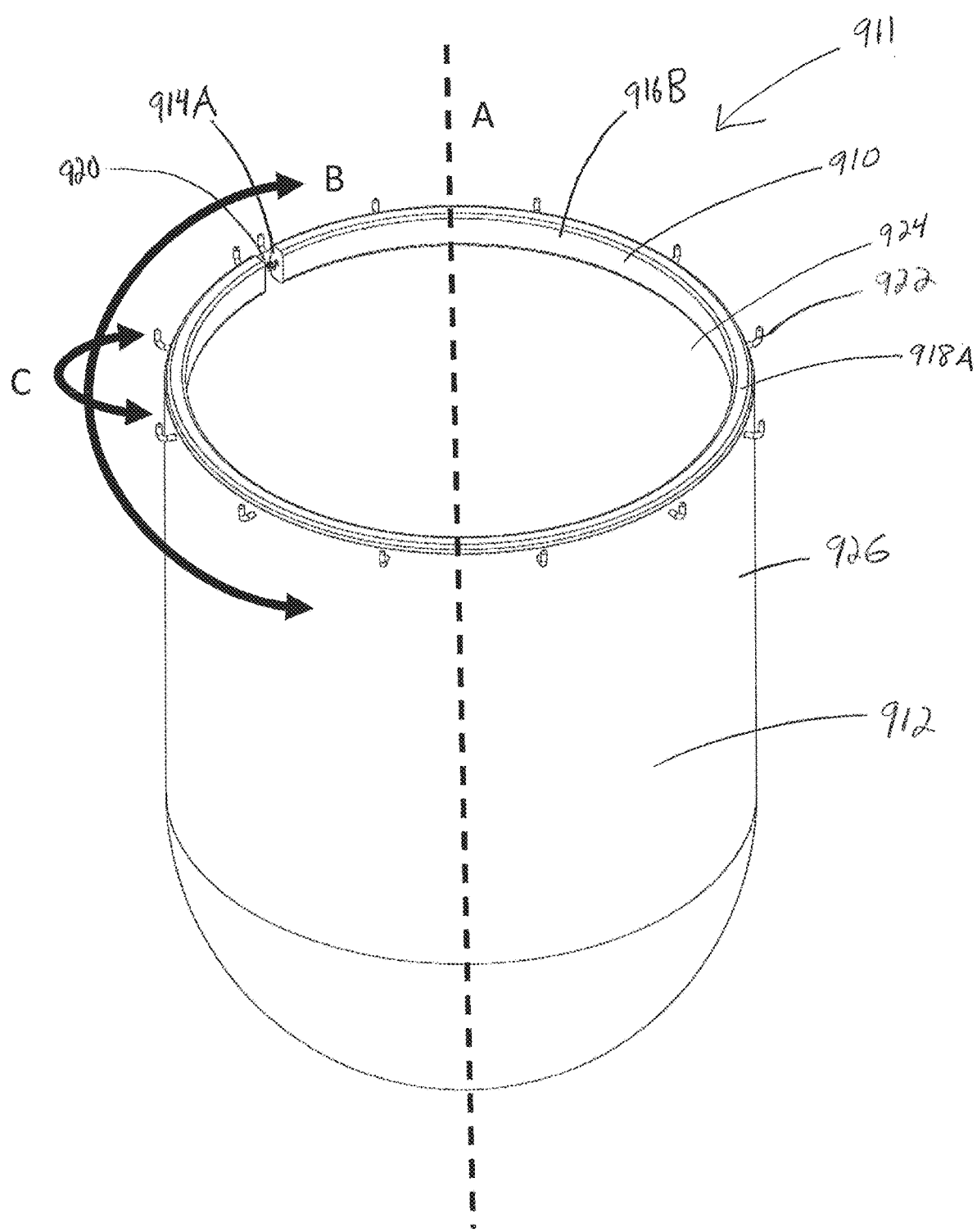
FIG. 88 is a perspective view of an exemplary bag assembly, in accordance with aspects of the present disclosure.
Figure 89:
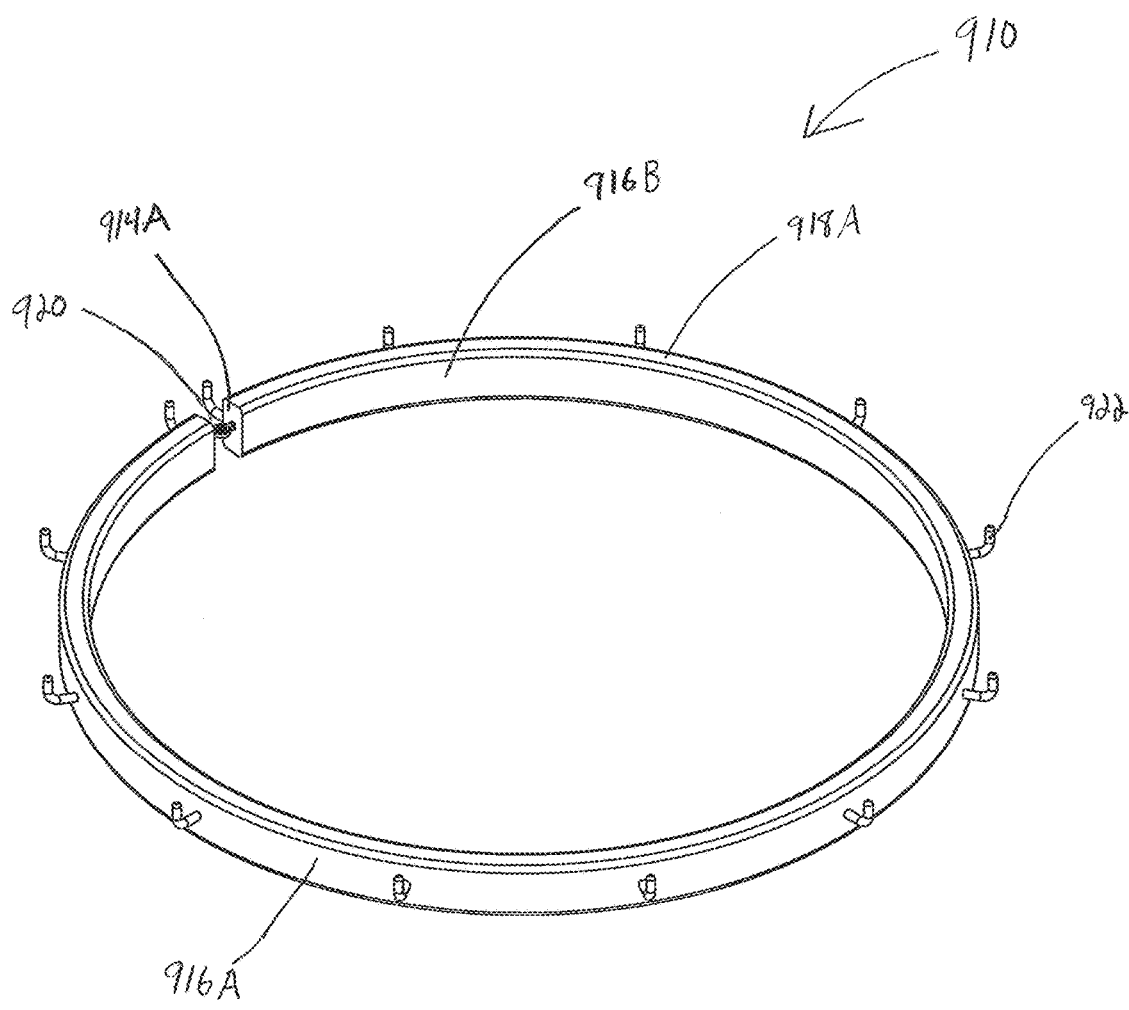
FIG. 89 is a perspective view of a retractor ring of the bag assembly of FIG. 88, in accordance with aspects of the present disclosure.
Figure 90:
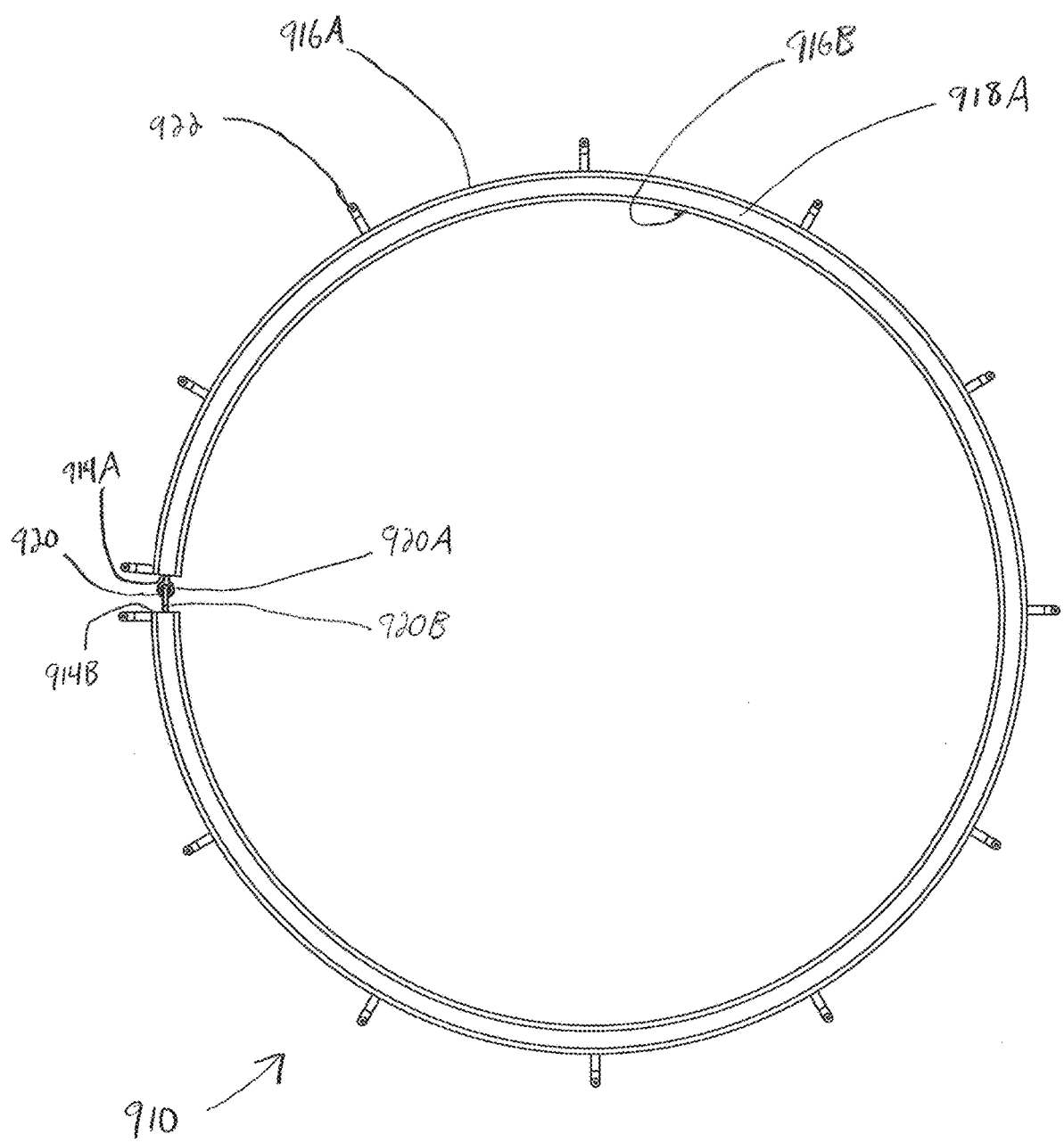
Figure 9Z:
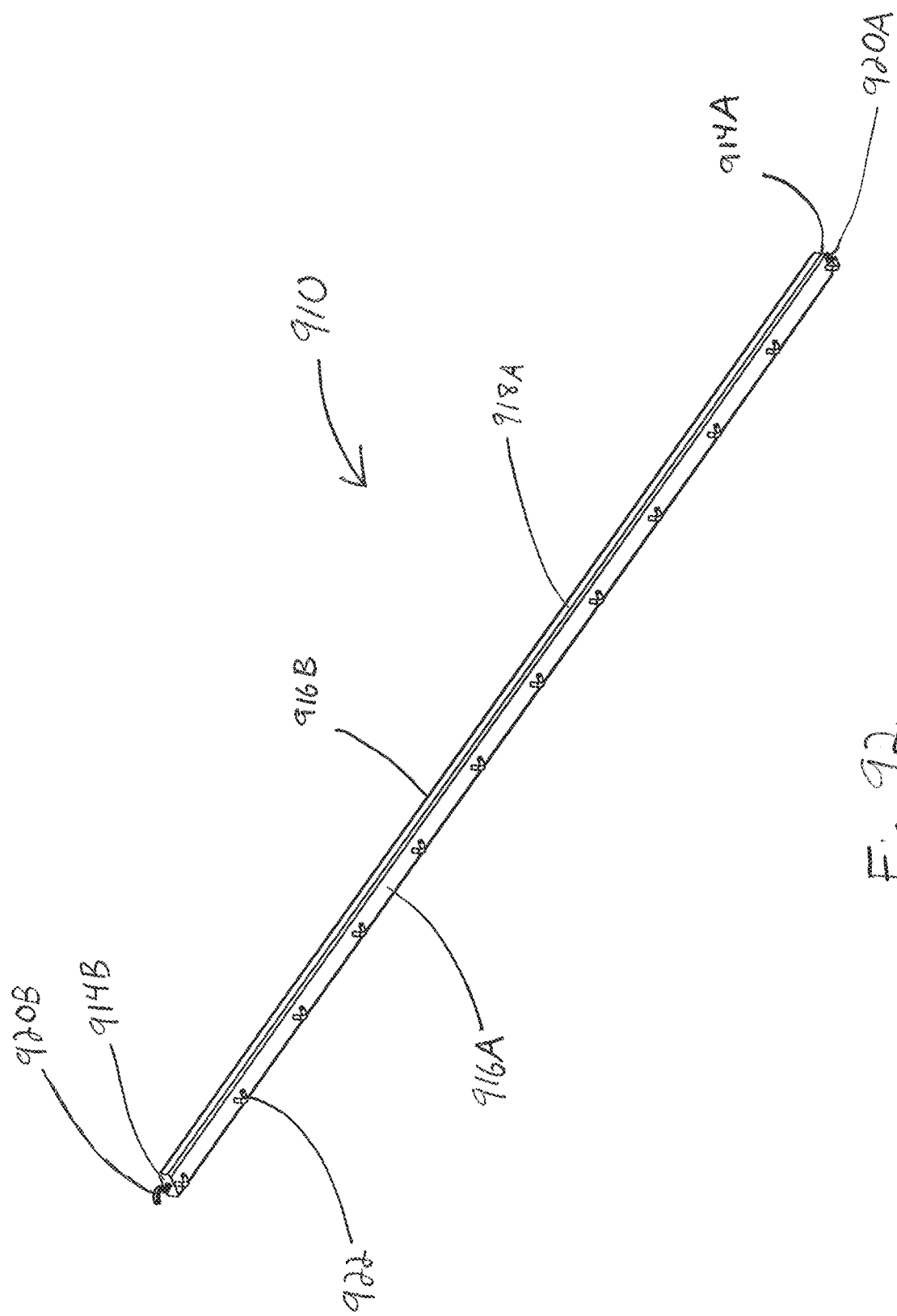
Figure 95:
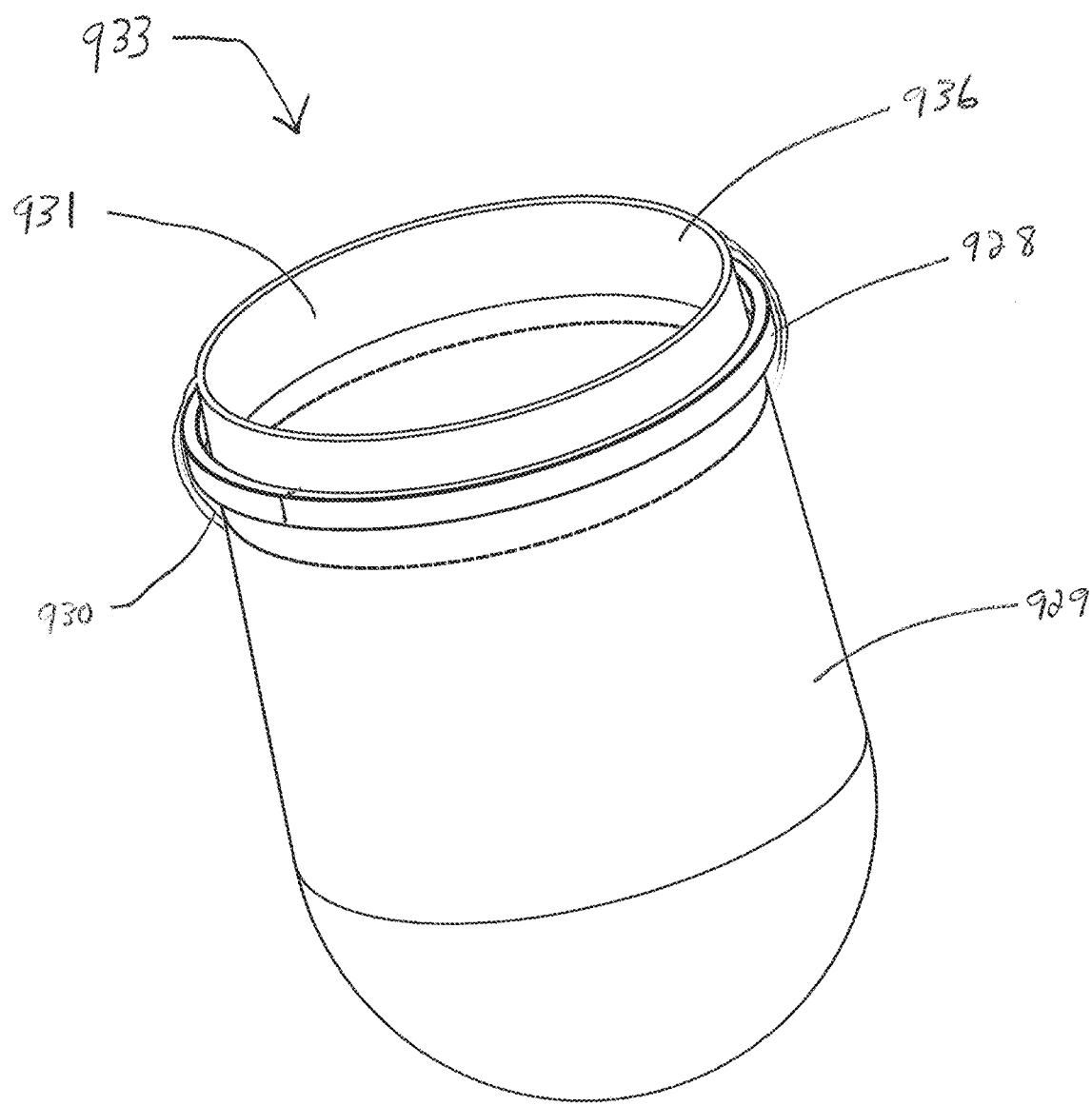
FIG. 95 is a perspective view of another exemplary bag assembly, in accordance with aspects of the present disclosure.
Figure 96:
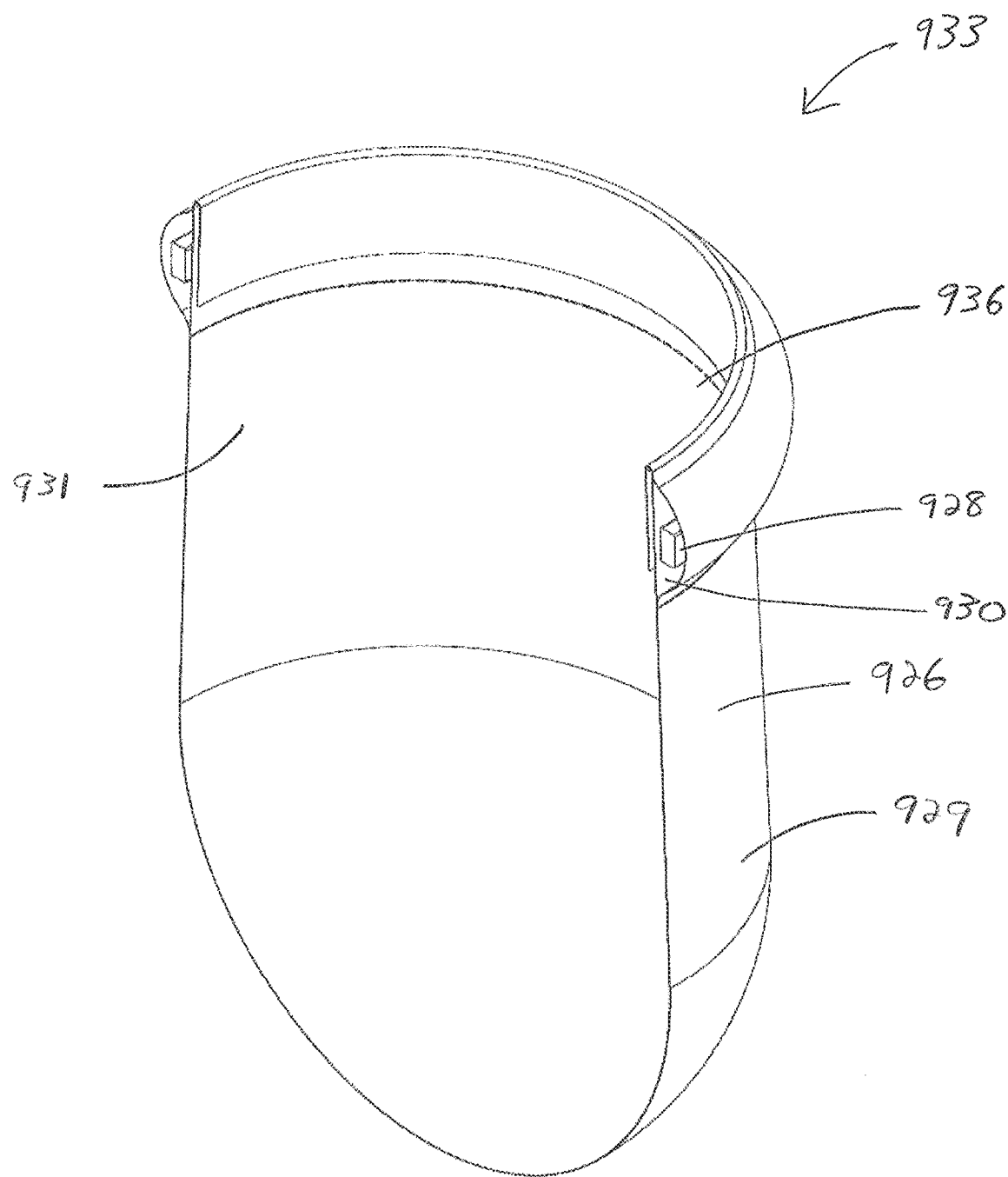
FIG. 96 is a cross-sectional perspective view of the bag assembly of FIG. 95, in accordance with aspects of the present disclosure.
Figure 97:
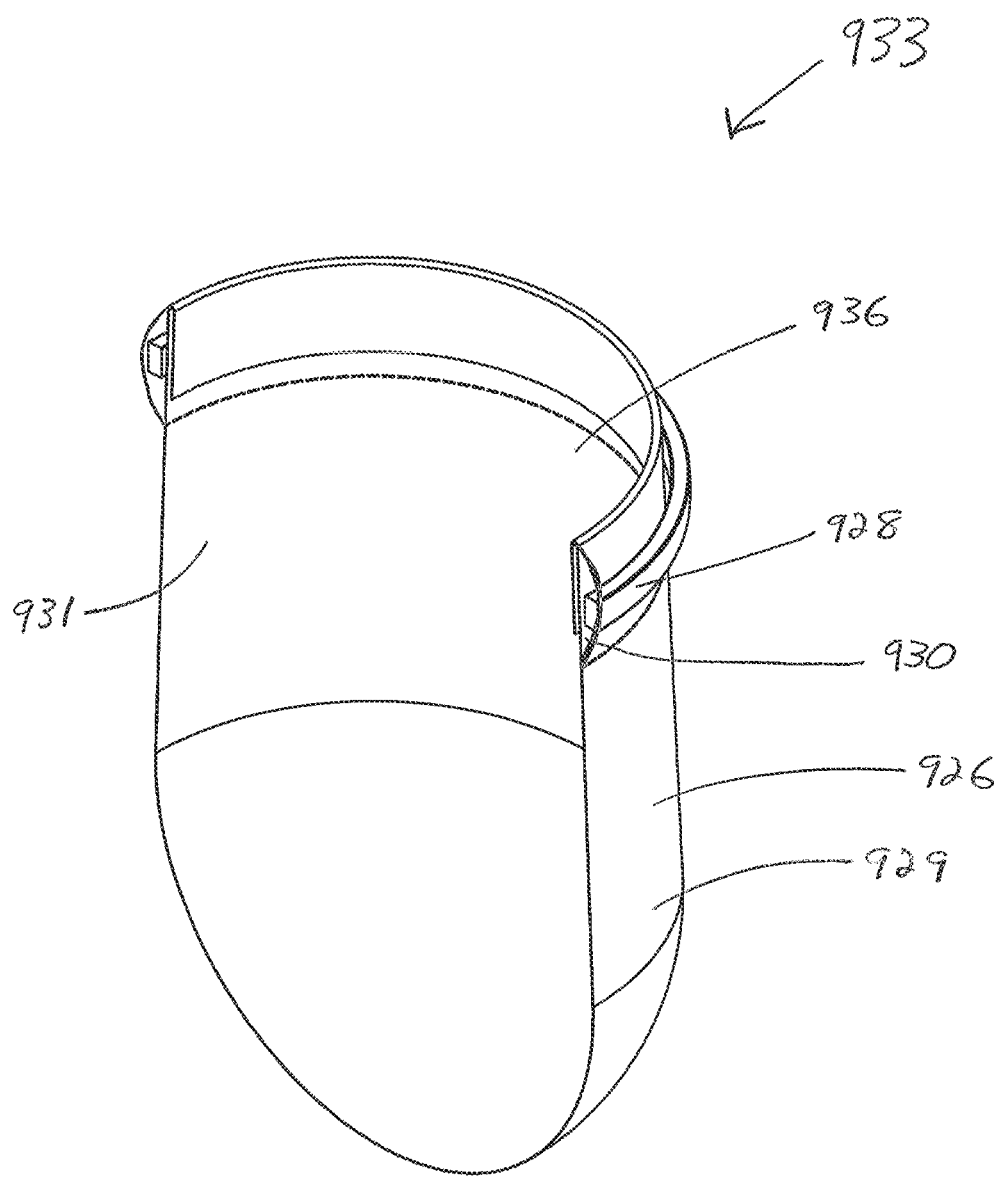
FIG. 97 is another cross-sectional perspective view of the bag assembly of FIG. 95, in accordance with aspects of the present disclosure.

FIG. 87 shows a cutting element 900 including a screw 902 with external threading 904, and a blade 906 that is coupled to the screw 902. Blade 906 may ride along threading 904. Screw 902 may be screwed into a tissue specimen 908, which may be contained in any of the aforementioned bags, and blade ride along threading 904 to cut tissue specimen 908.

In another example, any of the aforementioned mesh layers may be used to cut tissue. This may be achieved by pulling the mesh layers against tissue contained therein until the struts of the mesh layers cut into the tissue. The struts may include one or more sharpened edges to facilitate their entry into the tissue.

In another example, any of the aforementioned cutting elements may be operatively coupled to a transducer (not shown) that may vibrate one or more portions of the cutting elements at a high frequency (e.g., at an ultrasonic frequency). This vibration may facilitate cutting of tissue by the cutting elements. Additionally or alternatively, any of the aforementioned cutting elements may be operatively coupled to an electrosurgical unit that may provide electrical energy to one or more electrode portions of the cutting elements. Once electrified, the electrode portions may be able to cut through tissue more easily.

FIGS. 88-94B show aspects of an exemplary bag assembly 911. Bag assembly 911 may include a bag 912 and a retractor ring 910. For reference purposes, a central longitudinal axis (A) of bag assembly 911, bag 912, and/or retractor ring 910; a toroidal direction (B) of retractor ring 910, and a poloidal direction of retractor ring 910, also are shown. A central toroidal axis (not shown) of retractor ring 910 may include an axis running through a center of retractor ring 910 in toroidal direction B. When retractor ring 910 rotates (e.g., everts and/or inverts) about its central toroidal axis, the retractor ring 910 is rotating in the poloidal direction. These axes and directions also may be applicable to the other retractor rings disclosed herein.

Retractor ring 910 is shown in greater detail in FIGS. 89-92. Retractor ring 910 may include two end faces 914A and 914B (see, e.g., FIG. 90), two side faces 916A and 916B (see, e.g., FIG. 89), a top face 918A, a bottom face 918B (see, e.g., FIG. 91), a joining arrangement 920 (see, e.g., FIG. 90), and one or more hooks 922 (see, e.g., FIG. 89). One or more of the edges of retractor ring 910, formed where the various faces intersect, may be beveled, rounded, convex, or concave. Retractor ring 910 may be separate from bag 912, at least initially, and may be coupled to bag 912 when in use. It is contemplated, for example, that retractor ring 910 and bag 912 may be individual components of a kit.

When retractor ring 910 is coupled to bag 912 (see, e.g., FIG. 88), side face 916A may contact an interior surface 924 of bag 912. End faces 914A and 914B may extend transverse (e.g., substantially perpendicular) to side faces 916A and 916B. Joining arrangement 920 may link end face 914A to end face 914B to keep retractor ring 910 in its annular or toroidal form. Joining arrangement 920 may include, for example, one or more of an eye bolt, eye lag, u-bolt, j-bolt, and/or any other suitable fastener, that may be coupled to at least one of end faces 914A and end 914B, to secure end face 914A to end face 914B. In one example, joining arrangement 920 may include a first joining member 920A (see, e.g., FIG. 90) on end face 914A that may be selectively coupled to a second joining member 920B on end face 914B. Joining arrangement 920 may be used to constrain retractor ring 910 in its annular or toroidal configuration before, while, or after retractor ring 910 is coupled to bag 912.

Hooks 922 (see, e.g., FIG. 89), or other suitable fastening devices or materials on side face 916A, may couple retractor ring 910 to bag 912. Hooks 922 may curve or bend upward (proximally). The curve/bend may help ensure that retractor ring 910 and bag 912 stay coupled during rolling by preventing bag 912 from sliding off of hooks 922. Hooks 922 may be inserted into one or more apertures in bag 912, may puncture bag 912 to form apertures therein, and/or may be inserted into openings in a mesh bag (not shown) within bag 912 or used in place of bag 912. One advantage of having retractor ring 910 separate from bag 912, at least initially, is that retractor ring 910 need not be inserted into the subject's body with bag 912, allowing insertion of bag 912 through a smaller incision or opening. Further, retractor ring 910 will not be in the way while the tissue specimen is being inserted into bag 912, and/or while the proximal portion of bag 912 is being extracted from the subject's body. Rather, retractor ring 910 may be introduced after the proximal portion of bag 912 already has been withdrawn from the subject's body. It should be understood that the same advantage exists for the other embodiments of retractor ring described herein.

Retractor ring 910 may be rotated (e.g., inverted and/or everted) about its central toroidal axis to wrap bag 912 around retractor ring 910. Retractor ring 910 may move from one stable or equilibrium state to another one during rotation. An equilibrium state of retractor ring 910 is shown, for example, in FIGS. 88-90, where side faces 916A and 916B may extend substantially parallel to a central longitudinal axis of retractor ring 910. Retractor ring 910 may have two equilibrium states—a first equilibrium state where side face 916A faces radially-outwardly and side face 916B faces radially-inwardly, and a second equilibrium state where side face 916B faces radially-outwardly and side face 916A faces radially-inwardly. A non-equilibrium state of retractor ring 910 is not depicted, but may correspond to a configuration in which side faces 916A and 916B extend transverse (e.g., substantially perpendicular to) the central longitudinal axis of retractor ring 910. When retractor ring 910 is in the non-equilibrium state, internal forces in retractor ring 910 may bias retractor ring 910 to move toward an equilibrium state. As such, less of an external force may be needed to move retractor ring 910 from a non-equilibrium state to an equilibrium state than from an equilibrium state to a non-equilibrium state.

When retractor ring 910 is in its constrained configuration, and in an equilibrium state, one of side face 916A and side face 916B may face radially-outwardly, and may be in tension, while the other of side face 916A and side face 916B may face radially—inwardly, and may be in compression. The type of force associated with each of side faces 916A and 916B may reverse each time retractor ring 910 is rotated from one of its equilibrium states to the other.

Retractor ring 910 may have a tendency to straighten (see, e.g., FIGS. 92, 93A, and 94A). For example, retractor ring 910 may be self-biased to return to its expanded configuration in the absence of a constraining force holding retractor ring 910 in its annular or toroidal configuration. For example, retractor ring 910 may expand when joining arrangement 920 is undone. It may be easier, in some instances, for a user to connect retractor ring 910 to bag 912 when retractor ring 910 is in the expanded state than when retractor ring 910 is in the constrained state.

Rotating retractor ring 910 may roll a proximal portion of bag 912 onto retractor ring 910, and around retractor ring 910 in one or more layers, imparting tension in a distal portion of bag 912 that holds a tissue specimen. This may cause the distal portion to compress the tissue specimen. The user also may pull bag 912 proximally, by pulling retractor ring 910 proximally, to compress the distal portion of bag 912 on the tissue specimen, before, while, and/or after rolling bag 912 about retractor ring 910. Additionally or alternatively, the user may roll retractor ring 910 without pulling retractor ring 910 proximally.

FIGS. 95-100B show exemplary aspects of a bag assembly 933. Bag assembly 933 may include a bag 929 and a retractor ring 928. Bag 929 may include a channel 930 for receiving retractor ring 928, to couple retractor ring 928 to bag 929. Channel 930 may run transverse to a central longitudinal axis of bag 929. Channel 930 may project radially-outwardly from an exterior surface 926 (see, e.g., FIG. 96) of bag 929. Alternatively, channel 930 may project radially-inwardly from an interior surface 931 of bag 912. Channel 930 may be made of the same type of material as bag 929. Channel 930 may, for example, include a strip of material whose proximal and distal edges are sewn on, adhered to, or otherwise secured on/to exterior surface 926.

Channel 930 may have an opening (not shown), such as an aperture, slit, or other passage, for facilitating insertion of retractor ring 928 into channel 930. The user may slide retractor ring 928 into channel 930 while retractor ring 928 is in its expanded configuration (see, e.g., FIG. 100A). This insertion step may take place, for example, while the proximal portion of bag 929 is outside of the subject's body, and the distal portion of bag 929 is within the subject's body. Retractor ring 928 may bend into an annular or toroidal configuration to conform to channel 930. Alternatively, channel 930 may not have an opening, and retractor ring 928 may be pre-mounted within channel 930.

Channel 930 may be proximate to a bag opening 936 (see, e.g., FIG. 95) to assist the user with rolling a proximal portion of bag 929 and retractor ring 928. In use, the proximal portion of bag 929 may be wrapped around retractor ring 928, in one or more layers, by rotating (e.g., everting and/or inverting) retractor ring 928. Additionally or alternatively, the proximal portion of bag 929 may be wrapped around retractor ring 928 by rolling the proximal portion poloidally about retractor ring 928, in one or more layers, without rotating retractor ring 928.

Figure 98:
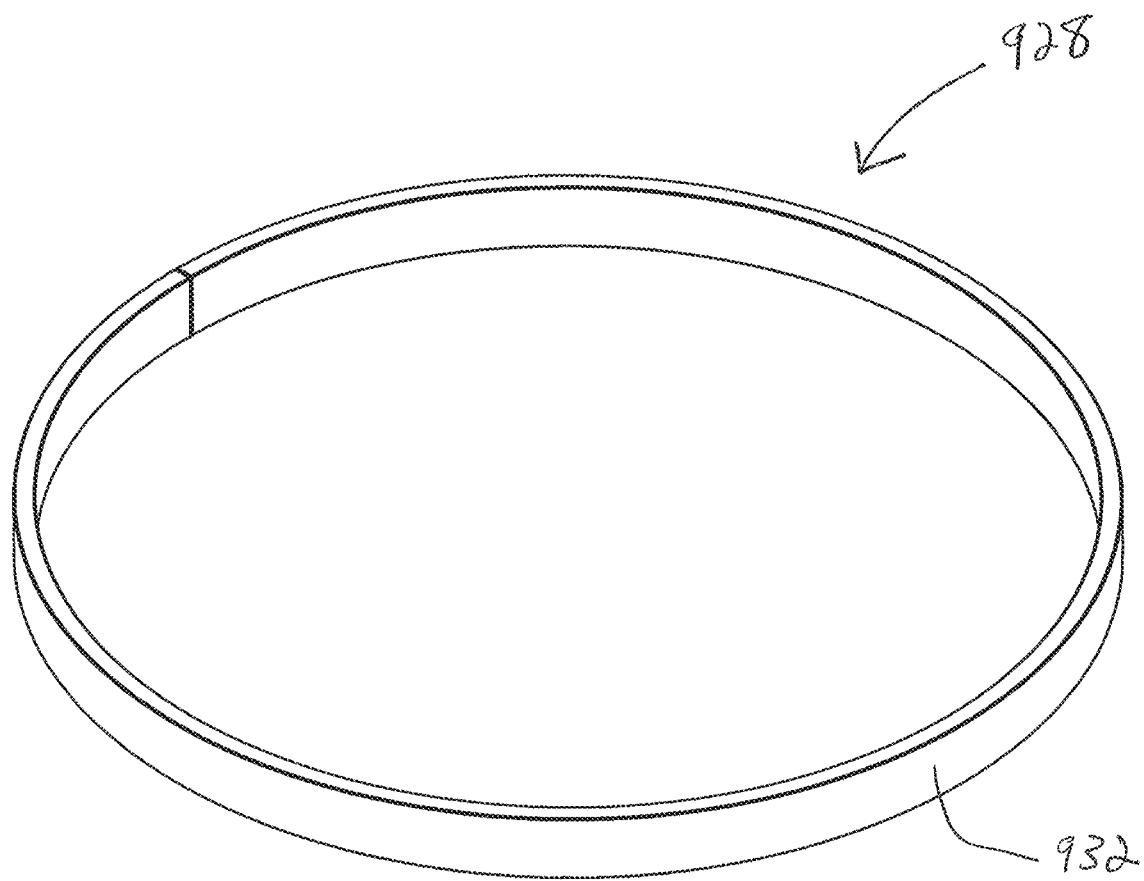
FIGS. 98, 99A, and 99B are perspective, top, and side views, respectively, of a retractor ring of the bag assembly of FIG. 95, in accordance with aspects of the present disclosure.
Figure 99A:
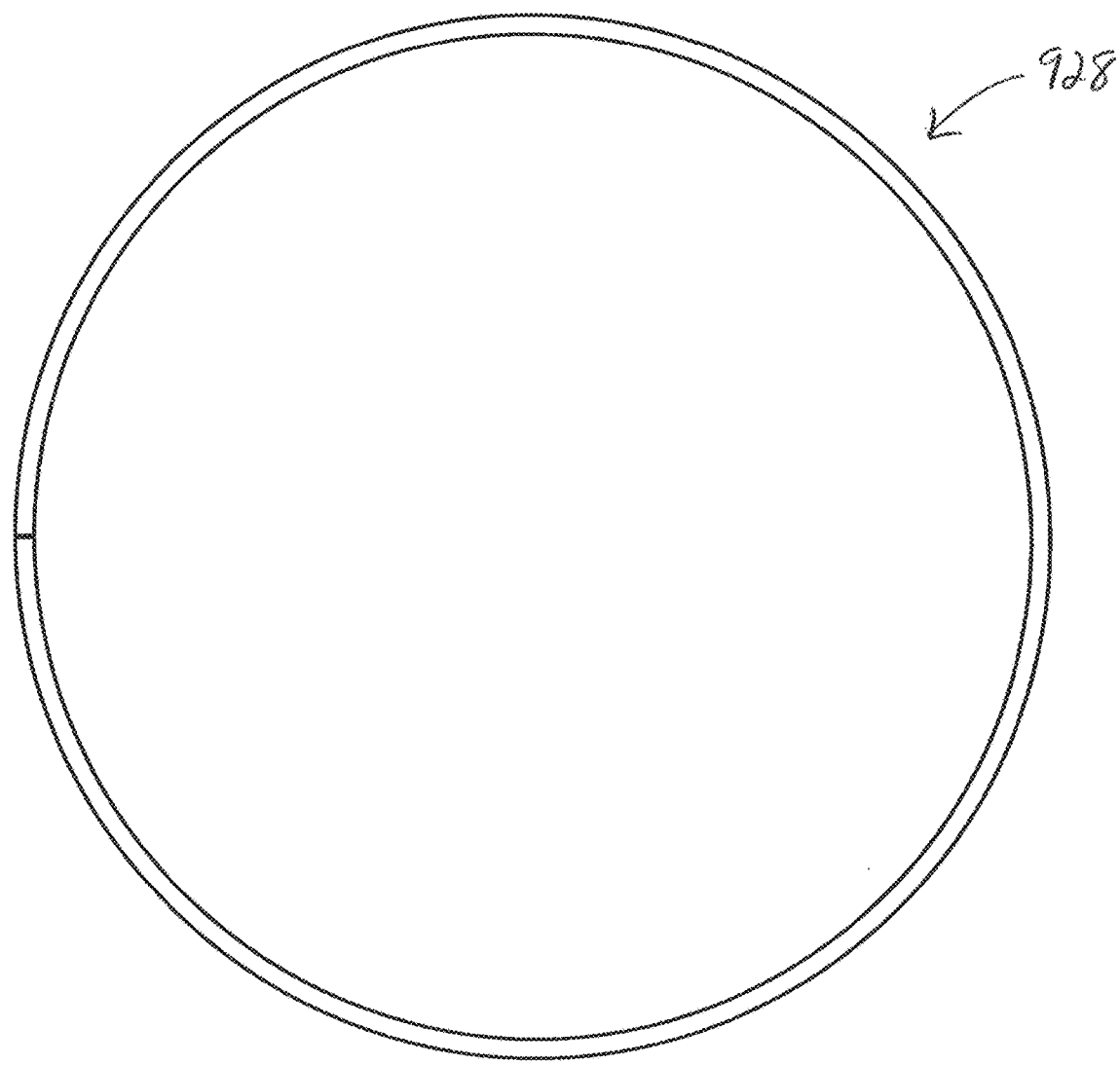
Figure 99B:
Figure 101:
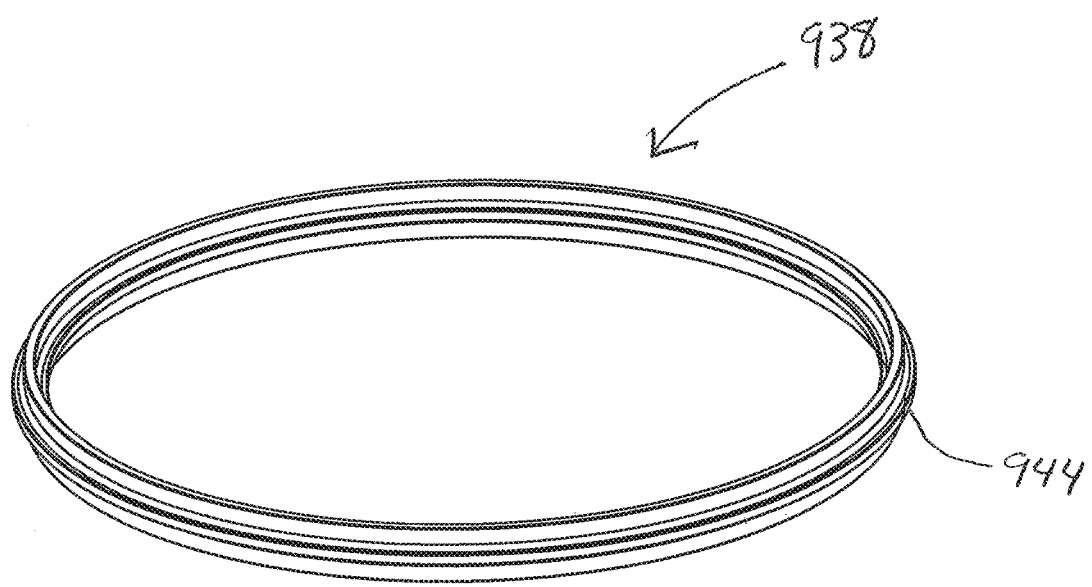
FIG. 101 is a perspective view of another exemplary retractor ring, in accordance with aspects of the present disclosure.

FIGS. 98-100 show aspects of retractor ring 928 in greater detail. In one example, retractor ring 928 may be similar to retractor ring 910 (FIG. 89), except retractor ring 928 may be free of hooks 922 and/or joining arrangement 920 to facilitate inserting retractor ring 928 into channel 930. End faces 934A and 934B (see, e.g., FIG. 100A) of retractor ring 928 may be coupled to give retractor ring 928 an annular or toroidal shape. End faces 934A and 934B may be coupled by glue or other adhesive. Additionally or alternatively, retractor ring 928 may be constrained in its annular or toroidal configuration by channel 930, in which case glue or adhesive may be omitted.

Figure 105:
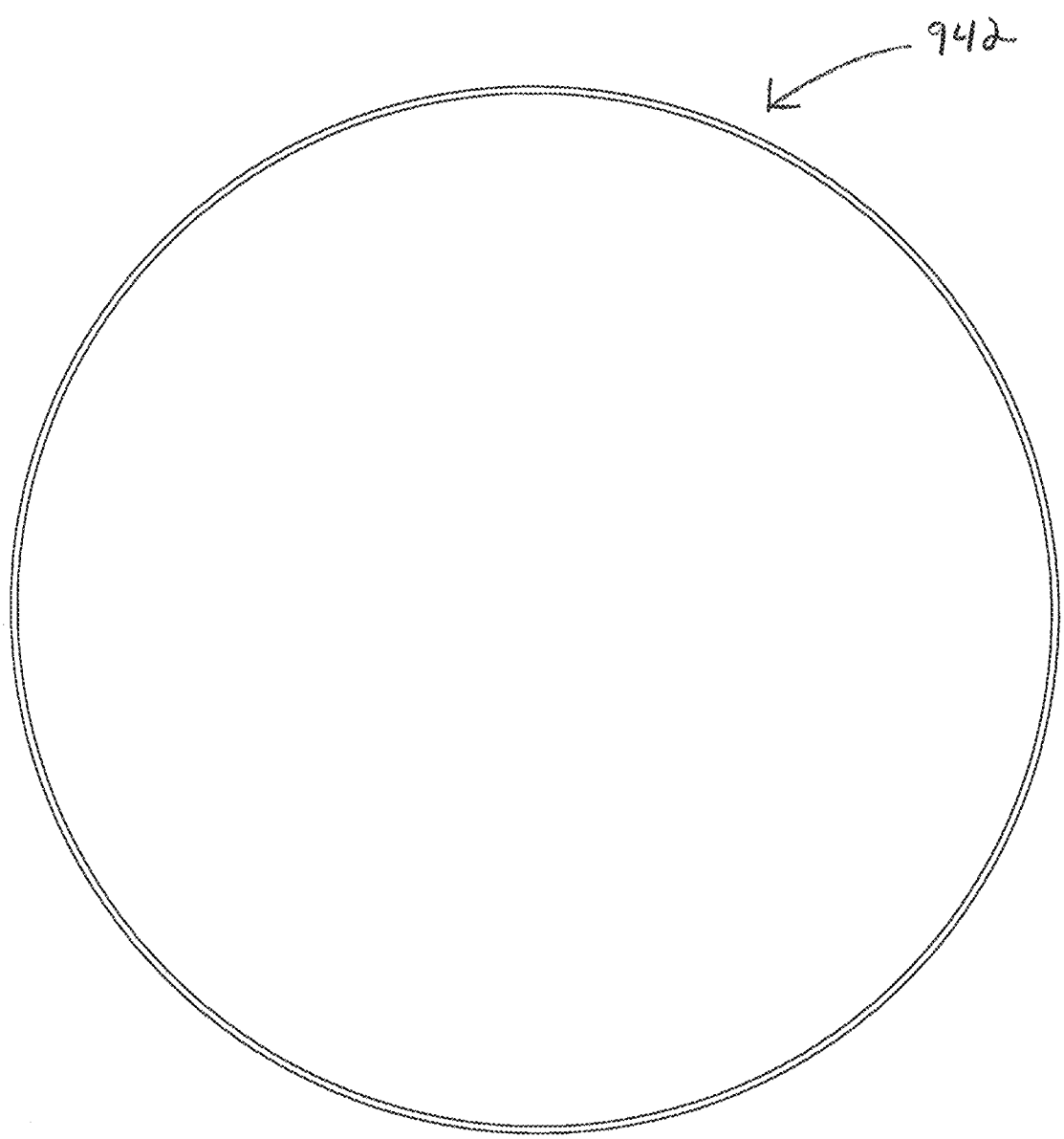
FIG. 105 is a top view of an exemplary inner reinforcement ring, in accordance with aspects of the present disclosure.

FIGS. 101-104B show aspects of an exemplary retractor ring 938. Retractor ring 938 may, at least initially, be separate from any of the bags (not shown) disclosed herein, but may be coupled to a proximal portion of the bag when the proximal portion of the bag is to be rolled. Once coupled to the bag, retractor ring 938 may be rotated (e.g., inverted and/or everted) to roll the proximal portion of the bag onto retractor ring 938 in one or more layers, thereby tightening a distal portion of the bag around a tissue specimen (not shown). In one example, retractor ring 938 may include an inner reinforcement ring 942 (see, e.g., FIG. 105) in its center or core that may increase the strength and/or stiffness of retractor ring 938. Inner reinforcement ring 942 may help retractor ring 938 maintain its annular or toroidal shape even when being subjected to forces exerted on retractor ring 938 by the user and/or the bag. Inner reinforcement ring 942 may slidably engage the rest of retractor ring 938, such that inner reinforcement ring 942 may not evert or invert as the rest of retractor ring 938 rotates poloidally about inner reinforcement ring 942.

Figure 102:
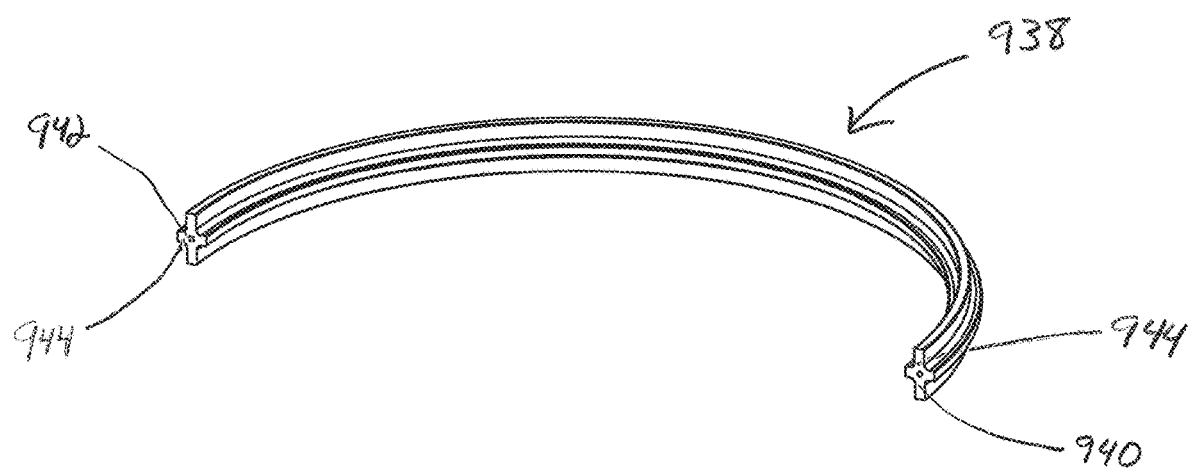
FIG. 102 is a cross-sectional perspective view of the retractor ring of FIG. 101, in accordance with aspects of the present disclosure.
Figure 103A:
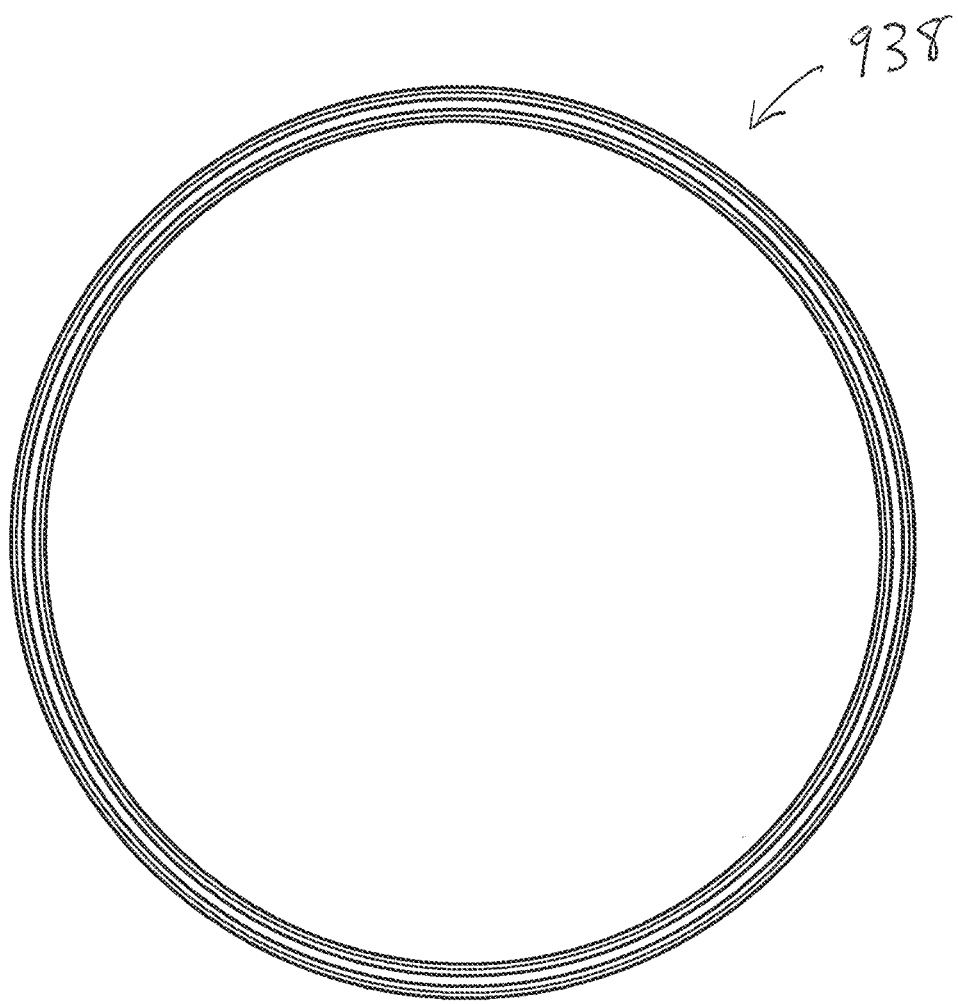
Figure 103B:
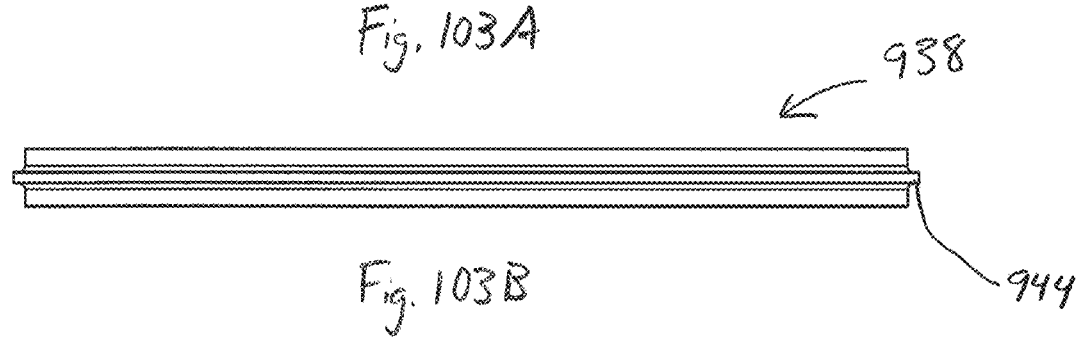

Retractor ring 938 may have a cross-shaped cross-section 940 (see, e.g., FIG. 102). More specifically, retractor ring 938 may have four splines 944 directed radially outwardly from its core. A first pair 944A of splines 944 may extend in opposite directions. A second pair 944B of splines 944 may also extend in opposite directions. The first pair 944A may extend transverse to the second pair 944B. For example, the first pair 944A may extend substantially perpendicular to the second pair 944B. Some of the splines 944 may be longer than the other splines 944. For example, the first pair 944A may be longer than the second pair 944B. Splines 944 may be rectangular in shape. Splines 944 may assist the user with rolling the ring by providing grips or holds by which to manipulate retractor ring 938, and/or also may assist with gripping the bag.

The retractor ring 938 may be coupled to the bag with hooks (similar to hooks 922 of FIG. 88), glue, or any other suitable means of attachment. Alternatively, retractor ring 938 may be coupled to the bag without a separate attachment means. For example, the user may press the proximal portion of the bag against retractor ring 938, start to roll the proximal portion of the bag about retractor ring 938 by inverting and/or everting retractor ring 938, then tuck a proximal end of the bag 912 under an oncoming rolled layer of the bag as the user continues to roll additional layers of the bag about retractor ring 938. Additionally or alternatively, retractor ring 938 may be inserted into or otherwise positioned in a channel (not shown, but similar to channel 930 of FIG. 96) on the bag.

FIGS. 106-116 show aspects of an exemplary retractor ring 946 that has an inner ring 948 (see, e.g., FIG. 107) and an outer ring 950. The act of rotating (e.g., inverting and/or everting) outer ring 946 around inner ring 948, may roll a bag (not shown) about retractor ring 946 in one or more layers. As with the other retractor rings and bags disclosed herein, retractor ring 946 may, at least initially, be separate from the bag. Retractor ring 946 may be coupled to a proximal portion of the bag in a similar manner to the other retractor rings, at the stage of a procedure where the proximal portion of the bag is to be rolled.

Figure 110:
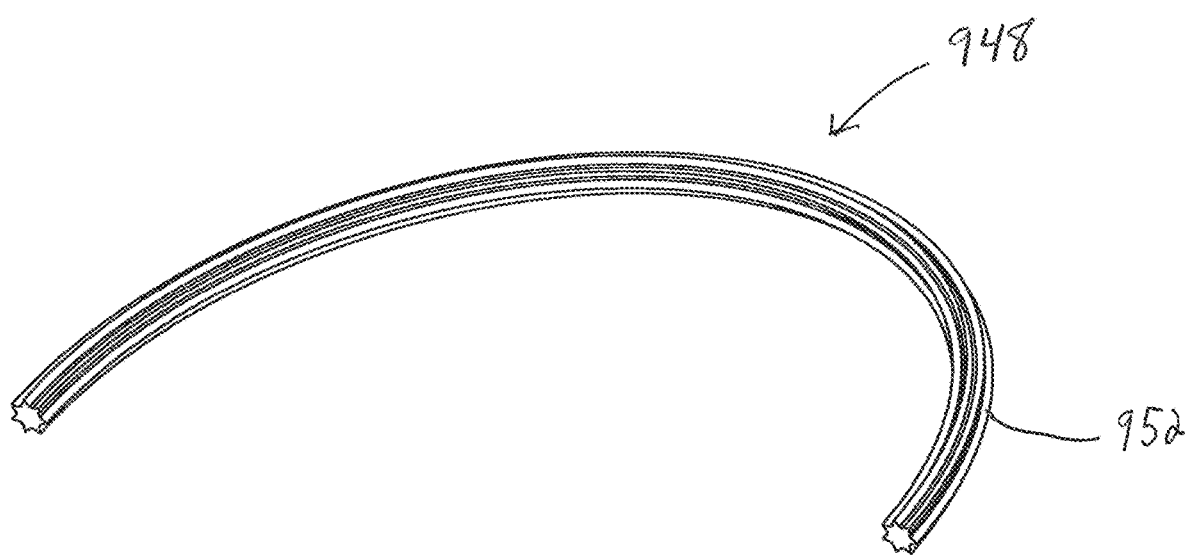
Figure 111A:
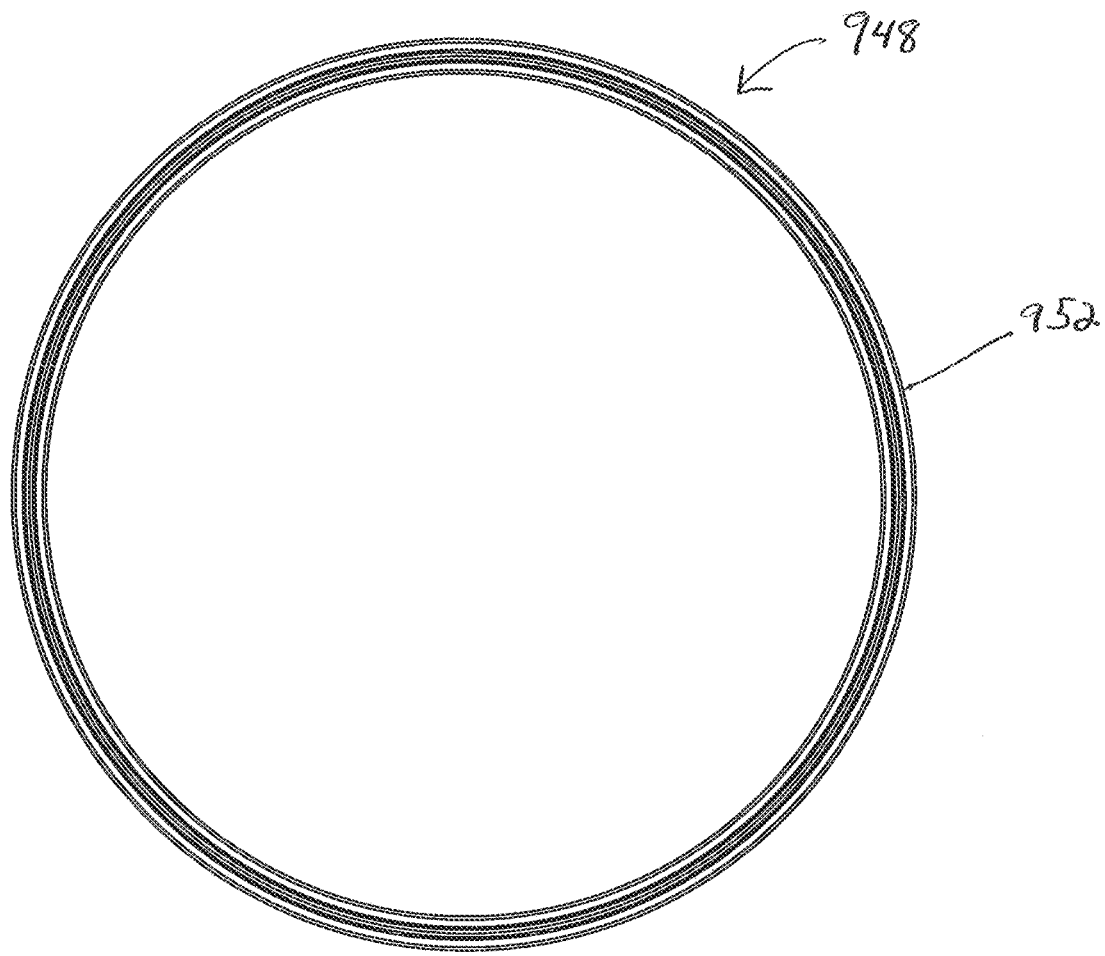
Figure 111B:
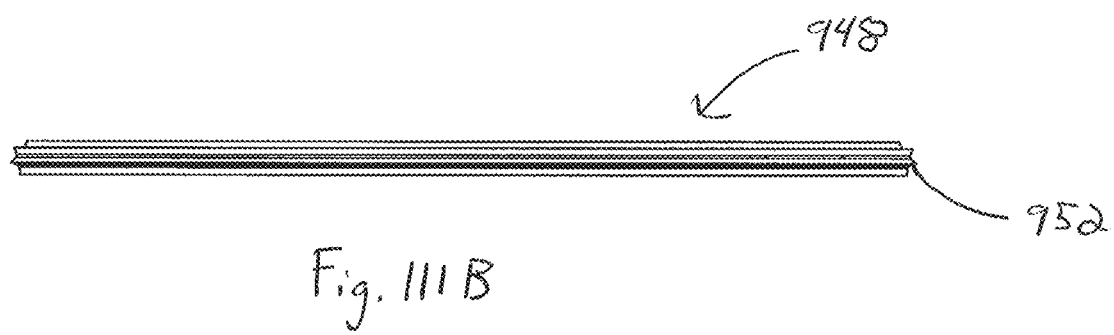

Inner ring 948 may have a plurality of radially-outwardly extending toroidal splines 952 (see, e.g., FIGS. 110 and 113). Splines 952 may form toroidal peaks 956 and troughs 954 that alternate about inner ring 948 in the poloidal direction. Splines 952 may have angled faces 955A and 955B, and/or may be triangular, convex, helical, crowned, parallel, involute, or ball splines. Inner ring 948 may be more rigid than outer ring 950 such that outer ring 950 may deform and rotate (e.g., invert and/or evert) around inner ring 948. The rigidity of inner ring 948 also may help retractor ring 946 keep its annular or toroidal shape.

Outer ring 950 may have a plurality of radially-inwardly extending toroidal splines 958, forming toroidal peaks 961 and troughs 959 that alternate about outer ring 950 in the poloidal direction (see, e.g., FIGS. 115B and 116). Splines 958 may circumscribe a channel 960 running through the center of outer ring 950, channel 960 being configured to receive inner ring 948. Channel 960 and inner ring 948 may be complementary in shape. Outer ring 950 may be more flexible than inner ring 948, and splines 958 may be capable of sliding over and across splines 952. Outer ring 950 may be coupled to the bag in any of the ways described in this disclosure (e.g., with hooks, glue, Velcro, adhesive, insertion into a channel, and/or other suitable form of coupling).

In use, retractor ring 946 may be coupled to a proximal portion of a bag in any of the ways described herein with respect to the other embodiments. Once coupled, outer ring 950 may rotate poloidally around inner ring 948 to roll the bag about outer ring 950. The flexibility of outer ring 950 may facilitate deformation and disengagement of splines 958 of outer ring 950 relative to splines 952 of inner ring 948. Outer ring 950 may lock onto inner ring 948 at certain orientations where peaks 961 of outer ring 950 are seated in troughs 954 of inner ring 948, and peaks 956 of inner ring 948 are seated in troughs 959 of outer ring 950. When in between the locking orientations, outer ring 950 may be inherently-biased to rotate into a locking orientation.

FIGS. 117-130 show aspects of another exemplary retractor ring 962 having an inner ring 964 (see, e.g., FIG. 118) and an outer ring 966. Retractor ring 962 may operate in a manner similar to retractor ring 946 (see, e.g., FIG. 106). As with the other retractor rings and bags disclosed herein, retractor ring 962 may, at least initially, be separate from the bag. Retractor ring 962 may be coupled to a proximal portion of the bag in a similar manner to the other retractor rings, at the stage of a procedure where the proximal portion of the bag is to be rolled.

Splines 968 (see, e.g., FIG. 126) of inner ring 964 (like splines 952 of inner ring 948) may have two faces. A difference between inner ring 948 and inner ring 964 is that one of the faces, a face 965A, of spline 968, may be steeper than a face 965B. Outer ring 966 of retractor ring 962 may be similar to outer ring 950 of retractor ring 946. However, splines 969 of outer ring 966 (see, e.g., FIG. 130) may be shaped such that they may be complementary to splines 968 of inner ring 964. For example, peaks 972 and troughs 974 of outer ring 966, surrounding an outer ring channel 976 of outer ring 966, may interlock in a complementary manner with troughs 974 and peaks 972, respectively, of inner ring 964 (see, e.g., FIG. 121). Like splines 968 of inner ring 964, splines 969 of outer ring 966 may have two faces 975A and 975B, with face 975A being steeper than face 975B.

Engagement between steeper faces 965A and 975A may prevent or otherwise limit rotation of outer ring 966 in one direction because steeper faces 965A and 975A may not be slidably forced past each other. Rotation may be carried out in the opposite direction because less steep faces 965B and 975B may be slidably forced past each other more easily. This unidirectional rotation may facilitate rolling of the bag about retractor ring 962, while preventing or otherwise limiting unrolling of the bag off of retractor ring 962.

FIGS. 131A-139 show aspects of an exemplary retractor ring 978 having an inner ring 980 (FIG. 131B) and an outer ring 982. As with the other retractor rings and bags disclosed herein, retractor ring 978 may, at least initially, be separate from the bag. Retractor ring 978 may be coupled to a proximal portion of the bag in a similar manner to the other retractor rings, at the stage of a procedure where the proximal portion of the bag is to be rolled.

Outer ring 982 may be rotated (e.g., inverted and/or everted) about inner ring 980. Inner ring 980 may have a flat rectangular cross-sectional shape with rounded corners (see, e.g., FIG. 137). Radially-inner and radially-outer ends of inner ring 980 may form splines 984A and 984B that may extend substantially perpendicular to a central longitudinal axis of inner ring 980. Inner ring 980 may be stiffer than outer ring 982.

Outer ring 982 may have a channel 988 (see, e.g., FIG. 139) running through its center. Channel 988 may be circumscribed by radially-inwardly extending toroidal splines 989 of outer ring 982. Splines 989 may form alternating peaks 991 and troughs 993 extending in a poloidal direction about channel 988. In one example, peaks 991 and troughs 993 may give channel 988 a cross shape. Each of troughs 993 may be approximately ninety-degrees offset from an adjacent trough to provide similarly offset locking positions between inner ring 980 and outer ring 982. Opposing troughs 993 may be at least partially complementary to splines 984A and 984B of inner ring 980. Outer ring 982 may be in a stable state when splines 984 of inner ring 980 are received in troughs 993, and may be in an unstable state when splines 984 are in engagement with peaks 991. When outer ring 982 is in an unstable state with respect to inner ring 980, outer ring 982 may be inherently biased to rotate toward a stable state. It should be understood that outer ring 982 may be coupled to the bag at, for example, a proximal portion of the bag, in any manner described herein.

FIGS. 140-150 show aspects of an exemplary retractor ring 990. As with the other retractor rings and bags disclosed herein, retractor ring 990 may, at least initially, be separate from the bag. Retractor ring 946 may be coupled to a proximal portion of the bag in a similar manner to the other retractor rings, at the stage of a procedure where the proximal portion of the bag is to be rolled.

Retractor ring 990 may have an outer ring 992 that receives an inner ring 994 (see, e.g., FIG. 141). Inner ring 994 may be similar to, or identical to, inner ring 980 (FIG. 134A). Outer ring 992 may be similar to outer ring 982 (FIG. 138B), except outer ring 992 may include a central channel 996 surrounded by more splines 991 (and thus, more peaks 995 and troughs 993) than outer ring 982. The additional splines 991 may provide smaller increments between locking/stable orientations of inner ring 994 and outer ring 992, allowing for greater precision when rolling a bag around outer ring 982.

FIGS. 151-157 show aspects of an exemplary retractor ring 1002 having an inner ring 1004 (see, e.g., FIG. 152) and an outer ring 1006. As with the other retractor rings and bags disclosed herein, retractor ring 1002 may, at least initially, be separate from the bag. Retractor ring 1002 may be coupled to a proximal portion of the bag in a similar manner to the other retractor rings, at the stage of a procedure where the proximal portion of the bag is to be rolled.

Outer ring 1006 may be similar to, or identical to, outer ring 992 (FIG. 150). Inner ring 1004 may be similar to inner ring 994 (FIG. 146). A difference between retractor ring 1002 and retractor ring 990 may be that inner ring 1004 may have an additional pair of splines 1012 (see, e.g., FIG. 154B) to provide additional contact points between outer ring 1006 and inner ring 1004. The addition of splines 1012 may result in inner ring 1004 having a cross-shaped cross-sectional shape.

FIGS. 158-170B show aspects of an exemplary bag assembly having a retractor ring 1014 coupled to a bag 1015. As with the other retractor rings and bags disclosed herein, retractor ring 1014 may, at least initially, be separate from bag 1015. Retractor ring 1014 may be coupled to a proximal portion of bag 1015 in a similar manner to the other retractor rings, at the stage of a procedure where the proximal portion of bag 1015 is to be rolled.

Retractor ring 1014 may have an inner ring 1016 (see, e.g., FIG. 161) and an outer ring 1018. A proximal portion of bag 1015 may be clamped between inner ring 1016 and outer ring 1018, and inner ring 1016 may rotate (e.g., evert and/or invert) around outer ring 1018 to roll the proximal portion of bag 1015 about retractor ring 1014 in one or more layers.

Inner ring 1016 may have a groove 1020 on a radially-outward facing surface 1019. Groove 1020 may receive a proximal portion of bag 1015 and outer ring 1018. Inner ring 1016 may be more flexible than outer ring 1018. Outer ring 1018 may have a discontinuity 1021 (see, e.g., FIG. 169) to facilitate mounting of outer ring 1018 onto inner ring 1016. For example, the user may be able to move ends 1017A and 1017B of outer ring 1018 apart, to help position outer ring 1018 around inner ring 1016 and within groove 1020 of inner ring 1016. Outer ring 1018 may be self-biased such that ends 1017A and 1017B may move back toward each other in the absence of a deforming force, thereby securing outer ring 1018 (and bag 1015) within groove 1020.

FIGS. 158-161 show bag 1015 clamped between outer ring 1018 and inner ring 1016. In use, bag 1015 may be positioned around radially-outward facing surface 1019 of inner ring 1016, and then bag 1015 may be pressed into groove 1020 by outer ring 1018. Inner ring 1016 may rotate (e.g., invert and/or evert) about outer ring 1018. Since a proximal portion of bag 1015 may be clamped between inner ring 1016 and outer ring 1018, the proximal portion of bag 1015 may be rolled about outer ring 1018 to tighten bag 1015 around a tissue specimen in a distal portion of bag 1015. Additionally or alternatively, bag 1015 may be tightened by pulling bag 1015 proximally as far as possible relative to inner ring 1016 before clamping bag 1015 between inner ring 1016 and outer ring 1018. In another example, groove 1020 may be on a radially-inward facing surface of inner ring 1016, and outer ring 1018 may be inserted therein to clamp bag 1015 therein.

FIGS. 171-185C show aspects of an exemplary bag assembly 1023 including a retractor ring 1022 and bag 1015. As with the other retractor rings and bags disclosed herein, retractor ring 1022 may, at least initially, be separate from bag 1015. Retractor ring 1022 may be coupled to a proximal portion of bag 1015 in a similar manner to the other retractor rings, at the stage of a procedure where the proximal portion of the bag is to be rolled.

Retractor ring 1022 may include an inner ring 1024 and an outer ring 1026 (see, e.g., FIG. 172). Outer ring 1024 may snap onto inner ring 1024, or inner ring 1024 may snap into outer ring 1026, to clamp bag 1015 between outer ring 1026 and inner ring 1024. Outer ring 1026 may have an elliptical cross-sectional shape (see, e.g., FIG. 178). Outer ring 1026 may be in a stable or equilibrium state whenever a major axis of its elliptical cross-sectional shape extends substantially parallel to a central longitudinal axis of outer ring 1026. Outer ring 1026 may have a slot 1028 extending along its radially-inner surface. Slot 1028 may open into a passage 1029 extending through a center of outer ring 1026. Slot 1028 may include sloped edges 1025A and 1025B to facilitate entry of inner ring 1024 through slot 1028 and into passage 1029. Engagement between inner ring 1024 and sloped edges 1025A and 1025B may expand a width of slot 1028. Passage 1029 may be at least partially complementary to inner ring 1024. Inner ring 1024 also may have an elliptical cross-sectional shape, smaller than, but similar to, outer ring 1026.

In use, bag 1015 may be placed around inner ring 1024, and then outer ring 1026 may be snapped onto inner ring 1025 and bag 1015, to clamp bag 1015 between inner ring 1025 and outer ring 1026. Alternatively, bag 1015 may be positioned across slot 1028 of outer ring 1026, and then inner ring 1024 may be snapped into slot 1028 and passage 1029 of outer ring 1026, to clamp bag 1015 between inner and outer rings 1024 and 1026. Once retractor ring 1022 is coupled to bag 1015, bag 1015 may be rolled around retractor ring 1022 by rotating (e.g., everting and/or inverting) retractor ring 1022 as a whole, or alternatively, by rotating (e.g., everting and/or inverting) outer ring 1026 about inner ring 1024. The elliptical cross-sectional shape of inner ring 1024 and outer ring 1026 may facilitate rolling of bag 1015 about retractor ring 1022 in discrete amounts as retractor ring 1022 seeks stable or equilibrium orientations where the major axis of inner ring 1024 and/or of outer ring 1026 may be substantially parallel to the central longitudinal axis retractor ring 1022. When in an unstable or non-equilibrium state, retractor ring 1022 may be inherently biased toward the stable or equilibrium state. Both of inner and outer rings 1024 and 1026 may be flexible enough to rotate as a unit to roll bag 1015. Alternatively, inner ring 1024 may be more rigid than outer ring 1026, and outer ring 1026 may rotate about inner ring 1024.

FIGS. 186-188 show aspects of an exemplary bag assembly 1033 having a retractor ring 1030 and bag 1015. As with the other retractor rings and bags disclosed herein, retractor ring 1030 may, at least initially, be separate from bag 1015. Retractor ring 1030 may be coupled to a proximal portion of bag 1015 in a similar manner to the other retractor rings, at the stage of a procedure where the proximal portion of bag 1015 is to be rolled.

Retractor ring 1030 may include an inner ring 1032 and an outer ring 1034. Outer ring 1034 may engage inner ring 1032 to clamp bag 1015 between outer ring 1034 and inner ring 1032. Inner ring 1032 may have a rectangular cross-sectional shape. In a stable or equilibrium state of inner ring 1032, side faces 1035 of inner ring 1032 may extend substantially parallel to a central longitudinal axis of inner ring 1032, and end faces 1037 of inner ring 1032 may extend transverse to (e.g., substantially perpendicular to) the central longitudinal axis. A radially-outwardly facing side face (hidden behind outer ring 1034 in FIGS. 186-188) of inner ring 1032 may engage bag 1015, clamping bag 1015 against a radially-inwardly facing side face (also hidden from view in FIGS. 186-188) of outer ring 1034.

Outer ring 1034 may have a shape similar to inner ring 1032, and a similar stable or equilibrium state. Outer ring 1034 may include a buckle 1036 on one side that may open to expand outer ring 1034 (to facilitate insertion of bag 1015 and inner ring 1032 into outer ring 1034) and close to constrict outer ring 1034 (to force outer ring 1034 against bag 1015 and inner ring 1032). Buckle 1036 may include a hinged actuation lever for selectively expanding and contracting outer ring 1034. Buckle 1036 may include a clasp, toggle clip, toggle buckle, lever, snap, button, spring loaded clasp, ratchet action clasp, a power clamp, a screw mechanism, a push-pull clamp, C-clamp, and/or any other suitable fastening means to selectively tighten and loosen outer ring 1034 relative to inner ring 1032.

Once outer ring 1034 is clamped onto bag 1015 and inner ring 1032, retractor ring 1030 may be rotated (e.g., everted and/or inverted) about its toroidal axis to wrap bag 1015 around ring retractor 1030 in one or more layers. It is contemplated that, in one example, inner ring 1032 and outer ring 1034 may be made of the same material, and thus, may have the same degree of flexibility. Additionally or alternatively, bag 1015 may be tightened another way. For example, a proximal portion of bag 1015 may be pulled proximally through a gap between an expanded outer ring 1034 and inner ring 1032. This pulling may create tension in a distal portion of bag 1015 that houses a tissue specimen. When a desired degree of tension has been imparted, the user may constrict outer ring 1034, by closing buckle 1036, to clamp bag 1015 against inner ring 1032. This process may be repeated one or more times during a procedure to pull more of bag 1015 out of the subject's body, and then secure bag 1015, thereby increasing tension in the distal portion of bag 1015. In such a scenario, inner ring 1032 and outer ring 1034 may have different degrees of stiffness. For example, outer ring 1034 may be more flexible than inner ring 1032. It is also contemplated that this pulling/sliding approach to tightening bag 1015 may be used in combination with the aforementioned rolling approach, or in place of it.

FIGS. 189-194B show aspects of an exemplary bag assembly 1037 having a retractor ring 1038 and bag 1015. As with the other retractor rings and bags disclosed herein, retractor ring 1038 may, at least initially, be separate from bag 1015. Retractor ring 1038 may be coupled to a proximal portion of bag 1015 in a similar manner to the other retractor rings, at the stage of a procedure where the proximal portion of bag 1015 is to be rolled.

Retractor ring 1038 may be similar to inner ring 1032 (FIGS. 186-188). Retractor ring 1038 may include an adhesive surface 1040 that may adhere to an interior surface 1041 of bag 1015 to couple retractor ring 1038 to bag 1015. Adhesive surface 1040 may help the user to easily and quickly couple retractor ring 1038 to bag 1015. Prior to application of retractor ring 1038 onto bag 1015, a removable strip 1042 may cover adhesive surface 1040. Removable strip 1042 may be peeled off by the user (see, e.g., FIG. 192) to expose adhesive surface 1040, so adhesive surface 1040 can be applied to any portion of interior surface 1041 of bag 1015 including, for example, a proximal portion of interior surface 1041. The adhesive may be an epoxy, polyurethane, polyimide, or other type of glue or adhesive. The adhesive may be pressure-sensitive, heat-sensitive, or may be specifically formulated in some other way to facilitate adherence to bag 1015.

Once retractor ring 1038 is coupled to bag 1015, the user may rotate (e.g., evert and/or invert) retractor ring 1038 to wrap the proximal portion of bag 1015 around retractor ring 1038 in one or more layers, thereby tightening a distal portion of bag 1015 around the tissue specimen contained therein. Retractor ring 1038 is shown in its stable or equilibrium state in FIGS. 189-194B. Retractor ring 1038 may be inherently biased toward a stable or equilibrium state when in an unstable or non-equilibrium state.

FIGS. 195-200 show aspects of an exemplary bag assembly 1045 having a retractor ring 1044 and a bag 1047. As with the other retractor rings and bags disclosed herein, retractor ring 1044 may, at least initially, be separate from bag 1047. Retractor ring 1044 may be coupled to a proximal portion of bag 1047 in a similar manner to the other retractor rings, at the stage of a procedure where the proximal portion of bag 1047 is to be rolled.

Retractor ring 1044 may include an inner ring 1046 and one or more outer ring segments 1048. Inner ring 1046 may be similar to any of the inner rings described herein. For example, inner ring 1046 may have an annular or toroidal shape, and may be more rigid than outer ring segments 1048, to facilitate rotation of outer ring segments 1048 poloidally around inner ring 1046. Inner ring 1046 may have a coating, such as a lubricant, that may facilitate the rotation of outer ring segments 1048 around inner ring 1046. Additionally or alternatively, inner ring 1046 may have a rough surface to enhance frictional engagement between inner ring 1046 and outer ring segments 1048. In one example, inner ring 1046 and outer ring segments 1048 may have splines (see, e.g., FIG. 198B) that are engaged, such that outer ring segments 1048 may lock onto inner ring 1046 in certain orientations, and/or may only rotate about inner ring 1046 in one direction.

Outer ring segments 1048 may rotate independently of each other around inner ring 1046. Outer ring segments 1048 may resemble an annulus or toroid when coupled to inner ring 1046, albeit one with gaps to create discrete segments. Each of outer ring segments 1048 may have a channel 1052 (see, e.g., FIG. 200) running therethrough. The cross-sectional shape of channel 1052 may be complimentary to a cross-sectional shape of inner ring 1046. In one example, outer ring channel 1052 may be defined by splines 1051 that engage with splines 1055 (see, e.g., FIG. 198B) of inner ring 1046, similar to retractor ring 962 (see, e.g., FIG. 121, showing outer ring splines 969 engaged with inner ring splines 968).

Retractor ring 1044 may be coupled to bag 1047 in any manner discussed in this disclosure. After retractor ring 1044 is coupled to bag 1047, outer ring segments 1048 may be rotated together, or individually, to wrap bag 1047 about outer ring segments 1048. Depending, for example, on the size, shape, and/or type of tissue the user seeks to remove from the subject's body, the user may want to tighten one region of bag 1047 independently of another region of bag 1047. If more tension is desired in one region/zone/sector of bag 1048 than another, the outer ring segment that rolls that region/zone/sector may be rotated more than other outer ring segments. If less tension is desired in one region/zone/sector than another, the outer ring segment for that region/zone/sector may be rotated less than other outer ring segments. This fine adjustment of tension allows the user to, for example, exert consistent compressive force on an irregularly-shaped tissue specimen.

FIGS. 201 and 202 show aspects of an exemplary bag assembly 1059. Bag assembly 1059 may include a bag 1057 and a retractor ring 1056. As with the other retractor rings and bags disclosed herein, retractor ring 1056 may, at least initially, be separate from bag 1057. Retractor ring 1056 may be coupled to a proximal portion of bag 1057 in a similar manner to the other retractor rings, at the stage of a procedure where the proximal portion of bag 1057 is to be rolled.

Retractor ring 1056 may have one or more annular slots or grooves 1058 along its outer surface. Grooves 1058 may run in the poloidal direction. The grooves 1058 may be evenly-spaced around the circumference of ring 1056, but other spacing arrangements also are contemplated. Grooves 1058 may be "T-track" grooves having a T-shaped cross-section (see, e.g., FIG. 202).

Grooves 1058 may receive anchors 1060 on a proximal end of bag 1057. Anchors 1060 may extend radially-outwardly from the proximal end of bag 1057. Anchors 1060 may be T-shaped, and may be complementary to portions of grooves 1058. Anchors 1060 may snap into grooves 1058, allowing retractor ring 1056 and bag 1057 to be coupled by the user during a procedure. Once in grooves 1058, anchors 1060 may slide through grooves 1058 in a poloidal direction to roll the proximal end of bag 1057 about retractor ring 1056 in one or more layers. Each anchor 1060 may slide independently of the other anchors 1060 so that different levels of tension may be imparted to different regions/zones/sectors of bag 1057.

FIGS. 203A and 203B show a mesh bag 1062 with cutters 1064 coupled to segments of the mesh. Mesh bag 1062 may, for example, be similar to the mesh bag(s) disclosed in U.S. Provisional Application No. 62/438,916. Cutters 1064 may be metal, plastic, or other material, and may have sharpened edges to facilitate cutting tissue. Cutters 1064 may be coupled to mesh bag 1062 by glue or other adhesive, may be fastened to mesh bag 1062 with clips, may be sewn onto mesh bag 1062, may be welded to mesh bag 1062, or may be fastened to mesh bag 1062 by other suitable means. Additionally or alternatively, cutters 1064 may include sharpened portions of segments forming the mesh of bag 1062. In one example, cutters 1064 may include blades similar to those disclosed in the '916 application. Cutters 1064 may line a bottom or distal portion of mesh bag 1062 to ensure contact with a tissue specimen inserted into mesh bag 1062. The user may actuate (e.g., expose and/or drive) cutters 1064 by compressing mesh bag 1062 against the tissue specimen. The compression may be imparted by use of any of the retractor rings described herein (FIG. 203B) to roll mesh bag 1062. Mesh bag 1062 may be contained in an outer bag 1063, such that pieces of the tissue specimen that have been cut by cutters 1064 may be contained in outer bag 1063.

FIGS. 204A and 204B show a plurality of cutting elements 1100-1 through 1100-7 (collectively referred to as 1100) having common ends 1102 and 1104. Cutting elements are disposed in an interior of bag 1106. FIG. 204A illustrates bag 1106 in an unfolded stated as indicated by the dashed line. Heat seals can be used to separate and/or keep the cutting elements substantially parallel in the bag. Cutting elements 1100 can have any of the structures described above in association with FIGS. 50A-73. A handle (not shown), such as handle 306, 310, 311, or 313 shown in FIGS. 47A-49, can be coupled to each of common ends 1102 and 1104. Common ends 1102 and 1104 can be pulled in a sawing motion such that multiple cutting elements (e.g., cutting elements 1100-3, 1100-4, and 1100-5) cut through a tissue specimen simultaneously. Although, FIG. 204A shows seven cutting elements and a rectangular bag 110, embodiments are not so limited. The size of the pieces into which the tissue specimen is cut can be dependent on the arrangement and/or spacing of cutting elements 1100, and/or the quantity of cutting elements 1100.

As illustrated in FIG. 204A, cutting elements 1100 can be substantially parallel to each other when coupled to bag 1106. However, when cutting elements 1100 are released from bag 1106, cutting elements 1100 expand (flare outwardly) as illustrated in FIG. 204B. Cutting elements 1100 can have a preformed shape to which cutting elements 1100 transition upon being released from bag 1106. One or more of cutting elements 1100 can be made of a shape memory alloy, such as Nitinol, and can expand outward when subjected to particular temperatures (e.g., body temperature).

FIG. 205A shows a perspective view of a bag including three strands 1108-1, 1108-2, and 1108-3 (collectively referred to as 1108). In the example of FIG. 205A, each of strands 1108 includes a plurality of cutting elements. FIG. 205B shows a plurality of cutting elements 1110-1 through 1110-4 (collectively referred to as 1110) of strand 1108-1 in an expanded arrangement. When a strand (e.g., 1108-1) is released from bag 1106, the cutting elements 1110 of strand 1108-1 expand (flare outwardly). Cutting elements 1110 can be analogous to cutting elements 1100 illustrated in FIGS. 204A and 204B. FIG. 205C illustrates cutting elements 1110-2, 1110-3, and 1110-4 of an expanded strand (e.g., strand 1108-1) in contact with tissue specimen 1112 (e.g., a fibroid). Cutting element 1110-1 is hidden by tissue specimen 1112.

FIG. 206 shows cutting elements 1114-1 through 1114-8 (collectively referred to as 1114) having a weaved (criss-crossed) pattern. Beneficially, the weaved pattern illustrated in FIG. 206 can cut a tissue specimen into smaller pieces than, for example, the substantially parallel pattern illustrated in FIG. 204A. However, the weaved pattern may require additional force to cut through a tissue specimen because of increased resistance from the additional contact of one or more cutting elements 1114 against the tissue specimen.

FIG. 207A shows barbed suture 1118, including barb 1120, that can serve as a cutting element (e.g., cutting elements 1100 illustrated in FIGS. 204A and 204B). FIG. 207B shows bladed suture 1122, including blade 1124, that can serve as a cutting element. Barb 1120 differs from blade 1124 in that barb 1122 provides resistance in one direction along the axis of barbed suture 1118. Barbed suture 1118 resists motion in the direction indicated by the arrow 1119. In contrast, bladed suture 1122 permits motion in both directions along the axis of bladed suture 1122 as indicated by the arrow 1123.

A concern with using a barbed or bladed suture as a cutting element is damaging the bag. However, at least one embodiment includes a bag including an inner layer that can be separated from an outer layer of the bag, such as double-layered bag 342 illustrated in FIGS. 30A-30D. As discussed above in association with FIG. 31, gap 348 between inner layer 346 and outer layer 344 of bag 302 can be inflated to separate outer layer 344 from inner layer 346. As a result, outer layer 344 is protected from the cutting elements.

FIG. 208A shows a side view of bag 1126 including inflatable ribs 1128-1, 1128-2, and 1128-3 (collectively referred to as 1128). Bag 1126 includes a fourth inflatable rib that is hidden by inflatable rib 1128-2. Inflatable ribs 1128 prevent outer layer of bag 1126 from being damaged by cutting elements (not shown) by separating the inner layer from the outer layer of bag 1126. Inflatable ribs 1128 can support a tissue specimen (not shown) in bag 1126 while the tissue specimen is being cut. Inflatable ribs 1128 can be inflated by injecting fluid (e.g., air, saline, carbon dioxide ($CO_2$) into inflatable ribs 1128 via inflating connection 1130.

FIG. 208B shows a bottom view of bag 1126 including inflated inflatable ribs 1128-1 through 1128-4. Inflatable ribs 1128 are inflated with fluid injected to inflating connection 1130. The lines on inflatable ribs 1128 that form an "X" are for illustration purposes only. Inflatable ribs 1128 can be coupled together as shown in FIG. 208B such that inflatable ribs 1128 are inflated simultaneously. In at least one embodiment, each of inflatable ribs 1128 can be a separate chamber, each rib having its own inflating connection. FIG. 208C shows a top view of bag 1126 including inflated inflatable ribs 1128-1 through 1128-4. As can be seen in FIGS. 208B and 208C, when inflatable ribs 1128 are inflated bag 1126 opens up and forms a bowl shape. FIG. 208D shows a side view of bag 1126 in a compressed state. In FIG. 208D, the inflatable ribs (not labeled) are deflated such that bag 1126 can be compressed.

FIG. 209 shows a cross-sectional view of bag 1132 including inflatable toroids (e.g., tori) 1134. FIG. 209 illustrates inflatable toroids in an inflated state such that inner layer 1133 is separated from outer layer 1135. Although FIG. 209 shows three toroids, embodiments are not so limited. Each of toroids 1134 can be a separate chamber such that each toroid is inflated individually. Alternatively, toroids 1134 can be coupled together such that toroids 1134 are inflated simultaneously.

FIG. 210 shows a cross-sectional view of bag 1136 including inflatable corrugation 1138. FIG. 210 illustrates inflatable corrugation 1138 in an inflated state such that inner layer 1137 is separated from outer layer 1139. Although FIG. 210 shows inflatable corrugation 1138 having a semi-circular profile, embodiments are not so limited. At least a portion of inflatable corrugation 1138 can be inflated. For example, the concave portion facing outer layer 1139 can be inflated, the concave portion facing inner layer 1137 can be inflated, or both portions can be inflated. A portion of inflatable corrugation can be coupled together such that the portion can be inflated simultaneously.

FIG. 211A shows a cross-sectional view of bag 1140 including inflatable cells 1142. FIG. 211 illustrates inflatable cells 1142 in an inflated state such that inner layer 1141 is separated from outer layer 1143. Inflatable cells 1142 can travel the circumference of bag 1140. FIG. 211B shows a side view of bag 1140 of FIG. 211B. Each of inflatable cells 1142 can be a separate chamber such that each cell is inflated individually. Alternatively, inflatable cells 1142 can be coupled together such that multiple ones of inflatable cells 1142 are inflated simultaneously. Not all of the inflatable cells 1142 have to be inflated; a subset of inflatable cells 1142 can be inflated.

FIG. 212A shows a perspective view of wound retractor 1170. Wound retractor 1170 includes inner ring 1158 and outer ring 1164. Inner ring 1158 fits within the annulus of outer ring 1164. Outer ring 1164 and inner ring 1158 each include at least one aperture, apertures 1180 and 1181, respectively, through which coupler 1162 can pass to couple inner ring 1158 to outer ring 1164. Inner ring 1158 can be removed and/or separated from outer ring 1164 by removing coupler 1162 from at least aperture 1181. In at least one embodiment coupler 1162 can be a spring plunger. As illustrated in FIG. 212A, inner ring 1158 has a funnel shape. Inner ring 1158 includes at least one retainer 1172 that can secure a strand or a cutting element. Retainers 1172 can each be a compliant mechanism made from the same material as inner ring 1158. A method of use of wound retractor 1170 is discussed below.

Wound retractor 1170 includes bag rolling ring 1166. Bag rolling ring 1166 is removably coupled to outer ring 1164 via at least one fastener 1176. Bag rolling ring 1166 includes at least one hook 1174 to which any of the bags disclosed herein can be coupled. Although FIG. 212A shows bag rolling ring 1166 including hooks 1174, embodiments are not so limited. For example, bag rolling ring 1166 can include pins, posts, and/or clips to couple a bag to bag rolling ring 1166. Bag rolling ring 1166 is used to roll the bag around bag rolling ring 1166 as described below. Bag rolling ring 1166 is made from a material with a firmness sufficient to prevent buckling during rolling the bag and to maintain optimal tension on a tissue specimen inside the bag.

FIG. 212B shows a sectional view of wound retractor 1170 of FIG. 212A. The section is taken at line 1171 illustrated in FIG. 212A. As shown in FIG. 212B, outer ring 1164 includes at least one retractor detent 1160. Retractor detent 1160 includes pawl (click) 1184 of a ratchet. The rack of the ratchet is on retractor arm 1150 discussed in association with FIGS. 213A-213D below. Retractor detent 1160 is coupled to outer ring 1164 such that pawl 1184 is positioned in channel 1178 of outer ring 1164. When retractor arm 1150 is position within channel 1178 (see FIG. 213B), pawl 1184 interfaces with rack 1183 on the retractor arm 1150.

Inner ring 1158 is coupled to outer ring 1164 via coupler 1162 positioned in apertures 1180 and 1181. Bag rolling ring 1166 is coupled to outer ring 1164 via fastener 1176. Fasteners 1176 can each be a compliant mechanism made from the same material as outer ring 1164. As discussed below, bag rolling ring 1166 should be able to rotate within fastener 1176.

FIG. 212C shows a perspective view of wound retractor 1170 with inner ring 1158 removed from outer ring 1164. Couplers 1162 are positioned in only aperture 1180 such that inner ring 1158 can be removed from outer ring 1164.

FIG. 213A shows a perspective view of outer ring 1164 of wound retractor 1170 and a plurality of retractors 1182-1, 1182-2, and 1182-3 (collectively referred to as 1182). Each of the retractors 1182 include retractor arm 1150 and retractor blade 1152. Retractor blade 1152 can be analogous or similar to petal 672 illustrated in FIG. 34R. FIG. 213A illustrates retractor 1182-3 positioned within the annulus of outer ring 1164 to be inserted in channel 1178.

FIG. 213B shows a sectional view of outer ring 1164 of wound retractor 1170 with retractor arm 1150 positioned within channel 1178. Pawl 1184 of retractor detent 1160 interfaces with rack 1183-3, permitting retractor 1182-3 to be pulled such that retractor blade 1152-3 is moved incrementally closer to outer ring 1164 while providing resistance to motion in the opposite direction.

FIG. 213C shows a perspective view of outer ring 1164 of wound retractor 1170 with retractors 1182 positioned within channels 1178 of outer ring 1164. As shown in FIG. 213C, edges of retractor blades 1152-1, 1152-2, and 1152-3 of retractors 1182-1, 1182-2, and 1182-3, respectively, overlap one another to cooperatively form an annulus.

FIG. 213D shows a perspective view of outer ring 1164 of wound retractor 1170 with retractors 1182 positioned within channels 1178 of outer ring 1164. As shown in FIG. 213D, retractor blades 1152 have been positioned closer to outer ring 1164 than shown in FIG. 213C. Edges of retractor blades 1152 still overlap one another to cooperatively form the annulus; however, the diameter of the annulus is greater than that shown in FIG. 213C.

FIG. 214 shows an exploded view of wound retractor 1170. Retractor detents 1160 can be coupled to outer ring 1164 via screws 1156. Each of the retractor blades 1152 can be coupled to each of the retractor arms 1150 via rivets 1154.

The following is an example method of use of wound retractor 1170 shown in FIGS. 212A-214. An incision (e.g., 2.5 centimeters (cm) long) is created in a patient's skin with a knife (e.g., scalpel). A cannula, for example, one having a 2.8 cm diameter, is inserted through the incision using a metal and/or plastic trocar (e.g., a taper point or cutting/trocar point). The inner diameter of the cannula should be at least the length of the incision (e.g., 2.5 cm). The trocar is then removed, but the cannula is left in place.

A bag, such as bag 1126, 1132, or 1136 shown in FIGS. 208A-210, contains a plurality of molded, flexible tracks/guides (e.g., four tracks) for a plurality of cutting elements, such as cutting elements 1100 illustrated in FIGS. 204A and 204B, and/or a plurality of strands, such as strands 1108 illustrated in FIGS. 205A-205C. In at least one embodiment, each of the cutting elements include a length of chainsaw having five links. Each cutting element or strand has a color-coded and/or numbered handle coupled to each end of the cutting elements or strands. For example, if there are four cutting elements then there are eight color-coded and numbered handles.

The upper portions of the cutting elements or strands are held in place against the sides of the bag (e.g., with plastic tabs) so that they do not become tangled when the bag is rolled or compressed. The plastic tabs can be perforated so as to facilitate freeing the cutting elements or strands from the bag. The handles can be staggered in height so as to facilitate passing the bag through the cannula.

The bag is inserted (pushed) into the patient's body (e.g., the patient's abdomen) through the cannula using an inserter with the bag rolled up (like an umbrella) inside the inserter. The cannula can include a seal that can be used as visual port, for example, for a camera. A camera can facilitate inserting a tissue specimen into the bag. The insertion of the bag can be analogous to the process described in association with FIGS. 46H-46L. Once the bag is inserted into the patient, the bag lies free. The tissue specimen is then inserted into the bag.

After inserting the tissue specimen in the bag, the neck of the bag is grasped (e.g., with a grasper) and pulled up through the incision. The cannula is then removed. Small tags can be fastened to the edge of the bag to facilitate this process. The handles and cutting elements and/or strands are pulled away/detached from the sides of the bag. The bag is attached to bag rolling ring 1166 via hooks 1174 and rolled taut. Rolling the bag with bag rolling ring 1166 may require four hands. To facilitate rolling the bag can be brought up taut against the underside of the incision (e.g., against the abdominal wall). Once the bag is rolled taut such that the tissue specimen is held against the underside of the incision, the cutting elements and/or strands are brought up through the annulus of bag rolling ring 1166. Outer ring 1164, including inner ring 1158, is coupled to (snapped onto) bag rolling ring 1166. The cutting elements and/or strands are attached to inner ring 1158 via retainers 1172 located at even intervals around the periphery of the outer portion of inner ring 1158.

If the bag includes an outer layer and an inner layer, such as bag 1126, inflatable ribs 1128 are inflated. For example, inflatable ribs 1128 can be inflated with $CO_2$ by connecting $CO_2$ tubing to inflating connection 1130, thereby expanding the outer layer and moving it away from the inner layer and the cutting elements and/or strands.

The cutting elements and/or strands are individually removed from fasteners 1172, one at a time, and pulled back and forth in a sawing motion. The cutting elements and/or strands quickly reduce the tissue specimen to smaller, manageable sized pieces. When one of the cutting elements and/or strands cuts all the way through the tissue specimen, that cutting element or strand is removed. The cutting elements and/or strands are utilized and removed sequentially according the numbers assigned to each of the handles. After all of the cutting elements and/or strands have cut through the tissue specimen and have been removed from inner ring 1158, inner ring 1158 is separated and/or removed from outer ring 1164.

Outer ring 1164 includes three retractor detents 1160, each located at the ten o'clock, two o'clock, and six o'clock positions. Retractor arms 1150 of three retractors 1182 are then positioned into channels 1178 of outer ring 1164. Retractors 1182 include retractor blades 1152 coupled to retractor arm 1150. Retractor arm 1150 is a knurled shaft including rack 1183 that interfaces with pawl 1184 of retractor detent 1160 to form a ratchet. The ratchet allows retractor arm 1150 to be tightened (pulled away from the center of the incision) and held in place. Retractor blades 1152 can each be a curved piece of semi-rigid, semi-flexible plastic. Retractor blades 1152 are inserted into the incision. As illustrated in FIGS. 213C and 213D, each one of the three retractor blades 1152 overlaps with the adjacent two retractor blades 1152, so as to form a collar that completely lines and protects the inside of the incision.

The cut pieces of the tissue specimen are extracted through the collar of retractor blades 1152 that protect the neck of the bag. If a cut piece of the tissue specimen is too large to fit through the collar, the cut piece can be cut again using a knife (e.g., scalpel). After the cut pieces have been extracted from the bag, the bag is removed along with outer ring 1164 and retractor arms 1182. If the bag is a dual layer bag, the space between the inner and outer layers and/or inflatable ribs 1128 are deflated and removed along with the inner layer.

FIG. 215A shows an exemplary cutter 1200 in accordance with the present disclosure, similar to previous embodiments illustrated in FIGS. 204A-206. Cutter 1200 includes strands 1202-1 and 1202-2 coupled to a plurality of cutting elements 1206. In the example of FIGS. 215A-215F, cutting elements 1206 includes a chain of cutting elements, or knives 1206, pivotally attached to, and interspersed with, links 1208. Although FIG. 215A shows five cutting elements, any suitable number of cutting elements 1206 can be used. While the term "cutting elements" is recited generally herein, those of skill in the art will recognize that they can be referred to as, and considered to be, blades or knives.

FIGS. 215B and 215C show a portion of cutter 1200 of FIG. 215A. Strand 1202-1 is coupled to link 1208-1 such as by routing strand 1202-1 around one of the pins disposed in link 1208-1. Link 1208-1 is pivotally coupled to cutting element 1206-1 by a pin proximate a first end thereof. Cutting element/knife/blade 1206-1 is in turn pivotally coupled to link 1208-2 proximate a second end of blade 1206-1 by a second pin. Cutting element 1206-2 is in turn coupled to links 1208-2 and 1208-3, respectively. Similarly, cutting element 1206-3 is coupled to links 1208-3 and 1208-4 and cutting element 1206-4 is coupled to links 1208-4 and 1208-4.

FIGS. 215D and 215E show a portion of a chain of cutting elements 1212-1 and 1212-2. Cutting elements 1212-1 and 1212-2 and links 1210-1 and 1210-2 can be analogous to cutting elements 1206 and links 1208 illustrated in FIGS. 215A-215C, respectively.

FIG. 215F shows a cutting element 1214 in accordance with the present disclosure. Cutting element 1214 can be analogous to cutting elements 1206 and 1212 illustrated in FIGS. 215A-215E. As shown in FIG. 215F, cutting element 1214 has a curved (arcuate, if desired) cutting edge 1216 that is formed along one edge of element 1214, whereas the opposing edge of element 1214 is presented as being concave, but may be straight or convex, if desired. By providing a cutting edge along one edge of elements 1214, sharp portions of the cutters can be oriented inwardly toward the center of the bag, thereby reducing the chance that the cutting edges 1216 will cut the bag. Moreover, by providing the cutters as a chain link with pins, similar in some manners to a bicycle chain, the links are constrained to move along a single plane, rather than being permitted to twist. Thus, in a chain of cutting elements, such as that shown in FIG. 215A, all of the cutting edges can be one side of the chain so to prevent a bag from being inadvertently cut. The cutting edges can face the interior space of a bag such that the cutting edges contact a tissue specimen (e.g., tissue specimen 1112 shown in FIG. 205C). Cutting element 1214 and cutting edge 1216 are curved with cutting edge 1216 located at the convex end of cutting element 1216. This location of cutting edge 1216 maximizes the surface area and/or length of cutting edge 1216. Cutter 1200 can be used in various arrangements as disclosed elsewhere herein. For example, cutter 1200 can be provided singularly and overlapped with other cutters and used individually in a predetermined order. In another embodiment, cutters 1200 can be used in place of any cutting elements described elsewhere in this disclosure, such as cutting elements 1114 in FIG. 206, or cutting elements 1110, cutting elements 1100, strands 1108, for example.

One or more components of embodiments of the present disclosure can be single-use and/or disposable.

It is contemplated that any of the rings disclosed herein may be made of silicone, polymer, metal, or any other suitable material. Where a ring has parts with different flexibilities/rigidities, the more flexible part may be made of a more flexible material (e.g., silicone), and the more rigid part may be made of a more rigid material (e.g., plastic or metal).

It will be apparent to those skilled in the art that various modifications and variations can be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

What is claimed is:

1. A tissue extraction device, comprising:
   an inner bag having an interior;
   an outer bag disposed about the inner bag;
   a plurality of elongate cutters extending through the interior of the inner bag along an inner surface of the inner bag, wherein each of the plurality of elongate cutters includes a strand and at least one cutting element on the strand, wherein the at least one cutting element includes a cutting edge to cut tissue as the cutter is drawn across tissue, wherein each of the plurality of elongate cutters is configured to be used individually from the other cutters to cut through a tissue specimen disposed in the inner bag using a reciprocating sawing motion; and
   a rolling retractor ring, wherein a proximal portion of the inner bag is configured to be rolled around the rolling retractor ring to pull the inner bag away from the outer bag and to pull the tissue specimen against the inner surface of the inner bag adjacent the plurality of cutters to facilitate engagement between each cutter of the plurality of cutters and the tissue specimen.

2. The tissue extraction device of claim 1, wherein the cutting element includes a blade on the strand.

3. The tissue extraction device of claim 1, further including a layer of material coupled to the inner surface of the inner bag, such that a channel is defined between the layer of material and the interior surface of the inner bag, wherein at least one of the elongate cutters extends through the channel.

4. The tissue extraction device of claim 1, wherein each of the elongate cutters includes eyelets.

5. The tissue extraction device of claim 4, wherein each of the elongate cutters further includes handles, and further wherein the handles are removably coupled to the eyelets.

6. The tissue extraction device of claim 1, wherein the rolling retractor ring includes a ring body defining at least one protrusion to engage a portion of the inner bag.

7. The tissue extraction device of claim 6, wherein a proximal portion of the inner bag defines one or more holes to receive the at least one protrusion of the rolling retractor ring.

8. The tissue extraction device of claim 1, further comprising a frame including at least one fastener to couple to and retain the rolling retractor ring in place against the frame after the inner bag has been rolled about the rolling ring a plurality of times.

9. The tissue extraction device of claim 8, wherein the frame defines a downwardly depending wound protector that in turn defines a central opening therethrough to permit the passage of the cutter therethrough, and at least one retainer to secure the cutter in place on the frame.

10. The tissue extraction device of claim 1, wherein the rolling retractor ring is configured to permit a user to evert the rolling retractor ring one or more times to induce tension on an inner layer of the inner bag so that the inner layer of the bag pulls a tissue specimen in the inner bag away from the outer layer of the bag and firmly hold onto the tissue specimen in preparation for cutting.

11. The tissue extraction device of claim 1, further comprising an inner ring that fits within an outer ring, wherein the rolling retractor ring is removably coupled to the outer ring by way of at least one fastener about a circumference of the outer ring.

12. The tissue extraction device of claim 11, wherein the inner ring is removably coupled to the outer ring by one or more further fasteners.

13. The tissue extraction device of claim 11, wherein the outer ring includes at least one retractor detent to receive a retractor arm of a retractor.

14. The tissue extraction device of claim 11, wherein the outer ring includes a plurality of retractor detents, each said retractor detent being configured to receive a retractor arm of a retractor, wherein edges of retractor blades disposed on the retractors overlap one another to cooperatively form an annulus proximate an incision in a patient.

15. The tissue extraction device of claim 1, wherein each of the plurality of elongate cutters includes a handle that bears indicia indicative of an order of progression for using each cutter.

\* \* \* \* \*